US012673947B2

(12) United States Patent
Wu et al.

(10) Patent No.: US 12,673,947 B2
(45) Date of Patent: Jul. 7, 2026

(54) PYRIDO-PYRAZINYL COMPOUNDS FOR TREATING ACUTE MYELOID LEUKEMIA

(71) Applicant: Cytosinlab Therapeutics Co., Ltd., Shanghai (CN)

(72) Inventors: Haiping Wu, Shanghai (CN); Meng Wang, Shanghai (CN); Yuan Mi, Shanghai (CN); Xingnian Fu, Shanghai (CN); Hui Shi, Shanghai (CN); Jiannan Guo, Shanghai (CN)

(73) Assignee: Cytosinlab Therapeutics Co. Ltd., Shanghai (CN)

( * ) Notice: Subject to any disclaimer, the term of this patent is extended or adjusted under 35 U.S.C. 154(b) by 736 days.

(21) Appl. No.: 17/999,295

(22) PCT Filed: Jul. 22, 2021

(86) PCT No.: PCT/CN2021/107759

§ 371 (c)(1),
(2) Date: Nov. 18, 2022

(87) PCT Pub. No.: WO2022/017434

PCT Pub. Date: Jan. 27, 2022

(65) Prior Publication Data

US 2023/0339936 A1 Oct. 26, 2023

(30) Foreign Application Priority Data

Jul. 23, 2020 (CN) ......................... 202010718607.9
Feb. 8, 2021 (CN) ......................... 202110172680.5

(51) Int. Cl.

| | |
|---|---|
| *C07D 471/04* | (2006.01) |
| *C07D 405/12* | (2006.01) |
| *C07D 405/14* | (2006.01) |
| *C07D 487/04* | (2006.01) |
| *C07D 519/00* | (2006.01) |

(52) U.S. Cl.
CPC ......... *C07D 471/04* (2013.01); *C07D 405/12* (2013.01); *C07D 405/14* (2013.01); *C07D 487/04* (2013.01); *C07D 519/00* (2013.01)

(58) Field of Classification Search
None
See application file for complete search history.

(56) References Cited

U.S. PATENT DOCUMENTS

2025/0101017 A1* 3/2025 Wu ....................... C07C 309/04

FOREIGN PATENT DOCUMENTS

| | | | | |
|---|---|---|---|---|
| CN | 1918158 A | 2/2007 | | |
| CN | 104822687 A | 8/2015 | | |
| CN | 106459042 A | 2/2017 | | |
| CN | 110944994 A | 3/2020 | | |
| WO | WO-2012167733 A1 * | 12/2012 | .............. | A61P 35/00 |
| WO | 2019062803 A1 | 4/2019 | | |

OTHER PUBLICATIONS

International Search Report issued Oct. 28, 2021 in PCT/CN2021/107759.

* cited by examiner

*Primary Examiner* — Jennifer A Berrios
*Assistant Examiner* — Sophia Reilly
(74) *Attorney, Agent, or Firm* — ICE MILLER LLP

(57) ABSTRACT

The present invention provides compounds having kinase inhibitory activity. Specifically, the present invention provides compounds having a structure represented by the following formula (II). The compound of the present invention has good inhibitory activity for a variety of kinases (e.g. ALK, AXL, EGFR, and FLT3), and therefore can be used for preparing a pharmaceutical composition for treating kinase activity-related diseases (e.g. acute myeloid leukemia, etc.).

14 Claims, No Drawings

PYRIDO-PYRAZINYL COMPOUNDS FOR TREATING ACUTE MYELOID LEUKEMIA

CROSS-REFERENCE TO RELATED APPLICATION

This application is a Section 371 of International Application No. PCT/CN2021/107759 filed Jul. 22, 2021, which was published in the Chinese language Jan. 27, 2022, under International Publication No. WO 2022/017434 A1, which claims priority to Chinese Patent Application No. 202010718607.9 filed Jul. 23, 2020, and to Chinese Patent Application No. 202110172680.5 filed Feb. 8, 2021, the disclosures of which are incorporated herein by reference in their entireties.

FIELD OF INVENTION

The present invention relates to the field of pharmaceutical chemistry and medicine, and in particular to FLT3 inhibitor compounds, preparation methods thereof and the use for treating diseases which is relevant to abnormal FLT3 activity or expression level, such as acute myeloid leukemia.

BACKGROUND OF INVENTION

The occurrence and development of malignant tumors is a complex process. The traditional therapeutic drugs include alkylating agents, antimetabolites, natural products and antibiotics, however, all of these types show poor efficiency and serious side effects. Small molecule kinase inhibitors are currently a hot field as potential cancer therapy. Protein kinases are catalysts that play a key role in almost every aspect of cell biology and biochemistry. These enzymes generate signaling modules that regulate cell cycle progression, proliferation, programmed cell death (apoptosis), cytoskeletal function, motility, differentiation, development, transcription, and translation. Protein kinases play several roles, and careful regulation of them is crucial, since abnormal actions of them can lead to cancer, cardiovascular disease, inflammation, and neurological disorders. Dysregulation, overexpression, and mutation of protein kinases are reasons for the pathogenesis of human diseases, which makes these enzymes attractive drug targets. Growth factor receptors with the activity of protein tyrosine kinases (PTKs) are called receptor tyrosine kinases. Protein receptor tyrosine kinases are a class of tightly regulated enzymes, and the abnormal activation of different members of the family is one of the markers of cancer. FLT3, same to receptors such as KIT, FMS, platelet-derived growth factor receptor (PDGFR), belongs to the family of receptor tyrosine kinases, and play important roles in the regulation of hematopoiesis.

FLT3 (FMS-like tyrosine kinase-3) is a specific cytokine receptor expressed on hematopoietic stem cells, which regulates the survival and growth of hematopoietic stem and progenitor cells, the maturation of dendritic cells, and the maintenance of regulatory T cell homeostasis. FLT3 gene mutations present in approximately 30% of patients with acute myeloid leukemia (AML), including FLT3 internal tandem duplication (FLT3-ITD) and FLT3 tyrosine kinase domain point mutation (FLT3-TKD). FLT3-ITD mutations lead to constitutive, ligand-independent activation of tyrosine kinase function and are known to have poor prognosis for patient survival, which exist in about 25% of AML patients, while FLT3-TKD exist in about 5% to 10% of such patients. FLT3 can dimerize on ligand binding and undergo autophosphorylation, thus initiating multiple intracellular signaling programs. FLT3 mutation can promote cell proliferation and inhibit cell apoptosis through MAPK, PI3K/AKT/Mtor and STAT5 pathway in vitro experiments. The high incidence and poor prognosis of FLT3 mutation suggest that it may be an important target for the treatment of AML.

In summary, there is an urgent need in the art to develop novel FLT3 kinase inhibitors.

SUMMARY OF INVENTION

The object of the present invention is to provide a novel FLT3 kinase inhibitor.

In the first aspect of the present invention, a compound of Formula I, or pharmaceutically acceptable salts or deuterated products thereof is provided:

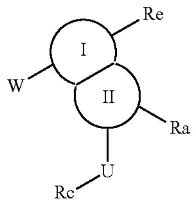

I

Wherein,

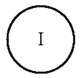

ring is an aza(5-6 membered heteroaromatic ring), and

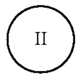

is a 5-6 membered aromatic ring or a heteroaromatic ring, and the

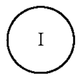

ring together with the

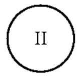

ring form a 9-10 membered heteroaromatic ring;

Ra is selected from the group consisting of H, halogen, a substituted or unsubstituted $C_1$-$C_6$ alkyl, a substituted or unsubstituted $C_2$-$C_6$ alkenyl, a substitute or unsubstitute $C_2$-$C_6$ alkynyl, a substitute or unsubstitute $C_3$-$C_8$ carbon ring (including saturated and partially unsaturated ring), a substituted or unsubstituted 5-9 membered heteroaromatic ring (including monocyclic or fused ring) containing 1-3 heteroatoms selected from oxygen, sulfur and nitrogen, a substituted or unsubstituted 3-8 membered heterocyclic ring containing 1-3 heteroatoms selected from oxygen, sulfur and nitrogen (which is saturated or partially unsaturated heterocyclic ring, preferably a substituted or unsubstituted $C_3$-$C_6$ cycloalkyl, a substituted or unsubstituted 3-6 membered heterocyclic ring containing 1-3 heteroatoms selected from oxygen, sulfur, and nitrogen), or a substituted and unsubstituted -$[L]_m$-H group; wherein, the L is each independently selected from the group consisting of —$CH_2$—, —O—, —NH—, or —S—;

m is selected from the group consisting of 1, 2, 3, 4, 5 and 6;

U is selected from the group consisting of a chemical bond, or —O—, —CHR—, carbonyl, S, —NH—, —NHC(O)—, —$NHS(O)_2$—, —NHC(O)NH—, —NHC(S)NH—, —COO—, and —O—$S(O)_2$—;

Rc is selected from the group consisting of H, a substituted or unsubstituted $C_1$-$C_6$ alkyl group, a substituted or unsubstituted $C_3$-$C_8$ carbocyclic ring (including saturated or partially unsaturated), a substituted or unsubstituted 3-8 membered heterocyclic ring containing 1-3 heteroatoms selected from oxygen, sulfur and nitrogen (saturated or partially unsaturated, including monocyclic, fused, bridged, or spirocyclic ring), a substituted or unsubstituted $C_6$-$C_{10}$ aryl group, a substituted or unsubstituted 5-12 membered heteroaromatic ring containing 1-3 heteroatoms selected from oxygen, sulfur, and nitrogen, or a substituted and unsubstituted -$[L]_m$-H group; wherein, the L is each independently selected from the group consisting of —$CH_2$—, —O—, —NH—, or —S—;

Re is selected from the group consisting of halogen, —NHR, —OR, a substituted or unsubstituted $C_1$-$C_6$ alkyl, a substituted or unsubstituted $C_1$-$C_6$ alkyl-NH—, a substituted or unsubstituted $C_1$-$C_6$ alkoxy, a substituted and unsubstituted $C_3$-$C_8$ carbocyclic ring (including saturated and partially unsaturated cases), or a substituted and unsubstituted -$[L]_m$-H group; wherein, the L is each independently selected from the group consisting of —$CH_2$—, —O—, —NH—, or —S—;

W is selected from the group consisting of H, —NHR, —OR, halogen, a substituted or unsubstituted $C_1$-$C_6$ alkyl group, a substituted or unsubstituted $C_1$-$C_6$ alkoxy group, a substitute or unsubstituted $C_2$-$C_6$ alkenyl group, a substitute or unsubstituted $C_2$-$C_6$ alkynyl group, a substituted or unsubstituted $C_3$-$C_8$ carbocyclic ring (including saturated and partially unsaturated cases), a substituted or unsubstituted $C_6$-$C_{10}$ aryl group, a substituted or unsubstituted 4-15 membered heterocyclic ring containing 1-3 heteroatoms selected from oxygen, sulfur and nitrogen (a saturated or partially unsaturated ring, including monocyclic, fused, bridged, or spirocyclic ring), a substituted or unsubstituted 5-12 membered heteroaromatic ring containing 1-3 heteroatoms selected from the group consisting of oxygen, sulfur, and nitrogen (including a monocyclic or fused ring), a substituted or unsubstituted —$C_1$-$C_6$ alkyl-phenyl, a substituted or unsubstituted $C_3$-$C_{12}$ cycloalkyl (including monocyclic, fused, bridged, or spirocyclic ring), a substituted or unsubstituted $C_2$-$C_{10}$ acyl group, a substituted or unsubstituted $C_2$-$C_{10}$ ester group, a substituted or unsubstituted $C_6$-$C_{10}$ aryloxy group, and a substituted or unsubstituted $C_1$-$C_6$ amide group;

The W group is substitute with at least one group having the structure -M-A, and the M is selected from the group consisting of a chemical bond, or —CHR—, carbonyl, S, O, —NH—, —NHC(O)—, —$NHS(O)_2$—, —NHC(O)NH—, —NHC(S)NH—, —COO—, and —O—$S(O)_2$—;

The A is selected from the group consisting of H, halogen, cyano, amino, nitro, hydroxyl, sulfhydryl, aldehyde, carboxyl, sulfonyl, a substituted or unsubstituted $C_1$-$C_6$ alkyl, a substituted or unsubstituted $C_1$-$C_6$ alkoxy, a substituted and unsubstituted $C_6$-$C_{10}$ aryl, a substituted or unsubstituted 4-12 membered heterocyclic ring containing 1-3 heteroatoms selected from oxygen, sulfur and nitrogen (including monocyclic ring, fused polycyclic ring, bridged ring, or spirocyclic ring), a substituted or unsubstituted 5-12 membered heteroaromatic ring containing 1-3 heteroatoms selected from oxygen, sulfur and nitrogen (including monocyclic ring or fused ring), a substituted or unsubstituted —$C_1$-$C_6$ alkyl-phenyl, a substituted or unsubstituted $C_3$-$C_{12}$ cycloalkyl, a substituted or unsubstituted $C_2$-$C_{10}$ acyl, a substituted or unsubstituted $C_2$-$C_{10}$ ester group, a substituted or unsubstituted $C_6$-$C_{10}$ aryloxy, a substituted or unsubstituted $C_1$-$C_6$ amide group, a substituted or unsubstituted $C_1$-$C_4$ alkyl-$S(O)_2$—, a substituted or unsubstituted $C_1$-$C_4$ alkyl-SO—;

In the group A, said substitution means substituted by one or more groups selected from group B, and the group B comprises H, halogen, =O, cyano, amino, nitro, hydroxyl, sulfhydryl, aldehyde, carboxyl, sulfonyl, a substituted or unsubstituted $C_1$-$C_6$ alkyl, a substituted or unsubstituted $C_1$-$C_6$ alkoxy, a substituted and unsubstituted $C_6$-$C_{10}$ aryl, a substituted or unsubstituted 3-12 membered (preferably 5-7 membered) heterocyclic ring containing 1-3 heteroatoms selected from oxygen, sulfur and nitrogen, a substituted or unsubstituted 5-12 membered heteroaromatic ring containing 1-3 heteroatoms selected from oxygen, sulfur and nitrogen, a substituted or unsubstituted —$C_1$-$C_6$ alkyl-phenyl, a substitute or unsubstituted $C_3$-$C_{12}$ cycloalkyl, a substitute or unsubstituted $C_2$-$C_{10}$ acyl, a substituted or unsubstituted $C_2$-$C_{10}$ ester group, a substituted or unsubstituted $C_6$-$C_{10}$ aryloxy, a substituted or unsubstituted $C_1$-$C_6$ amide, a substituted or unsubstituted $C_1$-$C_4$ alkyl-$S(O)_2$—, a substituted or unsubstituted $C_1$-$C_4$ alkyl-SO—; and in the group B, the substitution means substituted by one or more R groups;

R is selected from the group consisting of H, halogen, cyano, amino, nitro, hydroxyl, sulfhydryl, aldehyde, carboxyl, sulfonyl, a substituted or unsubstituted $C_1$-$C_6$ alkyl, a substituted or unsubstituted $C_1$-$C_6$ alkoxy, a substituted and unsubstituted $C_6$-$C_{10}$ aryl, a substituted or unsubstituted 5-7 membered heterocyclic ring containing 1-3 heteroatoms selected from oxygen, sulfur and nitrogen, a substituted or unsubstituted —$C_1$-$C_6$ alkyl-phenyl, a substitute or unsubstituted $C_3$-$C_{12}$ cycloalkyl, a substitute or unsubstituted $C_2$-$C_{10}$ acyl, a substituted or unsubstituted $C_2$-$C_{10}$ ester group, a substituted or unsubstituted $C_6$-$C_{10}$ aryloxy, a substituted or unsubstituted $C_1$-$C_6$ amide group, a substituted or unsubstituted $C_1$-$C_4$ alkyl-$S(O)_2$—, a substituted or unsubstituted $C_1$-$C_4$ alkyl-SO—;

Unless otherwise specified, in the above formulae, the substitution means that the hydrogen atom on the corresponding group is substituted by one or more substituents selected from the group consisting of deuterium, tritium, halogen, hydroxyl, carboxyl, sulfhydryl, benzyl, $C_1$-$C_{12}$ alkoxycarbonyl, $C_1$-$C_6$ aldehyde, amino, $C_1$-$C_6$ amide, nitro, cyano, an unsubstituted or halogenated $C_1$-$C_6$ alkyl, an unsubstituted or halogenated $C_3$-$C_8$ cycloalkyl, $C_2$-$C_{10}$ alkenyl, $C_1$-$C_6$ alkoxy, $C_1$-$C_6$ alkyl-amino, $C_6$-$C_{10}$ aryl, five or six membered heteroaryl, five or six membered nonaromatic heterocyclyl, —O—($C_6$-$C_{10}$ aryl), —O-(five and six membered heteroaryl), $C_1$-$C_{12}$ alkylaminocarbonyl, an unsubstituted or halogenated $C_2$-$C_{10}$ acyl, sulfonyl (—$SO_2$—OH), phosphoryl (—$PO_3$—OH), an unsubstituted or halogenated $C_1$-$C_4$ alkyl-S(O)$_2$—, an unsubstituted or halogenated $C_1$-$C_4$ alkyl-SO—.

In another preferred embodiment, the compound of the formula I has a structure as shown in the following formula II:

II

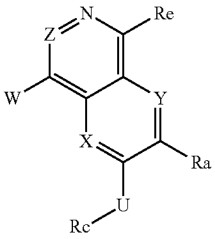

wherein, X, Y and Z are each independently selected from: N or CR.

In another preferred embodiment, the compound of the formula I has the structure as shown in the following formula IIa:

IIa

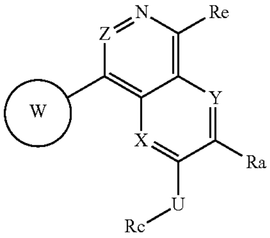

Wherein, the W ring is selected from the group consisting of a substituted and unsubstituted $C_6$-$C_{10}$ aryl, a substituted or unsubstituted 4-12 membered heterocyclic ring containing 1-3 heteroatoms selected from oxygen, sulfur and nitrogen, a substituted or unsubstituted 5-12 membered heteroaromatic ring containing 1-3 heteroatoms selected from oxygen, sulfur and nitrogen, a substituted or unsubstituted —$C_1$-$C_6$ alkyl-phenyl, a substitute or unsubstituted $C_3$-$C_{12}$ cycloalkyl; wherein, in the W group, said substitution means substitution by one or more groups selected from group A.

In another preferred embodiment, the W ring is selected from the group consisting of a substitute or unsubstituted 4-7 membered heterocyclic ring, a substituted or unsubstituted 5-6 membered heteroaromatic ring, a substituted or unsubstituted 9-10 membered heteroaromatic ring with a fused bicyclic structure, a substituted and unsubstituted phenyl, and a substituted and unsubstituted $C_3$-$C_6$ cycloalkyl.

In another preferred embodiment, the W ring is a substituted or unsubstituted ring structure selected from the group consisting of phenyl, cyclopentyl, cyclohexyl,

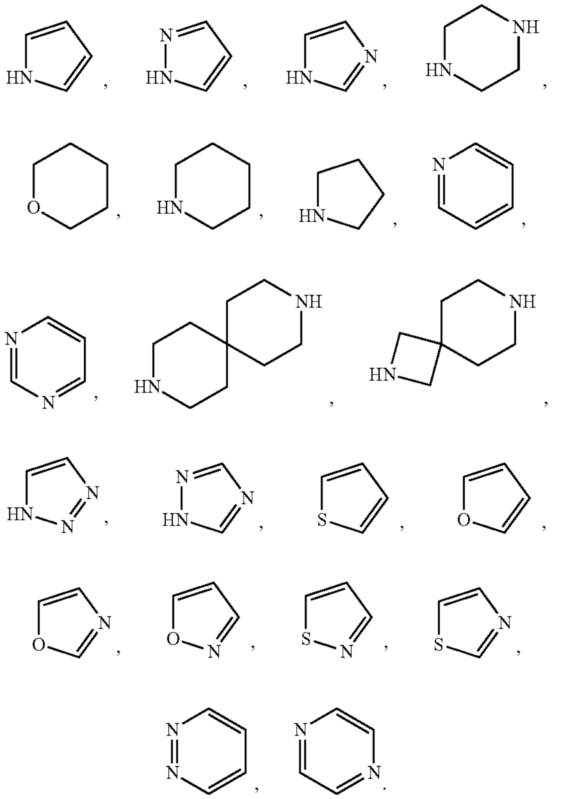

In another preferred embodiment, the compound of the formula I has the structure as shown in the following formula III:

III

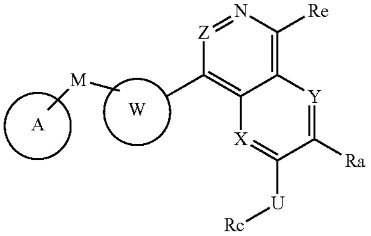

Wherein, the A ring is selected from the group consisting of a substituted or unsubstituted 4-12 membered heterocyclic ring containing 1-3 heteroatoms selected from oxygen, sulfur and nitrogen, a substituted or unsubstituted 5-12 membered heteroaromatic ring containing 1-3 heteroatoms selected from oxygen, sulfur and nitrogen, a substituted and unsubstituted $C_6$-$C_{10}$ aryl, a substituted or unsubstituted —$C_1$-$C_6$ alkyl-phenyl, a substituted or unsubstituted $C_3$-$C_{12}$ cycloalkyl; M is selected from the group consisting of a chemical bond, or —O—, —CHR—, carbonyl, S, —NH—, —NHC(O)—, —NHS(O)$_2$—, —NHC(O)NH—, —NHC(S)NH—, —COO—, —O—S(O)$_2$—.

In another preferred embodiment, the compound of the formula I has the structure as shown in the following formula:

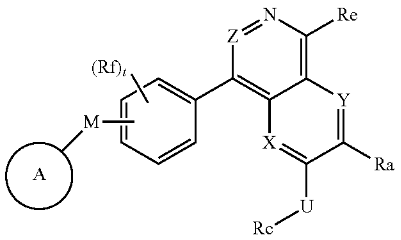

wherein,

Rf is selected from the group consisting of H, halogen, cyano, amino, nitro, hydroxyl, sulfhydryl, aldehyde, carboxyl, sulfonyl, $C_1$-$C_4$ alkyl-S(O)$_2$—, a substituted or unsubstituted $C_1$-$C_6$ alkyl, a substituted or unsubstituted $C_1$-$C_6$ alkoxy;

t is 0, 1, 2, 3 or 4;

the A ring is selected from the group consisting of a substituted or unsubstituted 5-12 membered saturated ring (including spirocyclic ring and bridged ring), a substituted or unsubstituted 5-12 membered heteroaromatic ring containing 1-3 heteroatoms selected from oxygen, sulfur and nitrogen, a substituted and unsubstituted $C_6$-$C_{10}$ aryl having at least one heteroatom selected from N or O on the ring.

In another preferred embodiment, at least one of the Rf is positioned at the meta position of the connecting site of the benzene ring and the parent nucleus.

In another preferred embodiment, the compound of the formula I has the structure as shown in the following formula:

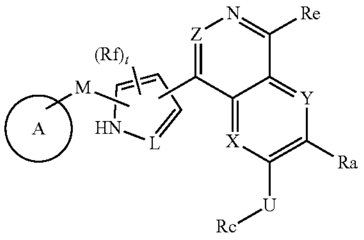

wherein,

Rf is selected from the group consisting of H, halogen, cyano, amino, nitro, hydroxyl, sulfhydryl, aldehyde, carboxyl, sulfonyl, $C_1$-$C_4$ alkyl-S(O)$_2$—, a substituted or unsubstituted $C_1$-$C_6$ alkyl, a substituted or unsubstituted $C_1$-$C_6$ alkoxy;

t is 0, 1, 2, 3 or 4;

L is N or CH;

the A ring is selected from the group consisting of a substituted or unsubstituted 4-12 membered heterocyclic ring containing 1-3 heteroatoms selected from oxygen, sulfur and nitrogen, a substituted or unsubstituted $C_3$-$C_{12}$ cycloalkyl, a substituted or unsubstituted 5-12 membered heteroaromatic ring containing 1-3 heteroatoms selected from oxygen, sulfur and nitrogen, a substituted and unsubstituted $C_6$-$C_{10}$ aryl.

Wherein, When the nitrogen atom on

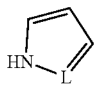

is the attachment site, said NH is N (i.e., the hydrogen atom on NH is absent to form the attachment site).

In another preferred embodiment, the compound of the formula I has the structure as shown in the following formula IV:

IV

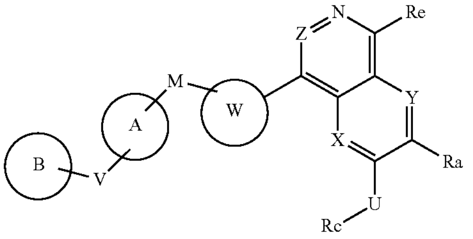

wherein, the A ring is selected from the group consisting of a substituted or unsubstituted 4-7 membered heterocyclic ring containing 1-3 heteroatoms selected from oxygen, sulfur and nitrogen, a substituted or unsubstituted 5-12 membered heteroaromatic ring containing 1-3 heteroatoms selected from oxygen, sulfur and nitrogen, a substituted and unsubstituted $C_6$-$C_{10}$ aryl, a substituted or unsubstituted —$C_1$-$C_6$ alkyl-phenyl group, a substituted or unsubstituted $C_3$-$C_{12}$ cycloalkyl group; M is selected from the group consisting of a chemical bond, or —O—, —CHR—, carbonyl, S, —NH—, —NHC(O)—, —NHS(O)$_2$—, —NHC(O)NH—, —NHC(S)NH—, —COO—, —O—S(O)$_2$—;

B ring is selected from the group consisting of a substituted or unsubstituted 4-12 membered heterocyclic ring containing 1-3 heteroatoms selected from oxygen, sulfur and nitrogen (including a monocyclic, fused, bridged, or spirocyclic ring), a substituted or unsubstituted 5-12 membered heteroaromatic ring containing 1-3 heteroatoms selected from oxygen, sulfur and nitrogen, a substituted and unsubstituted $C_6$-$C_{10}$ aryl, a substituted or unsubstituted $C_3$-$C_{12}$ carbocyclic ring;

V is selected from the group consisting of a chemical bond, or —O—, —CHR—, carbonyl, S, —NH—, —NHC(O)—, —NHS(O)$_2$—, —NHC(O)NH—, —NHC(S)NH—, —COO—, —O—S(O)$_2$—.

In another preferred embodiment, the compound of the formula I has a structure as shown in the following formula:

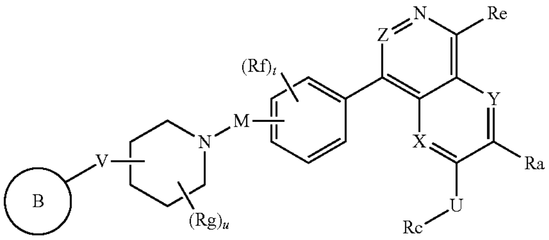

wherein, Rg is selected from the group consisting of halogen, cyano, amino, nitro, hydroxyl, sulfhydryl, aldehyde, carboxyl, sulfonyl, a substituted or unsubstituted $C_1$-$C_6$ alkyl, a substituted or unsubstituted $C_1$-$C_6$ alkoxy;

The B ring is selected from the group consisting of a substituted or unsubstituted 4-12 membered heterocyclic ring containing 1-3 heteroatoms selected from oxygen, sulfur and nitrogen (including monocyclic, fused, bridged, or spirocyclic ring), a substituted or unsubstituted 5-12 membered heteroaromatic ring containing 1-3 heteroatoms selected from oxygen, sulfur and nitrogen, a substituted and unsubstituted $C_6$-$C_{10}$ aryl, a substituted or unsubstituted $C_3$-$C_{12}$ carbocyclic ring;

u is 0, 1, 2, 3 or 4.

In another preferred embodiment, the compound of the formula I has a structure as shown in the following formula:

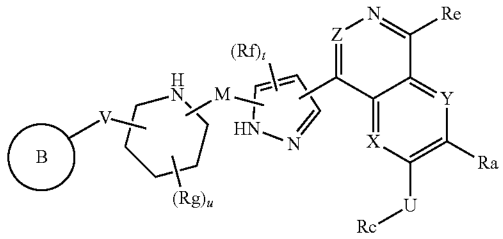

wherein, Rg is selected from the group consisting of halogen, cyano, amino, nitro, hydroxyl, sulfhydryl, aldehyde, carboxyl, sulfonyl, a substituted or unsubstituted $C_1$-$C_6$ alkyl, a substituted or unsubstituted $C_1$-$C_6$ alkoxy;

u is 0, 1, 2, 3 or 4.

In another preferred embodiment, the A ring has at least one substituent G, and the group G is selected from the group consisting of amino, =O, a substituted or unsubstituted 4-7 membered heterocyclic ring containing 1-3 heteroatoms selected from oxygen and nitrogen, a substituted or unsubstituted $C_2$-$C_{10}$ acyl group, a substituted and unsubstituted $C_2$-$C_{10}$ ester group, and a substituted and unsubstituted $C_1$-$C_6$ amide group.

Wherein, when the nitrogen atom on

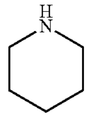

is the attachment site, said NH is N (i.e., the hydrogen atom on NH is lost to form the attachment site).

In another preferred embodiment, the compound of formula I has the structure selected from the group consisting of:

Ia

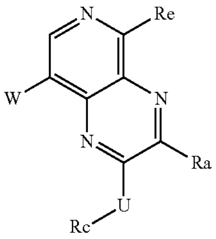

-continued

Ib

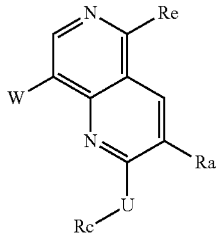

Ic

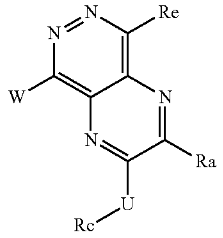

Id

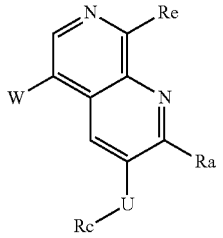

Ie

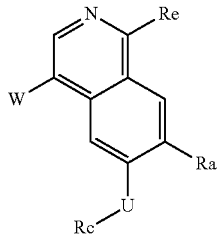

In another preferred embodiment, the W is selected from the group consisting of:

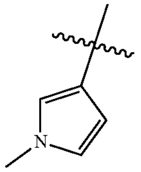

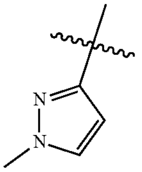

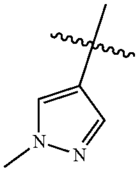

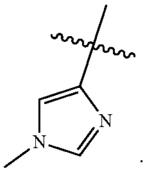

.

In another preferred embodiment, the W is selected from the group consisting of:

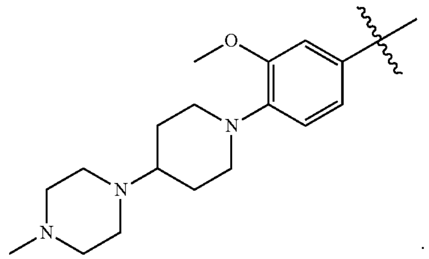 [SMILES: *c1ccc(N2CCC(N3CCN(C)CC3)CC2)c(OC)c1]
In another preferred embodiment, the Rc is selected from the group consisting of:
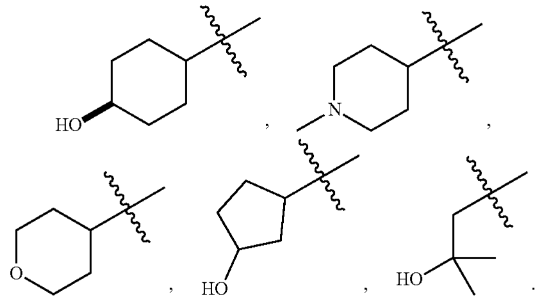
In another preferred embodiment, the URc is selected from the group consisting of:
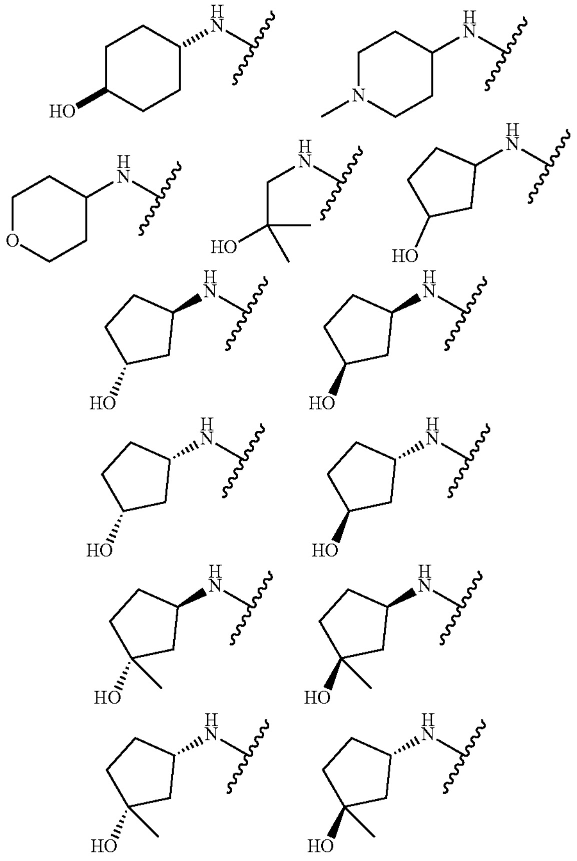
-continued
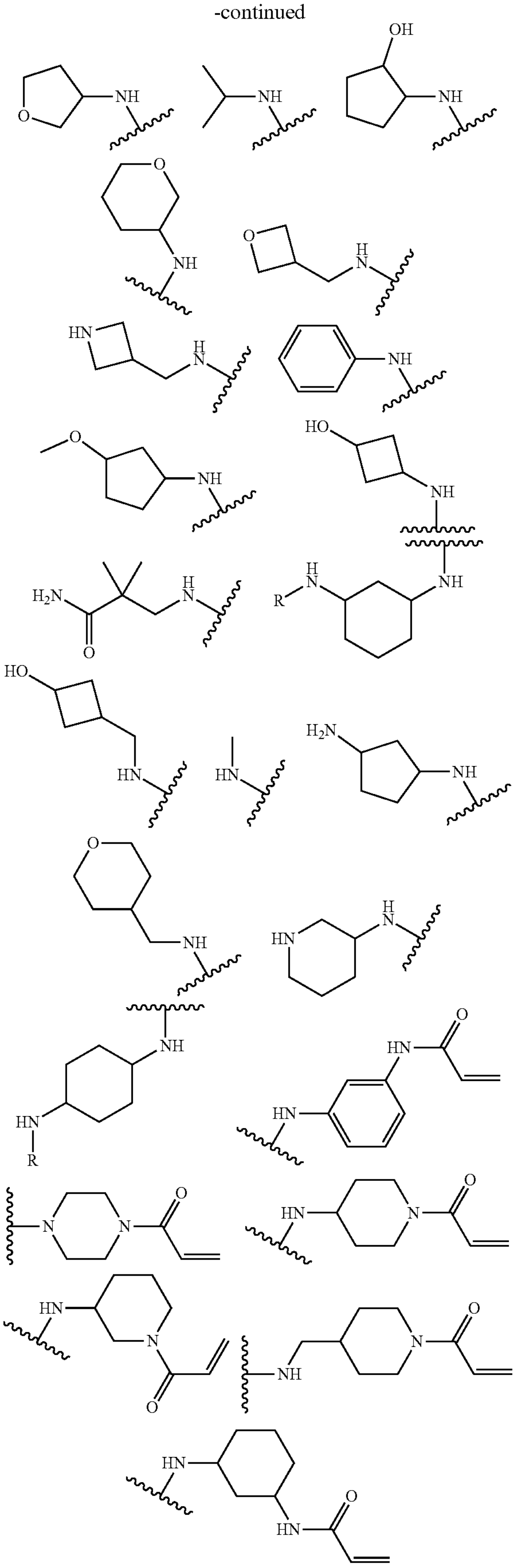

-continued

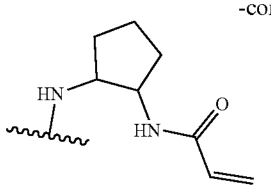

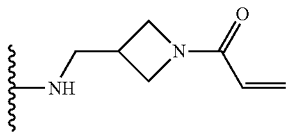

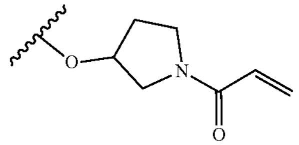

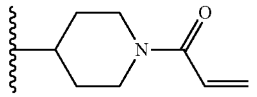

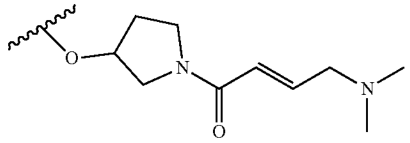

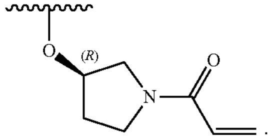

In another preferred embodiment, Re is selected from the group consisting of amino, a substituted or unsubstituted $C_1$-$C_6$ alkyl-NH—.

In the second aspect of the present invention, a pharmaceutical composition comprising a therapeutically effective amount of one or more compounds of formula I, pharmaceutically acceptable salts, racemates, R-isomers and S-isomers, stereoisomers or tautomers thereof, as described in the first aspect of the invention, and one or more pharmaceutically acceptable carriers, excipients, adjuvants, excipients and/or diluents is provided.

In the third aspect of the present invention, a use of the compounds of formula I, racemates, R-isomers, S-isomers or pharmaceutically acceptable salts thereof as described in the first aspect of the present invention is provided, which is in the manufacture of a medicament for the treatment or prevention of diseases associated with abnormal gene levels or abnormal expression (such as mutation, deletion of the corresponding nucleic acid, or ectopic or fusion or overexpression of said kinase) of kinases selected from the group consisting of FLT3, ALK, RET, ROS, AXL, EGFR.

In another preferred embodiment, the disease is selected from the group consisting of acute myeloid leukemia, neurofibroma type I, multiple myeloma, glioblastoma, non-small cell lung cancer, liver cancer, hepatocellular carcinoma, cervical cancer, lymphoma, bone metastases, hormone refractory prostate cancer, hormone dependent prostate cancer, thyroid adenoma, medullary thyroid carcinoma, mesothelioma, glioblastoma, sphincter metastases, Merkel cell carcinoma, urogenital tract tumor, Merkel cell carcinoma, bladder cancer, papillary thyroid cancer, breast cancer, soft tissue sarcoma, glioma, neuroendocrine tumor, renal cell carcinoma, advanced solid tumor, undifferentiated astrocytic cell carcinoma, gastrointestinal stromal tumor, Hipper-Lindau syndrome, small cell lung cancer, pancreatic cancer, pancreatic endocrine carcinoma, central nervous system tumor, metastatic renal cancer, endometrioid carcinoma, endometrioid adenocarcinoma, lung cancer, colorectal cancer, ovarian cancer, rhabdomyosarcoma, melanoma, retinoblastoma, tumors of the central and peripheral nervous system, acute leukemia, chronic leukemia, cholangiocarcinoma, bronchial carcinoma, esophageal cancer, testicular cancer, skin cancer, oral cancer, neuroblastoma, anaplastic large cell lymphoma.

In another aspect, the present invention provides a conjugate obtained by the compound according to the present invention and a small biomolecule or a monoclonal antibody through a chemical bond connection.

It should be understood that, within the scope of the present invention, each technical feature of the present invention described above and in the following (as examples) may be combined with each other to form a new or preferred technical solution, which is not listed here due to space limitations.

DETAILED DESCRIPTION

Through extensive and in-depth research, the inventors have unexpectedly found a class of compounds with kinase inhibitory activity (such as FLT3, ALK, AXL, EGFR) for the first time. The present invention was completed on this basis.

Terms

In the present invention, the halogen is F, Cl, Br or I.

In the present invention, unless otherwise indicated, the terms used herein have the general meaning known to those skilled in the art. In the present invention, unless otherwise specified, all chemical formula are intended to cover any possible optical or geometric isomers (R, S, or racemic forms, or cis and trans isomers of olefin, etc.)

In the present invention, the term "C1-C6 alkyl" refers to a straight or branched chain alkyl group having 1 to 6 carbon atoms, including but not limited to methyl, ethyl, propyl, isopropyl, butyl, isobutyl, sec-butyl, tert-butyl, pentyl, hexyl and the like; ethyl, propyl, isopropyl, butyl, isobutyl, sec-butyl and tert-butyl are preferred.

In the present invention, the term "C1-C6 alkoxy" refers to a linear or branched alkoxy group having 1 to 6 carbon atoms, including but not limited to methoxy, ethoxy, propoxy, isopropoxy, butoxy, etc.

In the present invention, the term "C2-C6 alkenyl" refers to a straight or branched chain alkenyl group containing a double bond having 2 to 6 carbon atoms, and includes, including but not limited to vinyl, propenyl, butenyl, isobutenyl, pentenyl and hexenyl etc.

In the present invention, the term "C2-C6 alkynyl" refers to a straight or branched chain alkynyl group containing a triple bond having 2 to 6 carbon atoms, including but not limited to ethynyl, propynyl, butynyl, isobutyny, pentynyl and hexynyl, etc.

In the present invention, the term "C3-C10 cycloalkyl" refers to a cyclic alkyl group having 3 to 10 carbon atoms in the ring, including but not limited to cyclopropyl, cyclobutyl, cyclopentyl, cyclohexyl, cycloheptyl, cyclooctyl and cyclodecyl and the like. The terms "$C_3$-$C_8$ cycloalkyl," "C3-C7 cycloalkyl," and "$C_3$-$C_6$ cycloalkyl" have the similar meaning.

In the present invention, the term "C3-C10 cycloalkenyl" refers to a cyclic alkenyl group having 3 to 10 carbon atoms in the ring, including but not limited to cyclopropenyl, cyclobutenyl, cyclopentenyl, cyclohexenyl, cycloheptenyl, cyclooctenyl, and cyclodecylene. The term "C3-C7 cycloalkenyl" has the similar meaning.

In the present invention, the term "C1-C12 alkoxycarbonyl" refers to an alkoxycarbonyl group having 1 to 12 carbon atoms in the alkyl chain, including but not limited to methoxycarbonyl, ethoxycarbonyl, propoxycarbonyl, isopropoxycarbonyl, tert-butoxycarbonyl, benzyloxycarbonyl and the like.

In the present invention, the term "C1-C12 alkylaminocarbonyl" refers to an alkylaminocarbonyl group having from 1 to 12 carbon atoms in the alkyl chain, including but not limited to methylamino carbonyl, ethylamino carbonyl, propylamino carbonyl, isopropylamino carbonyl, tert-butylamino carbonyl, benzylamino carbonyl, dimethylamino carbonyl and the like.

In the present invention, the term "C5-C9 furanosyl" refers to a furanosyl group having 5 to 9 carbon atoms, wherein the 1-position of the glycosyl group is attached to the main chain, including but not limited to ribofuranose group, deoxyribofuranose group, galactofuranoid group, and the like.

In the present invention, the term "C5-C9 pyranosyl" refers to a pyranosyl group having 5 to 9 carbon atoms, wherein the 1-position of the glycosyl group is attached to the main chain, including but not limited to glucopyranose group, glucuropyranose group, rhamnopyranosyl group, galactopyranosyl group, mannopyranosyl group, xylopyranosyl group and the like.

In the present invention, the terms "aromatic ring" or "aryl" have the same meaning, and preferably "aryl" is "C6-C12 aryl" or "C6-C10 aryl". The term "C6-C12 aryl" refers to an aromatic cyclic group having 6 to 12 carbon atoms without a heteroatom in the ring, such as phenyl, naphthyl, and the like. The term "C6-C10 aryl" has the similar meaning.

In the present invention, the terms "aromatic heterocycle" or "heteroaryl" have the same meaning and refer to a heteroaromatic group containing one to more heteroatoms. Heteroatoms referred to herein include oxygen, sulfur, and nitrogen. Such as furyl, thienyl, pyridyl, pyrazolyl, pyrrolyl, N-alkylpyrrolyl, pyrimidinyl, pyrazinyl, imidazolyl, tetrazolyl and the like. The heteroaryl ring may be fused to an aryl, heterocyclyl, or cycloalkyl ring, wherein the ring joined to the parent structure is the heteroaryl ring. Heteroaryl may be optionally substituted or unsubstituted.

In the present invention, the term "3 to 12 membered heterocyclic group" refers to a saturated or unsaturated 3 to 12 membered cyclic group containing 1 to 3 heteroatoms selected from oxygen, sulfur and nitrogen in the ring, for example, dioxolanyl and the like. The term "3-7 membered heterocyclyl" has the similar meaning.

In the present invention, the term "substitution" means that one or more hydrogen atoms on a specific group are replaced by a specific substituent. The specific substituents are the substituents described in the preceding text or the substituents present in the examples. Unless otherwise specified, a substituted group may have a substituent selected from the specified group at any substitutable position of the group, and the substituent may be the same or different at each position. A cyclic substituent, such as heterocycloalkyl, may be joined to another ring, such as a cycloalkyl group, to form a spiro-bicyclic ring system, for example, where the two rings have a common carbon atom. It will be understood by those skilled in the art that the combinations of substituents contemplated by the present invention are those that are stable or chemically achievable. The substituents may be (but not limited to): C1-8 alkyl, C2-8 alkenyl, C2-8 alkynyl, C3-8 cycloalkyl, 3 to 12 membered heterocyclyl, aryl, heteroaryl, halogen, hydroxyl, carboxyl (—COOH), C1-8 aldehyde, C2-10 acyl, C2-10 ester, C1-C12 alkoxycarbonyl, amino, alkoxy, C1-10 sulfonyl and the like.

FLT3 Inhibitor Compound

The invention provides a compound with FLT3 inhibitory activity:

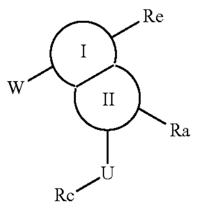

I

Wherein each group has the definition as described above.

Preferred compounds in the present application are compounds selected from the following Table 1:

TABLE 1

| No | Structure |
|---|---|
| 1 | 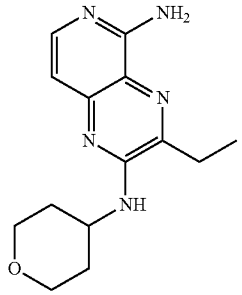 [SMILES: CCc1nc2c(N)nccc2nc1NC1CCOCC1] |

TABLE 1-continued
| No | Structure |
|---|---|
| 2 | 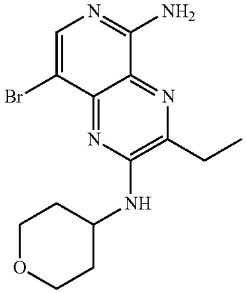 [SMILES: CCc1nc2c(N)ncc(Br)c2nc1NC1CCOCC1] |
| 3 | 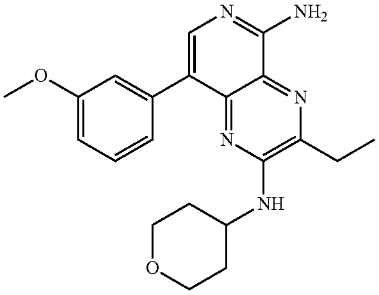 |
| 4 | 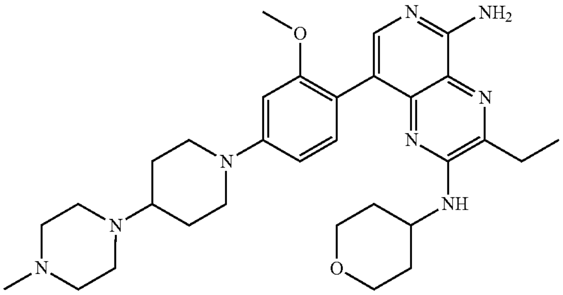 [SMILES: CCc1nc2c(N)ncc(-c3ccc(N4CCC(N5CCN(C)CC5)CC4)cc3OC)c2nc1NC1CCOCC1] |
| 5 | 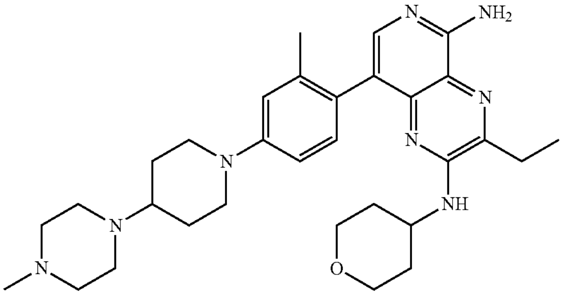 5 |
| 6 | 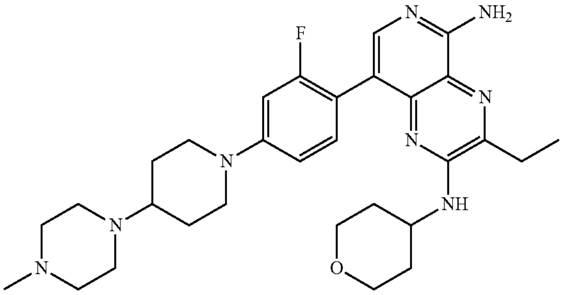 |

TABLE 1-continued
| No | Structure |
| --- | --- |
| 7 | 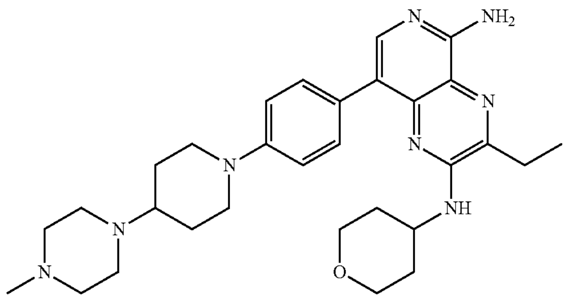 |
| 8 | 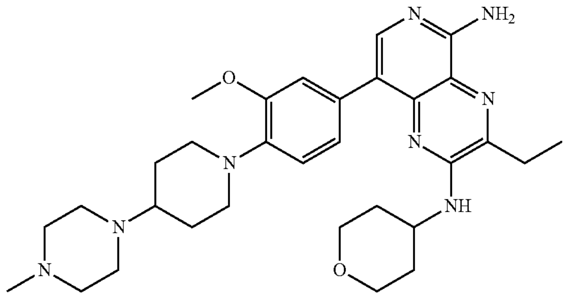 [SMILES: CCc1nc2c(N)ncc(-c3ccc(N4CCC(N5CCN(C)CC5)CC4)c(OC)c3)c2nc1NC1CCOCC1] |
| 9 | 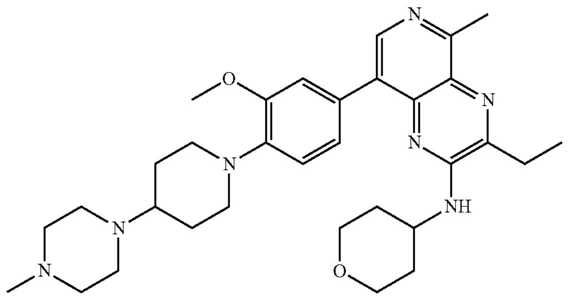 [SMILES: CCc1nc2c(C)ncc(-c3ccc(N4CCC(N5CCN(C)CC5)CC4)c(OC)c3)c2nc1NC1CCOCC1] |
| 10 | 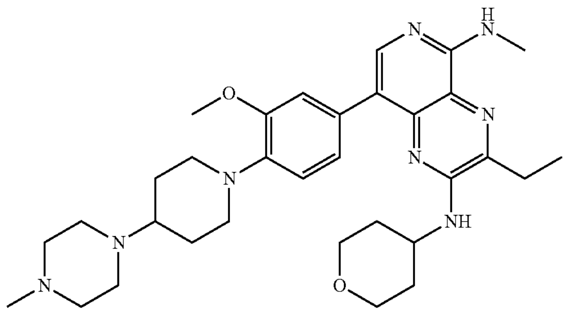 [SMILES: CCc1nc2c(NC)ncc(-c3ccc(N4CCC(N5CCN(C)CC5)CC4)c(OC)c3)c2nc1NC1CCOCC1] |
| 11 | 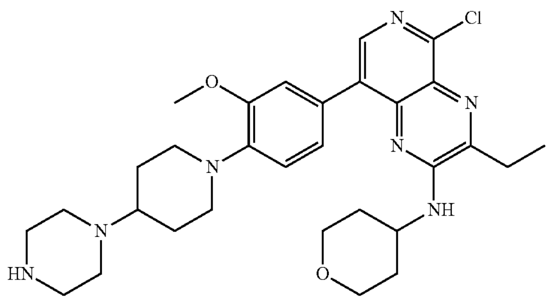 [SMILES: CCc1nc2c(Cl)ncc(-c3ccc(N4CCC(N5CCNCC5)CC4)c(OC)c3)c2nc1NC1CCOCC1] |

TABLE 1-continued
| No | Structure |
| --- | --- |
| 12 | 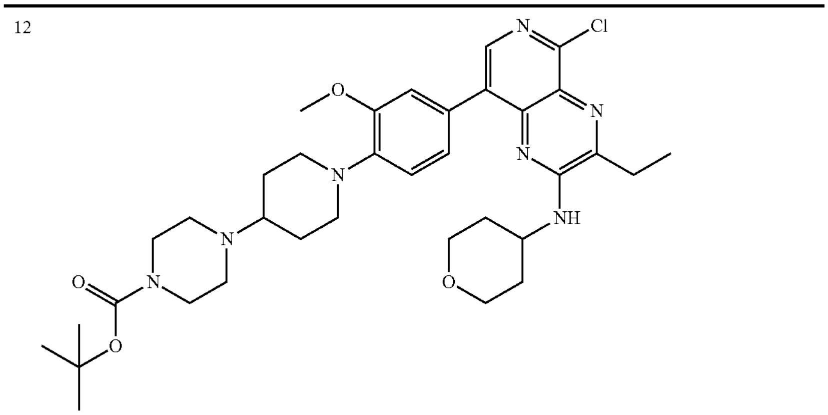 |
| 13 | 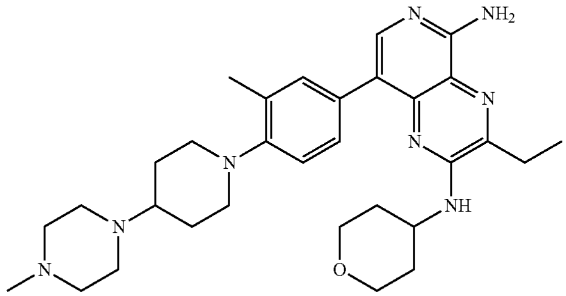 |
| 14 | 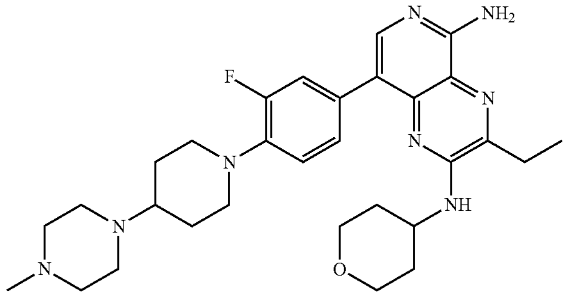 [SMILES: CCc1nc2c(N)ncc(-c3ccc(N4CCC(N5CCN(C)CC5)CC4)c(F)c3)c2nc1NC1CCOCC1] |
| 15 | 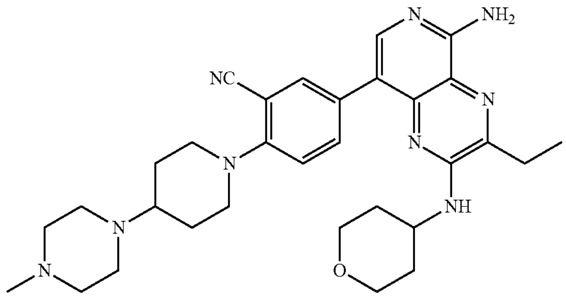 [SMILES: CCc1nc2c(N)ncc(-c3ccc(N4CCC(N5CCN(C)CC5)CC4)c(C#N)c3)c2nc1NC1CCOCC1] |
| 16 | 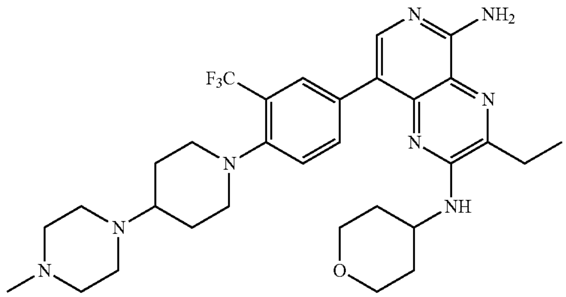 |

TABLE 1-continued
| No | Structure |
|---|---|
| 17 | 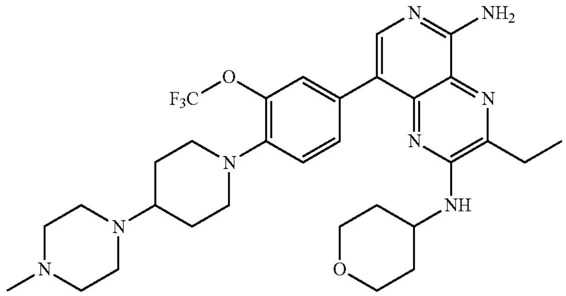 [SMILES: CCc1nc2c(N)ncc(-c3ccc(N4CCC(N5CCN(C)CC5)CC4)c(OC(F)(F)F)c3)c2nc1NC1CCOCC1] |
| 18 | 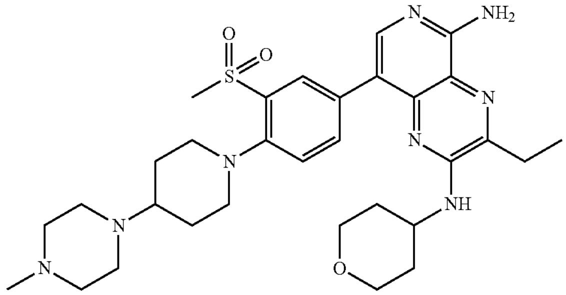 [SMILES: CCc1nc2c(N)ncc(-c3ccc(N4CCC(N5CCN(C)CC5)CC4)c(S(C)(=O)=O)c3)c2nc1NC1CCOCC1] |
| 19 | 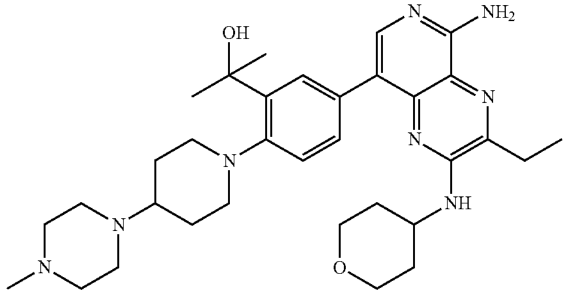 [SMILES: CCc1nc2c(N)ncc(-c3ccc(N4CCC(N5CCN(C)CC5)CC4)c(C(C)(C)O)c3)c2nc1NC1CCOCC1] |
| 20 | 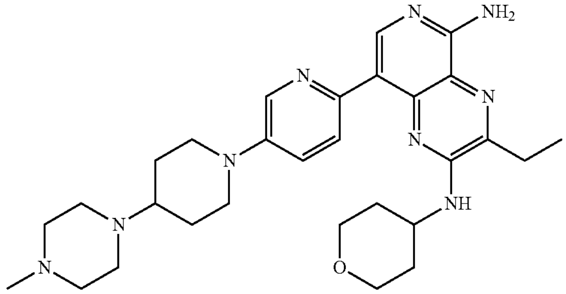 |
| 21 | 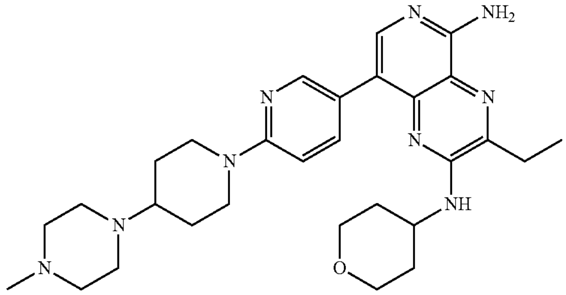 |

TABLE 1-continued
| No | Structure |
| --- | --- |
| 22 | 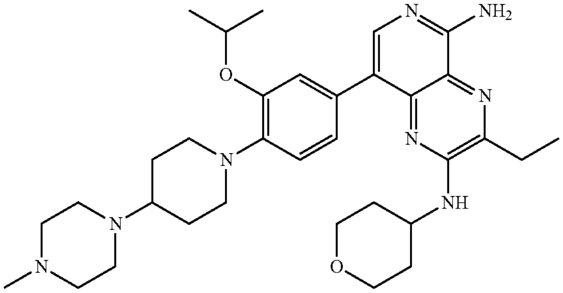 [SMILES: CCc1nc2c(N)ncc(-c3ccc(N4CCC(N5CCN(C)CC5)CC4)c(OC(C)C)c3)c2nc1NC1CCOCC1] |
| 23 | 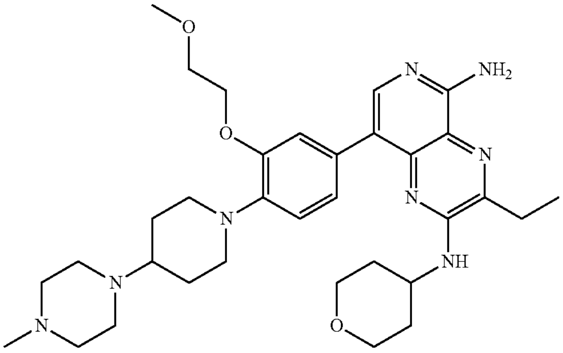 [SMILES: CCc1nc2c(N)ncc(-c3ccc(N4CCC(N5CCN(C)CC5)CC4)c(OCCOC)c3)c2nc1NC1CCOCC1] |
| 24 | 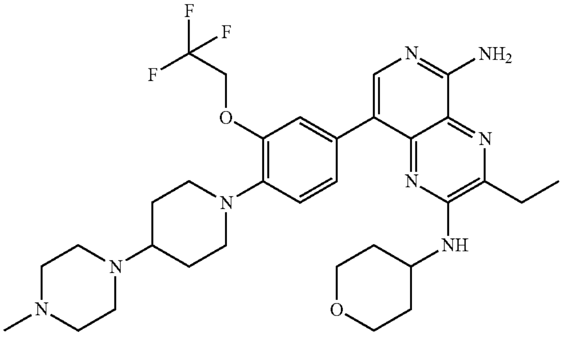 [SMILES: CCc1nc2c(N)ncc(-c3ccc(N4CCC(N5CCN(C)CC5)CC4)c(OCC(F)(F)F)c3)c2nc1NC1CCOCC1] |
| 25 | 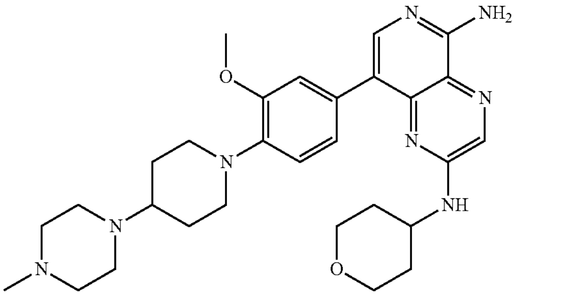 [SMILES: COc1cc(-c2cnc(N)c3ncc(NC4CCOCC4)nc23)ccc1N1CCC(N2CCN(C)CC2)CC1] |
| 26 | 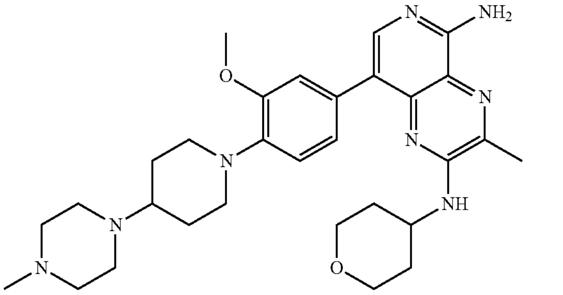 |

TABLE 1-continued
| No | Structure |
|---|---|
| 27 | 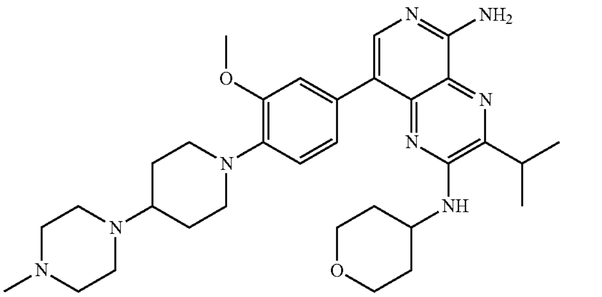 [SMILES: COc1cc(-c2cnc(N)c3nc(C(C)C)c(NC4CCOCC4)nc23)ccc1N1CCC(N2CCN(C)CC2)CC1] |
| 28 | 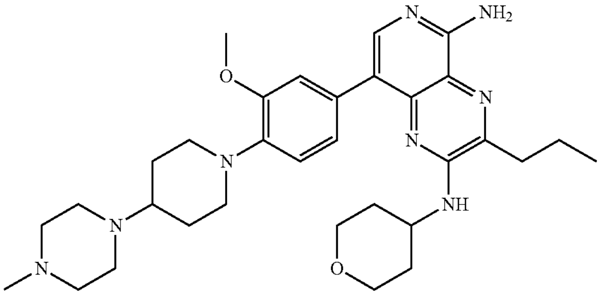 [SMILES: CCCc1nc2c(N)ncc(-c3ccc(N4CCC(N5CCN(C)CC5)CC4)c(OC)c3)c2nc1NC1CCOCC1] |
| 29 | 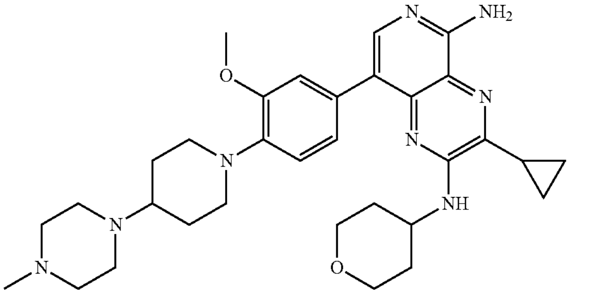 [SMILES: COc1cc(-c2cnc(N)c3nc(C4CC4)c(NC4CCOCC4)nc23)ccc1N1CCC(N2CCN(C)CC2)CC1] |
| 30 | 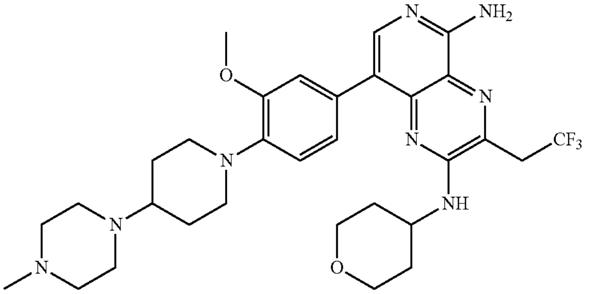 [SMILES: COc1cc(-c2cnc(N)c3nc(CC(F)(F)F)c(NC4CCOCC4)nc23)ccc1N1CCC(N2CCN(C)CC2)CC1] |
| 31 | 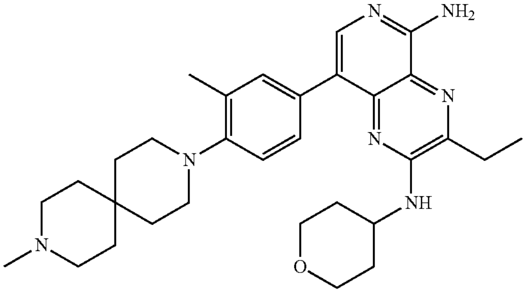 [SMILES: CCc1nc2c(N)ncc(-c3ccc(N4CCC5(CCN(C)CC5)CC4)c(C)c3)c2nc1NC1CCOCC1] |

TABLE 1-continued
| No | Structure |
|---|---|
| 32 | 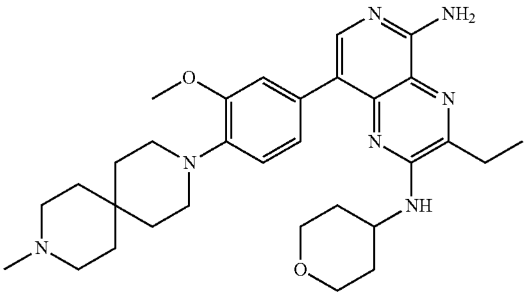 [SMILES: CCc1nc2c(N)ncc(-c3ccc(N4CCC5(CCN(C)CC5)CC4)c(OC)c3)c2nc1NC1CCOCC1] |
| 33 | 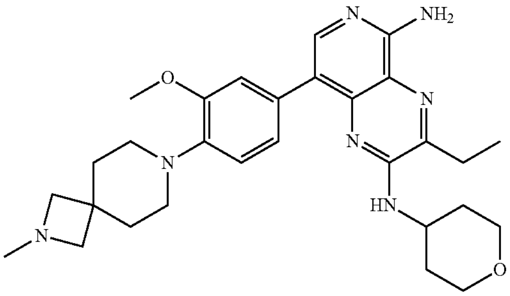 [SMILES: CCc1nc2c(N)ncc(-c3ccc(N4CCC5(CC4)CN(C)C5)c(OC)c3)c2nc1NC1CCOCC1] |
| 34 | 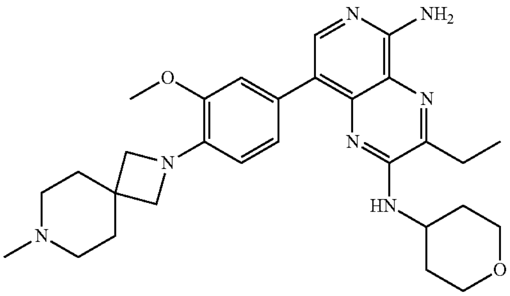 [SMILES: CCc1nc2c(N)ncc(-c3ccc(N4CC5(CCN(C)CC5)C4)c(OC)c3)c2nc1NC1CCOCC1] |
| 35 | 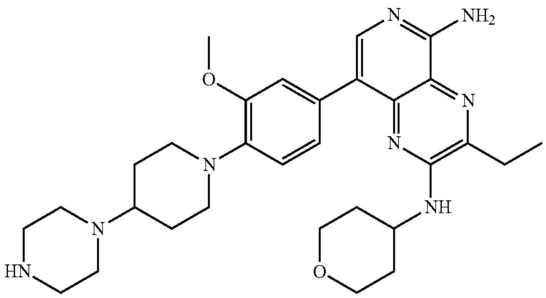 [SMILES: CCc1nc2c(N)ncc(-c3ccc(N4CCC(N5CCNCC5)CC4)c(OC)c3)c2nc1NC1CCOCC1] |
| 36 | 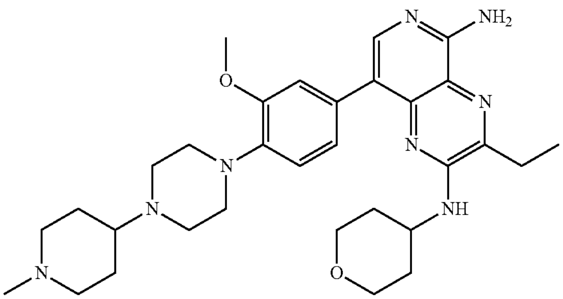 [SMILES: CCc1nc2c(N)ncc(-c3ccc(N4CCN(C5CCN(C)CC5)CC4)c(OC)c3)c2nc1NC1CCOCC1] |

TABLE 1-continued
| No | Structure |
|---|---|
| 37 | 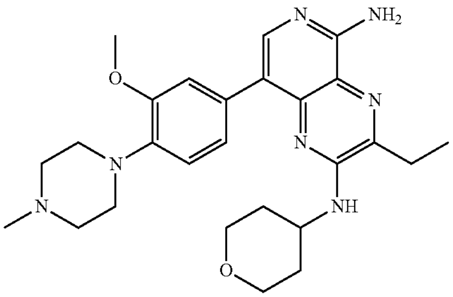 [SMILES: CCc1nc2c(N)ncc(-c3ccc(N4CCN(C)CC4)c(OC)c3)c2nc1NC1CCOCC1] |
| 38 | 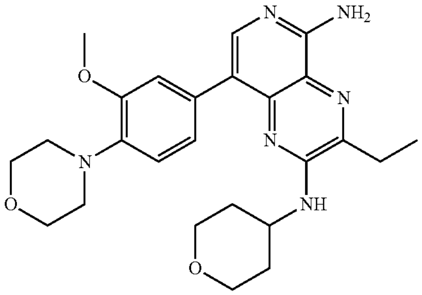 [SMILES: CCc1nc2c(N)ncc(-c3ccc(N4CCOCC4)c(OC)c3)c2nc1NC1CCOCC1] |
| 39 | 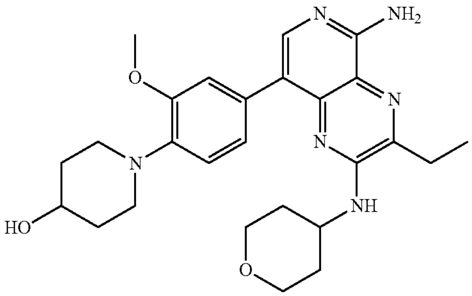 [SMILES: CCc1nc2c(N)ncc(-c3ccc(N4CCC(O)CC4)c(OC)c3)c2nc1NC1CCOCC1] |
| 40 | 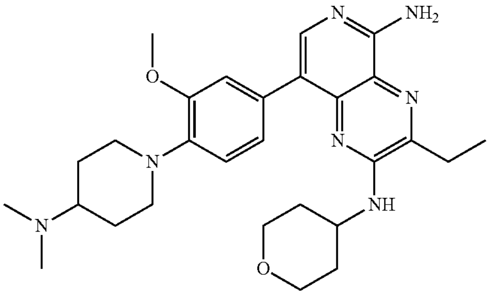 [SMILES: CCc1nc2c(N)ncc(-c3ccc(N4CCC(N(C)C)CC4)c(OC)c3)c2nc1NC1CCOCC1] |
| 41 | 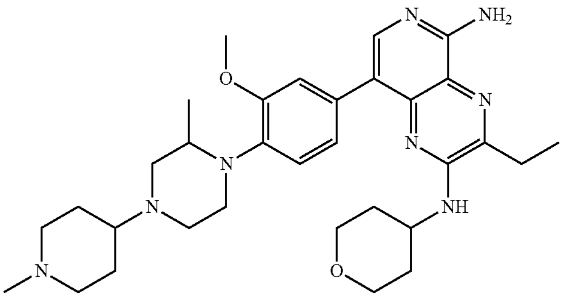 [SMILES: CCc1nc2c(N)ncc(-c3ccc(N4CCN(C5CCN(C)CC5)CC4C)c(OC)c3)c2nc1NC1CCOCC1] |

TABLE 1-continued
| No | Structure |
| --- | --- |
| 42 | 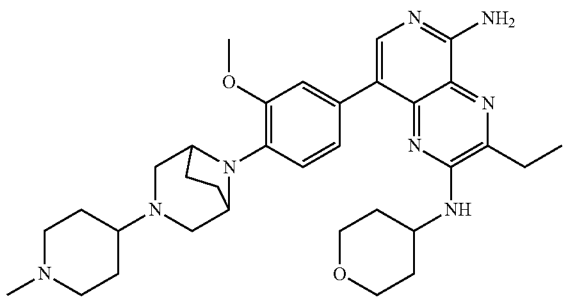 [SMILES: CCc1nc2c(N)ncc(-c3ccc(N4C5CCC4CN(C4CCN(C)CC4)C5)c(OC)c3)c2nc1NC1CCOCC1] |
| 43 | 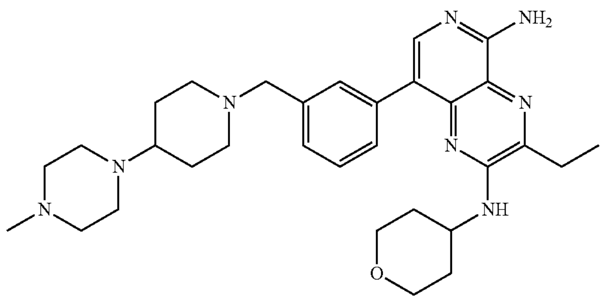 [SMILES: CCc1nc2c(N)ncc(-c3cccc(CN4CCC(N5CCN(C)CC5)CC4)c3)c2nc1NC1CCOCC1] |
| 44 | 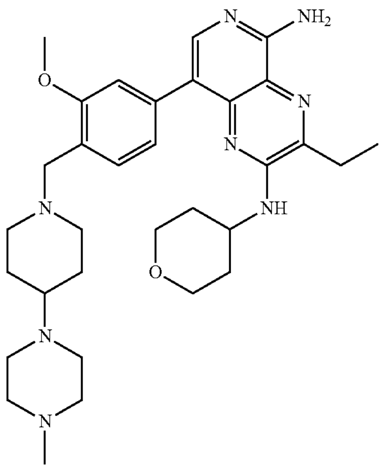 [SMILES: CCc1nc2c(N)ncc(-c3ccc(CN4CCC(N5CCN(C)CC5)CC4)c(OC)c3)c2nc1NC1CCOCC1] |
| 45 | 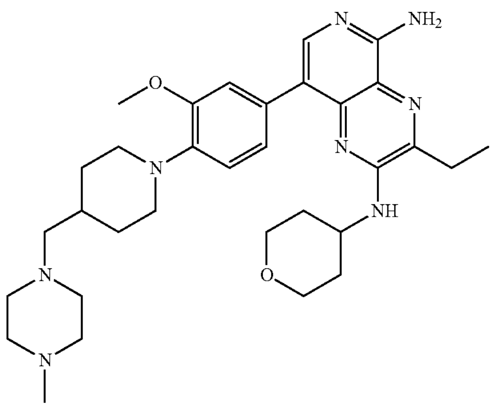 [SMILES: CCc1nc2c(N)ncc(-c3ccc(N4CCC(CN5CCN(C)CC5)CC4)c(OC)c3)c2nc1NC1CCOCC1] |

TABLE 1-continued
| No | Structure |
|---|---|
| 46 | 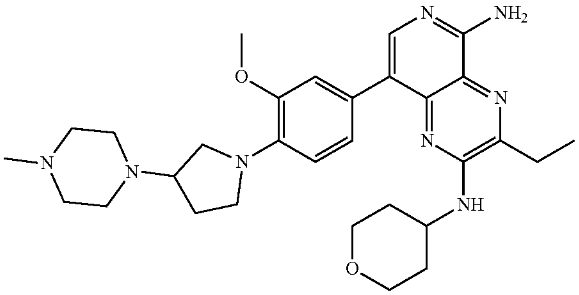 [SMILES: CCc1nc2c(N)ncc(-c3ccc(N4CCC(N5CCN(C)CC5)C4)c(OC)c3)c2nc1NC1CCOCC1] |
| 47 | 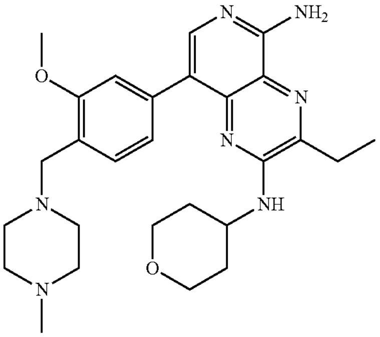 [SMILES: CCc1nc2c(N)ncc(-c3ccc(CN4CCN(C)CC4)c(OC)c3)c2nc1NC1CCOCC1] |
| 48 | 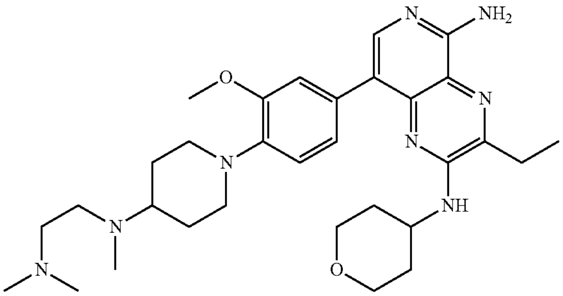 [SMILES: CCc1nc2c(N)ncc(-c3ccc(N4CCC(N(C)CCN(C)C)CC4)c(OC)c3)c2nc1NC1CCOCC1] |
| 49 | 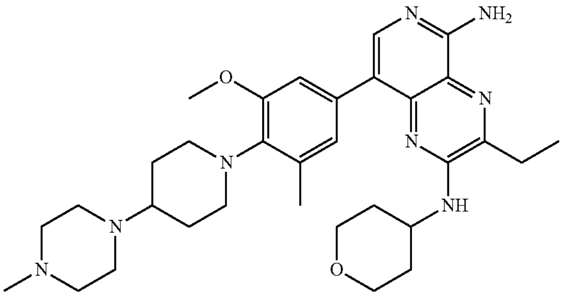 [SMILES: CCc1nc2c(N)ncc(-c3cc(C)c(N4CCC(N5CCN(C)CC5)CC4)c(OC)c3)c2nc1NC1CCOCC1] |
| 50 | 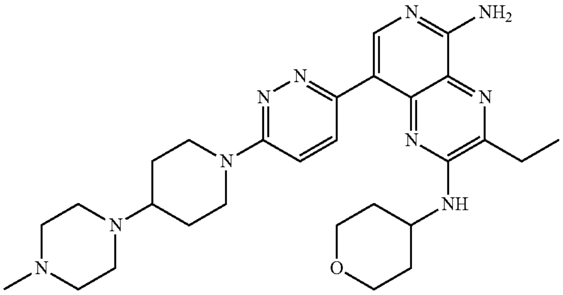 [SMILES: CCc1nc2c(N)ncc(-c3ccc(N4CCC(N5CCN(C)CC5)CC4)nn3)c2nc1NC1CCOCC1] |

TABLE 1-continued
| No | Structure |
|---|---|
| 51 | 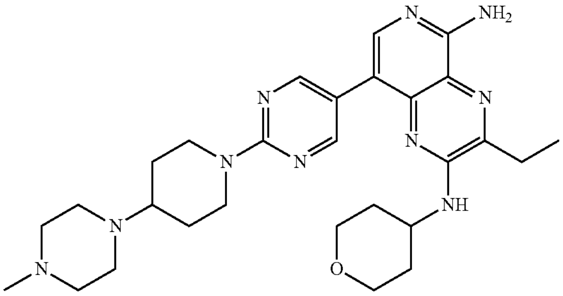 |
| 52 | 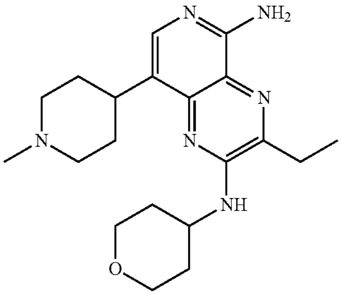 [SMILES: CCc1nc2c(N)ncc(C3CCN(C)CC3)c2nc1NC1CCOCC1] |
| 53 | 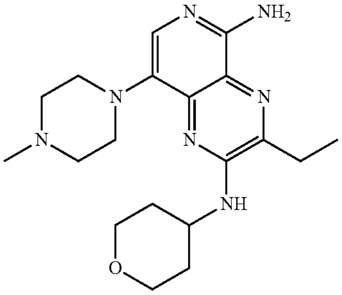 [SMILES: CCc1nc2c(N)ncc(N3CCN(C)CC3)c2nc1NC1CCOCC1] |
| 54 | 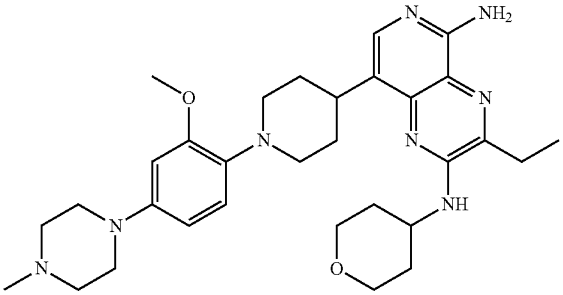 [SMILES: CCc1nc2c(N)ncc(C3CCN(c4ccc(N5CCN(C)CC5)cc4OC)CC3)c2nc1NC1CCOCC1] |
| 55 | 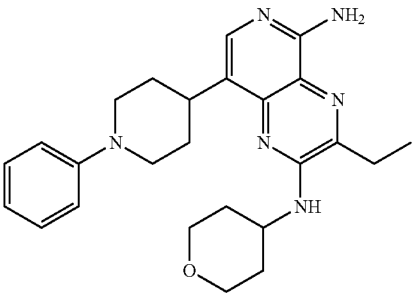 [SMILES: CCc1nc2c(N)ncc(C3CCN(c4ccccc4)CC3)c2nc1NC1CCOCC1] |

TABLE 1-continued
| No | Structure |
| --- | --- |
| 56 | 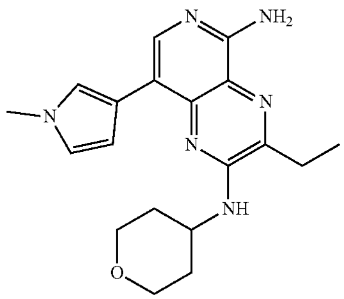 [SMILES: CCc1nc2c(N)ncc(-c3ccn(C)c3)c2nc1NC1CCOCC1] |
| 57 | 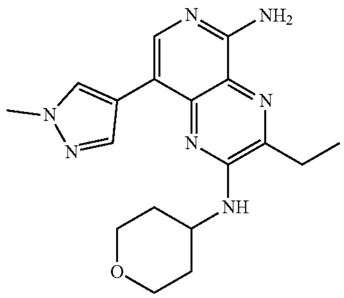 |
| 58 | 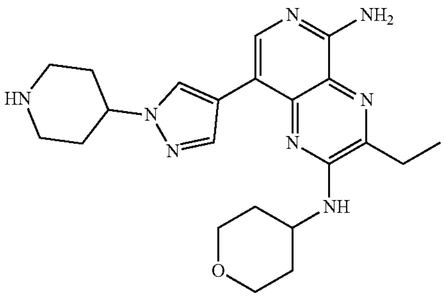 [SMILES: CCc1nc2c(N)ncc(-c3cnn(C4CCNCC4)c3)c2nc1NC1CCOCC1] |
| 59 | 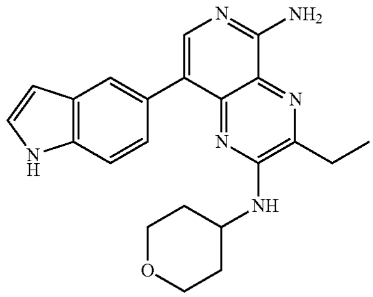 [SMILES: CCc1nc2c(N)ncc(-c3ccc4[nH]ccc4c3)c2nc1NC1CCOCC1] |
| 60 | 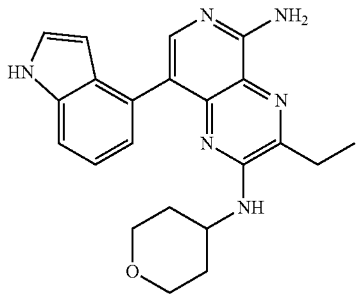 [SMILES: CCc1nc2c(N)ncc(-c3cccc4[nH]ccc34)c2nc1NC1CCOCC1] |

TABLE 1-continued
| No | Structure |
|---|---|
| 61 | 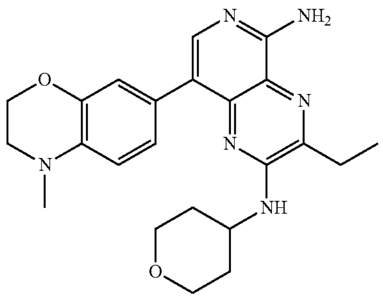 [SMILES: CCc1nc2c(N)ncc(-c3ccc4c(c3)OCCN4C)c2nc1NC1CCOCC1] |
| 62 | 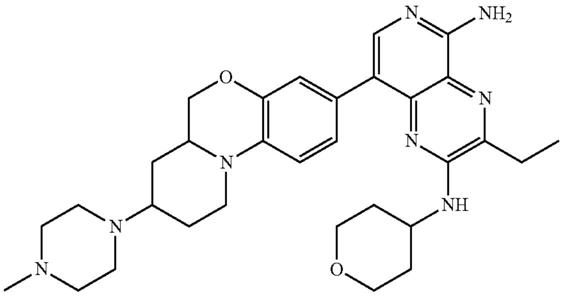 |
| 63 | 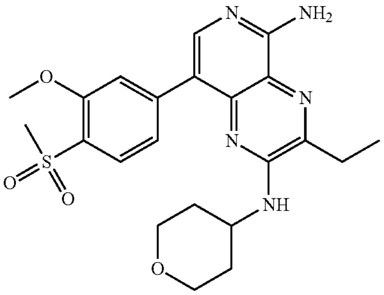 [SMILES: CCc1nc2c(N)ncc(-c3ccc(S(C)(=O)=O)c(OC)c3)c2nc1NC1CCOCC1] |
| 64 | 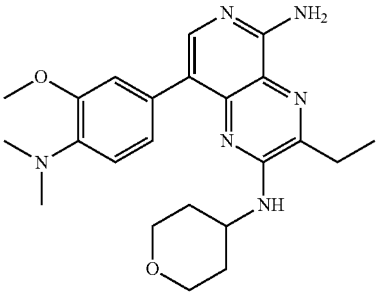 |
| 65 | 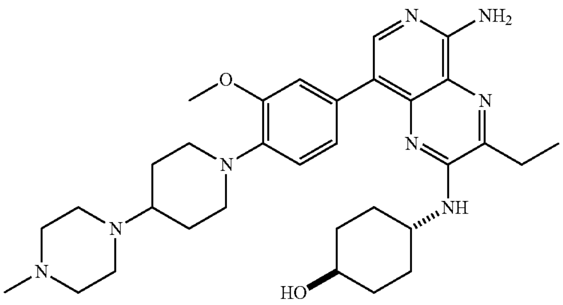 |

TABLE 1-continued
| No | Structure |
|---|---|
| 66 | 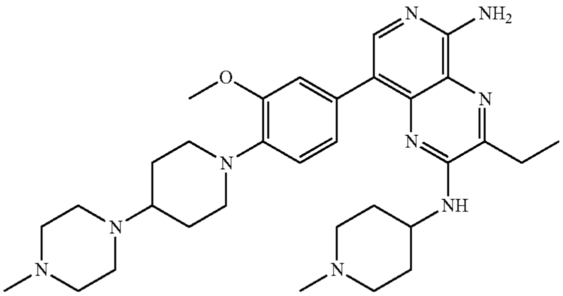 [SMILES: CCc1nc2c(N)ncc(-c3ccc(N4CCC(N5CCN(C)CC5)CC4)c(OC)c3)c2nc1NC1CCN(C)CC1] |
| 67 | 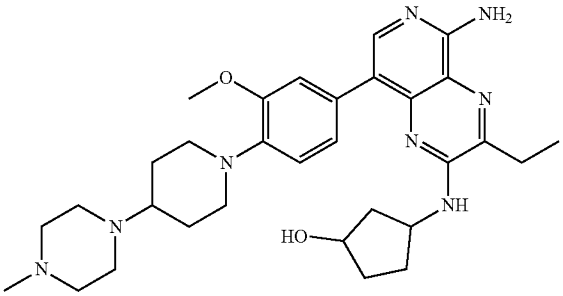 [SMILES: CCc1nc2c(N)ncc(-c3ccc(N4CCC(N5CCN(C)CC5)CC4)c(OC)c3)c2nc1NC1CCC(O)C1] |
| 68 | 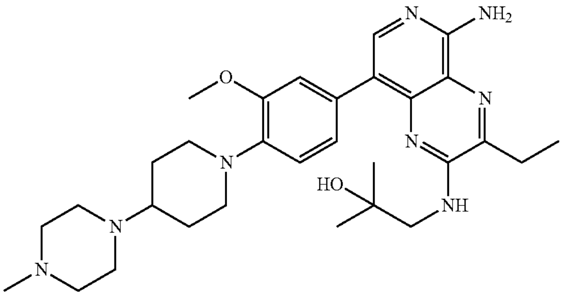 [SMILES: CCc1nc2c(N)ncc(-c3ccc(N4CCC(N5CCN(C)CC5)CC4)c(OC)c3)c2nc1NCC(C)(C)O] |
| 69 | 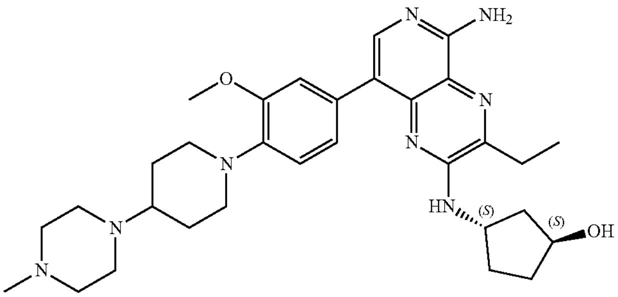 |
| 70 | 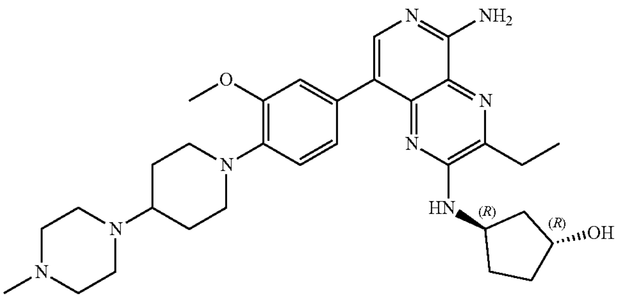 |

TABLE 1-continued
| No | Structure |
| --- | --- |
| 71 | 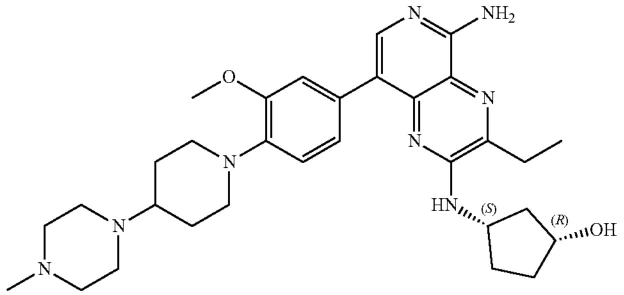 |
| 72 | 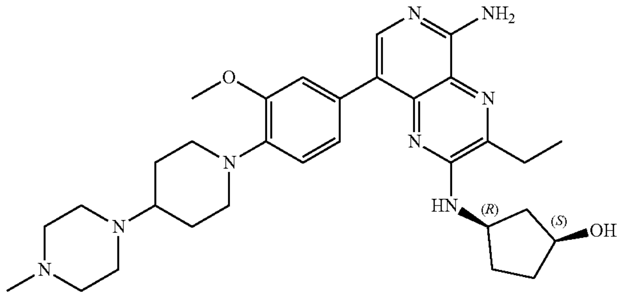 |
| 73 | 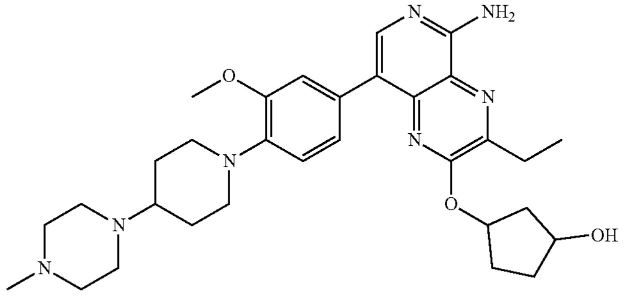 [SMILES: CCc1nc2c(N)ncc(-c3ccc(N4CCC(N5CCN(C)CC5)CC4)c(OC)c3)c2nc1OC1CCC(O)C1] |
| 74 | 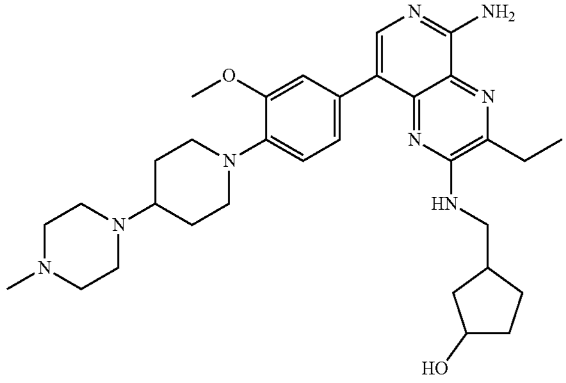 [SMILES: CCc1nc2c(N)ncc(-c3ccc(N4CCC(N5CCN(C)CC5)CC4)c(OC)c3)c2nc1NCC1CCC(O)C1] |

TABLE 1-continued
| No | Structure |
|---|---|
| 75 | 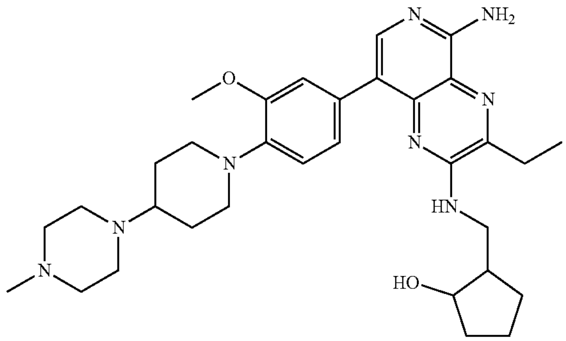 [SMILES: CCc1nc2c(N)ncc(-c3ccc(N4CCC(N5CCN(C)CC5)CC4)c(OC)c3)c2nc1NCC1CCCC1O] |
| 76 | 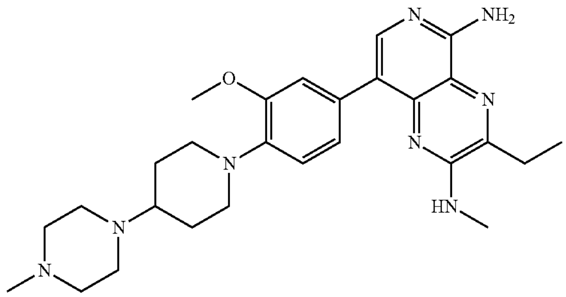 [SMILES: CCc1nc2c(N)ncc(-c3ccc(N4CCC(N5CCN(C)CC5)CC4)c(OC)c3)c2nc1NC] |
| 77 | 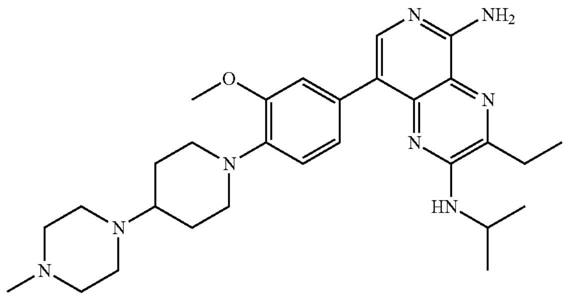 [SMILES: CCc1nc2c(N)ncc(-c3ccc(N4CCC(N5CCN(C)CC5)CC4)c(OC)c3)c2nc1NC(C)C] |
| 78 | 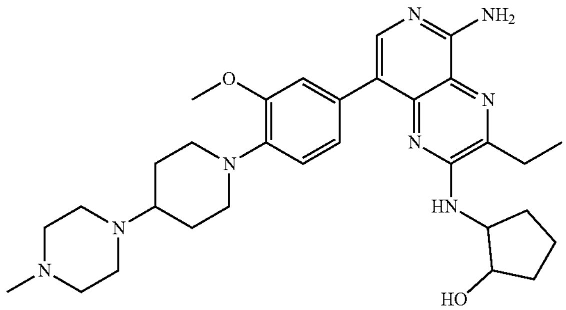 [SMILES: CCc1nc2c(N)ncc(-c3ccc(N4CCC(N5CCN(C)CC5)CC4)c(OC)c3)c2nc1NC1CCCC1O] |
| 79 | 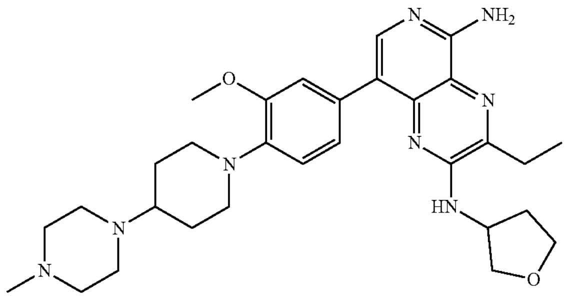 [SMILES: CCc1nc2c(N)ncc(-c3ccc(N4CCC(N5CCN(C)CC5)CC4)c(OC)c3)c2nc1NC1CCOC1] |

TABLE 1-continued
| No | Structure |
| --- | --- |
| 80 | 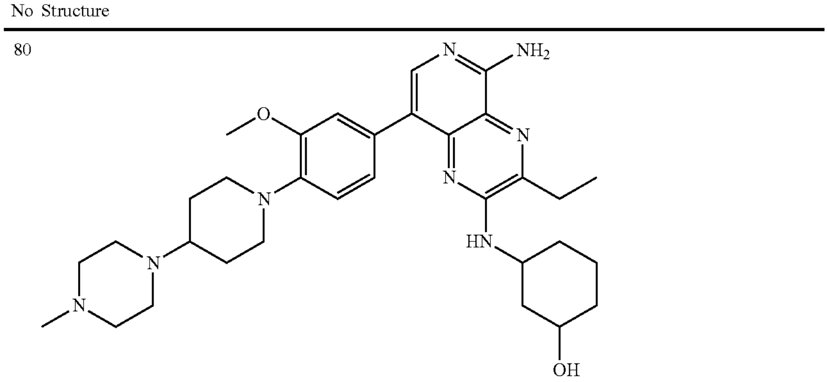 |
| 81 | 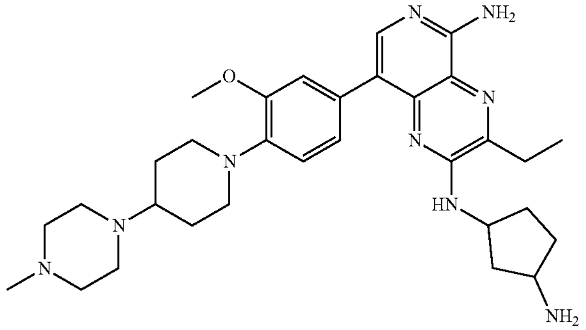 [SMILES: CCc1nc2c(N)ncc(-c3ccc(N4CCC(N5CCN(C)CC5)CC4)c(OC)c3)c2nc1NC1CCC(N)C1] |
| 82 | 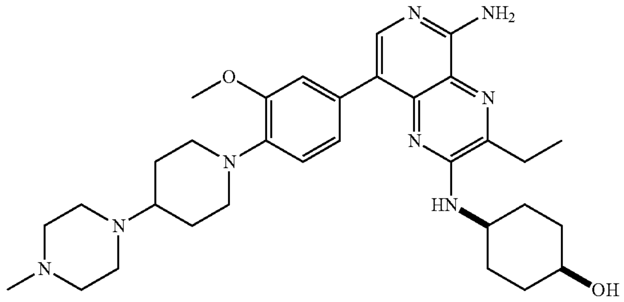 |
| 83 | 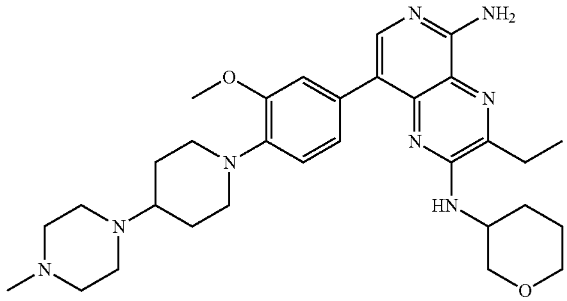 [SMILES: CCc1nc2c(N)ncc(-c3ccc(N4CCC(N5CCN(C)CC5)CC4)c(OC)c3)c2nc1NC1CCCOC1] |
| 84 | 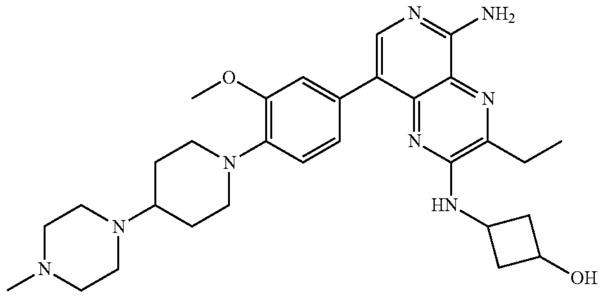 [SMILES: CCc1nc2c(N)ncc(-c3ccc(N4CCC(N5CCN(C)CC5)CC4)c(OC)c3)c2nc1NC1CC(O)C1] |

TABLE 1-continued
| No | Structure |
|---|---|
| 85 | 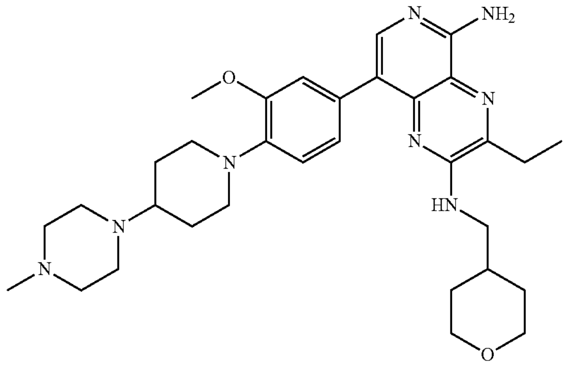 [SMILES: CCc1nc2c(N)ncc(-c3ccc(N4CCC(N5CCN(C)CC5)CC4)c(OC)c3)c2nc1NCC1CCOCC1] |
| 86 | 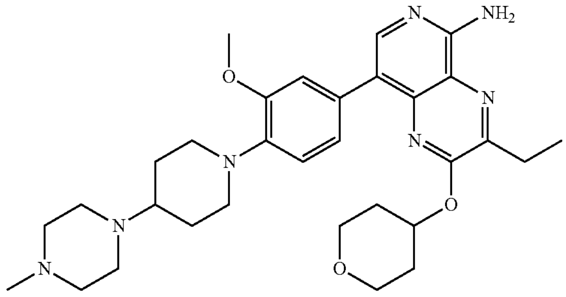 [SMILES: CCc1nc2c(N)ncc(-c3ccc(N4CCC(N5CCN(C)CC5)CC4)c(OC)c3)c2nc1OC1CCOCC1] |
| 87 | 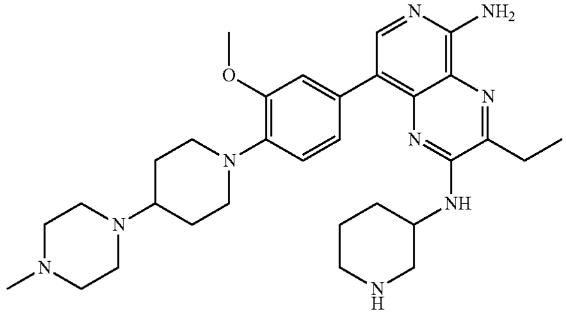 [SMILES: CCc1nc2c(N)ncc(-c3ccc(N4CCC(N5CCN(C)CC5)CC4)c(OC)c3)c2nc1NC1CCCNC1] |
| 88 | 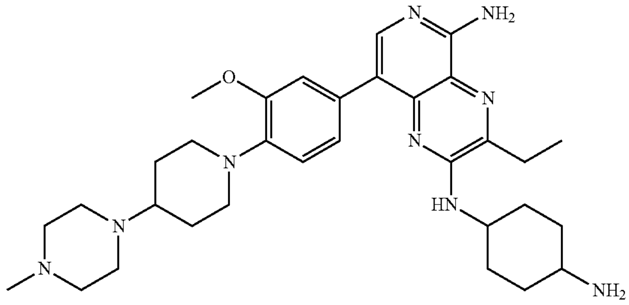 [SMILES: CCc1nc2c(N)ncc(-c3ccc(N4CCC(N5CCN(C)CC5)CC4)c(OC)c3)c2nc1NC1CCC(N)CC1] |

TABLE 1-continued
| No | Structure |
| --- | --- |
| 89 | 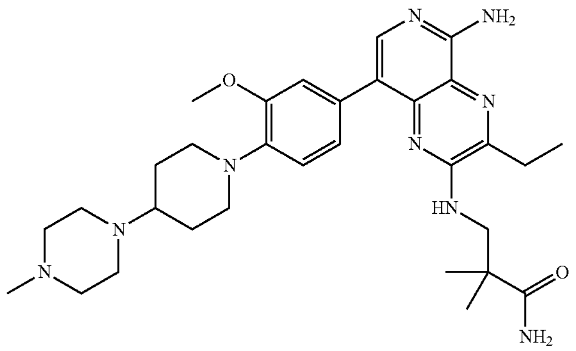 [SMILES: CCc1nc2c(N)ncc(-c3ccc(N4CCC(N5CCN(C)CC5)CC4)c(OC)c3)c2nc1NCC(C)(C)C(N)=O] |
| 90 | 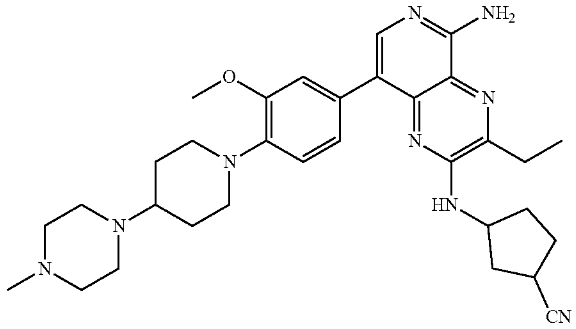 [SMILES: CCc1nc2c(N)ncc(-c3ccc(N4CCC(N5CCN(C)CC5)CC4)c(OC)c3)c2nc1NC1CCC(C#N)C1] |
| 91 | 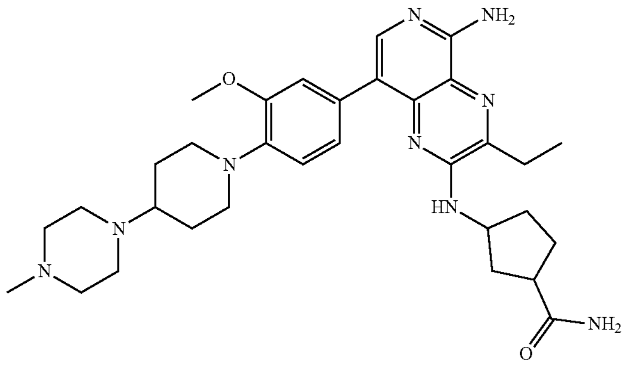 [SMILES: CCc1nc2c(N)ncc(-c3ccc(N4CCC(N5CCN(C)CC5)CC4)c(OC)c3)c2nc1NC1CCC(C(N)=O)C1] |
| 92 | 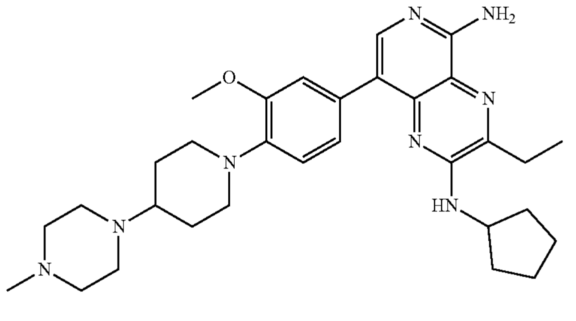 |

TABLE 1-continued
| No | Structure |
| --- | --- |
| 93 | 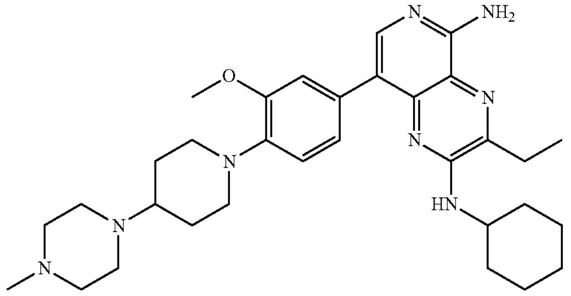 [SMILES: CCc1nc2c(N)ncc(-c3ccc(N4CCC(N5CCN(C)CC5)CC4)c(OC)c3)c2nc1NC1CCCCC1] |
| 94 | 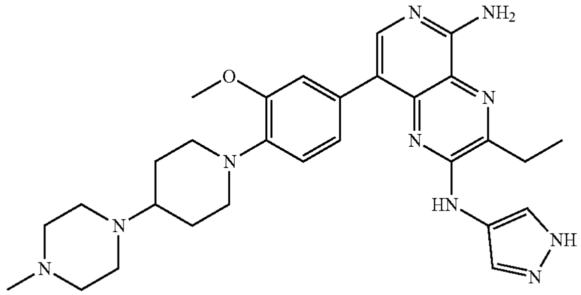 [SMILES: CCc1nc2c(N)ncc(-c3ccc(N4CCC(N5CCN(C)CC5)CC4)c(OC)c3)c2nc1Nc1cn[nH]c1] |
| 95 | 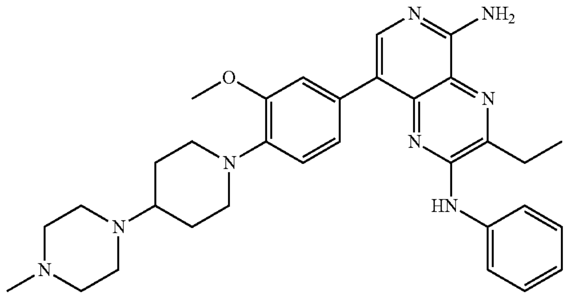 [SMILES: CCc1nc2c(N)ncc(-c3ccc(N4CCC(N5CCN(C)CC5)CC4)c(OC)c3)c2nc1Nc1ccccc1] |
| 96 | 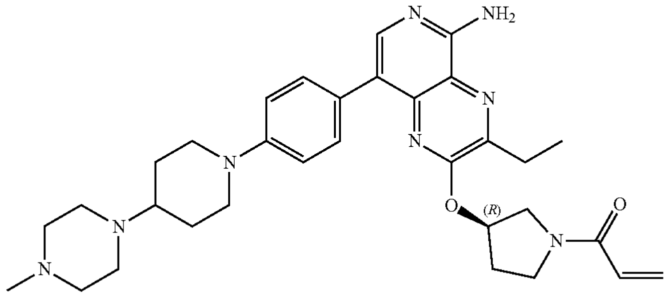 |
| 97 | 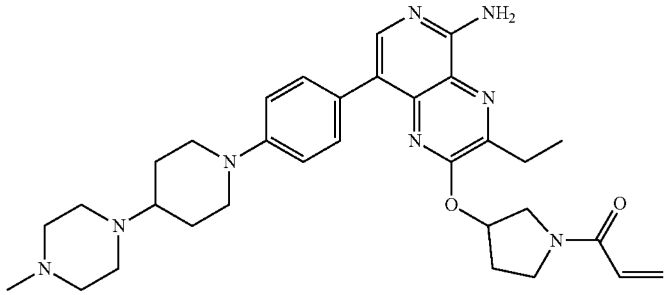 [SMILES: C=CC(=O)N1CCC(Oc2nc3c(-c4ccc(N5CCC(N6CCN(C)CC6)CC5)cc4)cnc(N)c3nc2CC)C1] |

TABLE 1-continued
| No | Structure |
|---|---|
| 98 | 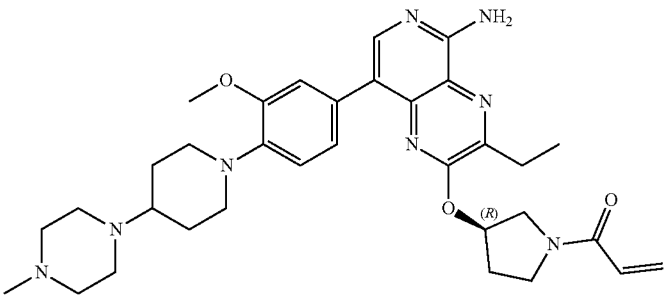 |
| 99 | 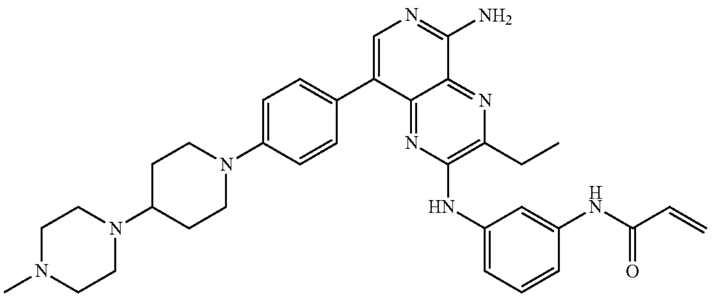 [SMILES: C=CC(=O)Nc1cccc(Nc2nc3c(-c4ccc(N5CCC(N6CCN(C)CC6)CC5)cc4)cnc(N)c3nc2CC)c1] |
| 100 | 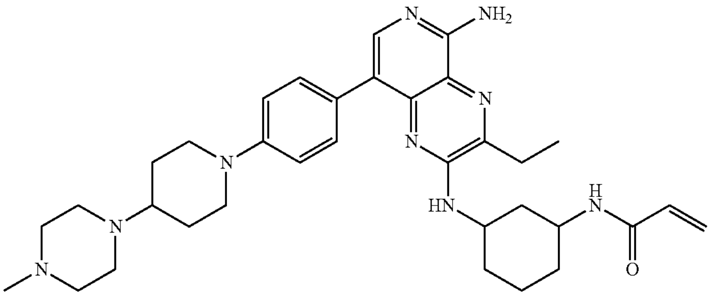 [SMILES: C=CC(=O)NC1CCCC(Nc2nc3c(-c4ccc(N5CCC(N6CCN(C)CC6)CC5)cc4)cnc(N)c3nc2CC)C1] |
| 101 | 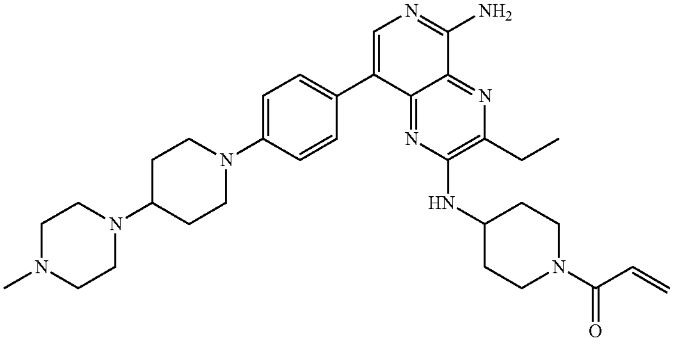 [SMILES: C=CC(=O)N1CCC(Nc2nc3c(-c4ccc(N5CCC(N6CCN(C)CC6)CC5)cc4)cnc(N)c3nc2CC)CC1] |

TABLE 1-continued
| No | Structure |
|---|---|
| 102 | 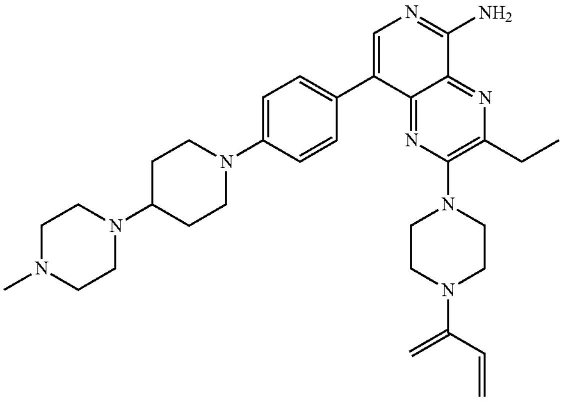 [SMILES: C=CC(=C)N1CCN(c2nc3c(-c4ccc(N5CCC(N6CCN(C)CC6)CC5)cc4)cnc(N)c3nc2CC)CC1] |
| 103 | 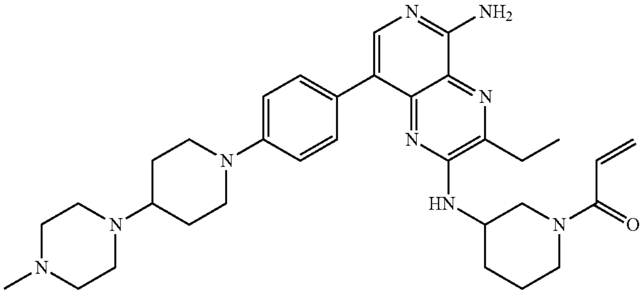 [SMILES: C=CC(=O)N1CCCC(Nc2nc3c(-c4ccc(N5CCC(N6CCN(C)CC6)CC5)cc4)cnc(N)c3nc2CC)C1] |
| 104 | 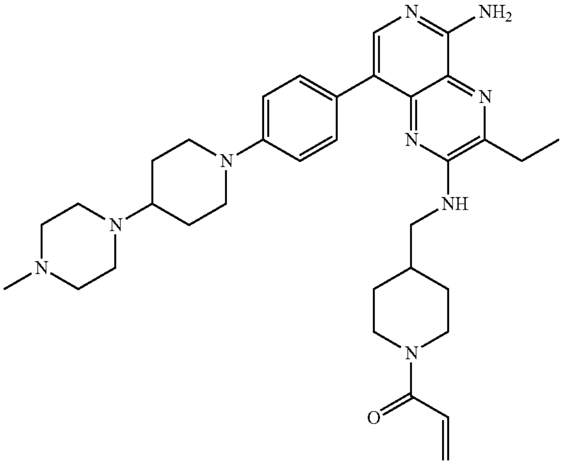 [SMILES: C=CC(=O)N1CCC(CNc2nc3c(-c4ccc(N5CCC(N6CCN(C)CC6)CC5)cc4)cnc(N)c3nc2CC)CC1] |
| 105 | 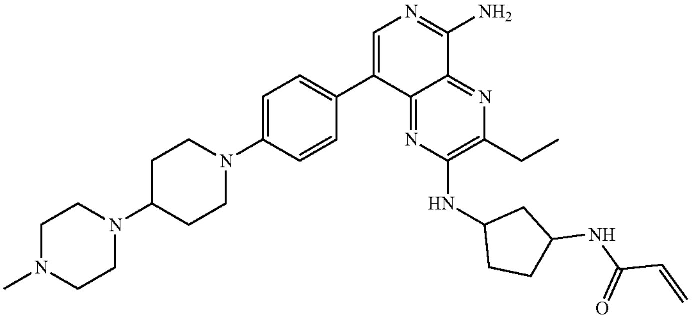 [SMILES: C=CC(=O)NC1CCC(Nc2nc3c(-c4ccc(N5CCC(N6CCN(C)CC6)CC5)cc4)cnc(N)c3nc2CC)C1] |

TABLE 1-continued
| No | Structure |
|---|---|
| 106 | 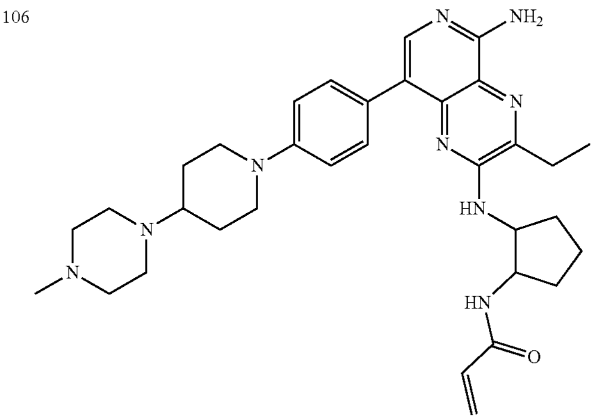 |
| 107 | 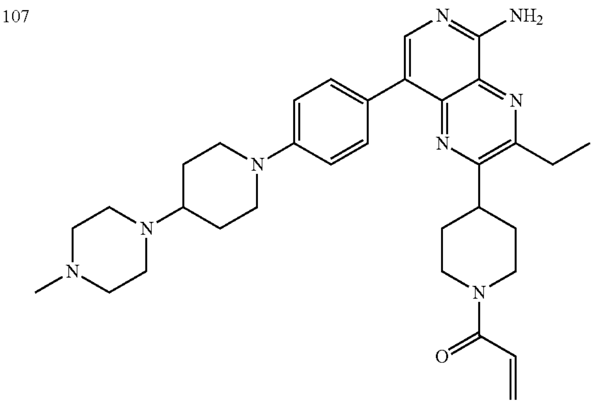 |
| 108 | 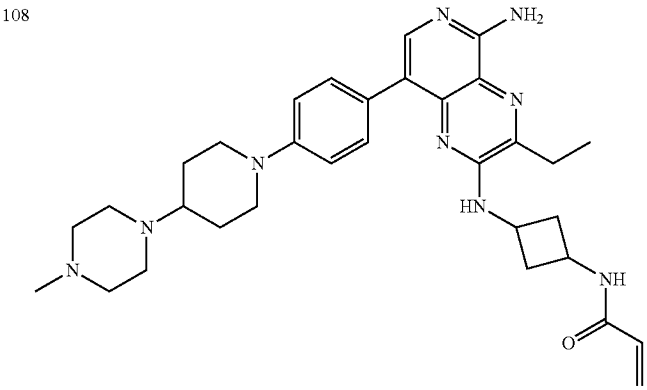 |

TABLE 1-continued
| No | Structure |
|---|---|
| 109 | 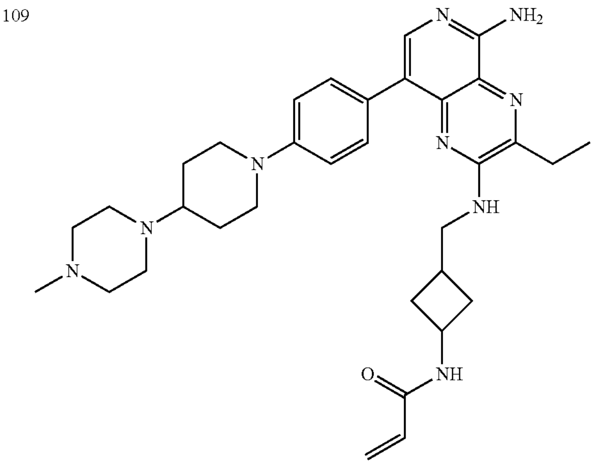 |
| 110 | 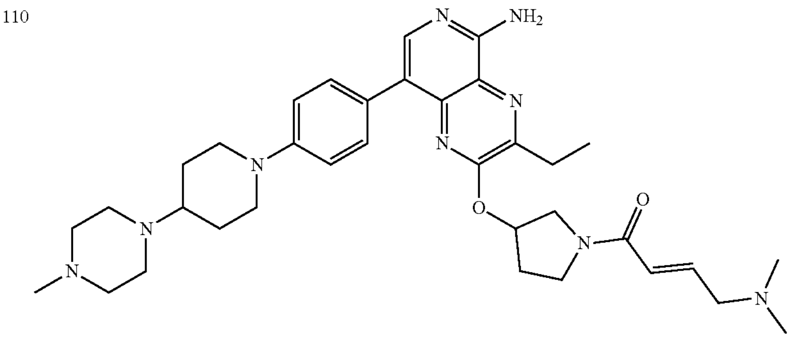 |
| 111 | 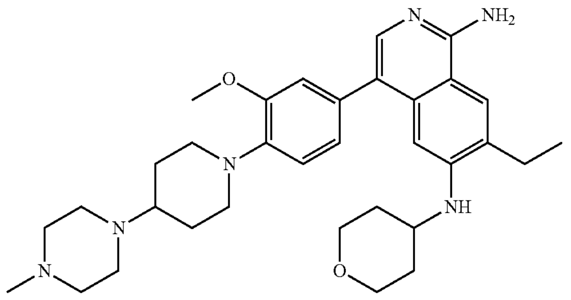 |
| 112 | 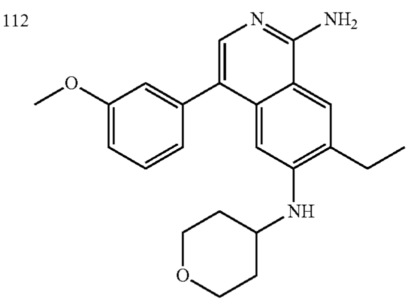 |

TABLE 1-continued
| No | Structure |
| --- | --- |
| 113 | 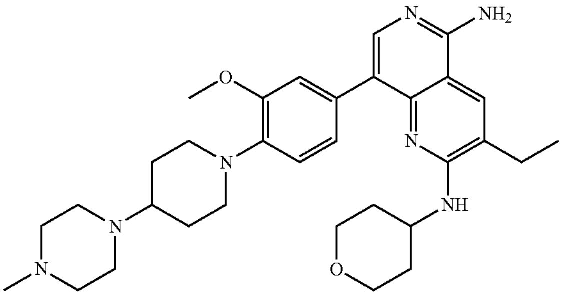 |
| 114 | 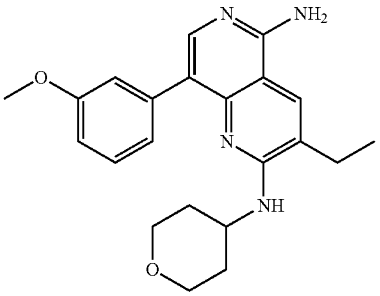 [SMILES: CCc1cc2c(N)ncc(-c3cccc(OC)c3)c2nc1NC1CCOCC1] |
| 115 | 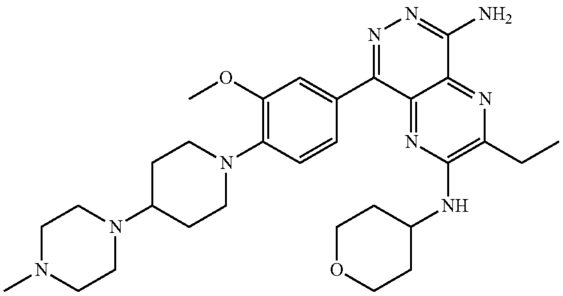 [SMILES: CCc1nc2c(N)nnc(-c3ccc(N4CCC(N5CCN(C)CC5)CC4)c(OC)c3)c2nc1NC1CCOCC1] |
| 116 | 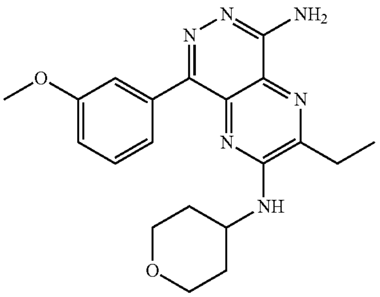 |
| 117 | 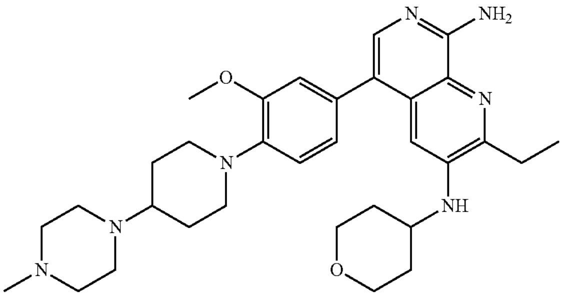 |

TABLE 1-continued
| No | Structure |
|---|---|
| 118 | 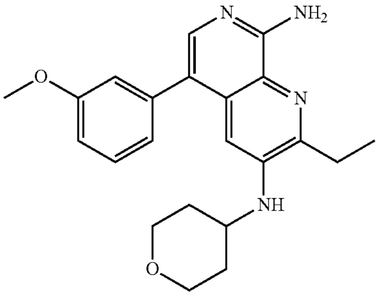 |
| 121 | 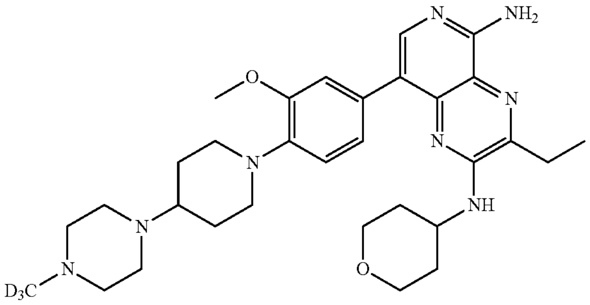 [SMILES: [2H]C([2H])([2H])N1CCN(C2CCN(c3ccc(-c4cnc(N)c5nc(CC)c(NC6CCOCC6)nc45)cc3OC)CC2)CC1] |
| 122 | 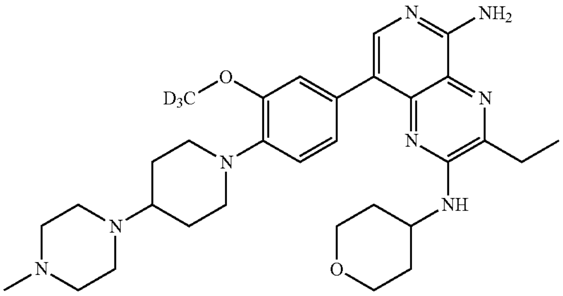 |
| 128 | 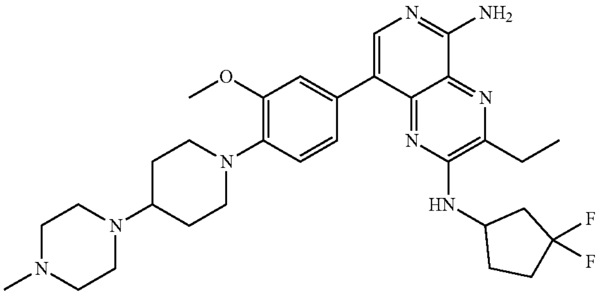 [SMILES: CCc1nc2c(N)ncc(-c3ccc(N4CCC(N5CCN(C)CC5)CC4)c(OC)c3)c2nc1NC1CCC(F)(F)C1] |
| 129 | 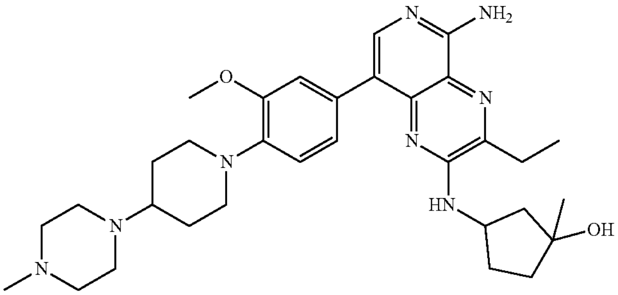 [SMILES: CCc1nc2c(N)ncc(-c3ccc(N4CCC(N5CCN(C)CC5)CC4)c(OC)c3)c2nc1NC1CCC(C)(O)C1] |

TABLE 1-continued
| No | Structure |
| --- | --- |
| 130 | 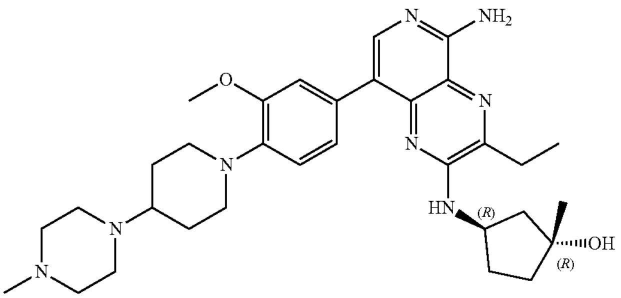 |
| 131 | 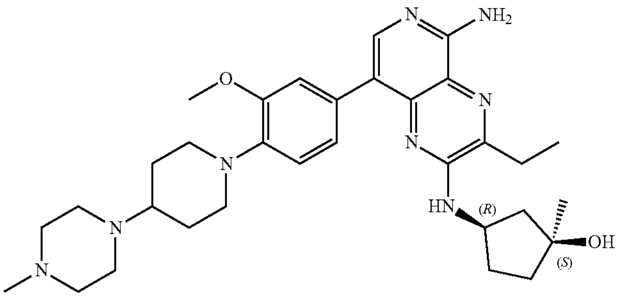 |
| 132 | 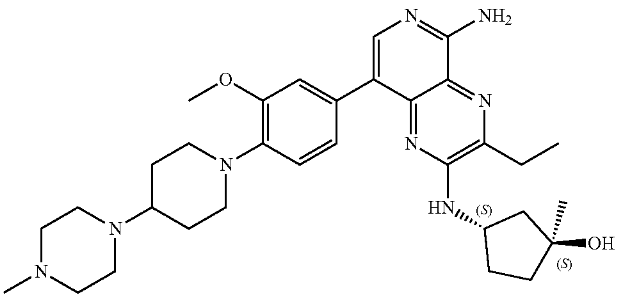 |
| 133 | 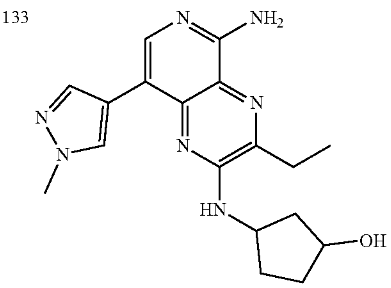 |

TABLE 1-continued
| No | Structure |
|---|---|
| 134 | 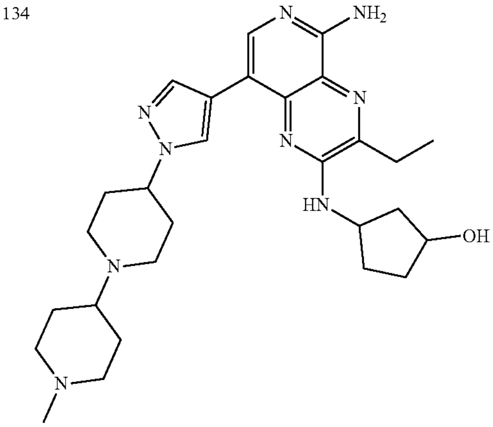 |
| 135 | 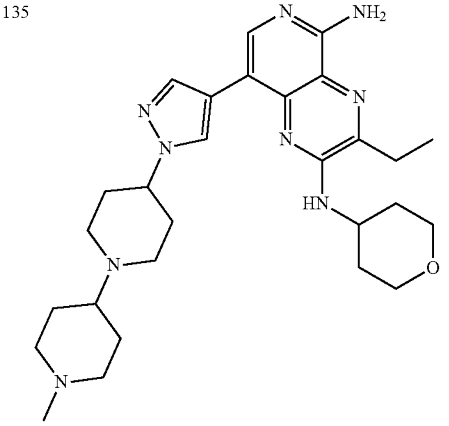 |
| 136 | 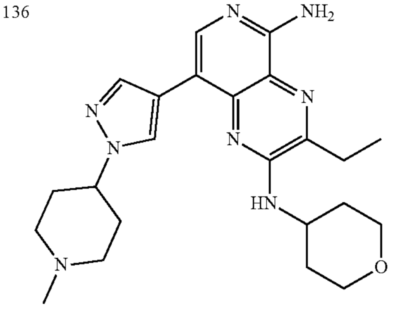 |
| 137 | 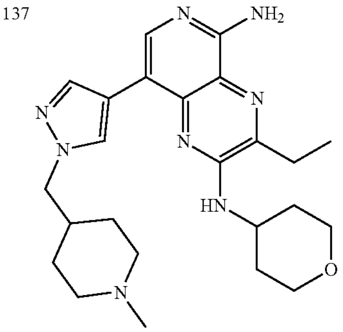 |

TABLE 1-continued
| No | Structure |
| --- | --- |
| 138 | 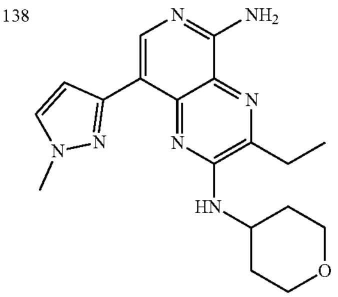 |
| 139 | 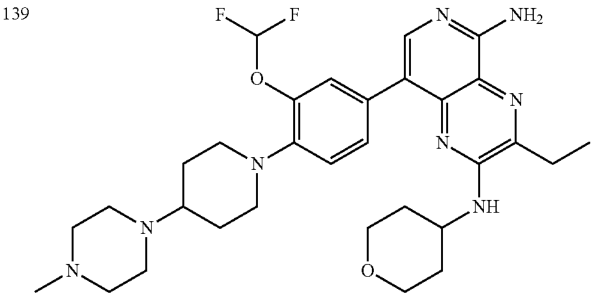 |
| 140 | 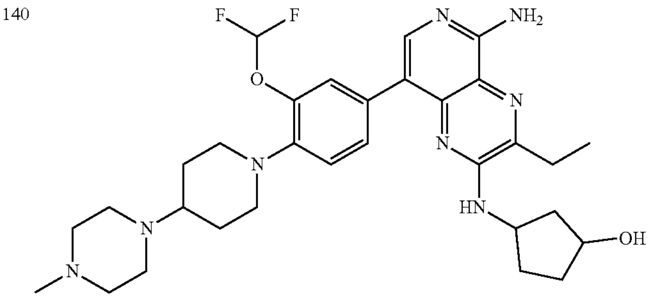 |
| 141 | 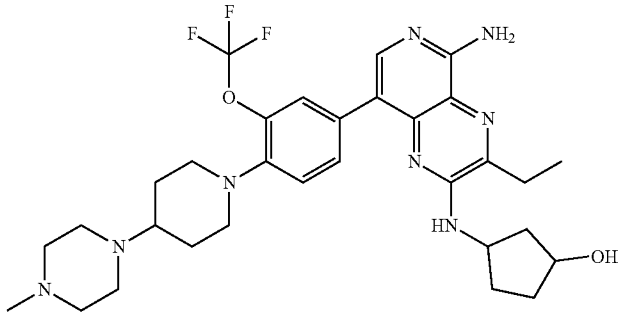 [SMILES: CCc1nc2c(N)ncc(-c3ccc(N4CCC(N5CCN(C)CC5)CC4)c(OC(F)(F)F)c3)c2nc1NC1CCC(O)C1] |
| 142 | 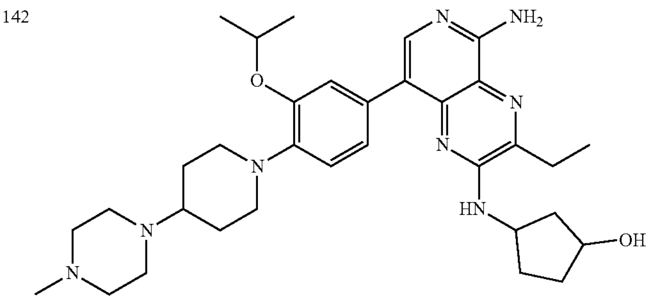 |

TABLE 1-continued
| No | Structure |
|---|---|
| 143 | 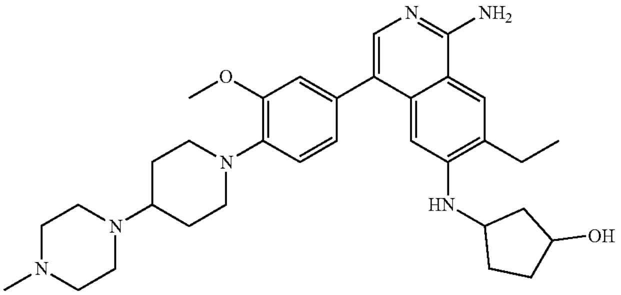 [SMILES: CCc1cc2c(N)ncc(-c3ccc(N4CCC(N5CCN(C)CC5)CC4)c(OC)c3)c2cc1NC1CCC(O)C1] |
| 144 | 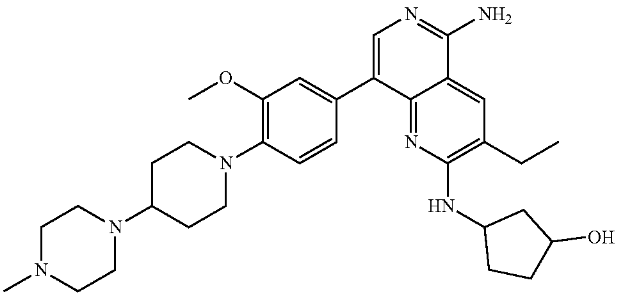 [SMILES: CCc1cc2c(N)ncc(-c3ccc(N4CCC(N5CCN(C)CC5)CC4)c(OC)c3)c2nc1NC1CCC(O)C1] |
| 145 | 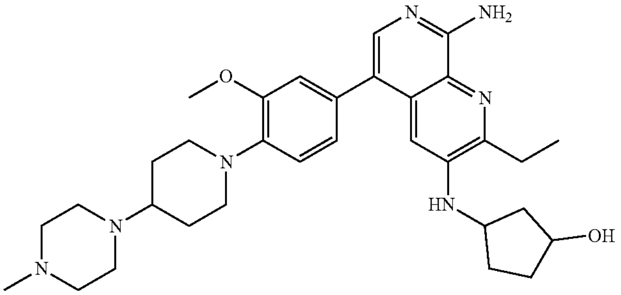 [SMILES: CCc1nc2c(N)ncc(-c3ccc(N4CCC(N5CCN(C)CC5)CC4)c(OC)c3)c2cc1NC1CCC(O)C1] |
| 146 | 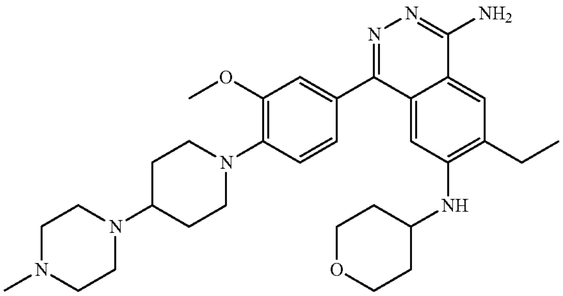 [SMILES: CCc1cc2c(N)nnc(-c3ccc(N4CCC(N5CCN(C)CC5)CC4)c(OC)c3)c2cc1NC1CCOCC1] |
| 147 | 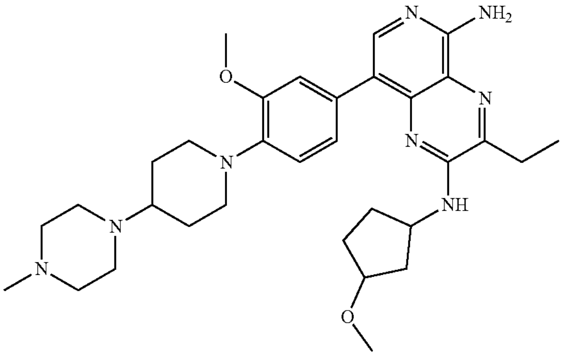 [SMILES: CCc1nc2c(N)ncc(-c3ccc(N4CCC(N5CCN(C)CC5)CC4)c(OC)c3)c2nc1NC1CCC(OC)C1] |

TABLE 1-continued
| No | Structure |
|---|---|
| 148 | 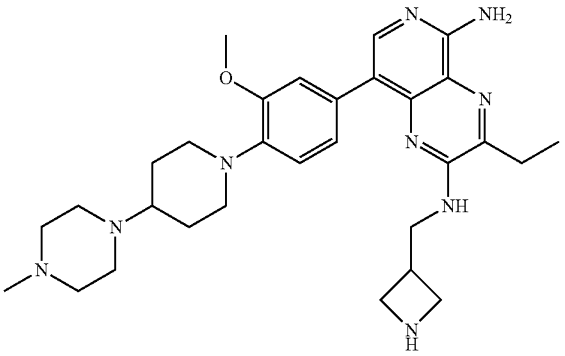 [SMILES: CCc1nc2c(N)ncc(-c3ccc(N4CCC(N5CCN(C)CC5)CC4)c(OC)c3)c2nc1NCC1CNC1] |
| 149 | 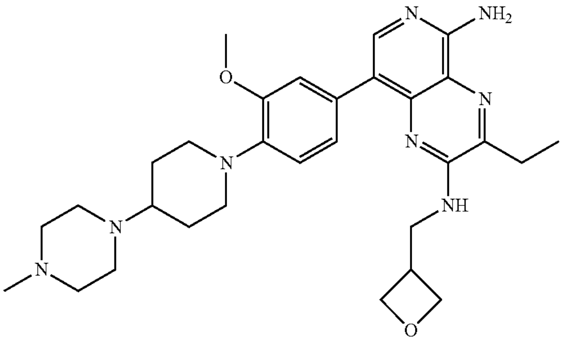 [SMILES: CCc1nc2c(N)ncc(-c3ccc(N4CCC(N5CCN(C)CC5)CC4)c(OC)c3)c2nc1NCC1COC1] |
| 150 | 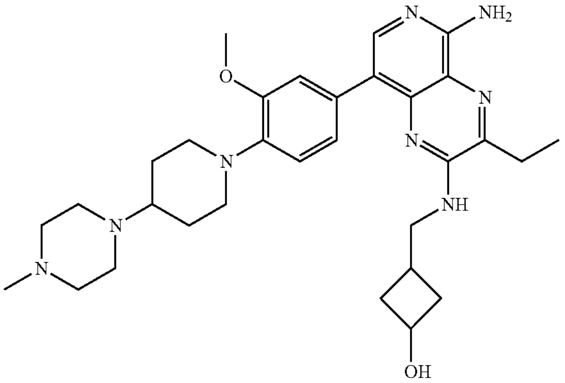 [SMILES: CCc1nc2c(N)ncc(-c3ccc(N4CCC(N5CCN(C)CC5)CC4)c(OC)c3)c2nc1NCC1CC(O)C1] |
| 151 | 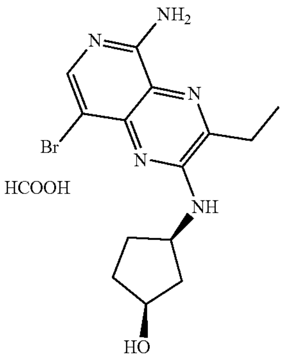 [SMILES: "HCOOH" ; CCc1nc2c(N)ncc(Br)c2nc1N[C@@H]1CC[C@H](O)C1] |

TABLE 1-continued
| No | Structure |
|---|---|
| 152 | 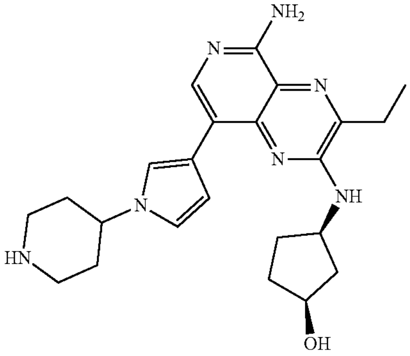 [SMILES: CCc1nc2c(N)ncc(-c3ccn(C4CCNCC4)c3)c2nc1N[C@@H]1CC[C@H](O)C1] |
| 153 | 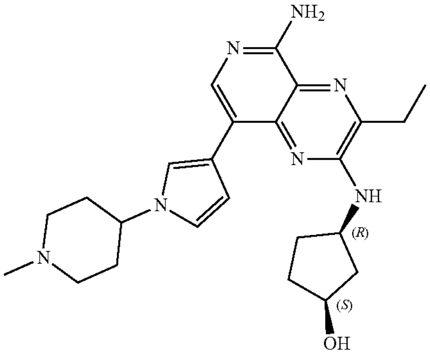 |
| 154 | 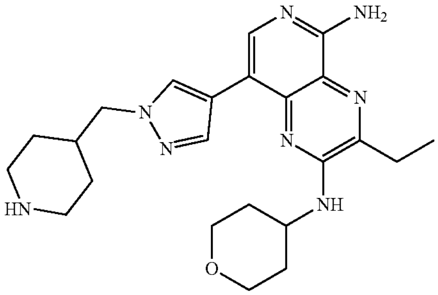 [SMILES: CCc1nc2c(N)ncc(-c3cnn(CC4CCNCC4)c3)c2nc1NC1CCOCC1] |
| 155 | 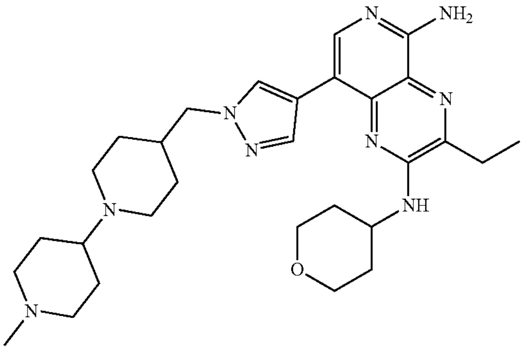 [SMILES: CCc1nc2c(N)ncc(-c3cnn(CC4CCN(C5CCN(C)CC5)CC4)c3)c2nc1NC1CCOCC1] |

TABLE 1-continued
| No | Structure |
| --- | --- |
| 156 | 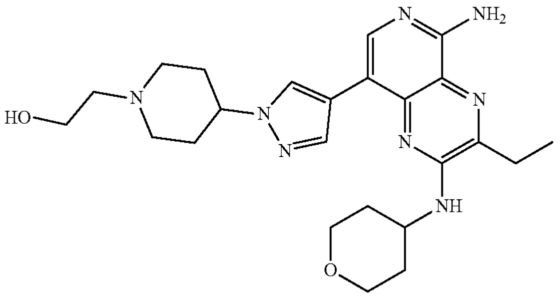 [SMILES: CCc1nc2c(N)ncc(-c3cnn(C4CCN(CCO)CC4)c3)c2nc1NC1CCOCC1] |
| 157 | 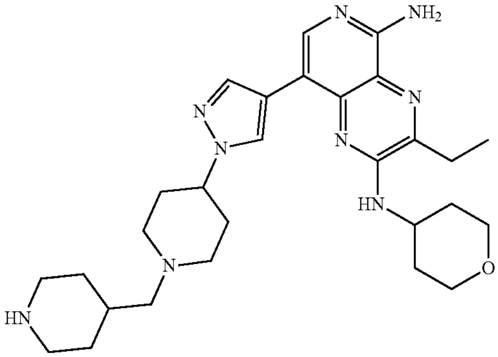 [SMILES: CCc1nc2c(N)ncc(-c3cnn(C4CCN(CC5CCNCC5)CC4)c3)c2nc1NC1CCOCC1] |
| 158 | 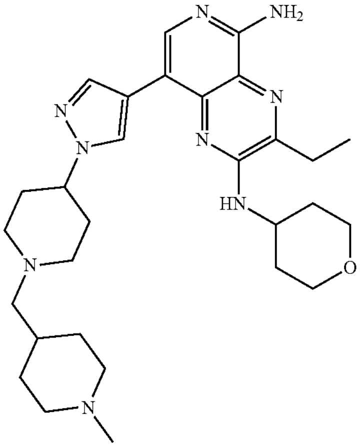 [SMILES: CCc1nc2c(N)ncc(-c3cnn(C4CCN(CC5CCN(C)CC5)CC4)c3)c2nc1NC1CCOCC1] |
| 159 | 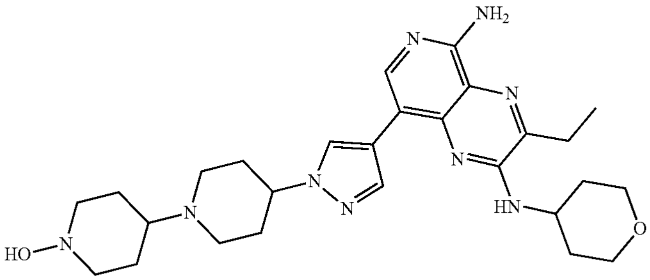 [SMILES: CCc1nc2c(N)ncc(-c3cnn(C4CCN(C5CCN(O)CC5)CC4)c3)c2nc1NC1CCOCC1] |

TABLE 1-continued
| No | Structure |
|---|---|
| 160 | 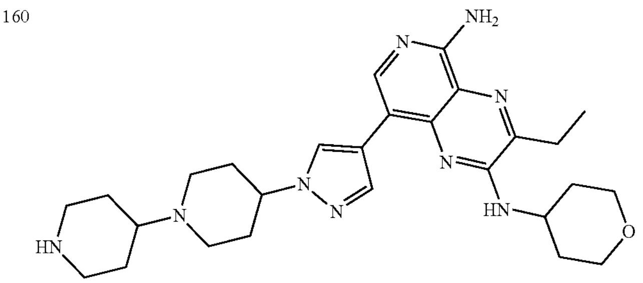 |
| 161 | 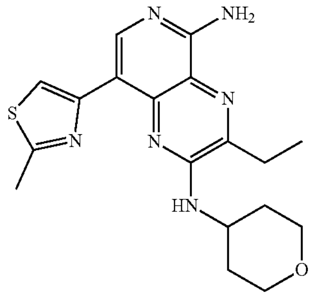 [SMILES: CCc1nc2c(N)ncc(-c3csc(C)n3)c2nc1NC1CCOCC1] |
| 162 | 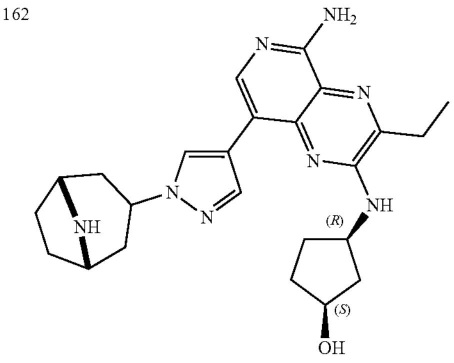 |
| 163 | 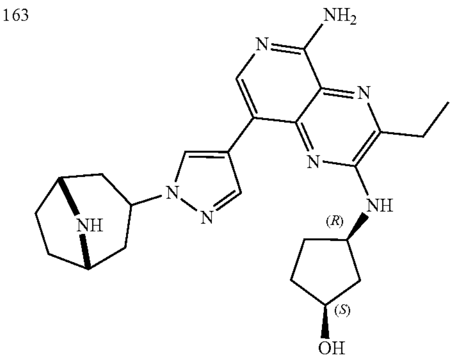 |

TABLE 1-continued
| No | Structure |
| --- | --- |
| 164 | 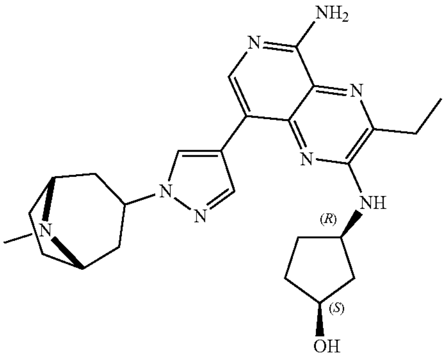 |
| 165 | 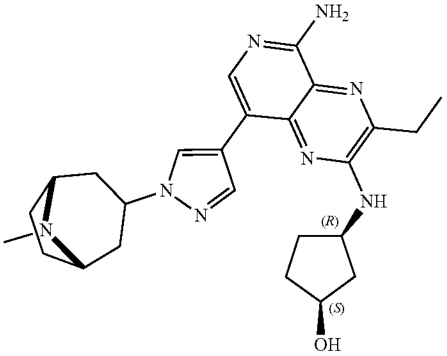 |
| 166 | 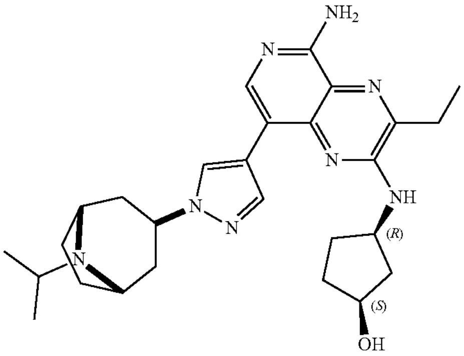 |
| 167 | 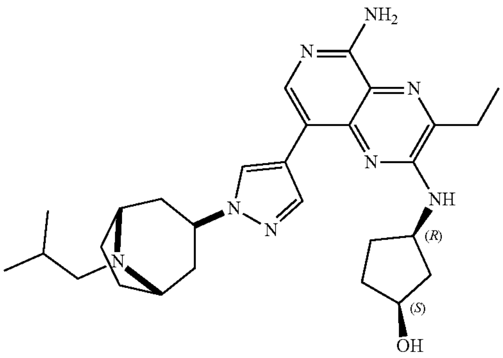 |

TABLE 1-continued
| No | Structure |
|---|---|
| 168 | 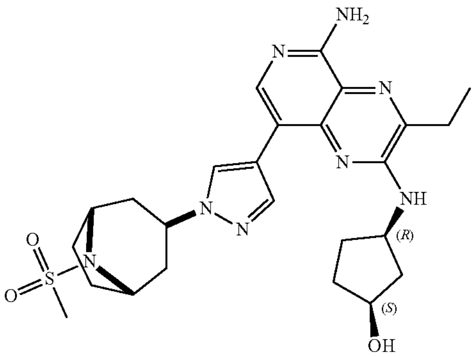 |
| 169 | 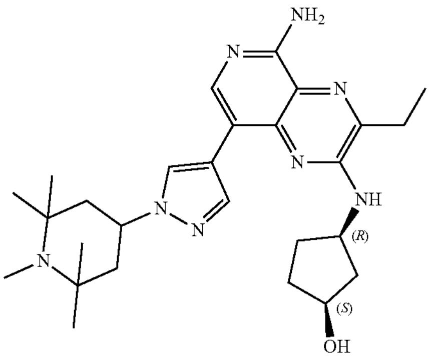 |
| 170 | 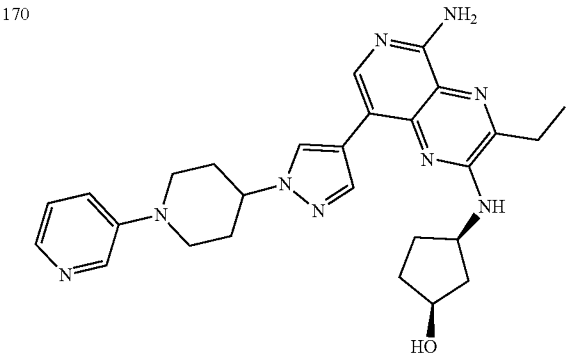 |
| 171 | 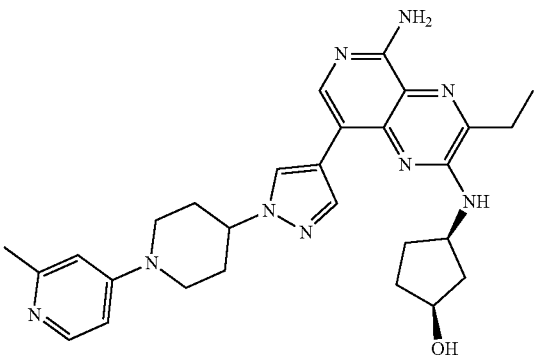 [SMILES: CCc1nc2c(N)ncc(-c3cnn(C4CCN(c5ccnc(C)c5)CC4)c3)c2nc1N[C@@H]1CC[C@H](O)C1] |

TABLE 1-continued
| No | Structure |
|---|---|
| 172 | 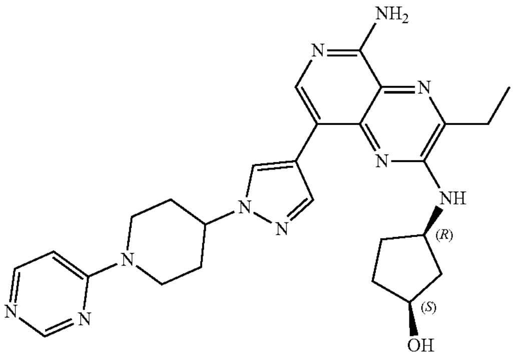 |
| 173 | 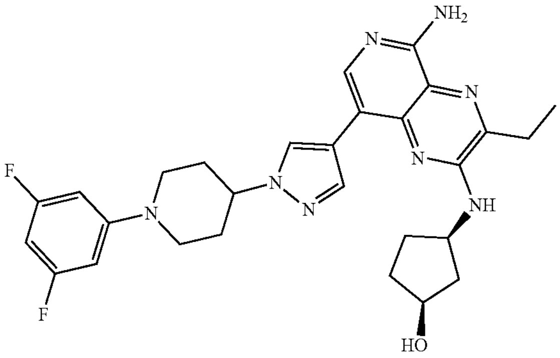 [SMILES: CCc1nc2c(N)ncc(-c3cnn(C4CCN(c5cc(F)cc(F)c5)CC4)c3)c2nc1N[C@@H]1CC[C@H](O)C1] |
| 174 | 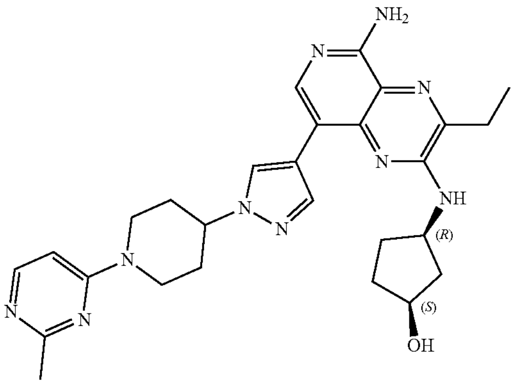 |
| 175 | 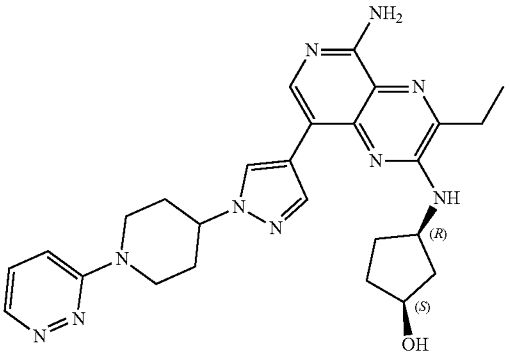 |

TABLE 1-continued
| No | Structure |
|---|---|
| 176 | 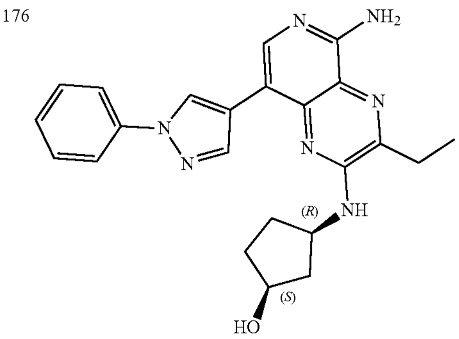 |
| 177 | 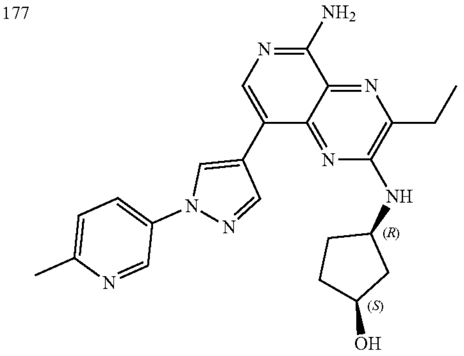 |
| 178 | 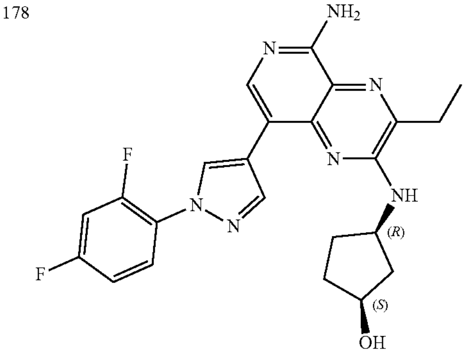 |
| 179 | 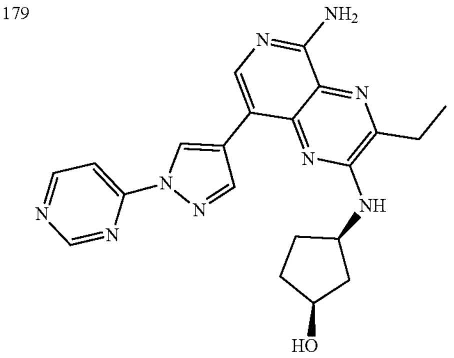 |

TABLE 1-continued
| No | Structure |
|---|---|
| 180 | 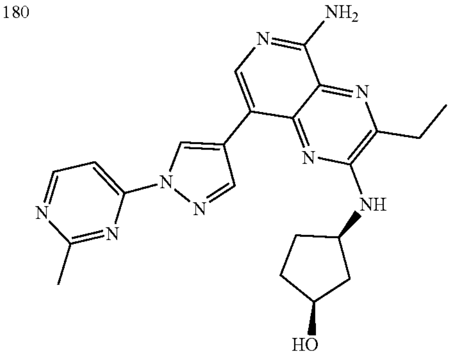 |
| 181 | 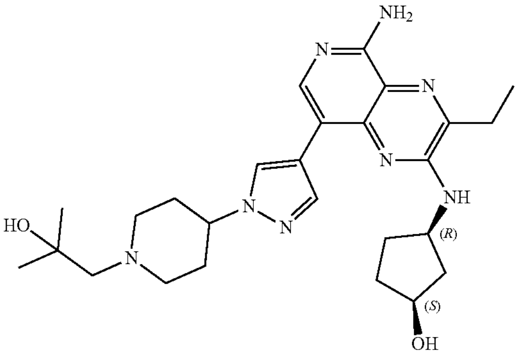 |
| 182 | 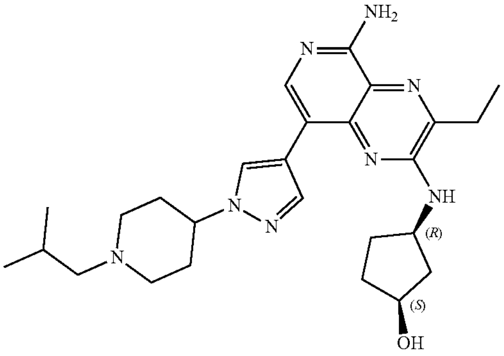 |
| 183 | 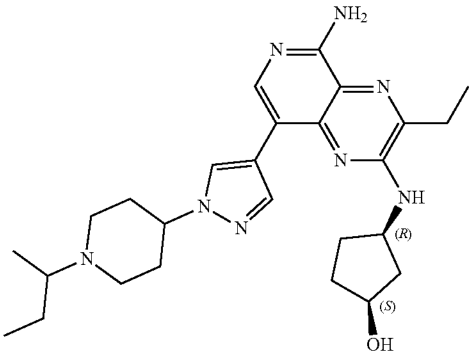 |

TABLE 1-continued
| No | Structure |
|---|---|
| 184 | 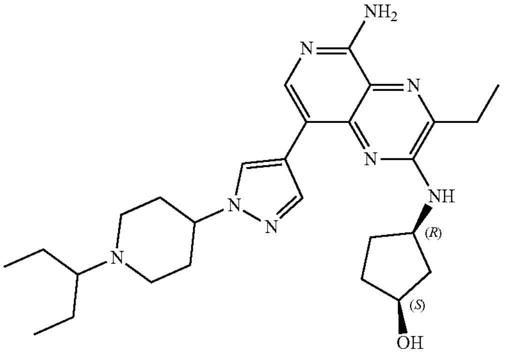 |
| 185 | 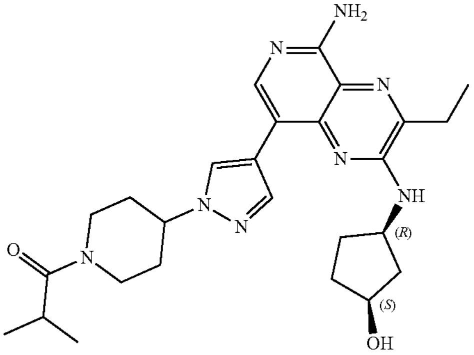 |
| 186 | 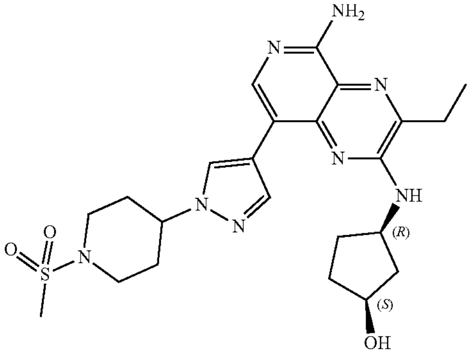 |
| 187 | 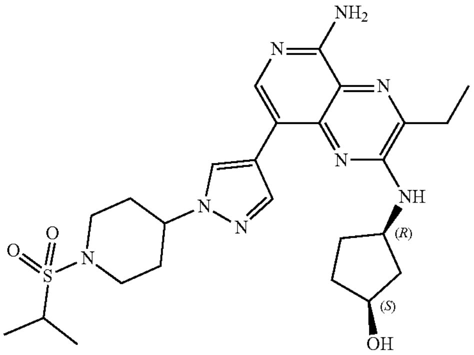 |

TABLE 1-continued
| No | Structure |
| --- | --- |
| 188 | 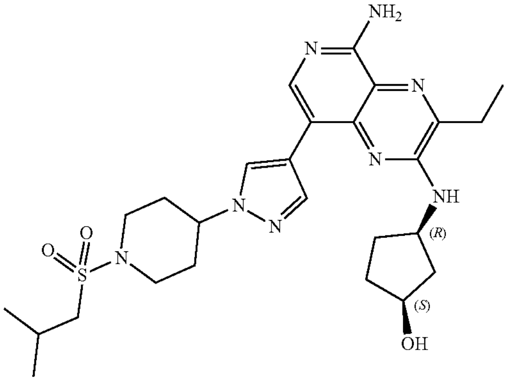 |
| 189 | 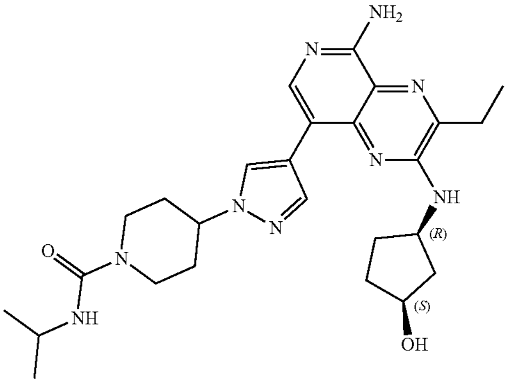 |
| 190 | 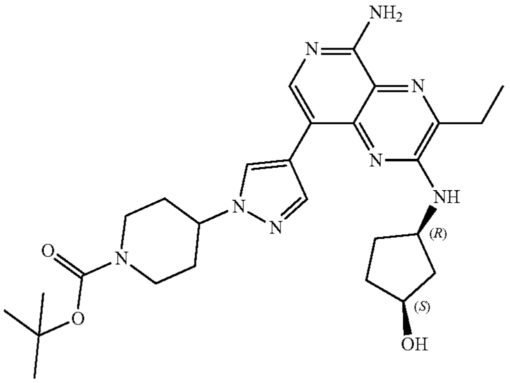 |
| 191 | 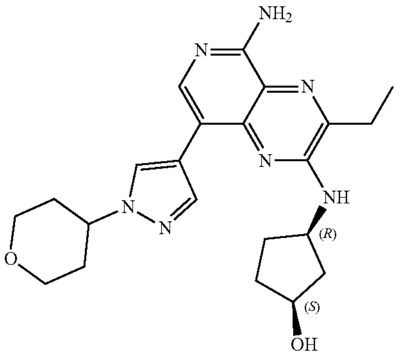 |

TABLE 1-continued
| No | Structure |
|---|---|
| 192 | 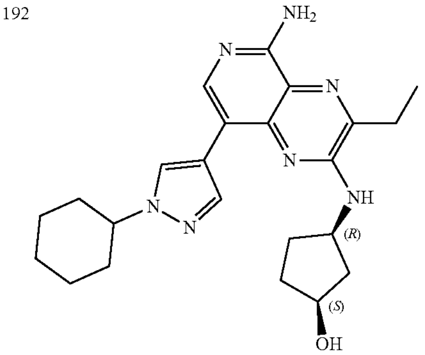 |
| 193 | 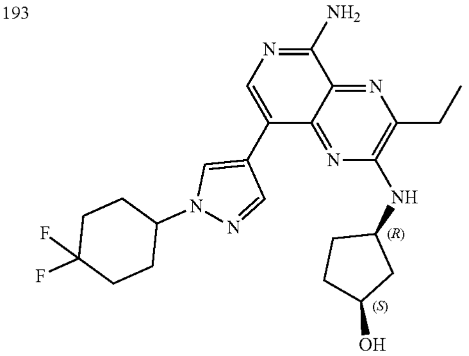 |
| 194 | 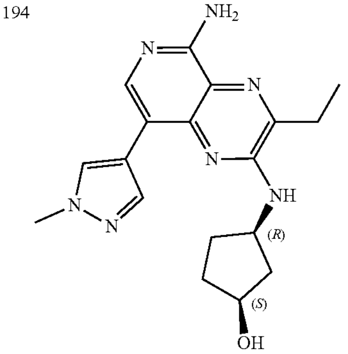 |
| 195 | 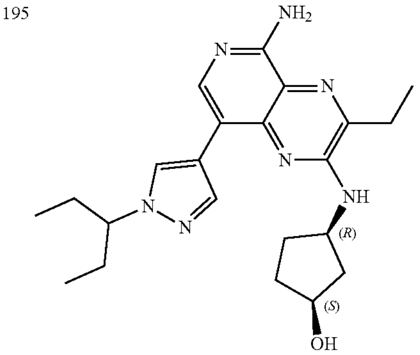 |

TABLE 1-continued
| No | Structure |
|---|---|
| 196 | 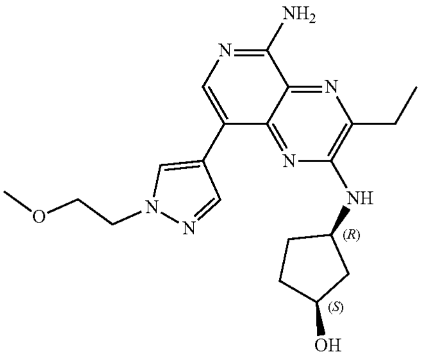 |
| 197 | 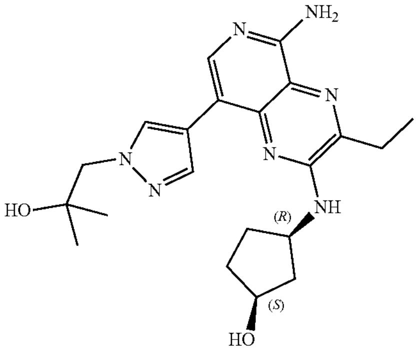 |
| 198 | 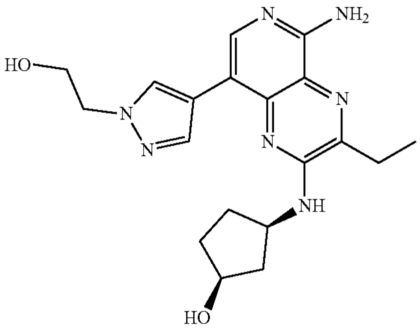 [SMILES: CCc1nc2c(N)ncc(-c3cnn(CCO)c3)c2nc1N[C@@H]1CC[C@H](O)C1] |
| 199 | 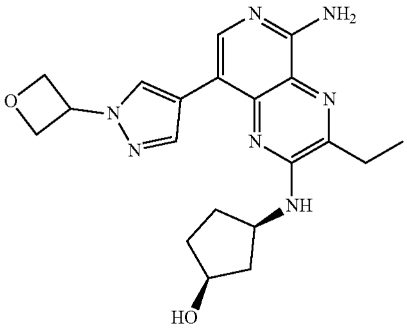 [SMILES: CCc1nc2c(N)ncc(-c3cnn(C4COC4)c3)c2nc1N[C@@H]1CC[C@H](O)C1] |

TABLE 1-continued
| No | Structure |
|---|---|
| 200 | 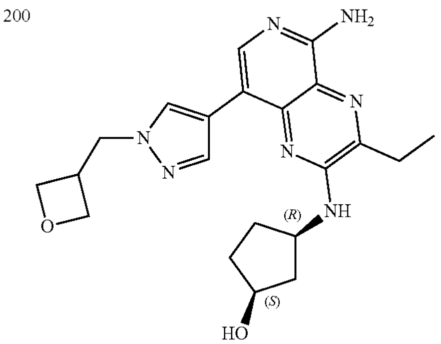 |
| 201 | 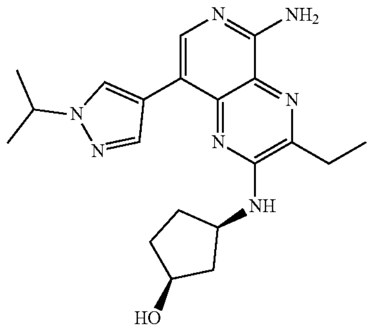 [SMILES: CCc1nc2c(N)ncc(-c3cnn(C(C)C)c3)c2nc1N[C@@H]1CC[C@H](O)C1] |
| 202 | 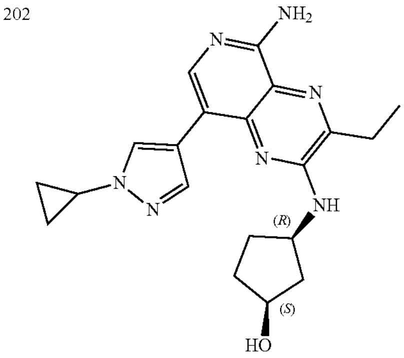 |
| 203 | 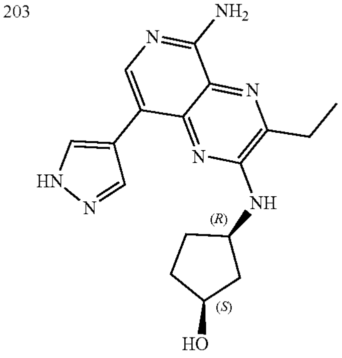 |

TABLE 1-continued
| No | Structure |
|---|---|
| 204 | 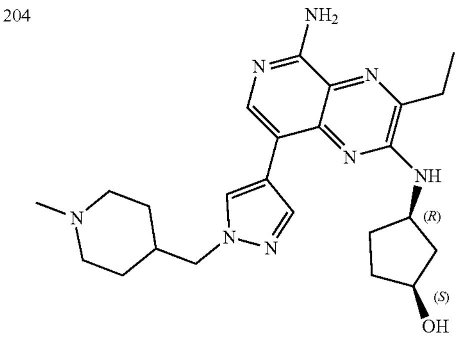 |
| 205 | 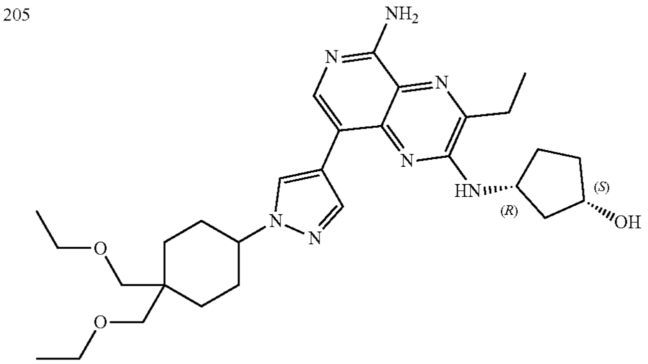 |
| 206 | 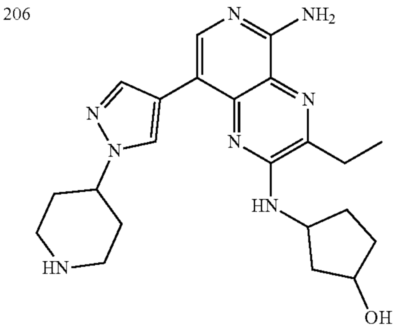 |
| 207 | 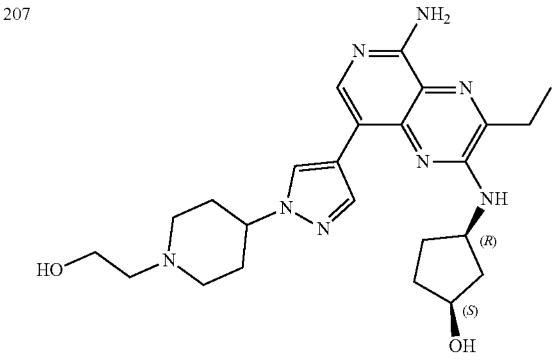 |

TABLE 1-continued
| No | Structure |
|---|---|
| 208 | 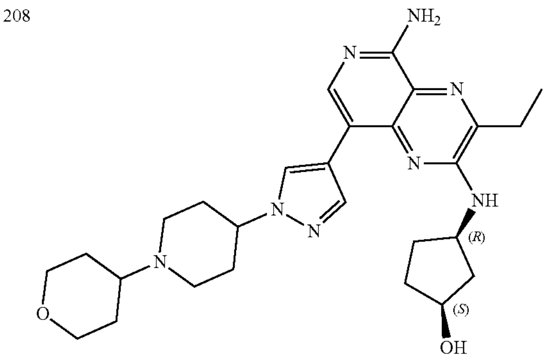 |
| 209 | 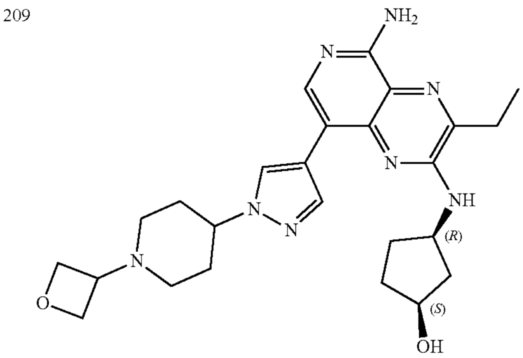 |
| 210 | 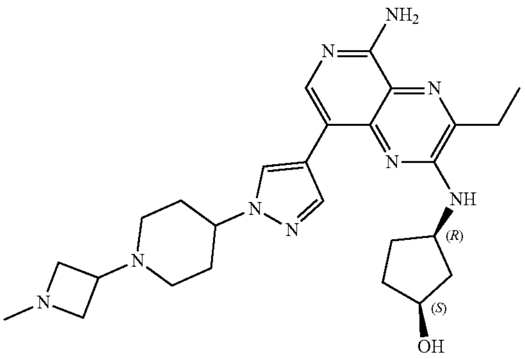 |
| 211 | 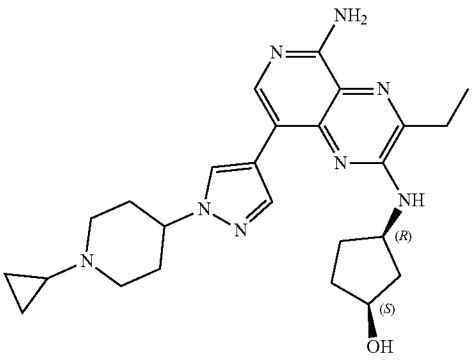 |

TABLE 1-continued
| No | Structure |
| --- | --- |
| 212 | 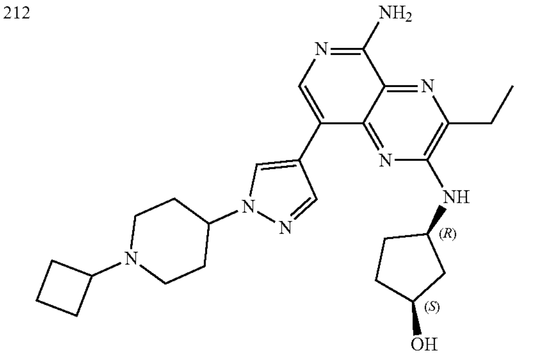 |
| 213 | 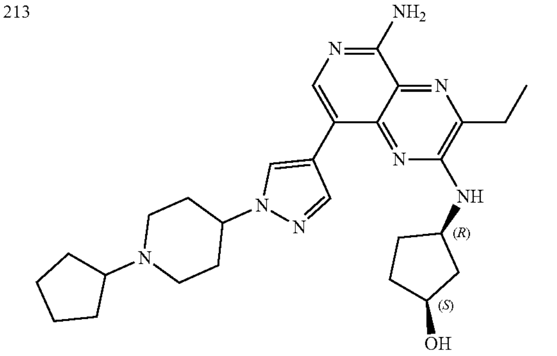 |
| 214 | 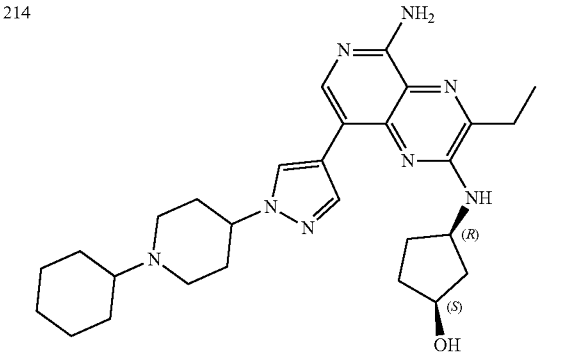 |
| 215 | 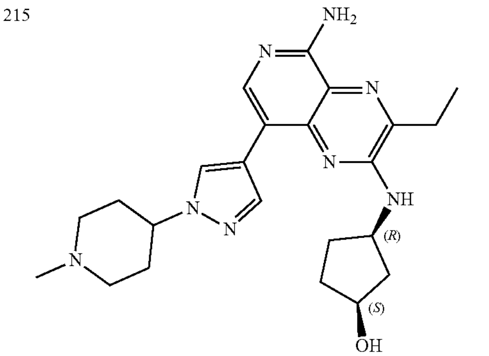 |

TABLE 1-continued
| No | Structure |
|---|---|
| 216 | 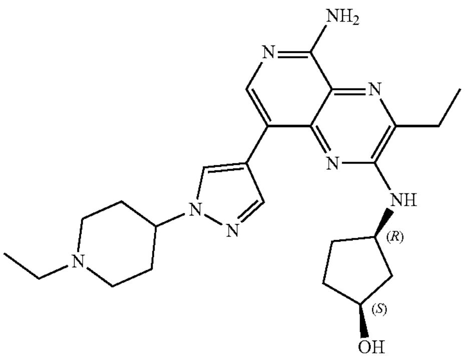 |
| 217 | 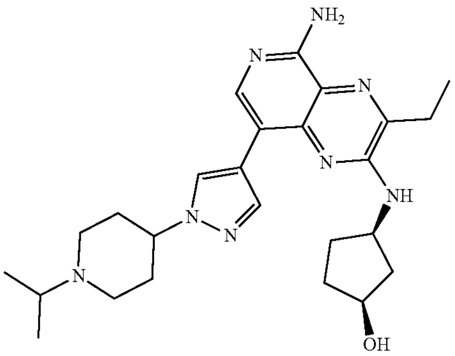 [SMILES: CCc1nc2c(N)ncc(-c3cnn(C4CCN(C(C)C)CC4)c3)c2nc1N[C@@H]1CC[C@H](O)C1] |
| 218 | 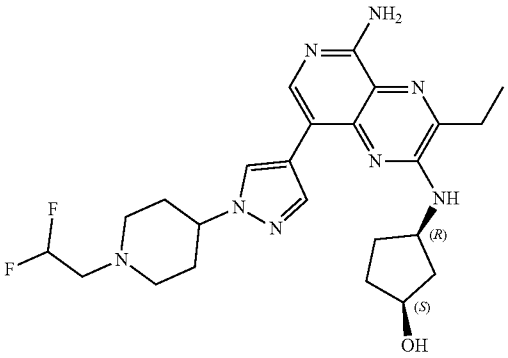 |
| 219 | 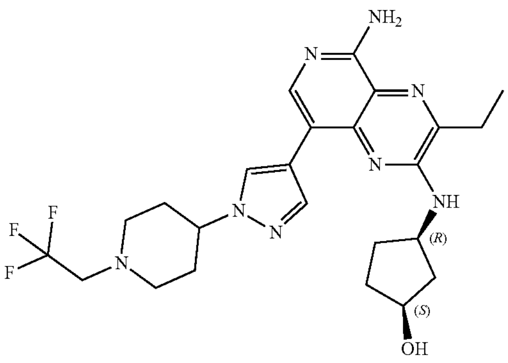 |

TABLE 1-continued
| No | Structure |
| --- | --- |
| 220 | 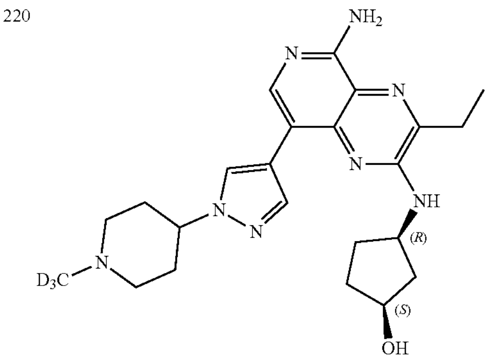 |
| 221 | 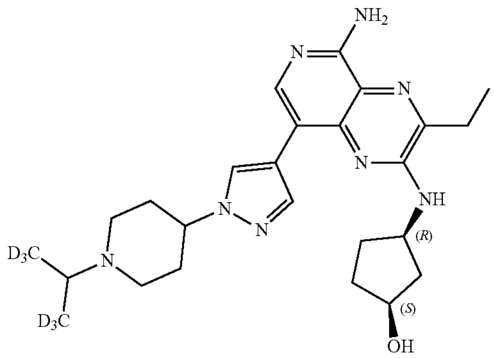 |
| 222 | 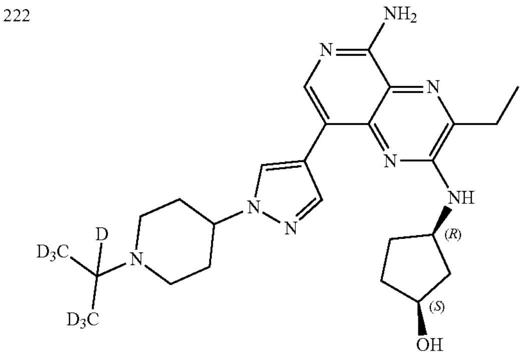 |
| 223 | 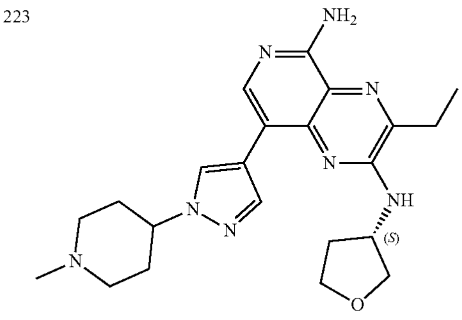 |

TABLE 1-continued
| No | Structure |
|---|---|
| 224 | 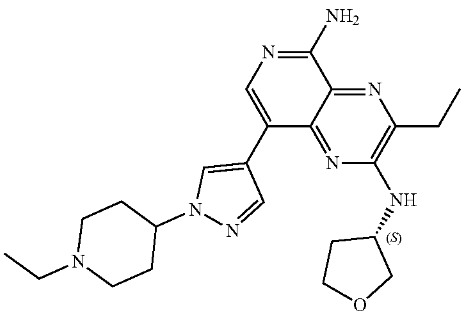 |
| 225 | 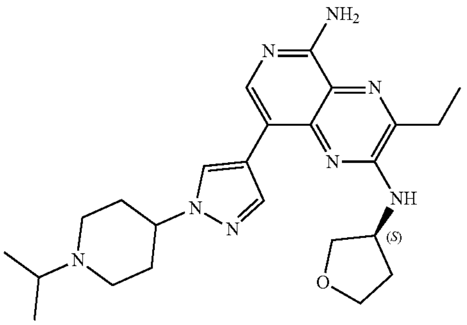 |
| 226 | 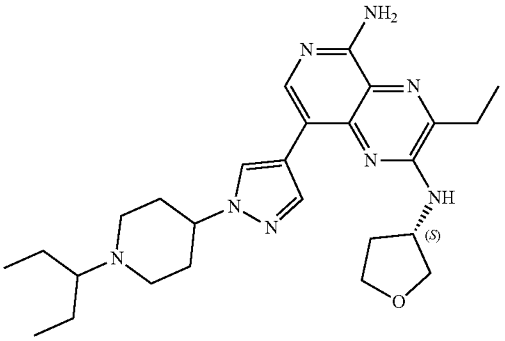 |
| 227 | 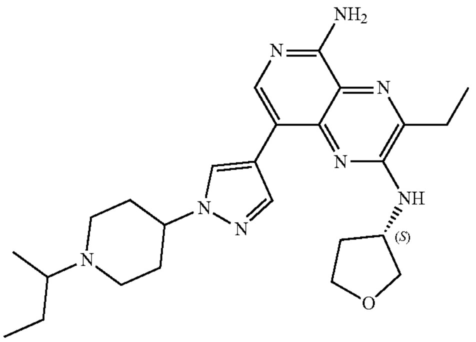 |

TABLE 1-continued
| No | Structure |
| --- | --- |
| 228 | 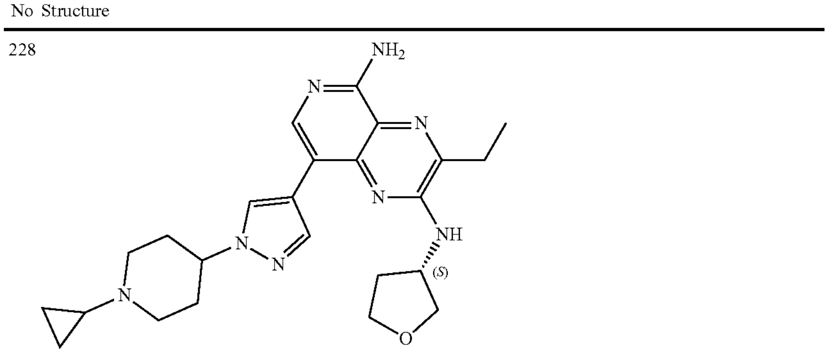 |
| 229 | 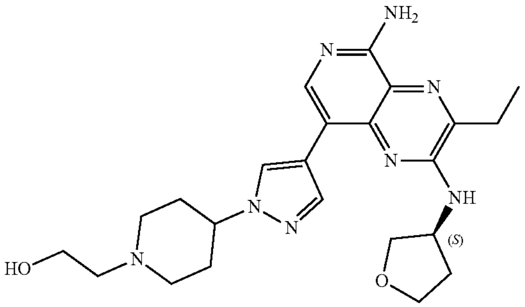 |
| 230 | 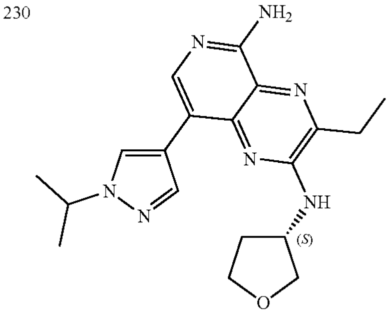 |
| 231 | 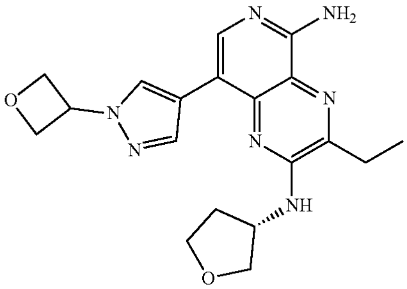 [SMILES: CCc1nc2c(N)ncc(-c3cnn(C4COC4)c3)c2nc1N[C@H]1CCOC1] |
| 232 | 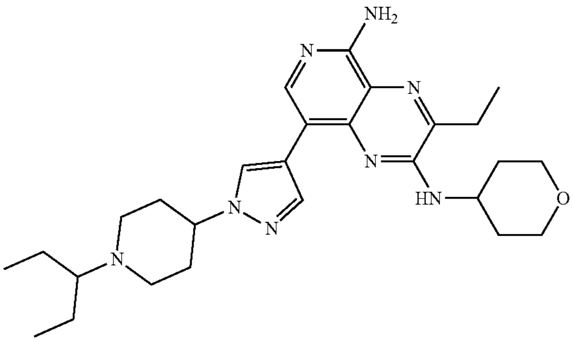 [SMILES: CCc1nc2c(N)ncc(-c3cnn(C4CCN(C(CC)CC)CC4)c3)c2nc1NC1CCOCC1] |

TABLE 1-continued
| No | Structure |
|---|---|
| 233 | 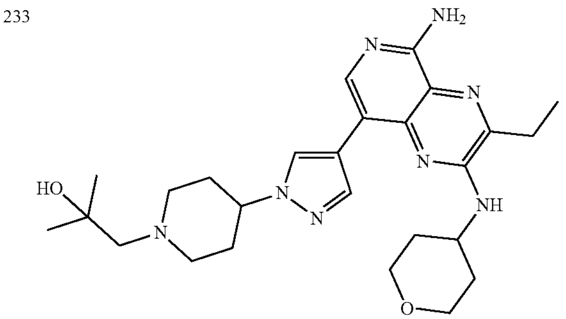 |
| 234 | 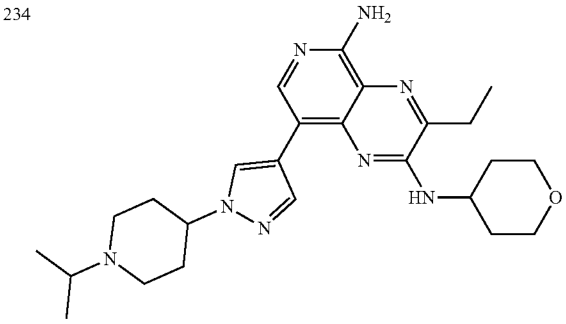 |
| 235 | 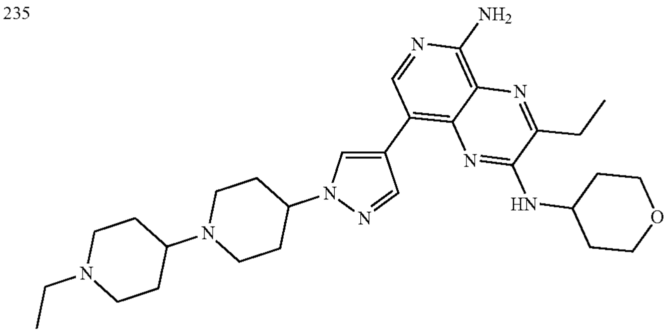 |
| 236 | 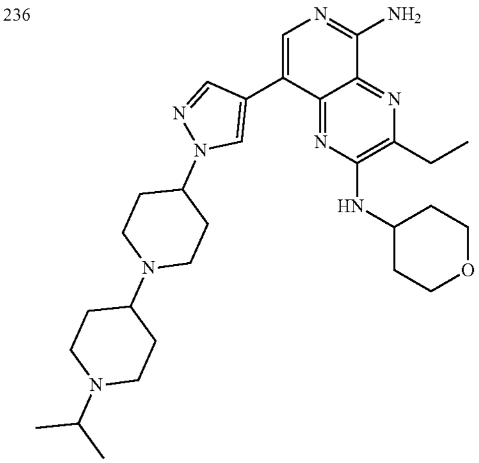 |

TABLE 1-continued
| No | Structure |
|---|---|
| 237 | 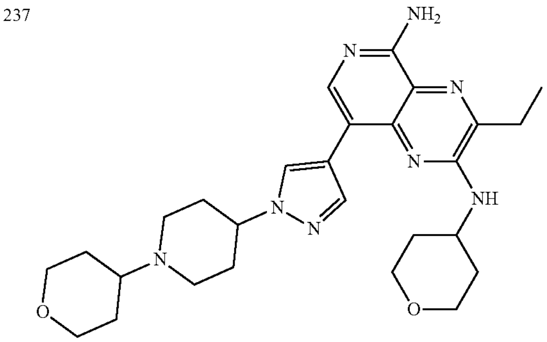 |
| 238 | 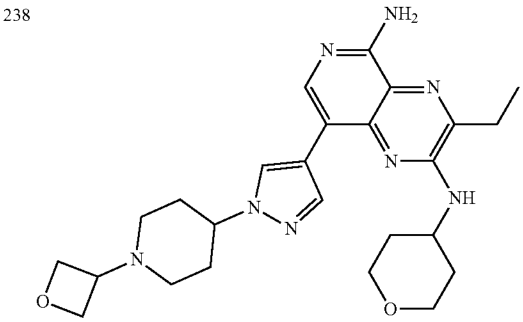 |
| 239 | 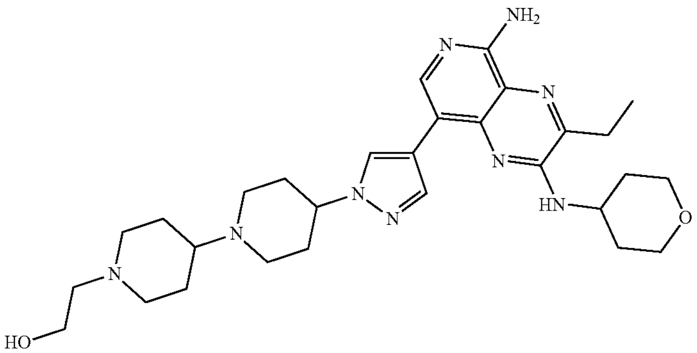 [SMILES: CCc1nc2c(N)ncc(-c3cnn(C4CCN(C5CCN(CCO)CC5)CC4)c3)c2nc1NC1CCOCC1] |
| 240 | 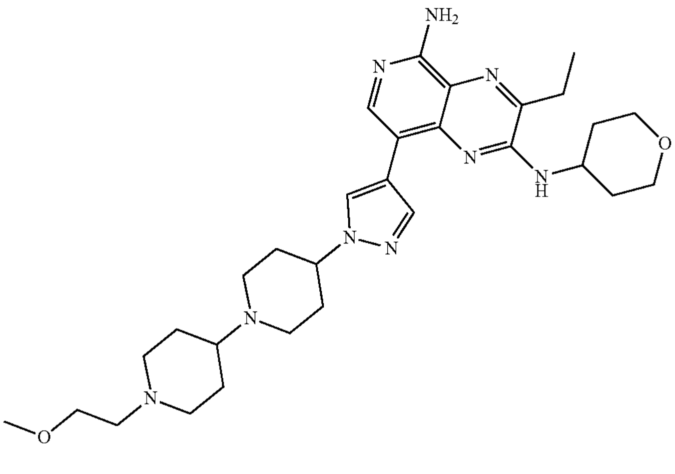 [SMILES: CCc1nc2c(N)ncc(-c3cnn(C4CCN(C5CCN(CCOC)CC5)CC4)c3)c2nc1NC1CCOCC1] |

TABLE 1-continued
| No | Structure |
|---|---|
| 241 | 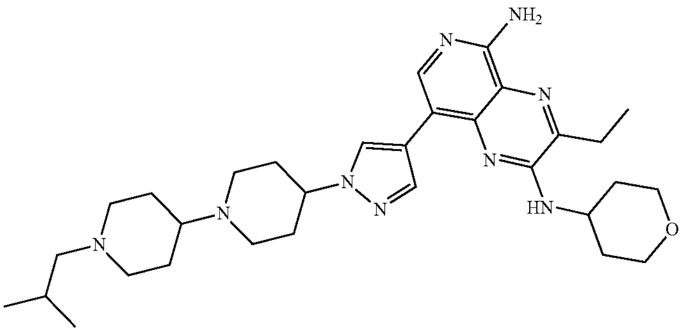 [SMILES: CCc1nc2c(N)ncc(-c3cnn(C4CCN(C5CCN(CC(C)C)CC5)CC4)c3)c2nc1NC1CCOCC1] |
| 242 | 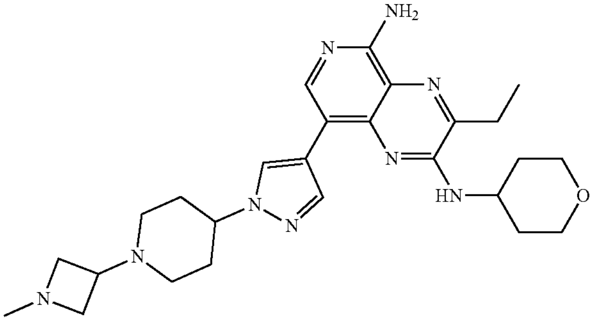 [SMILES: CCc1nc2c(N)ncc(-c3cnn(C4CCN(C5CN(C)C5)CC4)c3)c2nc1NC1CCOCC1] |
| 243 | 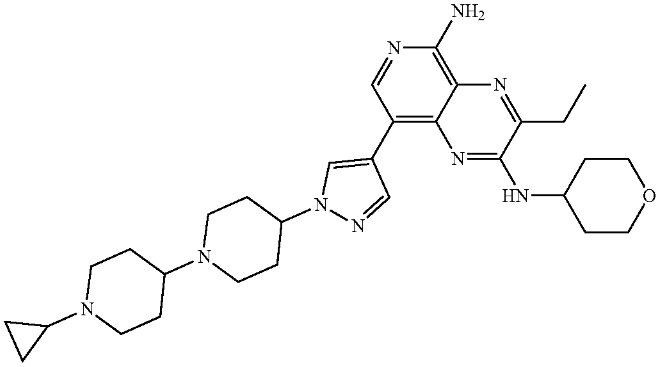 [SMILES: CCc1nc2c(N)ncc(-c3cnn(C4CCN(C5CCN(C6CC6)CC5)CC4)c3)c2nc1NC1CCOCC1] |
| 244 | 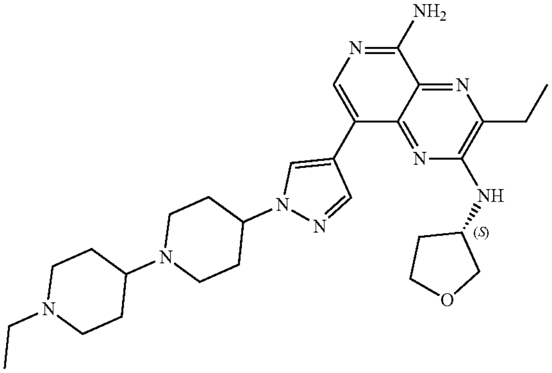 |

TABLE 1-continued
| No | Structure |
| --- | --- |
| 245 | 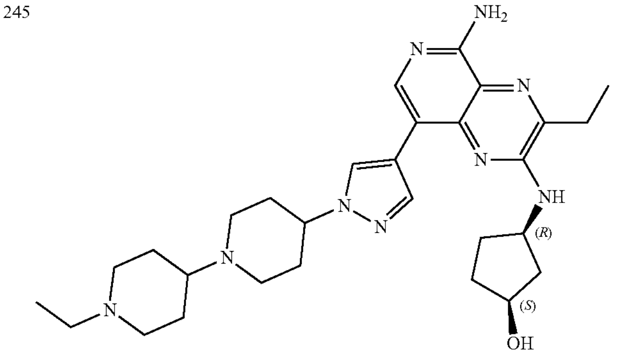 |
| 246 | 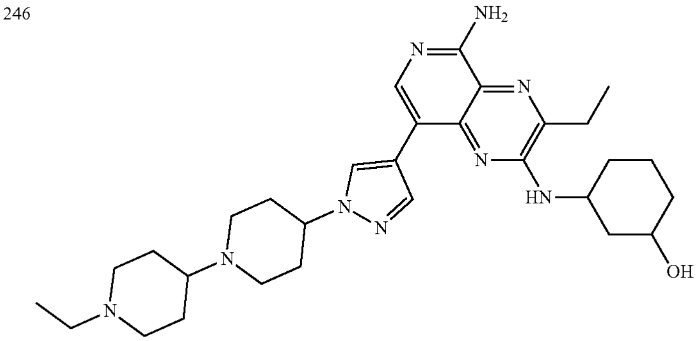 |
| 247 | 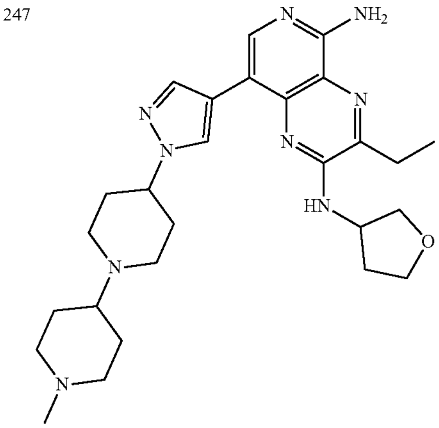 |
| 248 | 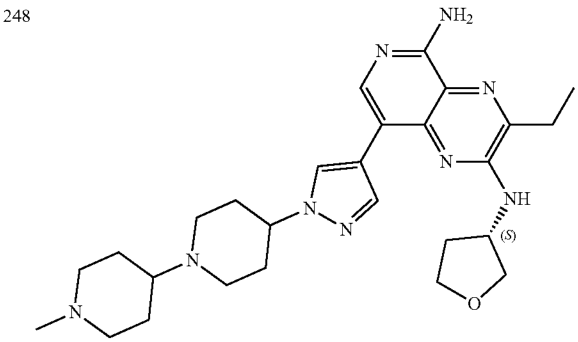 |

TABLE 1-continued
| No | Structure |
|---|---|
| 249 | 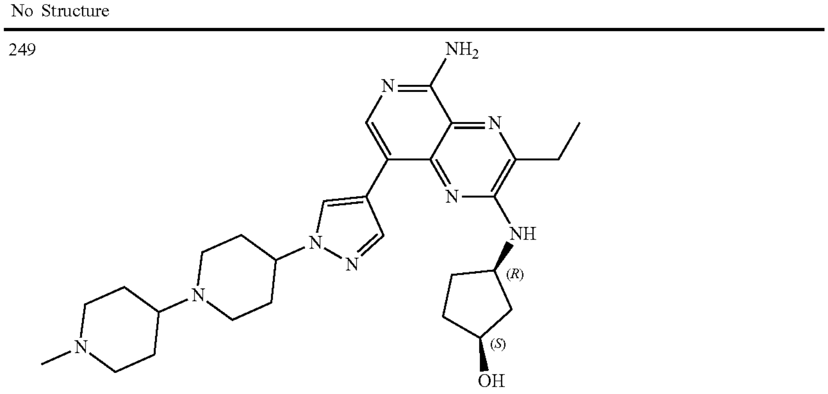 |
| 250 | 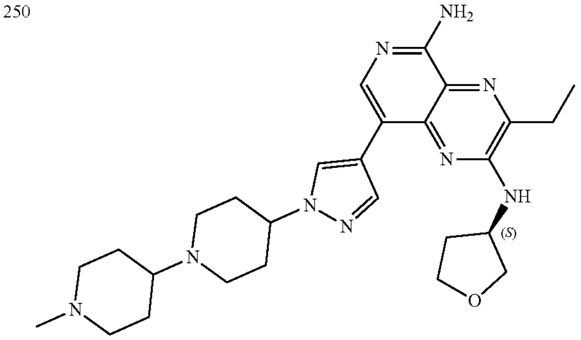 |
| 251 | 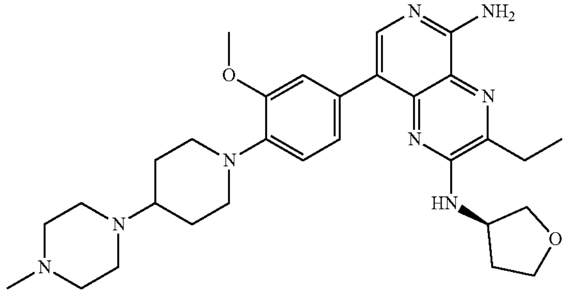 [SMILES: CCc1nc2c(N)ncc(-c3ccc(N4CCC(N5CCN(C)CC5)CC4)c(OC)c3)c2nc1N[C@@H]1CCOC1] |
| 252 | 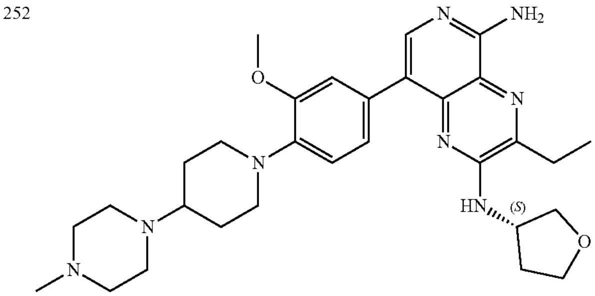 |
| 253 | 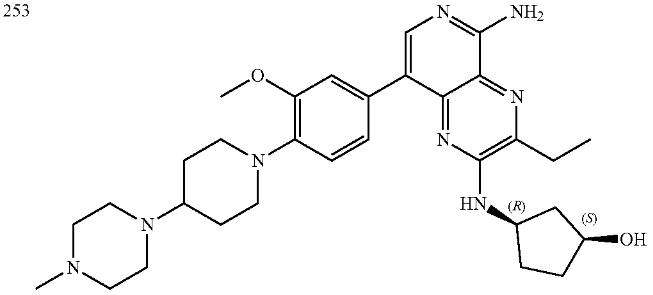 |

TABLE 1-continued
| No | Structure |
|---|---|
| 255 | 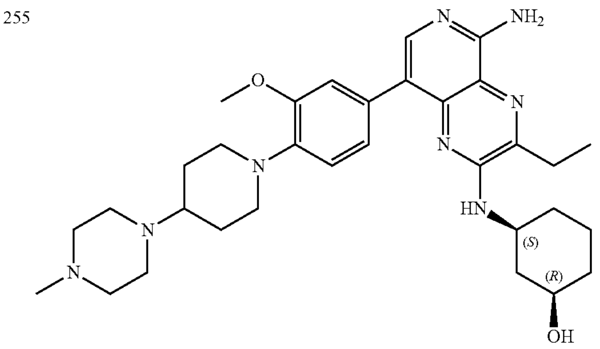 |
| 256 | 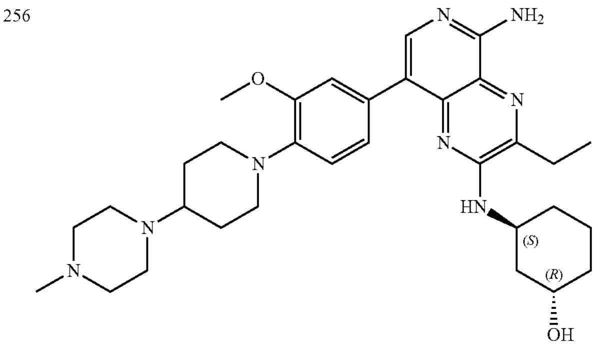 |
| 257 | 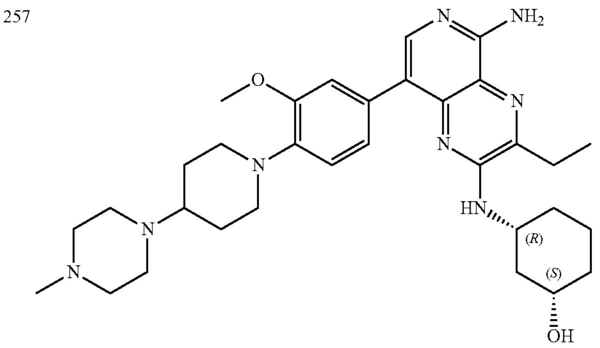 |
| 258 | 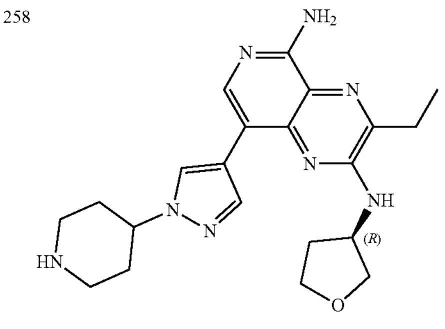 |

TABLE 1-continued
| No | Structure |
|---|---|
| 259 | 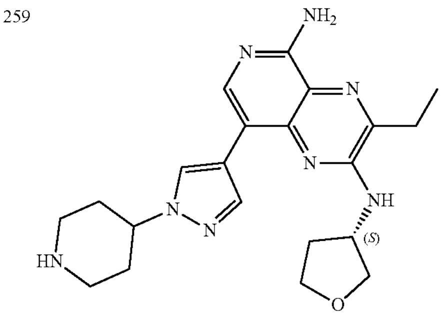 |
| 260 | 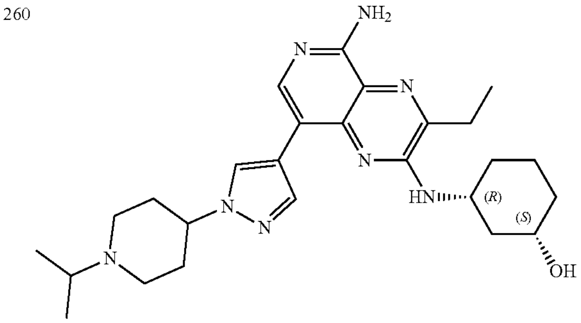 |
| 261 | 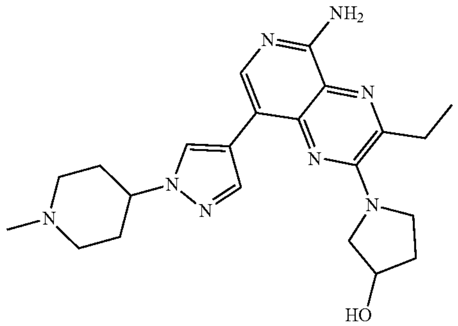 [SMILES: CCc1nc2c(N)ncc(-c3cnn(C4CCN(C)CC4)c3)c2nc1N1CCC(O)C1] |
| 262 | 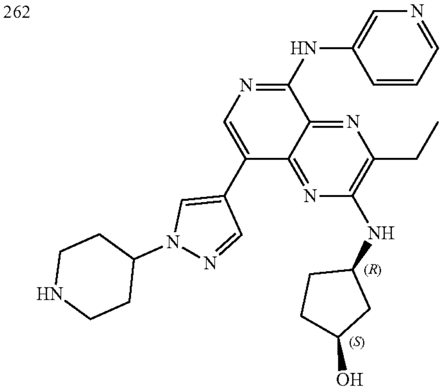 |

TABLE 1-continued
| No | Structure |
|---|---|
| 263 | 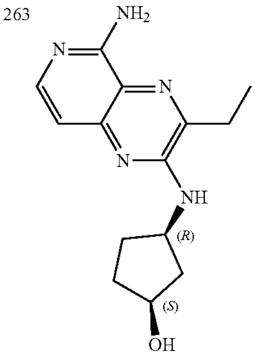 |
| 264 | 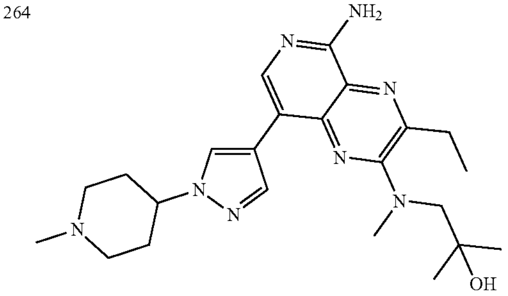 |
| 265 | 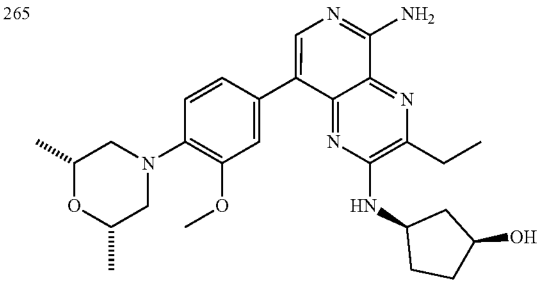 |
| 266 | 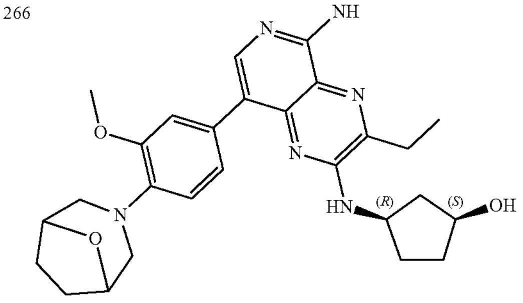 |
| 267 | 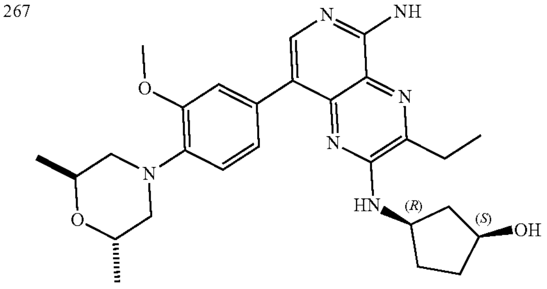 |

TABLE 1-continued
| No | Structure |
|---|---|
| 268 | 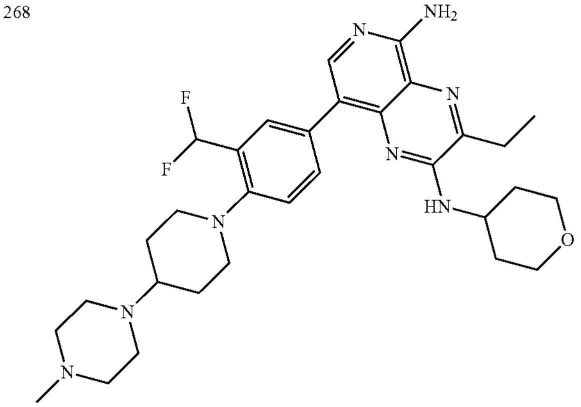 |
| 269 | 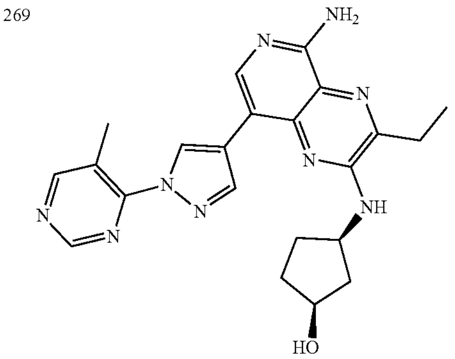 |
| 270 | 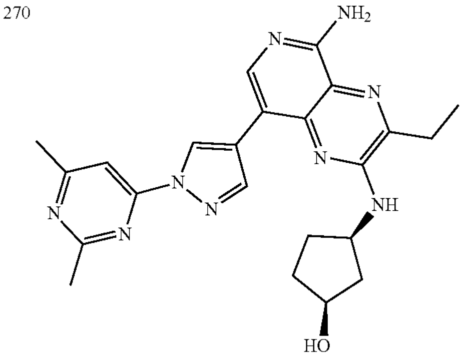 |
| 271 | 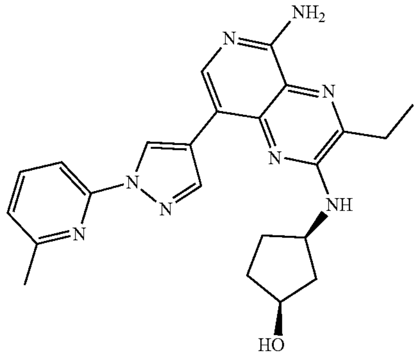 [SMILES: CCc1nc2c(N)ncc(-c3cnn(-c4cccc(C)n4)c3)c2nc1N[C@@H]1CC[C@H](O)C1] |

TABLE 1-continued
| No | Structure |
|---|---|
| 272 | 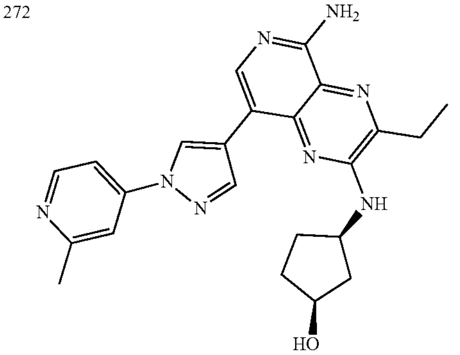 |
| 273 | 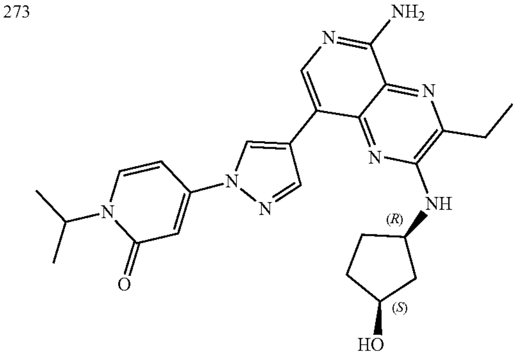 |
| 274 | 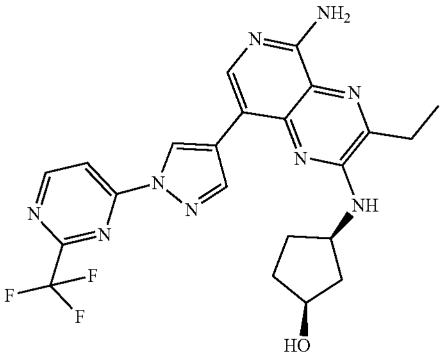 [SMILES: CCc1nc2c(N)ncc(-c3cnn(-c4ccnc(C(F)(F)F)n4)c3)c2nc1N[C@@H]1CC[C@H](O)C1] |
| 275 | 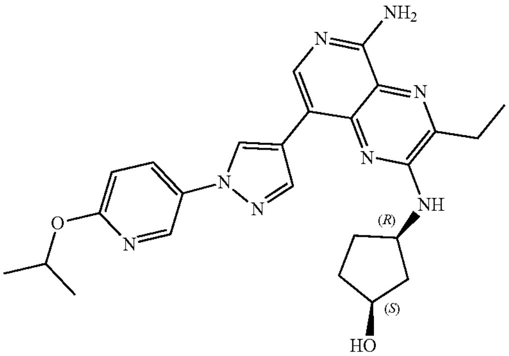 |

TABLE 1-continued
| No | Structure |
| --- | --- |
| 276 | 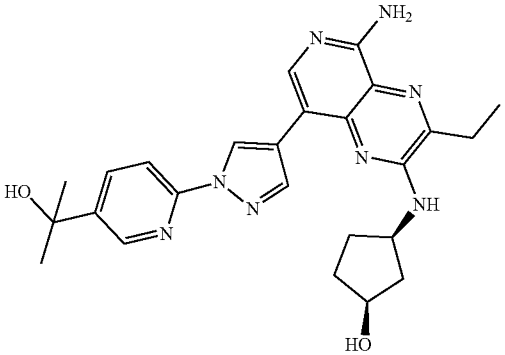 [SMILES: CCc1nc2c(N)ncc(-c3cnn(-c4ccc(C(C)(C)O)cn4)c3)c2nc1N[C@@H]1CC[C@H](O)C1] |
| 277 | 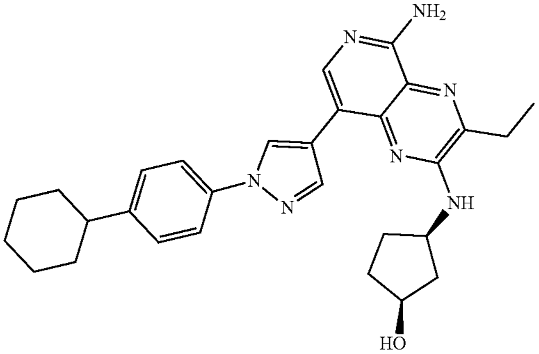 [SMILES: CCc1nc2c(N)ncc(-c3cnn(-c4ccc(C5CCCCC5)cc4)c3)c2nc1N[C@@H]1CC[C@H](O)C1] |
| 278 | 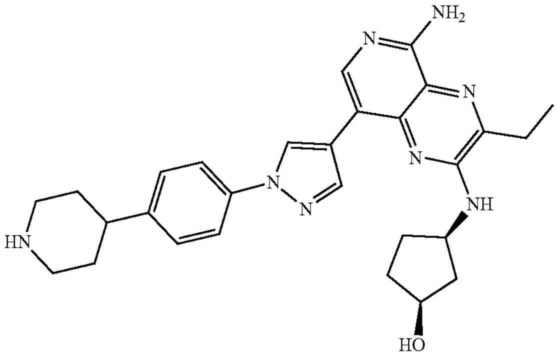 [SMILES: CCc1nc2c(N)ncc(-c3cnn(-c4ccc(C5CCNCC5)cc4)c3)c2nc1N[C@@H]1CC[C@H](O)C1] |
| 279 | 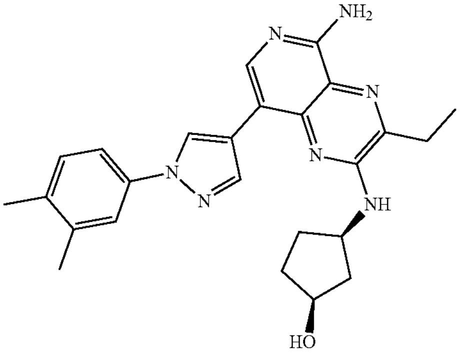 [SMILES: CCc1nc2c(N)ncc(-c3cnn(-c4ccc(C)c(C)c4)c3)c2nc1N[C@@H]1CC[C@H](O)C1] |

TABLE 1-continued
| No | Structure |
|---|---|
| 280 | 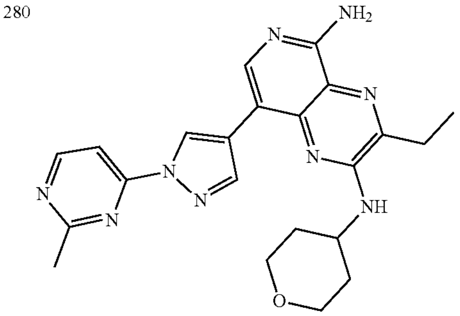 |
| 281 | 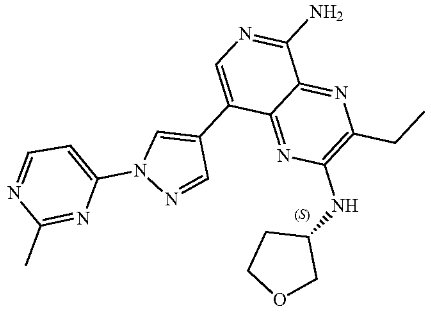 |
| 282 | 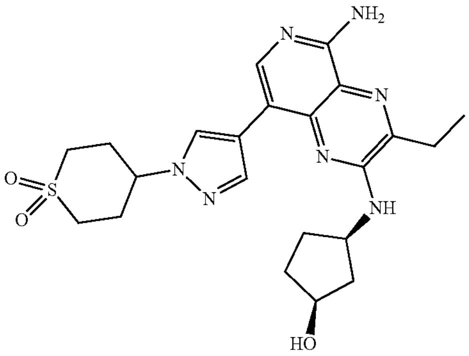 [SMILES: CCc1nc2c(N)ncc(-c3cnn(C4CCS(=O)(=O)CC4)c3)c2nc1N[C@@H]1CC[C@H](O)C1] |
| 283 | 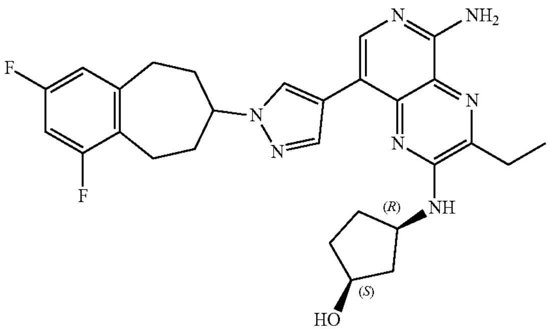 |

TABLE 1-continued
| No | Structure |
| --- | --- |
| 284 | 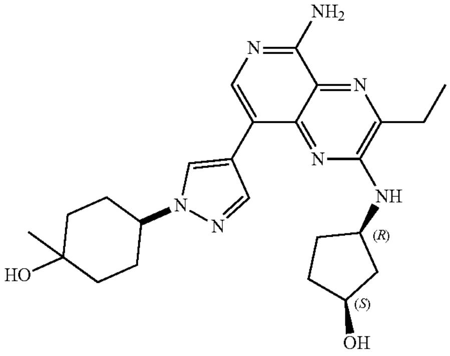 |
| 285 | 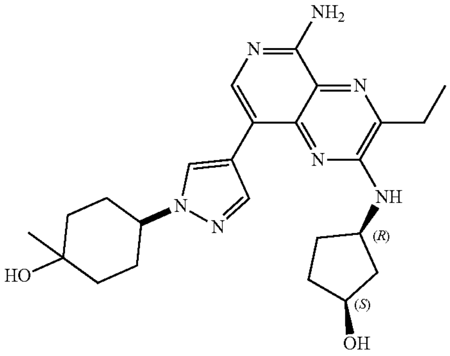 |
| 286 | 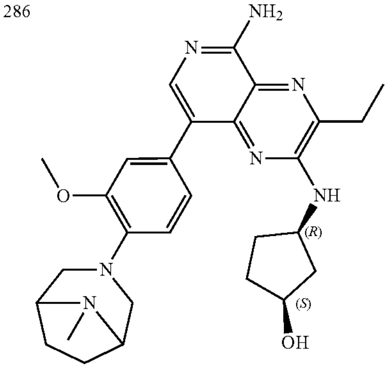 |
| 287 | 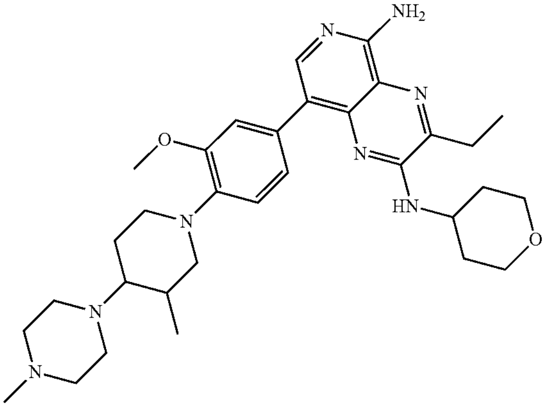 [SMILES: CCc1nc2c(N)ncc(-c3ccc(N4CCC(N5CCN(C)CC5)C(C)C4)c(OC)c3)c2nc1NC1CCOCC1] |

TABLE 1-continued
| No | Structure |
|---|---|
| 288 | 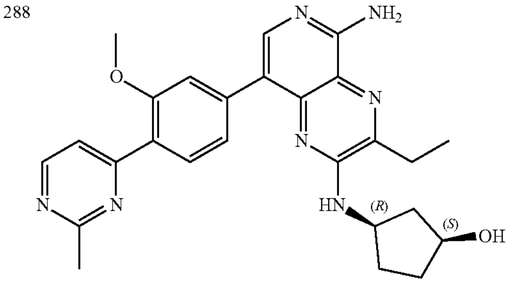 |
| 289 | 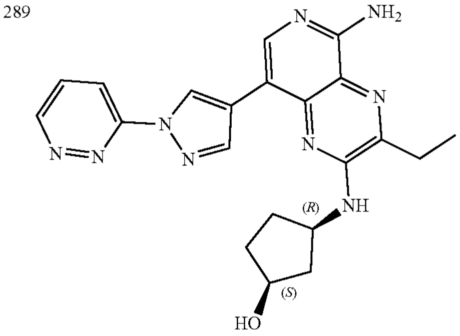 |
| 290 | 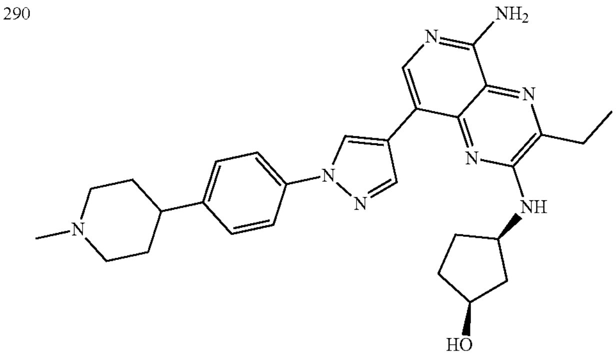 |
| 291 | 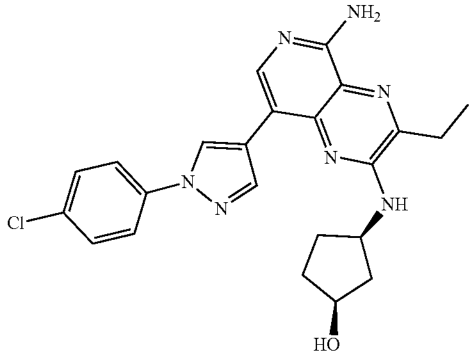 [SMILES: CCc1nc2c(N)ncc(-c3cnn(-c4ccc(Cl)cc4)c3)c2nc1N[C@@H]1CC[C@H](O)C1] |

TABLE 1-continued
| No | Structure |
|---|---|
| 292 | 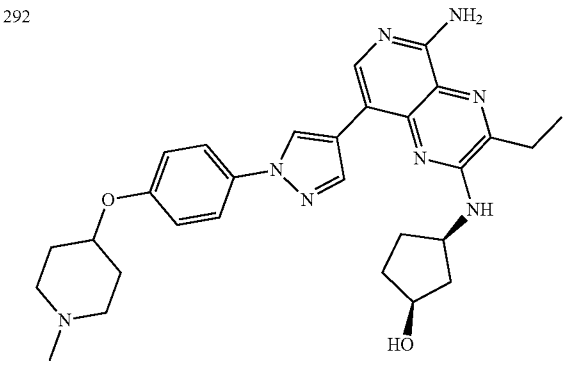 |
| 293 | 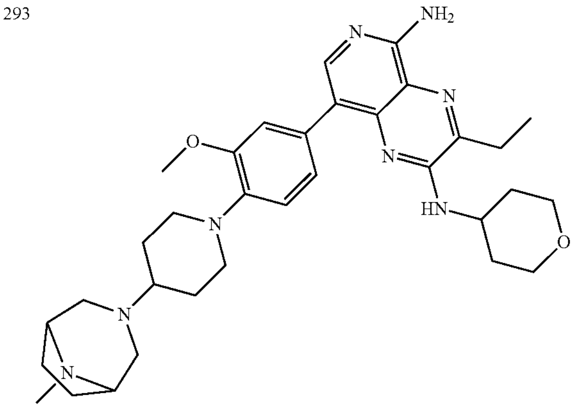 |
| 294 | 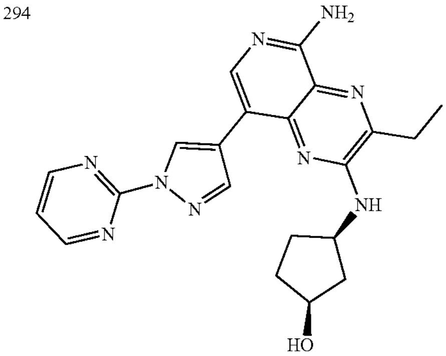 |
| 295 | 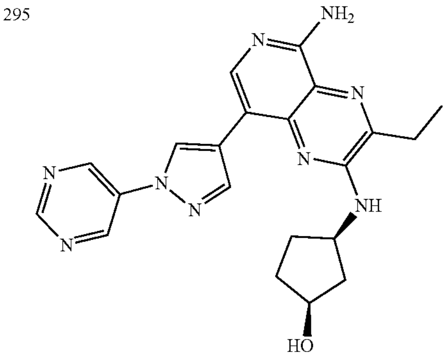 |

TABLE 1-continued
| No | Structure |
|---|---|
| 296 | 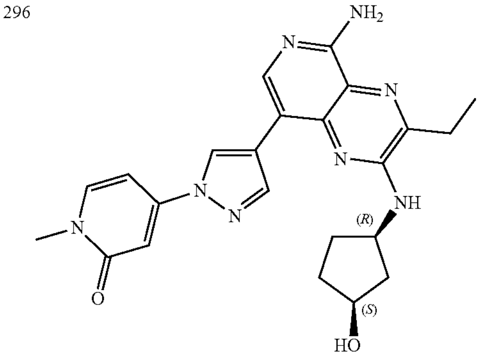 |
| 297 | 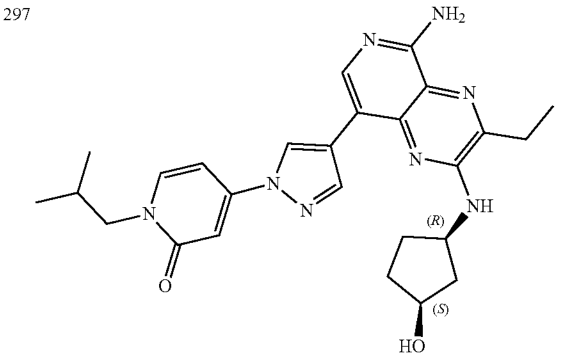 |
| 298 | 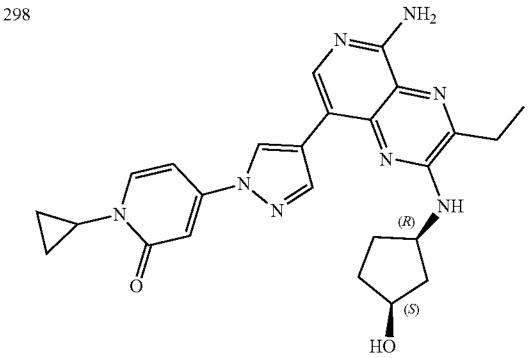 |
| 299 | 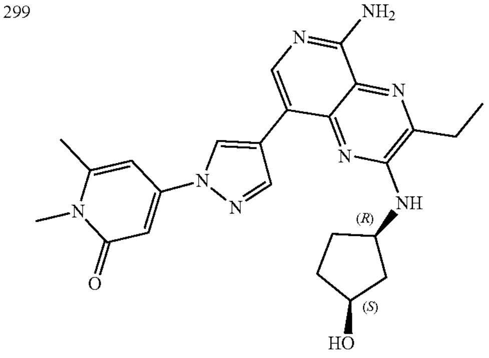 |

TABLE 1-continued
| No | Structure |
|---|---|
| 300 | 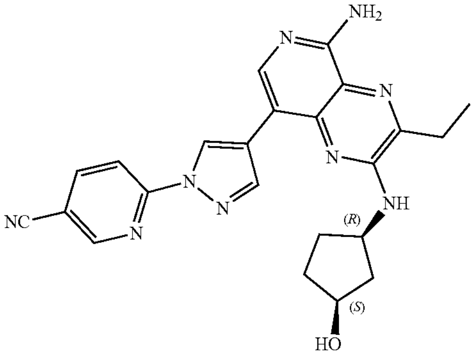 |
| 301 | 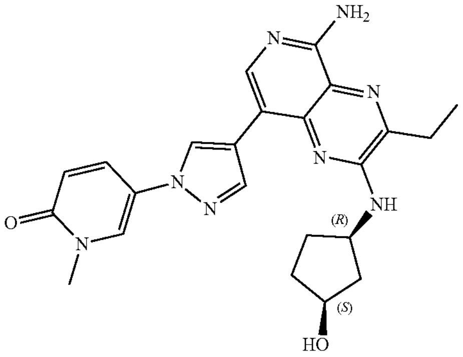 |
| 302 | 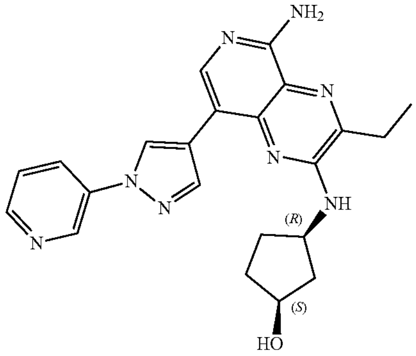 |
| 303 | 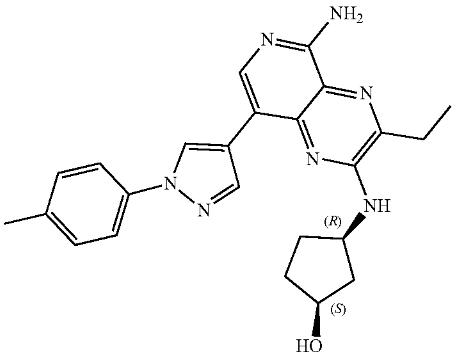 |

TABLE 1-continued
| No | Structure |
|---|---|
| 304 | 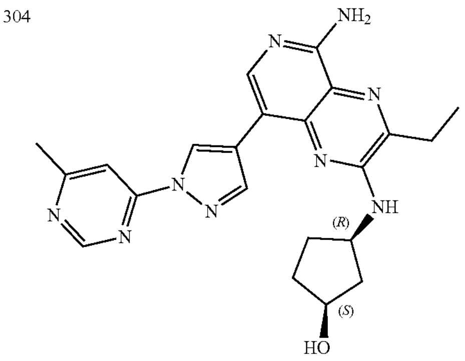 |
| 305 | 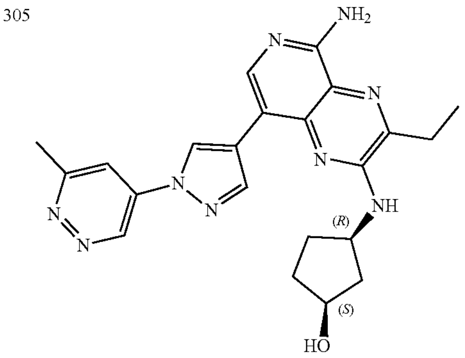 |
| 306 | 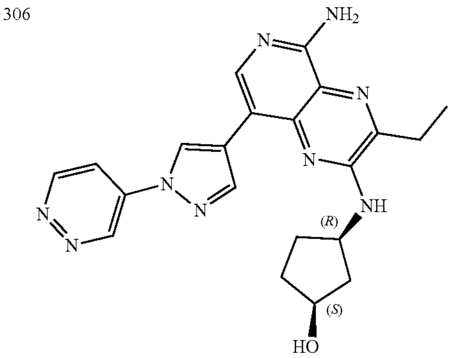 |
| 307 | 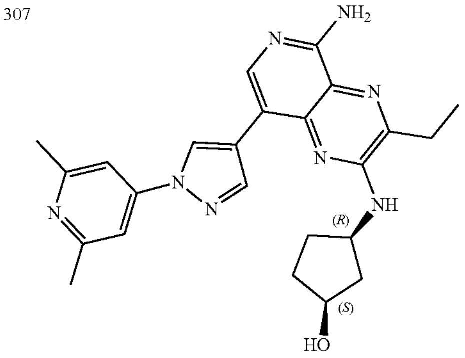 |

TABLE 1-continued
| No | Structure |
| --- | --- |
| 308 | 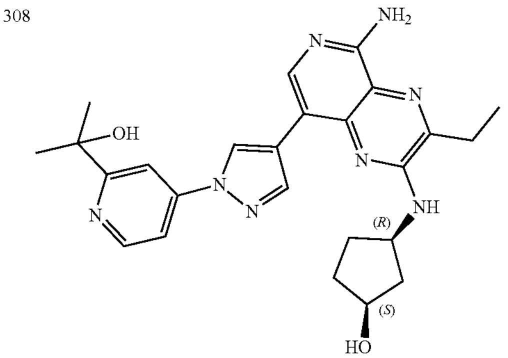 |
| 309 | 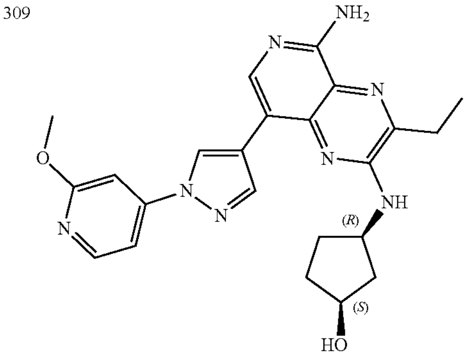 |
| 310 | 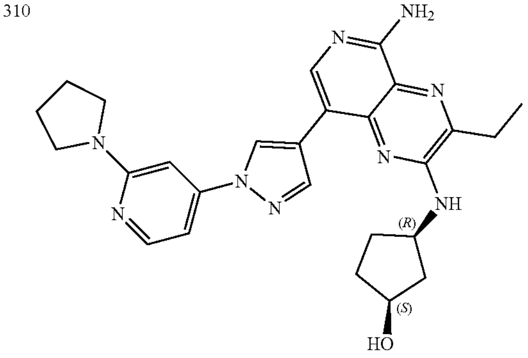 |
| 311 | 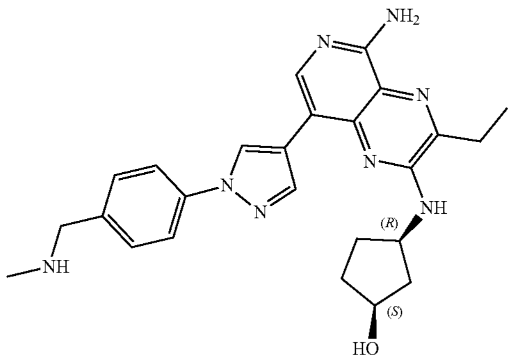 |

TABLE 1-continued
| No | Structure |
|---|---|
| 312 | 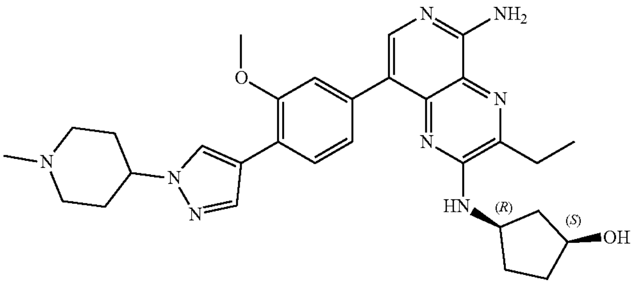 |
| 313 | 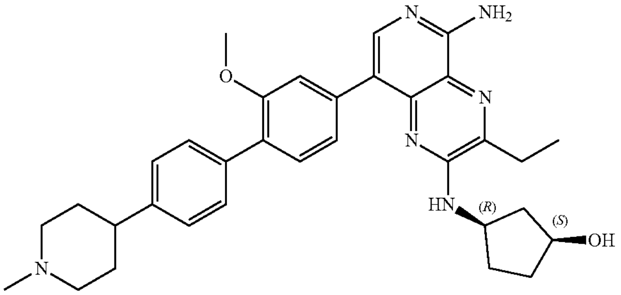 |
| 314 | 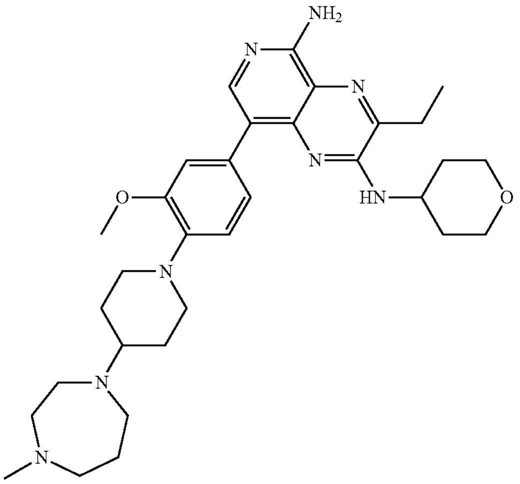 [SMILES: CCc1nc2c(N)ncc(-c3ccc(N4CCC(N5CCCN(C)CC5)CC4)c(OC)c3)c2nc1NC1CCOCC1] |
| 315 | 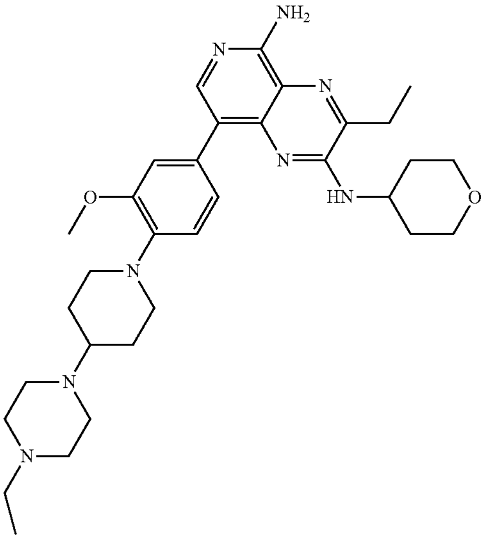 [SMILES: CCc1nc2c(N)ncc(-c3ccc(N4CCC(N5CCN(CC)CC5)CC4)c(OC)c3)c2nc1NC1CCOCC1] |

TABLE 1-continued
| No | Structure |
|---|---|
| 316 | 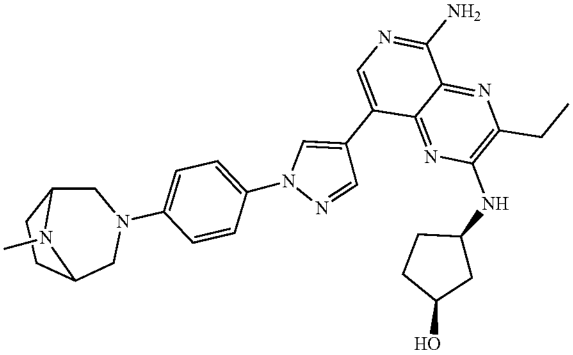 [SMILES: CCc1nc2c(N)ncc(-c3cnn(-c4ccc(N5CC6CCC(C5)N6C)cc4)c3)c2nc1N[C@@H]1CC[C@H](O)C1] |
| 317 | 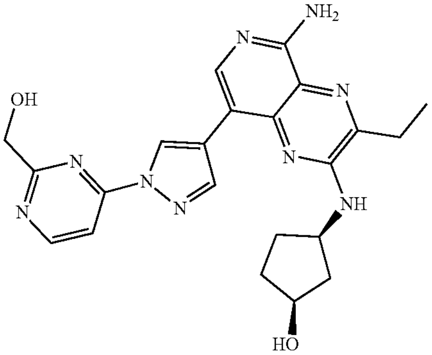 [SMILES: CCc1nc2c(N)ncc(-c3cnn(-c4ccnc(CO)n4)c3)c2nc1N[C@@H]1CC[C@H](O)C1] |
| 318 | 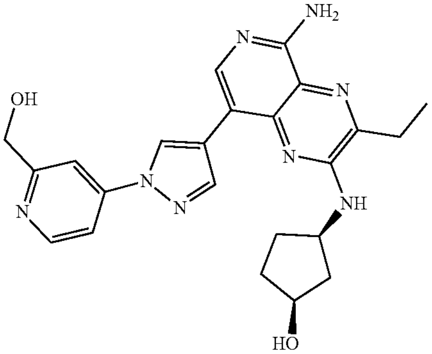 [SMILES: CCc1nc2c(N)ncc(-c3cnn(-c4ccnc(CO)c4)c3)c2nc1N[C@@H]1CC[C@H](O)C1] |
| 319 | 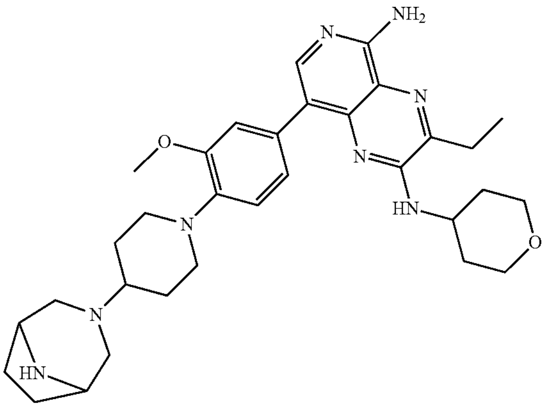 [SMILES: CCc1nc2c(N)ncc(-c3ccc(N4CCC(N5CC6CCC(C5)N6)CC4)c(OC)c3)c2nc1NC1CCOCC1] |

TABLE 1-continued
| No | Structure |
|---|---|
| 320 | 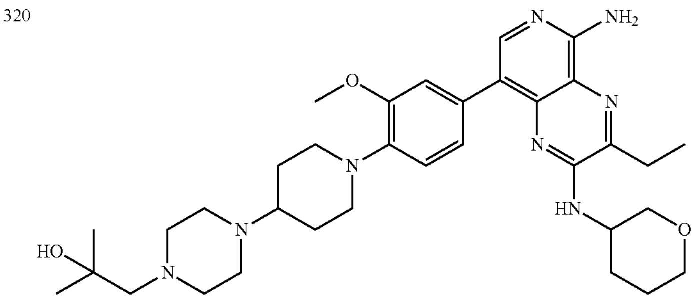 |
| 321 | 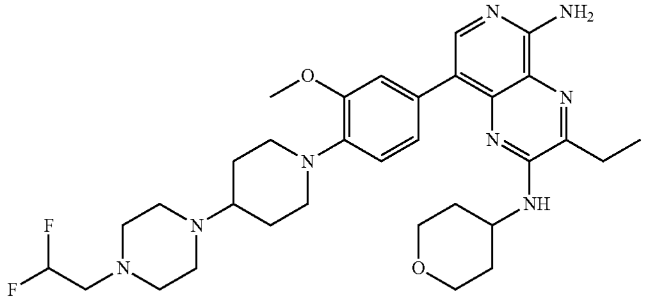 [SMILES: CCc1nc2c(N)ncc(-c3ccc(N4CCC(N5CCN(CC(F)F)CC5)CC4)c(OC)c3)c2nc1NC1CCOCC1] |
| 322 | 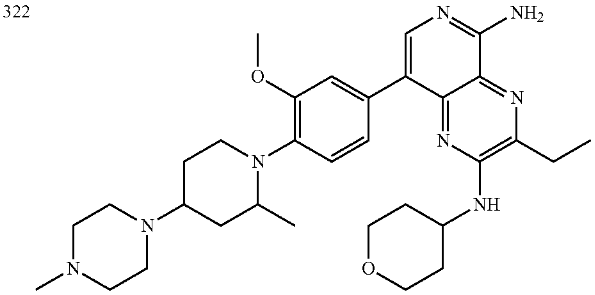 |
| 323 | 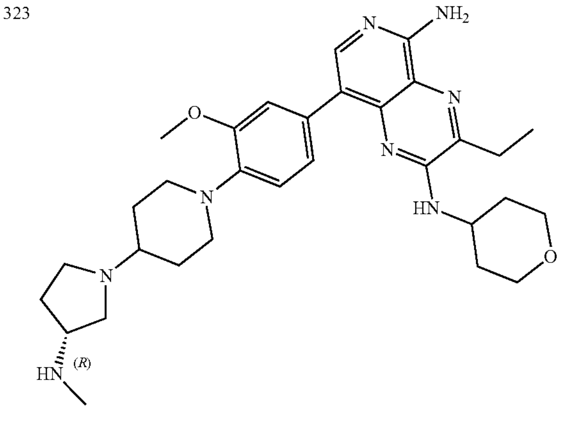 |

TABLE 1-continued
| No | Structure |
|---|---|
| 324 | 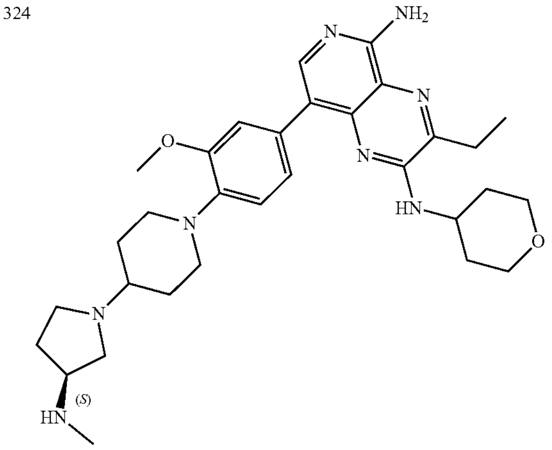 |
| 325 | 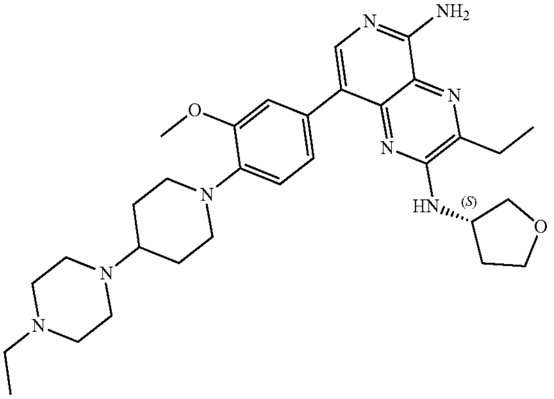 |
| 326 | 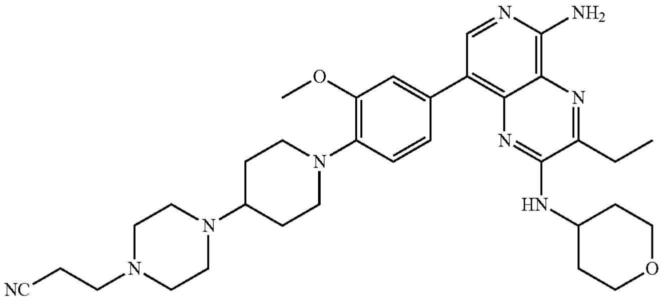 [SMILES: CCc1nc2c(N)ncc(-c3ccc(N4CCC(N5CCN(CCC#N)CC5)CC4)c(OC)c3)c2nc1NC1CCOCC1] |
| 327 | 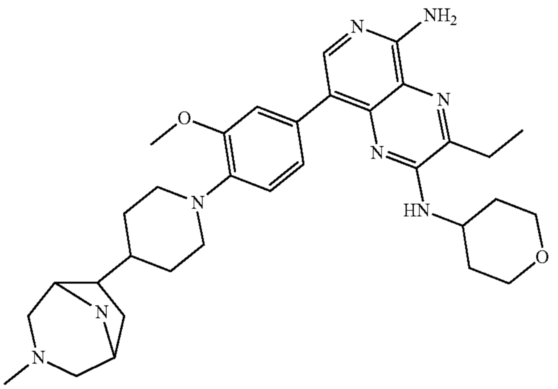 [SMILES: CCc1nc2c(N)ncc(-c3ccc(N4CCC(C5CC6CN(C)CC5N6)CC4)c(OC)c3)c2nc1NC1CCOCC1] |

TABLE 1-continued
| No | Structure |
|---|---|
| 328 | 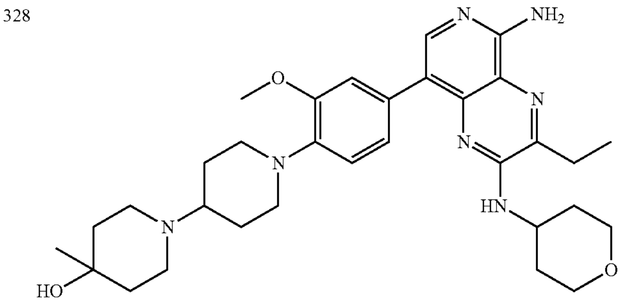 |
| 329 | 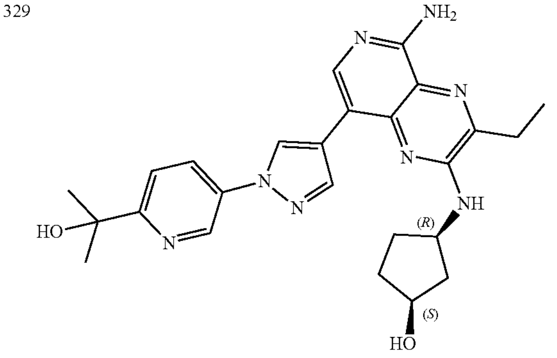 |
| 330 | 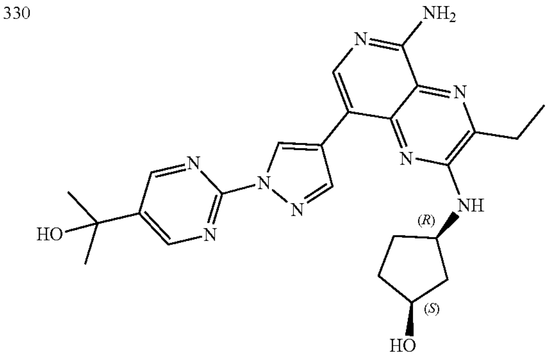 |
| 331 | 0.6 HCOOH 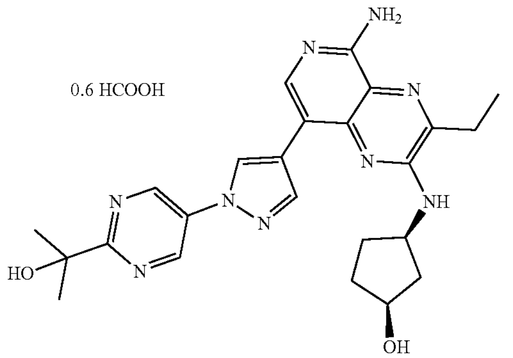 [SMILES: CCc1nc2c(N)ncc(-c3cnn(-c4cnc(C(C)(C)O)nc4)c3)c2nc1N[C@@H]1CC[C@H](O)C1] |

TABLE 1-continued
| No | Structure |
|---|---|
| 332 | 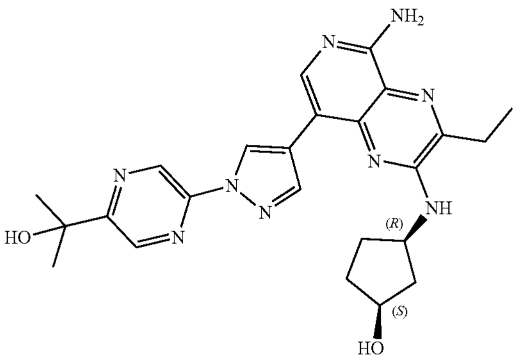 |
| 333 | 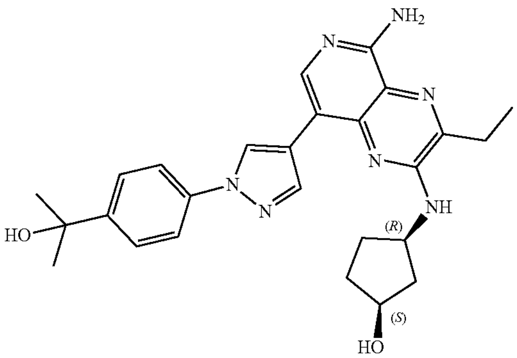 |
| 334 | 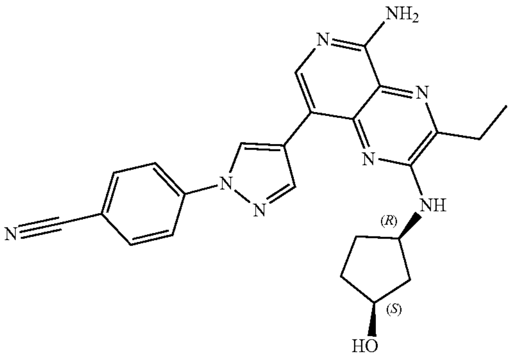 |
| 335 | 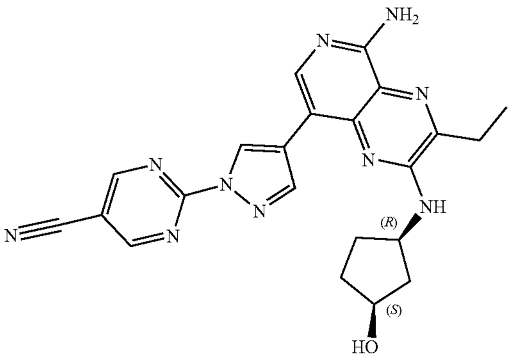 |

TABLE 1-continued
| No | Structure |
|---|---|
| 336 | 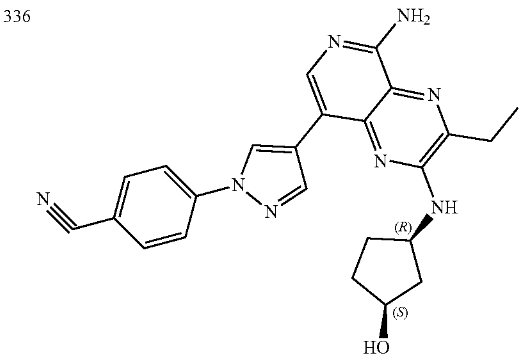 |
| 337 | 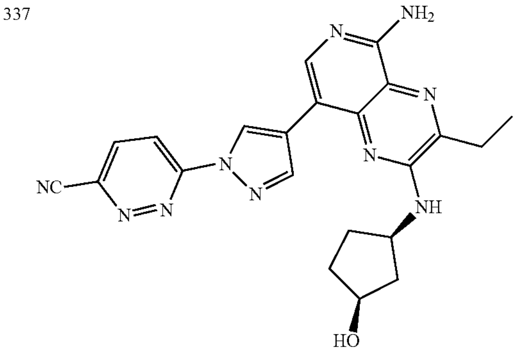 |
| 338 | 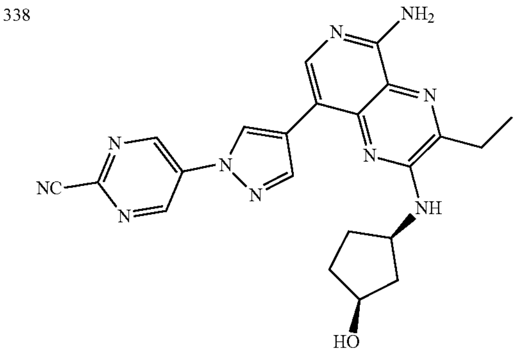 |
| 339 | 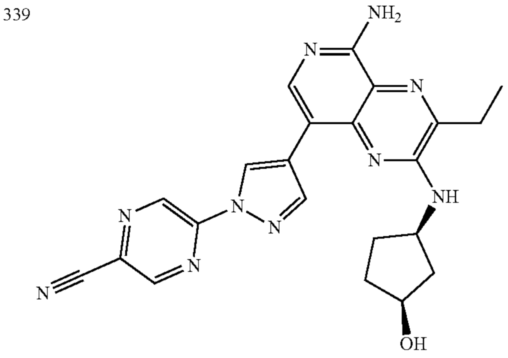 |

TABLE 1-continued
| No | Structure |
|---|---|
| 340 | 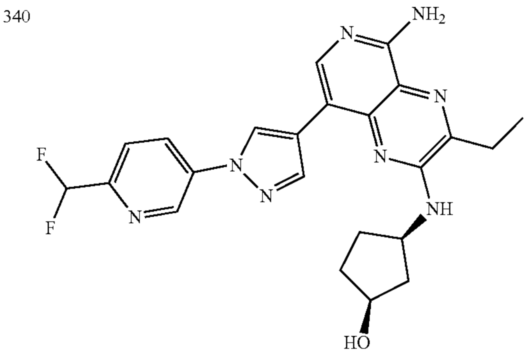 |
| 341 | 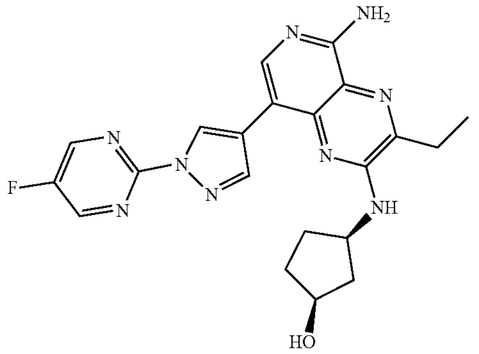 [SMILES: CCc1nc2c(N)ncc(-c3cnn(-c4ncc(F)cn4)c3)c2nc1N[C@@H]1CC[C@H](O)C1] |
| 342 | 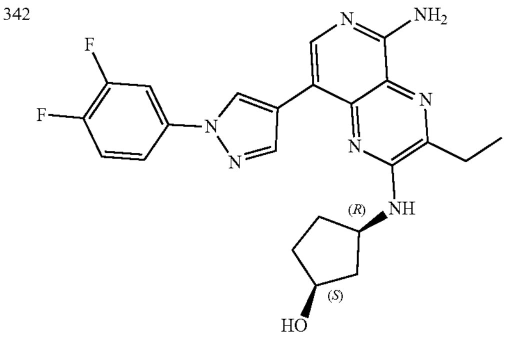 |
| 343 | 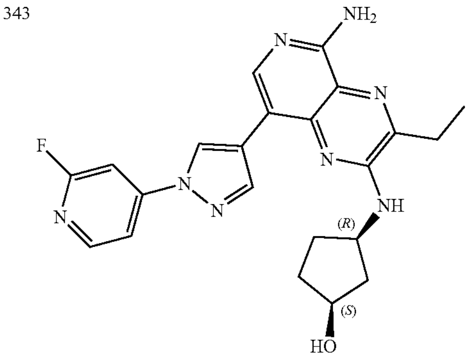 |

TABLE 1-continued
| No | Structure |
|---|---|
| 344 | 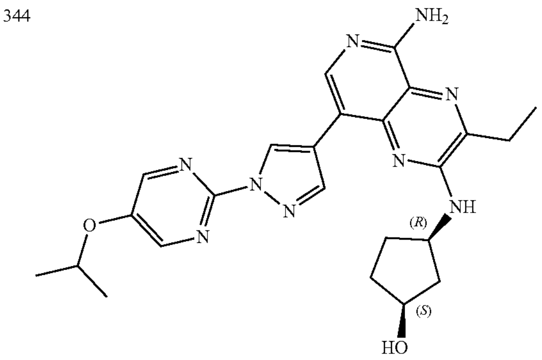 |
| 345 | 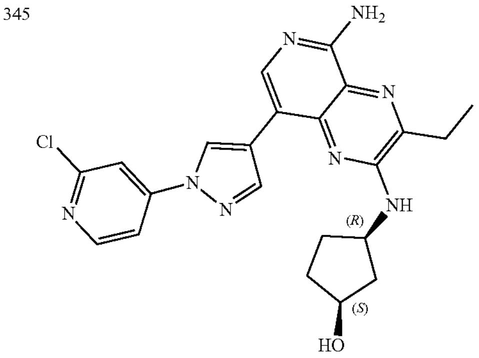 |
| 346 | 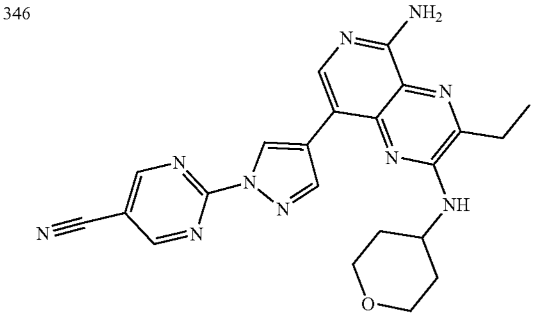 |
| 347 | 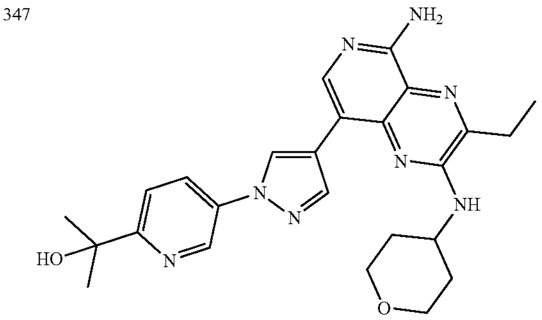 |

TABLE 1-continued
| No | Structure |
| --- | --- |
| 348 | 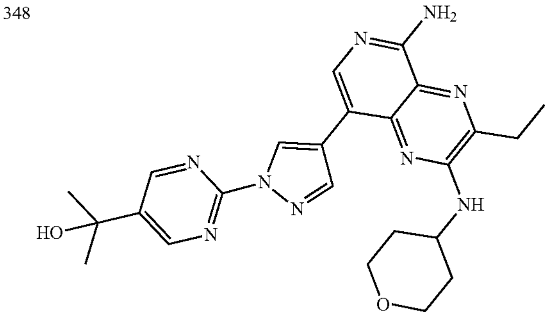 |
| 349 | 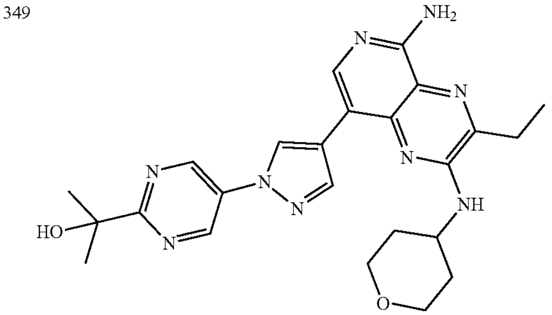 |
| 350 | 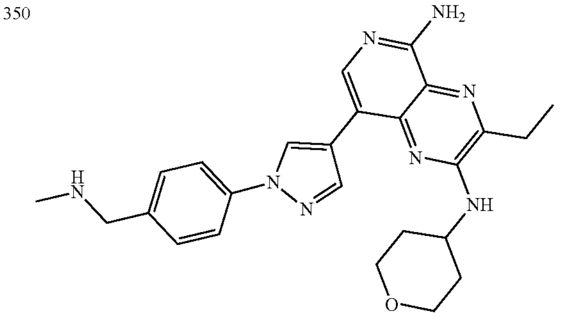 |
| 351 | 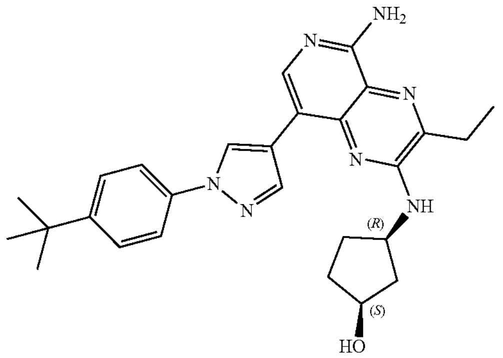 |

TABLE 1-continued
| No | Structure |
|---|---|
| 352 | 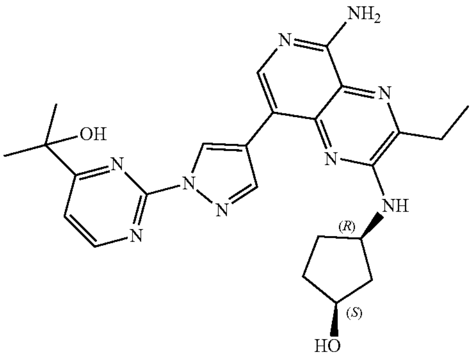 |
| 353 | 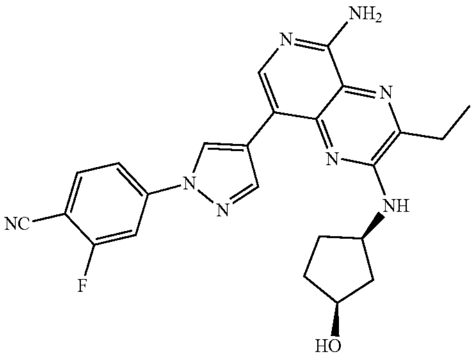 [SMILES: CCc1nc2c(N)ncc(-c3cnn(-c4ccc(C#N)c(F)c4)c3)c2nc1N[C@@H]1CC[C@H](O)C1] |
| 354 | 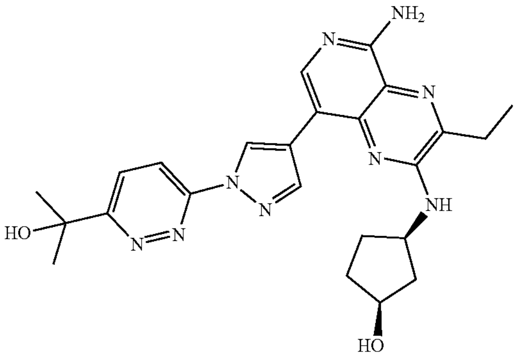 [SMILES: CCc1nc2c(N)ncc(-c3cnn(-c4ccc(C(C)(C)O)nn4)c3)c2nc1N[C@@H]1CC[C@H](O)C1] |
| 355 | 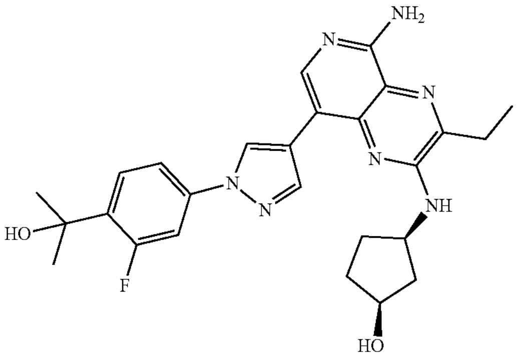 [SMILES: CCc1nc2c(N)ncc(-c3cnn(-c4ccc(C(C)(C)O)c(F)c4)c3)c2nc1N[C@@H]1CC[C@H](O)C1] |

TABLE 1-continued
| No | Structure |
| --- | --- |
| 356 | 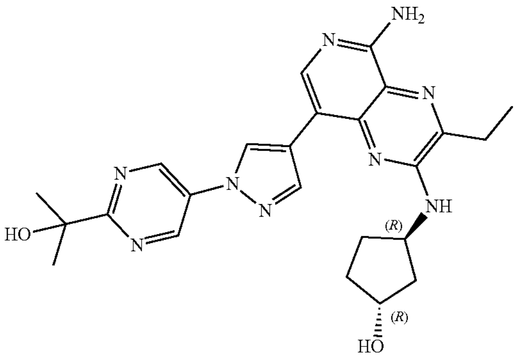 |
| 357 | 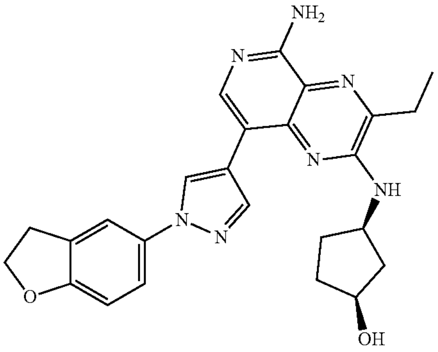 [SMILES: CCc1nc2c(N)ncc(-c3cnn(-c4ccc5c(c4)CCO5)c3)c2nc1N[C@@H]1CC[C@H](O)C1] |
| 358 | 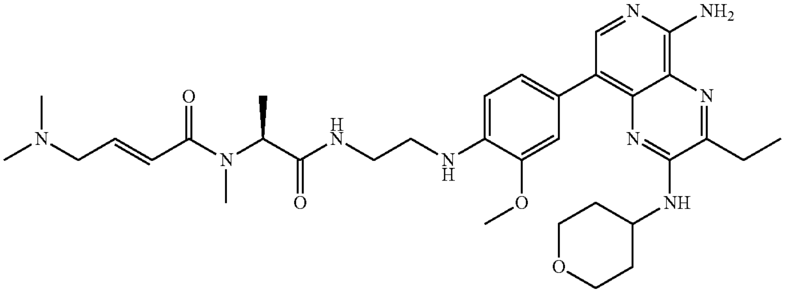 [SMILES: CCc1nc2c(N)ncc(-c3ccc(NCCNC(=O)[C@H](C)N(C)C(=O)/C=C/CN(C)C)c(OC)c3)c2nc1NC1CCOCC1] |

Wherein, compound 162 and 163 are

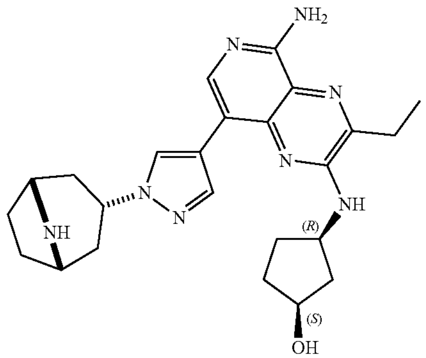

and

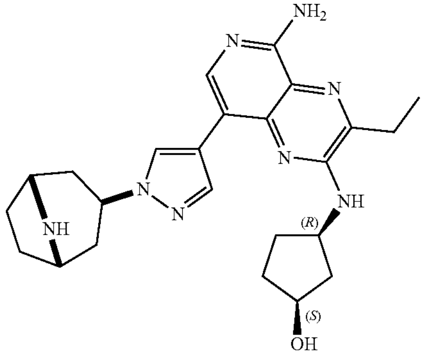

respectively, but the absolute configuration is unknown. Compound 164 and 165 are

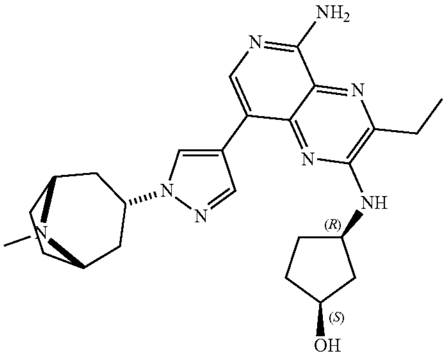

and

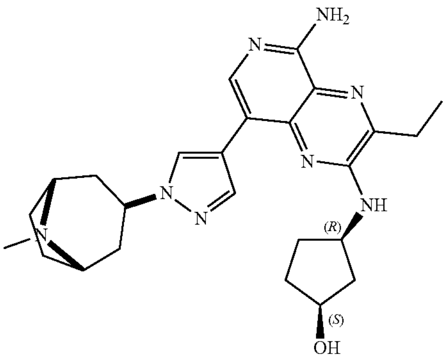

respectively, but the absolute configuration is unknown. Compound 284 and 285 are

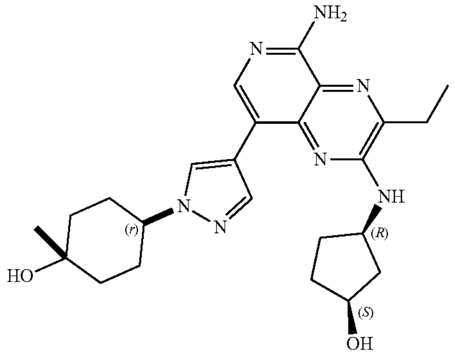

and

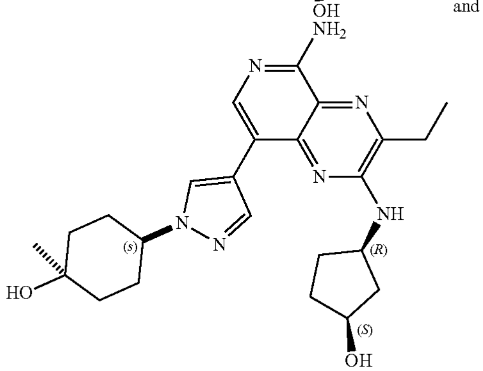

respectively, but the absolute configuration is unknown.

Pharmaceutical Compositions and Methods of Administration

Because the compounds of the invention have excellent kinase inhibition activity, the compounds of the invention and various crystal forms, pharmaceutically acceptable inorganic or organic salts, hydrates or solvates thereof, and a pharmaceutical composition containing the compound of the present invention as the main active ingredient can be used for treating, preventing and relieving related diseases caused by abnormal activity or expression level of kinases (such as FLT3).

The pharmaceutical composition of the present invention comprises a safe and effective amount of a compound of the present invention or a pharmacologically acceptable salt thereof, and a pharmacologically acceptable excipient or carrier. In which, "safe and effective amount" is meant that the amount of the compound is sufficient to significantly improve the condition without causing serious side effects. Generally, the pharmaceutical composition contains 1-2000 mg of the compound of the present invention/agent, more preferably, 5-200 mg of the compound of the present invention/agent. Preferably, the "agent" is a capsule or tablet.

The "pharmaceutically acceptable carrier" refers to: one or more compatible solids or liquid fillers or gel materials, which are suitable for people, and must have sufficient purity and low toxicity. "Compatibility" means that each component in the composition can be admixed with the compounds of the present invention and with each other without significantly reducing the efficacy of the compounds. Some examples of pharmaceutically acceptable carrier include cellulose and derivatives (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

The administration mode of the compound or pharmaceutical composition of the present invention is not particularly limited, and representative administration modes include, but are not limited to, oral, intratumoral, rectal, parenteral (intravenous, intramuscular or subcutaneous) and topical administration.

Solid dosage forms for oral administration include capsules, tablets, pills, powders and granules. In these solid dosage forms, the active ingredient is mixed with at least one conventional inert excipient (or carrier), such as sodium citrate or dicalcium phosphate, or mixed with any of the following components: (a) fillers or compatibilizer, for example, starch, lactose, sucrose, glucose, mannitol and silicic acid; (b) binders, for example, hydroxymethyl cellulose, alginate, gelatin, polyvinylpyrrolidone, sucrose and arabic gum; (c) humectants, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, calcium stearate, magnesium stearate, solid polyethylene glycol, sodium lauryl sulfate, or the mixture thereof. In capsules, tablets and pills, the dosage forms may also contain buffering agents.

Solid dosage forms such as tablets, dragees, capsules, pills and granules can be prepared with coatings and shells such as enteric coatings and other materials known in the art. They may contain opacifying agents and the release of the active compound or compound in such compositions may be released in a portion of the digestive tract in a delayed manner. Examples of embedding components that can be employed are polymeric materials and waxy materials. If necessary, the active compound may also be in microencapsulated form with one or more of the above-mentioned excipients.

Liquid dosage forms for oral administration include pharmaceutically acceptable emulsions, solutions, suspensions, syrups or tinctures. In addition to the active compound, the liquid dosage form may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures of these substances.

In addition to these inert diluents, the compositions may contain adjuvants such as wetting agents, emulsifying and suspending agents, sweetening agents, flavoring agents and spices.

In addition to the active compound, the suspension may contain suspending agent, for example, ethoxylated isooctadecanol, polyoxyethylene sorbitol and dehydrated sorbitan ester, microcrystalline cellulose, aluminum methoxide and agar, or the mixture thereof etc.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

Dosage forms for the compounds of the invention for topical administration include ointments, powders, patches, propellants and inhalants. The active ingredient is mixed under sterile conditions with a physiologically acceptable carrier and any preservatives, buffers, or propellants which may be required if necessary.

The compounds of the present invention may be administered alone or in combination with other pharmaceutically acceptable compounds. In some preferred embodiments, the compounds of the present invention may be administered with other small molecule compounds to form PROTAC, or with other large molecule compounds such as monoclonal antibodies to form ADC.

When the pharmaceutical composition is used, a safe and effective amount of the compound of the present invention is applied to a mammal in need of treatment (such as a human), wherein the dosage at the time of administration is the pharmaceutically effective dosage, for people having a body weight of 60 kg, the daily dose is usually 1-2000 mg, preferably 50-1000 mg. Of course, specific doses should also consider factors such as the administration route, the health of the patient, etc., which are within the skill of the skilled physician.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

The abbreviations are defined as follows:

Xantphos 4, 5-Didiphenylphosphine-9, 9-dimethyloxanthracene

NBS N-bromosuccinimide

Pd(dppf)$Cl_2$ 1, 1'-Didiphenylphosphine ferrocene palladium dichloride $Pd_2(dba)_3$ Tridibenzylidene acetone dipalladium $Pd(dba)_2$ Bis (dibenzylidene acetone) palladium BINAP 1, 1'-binaphthalene-2, 2'-bisdiphenylphosphine X-Phos 2-Dicyclohexylphosphorus-2', 4', 6'-triisopropylbiphenyl tBuXPhos 2-Di-tert-butylphosphino-2', 4', 6'-triisopropylbiphenyl tBuXPhos Pd G3 Methane sulfonic acid (2-di-tert-butylphosphino-2', 4', 6'-triisopropyl-1,1'-biphenyl)(2'-amino-1,1'-biphenyl-2-yl) palladium (II)

EDCI 1-(3-Dimethylaminopropyl)-3-ethylcarbodiimide hydrochloride

HOBT 1-Hydroxybenzotriazole

LDA Lithium diisopropylamide

HATU 2-(7-Azabenzotriazole)-N,N,N',N'-tetramethylureahexafluorophosphate

The starting materials may be obtained commercially or prepared by methods known or disclosed in the art.

The purification of intermediates and compounds is carried out by conventional chemical laboratory operations such as normal or reverse phase chromatography or recrystallization. The normal phase chromatography is a pre-packed silica gel chromatographic column or a preparative thin layer chromatography. Silica gel chromatographic columns are primarily glass columns or rapid preparative chromatographs. The mobile phase of the normal phase chromatography is selected from petroleum ether/ethyl acetate, dichloromethane/methanol or other proper solvents and is eluted according to the proportion. Reversed-phase preparative liquid chromatography is performed on a C18 column, using a preparative liquid chromatograph or a rapid preparative chromatograph, with 214 nM and 254 nM or preparative liquid chromatography-mass spectrometry combined instrument. 0.1% hydrochloric acid in water/acetonitrile, water/acetonitrile, 0.1% ammonium bicarbonate in water/acetonitrile, 0.1% formic acid in water/acetonitrile, 0.1% ammonia water/acetonitrile, 0.1% trifluoroacetic acid in water/acetonitrile or other suitable solvent systems are used as mobile phase for gradient elution.

The structures of intermediates and compounds are characterized by nuclear magnetic resonance (NMR) and mass spectrometry (LCMS). The NMR spectrometer used for NMR is Bruker Ascend 400 or Varian 400 or ZKNJ BIXI-1 300 MHz or Bruker Avance III 400 MHz or Bruker AVANCE Neo 400 MHz. The solvents used are deuterated dimethyl sulfoxide, deuterated chloroform, deuterated methanol or other labeled deuterated solvents. The spectral data are reported in the mode: chemical shift δ (number of splitting peaks, coupling constant J (Hz), number of hydrogens). Tetramethylsilane is used as an internal standard for the chemical shift and its chemical shift is set to zero (δ, 0 ppm). Some abbreviations mean: s (singlet), d (doublet), t (triplet), Q (quartet), m (multiplet), br (broad peak).

A representative method of liquid chromatography-mass spectrometry (LCMS) for structural characterization of intermediates and compounds is as follows:

Method I: performed on an Agilent LC1260 system coupled to a 6120 single quadrupole mass spectrometer Column: Waters CORTECS C-18, 2.7 μm, 4.6*30 mm. solvent A: 0.05% formic acid aqueous solution, solvent B: 0.05% formic acid acetonitrile solution, 5% acetonitrile to 95% acetonitrile within one minute, hold for one minute, total 2.5 minutes; flow rate: 1.8 mL/min; column temperature: 40° C.

Column: XSelect CSH C18, 3.5 μm, 4.6*50 mm. Solvent A: 0.05% ammonia water solution, solvent B: 0.05% ammonia acetonitrile solution, 5% acetonitrile to 95% acetonitrile within one minute, hold for one minute, total 2.5 minutes; flow rate: 1.8 mL/min; column temperature: 40° C.

Method II: performed on an Agilent LC/MSD 1200 system coupled to a quadrupole mass spectrometer. Column: ODS 2000 (50×4.6 mm, 5 μm) (ES (+) or (−) ionization mode), column temperature: 30° C.; flow rate 1.5 mL/min.

General Methods: Synthesis of Compound 8

Example 1: 3-ethyl-8-(3-methoxy-4-(4-(4-methylpiperazin-1-yl) piperidin-1-yl)phenyl)-N2-(tetrahydropyran-4-yl)pyrido[3,4-b]pyrazine-2,5-diamine trihydrochloride (Compound 8)

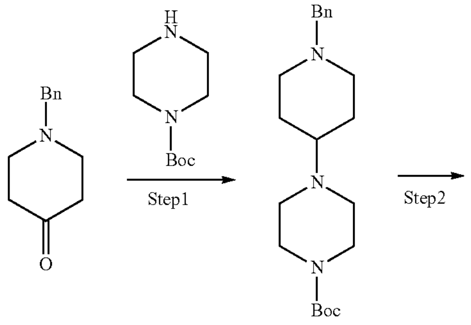

-continued

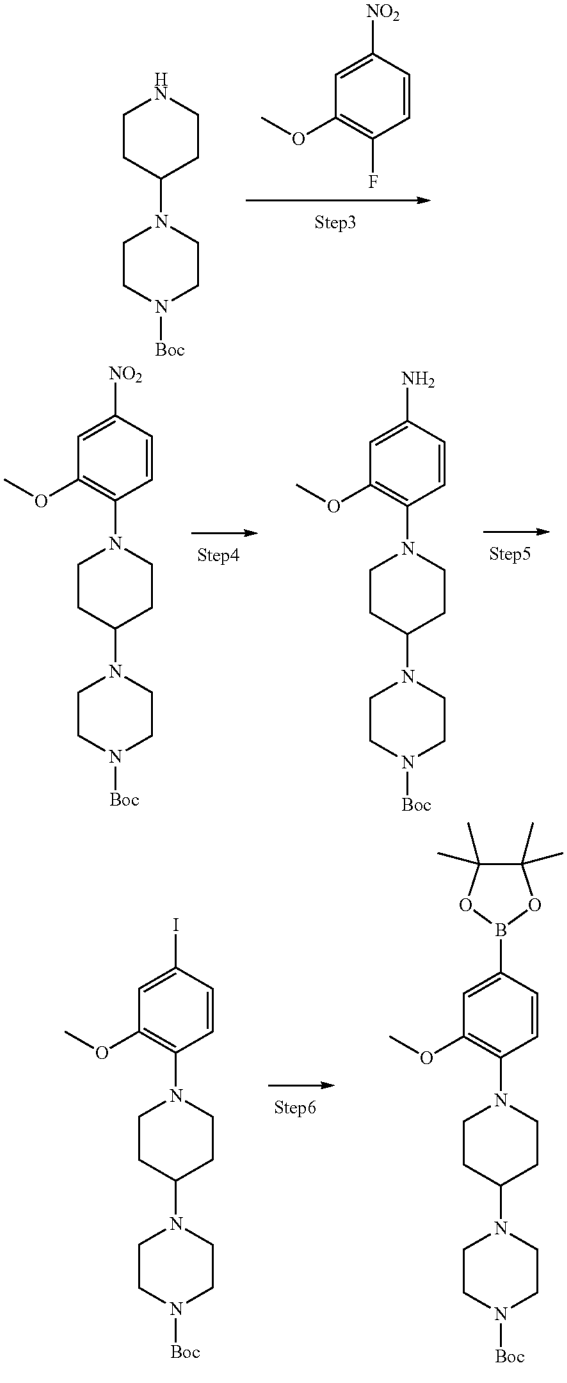

intermediateA

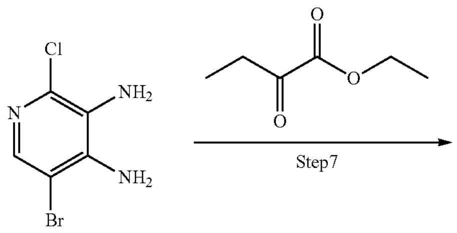

-continued
-continued
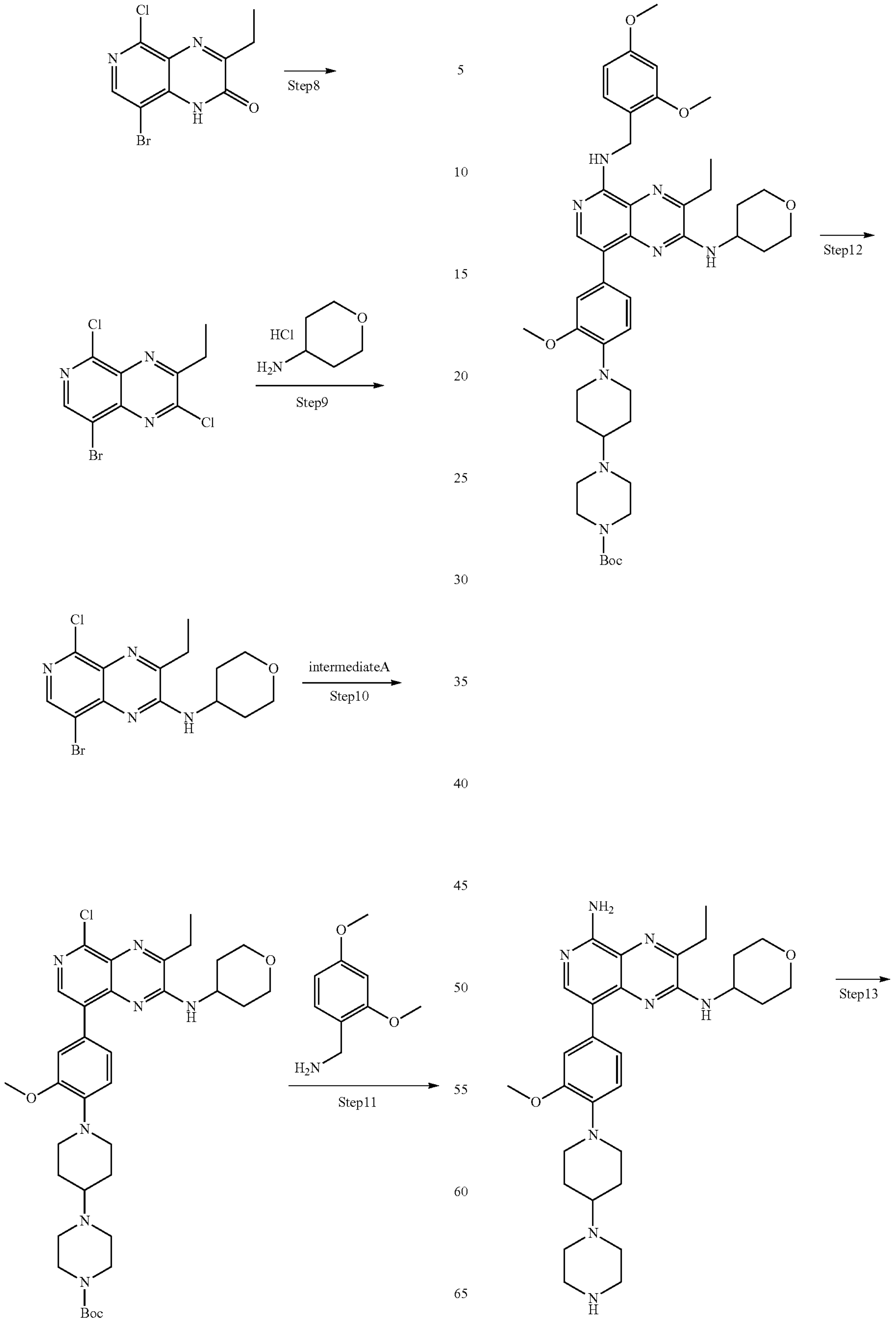

-continued

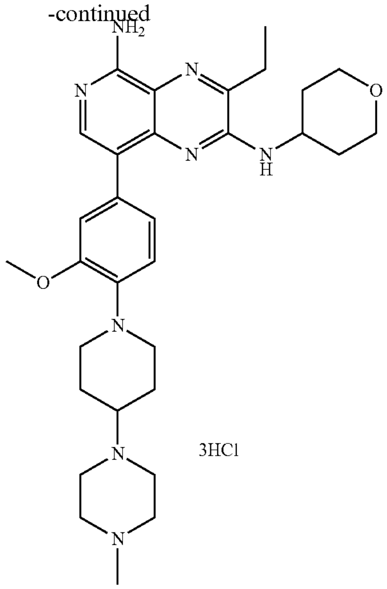

compound 8

Step 1: 1-benzyl-4-piperidone (5.00 g, 26.5 mmol) and 1-tert-butoxycarbonylpiperazine (5.41 g, 29.1 mmol) were dissolved in dichloromethane (100 mL). Acetic acid (2.38 g, 39.7 mmol) was added and then stirred at room temperature for 5 hours. Sodium triacetoxyborohydride (22.4 g, 106 mmol) was then added portionwise to this solution and the solution was stirred overnight at room temperature. The solution was concentrated, and water (100 mL) was added to the residue. The solution was adjusted to pH=10 with 5% sodium hydroxide and extracted three times with ethyl acetate (50 mL×3). The organic phases were combined, and washed with saturated saline (50 mL), dried over anhydrous sodium sulfate, filtered, and concentrated under reduced pressure. The resulting residue was purified by a C18 reversed-phase column (from water containing 50% acetonitrile to water containing 90% acetonitrile) to afford yellow solid tert-butyl ester 4-(1-benzylpiperidin-4-yl)piperazine-1-carboxylic acid (5.80 g, yield 61%). MS: 360.4 $[M+H]^+$.

Step 2: Tert-butyl 4-(1-benzylpiperidin-4-yl) piperazine-1-carboxylate (5.80 g, 16.1 mmol) was dissolved in methanol (100 mL) and 10 mol % palladium on carbon (1.5 g) was added. The mixture was stirred at 50° C. overnight under hydrogen (50 psi). At the end of the reaction, the solution was cooled to room temperature and filtered. The filtrate was concentrated under reduced pressure to afford white solid tert-butyl 4-(piperidine-4-yl)piperazine-1-formate (4.15 g, yield 96%). $^1$HNMR (300 MHz, $CDCl_3$): δ 3.44-3.41 (m, 4H), 3.17-3.13 (m, 2H), 2.63-2.58 (m, 2H), 2.55-2.49 (m, 4H), 2.41-2.31 (m, 1H), 1.82-1.78 (m, 2H), 1.46 (s, 9H), 1.43-4.33 (m, 2H).

Step 3: 1-Fluoro-2-methoxy-4-nitrobenzene (2.00 g, 11.7 mmol) and tert-butyl 4-(piperidin-4-yl)piperazine-1-carboxylate (3.46 g, 12.9 mmol) were dissolved in N, N-dimethylformamide (30 mL). Then potassium carbonate (3.23 g, 23.4 mmol) was added. The mixture was stirred at 100° C. for 2 hours. At the end of the reaction, the solution was cooled to room temperature, then water (100 mL) was added. The solution was extracted twice with ethyl acetate (30 mL×2). The organic phases were combined and washed twice with saturated saline (10 mL×2), dried over anhydrous sodium sulfate, filtered, and concentrated under reduced pressure to afford yellow solid tert-butyl 4-(1-(2-(2-methoxy-4-nitrophenyl)piperidin-4-yl)piperazine-1-carboxylate (4.90 g, yield 99%). 421.0 $[M+1]^+$.

Step 4: Tert-butyl 4-(1-(2-(2-methoxy-4-nitrophenyl) piperidin-4-yl) piperazine-1-carboxylate (4.90 g, 11.7 mmol) was dissolved in methanol (50 mL) and 10% palladium on carbon (0.5 g) was added. The mixture was stirred at 50° C. overnight under hydrogen (hydrogen balloon). At the end of the reaction, the mixture was cooled to room temperature, filtered, and the filtrate was concentrated under reduced pressure to afford purple solid tert-butyl 4-(1-(4-amino-2-methoxyphenyl) piperidin-4-yl) piperazine-1-carboxylate (4.50 g, yield 99%). $^1$HNMR (400 MHz, $CDCl_3$): δ 6.77 (d, J=8.4 Hz, 1H), 6.26-6.23 (m, 2H), 3.81 (s, 3H), 3.50-3.38 (m, 8H), 2.55-2.54 (m, 2H), 2.50-2.47 (m, 2H), 2.45-2.37 (m, 1H), 1.83-1.78 (m, 4H), 1.46 (s, 9H).

Step 5: Tert-butyl 4-(1-(4-amino-2-methoxyphenyl)piperidin-4-yl)piperazine-1-carboxylate (3.40 g, 8.72 mmol) and diiodomethane (7.00 g, 26.1 mmol) were dissolved in acetonitrile (100 mL). Isoamyl nitrite (1.53 g, 13.1 mmol) was added. The mixture was stirred at 80° C. for 4 hours under nitrogen protection. At the end of the reaction, the mixture was cooled to room temperature and concentrated under reduced pressure. Methylene chloride (30 mL), water (20 mL), and saturated sodium carbonate solution (10 mL) were added to the obtained residue. The mixture was extracted three times with dichloromethane (20 mL×3). The organic phases were combined, washed with saturated saline (10 mL), dried over anhydrous sodium sulfate, filtered, and the filtrate was concentrated under reduced pressure. The resulting residue was purified by silica gel chromatography (petroleum ether/ethyl acetate=2:1 to ethyl acetate) to afford brown solid tert-butyl 4-(4-(4-iodo-2-methoxyphenyl) cyclohexyl) piperazine-1-carboxylate (1.85 g, yield 42%). $^1$H NMR (300 MHz, $CDCl_3$) δ 7.21 (dd, J=8.1, 1.8 Hz, 1H), 7.09 (d, J=1.5 Hz, 1H), 6.65 (d, J=8.4 Hz, 1H), 3.84 (s, 3H), 3.52-3.48 (m, 2H), 3.46-3.42 (m, 4H), 2.56-2.47 (m, 6H), 2.42-2.38 (m, 1H), 1.87-1.74 (m, 4H), 1.46 (s, 9H). MS: 502.5 $[M+H]^+$.

Step 6: Tert-butyl 4-(4-(4-iodo-2-methoxyphenyl)cyclohexyl)piperazine-1-carboxylate (1.85 g, 3.69 mmol) was dissolved in N, N-dimethylformamide (100 mL). Pinacol diborate (1.13 g, 4.43 mmol), potassium acetate (1.09 g, 11.1 mmol), [1,1'-bis (diphenylphosphino) ferrocene]palladium dichloride (135 mg, 0.17 mmol) were added. The mixture was stirred at 100° C. for 5 hours under nitrogen protection. At the end of the reaction, the solution was cooled to room temperature and poured into water (100 mL). Saturated sodium carbonate solution (10 mL) was added. The mixture was extracted three times with ethyl acetate (30 mL×3). The organic phases were combined, washed with saturated saline (10 mL), dried over anhydrous sodium sulfate, filtered, and the filtrate was concentrated under reduced pressure. The resulting residue was purified by silica gel chromatography (petroleum ether/ethyl acetate=1:1 to ethyl acetate) to give yellow solid 4-(1-(2-methoxy-4-(4,4,5,5-tetramethyl-1,3,2-dioxaborolan-2-yl)phenyl)piperidin-4-yl)-1-tert-butoxycarbonylpiperazine (intermediate A, 1.30 g, yield 70%). $^1$H NMR (300 MHz, $CDCl_3$) δ 7.39 (d, J=7.8 Hz, 1H), 7.25 (s, 1H), 6.93 (d, J=7.8 Hz, 1H), 3.91 (s, 3H), 3.64-3.60 (m, 2H), 3.46-3.43 (m, 4H), 2.62-2.55 (m, 6H), 2.50-2.41 (m, 1H), 1.89-1.76 (m, 4H), 1.47 (s, 9H), 1.33 (s, 12H). MS: 502.6 $[M+H]^+$.

Step 7: 5-Bromo-2-chloropyridine-3,4-diamine (5.00 g, 22.5 mmol) and ethyl 2-oxobutyrate (3.51 g, 27.0 mmol) were dissolved in ethanol (100 mL) and acetic acid (0.2 mL) was added. The mixture was stirred at 90° C. for 36 hours under nitrogen protection. At the end of the reaction, the temperature was cooled to 50° C. The solution was filtered, and the filter cake was washed with ethanol (10 mL×3). The filtrate was concentrated under reduced pressure to give a residue and the residue was dissolved in ethanol (20 mL). The solution was heated to reflux for 10 minutes, then cooled to 50° C., filtered, and the filter cake was washed with ethanol (10 mL×2), dried to give yellow solid 8-bromo-5-chloro-3-ethylpyrido[3,4-b]pyrazin-2(1H)-one (4.1 g, yield 63%). $^{1}$H NMR (400 MHz, DMSO-$d_6$) δ 12.32 (br s, 1H), 8.50 (s, 1H), 2.86 (q, J=7.6 Hz, 2H), 1.25 (t, J=7.6 Hz, 3H).

Step 8: 8-Bromo-5-chloro-3-ethylpyrido[3,4-b]pyrazin-2(1H)-one (3.10 g, 10.7 mmol) was suspended in dichloromethane (50 mL) and 5 drops of N, N-dimethylformamide and oxalyl chloride (5.46 g, 43.0 mmol) were added. The mixture was stirred at 40° C. overnight under nitrogen protection. At the end of the reaction, the mixture was cooled to room temperature and concentrated under reduced pressure. Dichloromethane (50 mL), water (30 mL), and saturated sodium carbonate solution (10 mL) were added to the obtained residue. The mixture was extracted five times with dichloromethane (30 mL×5). The organic phases were combined, washed with saturated saline, dried over anhydrous sodium sulfate, filtered, and the filtrate was concentrated under reduced pressure to give yellow solid 8-bromo-2,5-dichloro-3-ethylpyrido[3,4-b]pyrazine (2.0 g, yield 61%). $^{1}$H NMR (300 MHz, DMSO-$d_6$) δ 8.91 (s, 1H), 3.20 (q, J=7.2 Hz, 2H), 1.39 (t, J=7.2 Hz, 3H).

Step 9: Tetrahydropyran-4-amine (1.35 g, 9.77 mmol) was suspended in ethanol (20 mL), and N, N-diisopropylethylamine (2.52 g, 19.5 mmol) was added. The solution was stirred at room temperature for half an hour. 8-Bromo-2,5-dichloro-3-ethylpyrido[3,4-b]pyrazine (2.00 g, 6.51 mmol) was suspended in ethanol (30 mL), and N,N-diisopropylethylamine (1.68 g, 13.0 mmol) was added. The solution was stirred at room temperature for half an hour. The two solutions were combined and stirred at 70° C. overnight. At the end of the reaction, the mixture was cooled to room temperature and concentrated under reduced pressure. Water (30 mL) was added to the residue and the solution was filtered. The filter cake was washed with dichloromethane/methanol=10/1 (5 mL×3) and dried to give yellow solid 8-bromo-5-chloro-3-ethyl-N-(tetrahydropyran-4-yl)pyrido[3,4-b]pyrazin-2-amine (1.2 g, yield 50%). $^{1}$H NMR (300 MHz, DMSO-$d_6$) δ 8.50 (s, 1H), 7.81 (d, J=7.2 Hz, 1H), 4.42-4.31 (m, 1H), 3.98-3.94 (m, 2H), 3.43 (t, J=7.5 Hz, 2H), 2.92 (q, J=7.2 Hz, 2H), 1.98-1.93 (m, 2H), 1.80-1.66 (m, 2H), 1.31 (t, J=7.2 Hz, 3H).

Step 10: An aqueous solution (5 mL) of sodium carbonate (824 mg, 7.78 mmol) and [1,1'-bis(diphenylphosphino)ferrocene]palladium dichloride (190 mg, 0.26 mmol) were added to the mixture of N, N-dimethylacetamide (50 mL) containing 8-bromo-5-chloro-3-ethyl-N-(tetrahydropyran-4-yl)pyrido[3,4-b]pyrazin-2-amine (0.960 g, 2.59 mmol) and 4-(1-(2-methoxy-4-(4,4,5,5-tetramethyl-1,3,2-dioxaboran-2-yl) phenyl) piperidin-4-yl)-1-tert-butoxycarbonylpiperazine (intermediate A, 1.30 g, 2.59 mmol). The mixture was stirred at 100° C. for 3 hours under nitrogen protection. At the end of the reaction, the mixture was cooled to room temperature and poured into water (150 mL). The mixture was extracted three times with ethyl acetate (30 mL×3). The organic phases were combined, washed with saturated saline (10 mL), dried over anhydrous sodium sulfate, filtered, and the filtrate was concentrated under reduced pressure. The resulting residue was purified by silica gel chromatography (ethyl acetate to dichloromethane/methanol/25% aqueous ammonia=30:1:0.1) to give the crude product. The crude product was purified by a C18 reverse-phase chromatography column (from water containing 50% acetonitrile to water containing 80% acetonitrile) to give yellow solid tert-butyl 4-(1-(4-(5-chloro-3-ethyl-2-((tetrahydro-2H-pyran-4-yl)amino)pyridyl[3,4-b]pyrazin-8-yl)-2-methoxyphenyl) piperidin-4-ylpiperazine-1-carboxylate (0.60 g, yield 35%). $^{1}$H NMR (300 MHz, DMSO-$d_6$) δ 8.32 (s, 1H), 7.56 (d, J=7.2 Hz, 1H), 7.30-7.28 (m, 2H), 6.97-6.95 (m, 1H), 4.19-4.11 (m, 1H), 3.93-3.89 (m, 2H), 3.83 (s, 3H), 3.52-3.49 (m, 2H), 3.31-3.30 (m, 4H), 3.25-3.22 (m, 2H), 2.90 (q, J=7.2 Hz, 2H), 2.61-2.57 (m, 2H), 2.50-2.41 (m, 4H), 2.38-2.32 (m, 1H), 1.88-1.81 (m, 4H), 1.71-1.55 (m, 4H), 1.40 (s, 9H), 1.32 (t, J=7.2 Hz, 3H). MS Found: 666.8 $[M+H]^+$.

Step 11: Tridibenzylideneacetone dipalladium (21 mg, 0.024 mmol) was added to the mixture of toluene (10 mL) containing tert-butyl 4-(1-(4-(5-chloro-3-ethyl-2-((tetrahydro-2H-pyran-4-yl)amino)pyridinyl[3,4-b]pyrazin-8-yl)-2-methoxyphenyl) piperidin-4-yl-piperazine-1-carboxylate (0.30 g, 0.45 mmol), (2,4-dimethoxyphenyl methylamine (113 mg, 0.680 mmol), 4,5-bis(diphenylphosphine)-9,9-dimethylxanthene (26 mg, 0.045 mmol) and sodium tert-butoxide (130 mg, 1.35 mmol). The mixture was stirred at 110° C. for 3 hours under nitrogen protection. At the end of the reaction, the mixture was cooled to room temperature and concentrated under reduced pressure. Ethyl acetate (20 mL) and water (30 mL) was added to the residue. The mixture was extracted three times with ethyl acetate (10 mL×3). The organic phases were combined, washed with saturated saline (10 mL), dried over anhydrous sodium sulfate, filtered, and the filtrate was concentrated under reduced pressure. The resulting residue was purified by silica gel chromatography (dichloromethane/methanol=30:1) to give the crude product. The crude product was purified by a C18 reverse-phase chromatography column (from water containing 40% acetonitrile to water containing 90% acetonitrile) to give yellow solid t-butyl 4-(1-(4-(5-((2,4-dimethoxybenzyl)amino)-3-ethyl-2-((tetrahydro-2H-pyran-4-yl)amino)pyridinyl[3,4-b]pyrazin-8-yl)-2-methoxyphenyl)piperidin-4-yl)piperazine-1-carboxylic acid (0.13 g, yield 36%). $^{1}$H NMR (400 MHz, $CDCl_3$) δ 8.16 (s, 1H), 7.35-7.33 (m, 1H), 7.30-7.27 (m, 1H), 7.16 (s, 1H), 6.96-6.94 (m, 2H), 6.50-6.49 (m, 1H), 6.46-6.43 (m, 1H), 4.80-4.78 (m, 2H), 4.76-4.74 (m, 1H), 4.25-4.16 (m, 1H), 4.01-3.98 (m, 2H), 3.89-3.88 (m, 6H), 3.80 (s, 3H), 3.62-3.59 (m, 2H), 3.50-3.45 (m, 6H), 2.70 (q, J=7.2 Hz, 2H), 2.64-2.59 (m, 6H), 2.53-2.45 (m, 1H), 2.08-2.05 (m, 2H), 1.89-1.82 (m, 4H), 1.56-1.52 (m, 2H), 1.47 (s, 9H), 1.41 (t, J=7.2 Hz, 3H). MS: 797.5 $[M+H]^+$.

Step 12: Trifluoroacetic acid (1 mL) was added to dichloromethane (2 mL) containing tert-butyl 4-(1-(4-(5-((2,4-dimethoxybenzyl)amino)-3-ethyl-2-((tetrahydro-2H-pyran-4-yl)amino)pyridinyl[3,4-b]pyrazin-8-yl)-2-methoxyphenyl)piperidin-4-yl)piperazine-1-carboxylic acid (0.13 g, 0.16 mmol). The reaction was stirred at 30° C. for 1 hour and concentrated. Water (2 mL) was added to the resulting residue, and the pH was adjusted to 10 with 5% sodium hydroxide. The solution was extracted six times (10 mL×6) with dichloromethane/methanol=10/1. The organic phases were combined, washed with saturated saline (5 mL), dried over anhydrous sodium sulfate, filtered and the filtrate was concentrated under reduced pressure to give yellow solid 3-ethyl-8-(3-methoxy-4-(4-(piperazin-1-yl)piperidin-1-yl)phenyl)-N2-(tetrahydro-2H-pyran-4-yl)pyridine[3,4-b]pyrazine-2,5-diamine (90 mg, yield 100%). MS: 547.6 $[M+H]^+$.

Step 13: 37% Aqueous formaldehyde (15 mg, 0.18 mmol) and 1 drop of acetic acid were added to the mixture of dichloromethane (2 mL) and methanol (1 mL) containing 3-ethyl-8-(3-methoxy-4-(4-(piperazin-1-yl)piperidin-1-yl) phenyl)-N2-(tetrahydro-2H-pyran-4-yl)pyridine[3,4-b] pyrazine-2,5-diamine (90 mg, 0.16 mmol). After stirred at room temperature for 20 minutes, sodium cyanoborohydride (31 mg, 0.49 mmol) was added. After stirred at room temperature for 30 minutes, water (2 mL) was added and alkalified to pH=10 with 5% sodium hydroxide. The mixture was extracted six times (10 mL×6) with dichloromethane/ methanol=10/1. The organic phases were combined and concentrated under reduced pressure to give the crude product. The crude product was purified by a C18 reverse-phase chromatography column (from water containing 10% acetonitrile to water containing 50% acetonitrile, the aqueous phase contained 0.1% hydrochloric acid) to give yellow solid 3-ethyl-8-(3-methoxy-4-(4-(4-methylpiperazin-1-yl) piperidin-1-yl)phenyl)-N2-(tetrahydro-2H-pyran-4-yl)pyridine[3,4-b]pyrazine-2,5-diaminetrihydrochloride (65 mg, yield 61%). $^1$H NMR (400 MHz, DMSO-$d_6$) δ 13.77 (s, 1H), 12.48-12.17 (m, 2H), 8.54 (s, 2H), 7.96-7.94 (i, 2H), 7.55 (br s, 1H), 7.43-7.32 (i, 2H), 4.14-4.05 (m, 1H), 3.95 (s, 3H), 3.92-3.89 (m 2H), 3.79-3.60 (i, 12H), 3.35-3.27 (s, 1H), 3.25-3.22 (m, 2H), 2.92-2.86 (m, 5H), 2.35-2.25 (i, 4H), 1.83-1.78 (i, 2H), 1.74-1.64 (m, 2H), 1.33 (t, J=7.2 Hz, 3H). MS: 561.4 $[M+H]^+$.

The compounds in the tables were prepared by using the same method and the corresponding starting materials.

The compounds in the following table were provided by the synthesis method of compound 8, while tetrahydropyran-4-amine in Step 9 was replaced with the corresponding starting materials in the table below:

| No | starting materials | structures | HNMR |
|---|---|---|---|
| 67 | 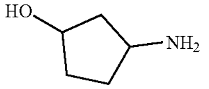 | 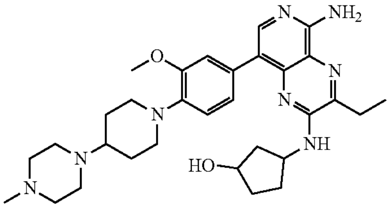 [SMILES: CCc1nc2c(N)ncc(-c3ccc(N4CCC(N5CCN(C)CC5)CC4)c(OC)c3)c2nc1NC1CCC(O)C1] | $^1$H NMR (400 MHz, $CD_3OD$) δ 7.89-7.80 (m, 2H), 7.63-7.60 (m, 1H), 7.53-7.47 (m, 1H), 4.55-4.47 (m, 1H), 4.32 (s, 1H), 4.11 (s, 3H), 3.98-3.58 (m, 13H), 3.06-3.01 (m, 3H), 2.88 (q, J = 7.2 Hz, 2H), 2.69-2.45 (m, 4H), 2.19-2.13 (m, 1H), 2.07-1.98 (m, 1H), 1.94-1.79 (m, 3H), 1.74-1.67 (m, 1H), 1.43 (t, J = 7.2Hz, 3H). hydrochloride |
| 68 | 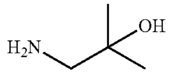 | 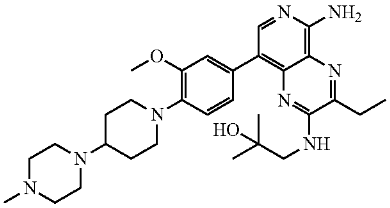 [SMILES: CCc1nc2c(N)ncc(-c3ccc(N4CCC(N5CCN(C)CC5)CC4)c(OC)c3)c2nc1NCC(C)(C)O] | $^1$H NMR (400 MHz, $CD_3OD$) δ 7.85 (d, J = 8.4 Hz, 1H), 7.80 (s, 1H), 7.62 (d, J = 1.6 Hz, 1H), 7.46 (dd, J = 8.4, 1.6 Hz, 1H), 4.13 (s, 3H), 4.00-3.66 (m, 13H), 3.60 (s, 2H), 3.05 (s, 3H), 2.94 (q, J = 7.2 Hz, 2H), 2.66-2.49 (m, 4H), 1.46 (t, J = 7.2 Hz, 3H), 1.15 (s, 6H). hydrochloride |
| 66 | 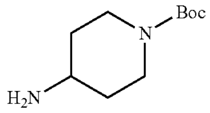 [SMILES: CC(C)(C)OC(=O)N1CCC(N)CC1] | 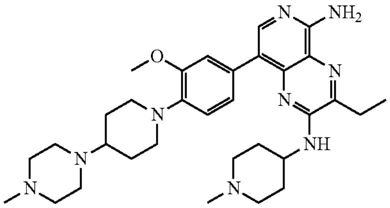 [SMILES: CCc1nc2c(N)ncc(-c3ccc(N4CCC(N5CCN(C)CC5)CC4)c(OC)c3)c2nc1NC1CCN(C)CC1] | $^1$H NMR (400 MHz, DMSO-$d_6$) δ 7.91 (s ,1H), 7.22-7.16 (m, 2H), 6.92 (d, J = 7.6 Hz, 1H), 6.88 (d, J = 8.0 Hz, 1H), 6.41 (br s, 1H), 3.94-3.86 (m, 1H), 3.82 (s, 3H), 3.47-3.44 (m, 2H), 2.82-2.75 (m, 4H), 2.57-2.51 (m, 6H), 2.36-2.25 (m, 5H), 2.14 (s, 6H), 1.84-1.80 (m, 6H), 1.65-1.53 (m, 4H), 1.30 (t, J = 7.6 Hz, 3H). |

The compounds in the following table were provided by the synthesis method of compound 8, while tetrahydropyran-4-amine in Step 9 was replaced with the corresponding starting materials in the table below, and the corresponding product in Step 11 was hydrolysized by alkaline to remove the acetyl protecting group:

| No | starting materials | structures | HNMR |
|---|---|---|---|
| 65 | 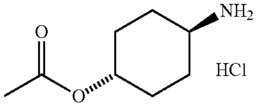 | 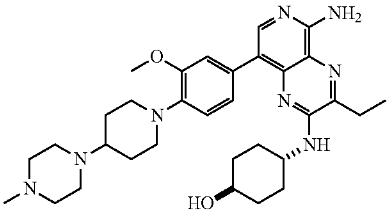 | $^1$H NMR (400 MHZ, $CD_3OD$) δ 7.75 (d, J = 8.4 Hz, 1H), 7.70 (s, 1H), 7.50 (s, 1H), 7.38 (d, J = 8.4, 1.6 Hz, 1H), 4.01 (s, 3H), 3.90-3.45 (m, 15H), 2.96 (s, 3H), 2.78-2.77 (m, 2H), 2.58-2.41 (m, 4H), 1.90-1.62 (m, 4H), 1.46-1.30 (m, 5H), 1.19-1.07 (m, 2H). Hydrochloride. |

The compounds in the following table were provided by the synthesis method of compound 8, while 1-fluoro-2-methoxy-4-nitrobenzene in Step 3 was replaced with the corresponding starting materials in the table below:

| No | starting materials | structures | HNMR |
|---|---|---|---|
| 4 | 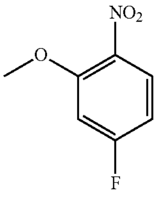 | 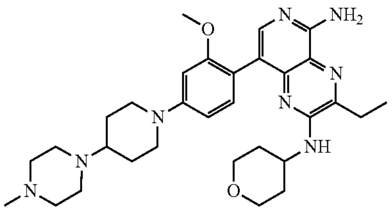 [SMILES: CCc1nc2c(N)ncc(-c3ccc(N4CCC(N5CCN(C)CC5)CC4)cc3OC)c2nc1NC1CCOCC1] | $^{1}$H NMR (400 MHZ, DMSO-d6) δ 13.27 (s, 1H), 12.48-11.95 (m, 2H), 8.43 (s, 2H), 7.78 (d, J = 6.4 Hz, 1H), 7.70 (d, J = 3.6 Hz, 1H), 7.21 (d, J = 8.4 Hz, 1H), 6.86-6.63 (m, 2H), 4.18-4.11 (m, 1H), 3.96-3.93 (m, 2H), 3.89-3.80 (m, 6H), 3.79-3.71 (m, 3H), 3.68 (s, 3H), 3.60-3.46 (m, 4H), 3.18-3.12 (m, 2H), 2.97-2.82 (m, 5H), 2.33-2.24 (m, 2H), 2.07-1.92 (m, 2H), 1.76-1.72 (m, 2H), 1.65-1.53 (m, 2H), 1.32 (t, J = 7.2 Hz, 3H). Hydrochloride. |
| 7 | 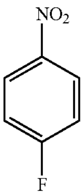 | 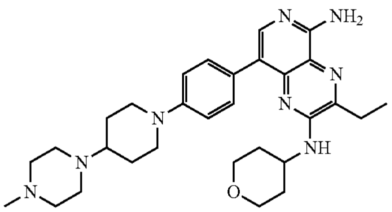 [SMILES: CCc1nc2c(N)ncc(-c3ccc(N4CCC(N5CCN(C)CC5)CC4)cc3)c2nc1NC1CCOCC1] | $^{1}$H NMR (400 MHz, $CD_3OD$) δ 7.55 (s , 1H), 7.46 (d, J = 8.4 Hz, 2H), 6.96 (d, J = 8.8 Hz, 2H), 4.17-4.09 (m, 1H), 3.91-3.87 (m, 2H), 3.79-3.76 (m 2H), 3.35-3.29 (m, 2H), 3.09-2.69 (m, 12H), 2.65-2.62 (m, 4H), 1.97-1.94 (m, 2H), 1.88-1.83 (m, 2H), 1.68-1.56 (m, 4H), 1.31 (t, J = 7.2 Hz, 3H). Hydrochloride. |
| 13 | 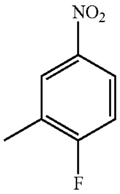 | 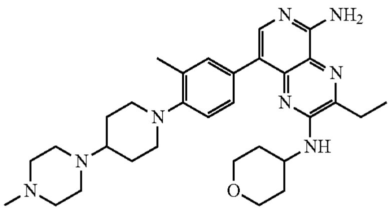 [SMILES: CCc1nc2c(N)ncc(-c3ccc(N4CCC(N5CCN(C)CC5)CC4)c(C)c3)c2nc1NC1CCOCC1] | $^{1}$H NMR (400 MHz, DMSO-$d_6$) δ 13.31 (s, 1H), 12.32-12.05 (m, 2H), 8.42 (s, 2H), 7.87-7.81 (m, 2H), 7.52-7.47 (m, 2H), 7.11 (d, J = 8.4 Hz, 1H), 4.12-4.06 (m, 1H), 3.92-3.78 (m, 6H), 3.69-3.43 (m, 5H), 3.29-3.24 (m, 4H), 2.90-2.85 (m, 5H), 2.78-2.67 (m, 2H), 2.33 (s, 3H), 2.26-2.23 (m, 2H), 2.01-1.97 (m, 2H), 1.84-1.80 (m, 2H), 1.73-1.66 (m, 2H), 1.33 (t, J = 7.2 Hz, 3H). Hydrochloride. |
| 14 | 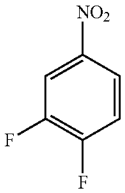 | 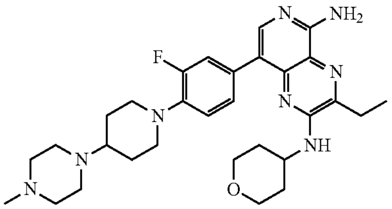 | $^{1}$H NMR (400 MHz, DMSO-$d_6$) δ 7.98 (s, 1H), 7.65 (d, J = 15.6 Hz, 1H), 7.39 (d, J = 8.4 Hz, 1H), 7.09 (d, J = 6.8 Hz, 1H), 7.03 (t, J = 8.8 Hz, 1H), 6.52 (s, 2H), 4.17-4.08 (m, 1H), 3.95-3.92 (m, 2H), 3.45-3.42 (m, 2H), 3.37-3.33 (m, 2H), 3.33-3.28 (m, 2H), 2.82 (q, J = 7.2 Hz, 2H), 2.71-2.65 (m, 2H), 2.60-2.54 (m, 2H), 2.47-2.39 (m, 4H), 2.36-2.29 (m, 1H), 2.21 (s, 3H), 1.91-1.83 (m, 4H), 1.69-1.55 (m, 4H), 1.31 (t, J = 7.2 Hz, 3H). |
| 15 | 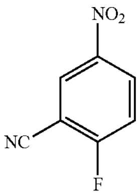 [SMILES: N#Cc1cc([N+](=O)[O-])ccc1F] | 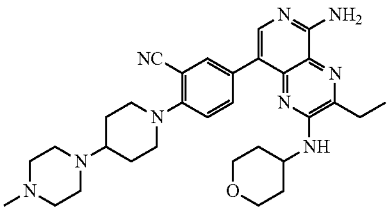 [SMILES: CCc1nc2c(N)ncc(-c3ccc(N4CCC(N5CCN(C)CC5)CC4)c(C#N)c3)c2nc1NC1CCOCC1] | $^{1}$H NMR (400 MHz, DMSO-$d_6$) δ 8.15 (d, J = 2.4 Hz, 1H), 7.99 (s , 1H), 7.85 (dd, J = 8.8, 2.4 Hz, 1H), 7.17 (d, J = 8.8 Hz, 1H), 7.12 (d, J = 8.8 Hz, 1H), 6.59 (br s, 2H), 4.15-4.07 (m, 1H), 3.93-3.90 (m, 2H), 3.59-3.56 (m, 2H), 3.41-3.25 (m, 4H), 2.86-2.79 (m, 4H), 2.67-2.55 (m, 6H), 2.44-2.40 (m 1H), 2.33 (s, 3H), 1.94-1.84 (m, 4H), 1.70-1.61 (m, 4H), 1.31 (t, J = 7.2 Hz, 3H). Hydrochloride. |
| 16 | 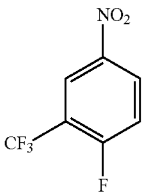 [SMILES: O=[N+]([O-])c1ccc(F)c(C(F)(F)F)c1] | 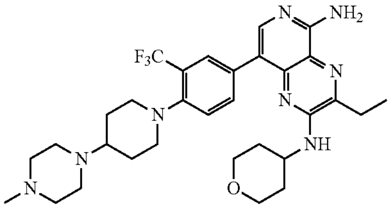 | $^{1}$HNMR (400 MHz, DMSO-$d_6$): δ 13.65 (brs, 1H), 12.45-12.20 (m, 2H), 8.56 (s, 2H), 8.04 (d, J = 1.6 Hz, 2H), 7.99 (s, 1H), 7.94-7.89 (m, 2H), 7.63 (d, J = 8.4 Hz, 1H), 4.14-4.06 (m, 1H), 3.90-3.83 (m, 4H), 3.76-3.73 (m, 2H), 3.64-3.53 (m, 4H), 3.49-3.40 (m, 1H), 3.23-3.12 (m, 4H), 2.91-2.85 (m, 7H), 2.27-2.24 (m, 2H), 1.92-1.84 (m, 2H), 1.76-1.63 (m, 4H), 1.33 (t, J = 7.6 Hz, 3H). Hydrochloride. |

-continued

| No | starting materials | structures | HNMR |
|---|---|---|---|
| 22 | 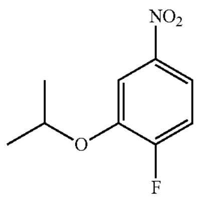 | 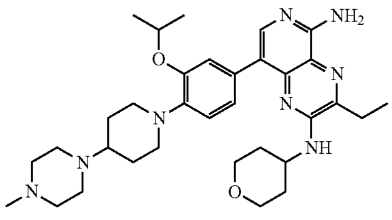 [SMILES: CCc1nc2c(N)ncc(-c3ccc(N4CCC(N5CCN(C)CC5)CC4)c(OC(C)C)c3)c2nc1NC1CCOCC1] | $^{1}$H NMR (400 MHz, DMSO-$d_6$): δ 13.53 (s, 1H), 12.16 (br s, 2H), 8.49 (s, 2H), 7.91 (s, 2H), 7.43-7.29 (m, 3H), 4.81-4.69 (m, 1H), 4.15-4.04 (m, 1H), 3.92-3.90 (m, 2H), 3.84-3.43 (m, 12H), 3.28-3.23 (m, 2H), 3.23-2.90 (m, 1H), 2.90-2.79 (m, 5H), 2.34-2.30 (m, 2H), 2.16 (br s, 2H), 1.82-1.79 (m, 2H), 1.72-1.62 (m, 2H), 1.35-1.31 (m, 9H). Hydrochloride. |

The compounds in the following table were provided by the synthesis method of compound 8, while intermediate A was replaced with the corresponding starting materials in the table below to react with 8-bromo-5-chloro-3-ethyl-N-(tetrahydropyran-4-yl)pyrido[3,4-b]pyrazin-2-amine:

| No | starting materials | structures | HNMR |
|---|---|---|---|
| 3 | 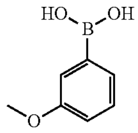 | 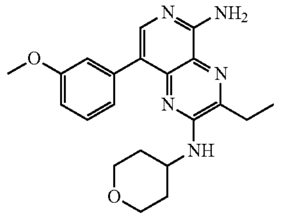 [SMILES: CCc1nc2c(N)ncc(-c3cccc(OC)c3)c2nc1NC1CCOCC1] | HNMR (CDCl3, 400 MHz): 8.12 (s, 1H), 7.35-7.28 (m, 3H), 6.89-6.86 (m, 1H), 5.64 (br s, 2H), 4.85 (d, J = 6.0 Hz, 1H), 4.26-4.16 (m, 1H), 4.03-3.99 (m, 2H), 3.85 (s, 3H), 3.53-3.46 (m, 2H), 2.73 (q, J = 7.2 Hz, 2H), 2.11-2.07 (m, 2H), 1.61-1.54 (m, 2H), 1.43 (t, J = 7.2 Hz, 3H). |
| 17 | 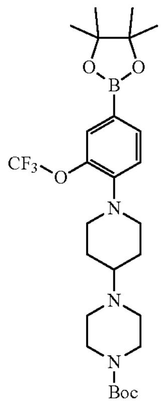 [SMILES: CC(C)(C)OC(=O)N1CCN(C2CCN(c3ccc(B4OC(C)(C)C(C)(C)O4)cc3OC(F)(F)F)CC2)CC1] | 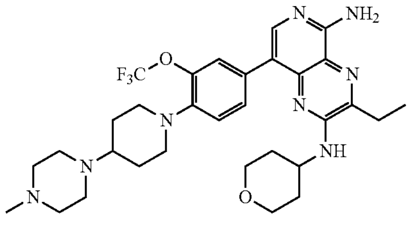 [SMILES: CCc1nc2c(N)ncc(-c3ccc(N4CCC(N5CCN(C)CC5)CC4)c(OC(F)(F)F)c3)c2nc1NC1CCOCC1] | 1HNMR (400 MHz, DMSO-d6): δ 13.40 (brs, 1H), 12.22-12.07 (m, 2H), 8.48 (s, 2H), 7.91 (s, 2H), 7.71 (s, 1H), 7.61-7.59 (m, 1H), 7.25 (d, J = 8.8 Hz, 1H), 4.14-4.07 (m, 1H), 3.93-3.73 (m, 6H), 3.59-3.40 (m, 7H), 3.30-3.24 (m, 2H), 2.90-2.76 (m, 7H), 2.30-2.27 (m, 2H), 1.92-1.65 (m, 6H), 1.33 (t, J = 7.6 Hz, 3H). Hydrochloride. |

The product of Step 10 of synthesis method of compound 8 was compound 12 in the following table:

| | | |
|---|---|---|
| 12 | 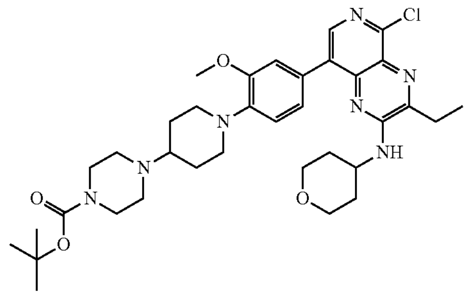 [SMILES: CCc1nc2c(Cl)ncc(-c3ccc(N4CCC(N5CCN(C(=O)OC(C)(C)C)CC5)CC4)c(OC)c3)c2nc1NC1CCOCC1] | $^{1}$H NMR (300 MHz, DMSO-$d_6$) ¿ 8.32 (s, 1H), 7.56 (d, J = 7.2 Hz, 1H), 7.30-7.28 (m, 2H), 6.97-6.95 (m, 1H), 4.19-4.11 (m, 1H), 3.93-3.89 (m, 2H), 3.83 (s, 3H), 3.52-3.49 (m, 2H), 3.31-3.30 (m, 4H), 3.25-3.22 (m, 2H), 2.90 (q, J = 7.2 Hz, 2H), 2.61-2.57 (m, 2H), 2.50-2.41 (m, 4H), 2.38-2.32 (m, 1H), 1.88-1.81 (m, 4H), 1.71-1.55 (m, 4H), 1.40 (s, 9H), 1.32 (t, J = 7.2 Hz, 3H) |

The compound 11 in the following table was provided by deprotection method of Step 12 in the synthesis method of compound 8, and compound 12 was used as the starting material:

| | | |
|---|---|---|
| 11 | 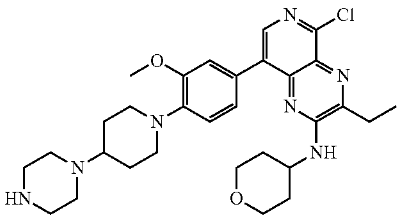 [SMILES: CCc1nc2c(Cl)ncc(-c3ccc(N4CCC(N5CCNCC5)CC4)c(OC)c3)c2nc1NC1CCOCC1] | $^1$H NMR (400 MHz, DMSO-$d_6$) δ 8.62 (s, 1H), 8.32 (s, 1H), 7.56 (d, J = 7.2 Hz, 1H), 7.30-7.28 (m, 2H), 6.96 (d, J = 8.4 Hz, 1H), 4.17-4.09 (m, 1H), 3.93-3.89 (m, 2H), 3.84 (s, 3H), 3.52-3.49 (m, 2H), 3.28-3.22 (m, 2H), 3.05-3.04 (m, 4H), 2.93-2.88 (m, 2H), 2.76-2.73 (m, 4H), 2.61-2.56 (m, 2H), 2.47-2.41 (m, 1H), 1.86-1.83 (m, 4H), 1.70-1.55 (m, 4H), 1.32 (t, J = 7.2 Hz, 3H) |

The compounds in the following table were provided by the synthesis method in example 11 and the corresponding starting materials in the table below were used:

| No | starting materials | structures | HNMR |
|---|---|---|---|
| 326 | 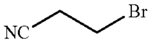 | 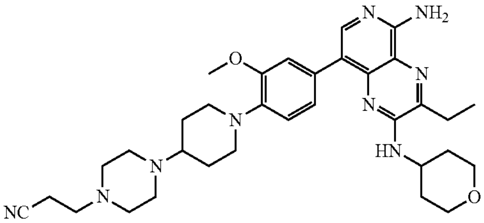 [SMILES: CCc1nc2c(N)ncc(-c3ccc(N4CCC(N5CCN(CCC#N)CC5)CC4)c(OC)c3)c2nc1NC1CCOCC1] | $^1$H NMR (400 MHz, DMSO-6) δ 8.19 (s, 1H), 7.92 (s, 1H), 7.23-7.17 (m, 2H), 7.00 (d, J = 7.2 Hz, 1H), 6.89 (d, J = 8.0 Hz, 1H), 6.44 (s, 2H), 4.13-4.11 (m, 1H), 3.90 (d, J = 8.0 Hz, 2H), 3.82 (s, 3H), 3.46-3.44 (m, 4H), 3.26-3.24 (m, 3H), 2.81 (q, J = 7.2 Hz, 2H), 2.68-2.65 (m, 2H), 2.58-2.54 (m, 4H), 2.46-2.40 (m, 4H), 2.36-2.29 (m, 2H), 1.89-1.81 (m, 4H), 1.66-1.57 (m, 4H), 1.31 (t, J = 7.2 Hz, 3H). Formate. |
| 321 | 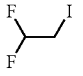 | 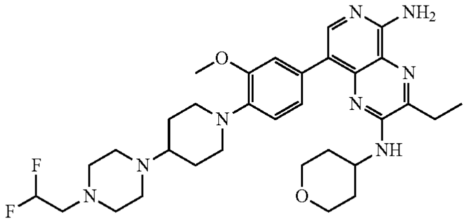 [SMILES: CCc1nc2c(N)ncc(-c3ccc(N4CCC(N5CCN(CC(F)F)CC5)CC4)c(OC)c3)c2nc1NC1CCOCC1] | $^1$H NMR (400 MHz, DMSO-$d_6$) δ 8.16 (s, 1H), 7.92 (s, 1H), 7.23-7.18 (m, 2H), 7.00 (d, J = 8.0 Hz, 1H), 6.89 (d, J = 8.0 Hz, 1H), 6.45 (s, 2H), 6.27 (t, J = 4.0 Hz, 0.25H), 6.13 (t, J = 4.0 Hz, 0.5H), 5.99 (t, J = 4.0 Hz, 0.25H), 4.17-4.09 (m, 1H), 3.90 (d, J = 8.0 Hz, 2H), 3.82 (s, 3H), 3.46-3.43 (m, 2H), 3.27-3.24 (m, 2H), 2.81 (q, J = 7.2 Hz, 2H), 2.75-2.66 (m, 3H), 2.54-2.51 (m, 8H), 2.47-2.44 (m, 1H), 2.32-2.30 (m, 1H), 1.85 (t, J = 10.4 Hz, 4H), 1.65-1.52 (m, 4H), 1.31 (t, J = 7.2 Hz, 3H). Formate. |

The compound in the following table was provided by the synthesis method of compound 8, while (2,4-dimethoxyphenyl) methylamine was replaced with trimethylboroxane and Suzuki reaction was used in Step 11:

| No | structures | HNMR |
|---|---|---|
| 9 | 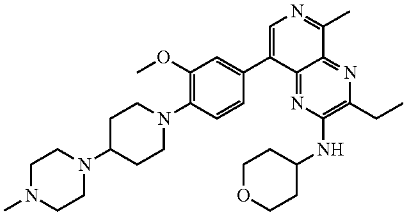 [SMILES: CCc1nc2c(C)ncc(-c3ccc(N4CCC(N5CCN(C)CC5)CC4)c(OC)c3)c2nc1NC1CCOCC1] | $^1$H NMR (400 MHz, DMSO-$d_6$) & 12.47-12.06 (br s, 2H), 8.53 (s, 1H), 8.39-8.37 (m, 1H), 7.39-7.36 (m, 2H), 7.07 (d, J = 7.6 Hz, 1H), 4.25-4.17 (m, 1H), 3.94-3.38 (m, 16H), 3.28-3.22 (m, 2H), 3.02 (s, 3H), 2.99-2.94 (m, 2H), 2.84 (s, 3H), 2.72-2.58 (m, 2H), 2.26-2.23 (m, 2H), 1.99-1.68 (m, 6H), 1.34 (t, J = 7.2 Hz, 3H). Hydrochloride. |

The compounds in the following table was provided by the synthesis method of compound 8, while ethyl 2-oxobutyrate was replaced with the corresponding starting materials in the following table:

| No | starting materials | structures | HNMR |
|---|---|---|---|
| 26 | Ethyl pyruvate | 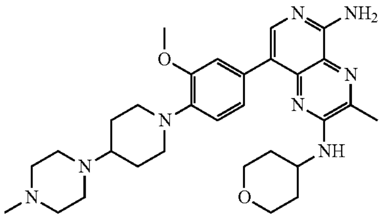 | $^1$H NMR (400 MHz, DMSO-$d_6$) δ 13.56 (s, 1H), 12.52-12.10 (m, 2H), 8.54 (s ,2H), 7.91 ( s, 2H), 7.28-7.15 (m, 3H), 4.15-4.03 (m, 1H), 3.92-3.83 (m 5H), 3.83-3.73 (m, 4H), 3.73-3.55 (m, 7H), 3.26-3.21 (m, 2H), 3.10-2.78 (m, 5H), 2.58 (s ,3H), 2.28-2.08 (m, 2H), 2.07-1.84 (m, 2H), 1.74-1.80 (m, 2H), 1.73-1.62 (m, 2H). Hydrochloride. |
| 27 | Ethyl 3-methyl-2-oxobutanoat | 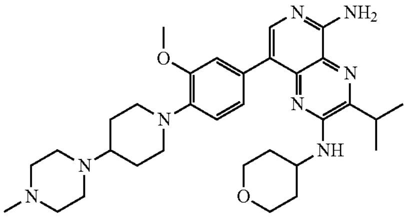 [SMILES: COc1cc(-c2cnc(N)c3nc(C(C)C)c(NC4CCOCC4)nc23)ccc1N1CCC(N2CCN(C)CC2)CC1] | $^1$H NMR (400 MHz, DMSO-$d_6$) δ 13.72 (s, 1H), 12.81-12.29 (m, 2H), 8.53 (s, 2H), 8.01-7.97 (m, 2H), 7.59-7.21 (m, 3H), 4.17-4.06 (m, 1H), 3.95-3.89 (m 5H), 3.80-3.50 (m, 13H), 3.45-3.21 (m, 3H), 2.86 (s, 3H), 2.34-2.19 (m, 4H), 1.82-1.59 (m, 4H), 1.28 (d, J = 6.4 Hz, 2H). Hydrochloride. |
| 28 | Ethyl 2-oxopentanoate | 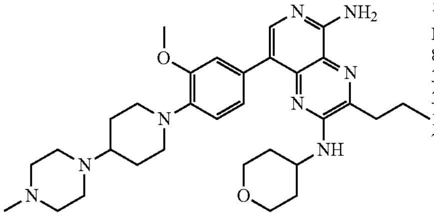 | $^1$H NMR (400 MHz, $CD_3OD$) δ 7.75 (d, J = 7.6 Hz, 1H), 7.71 (s ,1H), 7.47 (s, 1H), 7.38 (d, J = 8.0 Hz, 1H), 4.11-4.04 (m, 1H), 4.01 (s, 3H), 3.90-3.48 (m, 15H), 3.31-3.25 (m 2H), 2.95 (s, 3H), 2.78 (t, J = 7.6 Hz, 2H), 2.49-2.43 (m, 4H), 1.86-1.77 (m, 4H), 1.71-1.61 (m, 2H), 0.99 (t, J = 7.6 Hz, 3H). |

The compounds in the following table was provided by the synthesis method of compound 8, while tert-butyl 4-(piperidin-4-yl) piperazine-1-carboxylate was replaced with the corresponding starting materials in the following table:

| No | starting materials | structures | HNMR |
|---|---|---|---|
| 36 | 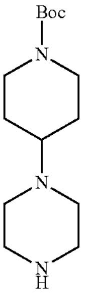 [SMILES: CC(C)(C)OC(=O)N1CCC(N2CCNCC2)CC1] | 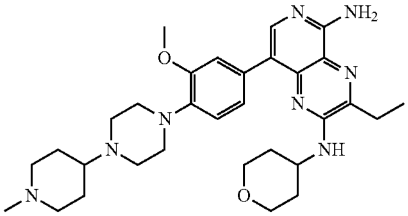 [SMILES: CCc1nc2c(N)ncc(-c3ccc(N4CCN(C5CCN(C)CC5)CC4)c(OC)c3)c2nc1NC1CCOCC1] | $^1$H NMR (400 MHz, $CD_3OD$) δ 7.58 (s , 1H), 7.19 (s, 1H), 7.15-7.12 (m, 1H), 7.02 (d, J = 8.0 Hz, 1H), 4.16-4.09 (m, 1H), 3.88-3.83 (m, 5H), 3.66-3.55 (m, 7H), 3.39-3.24 (m, 5H), 3.13-3.03 (m, 3H), 2.83-2.76 (m, 5H), 2.48-2.45 (m, 2H), 2.15-2.06 (m, 2H), 1.84-1.80 (m, 2H), 1.67-1.57 (m, 2H), 1.32 (t, J = 7.2 Hz, 3H). |
| 37 | 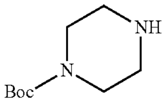 | 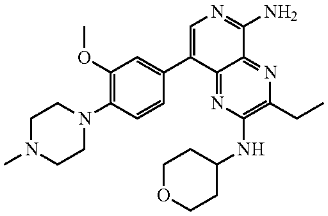 [SMILES: CCc1nc2c(N)ncc(-c3ccc(N4CCN(C)CC4)c(OC)c3)c2nc1NC1CCOCC1] | $^1$H NMR (400 MHz, DMSO-$d_6$) δ 13.58 (s, 1H), 11.20 (s, 1H), 8.47 (s, 2H), 7.91-7.89 (m, 2H), 7.29-7.23 (m, 2H), 7.01 (d, J = 8.8 Hz, 1H), 4.16-4.07 (m, 1H), 3.93-3.89 (m, 2H), 3.85 (s ,3H), 3.57-3.47 (m, 4H), 3.26-3.19 (m, 4H), 3.13-3.07 (m, 2H), 2.88 (q, J = 7.6 Hz, 2H), 2.80 (d, J = 4.8 Hz, 3H), 1.83-1.79 (m, 2H), 1.73-1.63 (m, 2H), 1.31 (t, J = 7.2 Hz, 3H). Hydrochloride. |

-continued

| No | starting materials | structures | HNMR |
|---|---|---|---|
| 38 | 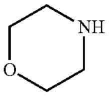 | 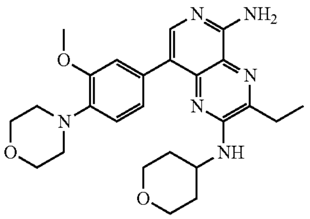 [SMILES: CCc1nc2c(N)ncc(-c3ccc(N4CCOCC4)c(OC)c3)c2nc1NC1CCOCC1] | $^{1}H$ NMR (400 MHz, DMSO-$d_6$) 6 7.93 (s, 1H), 7.25-7.21 (m, 2H), 7.02 (d, J = 7.2 Hz, 1H), 6.89 (d, J = 8.0 Hz, 1H), 6.49 (s, 2H), 4.16-4.09 (m, 1H), 3.92-3.89 (m, 2H), 3.83 (s, 3H), 3.76-3.74 (m, 4H), 3.30-3.25 (m, 2H), 3.00-2.98 (m, 4H), 2.81 (q, J = 7.2 Hz, 2H), 1.88-1.84 (m, 2H), 1.67-1.57 (m, 2H), 1.31 (t, J = 7.2 Hz, 3H). |

Example 2: The intermediate tert-butyl 4-(1-(4-(5-((2,4-dimethoxybenzyl)amino)-3-ethyl-2-((tetrahydro-2H-pyran-4-yl)amino)pyridino[3,4-b]pyrazine-8-yl)-2-methoxyphenyl)piperidine-4-yl)piperazine-1-carboxylic acid afforded in Step 11 of Example 1 can also be synthesized by the following method, and then compound 8 can be afforded through the Step 12 and 13 in Example 1:

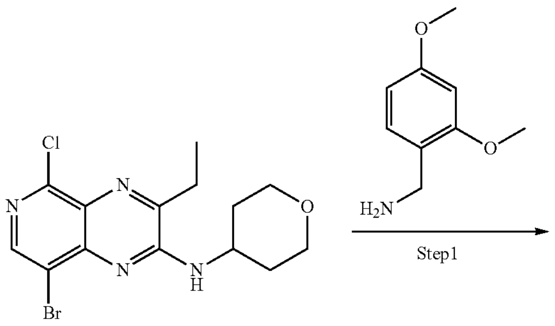

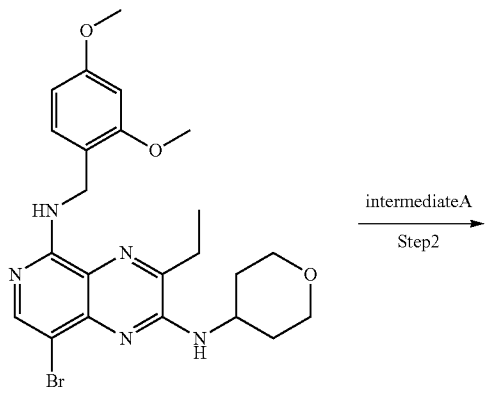

-continued

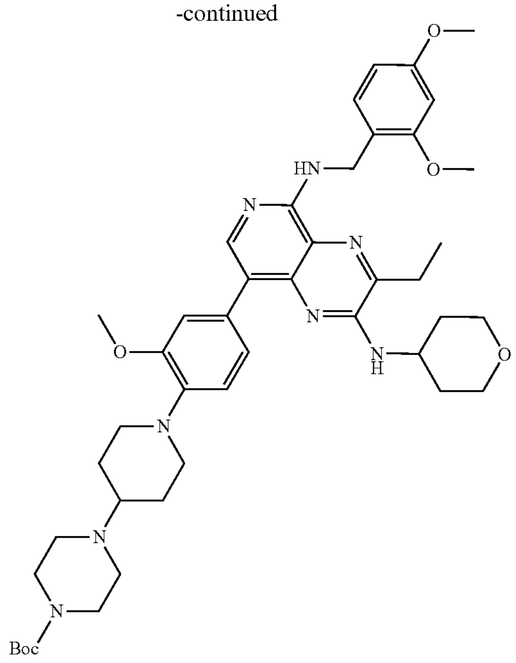

intermediateB

Step 1: The mixture of 8-bromo-5-chloro-3-ethyl-N-(tetrahydropyran-4-yl)pyridino[3,4-b]pyrazin-2-amine (6.00 g, 16.1 mmol) and 2,4-dimethoxybenzamine (15 g, 90 mmol) were stirred at 145° C. overnight. At the end of the reaction, the mixture was cooled to room temperature and purified by silica gel chromatography column (petroleum ether/ethyl acetate=5:1 to 3:1) to obtain yellow solid 8-bromo-N5-(2,4-dimethoxybenzyl)-3-ethyl-N2-(tetrahydro-2H-pyran-4-yl)pyridino[3,4-b]pyrazine-2,5-diamine (5.5 g, yield 68%). MS Found: 502.5 $[M+H]^+$.

Step 2: Cesium carbonate (5.20 g, 15.9 mmol) in water (15 mL) and Pd(dppf)$Cl_2$ (583 mg, 0.80 mmol) was added to 1, 4-dioxane (100 mL) mixture containing 8-bromo-N5-(2,4-dimethoxybenzyl)-3-ethyl-N2-(tetrahydro-2H-pyran-4-yl)pyridino[3,4-b]pyrazine-2,5-diamine (4.00 g, 7.97 mmol) and intermediate A (4.0 g, 7.97 mmol). This mixture was stirred and reacted at 110° C. for 3 hours under nitrogen protection. At the end of the reaction, the mixture was cooled to room temperature and concentrated under reduced pressure, and ethyl acetate (50 mL) and water (50 mL) were added. The solution was extracted three times (50 mL×3) with ethyl acetate. The combined organic phases was washed with saturated saline (10 m), dried over anhydrous sodium sulfate, filtered, and the filtrate was concentrated under reduced pressure. The resulting residue was purified by silicagel chromatography (petroleum ether/ethyl acetate=1:1 to 0:1 to ethyl acetate/methanol=20:1) to obtain yellow solid intermediate B (3.1 g, yield 49).

The compounds in the following table were provided by the Step 9 in Example 1, while tetrahydropyran-4-amine was replaced with the corresponding starting materials in the table below, and reacted with intermediate M according to the synthesis method of compound 8 in example 2:

| No | starting materials | structures | HNMR |
| --- | --- | --- | --- |
| 92 | 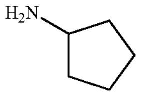 | 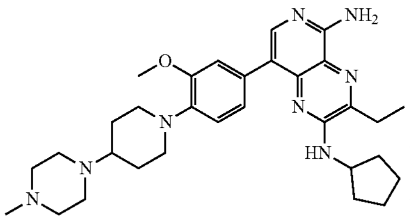 [SMILES: CCc1nc2c(N)ncc(-c3ccc(N4CCC(N5CCN(C)CC5)CC4)c(OC)c3)c2nc1NC1CCCC1] | $^1$H NMR (400 MHz, DMSO-$d_6$) δ 8.24 (s, 3H), 7.90 (s, 1H), 7.34 (d, J = 1.6 Hz, 1H), 7.18-7.16 (m, 1H), 7.00 (d, J = 6.4 Hz, 1H), 6.89 (d, J = 8.4 Hz, 1H), 6.45 (brs, 2H), 4.36 (d, J = 8.0 Hz, 1H), 3.91 (s, 3H), 3.43 (s, 2H), 2.84-2.78 (m, 2H), 2.64 (d, J = 28.0 Hz, 1H), 2.55 (d, J = 12.0 Hz, 4H), 2.40 (s, 4H), 2.32 (s, 2H), 2.20 (s, 3H), 1.94 (d, J = 6.4 Hz, 2H), 1.83 (d, J = 12.0 Hz, 2H), 1.69 (d, J = 6.4 Hz, 2H), 1.64-1.54 (m, 4H), 1.52-1.46 (m, 2H), 1.32-1.28 (m, 3H). Formate |
| 77 | 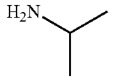 | 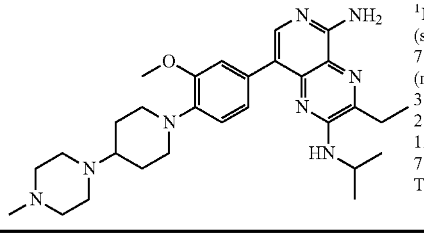 | $^1$H NMR (400 MHz, DMSO-$d_6$) δ 8.23 (s, 2H), 7.74 (s, 1H), 7.56 (d, J = 7.2 Hz, 1H), 7.30 (s, 1H), 7.21-7.15 (m, 1H), 6.98 (d, J = 8.4 Hz, 1H), 4.36-4.30 (m, 1H), 3.83 (s, 3H), 3.54 (d, J = 12.0 Hz, 2H), 3.20-3.11 (m, 8H), 2.90 (s, 1H), 2.90-2.83 (m, 2H), 2.72 (s, 3H), 2.67 (d, J = 12.0 Hz, 2H), 1.99 (d, J = 12.0 Hz, 2H), 1.71 (d, J = 12.0 Hz, 2H), 1.32 (t, J = 7.2 Hz, 3H), 1.21 (d, J = 6.4 Hz, 6H). Trifluoroacetate |

The compounds in the following table were provided by the synthesis method of compound 8 in example 1, while tetrahydropyran-4-amine was replaced with the corresponding starting materials in the table below in step 9, then afforded by the method of Example 2:

| No | starting materials | structures | HNMR |
| --- | --- | --- | --- |
| 69 | 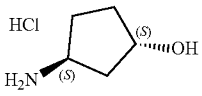 | 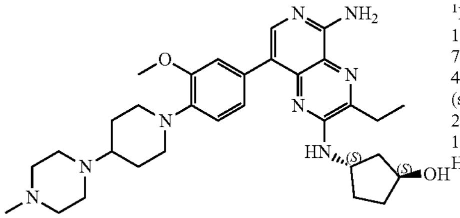 | $^1$H NMR (400 MHz, DMSO-$d_6$): δ 7.90 (s. 1H), 7.34 (d, J = 1.2 Hz, 1H), 7.17 (dd, J = 8.0, 2.0 Hz, 1H), 6.97 (d, J = 7.2 Hz, 1H), 6.90 (d, J = 8.4 Hz, 1H), 6.41 (br s, 2H), 4.63-4.58 (m, 1H), 4.47-4.46 (m, 1H), 4.25-4.20 (m, 1H), 3.83 (s, 3H), 3.46-3.43 (m 2H), 2.79 (q, J = 7.2 Hz, 2H), 2.56-2.50 (m, 5H), 2.36-2.26 (m, 5H), 2.15 (s, 3H), 2.13-2.08 (m 1H), 1.92-1.81 (m, 5H), 1.61-1.40 (m, 4H), 1.30 (t, J = 7.2 Hz, 3H). |
| 70 | 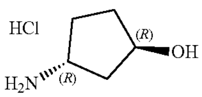 | 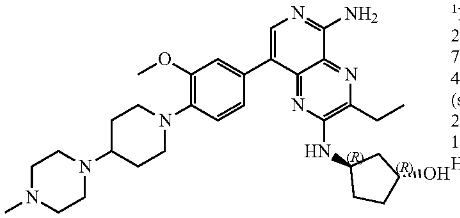 | $^1$H NMR (400 MHz, DMSO-$d_6$): δ 7.90 (s. 1H), 7.34 (d, J = 2.0 Hz, 1H), 7.17 (dd, J = 8.4, 1.6 Hz, 1H), 6.98 (d, J = 7.2 Hz, 1H), 6.89 (d, J = 8.8 Hz, 1H), 6.41 (br s, 2H), 4.63-4.58 (m, 1H), 4.48-4.47 (m, 1H), 4.25-4.19 (m, 1H), 3.83 (s, 3H), 3.46-3.43 (m 2H), 2.79 (q, J = 6.8 Hz, 2H), 2.56-2.53 (m, 3H), 2.37-2.25 (m, 5H), 2.15 (s, 3H), 2.15-2.07 (m 1H), 1.93-1.81 (m, 5H), 1.61-1.39 (m, 4H), 1.29 (t, J = 7.2 Hz, 3H). |

-continued

| No | starting materials | structures | HNMR |
|---|---|---|---|
| 71 | HCl 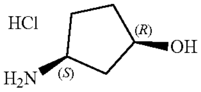 | 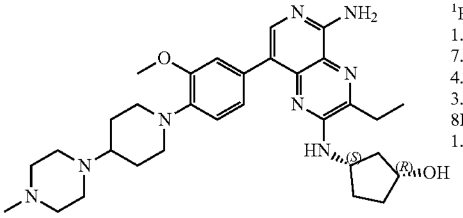 | $^1$H NMR (400 MHz, DMSO-$d_6$): δ 7.91 (s. 1H), 7.34 (d, J = 1.2 Hz, 1H), 7.17 (dd, J = 8.4, 2.0 Hz, 1H), 7.05 (d, J = 7.2 Hz, 1H), 6.90 (d, J = 8.4 Hz, 1H), 6.48 (s, 2H), 4.78-4.77 (m, 1H), 4.42-4.36 (m, 1H), 4.12 (s, 1H), 3.81 (s, 3H), 3.47-3.44 (m 3H), 2.79 (q, J = 7.2 Hz, 2H), 2.73-2.54 (m, 8H), 2.36 (s, 3H), 2.18-2.12 (m, 1H), 1.93-1.86 (m 3H), 1.80-1.56 (m, 6H), 1.31 (t, J = 7.2 Hz, 3H). |
| 72 | HCl 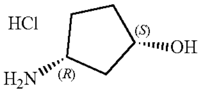 | 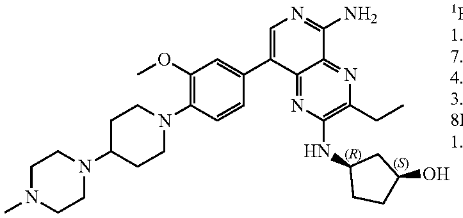 | $^1$H NMR (400 MHz, DMSO-$d_6$): δ 7.91 (s. 1H), 7.34 (d, J = 1.6 Hz, 1H), 7.17 (dd, J = 8.4, 1.6 Hz, 1H), 7.05 (d, J = 7.2 Hz, 1H), 6.90 (d, J = 8.8 Hz, 1H), 6.47 (s, 2H), 4.78-4.77 (m, 1H), 4.42-4.36 (m, 1H), 4.12 (s, 1H), 3.81 (s, 3H), 3.47-3.44 (m 3H), 2.79 (q, J = 7.2 Hz, 2H), 2.73-2.54 (m, 8H), 2.32 (s, 3H), 2.18-2.12 (m, 1H), 1.95-1.85 (m 3H), 1.80-1.56 (m, 6H), 1.31 (t, J = 7.2 Hz, 3H). |

The compound 10 in the following table was provided by synthesis method in example 2, while 2, 4-dimethoxybenzamine was replaced with methylamine.

| No | starting materials | structures | HNMR |
|---|---|---|---|
| 10 | Methylamine | 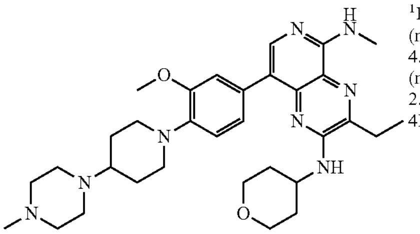 | $^1$H NMR (400 MHz, DMSO-$d_6$) δ 8.00 (s, 1H), 7.22-7.19 (m, 2H), 6.99-6.96 (m, 2H), 6.88 (d, J = 8.4 Hz, 1H), 4.16-4.07 (m, 1H), 3.92-3.88 (m, 2H), 3.82 (s, 3H), 3.47-3.24 (m, 9H), 3.00 (d, J = 5.2 Hz, 3H), 2.83-2.80 (m, 2H), 2.63-2.50 (m, 6H), 2.28(s, 3H), 1.87-1.84 (m, 4H), 1.66-1.56 (m, 4H), 1.31 (t, J = 7.2 Hz, 3H). |

The compound 23 in the following table was provided by the synthesis method of intermediate A in example 1 and synthesis method in example 2, while 1-fluoro-2-methoxy-4-nitrobenzene was replaced with the starting material in the following table:

| No | starting materials | structures | HNMR |
|---|---|---|---|
| 23 | 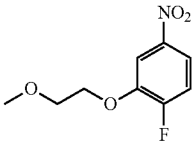 | 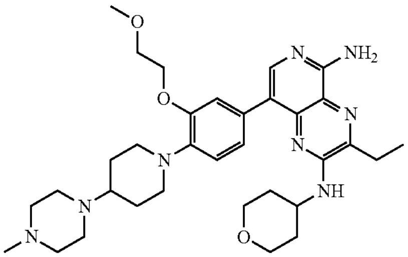 [SMILES: CCc1nc2c(N)ncc(-c3ccc(N4CCC(N5CCN(C)CC5)CC4)c(OCCOC)c3)c2nc1NC1CCOCC1] | $^1$H NMR (400 MHz, DMSO-$d_6$) δ 7.91 (s. 1H), 7.23-7.21 (m, 2H), 7.05 (d, J = 7.2 Hz, 1H), 6.89 (d, J = 8.0 Hz, 1H), 6.55 (s, 2H), 4.13-4.11 (m, 3H), 3.91-3.88 (m, 2H), 3.70-3.68 (m, 2H), 3.57-3.54 (m 2H), 3.32-3.25 (m, 8H), 2.91-2.74 (m, 8H), 2.59-2.50 (m 3H), 2.48-2.42 (m, 2H), 1.93-1.84 (m, 4H), 1.67-1.57 (m, 4H), 1.31 (t, J = 7.2 Hz, 3H). |

The compound 31 in the following table was provided by the synthesis method of intermediate A in example 1 and synthesis method in example 2, while 1-fluoro-2-methoxy-4-nitrobenzene and tert-butyl 4-(piperidin-4-yl)piperazine-1-carboxylate were replaced with 1-fluoro-2-methyl-4-nitrobenzene and tert-butyl 3,9-diazaspiro[5.5]undecane-3-carboxylate in the following table respectively.

| No | starting materials | structures | HNMR |
| --- | --- | --- | --- |
| 31 | 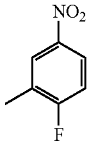, 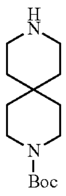 | 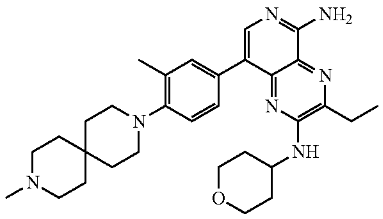 [SMILES: CCc1nc2c(N)ncc(-c3ccc(N4CCC5(CCN(C)CC5)CC4)c(C)c3)c2nc1NC1CCOCC1] | $^{1}$H NMR (400 MHz, DMSO-$d_6$) δ 13.53 (br, 1H), 10.58 (br s, 1H), 8.50 (s, 2H), 7.91-7.89 (m, 2H), 7.62-7.56 (m, 1H), 7.45-7.26 (m, 1H), 4.13-4.08 (m, 2H), 3.91-3.86 (m, 8H), 3.29-3.24 (m, 5H), 3.13-3.04 (m 3H), 2.88 (q, J = 7.2 Hz, 2H), 2.73 (d, J = 4.8 Hz, 3H), 2.12-1.97 (m, 2H), 1.83-1.75 (m, 3H), 1.71-1.65 (m, 5H), 1.33 (t, J = 7.2 Hz, 3H). Hydrochloride |

The compounds in the following table were provided by the synthesis method of intermediate A in example 1 and synthesis method in example 2, while 2, 4-(piperidin-4-yl) piperazine-1-carboxylic acid tert-butyl ester was replaced with the corresponding starting materials in the following table.

| No | starting materials | structures | HNMR |
| --- | --- | --- | --- |
| 32 | 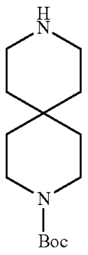 [SMILES: CC(C)(C)OC(=O)N1CCC2(CCNCC2)CC1] | 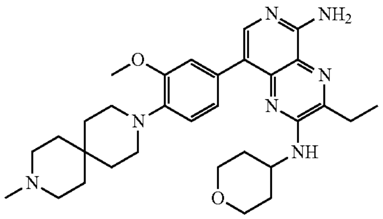 [SMILES: CCc1nc2c(N)ncc(-c3ccc(N4CCC5(CCN(C)CC5)CC4)c(OC)c3)c2nc1NC1CCOCC1] | HNMR ($CDCl_3$, 400 MHz): 7.99 (s, 1H), 7.26-7.24 (m, 1H), 7.14 (d, J = 1.6 Hz, 1H), 6.96 (d, J = 8.4 Hz, 1H), 6.05 (br s, 2H), 4.96 (d, J = 7.2 Hz, 1H), 4.26-4.15 (m, 1H), 4.01-3.98 (m, 2H), 3.89 (s, 3H), 3.49-3.42 (m, 2H), 3.07-3.05 (m, 4H), 3.04-2.99 (m, 4H), 2.75 (q, J = 7.2 Hz, 2H), 2.69 (s, 3H), 2.07-2.04 (m, 2H), 2.00-1.93 (m, 4H), 1.80-1.78 (m, 4H), 1.62-1.52 (m, 2H), 1.44 (t, J = 7.2 Hz, 3H). |
| 33 | 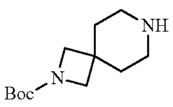 [SMILES: CC(C)(C)OC(=O)N1CC2(CCNCC2)C1] | 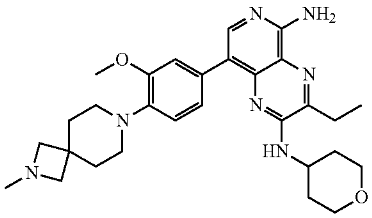 [SMILES: CCc1nc2c(N)ncc(-c3ccc(N4CCC5(CC4)CN(C)C5)c(OC)c3)c2nc1NC1CCOCC1] | $^{1}$H NMR (400 MHz, DMSO-$d_6$) δ 10.50 (br s, 1H), 7.89 (s, 1H), 7.23-7.18 (m, 2H), 6.91-6.78 (m, 2H), 4.17-4.07 (m, 1H), 3.92-3.89 (m, 4H), 3.82 (s, 3H), 3.26-3.23 (m, 5H), 2.97-2.89 (m, 3H), 2.84-2.80 (m, 5H), 1.95-1.89 (m, 4H), 1.81-1.70 (m, 2H), 1.55-1.33(m, 2H), 1.42 (t, J = 7.2 Hz, 3H). Hydrochloride |
| 39 | 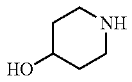 | 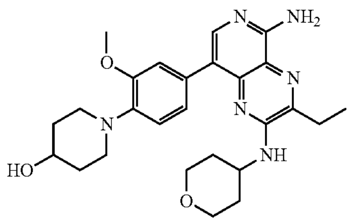 [SMILES: CCc1nc2c(N)ncc(-c3ccc(N4CCC(O)CC4)c(OC)c3)c2nc1NC1CCOCC1] | $^{1}$H NMR (400 MHz, DMSO-$d_6$): 7.92 (s, 1H), 7.22-7.18 (m, 2H), 7.00 (d, J = 6.8 Hz, 1H), 6.89 (d, J = 8.4 Hz, 1H), 6.44 (s, 2H), 4.64 (d, J = 4.4 Hz, 1H), 4.17-4.08 (m, 1H), 3.92-3.89 (m, 2H), 3.82 (s, 3H), 3.64-3.55 (m, 1H), 3.30-3.25 (m, 4H), 2.81 (q, J = 6.8 Hz, 2H), 2.67 (t, J = 9.6 Hz, 2H), 1.88-1.84 (m, 4H), 1.67-1.51 (m, 4H), 1.31 (t, J = 6.8 Hz, 3H). |

The compounds in the following table were provided by the synthesis method of intermediate A in example 1 and synthesis method in example 2, while 1-benzyl-4-piperidone was replaced with the starting material in the table below.

| No | starting materials | structures | HNMR |
|---|---|---|---|
| 322 | 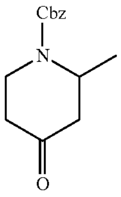 [SMILES: CC1CC(=O)CCN1C(=O)OCc1ccccc1] | 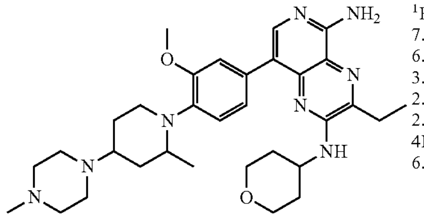 | $^1$H NMR (400 MHz, DMSO-$d_6$) δ 7.95-7.92 (m, 1H), 7.20-7.17 (m, 2H), 7.06-7.00 (m, 1.9H), 6.85-6.83 (m, 0.1H), 6.47-6.43 (m, 2H), 4.14-4.06 (m, 1H), 3.90-3.88 (m, 2H), 3.81 (s, 3H), 3.27-3.20 (m, 2H), 3.12-3.09 (m, 2H), 2.83-2.78 (m, 2H), 2.67-2.64 (m, 1H), 2.61-2.51 (m, 4H), 2.50-2.49 (m,1H), 2.37-2.31 (m, 5H), 2.14 (s, 3H), 1.88-1.75 (m, 4H), 1.65-1.46 (m, 3H), 1.31 (t, J = 7.2 Hz, 3H), 0.88 (d, J = 6.0 Hz, 3H). |

The compounds in the following table were provided by the method of example 1, while 2-oxobutyrate ethyl ester was replaced with the starting material in the following-table in step 7, then afforded by the method of Example 2

| No | starting materials | structures | HNMR |
|---|---|---|---|
| 25 | Ethyl glyoxylate (50% toluene solution) | 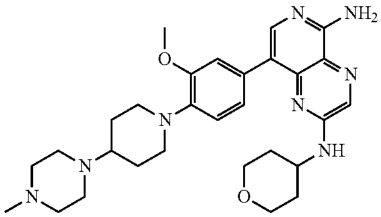 [SMILES: COc1cc(-c2cnc(N)c3ncc(NC4CCOCC4)nc23)ccc1N1CCC(N2CCN(C)CC2)CC1] | $^1$H NMR (400 MHz, $CD_3OD$) δ 8.14 (s, 1H), 7.82 (s, 1H), 7.28 (d, J = 1.2 Hz, IH), 7.18-7.16 (m, 1H), 7.06-7.04 (m, 1H), 4.12-4.05 (m, 1H), 3.99-3.96 (m, 2H), 3.93 (s, 3H), 3.61-3.58 (m, 2H), 3.47-3.42 (m, 2H), 3.11-2.84 (m, 8H), 2.71-2.66 (m, 3H), 2.63 (s, 3H), 2.07-2.00 (m, 4H), 1.88-1.78 (m, 2H), 1.65-1.55 (m, 2H). |

The compounds in the following table was provided by the synthesis method of intermediate A in example 1 and synthesis method in example 2, while 4-(4-(4-iodo-2-methoxyphenyl) cyclohexyl) piperazine-1-tert-butyl formate was replaced with the starting material in the table below.

| No | starting materials | structures | HNMR |
|---|---|---|---|
| 44 | 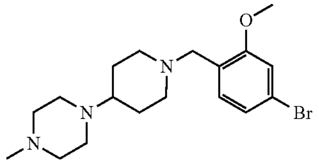 | 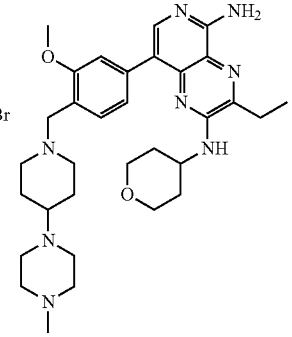 | $^1$H NMR (400 MHz, DMSO-$d_6$) δ 8.25 (brs, 2 H), 7.98 (s, 1H), 7.31-7.26 (m, 2H), 7.22 (s, 1H), 7.08 (d, J = 8.0 Hz, 1H), 6.61 (s, 2H), 4.13-4.09 (m, 1H), 3.90 (d, J = 8.0 Hz, 2H), 3.82 (s, 3H), 3.59 (s, 2H), 3.27-3.21 (m, 2H), 2.98-2.88 (m, 2H), 2.84-2.79 (m, 2H), 2.55 (s, 1H), 2.51-2.43 (m, 8H), 2.25 (s, 3H), 2.11-2.06 (m, 2H), 1.84 (d, J = 12.0 Hz, 2H), 1.75 (d, J = 12.0 Hz, 2H), 1.68-1.55 (m, 2H), 1.52-1.37 (m, 2H), 1.33-1.29 (m, 3H). LC-MS: (ESI) m/z. 575.3 [M + 1]$^+$. Formate |

Example 3: 3-ethyl-8-(6-(4-(4-methylpiperazine-1-yl) piperidine-1-yl) pyridin-3-yl)-N2-tetrahydro-2H-pyran-4-yl) pyridino [3,4-b] pyrazine-2,5-diamine (Compound 21)
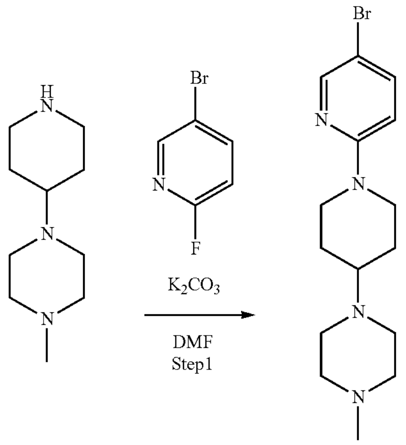
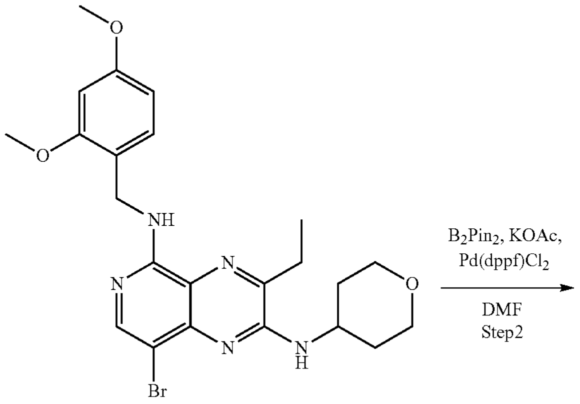
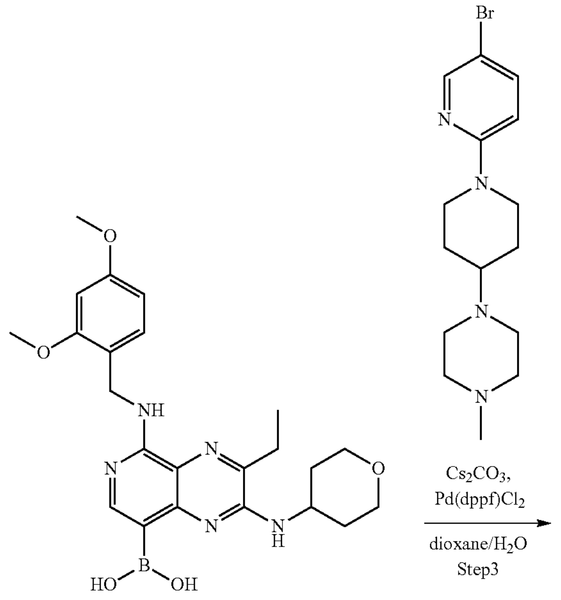
intermediateC
-continued
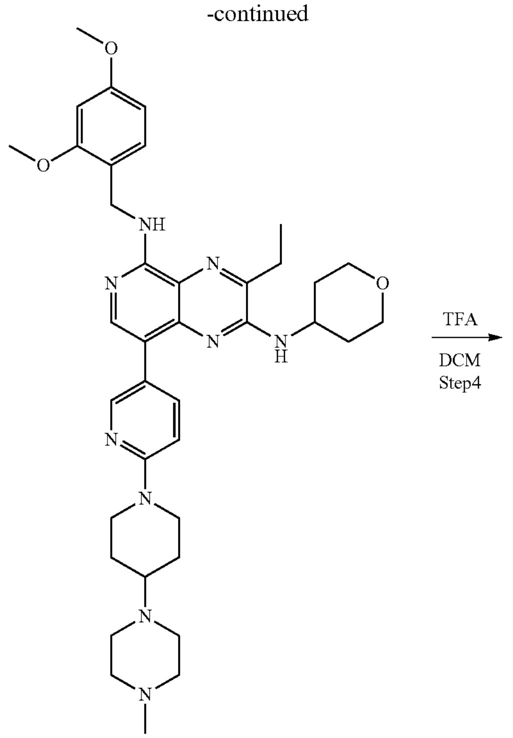
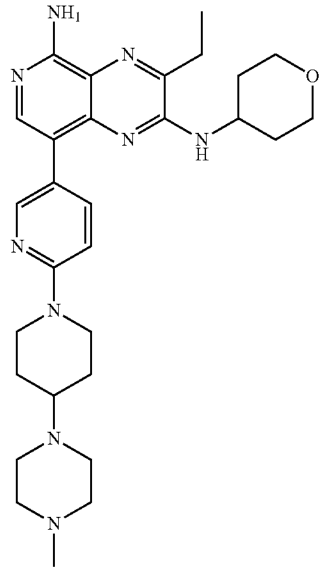
compound 21

Step 1: 5-Bromo-2-fluoropyridine (500 mg, 2.84 mmol) and 1-methyl-4-(4-piperidinyl) piperazine (520 mg, 2.84 mmol) was dissolved in N,N-dimethylformamide (10 mL), and potassium carbonate (784 mg, 5.68 mmol) was added. This mixture was stirred and reacted at 110° C. for 6 hours. At the end of the reaction, the mixture was cooled to room temperature and water (50 mL) was added. The solution was extracted with ethyl acetate (20 mL×3). The organic phases were combined, washed with saturated saline (30 mL), dried over anhydrous sodium sulfate, filtered, and the filtrate was concentrated under reduced pressure. The resulting residue was purified by silica gel chromatography (dichloromethane:methanol=20:1 to 10:1) to obtain white solid (800 mg, yield 83%). $^1$H NMR (400 MHz, $CDCl_3$): δ 8.16 (d, J=2.0 Hz, 1H), 7.49 (dd, J=8.8, 2.0 Hz, 1H), 6.56 (d, J=8.8 Hz, 1H), 4.29-4.26 (m, 2H), 2.86-2.79 (m, 2H), 2.71-2.55 (m, 4H), 2.49-2.42 (m, 5H), 2.28 (s, 3H), 1.93-1.85 (m, 2H), 1.57-1.47 (m, 2H).

Step 2: Potassium acetate (364 mg, 3.19 mmol) and $Pd(dppf)Cl_2$ (117 mg, 0.16 mmol) were added to the N-dimethylformamide (5 mL) mixture containing 8-bromo-N5-(2,4-dimethoxybenzyl)-3-ethyl-N2-(tetrahydro-2H-pyran-4-yl) pyridino [3,4-b] pyrazine-2,5-diamine (800 mg, 1.59 mmol) and divaleryl diboron (810 mg, 3.19 mmol). This mixture was stirred and reacted at 110° C. for 5 hours under nitrogen protection. At the end of the reaction, the mixture was cooled to room temperature and water (30 mL) was added. The solution was extracted three times (20 mL×3) with ethyl acetate. The organic phases were combined, washed with saturated saline (5 mL), dried over anhydrous sodium sulfate, filtered, and the filtrate was concentrated under reduced pressure. The resulting residue was purified by silica gel chromatography (petroleum ether/ethyl acetate=1:1 to 0:1 to ethyl acetate/methanol=10:1) to obtain brown solid intermediate C (230 mg, yield 31%). MS Found: 468.6 $[M+H]^+$.

Step 3: The synthesis method of step 2 in Example 2 was referred, 1-(1-(5-bromopyridine-2-yl) piperidine-4-yl)-4-methylpiperazine (87 mg, 0.26 mmol) was reacted with intermediate C (100 mg, 0.21 mmol) to obtain yellow solid N5-(2,4-Dimethoxybenzyl)-3-ethyl-8-(6-(4-(4-methylpiperazine-1-yl)piperidine-1-yl)pyridin-3-yl)-N2-(tetrahydro-2H)pyran-4-yl)pyridino[3,4-b]pyrazine-2,5-diamine (70 mg, yield 49%). MS Found: 682.6 $[M+H]^+$.

Step 4: The method of Step 12 of Example 1 was referred, N5-(2,4-dimethoxybenzyl)-3-ethyl-8-(6-(4-(4-methylpiperazine-1-yl)piperidine-1-yl)pyridin-3-yl)-N2-(tetrahydro-2H)pyran-4-yl)pyridino[3,4-b]pyrazine-2,5-diamine (70 mg, 0.1 mmol) reacted to yellow solid compound 21 (70 mg, 0.1 mmol). $^1$H NMR (400 MHz, DMSO-$d_6$): δ 8.38 (d, J=2.0 Hz, 1H), 7.92-7.88 (m, 2H), 7.05 (d, J=6.8 Hz, 1H), 6.85 (d, J=8.8 Hz, 1H), 6.45 (s, 2H), 4.35-4.31 (m, 2H), 4.11-4.03 (m, 1H), 3.93-3.91 (m, 2H), 3.40-3.28 (m, 4H), 2.83-2.78 (m, 4H), 2.42-2.30 (m, 7H), 2.14 (s, 3H), 1.89-1.80 (m 4H), 1.66-1.57 (m, 2H), 1.44-1.34 (m, 2H), 1.31 (t, J=7.2 Hz, 3H). MS Found: 532.3$[M+H]^+$.

Example 4: 3-ethyl-8-(4-(4-(4-methylpiperazine-1-yl) piperidine-1-yl)-3-(methylsulfyl)phenyl)-N2-(tetrahydro-2H-pyran-4-yl) pyridino [3,4-b] pyrazine-2, 5-diamine (Compound 18)

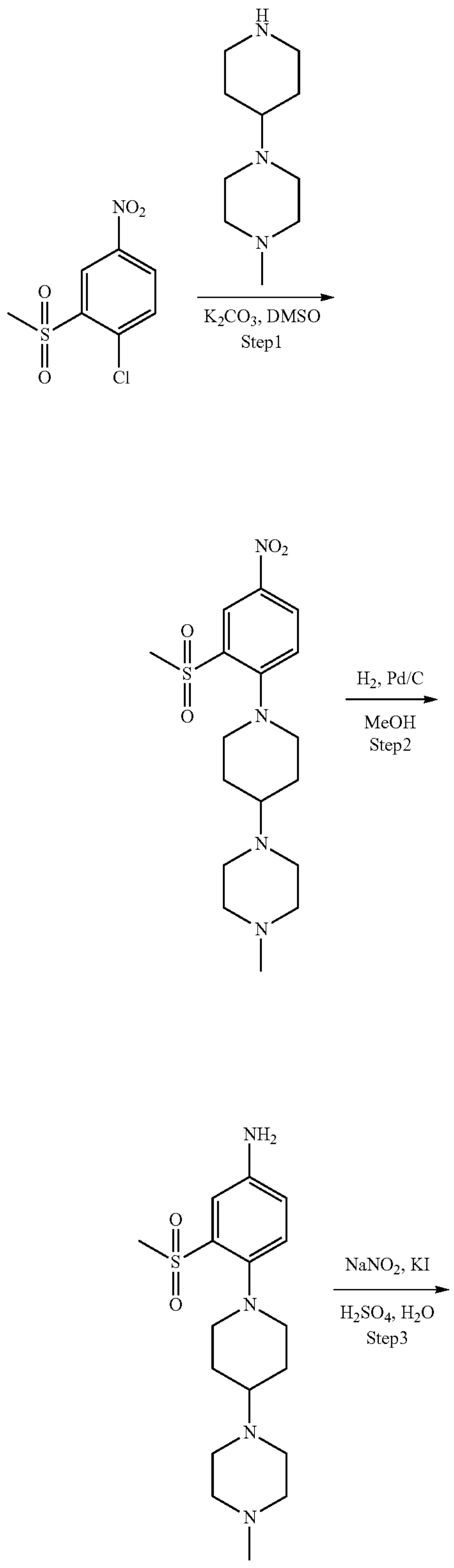

-continued

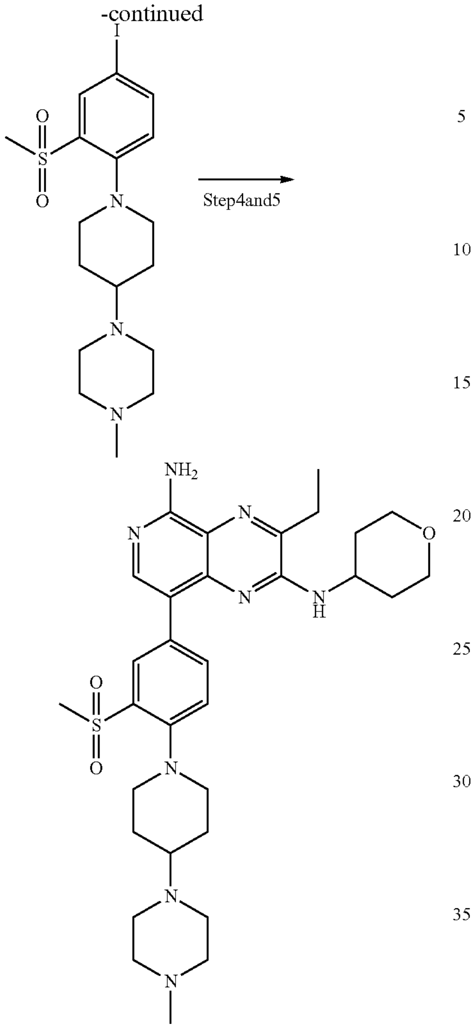

compound18

Step 1: Commercially available 1-chloro-2-(methylsulfone)-4-nitrobenzene (1.20 g, 5.08 mmol) and 1-methyl-4-(4-piperidinyl) piperazine (931 mg, 5.08 mmol) was dissolved in dimethyl sulfoxide (20 mL), and potassium carbonate (1.40 g, 10.2 mmol) was added. This mixture was stirred and reacted at 100° C. for 2 hours. At the end of the reaction, the mixture was cooled to room temperature and added to water (100 mL). The solution was extracted with ethyl acetate (20 mL×5). The organic phases were combined, washed with saturated saline (10 mL×2), and concentrated under reduced pressure. Dichloromethane (20 mL) was added, and the solution was poured into concentrated hydrochloric acid (3 mL) aqueous solution (30 mL), and washed with dichloromethane (20 mL). The aqueous phase was basified with 5% sodium hydroxide solution and extracted with dichloromethane (20 mL×4). The organic phases were combined, washed with saturated saline (5 mL), dried over anhydrous sodium sulfate, filtered, and the filtrate was concentrated under reduced pressure to obtain brown solid (1.70 g, yield 87%). $[M+H]^+$. $^1H$ NMR (400 MHz, $CDCl_3$) δ 8.95 (d, J=2.8 Hz, 1H), 8.42 (dd, J=8.8, 2.8 Hz, 1H), 7.44 (d, J=9.2 Hz, 1H), 3.55-3.52 (m, 2H), 3.32 (s, 3H), 2.87-2.81 (m, 2H), 2.73-2.65 (m, 4H), 2.58-2.50 (m, 4H), 2.43-2.34 (m, 1H), 2.30 (s, 1H), 2.08-2.05 (m, 2H), 1.82-1.72 (m, 2H). MS Found: 383.2.

Step 2: The method of Step 4 in Example 1 was referred, 1-methyl-4-(1-(2-(methylsulfonyl)-4-nitrophenyl)piperidin-4-yl)piperazine was used as starting material to obtain white solid 4-(4-(4-methylpiperazine-1-yl)piperidine-1-yl)-3-(methylsulfonyl)aniline (1.50 g, yield 96%). MS Found: 353.5 $[M+H]^+$.

Step 3: 4-(4-(4-methylpiperazine-1-yl) piperidine-1-yl)-3-(methylsulfonyl) aniline (600 mg, 1.70 mmol) was dissolved in aqueous solution (5 mL) of concentrated sulfuric acid (834 mg, 8.51 mmol). The solution was reduced to 0° C., and sodium nitrite (117 mg, 8.51 mmol) aqueous solution (0.5 mL) was added dropwise to the solution. The solution was stirred at 0-5° C. for 10 minutes, then potassium iodide (565 mg, 3.40 mmol) aqueous solution (2 mL) was added dropwise to the solution. The solution was stirred at 5° C. for 30 minutes, and then poured into water (5 mL). The solution was basified to pH=10 with 5% sodium hydroxide solution and extracted with dichloromethane (20 mL×3). The organic phases were combined, washed with saturated saline (5 mL), dried over anhydrous sodium sulfate, filtered, and the filtrate was concentrated under reduced pressure. The resulting residue was purified by silica gel chromatography (dichloromethane/methanol=10:1) and C18 column (40-80% acetonitrile aqueous solution) to obtain yellow solid (250 mg, 32% yield). MS Found: 464.1 $[M+H]^+$.

Step 4 and 5: The method of Step 3 and Step 4 in Example 3 was referred. 1-(1-(4-Iodo-2-(methylsulfone)phenyl)piperidin-4-yl)-4-methylpiperazine (87 mg, 0.26 mmol) was reacted with intermediate C (200 mg, 0.43 mmol) to give yellow solid compound 18 (60 mg, two-step yield 46%). $^1H$ NMR (400 MHz, DMSO-$d_6$) δ 8.46 (d, J=1.2 Hz, 1H), 7.98 (s, 1H), 7.91 (d, J=8.4 Hz, 1H), 7.55 (d, J=8.4 Hz, 1H), 7.06 (d, J=7.6 Hz, 1H), 6.62 (s, 2H), 4.28-4.18 (m, 1H), 3.84-3.82 (m, 2H), 3.40 (s, 3H), 3.38-3.32 (m, 4H), 3.26-3.23 (m, 2H), 2.84-2.77 (m, 5H), 2.73-2.59 (m, 6H), 2.37 (s, 3H), 1.93-1.91 (m, 2H), 1.82-1.79 (m, 2H), 1.64-1.57 (m, 4H), 1.31 (t, J=7.2 Hz, 3H). MS Found: 609.4 $[M+H]^+$.

Example 5: 2-(5-(5-amino-3-ethyl-2-((tetrahydro-2H-pyran-4-yl)amino)pyridino[3,4-b]pyrazine-8-yl)-2-(4-(4-methylpiperazine-1-yl)piperidine-1-yl)phenyl)propan-2-ol (Compound 19)

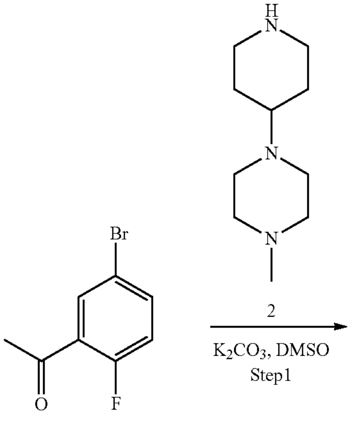

-continued

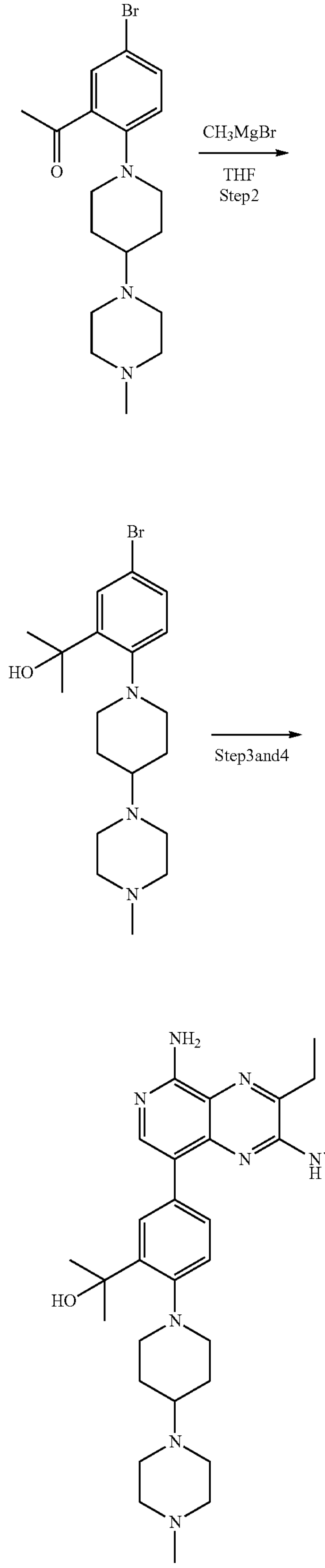

compound19

Step 1: The method of Step 1 in Example 4 was referred, 1-(5-bromo-2-fluorophenyl)ethanone (1.20 g, 5.53 mmol) was reacted with 1-methyl-4-(4-piperidinyl)piperazine (1.01 g, 5.53 mmol) to obtain yellow solid (1.40 g, yield 67%). MS Found: 380.1 $[M+H]^+$.

Step 2: Tetrahydrofuran solution (3.0 M, 1.05 mL, 3.16 mmol) of methylmagnesium bromide solution was added dropwise to 1-(5-bromo-2-(4-(4-methylpiperazine-1-yl)piperidine-1-yl)phenyl)ethyl-1-one (400 mg, 1.05 mmol) in tetrahydrofuran solution (10 mL) at 0° C. under nitrogen protection. The reaction was stirred at 0-5° C. for 10 minutes, then poured into water (10 mL) and extracted with dichloromethane/methanol (10/1, 10 mL×3). The organic phases were combined and concentrated under reduced pressure. The resulting residue was purified by C18 column (aqueous solution of 10-60% acetonitrile) to obtain white solid (170 mg, yield 41%).

Steps 3 and 4: The method of Step 3 and Step 4 in Example 3 was referred, 2-(5-bromo-2-(4-(4-methylpiperazine-1-yl) piperidine-1-yl) phenyl) propan-2-ol (102 mg, 0.26 mmol) was reacted with intermediate C (120 mg, 0.26 mmol) to obtain white solid compound 19 (60 mg, two-step yield 30%). $^1H$ NMR (400 MHz, DMSO-$d_6$): δ 7.92 (s. 1H), 7.64-7.61 (m, 2H), 7.54 (br, 1H), 7.39 (d, J=8.0 Hz, 1H), 7.01 (d, J=7.2 Hz, 1H), 6.52 (s, 2H), 4.20-4.12 (m, 1H), 3.90-3.88 (m, 2H), 3.30-3.27 (m, 4H), 2.97-2.88 (m, 4H), 2.81 (q, J=7.2 Hz, 2H), 2.74-2.59 (m, 7H), 2.37 (s, 3H), 1.95-1.92 (m 2H), 1.84-1.80 (m, 2H), 1.67-1.58 (m, 2H), 1.57-1.48 (m, 8H), 1.31 (t, J=7.2 Hz, 3H). MS Found: 589.4$[M+H]^+$.

Example 6: 3-ethyl-8-(3-((4-(4-methylpiperazine-1-yl)piperidine-1-yl)methyl)phenyl)-N2-(tetrahydro-2H-pyran-4-yl)pyrido[3, 4-b]pyrazine-2,5-diamine (Compound 43)

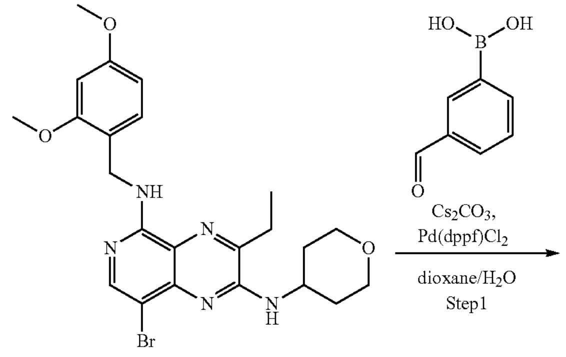

-continued

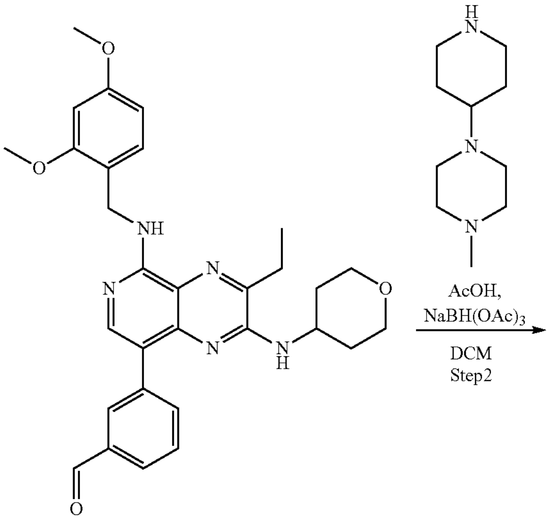

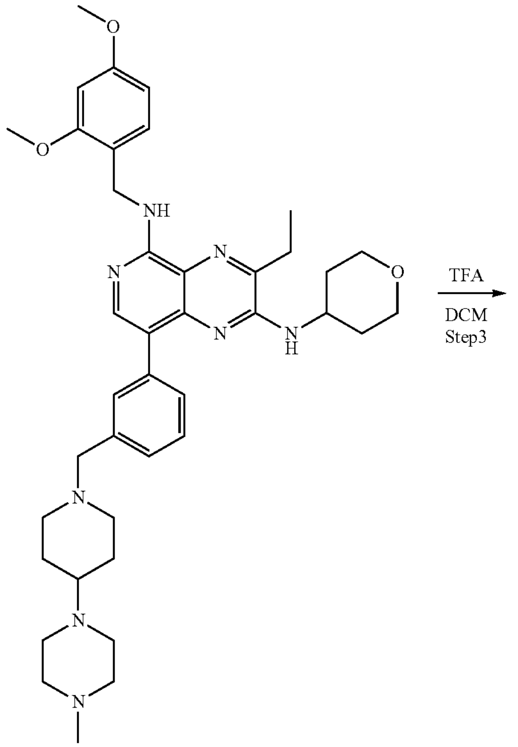

-continued

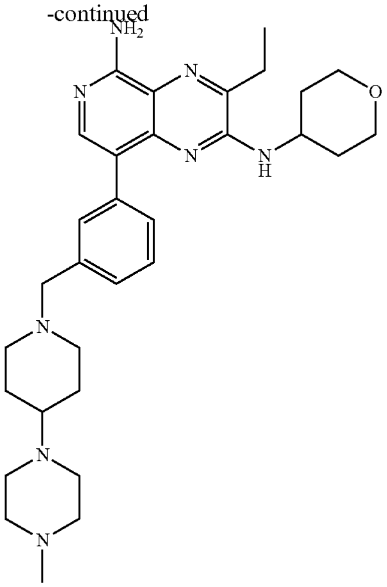

compound43

Step 1: The method of Step 2 of Example 2 was referred, 8-bromo-N5-(2,4-dimethoxybenzyl)-3-ethyl-N2-(tetrahydro-2H-pyran-4-yl)pyridino[3,4-b]pyrazine-2,5-diamine (150 mg, 0.3 mmol) was reacted with 3-formylphenylboronic acid (54 mg, 0.36 mmol) to obtain yellow solid intermediate B (110 mg, yield 69%).

Step 2: 1 A drop of acetic acid was added to dichloromethane (5 mL) mixture containing 3-(5-((2,4-dimethoxybenzyl)amino)-3-ethyl-2-((tetrahydro-2H-pyran-4-yl)amino)pyridino[3,4-b]pyrazin-8-yl)benzaldehyde (110 mg, 0.21 mmol) and 1-methyl-4-(piperidin-4-yl) piperazine (57 mg, 0.31 mmol). The reaction was stirred at room temperature for 5 hours and sodium triacetoxyborohydride (133 mg, 0.63 mmol) was added. After stirred at room temperature overnight, water (5 mL) was added. The mixture was extracted with dichloromethane (15 mL×4), and the organic phases were combined, washed with saturated saline (5 mL), dried over anhydrous sodium sulfate, filtered, and the filtrate was concentrated under reduced pressure. The resulting residue was purified by silica gel chromatography (dichloromethane/methanol=30:1 to 15:1) to obtain yellow solid (100 mg, yield 69%). MS Found: 695.7 $[M+H]^+$.

Step 3: The deprotection method of Step 12 in the synthesis method of compound 8 was referred, N5-(2,4-dimethoxybenzyl)-3-ethyl-8-(3-((4-(4-methylpiperazine-1-yl) piperidine-1-yl) methyl)phenyl)-N2-(tetrahydro-2H-pyran-4-yl)pyridino[3,4-b]pyrazine-2,5-diamine (80 mg, 0.12 mmol) was used as the starting material to obtain white solid compound 43 (40 mg, yield 61%). $^1$H NMR (400 MHz, DMSO-$d_6$) δ 8.01 (s. 1H), 7.76-7.71 (m, 2H), 7.42-7.38 (m, 2H), 7.16 (d, J=7.2 Hz, 2H), 6.75 (s, 2H), 4.13-4.04 (m, 1H), 3.93-3.90 (m, 3H), 3.32-3.26 (m, 5H), 3.15-3.06 (m, 3H), 2.93-2.72 (m, 10H), 2.54 (s, 3H), 1.86-1.84 (m 4H), 1.70-1.61 (m, 4H), 1.31 (t, J=7.2 Hz, 3H). MS Found: 545.3 $[M+H]^+$.

Example 7: 3-ethyl-8-(3-methoxy-4-(4-((4-methylpiperazine-1-yl)methyl)piperidine-1-yl)phenyl)-N2-(tetrahydro-2H-pyran-4-yl)pyridino[3,4-b]pyrazine-2,5-diamine (Compound 45)
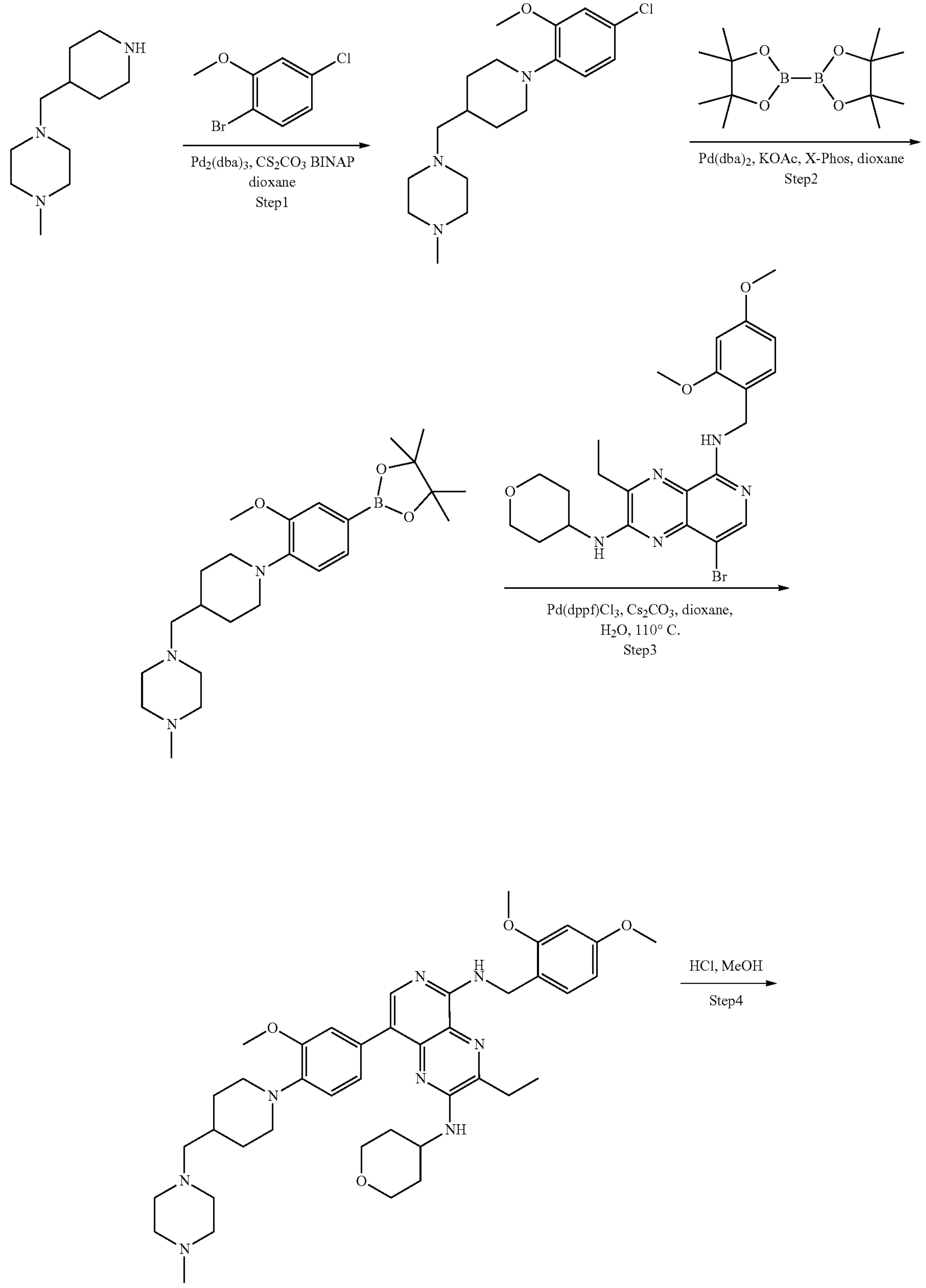

-continued

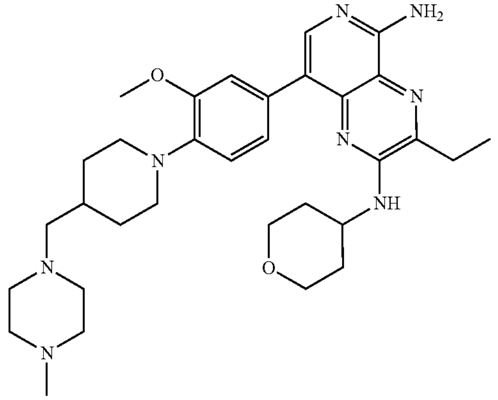

compound45

Step 1: Cesium acetate (5.0 g, 15 mmol), $Pd_2(dba)_3$ (0.50 g, 0.50 mmol), BINAP (0.60 g, 1.0 mmol) were added to 1, 4-dioxane (15 mL) mixture containing 1-methyl-4-(piperidin-4-ylmethyl) piperazine (1.0 g, 5.1 mmol) and 1-bromo-4-chloro-2-methoxybenzene (1.1 g, 5.1 mmol). This mixture was stirred and reacted at 110° C. for 3 hours under nitrogen protection. At the end of the reaction, the mixture was cooled to room temperature and water (30 mL) was added. The mixture was extracted three times (20 mL×3) with ethyl acetate. The organic phases were combined, dried over anhydrous sodium sulfate, filtered, and the filtrate was concentrated under reduced pressure. The resulting residue was purified by silica gel chromatography (dichloromethane/methanol=4:1) to obtain yellow oil (620 mg, yield 35%). (ESI) m/z 338.1. $[M+H]^+$.

Step 2: Potassium acetate (291 mg, 3.6 mmol), $pd(dba)_2$ (14 mg, 0.020 mmol) and X-Phos (11 mg, 0.020 mmol) were added to 1, 4-dioxane (10 mL) mixture containing 1-((1-(4-chloro-2-methoxyphenyl)piperidin-4-yl)methyl)-4-methylpiperazine (400 mg, 1.2 mmol) and divaleryl diboron (601 mg, 2.4 mmol). This mixture was stirred at 110° C. for 16 hours under nitrogen protection. At the end of the reaction, the mixture was cooled to room temperature, filtered, and concentrated under reduced pressure. The resulting residue was purified by silica gel chromatography (dichloromethane/methanol=4:1) to obtain yellow oil (400 mg, yield 75%). (ESI) m/z 430.2. $[M+H]^+$.

Step 3: The method of Step 2 of Example 2 was referred, 1-((1-(2-methoxy-4-(4,4,5,5-tetramethyl-1,3,2-dioxorane-2-yl)phenyl)piperidin-4-yl)methyl)-4-methylpiperazine (137 mg, 0.31 mmol) was reacted with 8-bromo-N5-(2,4-dimethoxybenzyl)-3-ethyl-N2-(tetrahydro-2H-pyran-4-yl)pyridino[3,4-b]pyrazine-2,5-diamine (100 mg, 0.21 mmol) to obtain yellow oil (112 mg, yield 79%). (ESI) m/z 725.3. $[M+H]^+$.

Step 4: N5-(2,4-dimethoxybenzyl)-3-ethyl-8-(3-methoxy-4-(4-((4-methylpiperazine-1-yl)methyl)piperidine-1-yl)phenyl)-N2-(tetrahydro-2H-pyran-4-yl)pyridino [3,4-b]pyrazine-2,5-diamine (112 mg, 0.16 mmol) was dissolved in methanol solution (4 M, 5 mL) of hydrochloric acid. The solution was stirred at 25° C. for 16 hours. At the end of the reaction, the solution was cooled to room temperature and quenched with saturated sodium bicarbonate solution (10 mL). The mixture was extracted three times (10 mL×3) with ethyl acetate. The organic phases were combined, dried over anhydrous sodium sulfate, filtered, and the filtrate was concentrated under reduced pressure. The resulting residue was purified by preparative liquid chromatography to obtain yellow solid, which is a formate of compound 45 (19 mg, yield 20%). $^1H$ NMR (400 MHz, DMSO-$d_6$) δ 8.25 (s, 1H), 7.92 (s, 1H), 7.24-7.17 (m, 2H), 7.00 (d, J=7.2 Hz, 1H), 6.89 (d, J=8.0 Hz, 1H), 6.44 (s, 2H), 4.14-4.10 (m, 1H), 3.90 (d, J=8.4 Hz, 2H), 3.81 (s, 3H), 3.24 (s, 6H), 2.83-2.78 (m, 2H), 2.54 (d, J=12.8 Hz, 3H), 2.43-2.22 (m, 5H), 2.17 (d, J=7.2 Hz, 2H), 2.15 (s, 3H), 1.86 (d, J=12.4 Hz, 2H), 1.77 (d, J=12.0 Hz, 2H), 1.68-1.56 (m, 3H), 1.33-1.22 (m, 5H). (ESI) m/z 575.3. $[M+H]^+$.

The method of Step 1 in Example 7 was referred, 1-bromo-4-chloro-2-methoxybenzene was replaced with the starting material of the following table to obtain the corresponding intermediate, and then the method of Example 7 was referred, 1-methyl-4-(piperidin-4-ylmethyl) piperazine was replaced with 1-methyl-4-(4-piperidinyl) to obtain the compound in following table

| No | starting materials | structures | HNMR |
|---|---|---|---|
| 139 | 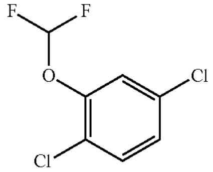 [SMILES: FC(F)Oc1cc(Cl)ccc1Cl] | 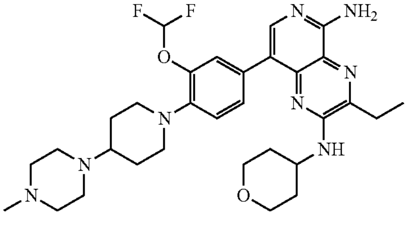 [SMILES: CCc1nc2c(N)ncc(-c3ccc(N4CCC(N5CCN(C)CC5)CC4)c(OC(F)F)c3)c2nc1NC1CCOCC1] | $^1H$ NMR (400 MHz, DMSO-$d_6$) δ 7.94 (s, 1H), 7.59 (d, J = 2.0 Hz, 1H), 7.51-7.49 (m, 1H), 7.25-6.87 (m, 3H), 6.51 (s, 2H), 4.17-4.09 (m, 1H), 3.90-3.87 (m, 2H), 2.83-2.81 (m, 2H), 2.67-2.65 (m, 2H), 2.64-2.61 (m, 3H), 2.51-2.50 (m, 4H), 2.48-2.46 (m, 1H), 2.32-2.25 (m, 5H), 2.13 (s, 3H), 1.88-1.83 (m, 4H), 1.66-1.54 (m, 4H), 1.29 (t, J = 7.2 Hz, 3H). |

The method of Step 9 in Example 1 and the method of Step 1 in Example 2 were referred, tetrahydropyran-4-amine was replaced with the starting materials of the following table to obtain the corresponding intermediates, and then the method of Example 7 was referred, 1-methyl-4-(piperidin-4-ylmethyl) piperazine was replaced with 1-methyl-4-(4-piperidinyl) to obtain the compounds of following table:

| No | starting materials | structures | HNMR |
|---|---|---|---|
| 255 | 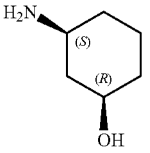 | 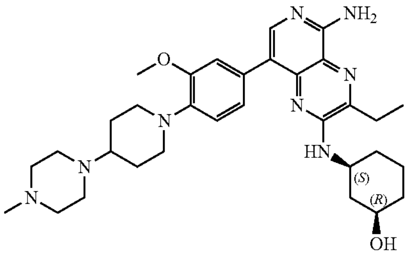 | $^1$H NMR (400 MHz, DMSO-$d_6$) $\delta$ 8.19 (brs, 1H), 7.91 (s, 1H), 7.25 (d, J = 2.0 Hz, 1H), 7.21-7.19 (m, 1H), 7.07 (t, J = 7.6 Hz, 1H), 6.89 (d, J = 8.0 Hz, 1H), 6.46 (s, 2H), 4.03-4.01 (m, 1H), 3.81 (s, 3H), 3.44 (d, J = 11.2 Hz, 5H), 2.81-2.75 (m, 2H), 2.57-2.54 (m, 4H), 2.52-2.50 (m, 3H), 2.46-2.44 (m, 3H), 2.33-2.32 (m, 1H), 2.23 (s, 3H), 2.04 (d, J = 12.0 Hz, 1H), 1.85-1.80 (m, 4H), 1.73-1.70 (m, 1H), 1.63-1.54 (m, 2H), 1.46-1.34 (m, 1H), 1.31 (t, J = 7.2 Hz, 3H), 1.17-1.13 (m, 2H). Formate |
| 76 | Methylamine | 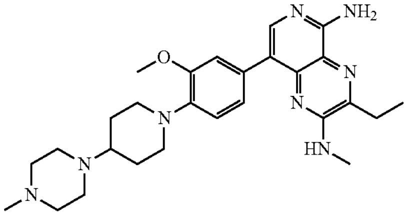 [SMILES: CCc1nc2c(N)ncc(-c3ccc(N4CCC(N5CCN(C)CC5)CC4)c(OC)c3)c2nc1NC] | $^1$H NMR (400 MHz, DMSO-$d_6$) $\delta$ 7.93 (s, 1H), 7.45 (d, J = 1.6 Hz, 1H), 7.38 (d, J = 4.8 Hz, 1H), 7.19-7.16 (m, 1H), 6.90 (d, J = 8.4 Hz, 1H), 6.43 (s, 2H), 3.81 (s, 3H), 3.44 (d, J = 11.2 Hz, 2H), 2.95-2.88 (m, 3H), 2.81-2.72 (m, 2H), 2.55 (d, J = 10.8 Hz, 6H), 2.36-2.30 (m, 5H), 2.16 (s, 3H), 1.87-1.80 (m, 2H), 1.60-1.52 (m, 2H), 1.33-1.29 (m, 3H). |
| 78 | 2-Aminocyclopentanol | 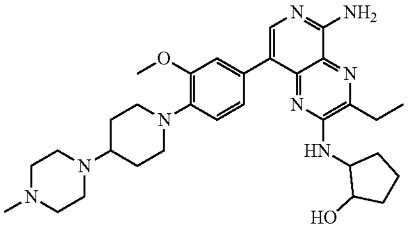 [SMILES: CCc1nc2c(N)ncc(-c3ccc(N4CCC(N5CCN(C)CC5)CC4)c(OC)c3)c2nc1NC1CCCC1O] | $^1$H NMR (400 MHz, DMSO-$d_6$) $\delta$ 8.15 (brs, 1H), 7.89 (s, 1H), 7.33 (d, J = 2.0 Hz, 1H), 7.17-1.13 (m, 1H), 7.01 (d, J = 6.8 Hz, 1H), 6.90 (d, J = 8.4 Hz, 1H), 6.48 (s, 2H), 4.58 (s, 1H), 4.14-4.09 (m, 2H), 3.84 (s, 3H), 3.47 (s, 3H), 2.85-2.80 (m, 3H), 2.67 (s, 6H), 2.56 (d, J = 12.0 Hz, 3H), 2.36 (s, 3H), 2.04 (m, 1H), 1.92-1.80 (m, 3H), 1.63-1.57 (m, 4H), 1.54-1.45 (m, 1H), 1.45-1.36 (m, 1H), 1.31 (m, 3H), 1.23 (d, J = 6.8 Hz, 1H). formate |
| 79 | 3-Aminotetrahydrofuran | 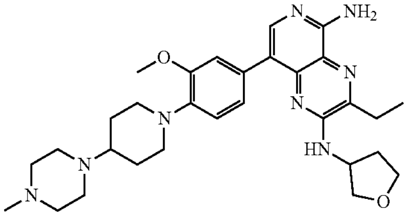 [SMILES: CCc1nc2c(N)ncc(-c3ccc(N4CCC(N5CCN(C)CC5)CC4)c(OC)c3)c2nc1NC1CCOC1] | $^1$H NMR (400 MHz, DMSO-$d_6$) $\delta$ 8.17 (brs, 2H), 7.91 (s, 1H), 7.27 (d, J = 4.0 Hz, 1H), 7.21 (d, J = 4.0 Hz, 1H), 7.17-7.15 (m, 1H), 6.90 (d, J = 8.0 Hz, 1H), 6.48 (s, 1H), 4.51-4.47 (m, 1H), 3.90-3.84 (m, 2H), 3.81 (s, 3H), 3.72-3.67 (m, 2H), 3.61-3.58 (m, 2H), 3.46 (d, J = 8.0 Hz 2H), 2.86-2.81 (m, 2H), 2.60-2.50 (m, 4H), 2.47-2.40 (m, 2H), 2.37-2.31 (m, 2H), 2.22 (s, 3H), 2.21-2.11 (m, 2H), 2.04-2.00 (m, 1H), 1.85-1.82(m, 2H), 1.61-1.53 (m, 2H), 1.31 (t, J = 7.2 Hz, 3H). formate |
| 80 | 3-Aminocyclohexa | 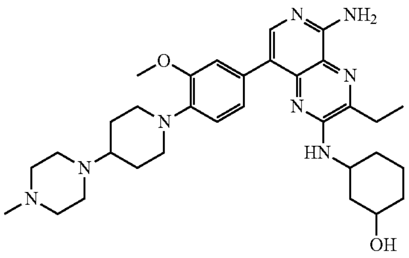 [SMILES: CCc1nc2c(N)ncc(-c3ccc(N4CCC(N5CCN(C)CC5)CC4)c(OC)c3)c2nc1NC1CCCC(O)C1] | $^1$H NMR (400 MHz, DMSO-$d_6$) $\delta$ 8.17 (brs, 1H), 7.90 (s, 1H), 7.27 (d, J = 2.0 Hz, 1H), 7.22 (dd, J = 8.4, 2.0 Hz, 1H), 6.89 (d, J = 8.4 Hz, 1H), 6.72 (d, J = 7.6 Hz, 1H), 6.44 (brs, 2H), 4.41-4.29 (m, 2H), 4.00 (s, 1H), 3.83 (s, 3H), 3.51-3.40 (m, 9H), 2.80 (q, J = 7.2 Hz, 2H), 2.62-2.49 (m, 4H), 2.40-2.30 (m, 2H), 2.25 (s, 3H), 1.99-1.80 (m, 5H), 1.76-1.26 (m, 6H), 1.30 (t, J = 7.2 Hz, 3H). formate |

-continued

| No | starting materials | structures | HNMR |
|---|---|---|---|
| 257 | 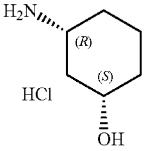 HCl | 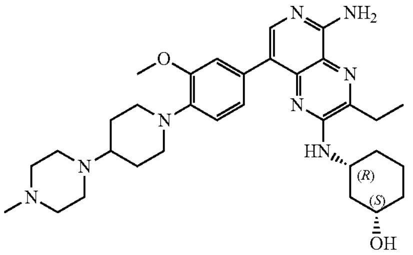 | $^1H$ NMR (400 MHz, DMSO-$d_6$) δ 8.14 (brs, 1H), 7.91 (s, 1H), 7.26 (d, J = 1.6 Hz, 1H), 7.22-7.19 (m, 1H), 7.10 (d, J = 7.2 Hz, 1H), 6.90 (d, J = 8.0 Hz, 1H), 6.52 (brs, 2H), 4.73 (s, 1H), 4.02 (d, J = 7.2 Hz, 1H), 3.82 (s, 3H), 3.51 (s, 2H), 3.26-3.03 (m, 4H), 2.78 (s, 6H), 2.63-2.53 (m, 4H), 2.45 (s, 3H), 2.04 (d, J = 12.0 Hz, 1H), 1.88 (d, J = 12.0 Hz, 2H), 1.84-1.68 (m, 3H), 1.65-1.57 (m, 2H), 1.47-1.32 (m, 2H), 1.29 (d, J = 7.2 Hz, 3H), 1.15 (s, 2H). formate |
| 256 | 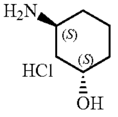 HCl | 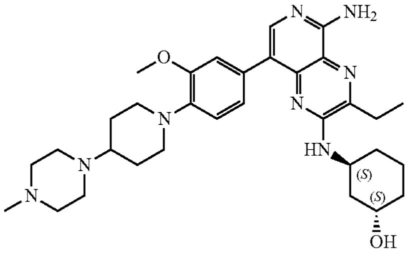 | $^1H$ NMR (400 MHz, DMSO-$d_6$) δ 8.14 (brs, 2H), 7.90 (s, 1H), 7.27 (d, J = 2.0 Hz, 1H), 7.24-7.18 (m, 1H), 6.90 (d, J = 8.0 Hz, 1H), 6.74 (d, J = 8.0 Hz, 1H), 6.46 (brs, 2H), 4.33 (s, 1H), 4.00 (s, 1H), 3.84 (s, 3H), 3.49-3.39 (m, 6H), 2.80 (d, J = 8.0 Hz, 2H), 2.52 (d, J = 2.0 Hz, 6H), 2.38 (s, 3H), 1.93 (s, 1H), 1.86 (d, J = 12.0 Hz, 2H), 1.74 (s, 2H), 1.65-1.59 (m, 5H), 1.40-1.37 (m, 2H), 1.31-1.28 (m, 3H), 1.15 (s, 2H). formate |
| 82 | 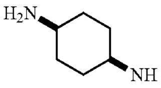 | 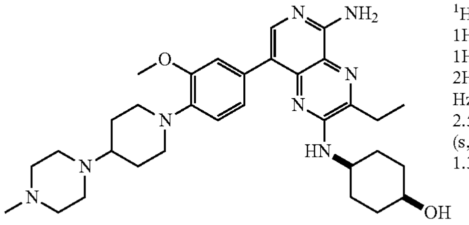 | $^1H$ NMR (400 MHz, DMSO-$d_6$) δ 8.23 (brs, 3H), 7.90 (s, 1H), 7.26 (d, J = 1.6 Hz, 1H), 7.19 (dd, J = 8.0, 1.6 Hz, 1H), 6.88 (d, J = 8.0 Hz, 2H), 6.49 (s, 2H), 3.97-3.90 (m, 2H), 3.81 (s, 3H), 3.75-3.70 (m, 1H), 3.44 (d, J = 11.2 Hz, 2H), 2.82 (q, J = 7.2 Hz, 2H), 2.64-2.55 (m, 4H), 2.53 (s, 1H), 2.46-2.44 (m, 1H), 2.37-2.31 (m, 1H), 2.24 (s, 3H), 1.89-1.75 (m, 4H), 1.73-1.55 (m, 6H), 1.46-1.35 (m, 2H), 1.29 (t, J = 7.2 Hz, 3H). formate |
| 83 | 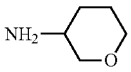 | 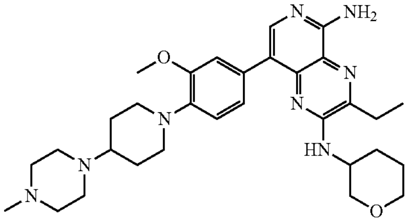 [SMILES: CCc1nc2c(N)ncc(-c3ccc(N4CCC(N5CCN(C)CC5)CC4)c(OC)c3)c2nc1NC1CCCOC1] | $^1H$ NMR (400 MHz, DMSO-$d_6$) δ 8.20 (brs, 2H), 7.90 (s, 1H), 7.35 (d, J = 1.6 Hz, 1H), 7.11-7.09 (m, 1H), 6.89 (d, J = 8.4 Hz, 1H), 6.85 (d, J = 8.0 Hz, 1H), 6.48 (brs, 2H), 4.18 (s, 1H), 3.83 (s, 3H), 3.78 (d, J = 12.0 Hz, 4H), 3.46 (s, 4H), 3.30-3.20 (m, 2H), 2.83-2.77 (m, 2H), 2.57 (s, 2H), 2.42 (s, 2H), 2.33 (d, J = 1.6 Hz, 2H), 2.21 (s, 3H), 1.96 (d, J = 8.4 Hz, 1H), 1.84 (d, J = 12.0 Hz, 2H), 1.714-1.68 (m, 2H), 1.60 (d, J = 12.0 Hz, 2H), 1.56-1.49 (m, 2H), 1.32-1.28 (m, 3H). formate |
| 85 | 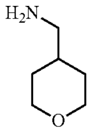 | 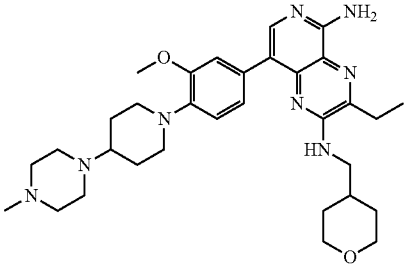 [SMILES: CCc1nc2c(N)ncc(-c3ccc(N4CCC(N5CCN(C)CC5)CC4)c(OC)c3)c2nc1NCC1CCOCC1] | $^1H$ NMR (400 MHz, DMSO-$d_6$) δ 8.22 (s, 5H), 7.90 (s, 1H), 7.45-7.53 (m,1H), 7.26 (d, J = 1.2 Hz, 1H), 7.21-7.16 (m, 1H), 6.89-6.85 (m, 1H), 6.55 (brs, 2H), 3.82 (s, 3H), 3.79 (s, 2H), 3.43 (d, J = 12.0 Hz, 2H), 3.36 (d, J = 12.0 Hz, 1H), 3.28-3.25 (m, 2H), 3.21-3.15 (m, 2H), 2.82-2.76 (m, 2H), 2.63 (s, 4H), 2.53 (s, 2H), 2.41 (s, 2H), 2.37 (d, J = 12.0 Hz, 2H), 2.28 (d, J = 6.4 Hz, 3H), 1.95 (s, 1H), 1.85 (d, J = 12.0 Hz, 2H), 1.61-1.50 (m, 4H), 1.32-1.28 (m, 3H), 1.19-1.11 (m, 2H). formate |
| 251 | 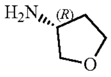 | 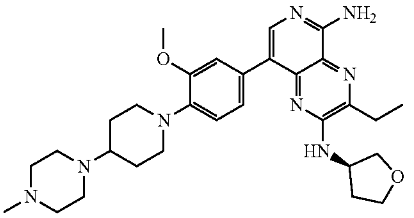 [SMILES: CCc1nc2c(N)ncc(-c3ccc(N4CCC(N5CCN(C)CC5)CC4)c(OC)c3)c2nc1N[C@@H]1CCOC1] | $^1H$ NMR (400 MHz, DMSO-$d_6$) δ 8.17 (brs, 2H), 7.91 (s, 1H), 7.27 (d, J = 4.0 Hz, 1H), 7.21 (d, J = 4.0 Hz, 1H), 7.17-7.15 (m, 1H), 6.90 (d, J = 8.0 Hz, 1H), 6.48 (s, 1H), 4.51-4.47 (m, 1H), 3.90-3.84 (m, 2H), 3.81 (s, 3H), 3.72-3.67 (m, 2H), 3.61-3.58 (m, 2H), 3.46 (d, J = 8.0 Hz 2H), 2.86-2.81 (m, 2H), 2.60-2.50 (m, 4H), 2.47-2.40 (m, 2H), 2.37-2.31 (m, 2H), 2.22 (s, 3H), 2.21-2.11 (m, 2H), 2.04-2.00 (m, 1H), 1.85-1.82(m, 2H), 1.61-1.53 (m, 2H), 1.31 (t, J = 7.2 Hz, 3H). formate |

The method of Example 7 was referred, 1-methyl-4-(piperidin-4-ylmethyl)piperazine was replaced with the starting materials in the following table to obtain the following compounds:

| No | starting materials | structures | HNMR |
|---|---|---|---|
| 48 | 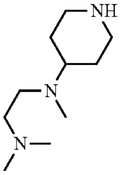 | 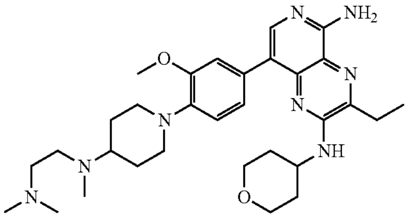 [SMILES: CCc1nc2c(N)ncc(-c3ccc(N4CCC(N(C)CCN(C)C)CC4)c(OC)c3)c2nc1NC1CCOCC1] | $^1$H NMR (400 MHz, DMSO-d$_6$) δ 8.25 (s, 1H),7.92 (s, 1H), 7.24-7.17 (m, 2H), 7.00 (d, J = 7.2 Hz, 1H), 6.89 (d, J = 8.0 Hz, 1H), 6.44 (s, 2H), 4.14-4.10 (m, 1H), 3.90 (d, J = 8.4 Hz, 2H), 3.81 (s, 3H), 3.24 (s, 6H), 2.83-2.78 (m, 2H), 2.54 (d, J = 12.8 Hz, 3H), 2.43-2.22 (m, 5H), 2.17 (d, J = 7.2 Hz, 2H), 2.15 (s, 3H), 1.86 (d, J = 12.4 Hz, 2H), 1.77 (d, J = 12.0 Hz, 2H), 1.68-1.56 (m, 3H), 1.33-1.22 (m, 5H). formate |
| 46 | 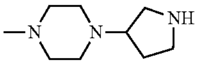 | 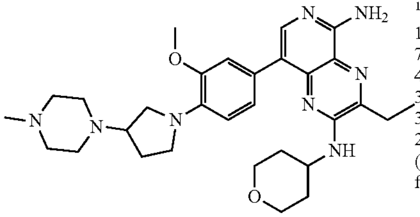 | $^1$H NMR (400 MHz, DMSO-d$_6$) δ 8.19 (brs, 2H), 7.90 (s, 1H), 7.24 (d, J = 1.8 Hz, 1H), 7.18-7.16 (m, 1H), 7.00 (d, J = 7.2 Hz, 1H), 6.68 (d, J = 8.2 Hz, 1H), 6.45 (brs, 2H), 4.17-4.12 (m, 1H), 3.91 (d, J = 11.2 Hz, 2H), 3.78 (s, 3H), 3.42 (d, J = 7.2 Hz, 2H), 3.36-3.27 (m, 4H), 3.23-3.19 (m, 2H), 2.84-2.78 (m, 3H), 2.47-2.31 (m, 6H), 2.21 (s, 3H), 2.11-2.04 (m, 1H), 1.86 (s, 2H), 1.75-1.70 (m, 1H), 1.63 (d, J = 12 Hz, 2H), 1.33-1.29 (m, 3H). formate |

The method of Example 7 and the method of catalytic hydrogenation in Step 4 of Example 1 was referred, 1-((1-(2-methoxy-4-(4,4,5,5-tetramethyl-1,3,2-dioxyboran-2-yl)phenyl)piperidin-4-yl)methyl)-4-methylpiperazine was replaced with the starting material in the table below to obtain the compound in the following table:

| No | starting materials | structures | HNMR |
|---|---|---|---|
| 52 | 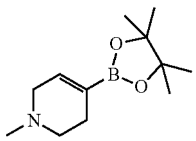 | 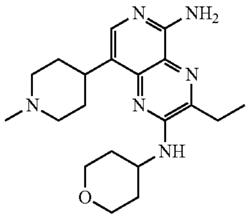 [SMILES: CCc1nc2c(N)ncc(C3CCN(C)CC3)c2nc1NC1CCOCC1] | $^1$H NMR (400 MHz, DMSO-d$_6$) δ 8.26 (brs, 2H), 7.64 (s, 1H), 7.00 (d, J = 7.2 Hz, 1H), 6.22 (brs, 2H), 4.23-4.14 (m, 1H), 3.98-3.93 (m, 2H), 3.59 (s, 1H), 3.08-2.97 (m, 2H), 2.95-2.87 (m, 2H), 2.79 (q, J = 7.2 Hz, 2H), 2.23 (s, 3H), 2.07-1.98 (m, 2H), 1.97-1.90 (m, 2H), 1.84-1.73 (m, 4H), 1.69-1.60 (m, 2H), 1.28 (t, J = 7.2 Hz, 3H). |

The method of Step 2 in Example 2 was referred, and then method of Step 12 in Example 1 was referred to remove the protecting group, 1-((1-(2-methoxy-4-(4,4,5,5-tetramethyl-1,3,2-dioxyboran-2-yl)phenyl)piperidin-4-yl)methyl)-4-methylpiperazine was replaced with the starting material in the table below to obtain the compound in the following table:

| No | starting materials | structures | HNMR |
|---|---|---|---|
| 161 | 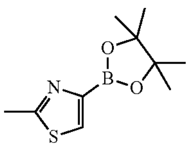 | 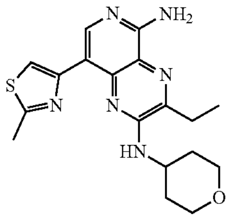 [SMILES: CCc1nc2c(N)ncc(-c3csc(C)n3)c2nc1NC1CCOCC1] | $^1$H NMR (400 MHz, DMSO-d$_6$) δ 8.32 (s, 2H), 8.30(brs,1H), 8.19 (d, J = 6.8 Hz, 1H), 8.07 (s, 1H), 7.08 (d, J = 7.2 Hz, 1H), 6.39 (brs, 2H), 4.34-4.22 (m, 2H), 4.02-3.98 (m, 6H), 3.47 (t, J = 11.2 Hz, 2H), 3.19 (d, J = 12.4 Hz, 2H), 2.88-2.70 (m, 4H), 2.10-2.08 (m, 1H), 2.01-1.85 (m, 2H), 1.81-1.59 (m, 4H), 1.42-1.27 (m, 5H). formate |

The method of Example 7 was referred, 1-((1-(2-methoxy-4-(4,4,5,5-tetramethyl-1,3,2-dioxorane-2-yl)phenyl)piperidin-4-yl)methyl)-4-methylpiperazine was replaced with the starting materials in the following table to obtain the compounds in the following table:

| No | starting materials | structures | HNMR |
|---|---|---|---|
| 154 | 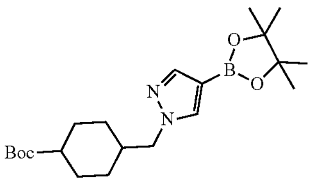 [SMILES: CC(C)(C)OC(=O)C1CCC(Cn2cc(B3OC(C)(C)C(C)(C)O3)cn2)CC1] | 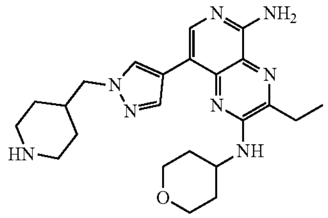 [SMILES: CCc1nc2c(N)ncc(-c3cnn(CC4CCNCC4)c3)c2nc1NC1CCOCC1] | $^1$H NMR (400 MHz, DMSO-$d_6$) δ 8.32 (s, 2H), 8.30(brs,1H), 8.19 (d, J = 6.8 Hz, 1H), 8.07 (s, 1H), 7.08 (d, J = 7.2 Hz, 1H), 6.39 (brs, 2H), 4.34-4.22 (m, 2H), 4.02-3.98 (m, 6H), 3.47 (t, J = 11.2 Hz, 2H), 3.19 (d, J = 12.4 Hz, 2H), 2.88-2.70 (m, 4H), 2.10-2.08 (m, 1H), 2.01-1.85 (m, 2H), 1.81-1.59 (m, 4H), 1.42-1.27 (m, 5H). formate |
| 56 | 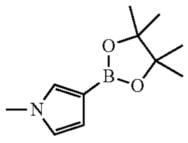 | 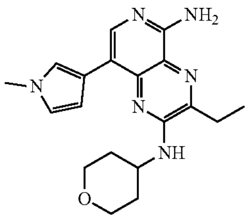 [SMILES: CCc1nc2c(N)ncc(-c3ccn(C)c3)c2nc1NC1CCOCC1] | $^1$H NMR (400 MHz, DMSO-$d_6$) δ 8.10 (s, 1H), 7.57-7.53 (m, 1H), 7.01 (d, J = 7.2 Hz, 1H), 6.73-6.69 (m, 1H), 6.54-6.50 (m, 1H), 6.22 (s, 2H), 4.30-4.24 (m, 1H), 4.03-3.96 (m, 2H), 3.66 (s, 3H), 3.51-3.47 (m, 2H), 2.84-2.79 (m, 2H), 2.02-1.95 (m, 2H), 1.73-1.67 (m, 2H), 1.31 (t, J = 7.6 Hz, 3H). |
| 57 | 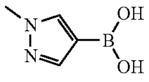 | 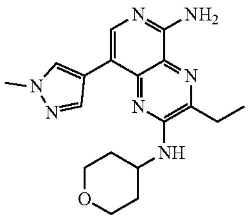 [SMILES: CCc1nc2c(N)ncc(-c3cnn(C)c3)c2nc1NC1CCOCC1] | $^1$H NMR (400 MHz, DMSO-$d_6$) δ 8.25 (s, 1H), 8.17 (s, 1H), 7.99 (s, 1H), 7.08 (d, J = 7.2 Hz, 1H), 6.37 (brs, 2H), 4.28-4.23 (m, 1H), 4.01-3.95 (m, 2H), 3.88 (s, 3H), 3.52-3.45 (m, 2H), 2.82 (q, J = 7.2 Hz, 2H), 2.02-1.93 (m, 2H), 1.74-1.66(m, 2H), 1.31 (t, J = 7.2 Hz, 3H). |
| 58 | 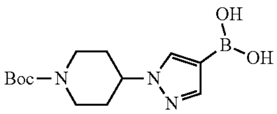 [SMILES: CC(C)(C)OC(=O)N1CCC(n2cc(B(O)O)cn2)CC1] | 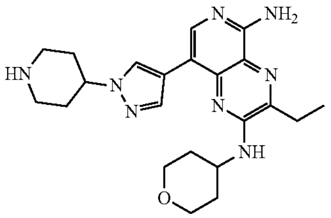 [SMILES: CCc1nc2c(N)ncc(-c3cnn(C4CCNCC4)c3)c2nc1NC1CCOCC1] | $^1$H NMR (400 MHz, DMSO-$d_6$) δ 8.32 (s, 1H), 8.29 (s, 1H), 8.19 (brs, 1H), 8.07 (s, 1H), 7.06 (d, J = 7.2 Hz, 1H), 6.41 (s, 2H), 4.42-4.35 (m, 1H), 4.29-4.24 (m, 1H), 4.01-3.95 (m, 2H), 3.50 (m, 2H), 3.32-3.25 (m, 2H), 2.97-2.88 (m, 2H), 2.83 (q, J = 7.2 Hz, 2H), 2.19-2.01 (m, 4H), 1.98-1.91 (m, 2H), 1.77-1.64 (m, 2H), 1.31 (t, J = 7.2 Hz, 3H). |
| 61 | 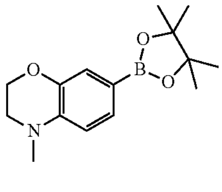 [SMILES: CN1CCOc2cc(B3OC(C)(C)C(C)(C)O3)ccc21] | 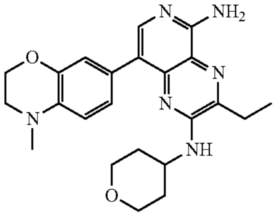 [SMILES: CCc1nc2c(N)ncc(-c3ccc4c(c3)OCCN4C)c2nc1NC1CCOCC1] | $^1$H NMR (400 MHz, DMSO-$d_6$) δ 8.18 (brs, 1H), 7.89 (s, 1H), 7.21 (d, J = 2.0 Hz, 1H), 7.12-7.05 (m, 1H), 7.03 (d, J = 7.2 Hz, 1H), 6.70 (d, J = 8.4 Hz, 1H), 6.45 (brs, 2H), 4.28-4.23 (m, 2H), 4.16-4.10 (m, 1H), 3.95-3.90 (m, 2H), 3.43-3.33 (m, 2H), 3.27-3.22 (m, 2H), 2.84 (s, 3H), 2.83-2.78 (m, 2H), 1.95-1.85 (m, 2H), 1.68-1.56 (m, 2H), 1.30 (t, J = 7.2 Hz, 3H). |

-continued

| No | starting materials | structures | HNMR |
|---|---|---|---|
| 137 | 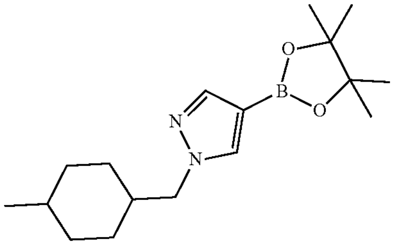 | 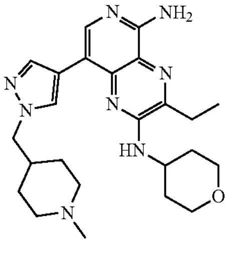 [SMILES: CCc1nc2c(N)ncc(-c3cnn(CC4CCN(C)CC4)c3)c2nc1NC1CCOCC1] | $^1$H NMR (400 MHz, DMSO-$d_6$) δ 8.28 (s, 1H), 8.20 (s, 3H), 8.19 (s,1H), 8.02 (s, 1H), 7.08 (d, J = 7.2 Hz, 1H), 6.39 (s, 2H), 4.32-4.23 (m,1H), 4.01-3.98 (m, 4H), 3.48-3.45 (m, 2H), 2.83-2.80 (m, 4H), 2.21 (s, 3H), 1.95-1.92 (m, 4H), 1.88-1.66 (m, 4H), 1.53-1.50 (m, 2H), 1.32-1.22 (m, 5H). formate |
| 138 | 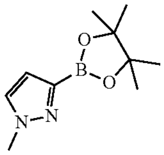 | 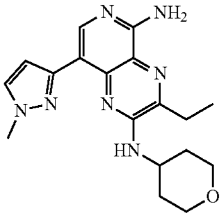 [SMILES: CCc1nc2c(N)ncc(-c3ccn(C)n3)c2nc1NC1CCOCC1] | $^1$H NMR (400 MHz, DMSO-$d_6$) δ 8.42 (s, 1H), 8.16 (s, 1H), 7.69 (d, J = 4.0 Hz, 1H), 7.08 (d, J = 7.2 Hz, 1H), 7.03 (d, J = 4.0 Hz, 1H), 6.48 (brs, 2H), 4.24 (d, J = 7.2 Hz, 1H), 3.98-3.87 (m, 2H), 3.87 (s, 3H), 3.62-3.44 (m, 2H), 2.85-2.79(m, 2H), 1.97-19.4 (m, 2H), 1.69-1.65 (m, 2H), 1.33-1.29 (m, 3H). formate |

The method of Step 9 in Example 1 was referred, tetrahydropyran-4-amine was replaced with the following starting material 2 to obtain the corresponding intermediate, and then the method from Step 3 to the end of Example 7 was referred, 1-((1-(2-methoxy-4-(4,4,5,5-tetramethyl-1,3,2-dioxorane-2-yl)phenyl)piperidin-4-yl)methyl)-4-methylpiperazine was replaced with the following starting material 1 to obtain the compound in the following table:

| No | starting materials 1 | starting materials 2 | structures | HNMR |
|---|---|---|---|---|
| 206 | 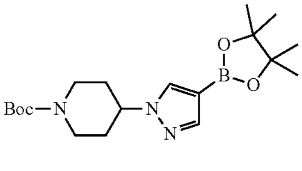 [SMILES: CC(C)(C)OC(=O)N1CCC(n2cc(B3OC(C)(C)C(C)(C)O3)cn2)CC1] | 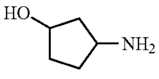 | 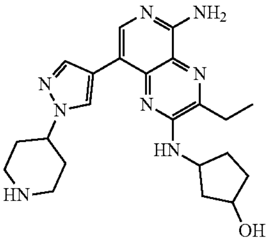 [SMILES: CCc1nc2c(N)ncc(-c3cnn(C4CCNCC4)c3)c2nc1NC1CCC(O)C1] | $^1$H NMR (400 MHz, DMSO-$d_6$) δ 8.39 (s, 1H), 8.28 (brs, 2H), 8.20 (s, 1H), 8.08 (s, 1H), 7.09 (d, J = 7.2 Hz, 1H), 6.39 (brs, 2H), 4.52-4.45 (m, 1H), 4.40-4.36 (m, 1H), 4.25-4.20 (m, 1H), 3.32-3.22 (m, 2H), 2.95-2.88 (m, 2H), 2.80 (q, J = 7.2 Hz, 2H), 2.53-2.52 (m, 1H), 2.30-2.26 (m, 1H), 2.19-2.13 (m, 2H), 2.10-1.94 (m, 4H), 1.88-1.80 (m, 2H), 1.71-1.63 (m, 2H), 1.31 (t, J = 7.2 Hz, 3H) formate |

Example 8: 3-ethyl-8-(4-methylpiperazine-1-yl)-N2-(tetrahydro-2H-pyran-4-yl)pyridino[3,4-b]pyrazine-2,5-diamine (Compound 53)

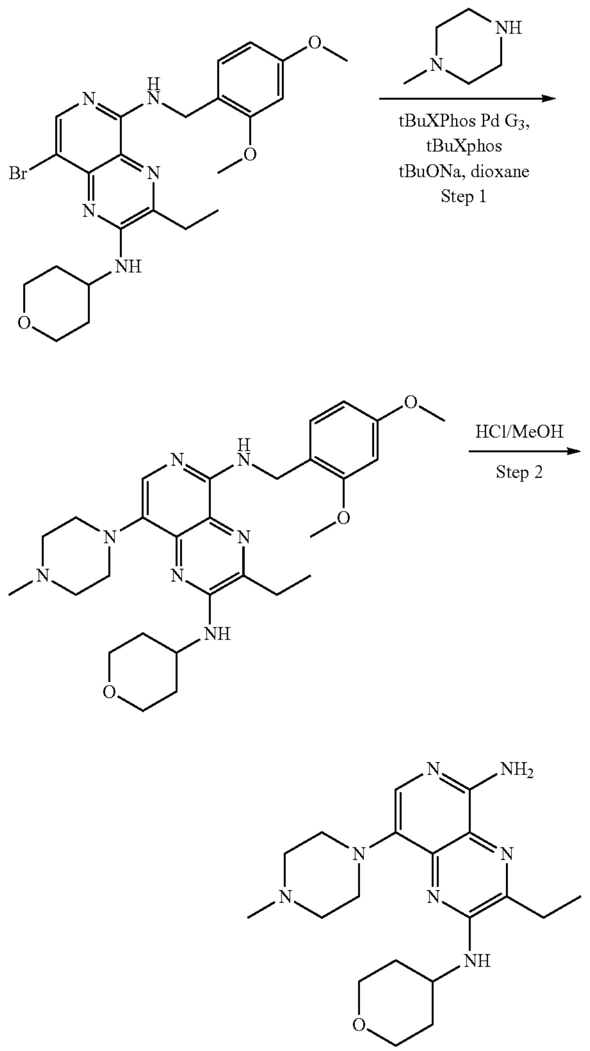

compound 53

Step 1: Potassium tert-butoxide (43 mg, 0.45 mmol), tBuXPhos Pd G3 (27 mg, 0.030 mol) and tBuXPhos (28 mg, 0.060 mmol) were added to 1, 4-dioxane (5 mL) mixture containing 8-bromo-N5-(2,4-dimethoxybenzyl)-3-ethyl-N2-(tetrahydro-2H-pyran-4-yl)pyridino[3,4-b]pyrazine-2,5-diamine (75 mg, 0.15 mmol) and 1-methylpiperazine (30 mg, 0.30 mmol). The mixture was stirred at 110° C. for 14 hours under nitrogen protection. At the end of the reaction, the mixture was cooled to room temperature and water (10 mL) was added. The mixture was extracted three times (10 mL×3) with ethyl acetate. The organic phases were combined, dried over anhydrous sodium sulfate, filtered, and the filtrate was concentrated under reduced pressure. The resulting residue was purified by silica gel chromatography (dichloromethane/methanol=10:1) to obtain brown oil (50 mg, yield 64%). (ESI) m/z 522.2. $[M+1]^+$.

Step 2: The method of Step 4 in Example 7 was referred, N5-(2,4-dimethoxybenzyl)-3-ethyl-8-(4-methylpiperazine-1-yl)-N2-(tetrahydro-2H-pyran-4-yl)pyridino[3,4-b]pyrazine-2,5-diamine (50 mg, 0.096 mmol) was reacted to obtain yellow solid compound 53 (15 mg, 42%). 1H NMR (400 MHz, DMSO-$d_6$) δ 8.18 (brs, 2H), 7.37 (s, 1H), 7.05 (d, J=7.2 Hz, 1H), 6.16 (brs, 2H), 4.25-4.19 (m, 1H), 3.98-3.94 (m, 2H), 3.41-3.35 (m, 2H), 3.22-3.06 (m, 2H), 2.79 (d, J=7.2 Hz, 2H), 2.59-2.52 (m, 4H), 2.28 (s, 3H), 1.93-1.87 (m, 2H), 1.72-1.62 (m, 2H), 1.28 (t, J=7.2 Hz, 4H). (ESI) m/z 373.1. $[M+1]^+$.

Example 9: 3-((5-amino-3-ethyl-8-(1-(1'-methyl-[1,4'-bipiperidine]-4-yl)-1H-pyrazol-4-yl)pyridino[3,4-b]pyrazine-2-yl)amino)cyclopentan-1-ol (Compound 134)

The method of Step 2 in Example 6 was referred, the starting material in the following table was reacted with compound 206 to obtain the following table compound:

| No | starting materials | structures | HNMR |
|---|---|---|---|
| 134 | 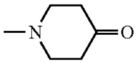 | 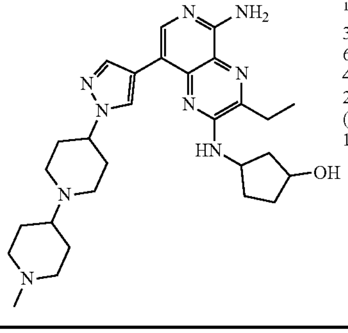 | $^1H$ NMR (400 MHz, DMSO-$d_6$) δ 8.43 (s, 1H), 8.20 (brs, 3H), 8.18 (s, 1H), 8.02 (s, 1H), 7.13 (d, J = 7.2 Hz, 1H), 6.41 (brs, 2H), 4.51-4.45 (m, 1H), 4.25-4.20 (m, 1H), 4.14-4.11 (m, 1H), 3.02-2.94 (m, 4H), 2.83-2.77 (m, 2H), 2.53-2.52 (m, 1H), 2.35-2.29 (m, 7H), 2.23-2.14 (m, 2H), 2.12-2.03 (m, 3H), 1.91-1.75 (m, 6H), 1.70-1.50 (m, 4H), 1.30 (t, J = 7.2 Hz, 3H). formate |

Example 10: The method of Step 2 in Example 6 was referred, the following starting materials were used to react with compound 58 to obtain the following table compounds:

| No | starting materials | structures | HNMR |
|---|---|---|---|
| 240 | 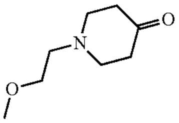 | 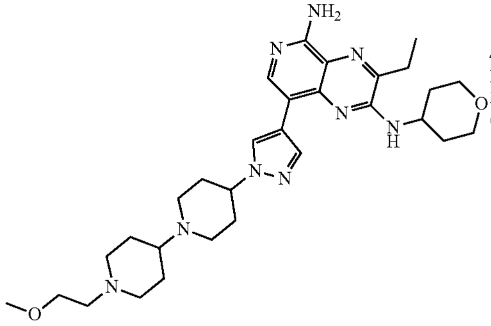 | $^1$H NMR (400 MHz, DMSO-$d_6$) δ 8.36 (s, 1H), 8.18 (s, 1H), 8.00 (s, 1H), 7.04 (d, J = 7.6 Hz, 1H), 6.37 (s, 2H), 4.36-4.25 (m, 2H), 4.16-4.06 (m, 1H), 3.97 (d, J = 8.8 Hz, 1H), 3.50-3.45 (m, 2H), 3.42-3.39 (m, 3H), 3.22 (s, 3H), 3.00-2.90 (m, 4H), 2.85-2.79 (m, 2H), 2.46-2.43 (m, 2H), 2.32-2.26 (m, 3H), 2.07-2.04 (m, 2H), 1.98-1.92 (m, 5H), 1.76-1.69 (m, 4H), 1.48-1.40 (m, 2H), 1.31 (t, J = 7.2 Hz, 3H). |
| 241 | 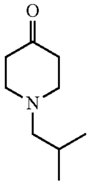 | 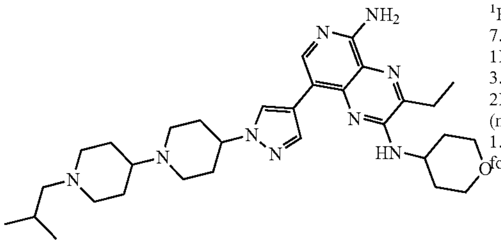 | $^1$H NMR (400 MHz, DMSO-$d_6$) δ 8.36 (s, 1H), 8.19 (d, J = 7.2 Hz, 3H), 8.18 (s, 1H), 8.00 (s, 1H), 7.05 (d, J = 7.6 Hz, 1H), 6.41 (s, 2H), 4.36-4.27 (m, 1H), 4.13-4.10 (m, 1H), 3.98-3.95 (m, 2H), 3.47-3.44 (m, 2H), 3.01-2.98 (m, 2H), 2.84-2.78 (m, 4H), 2.38-2.26 (m, 4H), 2.15-2.01 (m, 4H), 1.99-1.83 (m, 6H), 1.80-1.66 (m, 4H), 1.55-1.45 (m, 2H), 1.31 (t, J = 7.2 Hz, 3H), 0.91-0.79 (m, 6H). formate |
| 237 | 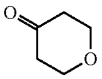 | 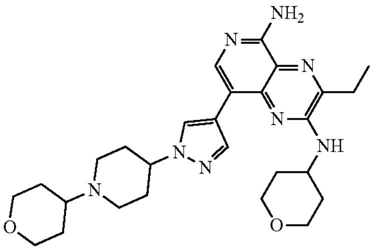 [SMILES: CCc1nc2c(N)ncc(-c3cnn(C4CCN(C5CCOCC5)CC4)c3)c2nc1NC1CCOCC1] | $^1$H NMR (400 MHz, DMSO-$d_6$) δ 8.36 (s, 1H), 8.19 (s, 1H), 8.17 (s, 2H), 8.00 (s, 1H), 7.05 (d, J = 7.6 Hz, 1H), 6.40 (brs, 2H), 4.35-4.26 (m, 1H), 4.16-4.13 (m, 1H), 4.02-3.94 (m, 5H), 3.92-3.88 (m, 2H), 3.70-3.60 (m, 2H), 3.59-3.44 (m, 2H), 3.29-3.25 (m, 2H), 3.04-3.00 (m, 2H), 2.82 (q, J = 7.2 Hz, 2H), 2.32-3.30 (m, 2H), 2.08-2.05 (m, 2H), 2.01-1.89 (m, 4H), 1.77-1.65 (m, 3H), 1.47-1.44 (m, 2H), 1.31 (t, J = 7.2 Hz, 3H). formate |
| 234 | Acetone | 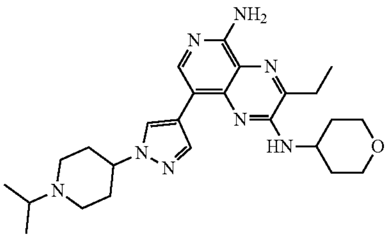 [SMILES: CCc1nc2c(N)ncc(-c3cnn(C4CCN(C(C)C)CC4)c3)c2nc1NC1CCOCC1] | $^1$H NMR (400 MHz, DMSO-$d_6$) δ 8.36 (s, 1H), 8.21-8.14 (m, 4H), 8.02 (s, 1H), 7.05 (d, J = 7.6 Hz, 1H), 6.42 (brs, 2H), 4.35-4.25 (m, 1H), 4.20-4.16 (m, 1H), 3.99-3.94 (m, 2H), 3.52-3.43 (m, 2H), 3.02-2.97 (m, 2H), 2.91-2.86 (m, 1H), 2.85-2.79 (m, 2H), 2.44-2.38 (m, 2H), 2.13-2.08 (m, 2H), 2.05-1.91 (m, 4H), 1.77-1.65 (m, 2H), 1.31 (t, J = 7.2 Hz, 3H), 1.04 (d, J = 6.8 Hz, 6H). formate |
| 135 | 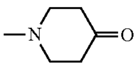 | 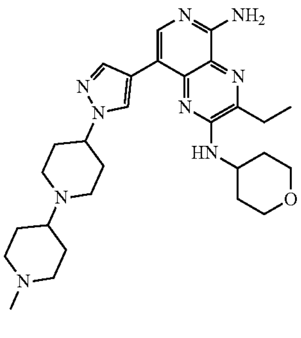 [SMILES: CCc1nc2c(N)ncc(-c3cnn(C4CCN(C5CCN(C)CC5)CC4)c3)c2nc1NC1CCOCC1] | $^1$H NMR (400 MHz, DMSO-$d_6$) δ 8.36 (d, J = 2.4 Hz, 1H), 8.24 (s, 2H), 8.18 (s, 1H), 8.01 (t, J = 3.6 Hz, 1H), 7.05 (d, J = 7.6 Hz, 1H), 6.40 (s, 2H), 4.33-4.32 (m, 1H), 4.18-4.11 (m, 1H), 3.97-3.92 (m, 2H), 3.51-3.43 (m, 1H), 3.34-3.30 (m, 1H), 2.98-2.92 (m, 2H), 2.82 (dd, J = 14.5, 7.2 Hz, 2H), 2.35-2.31 (m, 4H), 2.14-1.82 (m, 8H), 1.79-1.63 (m, 5H), 1.51-1.38 (m, 2H), 1.31 (t, J = 7.2 Hz, 3H), 1.23-1.03 (m, 2H). formate |

-continued

| No | starting materials | structures | HNMR |
|---|---|---|---|
| 136 | paraformaldehyde | 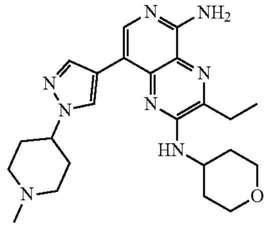 [SMILES: CCc1nc2c(N)ncc(-c3cnn(C4CCN(C)CC4)c3)c2nc1NC1CCOCC1] | $^1$H NMR (400 MHz, DMSO-$d_6$) δ 8.34 (s, 1H), 8.27 (brs, 3H), 8.18 (s, 1H), 8.02 (s, 1H), 7.05 (d, J = 7.6 Hz, 1H), 6.39 (s, 2H), 4.33-4.26 (m, 1H), 4.13 (s, 1H), 3.98 (d, J = 9.2 Hz, 2H), 3.69 (s, 5H), 2.90 (d, J = 11.2 Hz, 2H), 2.82 (q, J = 7.2 Hz, 2H), 2.24 (s, 3H), 2.11-2.03 (m, 4H), 1.98-1.92 (m, 2H), 1.71 (dd, J = 11.2, 3.6 Hz, 2H), 1.31 (t, J = 7.2 Hz, 3H). formate |
| 238 | 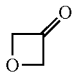 | 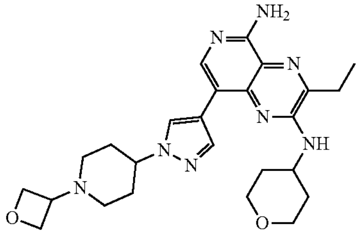 [SMILES: CCc1nc2c(N)ncc(-c3cnn(C4CCN(C5COC5)CC4)c3)c2nc1NC1CCOCC1] | $^1$H NMR (400 MHz, DMSO-$d_6$) δ 8.37 (s, 1H), 8.22 (brs, 3H), 8.18 (s, 1H), 8.02 (s, 1H), 7.05 (d, J = 7.6 Hz, 1H), 6.40 (brs, 2H), 4.55 (t, J = 6.4 Hz, 2H), 4.45 (t, J = 6.4 Hz, 2H), 4.33-4.29 (m, 1H), 4.21-4.15 (m, 1H), 4.00-3.96 (m, 2H), 3.47-3.44 (m, 5H), 2.84-2.79 (m, 4H), 2.09-2.05 (m, 2H), 2.00-1.93 (m, 4H), 1.78-1.65 (m, 2H), 1.31 (t, J = 7.2 Hz, 3H). formate |
| 236 | 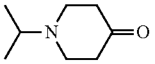 | 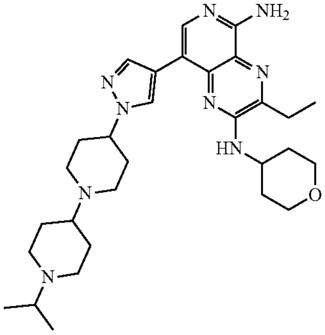 [SMILES: CCc1nc2c(N)ncc(-c3cnn(C4CCN(C5CCN(C(C)C)CC5)CC4)c3)c2nc1NC1CCOCC1] | $^1$H NMR (400 MHz, DMSO-$d_6$) δ 8.36 (s, 1H), 8.23 (brs, 4H), 8.18 (s, 1H), 8.00 (s, 1H), 7.04 (d, J = 7.6 Hz, 1H), 6.39 (brs, 2H), 4.35-4.28 (m, 2H), 4.18-4.10 (m, 2H), 3.98 (d, J = 8.4 Hz, 2H), 3.48-3.44 (m, 2H), 2.97-2.91 (m, 4H), 2.86-2.79 (m, 3H), 2.36-2.26 (m, 5H), 2.07-2.04 (m, 2H), 1.99-1.89 (m, 4H), 1.81-1.70 (m, 4H), 1.55-1.46 (m, 2H), 1.31 (t, J = 7.2 Hz, 3H), 1.02 (d, J = 6.4 Hz, 6H). formate |
| 235 | 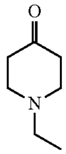 | 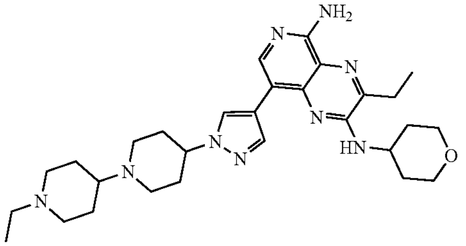 [SMILES: CCc1nc2c(N)ncc(-c3cnn(C4CCN(C5CCN(CC)CC5)CC4)c3)c2nc1NC1CCOCC1] | $^1$H NMR (400 MHz, DMSO-$d_6$) δ 8.37 (s, 1H),8.19 (brs, 4H), 8.01 (s, 1H), 7.06 (d, J = 7.6 Hz, 1H), 6.40 (s, 2H), 4.36-4.25 (m, 2H), 4.16-4.14 (m, 2H), 4.03-3.95 (m, 2H), 3.48-3.45 (m, 2H), 3.07-2.97 (m, 4H), 2.82-2.79 (m, 2H), 2.39-2.29 (m, 3H), 2.17-2.04 (m, 4H), 1.99-1.89 (m, 4H), 1.82-1.67 (m, 4H), 1.53 (d, J = 9.6 Hz, 2H), 1.31 (t, J = 7.2 Hz, 3H), 1.04 (t, J = 7.2 Hz, 3H). formate |
| 243 | 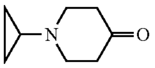 | 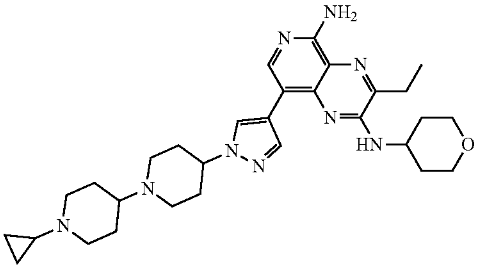 [SMILES: CCc1nc2c(N)ncc(-c3cnn(C4CCN(C5CCN(C6CC6)CC5)CC4)c3)c2nc1NC1CCOCC1] | $^1$H NMR (400 MHz, DMSO-$d_6$) δ 8.35 (s, 1H), 8.17 (s, 1H), 8.15 (d, J = 4.0 Hz, 2H), 8.02 (s, 1H), 7.07 (d, J = 4.0 Hz, 1H), 6.49-6.42 (m, 2H), 4.34-4.27 (m, 1H), 4.20 (s, 1H), 3.97 (d, J = 12.0 Hz, 2H), 3.49 (s, 2H), 3.08 (s, 2H), 2.99 (d, J = 12.0 Hz, 2H), 2.85-2.80 (m, 2H), 2.52 (d, J = 4.0 Hz, 2H), 2.46-2.44 (m, 1H), 2.21-2.08 (m, 4H), 2.03-1.91 (m, 4H), 1.79-1.68 (m, 4H), 1.61 (d, J = 4.0 Hz, 1H), 1.47-1.37 (m, 2H), 1.33-1.29 (m, 3H), 0.43-0.41 (m, 2H), 0.32-0.28 (m, 2H). formate |
| 159 | 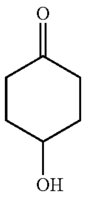 | 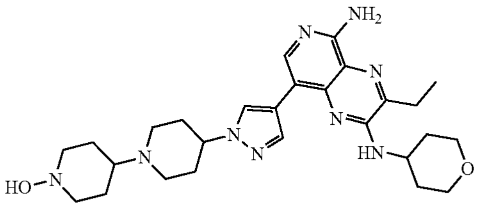 [SMILES: CCc1nc2c(N)ncc(-c3cnn(C4CCN(C5CCN(O)CC5)CC4)c3)c2nc1NC1CCOCC1] | $^1$H NMR (400 MHz, DMSO-$d_6$) δ 8.36 (d, J = 2.4 Hz, 1H), 8.24 (s, 2H), 8.18 (s, 1H), 8.01 (t, J = 3.6 Hz, 1H), 7.05 (d, J = 7.6 Hz, 1H), 6.40 (s, 2H), 4.33-4.32 (m, 1H), 4.18-4.11 (m, 1H), 3.97-3.92 (m, 2H), 3.51-3.43 (m, 1H), 3.34-3.30 (m, 1H), 2.98-2.92 (m, 2H), 2.82 (dd, J = 14.5, 7.2 Hz, 2H), 2.35-2.31 (m, 4H), 2.14-1.82 (m, 8H), 1.79-1.63 (m, 5H), 1.51-1.38 (m, 2H), 1.31 (t, J = 7.2 Hz, 3H), 1.23-1.03 (m, 2H). formate |

The method of Step 2 in Example 6 was referred, the following starting materials were used to react with compound 58, then referring to the method of Step 4 in Example 7 to remove the protective group to obtain the following table compounds:

| No | register No# starting materials | structures | HNMR |
| --- | --- | --- | --- |
| 157 | 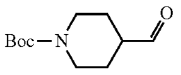 | 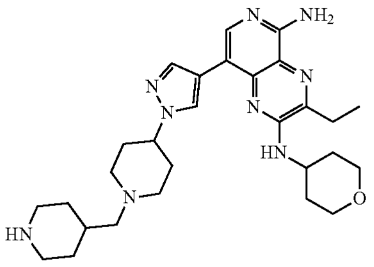 [SMILES: CCc1nc2c(N)ncc(-c3cnn(C4CCN(CC5CCNCC5)CC4)c3)c2nc1NC1CCOCC1] | $^1$H NMR (400 MHz, DMSO-$d_6$) δ 8.37 (s, 1H), 8.27 (brs, 3H), 8.19 (s, 1H), 8.00 (s, 1H), 7.06 (d, J = 7.6 Hz, 1H), 6.40 (brs, 2H), 4.34-4.30 (m, 1H), 4.20-4.14 (m, 1H), 4.02-3.86 (m, 2H), 3.76-3.60 (m, 4H), 3.50-3.44 (m, 2H), 3.23 (d, J = 12.4 Hz, 2H), 2.96 (d, J = 10.8 Hz, 2H), 2.87-2.77 (m, 4H), 2.19 (d, J = 6.8 Hz, 2H), 2.13-2.01 (m, 4H), 1.98 (s, 1H), 1.97-1.92 (m, 2H), 1.91-1.80 (dm, 2H), 1.76-1.67 (m, 2H), 1.33-1.29 (m, 3H), 1.26-1.21 (m, 1H). formate |
| 160 | 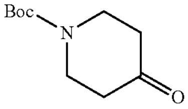 | 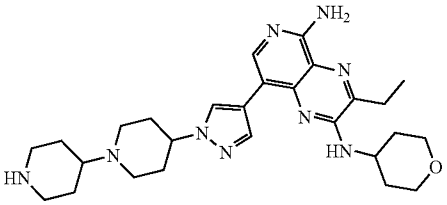 [SMILES: CCc1nc2c(N)ncc(-c3cnn(C4CCN(C5CCNCC5)CC4)c3)c2nc1NC1CCOCC1] | $^1$H NMR (400 MHz, DMSO-$d_6$) δ 8.37 (s, 1H), 8.32 (s, 2H), 8.18 (s, 1H), 8.01 (s, 1H), 7.10 (d, J = 7.6 Hz, 1H), 6.51 (s, 2H), 4.35-4.28 (m, 1H), 4.20-4.05 (m, 2H), 3.98-3.92 (m, 2H), 3.45-3.42 (m, 2H), 3.29-3.25 (m, 2H), 2.96-2.92 (m, 2H), 2.83-2.80 (m, 4H), 2.59-2.55 (m, 1H), 2.32-2.28 (m, 2H), 2.07-2.04 (m, 2H), 2.03-1.81 (m, 6H), 1.72-1.68 (m, 4H), 1.31 (t, J = 7.2 Hz, 3H). formate |

The method of Step 2 in Example 6 was referred, the following starting material was used to react with compound 58, then the method of Step 12 in Example 1 was referred to remove the protective group, and finally the method of step 2 of compound 6 was referred to react with formaldehyde to obtain the following table compound:

| No | starting materials | structures | HNMR |
| --- | --- | --- | --- |
| 242 | 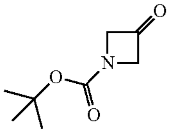 | 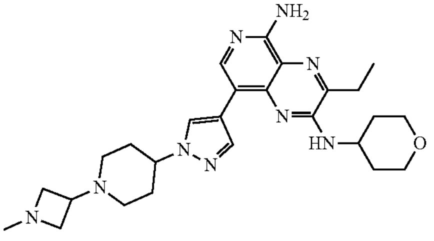 [SMILES: CCc1nc2c(N)ncc(-c3cnn(C4CCN(C5CN(C)C5)CC4)c3)c2nc1NC1CCOCC1] | $^1$H NMR (400 MHz, DMSO-$d_6$) δ 8.38 (s, 1H), 8.28 (s, 1H), 8.18 (s, 1H), 8.00 (s, 1H), 7.04 (d, J = 7.6 Hz, 1H), 6.37 (s, 2H), 4.32-4.30 (m, 1H), 4.16-4.14 (m, 1H), 3.99-3.96 (m, 2H), 3.53-3.41 (m, 3H), 2.91-2.73 (m, 7H), 2.55-2.50(m, 1H), 2.23 (s, 3H), 1.96-1.90 (m, 8H), 1.72-1.70 (m, 2H), 1.31 (t, J = 7.2 Hz, 3H). formate |

The method of step 2 in Example 6 was referred, paraformaldehyde was reacted with compound 157 to obtain the following compound:

| | | |
|---|---|---|
| 158 | 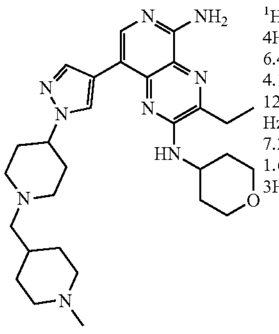 | $^1$H NMR (400 MHz, DMSO-$d_6$) δ 8.37 (s, 1H), 8.25 (brs, 4H), 8.19 (s, 1H), 8.00 (s, 1H), 7.06 (d, J = 7.6 Hz, 1H), 6.43 (brs, 2H), 4.33-4.28 (m, 1H), 4.18-4.13 (m, 1H), 4.10-3.88 (m, 2H), 3.76-3.69 (m, 1H), 3.47 (dd, J = 12.0, 10.4 Hz, 2H), 3.10-2.87 (m, 4H), 2.82 (q, J = 7.2 Hz, 2H), 2.37 (s, 3H), 2.27 (t, J = 11.2 Hz, 2H), 2.18 (d, J = 7.2 Hz, 2H), 2.16-1.99 (m, 4H), 1.98-1.92 (m, 3H), 1.79-1.69 (m, 4H), 1.61-1.50 (m, 1H), 1.31 (t, J = 7.2 Hz, 3H), 1.25-1.16 (m, 2H). formate |

Example 11: 3-Ethyl-8-(1-(1-(pent-3-yl)piperidin-4-yl)-1H-pyrazol-4-yl)-N2-(tetrahydro-2H-pyran-4-yl) pyridino [3,4-b]pyrazine-2,5-diamine (Compound 232)

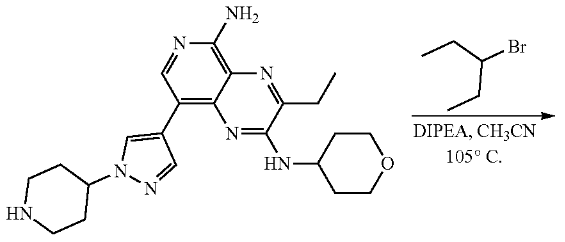

compound58

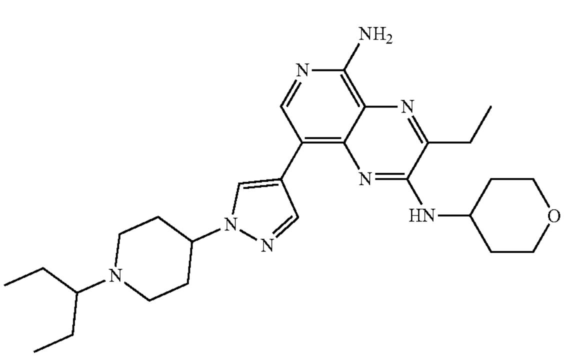

compound232

3-bromopentane (360 mg, 2.4 mmol) and diisopropylethylamine (90 mg, 0.70 mmol) were added to acetonitrile (3 mL) solution of compound 58 (100 mg, 0.20 mmol). This mixture was stirred and reacted at 105° C. for 16 hours in schlenk tube. At the end of the reaction, the mixture was cooled to room temperature and water (10 mL) was added. The mixture was extracted three times (10 mL×3) with ethyl acetate. The organic phases were combined, dried over anhydrous sodium sulfate, filtered, and the filtrate was concentrated under reduced pressure. The resulting residue was purified by preparative liquid chromatography to obtain formate of yellow solid compound 232 (30 mg, yield 23%). $^1$H NMR (400 MHz, DMSO-$d_6$) δ 8.34 (s, 1H), 8.17 (brs, 4H), 8.01 (s, 1H), 7.05 (d, J=8.0 Hz, 1H), 6.44 (brs, 2H), 4.35-4.26 (m, 1H), 4.17-4.09 (m, 1H), 4.01-3.94 (m, 2H), 3.49-3.43 (m, 2H), 2.83-2.82 (m, 4H), 2.46 (d, J=12.0 Hz, 2H), 2.30-2.23 (m, 1H), 2.06 (d, J=8.0 Hz, 2H), 1.99-1.88 (m, 4H), 1.74-1.70 (m, 2H), 1.52-1.45 (m, 2H), 1.37-1.24 (m, 5H), 0.91-0.87 (m, 6H). (ESI) m/z. 493.2 [M+1]$^+$.

Example 12: 3-ethyl-8-(5-(4-(4-methylpiperazine-1-yl)piperidine-1-yl)pyridin-2-yl)-N2-(tetrahydro-2H-pyran-4-yl)pyridino[3,4-b]pyrazine-2,5-diamine (Compound 20)

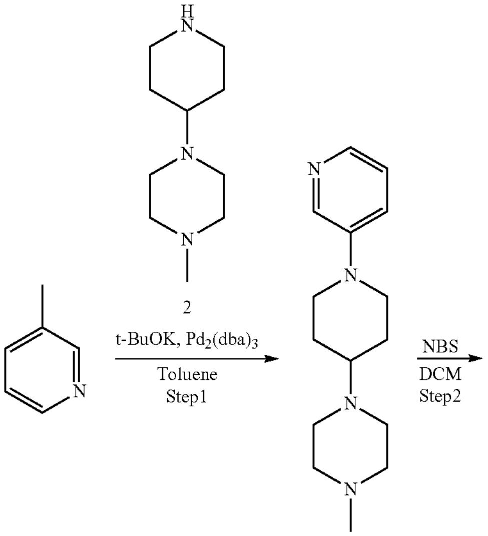

-continued

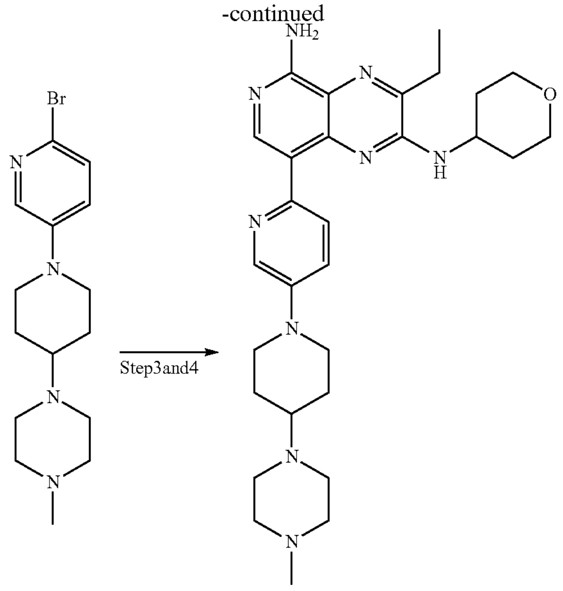

compound 20

Step 1: Tridibenzylidene acetone dipalladium (447 mg, 0.49 mmol) was added to toluene mixture (20 mL) containing 3-iodopyridine (1.00 g, 4.88 mmol), 1-methyl-4-(4-piperidinyl)piperazine (893 mg, 4.88 mmol), Xantphos (282 mg, 0.49 mmol) and potassium tert-butoxide (1.09 g, 9.76 mmol). This mixture was stirred to react at 108° C. for 4 hours under nitrogen. At the end of the reaction, the mixture was cooled to room temperature and methylene chloride (20 mL) and water (20 mL) were added. The mixture was extracted three times (20 mL×3) with dichloromethane. The organic phases were combined, washed with saturated saline (10 mL), dried over anhydrous sodium sulfate, filtered, and the filtrate was concentrated under reduced pressure. The residue was purified by silica gel chromatography (dichloromethane/methanol=10:1 to dichloromethane/methanol/25% ammonia solution=10:1:0.1) to obtain yellow solid (750 mg, yield 59%). $^1$H NMR (400 MHz, $CDCl_3$) δ 8.30 (d, J=2.8 Hz, 1H), 8.07-8.05 (m, 1H), 7.20-7.17 (m, 1H), 7.15-7.12 (m, 1H), 3.77-3.74 (m, 2H), 2.81-2.74 (m, 2H), 2.65-2.60 (m, 4H), 2.51-2.44 (m, 2H), 2.41-2.38 (m, 1H), 2.31 (s, 3H), 2.19-2.06 (m, 2H), 1.98-1.95 (m, 2H), 1.72-1.62 (m, 2H).

Step 2: NBS (770 mg, 4.33 mmol) was added in portions to dichloromethane mixture (30 mL) containing 1-methyl-4-(1-(pyridine-3-yl)piperidine-4-yl)piperazine (750 mg, 2.88 mmol) in ice bath. The reaction was stirred for 2 hours under 5-20° C., and then poured into water (20 mL). The solution was extracted with dichloromethane (20 mL×4). The organic phases were combined, washed with saturated saline (5 mL), dried over anhydrous sodium sulfate, filtered, and the filtrate was concentrated under reduced pressure. The resulting residue was purified by silica gel chromatography (dichloromethane/methanol=20:1 to 10:1) to obtain yellow solid (500 mg, yield 51%). $^1$H NMR (400 MHz, $CDCl_3$) δ 8.00 (d, J=3.2 Hz, 1H), 7.28-7.16 (m, 1H), 7.07 (dd, J=8.8, 3.2 Hz, 1H), 3.71-3.68 (m, 2H), 2.80-2.74 (m, 2H), 2.63-2.36 (m, 9H), 2.30 (s, 3H), 1.97-1.94 (m, 2H), 1.69-1.59 (m, 2H). MS Found: 339.1 [M+H]$^+$.

Steps 3 and 4: The method of Step 3 and Step 4 of Example 3 was referred, 1-(1-(6-Bromopyridine-3-yl)piperidine-4-yl)-4-methylpiperazine (145 mg, 0.43 mmol) was reacted with intermediate C (200 mg, 0.43 mmol) to give yellow solid compound 20 (60 mg, two-step yield 26%). $^1$H NMR (400 MHz, DMSO-$d_6$) δ 8.46 (s, 1H), 8.35-8.31 (m, 2H), 7.39-7.36 (m, 1H), 7.24-7.22 (m, 1H), 6.82 (s, 2H), 4.22-4.14 (m, 1H), 3.96-3.94 (m, 2H), 3.88-3.85 (m, 2H), 3.46-3.40 (m, 3H), 3.07-2.73 (m, 12H), 2.58 (s, 3H), 1.94-1.91 (m, 4H), 1.72-1.58 (m, 4H), 1.32 (t, J=7.2 Hz, 3H). MS Found: 532.2 [M+H]$^+$.

Example 13: (1S, 3R)-3-((5-amino-8-bromo-3-ethylpyridino[3,4-b]pyrazine-2-yl)amino)cyclopentan-1-ol (Compound 151)

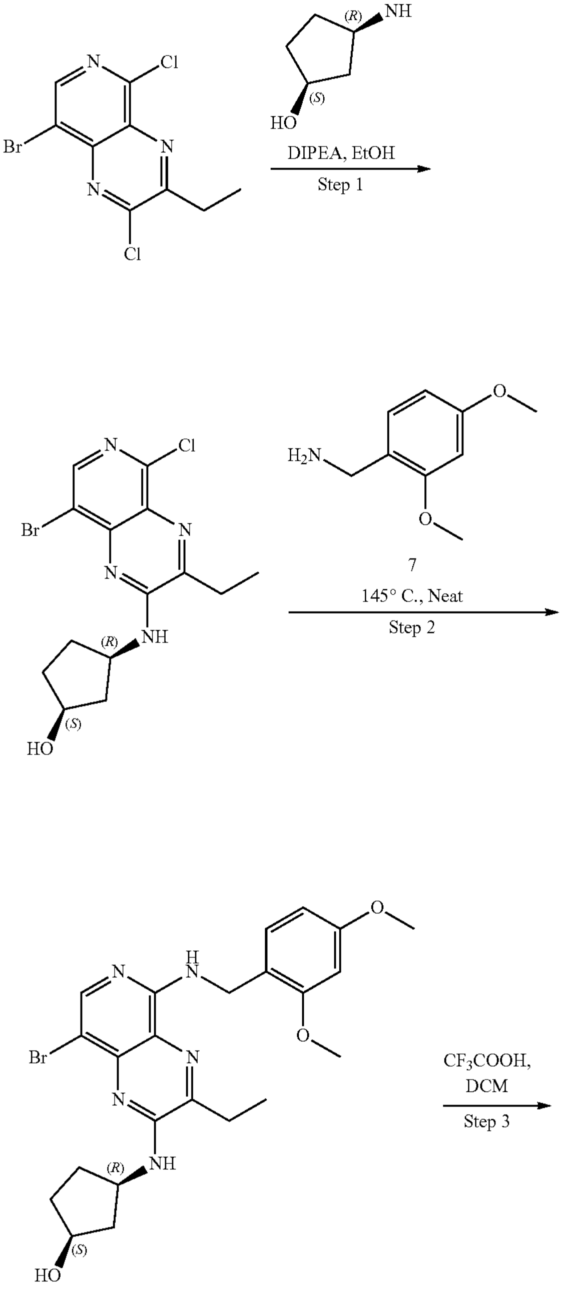

intermediate D

-continued

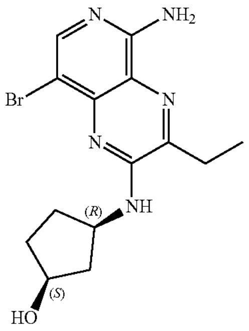

compound 151

Steps 1 and 2, synthesis of intermediate D: The methods of Step 9 of Example 1 and Step 1 of Example 2 were referred, (1S, 3R)-3-aminocyclopentanol hydrochloride was used to provide yellow solid intermediate D (two-step yield 40%). $^{1}$H NMR (400 MHz, DMSO-$d_6$) δ 8.01 (s, 1H), 7.31-7.17 (m, 2H), 7.07 (d, J=8.0 Hz, 1H), 6.56 (s, 1H), 6.44-6.38 (m, 1H), 5.76 (s, 1H), 4.74 (d, J=3.6 Hz, 1H), 4.56 (d, J=6.0 Hz, 2H), 4.52-4.41 (m, 1H), 3.83 (s, 3H), 3.72 (s, 3H), 2.83-2.77 (m, 2H), 2.13-1.99 (m, 2H), 1.83-1.72 (m, 2H), 1.68-1.56 (m, 2H), 1.30 (t, J=7.2 Hz, 3H). (ESI) m/z 502.0 $[M+H]^+$.

Step 3: The method of Step 12 in Example 1 was referred, intermediate D (100 mg, 0.20 mmol) was used to provide yellow solid compound 151 (56 mg, yield 79%). $^{1}$H NMR (400 MHz, DMSO-$d_6$) δ 8.14 (brs, 1H), 8.00 (s, 1H), 7.43 (d, J=6.8 Hz, 1H), 6.98 (brs, 2H), 4.76 (s, 1H), 4.55-4.45 (m, 1H), 4.22-4.13 (m, 1H), 2.81 (q, J=7.2 Hz, 2H), 2.36-2.27 (m, 1H), 2.12-2.01 (m, 1H), 1.87-1.73 (m, 2H), 1.70-1.58 (m, 2H), 1.30 (t, J=7.2 Hz, 3H). (ESI) m/z 352.1. $[M+H]^+$.

Example 14: The method of Step 2 in Example 2 was referred, and the starting materials in the following table were used to react with compound 151 to obtain the corresponding compounds:

| No | starting materials | structures | HNMR |
|---|---|---|---|
| 200 | 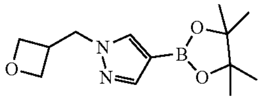 [SMILES: CC1(C)OB(c2cnn(CC3COC3)c2)OC1(C)C] | 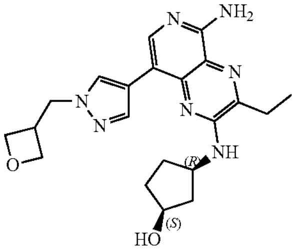 | $^{1}$H NMR (400 MHz, DMSO-$d_6$) δ 8.32 (s, 1H), 8.19-8.15 (m, 2H), 8.05 (s, 1H), 7.06 (d, J = 7.2 Hz, 1H), 6.38 (brs, 2H), 4.69-4.64 (m, 2H), 4.54-4.48 (m, 1H), 4.46-4.42 (m, 4H), 4.26-4.21 (m, 1H), 3.46-3.40 (m, 2H), 2.79 (q, J = 7.2 Hz, 2H), 2.29-2.22 (m, 1H), 2.08-2.01 (m, 1H), 1.86-1.79 (m, 2H), 1.71-1.64 (m, 2H), 1.30 (t, J = 7.2 Hz, 3H). Formate |
| 202 | 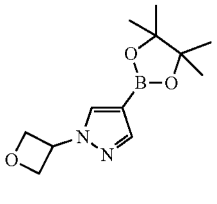 [SMILES: CC1(C)OB(c2cnn(C3COC3)c2)OC1(C)C] | 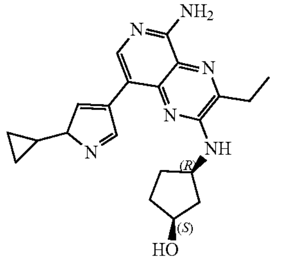 | $^{1}$H NMR (400 MHz, DMSO-$d_6$) δ 8.37 (s, 1H), 8.21-8.14 (m, 2H), 8.03 (s, 1H), 7.12-7.06 (m, 1H), 6.47-6.35 (m, 2H), 4.52-4.43 (m, 1H), 4.27-4.20 (m, 1H), 3.75-3.68 (m, 1H), 2.80 (q, J = 7.2 Hz, 2H), 2.30-2.23 (m, 1H), 2.10-2.01 (m, 1H), 1.91-1.61 (m, 5H), 1.30 (t, J = 7.2 Hz, 3H), 1.07-1.02 (m, 2H), 1.00-0.95 (m, 2H). Formate |
| 196 | 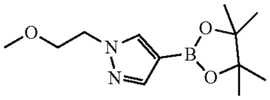 | 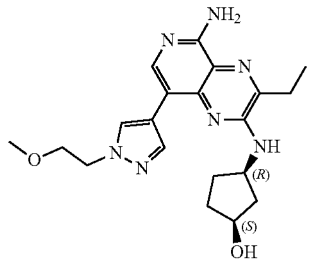 | $^{1}$H NMR (400 MHz, DMSO-$d_6$) δ 8.35 (s, 1H), 8.18 (brs, 1H), 8.15 (s, 1H), 8.04 (s, 1H), 7.06 (d, J = 7.2 Hz, 1H), 6.39 (brs, 2H), 4.52-4.46 (m, 1H), 4.28 (t, J = 5.2 Hz, 2H), 4.25-4.20 (m, 1H), 3.70 (t, J = 5.2 Hz, 2H), 3.24 (s, 3H), 2.80 (q, J = 7.2 Hz, 2H), 2.55-2.53 (m, 1H), 2.30-2.23 (m, 1H), 2.11-2.02 (m, 1H), 1.88-1.78 (m, 2H), 1.72-1.64 (m, 2H), 1.31 (t, J = 7.2 Hz, 3H). Formate |

-continued

| No | starting materials | structures | HNMR |
|---|---|---|---|
| 192 | 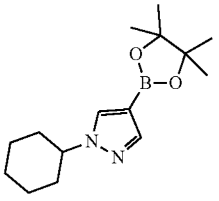 [SMILES: CC1(C)OB(c2cnn(C3CCCCC3)c2)OC1(C)C] | 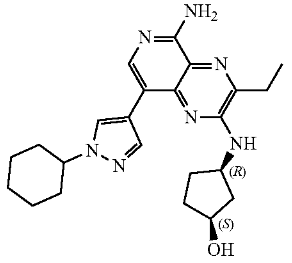 | $^1$H NMR (400 MHz, DMSO-$d_6$) δ 8.41 (s, 1H), 8.18 (brs, 1H), 8.14 (s, 1H), 8.00 (s, 1H), 7.12 (d, J = 7.2 Hz, 1H), 6.39 (brs, 2H), 4.54-4.44 (m, 1H), 4.26-4.09 (m, 2H), 2.80 (q, J = 7.2 Hz, 2H), 2.33-2.28 (m, 1H), 2.13-2.03 (m, 3H), 1.87-1.62 (m, 10H), 1.49-1.37 (m, 2H), 1.30 (t, J = 7.2 Hz, 3H), 1.25-1.18 (m, 1H). Formate |
| 191 | 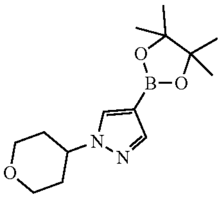 [SMILES: CC1(C)OB(c2cnn(C3CCOCC3)c2)OC1(C)C] | 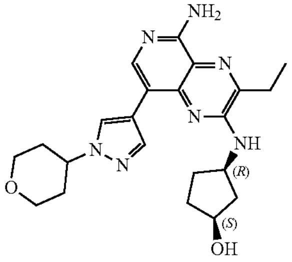 | $^1$H NMR (400 MHz, DMSO-$d_6$) δ 8.43 (s, 1H), 8.19 (s, 1H), 8.16 (brs, 1H), 8.06 (s, 1H), 7.10 (d, J = 7.2 Hz, 1H), 6.38 (brs, 2H), 4.51-4.37 (m, 2H), 4.25-4.18 (m, 1H), 4.03-3.95 (m, 2H), 3.54-3.45 (m, 3H), 2.80 (q, J = 7.2 Hz, 2H), 2.32-2.26 (m, 1H), 2.09-2.01 (m, 3H), 1.97-1.79 (m, 4H), 1.74-1.62 (m, 2H), 1.31 (t, J = 7.2 Hz, 3H). Formate |
| 201 | 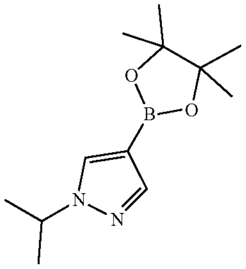 [SMILES: CC(C)n1cc(B2OC(C)(C)C(C)(C)O2)cn1] | 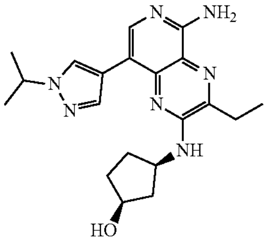 [SMILES: CCc1nc2c(N)ncc(-c3cnn(C(C)C)c3)c2nc1N[C@@H]1CC[C@H](O)C1] | $^1$H NMR (400 MHz, DMSO-$d_6$) δ 8.39 (s, 1H), 8.19 (s, 2H), 8.02 (s, 1H), 7.08 (d, J = 6.8 Hz, 1H), 6.37 (d, J = 7.2 Hz, 2H), 4.50-4.45 (m, 2H), 4.27-4.18 (m, 1H), 2.80 (q, J = 7.2 Hz, 2H), 2.28-2.23 (m, 1H), 2.05-1.99 (m, 1H), 1.90-1.62 (m, 5H), 1.46 (d, J = 6.8 Hz, 6H), 1.31 (t, J = 7.2 Hz, 3H). Formate |
| 203 | 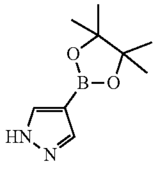 | 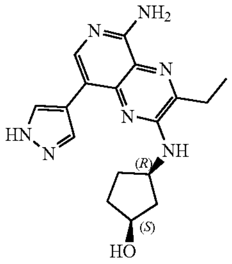 | $^1$H NMR (400 MHz, DMSO-$d_6$) δ 8.27-8.13 (m, 4H), 7.06 (d, J = 8.0 Hz, 1H), 6.40 (brs, 2H), 4.50-4.45 (m, 1H), 4.26-4.18 (m, 1H), 2.83-2.77 (m, 2H), 2.29-2.22 (m, 1H), 2.09-2.00 (m, 1H), 1.88-1.77 (m, 2H), 1.73-1.63 (m, 2H), 1.33-1.29 (m, 3H). Formate |
| 199 | 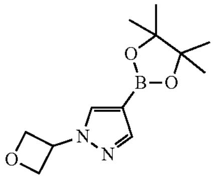 [SMILES: CC1(C)OB(c2cnn(C3COC3)c2)OC1(C)C] | 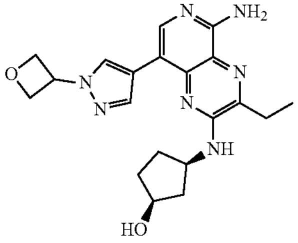 [SMILES: CCc1nc2c(N)ncc(-c3cnn(C4COC4)c3)c2nc1N[C@@H]1CC[C@H](O)C1] | $^1$H NMR (400 MHz, DMSO-$d_6$) δ 8.56 (s, 1H), 8.21 (d, J = 8.0 Hz, 2H), 8.16 (brs, 1H), 7.09 (d, J = 8.0 Hz, 1H), 6.42 (brs, 2H), 5.64-5.54 (m, 1H), 4.99-4.96 m, 2H), 4.92-4.89 (m, 2H), 4.53-4.48 (m, 1H), 4.26-4.20 (m, 1H), 2.83-2.77 (m, 2H), 2.33-2.25 (m, 1H), 2.08-2.02 (m, 1H), 1.88-1.78 (m, 2H), 1.72-1.62 (m, 2H), 1.33-1.29 (m, 3H). Formate |

-continued

| No | starting materials | structures | HNMR |
|---|---|---|---|
| 198 | 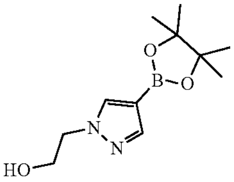 [SMILES: CC1(C)OB(c2cnn(CCO)c2)OC1(C)C] | 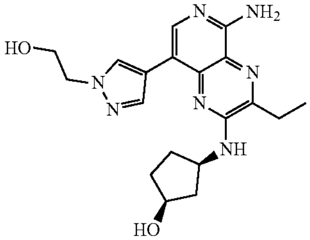 [SMILES: CCc1nc2c(N)ncc(-c3cnn(CCO)c3)c2nc1N[C@@H]1CC[C@H](O)C1] | $^1$H NMR (400 MHz, DMSO-$d_6$) δ 8.38 (s, 1H), 8.16 (brs, 1H), 8.04 (s, 1H), 7.11 (d, J = 4.0 Hz, 1H), 6.48 (brs, 2H), 4.93-4.91 (m, 1H), 4.78 (d, J = 4.0 Hz, 1H), 4.52-4.48 (m, 1H), 4.27-4.13 (m, 3H), 3.78-3.74 (m, 2H), 2.83-2.77 (m, 2H), 2.31-2.22 (m, 1H), 2.12-2.02 (m, 1H), 1.88-1.78 (m, 2H), 1.69-1.63 (m, 2H), 1.33-1.29 (m, 3H). |
| 194 | 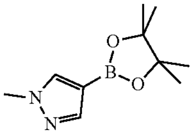 | 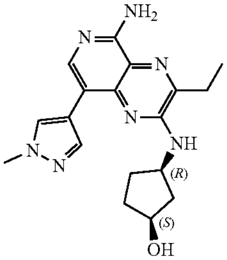 | $^1$H NMR (400 MHz, DMSO-$d_6$) δ 8.26 (s, 1H), 8.21 (brs, 2H), 8.15 (s, 1H), 8.03 (s, 1H), 7.06 (d, J = 7.2 Hz, 1H), 6.37 (brs, 2H), 4.49-4.44 (m, 1H), 4.24-4.21 (m, 1H), 3.87 (s, 3H), 2.82-2.77 (m, 2H), 2.54-2.52 (m, 1H), 2.33-2.24 (m, 1H), 2.08-2.04 (m, 1H), 1.86-1.80 (m, 2H), 1.70-1.64 (m, 2H), 1.30 (t, J = 7.2 Hz, 3H). Formate |
| 190 | 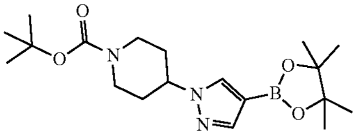 [SMILES: CC(C)(C)OC(=O)N1CCC(n2cc(B3OC(C)(C)C(C)(C)O3)cn2)CC1] | 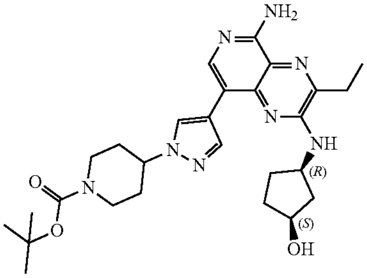 | $^1$H NMR (400 MHz, DMSO-$d_6$) δ 8.42 (s, 1H), 8.16 (s, 1H), 8.05 (s, 1H), 7.26-7.17 (m, 1H), 6.64 (brs, 2H), 4.79 (d, J = 3.6 Hz, 1H), 4.52-4.43 (m, 1H), 4.42-4.32 (m, 1H), 4.25-4.18 (m, 1H), 4.12-3.98 (m, 2H), 3.02-2.88 (m, 2H), 2.81 (q, J = 7.2 Hz, 2H), 2.32-2.25 (m, 1H), 2.12-2.00 (m, 3H), 1.90-1.57 (m, 7H), 1.42 (s, 9H), 1.31 (t, J = 7.2 Hz, 3H). |
| 176 | 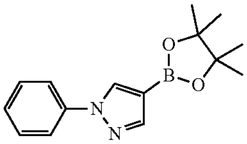 [SMILES: CC1(C)OB(c2cnn(-c3ccccc3)c2)OC1(C)C] | 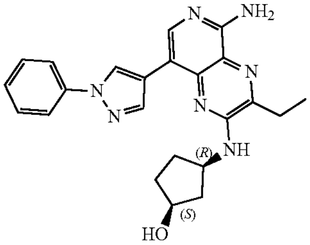 | $^1$H NMR (400 MHz, dmso-$d_6$) δ 9.07 (s, 1H), 8.42 (s, 1H), 8.34 (s, 1H), 8.18 (brs, 1H), 7.86-7.80 (m, 2H), 7.55-7.49 (m, 2H), 7.33-7.29 (m, 1H), 7.16 (d, J = 7.2 Hz, 1H), 6.49 (brs, 2H), 4.58-4.52 (m, 1H), 4.25-4.17 (m, 1H), 2.85-2.80 (m, 2H), 2.37-2.29 (m, 1H), 2.13-2.07 (m, 1H), 1.91-1.76 (m, 2H), 1.72-1.65 (m, 2H), 1.34-1.30 (m, 3H). Formate |

Example 15: (1S,3R)-3-((5-amino-3-ethyl-8-(1-(piperidin-4-yl)-1H-pyrrole-3-yl)pyrido[3,4-b]pyrazin-2-yl)amino)cyclopentan-1-ol (Compound 152) and (1S,3R)-3-((5-amino-3-ethyl-8-(1-(1-methylpiperidine-4-yl)-1H-pyrrole-3-yl)pyrido[3,4-b]pyrazine-2-yl)amino)cyclopentan-1-ol (Compound 153)

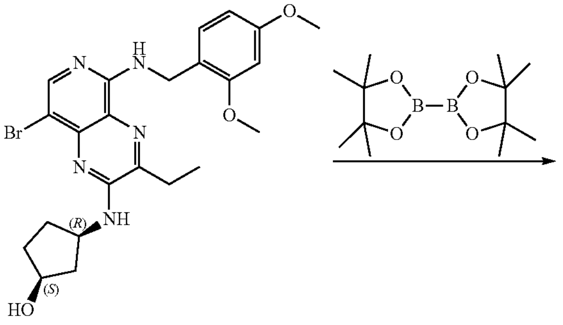

intermediate D

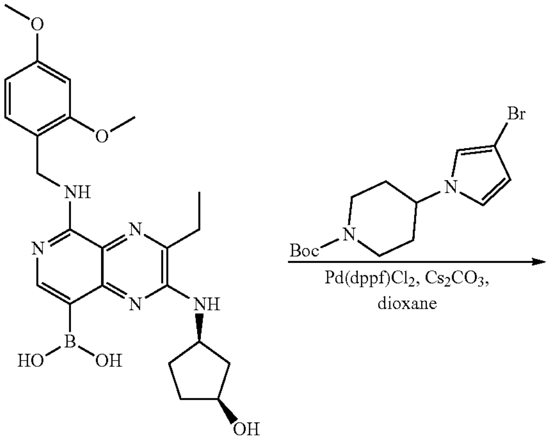

intermediate E

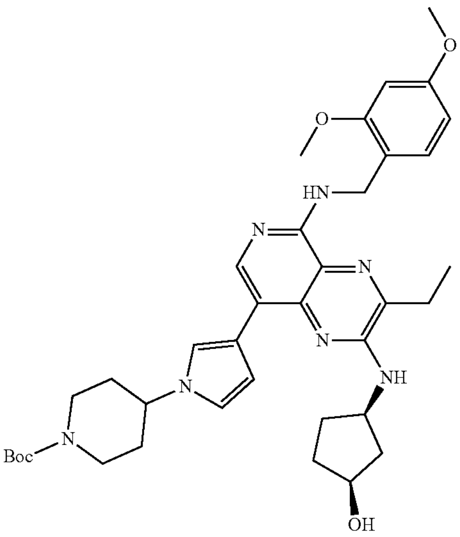

-continued

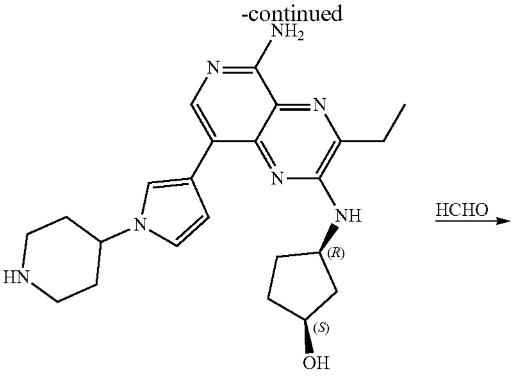

compound152

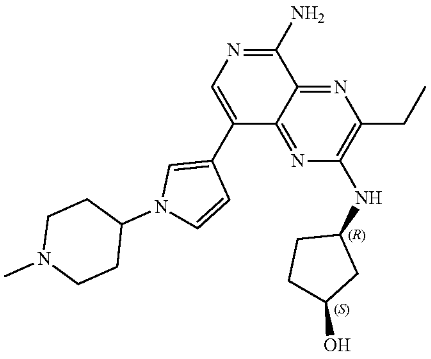

compound153

The method of Example 3 was referred, in which intermediate E was prepared from intermediate D, and then reacted with tert-butyl 4-(3-bromo-1H-pyrrole-1-yl) piperidin-1-carboxylate ester. The obtained product was deprotected according to the method of Step 12 of Example 1 to obtain yellow solid compound 152. Compound 152 was reacted with formaldehyde according to the method of Step 2 of Example 6 to obtain yellow solid compound 153.

Compound 152: 1H NMR (400 MHz, DMSO-$d_6$) δ 7.68 (s, 1H), 6.96 (d, J=7.2 Hz, 1H), 6.88 (s, 1H), 6.49 (s, 2H), 6.07 (t, J=4.0 Hz, 1H), 5.87 (s, 1H), 4.77 (d, J=3.6 Hz, 1H), 4.31 (d, J=6.4 Hz, 1H), 4.09 (s, 1H), 3.80 (s, 1H), 2.92 (d, J=12.0 Hz, 2H), 2.77-2.72 (m, 2H), 2.24 (s, 1H), 2.00-1.90 (m, 1H), 1.81-1.47 (m, 11H), 1.29 (t, J=7.2 Hz, 3H). (ESI) m/z. 422.2 $[M+1]^+$.

Compound 153: 1H NMR (400 MHz, DMSO-$d_6$) δ 7.69 (s, 1H), 7.00 (d, J=7.2 Hz, 1H), 6.90 (s, 1H), 6.55 (s, 2H), 6.10 (t, J=4.0 Hz, 1H), 5.90-5.89 (m, 1H), 4.79 (d, J=3.6 Hz, 1H), 4.37-4.24 (m, 1H), 4.09 (d, J=4.0 Hz, 1H), 3.80 (s, 1H), 2.95 (s, 2H), 2.77-2.72 (m, 2H), 2.30 (s, 3H), 2.02-1.57 (m, 11H), 1.55-1.49 (m, 1H), 1.30 (t, J=7.2 Hz, 3H). (ESI) m/z. 436.2 $[M+1]^+$.

Example 16: The method of Step 2 in Example 6 was referred, the starting material of the following table was used to react with the compound 154 to obtain the corresponding compounds:

| No | register No# starting material | structure | HNMR |
|---|---|---|---|
| 155 | 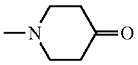 | 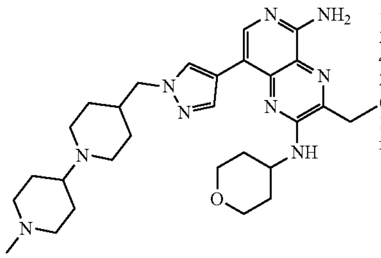 | $^1$H NMR (400 MHz, DMSO-$d_6$) δ 8.27 (s, 1H), 8.19 (s, 3H), 8.01 (s, 1H), 7.07 (d, J = 7.2 Hz, 1H), 6.39 (brs, 2H), 4.33-4.28 (m, 2H), 4.00-3.95 (m, 5H), 3.53-3.44 (m, 2H), 2.92-2.76 (m, 7H), 2.25-2.08 (m, 6H), 1.97-1.94 (m, 4H), 1.90-1.88 (m, 1H), 1.81-1.64 (m, 4H), 1.76-1.65 (m, 4H), 1.56-1.37 (m, 5H), 1.49-1.39 (m, 2H). formate |

Example 17: (1S,3R)-3-((5-amino-3-ethyl-8-(1-(1,2,2,6,6-pentamethylpiperidine-4-yl)-1H-pyrazol-4-yl)pyridino[3,4-b]pyrazine-2-yl)amino)cyclopentan-1-ol (Compound 169)

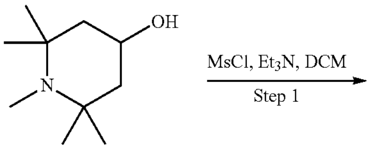

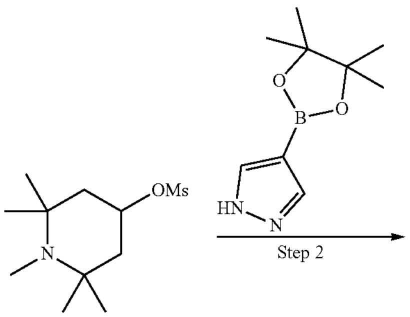

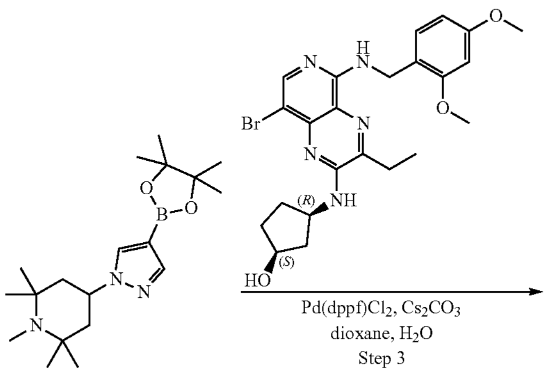

-continued

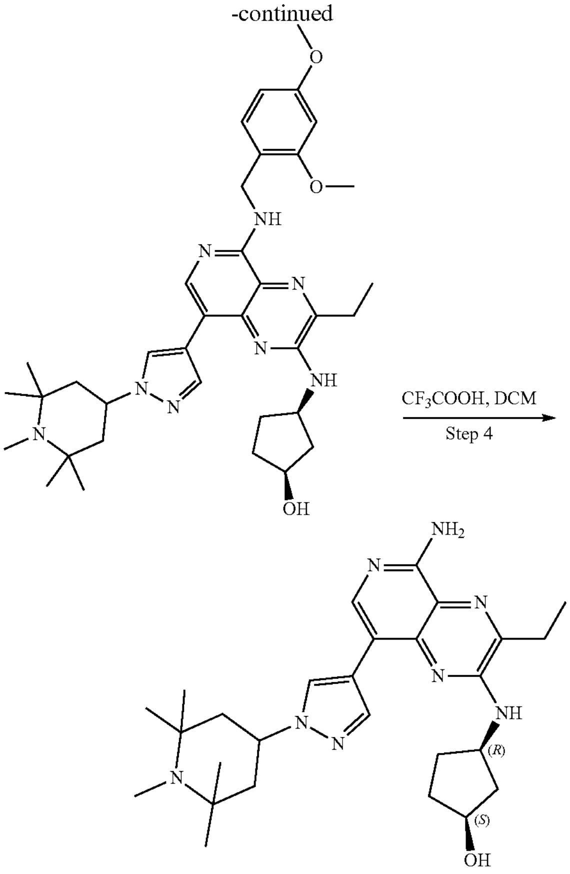

Step 1: Triethylamine (8.9 g, 88 mmol) and methanesulfonyl chloride (2.4 g, 21 mmol) were added to dichloromethane solution (30 mL) containing 4-hydroxy-1,2,2,6,6-pentamethylpiperidine (3 g, 18 mmol) at 0° C. The reaction was stirred at 25° C. for 6 hours and quenched with saturated sodium bicarbonate solution after the reaction. The solution was extracted twice (30 mL×2) with dichloromethane. The organic phases were combined, dried over anhydrous sodium sulfate, filtered, and the filtrate was concentrated under reduced pressure to obtain yellow oil (74.2 g, yield 96%), which is directly used for the next reaction. (ESI) m/z 250.2. $[M+H]^+$.

Step 2: Sodium hydride (0.48 g, 12 mmol) was added to the solution of N,N-dimethylformamide (20 mL) containing 4-pyrazole borate (2.3 g, 12 mmol). After stirring at 25° C.

for 1 hour, the product of step 1 (1,2,2,6, 6-pentamethylpiperidine-4-yl)mesylate (2.0 g, 8.0 mol) was added. The solution was stirred at 110° C. for 12 hours. The mixture was cooled to room temperature and extracted with ethyl acetate (30 mL×3). The organic phases were combined, dried over anhydrous sodium sulfate, filtered, and the filtrate was concentrated under reduced pressure. The residue was purified by preparative liquid chromatography to obtain yellow oil (23 mg, 1.3%) (ESI) m/z. 348.2 $[M+H]^+$.

Steps 3 and 4: The method of Step 2 in Example 2 was referred, and then method of removing the protective group of Step 12 in Example 1 was referred, Intermediate D (15 mg, 0.03 mmol) was reacted with the product of Step 2 (26 mg, 0.075 mmol) to obtain yellow solid compound 169 (4.5 mg, two-step yield 28%). $^1$H NMR (400 MHz, DMSO-$d_6$) δ 8.44 (s, 1H), 8.20 (d, J=8.0 Hz, 4H), 8.02 (s, 1H), 7.10 (d, J=8.0 Hz, 1H), 6.38 (s, 2H), 4.54-4.49 (m, 2H), 4.25-4.20 (m, 1H), 2.81-2.78 (m, 2H), 2.33-2.29 (m, 1H), 2.25 (s, 3H), 2.09-2.05 (m, 1H), 2.00-1.97 (m, 2H), 1.89-1.80 (m, 5H), 1.71-1.61 (m, 2H), 1.32-1.29 (m, 3H), 1.16 (s, 6H), 1.11 (s, 6H). (ESI) m/z. 493.3 $[M+H]^+$.

The method of Example 17 staffing from Step 3 was referred, the starting material in following table was reacted with intermediate D, then reacted with methyl iodide according to method of Example 17 to obtain the following table compound:

| No | register No# starting material | structure | HNMR |
|---|---|---|---|
| 204 | 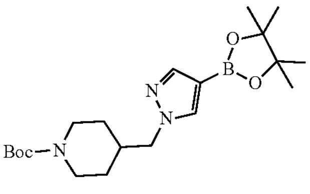 [SMILES: CC(C)(C)OC(=O)N1CCC(Cn2cc(B3OC(C)(C)C(C)(C)O3)cn2)CC1] | 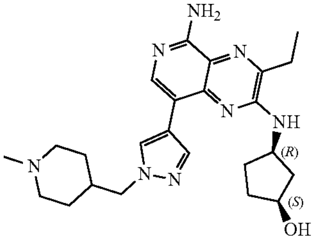 | $^1$H NMR (400 MHz, DMSO-$d_6$) δ 8.32 (s, 1H), 8.22 (s, 3H), 8.17 (s, 1H), 8.02 (s, 1H), 7.08 (d, J = 8.0 Hz, 1H), 6.39 (brs, 2H), 4.51-4.46 (m, 1H), 4.26-4.20 (m, 1H), 4.02 (d, J = 8.0 Hz, 2H), 2.85-2.77 (m, 4H), 2.51 (s, 2H), 2.29-2.19 (m, 4H), 2.09-1.93 (m, 4H), 1.85-1.79 (m, 2H), 1.71-1.63 (m, 2H), 1.52 (d, J = 12.0 Hz, 2H), 1.32-1.29 (m, 3H). formate |

The step 3 to the end of method of Example 17 was referred, the starting materials in the following table were used to obtain the corresponding compounds:

| No | starting materials | structures | HNMR |
|---|---|---|---|
| 197 | 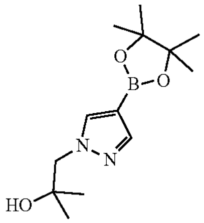 [SMILES: CC(C)(O)Cn1cc(B2OC(C)(C)C(C)(C)O2)cn1] | 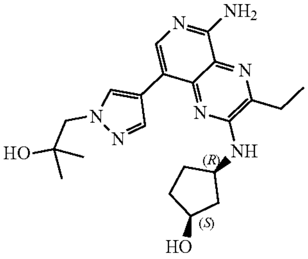 | $^1$H NMR (400 MHz, DMSO-$d_6$) δ 8.38 (s, 1H), 8.18 (s, 2H), 8.01 (s, 1H), 7.05 (d, J = 7.2 Hz, 1H), 6.39 (brs, 2H), 4.70 (s, 1H), 4.54-4.49 (m, 1H), 4.27-4.19 (m, 1H), 4.03 (s, 2H), 2.82-2.77 (m, 2H), 2.54 (s, 1H), 2.30-2.19 (m, 1H), 2.08-2.02 (m, 1H), 1.88-1.76 (m, 2H), 1.72-1.60 (m, 2H), 1.31 (t, J = 7.2 Hz, 3H), 1.10 (s, 6H). formate |
| 195 | 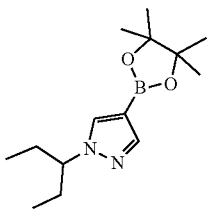 [SMILES: CCC(CC)n1cc(B2OC(C)(C)C(C)(C)O2)cn1] | 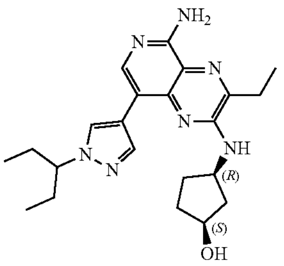 | $^1$H NMR (400 MHz, DMSO-$d_6$) δ 8.35 (s, 1H), 8.18 (s, 1H), 8.14 (brs, 1H), 8.02 (s, 1H), 7.11 (d, J = 8.0 Hz, 1H), 6.43 (brs, 2H), 4.80 (s, 1H), 4.52-4.47 (m, 1H), 4.25-4.17 (m, 1H), 4.01-3.94 (m, 1H), 2.83-2.78 (m, 2H), 2.31-2.24 (s, 1H), 2.09-2.00 (m, 1H), 1.88-1.75 (m, 6H), 1.74-1.63 (m, 2H), 1.32-1.29 (m, 3H), 0.75-0.71 (m, 6H). formate |

-continued

| No | starting materials | structures | HNMR |
|---|---|---|---|
| 186 | 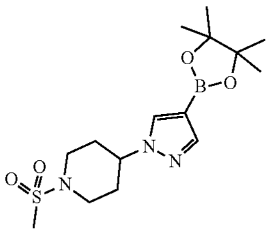 [SMILES: CC1(C)OB(c2cnn(C3CCN(S(C)(=O)=O)CC3)c2)OC1(C)C] | 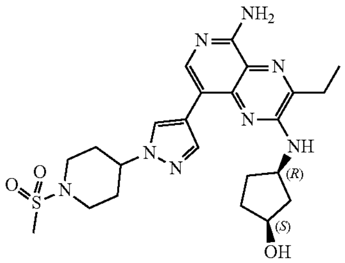 | $^1$H NMR (400 MHz, DMSO-$d_6$) δ 8.43 (s, 1H), 8.18 (s, 1H), 8.14 (brs, 1H), 8.08 (s, 1H), 7.14 (d, J = 4.0 Hz, 1H),<br>6.50 (brs, 2H), 4.78 (s, 1H), 4.51-4.46 (m, 1H), 4.39-4.29 (m, 1H), 4.22 (s, 1H), 3.68 (d, J = 12.0 Hz, 2H), 3.02<br>-2.90 (m, 5H), 2.83-2.78 (m, 2H), 2.31-2.25 (m, 1H), 2.20 (d, J = 8.0 Hz, 2H), 2.08-1.94 (m, 3H), 1.89-1.76 (m, 2H), 1.73-1.61 (m, 2H), 1.32-1.29 (m, 3H). formate |

The step 2 to the end of method of Example 17 was referred, the starting materials in the following table were used to obtain the corresponding compounds

| No | starting materials | structures | HNMR |
|---|---|---|---|
| 306 | 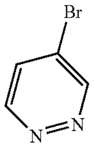 | 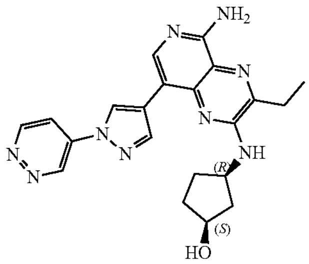 | $^1$H NMR (400 MHz, DMSO-$d_6$) δ 9.80 (s, 1H), 9.28 (s, 2H), 8.65 (s, 1H), 8.34 (s, 1H), 8.14 (brs, 1H), 8.05-8.02 (m, 1H), 7.19 (d, J = 7.2 Hz, 1H), 6.62 (s, 2H), 4.80 (s, 1H), 4.59-4.54 (m, 1H), 4.24-4.19 (m, 1H), 2.85-2.79 (m, 2H), 2.33-2.27 (m, 1H), 2.11-2.03 (m, 1H), 1.91-1.77 (m, 2H), 1.73-1.64 (m, 2H), 1.32 (t, J = 7.2 Hz, 3H). formate |
| 179 | 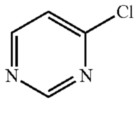 | 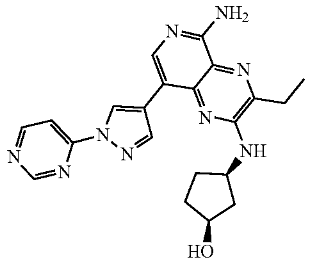 [SMILES: CCc1nc2c(N)ncc(-c3cnn(-c4ccncn4)c3)c2nc1N[C@@H]1CC[C@H](O)C1] | $^1$H NMR (400 MHz, DMSO-$d_6$) δ 9.59 (s, 1H), 9.05 (s, 1H), 8.89 (d, J = 5.6 Hz, 1H), 8.61 (s, 1H), 8.35 (s, 1H), 7.97-7.95 (m, 1H), 7.65 (d, J = 6.4 Hz, 1H), 7.53 (s, 2H), 4.81 (d, J = 3.2 Hz, 1H), 4.57-4.52 (m, 1H), 4.31 (s, 1H), 2.89-2.83 (m, 2H), 2.46-2.40 (m, 1H), 2.21-2.13 (m, 1H), 1.96-1.86 (m, 2H), 1.75-1.66 (m, 2H), 1.33 (t, J = 7.2 Hz, 3H). |
| 341 | 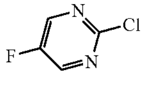 | 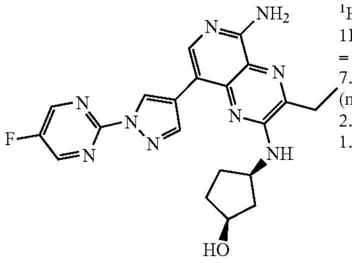 | $^1$H NMR (400 MHz, DMSO-$d_6$) δ 9.48 (s, 1H), 8.93 (s, 1H), 8.50 (s, 1H), 8.40 (s, 1H), 8.22 (brs, 1H), 7.21 (d, J =<br>7.2 Hz, 1H), 6.54 (s, 2H), 4.59-4.49 (m, 1H), 4.31-4.26 (m, 3H), 2.85-2.80 (m, 2H), 2.43-2.38 (m, 1H), 2.20-2.12 (m, 1H), 1.94-1.82 (m, 2H), 1.74-1.65 (m, 2H), 1.32 (t, J = 7.2 Hz, 3H). formate |

The method of Example 17 was referred, and 4-hydroxy-1,2,2,6,6-pentamethylpiperidine was replaced with the starting materials in the following table to obtain the corresponding compounds:

| No | starting materials | structures | HNMR |
|---|---|---|---|
| 283 | 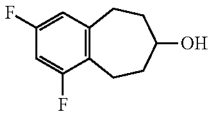 [SMILES: OC1CCc2cc(F)cc(F)c2CC1] | 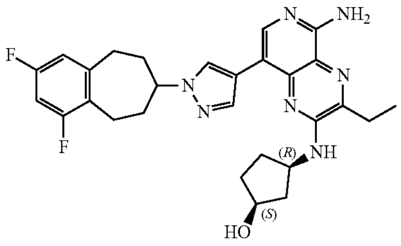 | $^1$H NMR (400 MHz, DMSO-$d_6$) δ 8.38 (s, 1H), 8.17 (brs, 2H), 8.00 (s, 1H), 7.05-7.00 (m, 3H), 6.38 (brs, 2H), 4.58 -4.54 (m 1H), 4.41-4.38 (m, 1H), 4.04-4.01 (m, 1H), 3.18-3.15 (m, 1H), 3.02-2.87 (m, 2H), 2.79 (q, J = 7.2 Hz, 2H), 2.69-2.59 (m, 1H), 2.33-2.30 (m, 2H), 2.23-2.20 (m, 1H), 2.03-1.90 (m, 1H), 1.88-1.51 (m, 7H), 1.29 (t, J = 7.2 Hz, 3H). formate |
| 193 | 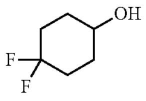 | 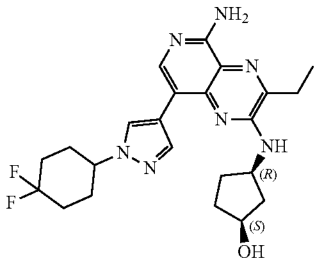 | $^1$H NMR (400 MHz, DMSO-$d_6$) δ 8.42 (s, 1H), 8.20 (s, 1H), 8.17 (s, 1H), 8.06 (s, 1H), 7.10 (d, J = 8.0 Hz, 1H), 6.39 (brs, 2H), 4.99-4.43 (m, 2H), 4.24-4.19 (m, 1H), 2.83-2.77 (m, 2H), 2.52 (d, J = 4.0 Hz, 1H), 2.30-2.25 m, 1H), 2.21-1.92 (m, 9H), 1.90-1.75 (m, 2H), 1.72-1.63 (m, 2H), 1.30-1.29 (m, 3H). formate |
| 170 | 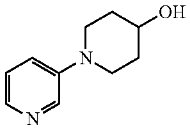 [SMILES: OC1CCN(c2cccnc2)CC1] | 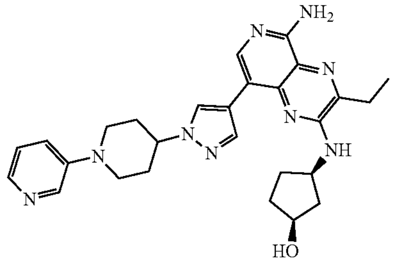 [SMILES: CCc1nc2c(N)ncc(-c3cnn(C4CCN(c5cccnc5)CC4)c3)c2nc1N[C@@H]1CC[C@H](O)C1] | $^1$H NMR (400 MHz, DMSO-$d_6$) δ 8.45 (s, 1H), 8.37 (d, J = 4.0 Hz, 1H), 8.13 (s, 1H), 8.08 (s, 1H), 8.00 (d, J = 4.0 Hz, 1H), 7.40-7.38 (m, 2H), 7.25-7.21 (m, 1H), 7.03 (s, 2H), 4.81 (d, J = 3.2 Hz, 1H), 4.50-4.40 (m, 2H), 4.20 (d, J = 4.0 Hz, 1H), 3.91 (d, J = 12.0 Hz, 2H), 2.98 (t, J = 12.0 Hz, 2H), 2.81 (t, J = 7.2 Hz, 2H), 2.26-2.14 (m, 3H), 2.05-1.99 (m, 3H), 1.89-1.79 (m, 2H), 1.71-1.63 (m, 2H), 1.31 (t, J = 7.2 Hz, 2H). |
| 173 | 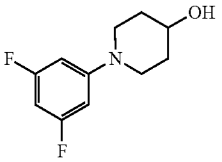 [SMILES: OC1CCN(c2cc(F)cc(F)c2)CC1] | 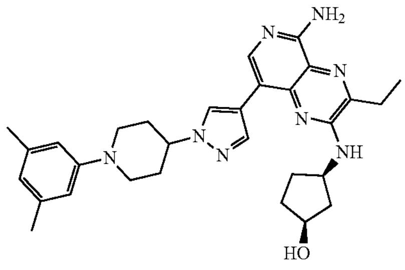 [SMILES: CCc1nc2c(N)ncc(-c3cnn(C4CCN(c5cc(C)cc(C)c5)CC4)c3)c2nc1N[C@@H]1CC[C@H](O)C1] | $^1$H NMR (400 MHz, DMSO-$d_6$) δ 8.41 (s, 1H), 8.25 (brs, 1H), 8.19 (s, 1H), 8.06 (s, 1H), 7.04 (d, J = 7.2 Hz, 1H), 6.70-6.66 (m, 2H), 6.49-6.43 (m, 1H), 6.36 (brs, 2H), 4.80 (s, 1H), 4.47-4.40 (m, 2H), 4.22-4.17 (m, 1H), 3.94 (d, J = 13.2 Hz, 2H), 3.05-2.99 (m, 2H), 2.81-2.76 (m, 2H), 2.24-2.17 (m, 1H), 2.13-2.10 (m, 2H), 1.99-1.74 (m, 5H), 1.70-1.62 (m, 2H), 1.30 (t, J = 7.2 Hz, 3H). formates |

Example 18

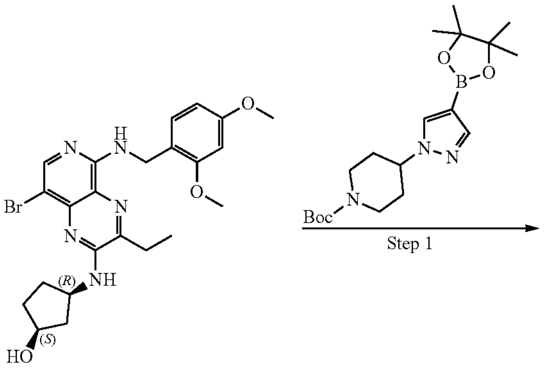

intermediate D

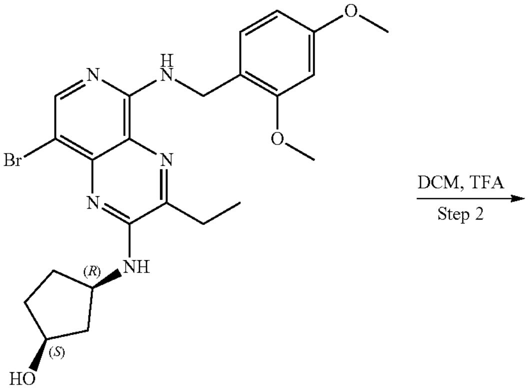

-continued

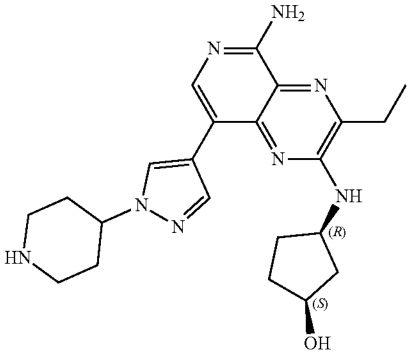

intermediate F

Step 1: The method of Step 2 of Example 2 was referred, intermediate D (0.30 g, 0.60 mmol) was used as the starting material to react with tert-butyl 4-(4-(4,4,5,5-tetramethyl-1,3,2-dioxaborolan-2-yl)-1H-pyrazol-1-yl)piperidine-1-carboxylate (0.45 g, 1.2 mmol) to obtain yellow solid (180 mg, yield 45%). (ESI) m/z 673.3. $[M+H]^+$.

Step 2: The method of Step 12 in Example 1 was referred, the product of Step 1 (0.18 g, 0.27 mmol) was used as the starting material to obtain yellow solid intermediate F (80 mg, yield 71%). (ESI) m/z 423.3. $[M+H]^+$.

The method of Step 2 in Example 6, the starting materials in the following table were used to react with the intermediate F, then the protecting group was removed according to the method of Step 12 in Example 1, and finally reacted with paraformaldehyde according to the method of Step 2 in Example 6 to obtain the compound of following table:

| No | starting materials | structures | HNMR |
|---|---|---|---|
| 210 | 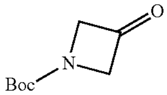 | 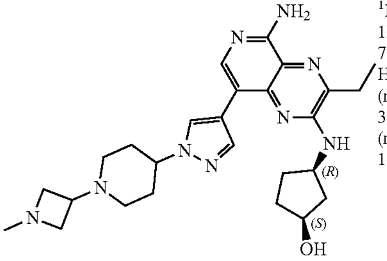 | $^1$H NMR (400 MHz, DMSO-$d_6$) δ 8.43 (s, 1H), 8.18 (s, 1H), 8.16 (s, 2H), 8.05 (d, J = 4.0 Hz, 1H), 7.15 (d, J = 7.2 Hz, 1H), 6.45 (brs, 2H), 4.48-4.45 (m, 1H), 4.20-4.17 (m, 2H), 3.98-3.88 (m, 1H), 3.60-3.58 (m, 1H), 3.17-3.14 (m, 2H), 2.82-2.78 (m, 3H), 2.67 (s, 3H), 2.31-2.28 (m, 2H), 1.93-1.75 (m, 10H), 1.73-1.61 (m, 2H), 1.33-1.25 (m, 3H). formate |

The following starting materials were used to react with the intermediate F according to the method of step 2 in Example 6 to obtain the compounds of following table:

| No | starting materials | structures | HNMR |
|---|---|---|---|
| 211 | 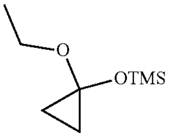 | 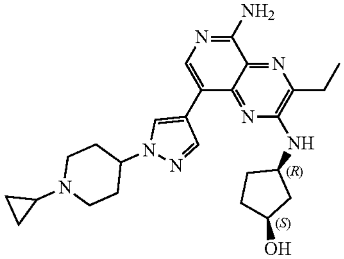 | $^1$H NMR (400 MHz, DMSO-$d_6$) δ 8.43 (s, 1H), 8.19-8.16 (m, 3H), 8.01 (s, 1H), 7.15-7.09 (m, 1H), 6.40 (brs, 2H), 4.50-4.42 (m, 1H), 4.24-4.10 (m, 3H), 3.05-3.00 (m, 2H), 2.80 (q, J = 7.2 Hz, 2H), 2.37-2.30 (m, 3H), 2.09-2.01 (m, 3H), 1.88-1.76 (m, 4H), 1.70-1.61 (m, 3H), 1.30 (t, J = 7.2 Hz, 3H), 0.46-0.41 (m, 2H), 0.34-0.31 (m, 2H). formate |

-continued

| No | starting materials | structures | HNMR |
| --- | --- | --- | --- |
| 214 | 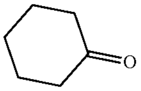 | 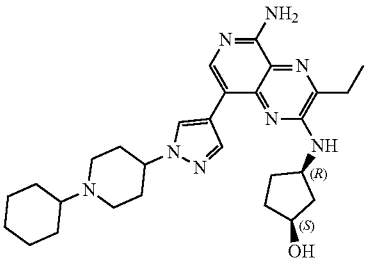 | $^1$H NMR (400 MHz, DMSO-$d_6$) δ 8.42 (s, 1H), 8.22 (brs, 2H), 8.18 (s, 1H), 8.04 (s, 1H), 7.14 (d, J = 7.2 Hz, 1H), 6.51 (brs, 2H), 4.51-4.46 (m, 2H), 4.25-4.16 (m, 2H), 3.05 (d, J = 11.6 Hz, 2H), 2.83-2.78 (m, 2H), 2.59-2.50 (m, 2H), 2.35-2.28 (m, 1H), 2.14-1.95 (m, 5H), 1.88-1.57 (m, 10H), 1.33-1.17 (m, 7H), 1.13-1.04 (m, 1H). formate |
| 213 | 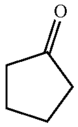 | 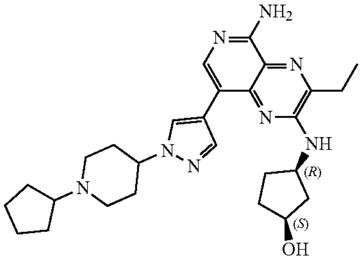 | $^1$H NMR (400 MHz, DMSO-$d_6$) δ 8.43 (s, 1H), 8.19-8.17 (m, 4H), 8.04 (s, 1H), 7.12 (d, J = 7.2 Hz, 1H), 6.43 (brs, 2H), 4.51-4.45 (m, 1H), 4.25-4.22 (m, 1H), 4.20-4.13 (m, 1H), 3.09 (d, J = 9.6 Hz, 2H), 2.80 (q, J = 7.2 Hz, 2H), 2.53-2.52 (m, 2H), 2.26-2.17 (m, 2H), 2.15-1.88 (m, 6H), 1.87-1.79 (m, 4H), 1.71-1.60 (m, 4H), 1.55-1.47 (m, 2H), 1.45-1.36 (m, 2H), 1.30 (t, J = 7.2 Hz, 3H). formate |
| 215 | paraformaldehyde | 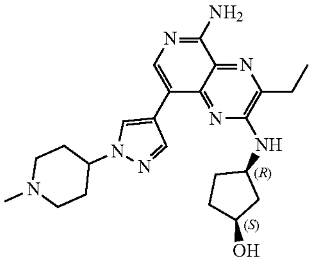 | $^1$H NMR (400 MHz, DMSO-$d_6$) δ 8.41 (s, 1H), 8.19 (s, 1H), 8.15 (brs, 2H), 8.07 (s, 1H), 7.12 (d, J = 7.2 Hz, 1H), 6.46 (brs, 2H), 4.55-4.45 (m, 1H), 4.25-4.17 (m, 2H), 3.13-3.03 (m, 3H), 2.80 (q, J = 7.2 Hz, 2H), 2.53-2.52 (m, 2H), 2.41 (s, 3H), 2.30-2.25 (m, 1H), 2.17-2.10 (m, 2H), 2.08-2.00 (m, 3H), 1.88-1.79 (m, 2H), 1.72-1.63 (m, 2H), 1.31 (t, J = 7.2 Hz, 3H). formate |
| 245 | 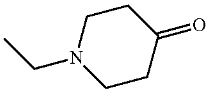 | 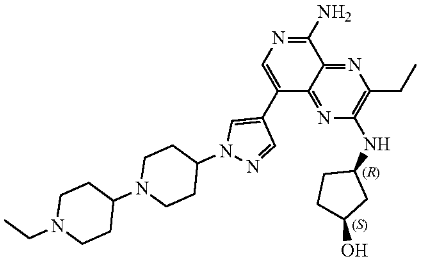 | $^1$H NMR (400 MHz, DMSO-$d_6$) δ 8.44 (s, 1H), 8.22 (s, 3H), 8.19 (s, 1H), 8.02 (s, 1H), 7.13 (d, J = 7.2 Hz, 1H), 6.42 (brs, 2H), 4.48-4.45 (m, 1H), 4.23-4.20 (m, 1H), 4.13-4.10 (m, 1H), 3.08-3.05 (m, 2H), 2.98-2.95 (m, 2H), 2.80-2.78 (m, 2H), 2.56-2.50 (m, 3H), 2.41-2.03 (m, 9H), 1.94-1.49 (m, 10H), 1.30 (t, J = 7.2 Hz, 3H), 1.11-1.02 (m, 3H). formate |
| 208 | 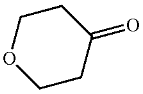 | 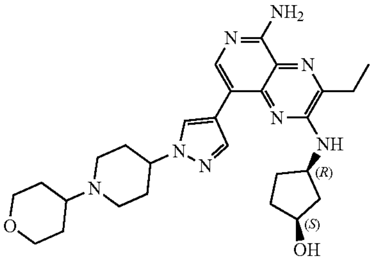 | $^1$H NMR (400 MHz, DMSO-$d_6$) δ 8.44 (s, 1H), 8.25 (brs, 3H), 8.19 (s, 1H), 8.02 (s, 1H), 7.13 (d, J = 7.2 Hz, 1H), 6.40 (brs, 2H), 4.52-4.45 (m, 1H), 4.24-4.21 (m, 1H), 4.14-4.11 (m, 1H), 3.94-3.90 (m, 2H), 3.80-3.75 (m, 1H), 3.65-3.60 (m, 1H), 3.35-3.25 (m, 2H), 3.00 (d, J = 11.6 Hz, 2H), 2.83-2.78 (m, 2H), 2.37-2.27 (m, 3H), 2.12-2.02 (m, 3H), 1.92-1.79 (m, 4H), 1.73-1.60 (m, 4H), 1.50-1.40 (m, 2H), 1.30 (t, J = 7.2 Hz, 3H). formate |

-continued

| No | starting materials | structures | HNMR |
|---|---|---|---|
| 249 | 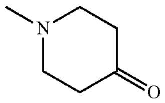 | 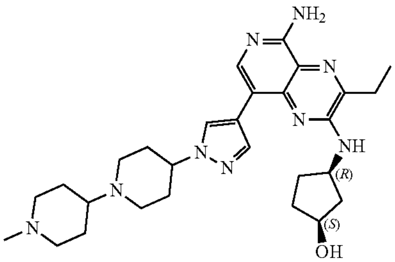 | $^1$H NMR (400 MHz, DMSO-$d_6$) δ 8.43 (s, 1H), 8.21 (s, 4H), 8.18 (s, 1H), 8.03 (s, 1H), 7.14 (d, J = 7.2 Hz, 1H), 6.45 (brs, 2H), 4.48-4.45 (m, 1H), 4.23-4.20 (m, 2H), 4.13-4.10 (m, 2H), 3.07-2.95 (m, 4H), 2.92-2.88 (m, 2H), 2.80-2.75 (m, 7H), 2.13-2.02 (m, 3H), 1.95-1.60 (m, 7H), 1.59-1.38 (m, 6H), 1.30 (t, J = 7.2 Hz, 3H). formate |
| 221 | 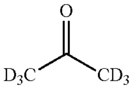 | 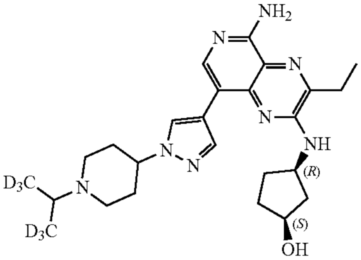 | $^1$H NMR (400 MHz, DMSO-$d_6$) δ 8.38 (s, 1H), 8.18 (s, 1H), 8.15-8.11 (m, 3H), 7.16 (d, J = 7.2 Hz, 1H), 6.55 (s, 2H), 4.52-4.42 (m, 2H), 4.26-4.20 (m, 1H), 3.07-2.97 (m, 2H), 2.80 (q, J = 7.2 Hz, 2H), 2.54-2.52 (m, 2H), 2.32-<br>2.24 (m, 3H), 2.20-1.97 (m, 5H), 1.89-1.78 (m, 2H), 1.72-1.63 (m, 2H), 1.31 (t, J = 7.2 Hz, 3H). formate |
| 217 | 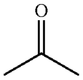 | 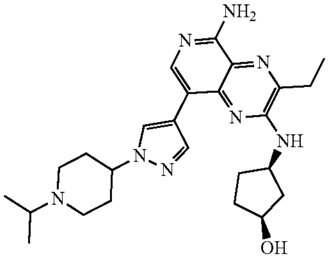 [SMILES: CCc1nc2c(N)ncc(-c3cnn(C4CCN(C(C)C)CC4)c3)c2nc1N[C@@H]1CC[C@H](O)C1] | $^1$H NMR (400 MHz, DMSO-$d_6$) δ 8.43 (s, 1H), 8.19 (s, 2H), 8.18 (brs, 2H), 8.02 (s, 1H), 7.11 (d, J = 7.2 Hz, 1H),<br>6.37 (brs, 2H), 4.51-4.45 (m, 1H), 4.24-4.21 (m, 1H), 4.15-4.11 (m, 1H), 2.94-2.90 (m, 2H), 2.82-2.77 (m, 3H), 2.37-2.26 (m, 4H), 2.12-2.02 (m, 3H), 1.93-1.80 (m, 4H), 1.72-1.61 (m, 2H), 1.30 (t, J = 7.2 Hz, 3H), 1.01 (d, J = 6.8 Hz, 6H). formate |
| 212 | 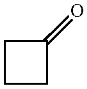 | 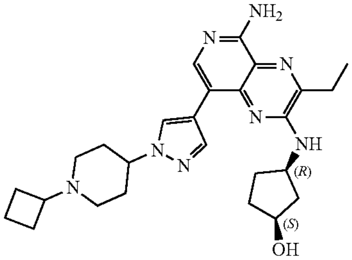 | $^1$H NMR (400 MHz, DMSO-$d_6$) δ 8.43 (s, 1H), 8.18 (brs, 2H), 8.03 (d, J = 4.8 Hz, 1H), 7.11 (d, J = 7.2 Hz, 1H), 6.35<br>(brs, 2H), 4.79-4.77 (m, 1H), 4.48-4.45 (m, 1H), 4.23-4.20 (m, 1H), 4.12-4.10(m, 1H), 2.86-2.83 (m, 2H), 2.80 (q, J = 7.2 Hz, 2H), 2.76-2.70 (m, 2H), 2.32-2.24 (m, 1H), 2.13-1.94 (m, 6H), 1.84-1.72 (m, 7H), 1.72-1.58 (m, 4H), 1.30 (t, J = 7.2 Hz, 3H). |
| 216 | CH3CHO | 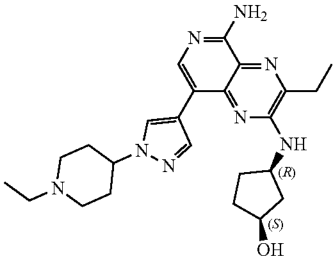 | $^1$H NMR (400 MHz, DMSO-$d_6$) $^1$H NMR (400 MHz, DMSO) δ 8.42 (s, 1H), 8.19 (s, 3H), 8.02 (s, 1H), 7.11 (d,<br>J = 7.2 Hz, 1H), 6.38 (brs, 2H), 4.48-4.45 (m, 1H), 4.25-4.11 (m, 3H), 3.00-2.96 (m, 2H), 2.80-2.76 (m, 2H), 2.42-2.40 (m, 2H), 2.33-2.28 (m, 1H), 2.08-2.05 (m, 5H), 2.00-1.78 (m, 4H), 1.74-1.60 (m, 2H), 1.30 (t, J = 7.2 Hz, 3H), 1.04 (t, J = 7.2 Hz, 3H). formate |

-continued

| No | starting materials | structures | HNMR |
|---|---|---|---|
| 209 | 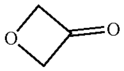 | 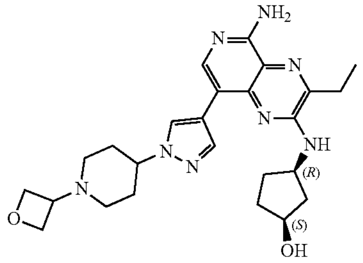 | $^1$H NMR (400 MHz, DMSO-$d_6$) δ 8.44 (s, 1H), 8.19 (s, 1H), 8.16 (brs, 2H), 8.04 (s, 1H), 7.12 (d, J = 7.2 Hz, 1H), 6.38 (s, 2H), 4.55-4.50 (m, 2H), 4.51-4.40 (m, 3H), 4.27 -4.09 (m, 2H), 3.46-3.40 (m, 1H), 2.80-2.76 (m, 4H), 2.33-2.31 (m, 1H), 2.09-2.01 (m, 4H), 2.00-1.91 (m, 3H), 1.89-1.78 (m, 3H), 1.74-1.61 (m, 2H), 1.31 (t, J = 7.2 Hz, 3H). formate |
| 182 | 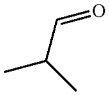 | 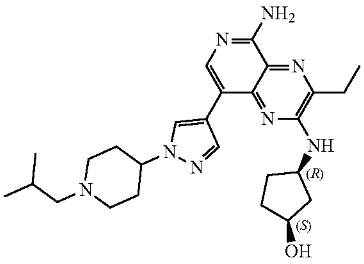 | $^1$H NMR (400 MHz, DMSO-$d_6$) δ 8.43 (s, 1H), 8.16 (s, 1H), 8.14 (brs, 2H), 8.07 (s, 1H), 7.25 (d, J = 6.8 Hz, 1H), 6.71 (brs, 2H), 4.80-4.78 (m, 2H), 4.49-4.45 (m, 1H), 4.23-4.18 (m, 2H), 3.13-3.10 (m, 2H), 2.81 (q, J = 7.2 Hz, 2H), 2.35-2.24 (m, 2H), 2.21-1.99 (m, 6H), 1.94-1.76 (m, 4H), 1.69-1.65 (m, 2H), 1.31 (t, J = 7.2 Hz, 3H). 0.91 (d, J = 6.8 Hz, 6H). formate |
| 183 | 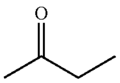 | 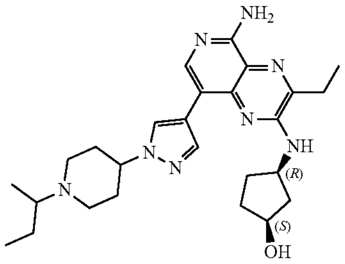 | $^1$H NMR (400 MHz, DMSO-$d_6$) δ 8.41 (s, 1H), 8.17 (d, J = 16.0 Hz, 3H), 8.06 (s, 1H), 7.13 (d, J = 8.0 Hz, 1H), 6.47 (brs, 2H), 4.51-4.44 (m, 1H), 4.28-4.18 (m, 2H), 3.02 (d, J = 12.0 Hz, 2H), 2.82-2.72 (m, 3H), 2.62-2.52 (m, 2H), 2.35-2.22 (m, 2H), 2.16 (d, J = 12.0 Hz, 2H), 2.08-1.95 (m, 3H), 1.84-1.77 (m, 2H), 1.73-1.56 (m, 3H), 1.41-1.26 (m, 4H), 1.04 (d, J = 4.0 Hz, 3H), 0.91-0.88 (m, 3H). formate |

The following starting materials were used to react with intermediate F according to the method of Example 11 to obtain the following table compounds:

| No | starting materials | structures | HNMR |
|---|---|---|---|
| 171 | 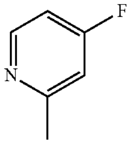 | 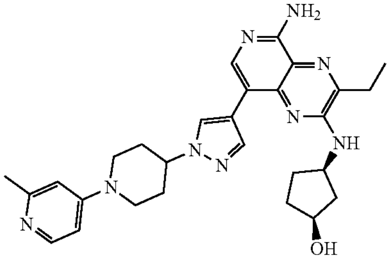 [SMILES: CCc1nc2c(N)ncc(-c3cnn(C4CCN(c5ccnc(C)c5)CC4)c3)c2nc1N[C@@H]1CC[C@H](O)C1] | $^1$H NMR (400 MHz, DMSO-$d_6$) δ 8.40 (s, 1H), 8.19 (, 1H), 8.11 (d, J = 4.0 Hz, 1H), 8.07 (s, 1H), 7.08 (d, J = 4.0 Hz, 1H), 6.99 (s, 1H), 6.94 (d, J = 8.0 Hz, 1H), 6.40 (brs, 2H), 4.79 (d, J = 4.0 Hz, 1H), 4.60-4.54 (m, 1H), 4.47-4.41 (m, 1H), 4.23-4.15 (m, 3H), 3.33-3.20 (m, 2H), 2.82-2.76 (m, 2H), 2.41 (s, 3H), 2.21-2.16 (m, 2H), 2.01-1.79 (m, 5H), 1.72-1.61 (m, 3H), 1.30-1.23 (m, 3H). |
| 172 | 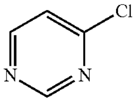 | 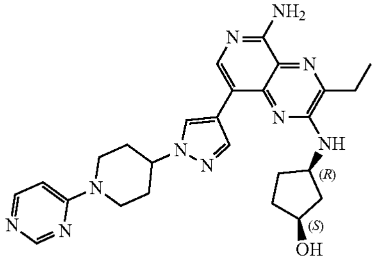 | $^1$H NMR (400 MHz, DMSO-$d_6$) δ 8.52 (s, 1H), 8.42 (s, 1H), 8.20 (d, J = 4.0 Hz, 1H), 8.16 (s, 1H), 8.06 (s, 1H), 7.16 (d, J = 8.0 Hz, 1H), 6.93-6.92 (m, 1H), 6.60 (brs, 2H), 4.77 (d, J = 4.0 Hz, 1H), 4.58-4.53 (m, 2H), 4.47-4.42 (m, 1H), 4.16 (d, J = 4.0 Hz, 1H), 3.16-3.11 (m, 2H), 2.82-2.77 (m, 2H), 2.24-2.15 (m, 3H), 1.99-1.92 (m, 1H), 1.87-1.78 (m, 3H), 1.75-1.61 (m, 4H), 1.32-1.28 (m, 3H). |

-continued

| No | starting materials | structures | HNMR |
| --- | --- | --- | --- |
| 174 | 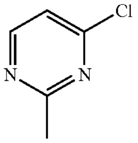 | 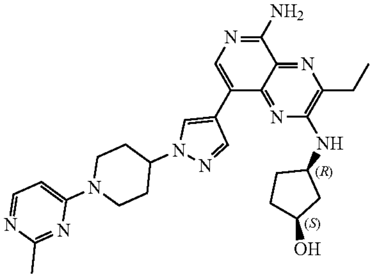 | $^{1}$H NMR (400 MHz, DMSO-$d_6$) δ 8.43 (s, 1H), 8.13-8.11 (m, 3H), 8.07 (s, 1H), 7.35 (d, J = 7.2 Hz, 1H), 7.06 (s, 2H), 6.76 (d, J = 6.4 Hz, 1H), 4.78 (s, 1H), 4.58-4.53 (m, 3H), 4.48-4.43 (m, 1H), 4.18-4.13 (m, 1H), 3.12 (t, J = 12.0 Hz, 2H), 2.39 (s, 3H), 2.25-2.15 (m, 3H), 2.01-1.93 (m, 1H), 1.89-1.80 (m, 3H), 1.70-1.62 (m, 3H), 1.30 (t, J = 7.2 Hz, 3H). formate |
| 175 | 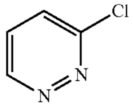 | 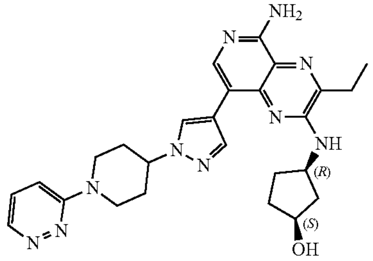 | $^{1}$H NMR (400 MHz, DMSO-$d_6$) δ 8.52 (s, 1H), 8.42 (s, 1H), 8.20 (d, J = 4.0 Hz, 1H), 8.16 (s, 1H), 8.06 (s, 1H), 7.16 (d, J = 8.0 Hz, 1H), 6.93-6.92 (m, 1H), 6.60 (brs, 2H), 4.77 (d, J = 4.0 Hz, 1H), 4.58-4.53 (m, 2H), 4.47-4.42 (m, 1H), 4.16 (d, J = 4.0 Hz, 1H), 3.16-3.11 (m, 2H), 2.82-2.77 (m, 2H), 2.24-2.15 (m, 3H), 1.99-1.91 (m, 1H), 1.83-1.78 (m, 3H), 1.75-1.61 (m, 4H), 1.32-1.28 (m, 3H). |
| 184 | 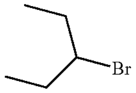 | 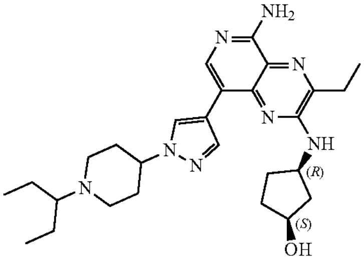 | $^{1}$H NMR (400 MHz, DMSO-$d_6$) δ 8.44 (s, 1H), 8.19 (d, J = 4.0 Hz, 4H), 8.02 (s, 1H), 7.11 (d, J = 8.0Hz, 1H), 6.42 (brs, 2H), 4.51-4.46 (m, 1H), 4.24-4.20 (m, 1H), 4.14-4.06 (m, 1H), 2.83-2.78 (m, 1H), 2.60-2.50 (m, 2H), 2.43 (d, J = 12.0 Hz, 2 H), 2.32-2.21 (m, 2H), 2.11-2.01 (m, 3H), 1.91-1.76 (m, 4H), 1.74-1.61 (m, 2H), 1.50-1.41 (m, 2H), 1.35-1.21 (m, 5H), 0.90-0.87 (m, 6H) . formate |
| 218 | 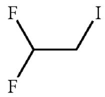 | 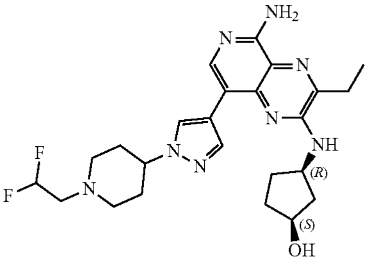 | $^{1}$H NMR (400 MHz, DMSO-$d_6$) δ 8.42 (s, 1H), 8.16 (brs, 3H), 8.04 (s, 1H), 7.12 (d, J = 7.2 Hz, 1H), 6.42 (brs, 2H), 6.30-6.00 (m, 1H), 4.80 (s, 1H), 4.53-4.46 (m, 1H), 4.27-4.12 (m, 2H), 3.01 (d, J = 12.0 Hz, 2H), 2.85-2.75 (m, 4H), 2.41-2.27 (m, 3H), 2.08-2.01 (m, 3H), 1.97-1.79 (m, 4H), 1.73-1.60 (m, 2H), 1.32-1.29 (m, 3H). formate |
| 219 | 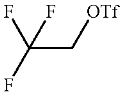 | 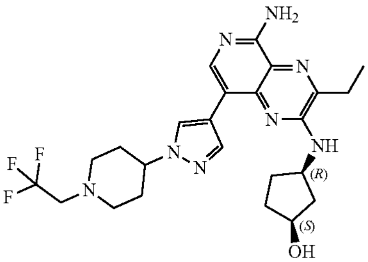 | $^{1}$H NMR (400 MHz, DMSO-$d_6$) δ 8.43 (s, 1H), 8.18 (s, 1H), 8.14 (brs, 1H), 8.04 (s, 1H), 7.14 (d, J = 7.2 Hz, 1H), 6.46 (brs, 2H), 4.77 (s, 1H), 4.53-4.44 (m, 1H), 4.24-4.13 (m, 2H), 3.24 (d, J = 10.0 Hz, 2H), 3.02 (d, J = 12.0 Hz, 2H), 2.80 (q, J = 7.2 Hz, 2H), 2.60-2.55 (m, 1H), 2.32-2.25 (m, 1H), 2.10-2.02 (m, 3H), 2.00-1.91 (m, 2H), 1.90-1.72 (m, 3H), 1.71-1.59 (m, 2H), 1.31 (t, J = 7.2 Hz, 3H). formate |

-continued

| No | starting materials | structures | HNMR |
|---|---|---|---|
| 220 | $CD_3I$ | 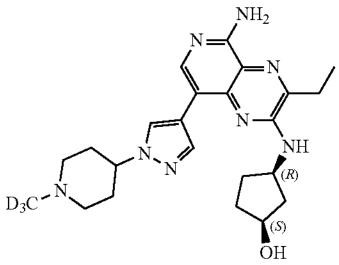 | $^1H$ NMR (400 MHz, DMSO-$d_6$) δ 8.41 (s, 1H), 8.19 (brs, 1H), 8.07 (s, 1H), 7.11 (d, J = 7.2 Hz, 1H), 6.41 (brs, 2H), 4.80 (s, 1H), 4.49-4.46 (m, 1H), 4.23-4.19 (m, 2H), 3.07-3.05 (m, 2H), 2.83-2.77 (m, 2H), 2.45-2.44 (m, 1H), 2.33-2.26 (m, 2H), 2.15-2.12 (m, 2H), 2.07-2.03 (m, 3H), 1.84-1.79 (m, 2H), 1.71-1.63 (m, 2H), 1.30 (t, J = 7.2 Hz, 3H). |
| 222 | 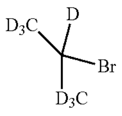 | 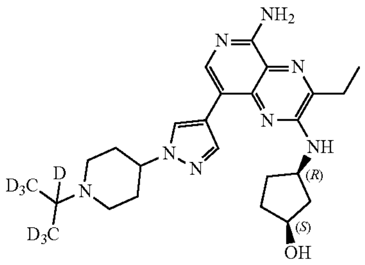 | $^1H$ NMR (400 MHz, DMSO-$d_6$) δ 8.41 (s, 1H), 8.19 (s, 1H), 8.07 (s, 1H), 7.11 (d, J = 8.0 Hz, 1H), 6.40 (brs, 2H), 4.79 (d, J = 4.0 Hz, 1H), 4.50-4.45 (m, 1H), 4.22 (s, 1H), 3.20-3.00 (m, 2H), 2.83-2.77 (m, 2H), 2.62-2.40 (m, 2H), 2.33-1.96 (m, 6H), 1.89-1.77 (m, 2H), 1.75-1.62 (m, 2H), 1.32-1.29 (m, 3H). |

The following starting material was used to react with intermediate F according to the method of Step 3 in Example 35 to obtain the following table compound:

| No | starting materials | structures | HNMR |
|---|---|---|---|
| 262 | 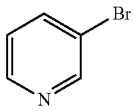 | 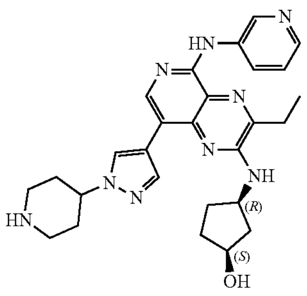 | $^1H$ NMR (400 MHz, DMSO-$d_6$) δ 9.10 (d, J = 2.4 Hz, 1H), 9.01 (s, 1H), 8.52-8.47 (m, 2H), 8.44 (s, 1H), 8.17-8.16 (m, 1H), 8.13 (s, 1H), 7.37-7.28 (m, 2H), 4.54-4.49 (1, 1H), 4.31-4.16 (m, 2H), 3.09 (d, J = 12.4 Hz, 2H), 2.94-2.89 (m, 2H), 2.71-2.52 (m, 2H), 2.36-2.32 (m, 2H), 2.06 (d, J = 12.0 Hz, 3H), 1.91-1.76 (m, 5H), 1.73-1.66 (m, 2H), 1.38 (t, J = 7.2 Hz, 3H). |

Example 19: (1S,3R)-3-((5-amino-3-ethyl-8-(1-(2-hydroxy-2-methylpropyl)piperidin-4-yl)-1H-pyrazol-4-yl)pyridino[3,4-b]pyrazine-2-yl)amino)cyclopentan-1-ol (Compound 181)

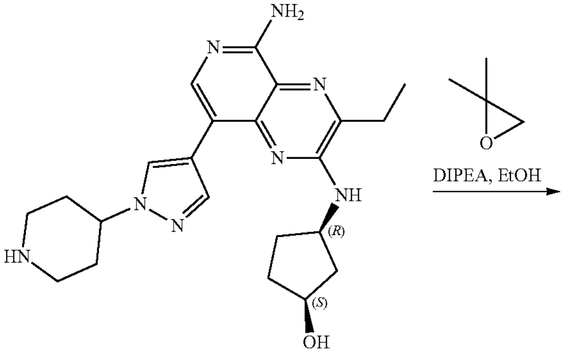

intermediate F

-continued

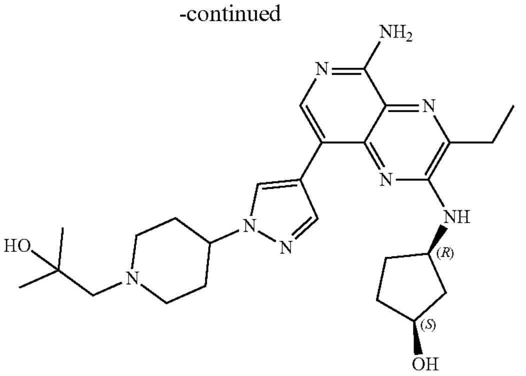

compound 181

The ethanol (10 mL) solution of the intermediate F (90 mg, 0.21 mmol) and 2,2-dimethylethylene oxide (46 mg, 0.64 mmol) was stirred at 80° C. for 12 hours. At the end of the reaction, the mixture was cooled to room temperature and concentrated under reduced pressure. The resulting residue was purified by silica gel chromatography column (dichloromethane/methanol=70%: 30%) to obtain yellow solid compound 181 (65 mg, yield 59%). $^1$H NMR (400 MHz, DMSO-$d_6$) δ 8.44 (s, 1H), 8.20 (s, 1H), 8.02 (s, 1H), 7.11 (d, J=7.2 Hz, 1H), 6.37 (brs, 2H), 4.79 (d, J=3.6 Hz, 1H), 4.54-4.44 (m, 1H), 4.28-4.20 (m, 1H), 4.17-4.05 (m, 2H), 3.11-2.99 (m, 2H), 2.80 (q, J=7.2 Hz, 2H), 2.38-2.21 (m, 5H), 2.12-1.77 (m, 7H), 1.75-1.60 (m, 2H), 1.31 (t, J=7.2 Hz, 3H), 1.11 (s, 6H). (ESI) m/z. 495.2 [M+1]$^+$.

The following starting materials were used to obtain the following table compound according to the method of Example 19:

| No | starting materials | structures | HNMR |
|---|---|---|---|
| 233 | 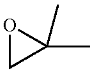 and compound 58 | 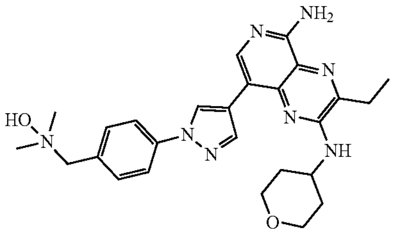 | $^1$H NMR (400 MHz, DMSO-$d_6$) δ 8.36 (s, 1H), 8.19 (s, 1H), 8.00 (s, 1H), 7.05 (d, J = 7.6 Hz, 1H), 6.38 (s, 2H), 4.40-4.25 (m, 1H), 4.11-4.09 (m, 2H), 4.02-3.94 (m, 2H), 3.48-3.45(m, 2H), 3.14-3.02 (m, 2H), 2.82-2.79 (m, 2H), 2.31-2.26 (m, 4H), 2.10-1.90 (m, 6H), 1.72-1.69 (m, 2H), 1.36-1.26 (m, 3H), 1.13 (d, J = 14.9 Hz, 6H). |
| 320 | 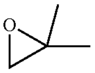 and compound 11 | 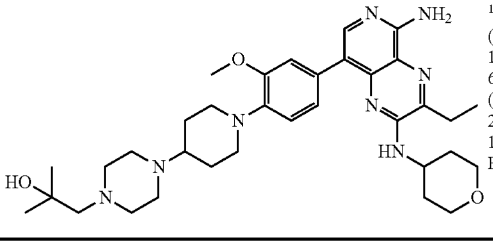 | $^1$H NMR (400 MHz, DMSO-$d_6$) δ 7.92 (s, 1H), 7.23-7.19 (m, 2H), 7.04 (d, J = 7.2 Hz, 1H), 6.90 (d, J = 8.4 Hz, 1H), 6.51 (s, 2H), 4.16-4.08 (m, 1H), 3.92-3.89 (m, 2H), 3.82 (s, 3H), 3.50-3.47 (m, 3H), 3.29-3.24 (m, 6H), 2.83-2.78 (m, 3H), 2.59-2.53 (m, 6H), 2.29-2.23 (m, 2H), 1.88-1.84 (m, 4H), 1.67-1.57 (m, 4H), 1.31 (t, J = 7.2 Hz, 3H), 1.10 (s, 6H). |

Example 20: 4-(4-(5-amino-3-ethyl-2-(((1R,3S)-3-hydroxycyclopentyl)amino)pyridino[3,4-b]pyrazin-8-yl)-1H-pyrazol-1-yl)-N-isopropylpiperazine-1-formamide (Compound 189)

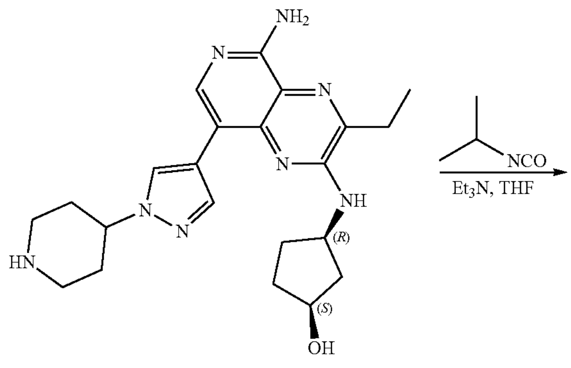

intermediate F

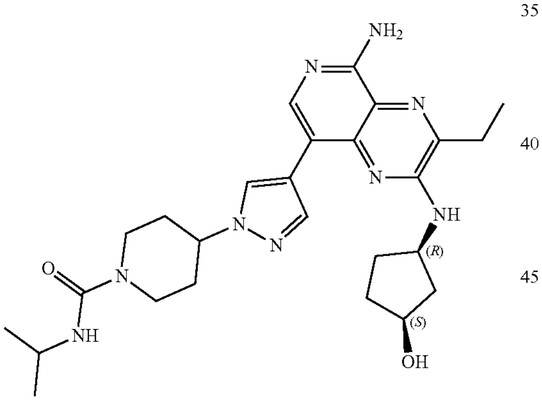

compound 189

Isopropyl isocyanate (19 mg, 0.23 mmol) was added to tetrahydrofuran (10 mL) solution of intermediate F (80 mg, 0.19 mmol) and triethylamine (57 mg, 0.57 mmol). The mixture was stirred at 25° C. for 2 hours and concentrated under reduced pressure. The resulting residue was purified by silica gel chromatography column (dichloromethane/methanol=70%: 30%) to obtain yellow solid compound 189 (38 mg, yield 37%). $^{1}$H NMR (400 MHz, DMSO-$d_6$) δ 8.40 (s, 1H), 8.17 (s, 1H), 8.05 (s, 1H), 7.13 (d, J=6.9 Hz, 1H), 6.47 (brs, 2H), 6.24 (d, J=7.6 Hz, 1H), 4.79 (d, J=3.6 Hz, 1H), 4.51-4.42 (m, 1H), 4.38-4.28 (m, 1H), 4.25-4.18 (m, 1H), 4.14-4.06 (m, 2H), 3.77 (dd, J=13.4, 6.8 Hz, 1H), 2.89-2.73 (m, 4H), 2.27 (dd, J=13.4, 6.8 Hz, 1H), 2.10-1.98 (m, 3H), 1.89-1.61 (m, 7H), 1.30 (t, J=7.2 Hz, 3H), 1.07 (d, J=6.8 Hz, 6H). (ESI) m/z 508.3. $[M+1]^+$.

Example 21: 1-(4-(4-(5-amino-3-ethyl-2-(((1R,3S)-3-hydroxycyclopentyl)amino)pyridino[3,4-b]pyrazin-8-yl)-1H-pyrazol-1-yl)piperidin-1-yl)-2-methylpropyl-1-one (Compound 185)

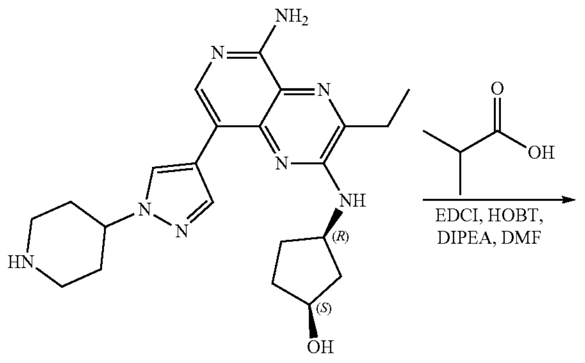

intermediate F

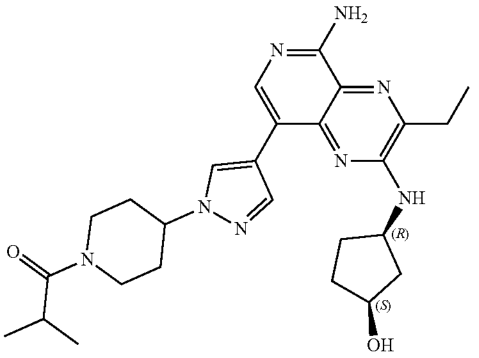

compound 185

N,N-dimethylformamide (5 mL) solution of isobutyric acid (25 mg, 0.28 mmol), EDCI (109 mg, 0.57 mmol), HOBT (77 mg, 0.57 mmol) and diisopropylethylamine (147 mg, 1.1 mmol) were stirred at 0° C. for half an hour, and then intermediate F (80 mg, 0.19 mmol) was added. The mixture was stirred at 25° C. for 2 hours, and water (20 mL) was added after the reaction. The solution was extracted three times (20 mL×3) with ethyl acetate. The organic phases were combined, dried over anhydrous sodium sulfate, filtered, and the filtrate was concentrated under reduced pressure. The resulting residue was purified by silica gel chromatography column (dichloromethane/methanol=95%: 5%) to obtain yellow solid compound (50 mg, yield 51%). $^{1}$H NMR (400 MHz, DMSO-$d_6$) δ 8.40 (s, 1H), 8.19 (s, 1H), 8.06 (s, 1H), 7.08 (d, J=7.2 Hz, 1H), 6.37 (brs, 2H), 4.79 (d, J=3.6 Hz, 1H), 4.56-4.40 (m, 3H), 4.25-4.17 (m, 1H), 4.12-4.02 (m, 1H), 3.27-3.18 (m, 1H), 2.96-2.89 (m, 1H), 2.80 (q, J=7.2 Hz, 2H), 2.53-2.52 (m, 1H), 2.31-2.22 (m, 1H), 2.17-2.00 (m, 3H), 1.88-1.63 (m, 6H), 1.30 (t, J=7.2 Hz, 3H), 1.06-0.99 (m, 6H). (ESI) m/z 493.3. $[M+1]^+$.

Example 22: (1S,3R)-3-((5-amino-3-ethyl-8-(1-(6-methylpyridin-3-yl)-1H-pyrazol-4-yl)pyridino[3,4-b]pyrazin-2-yl)amino)cyclopentan-1-ol (Compound 177)

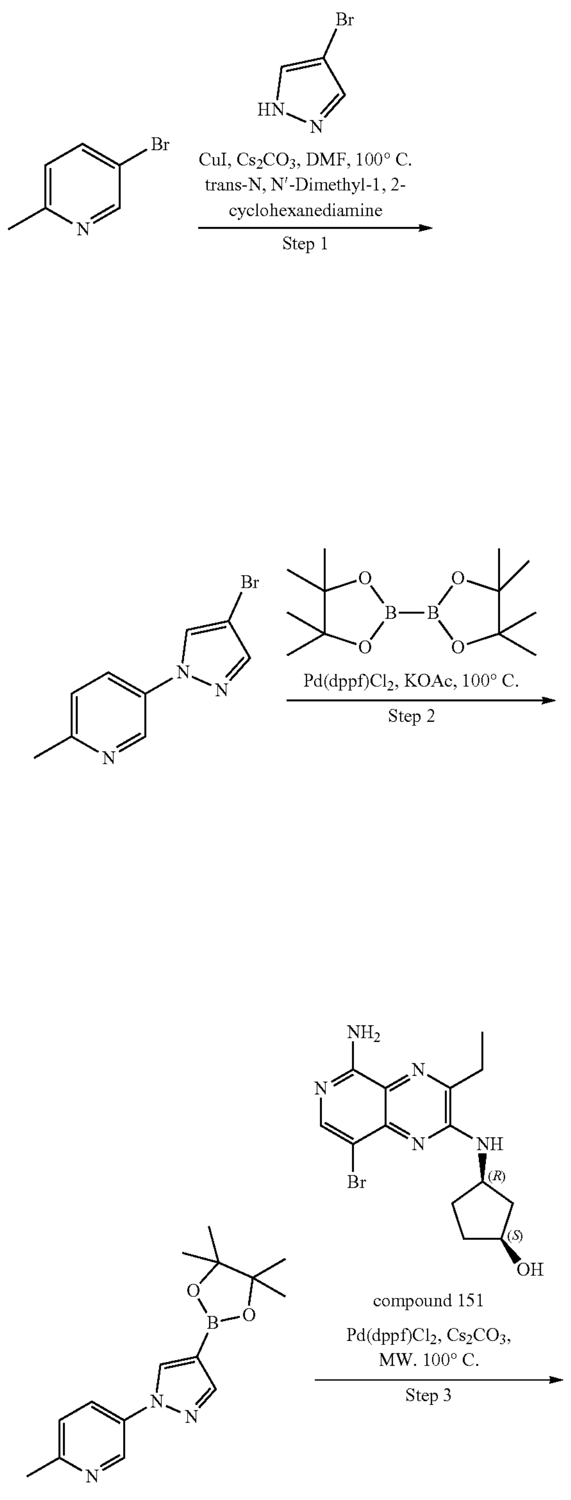

-continued

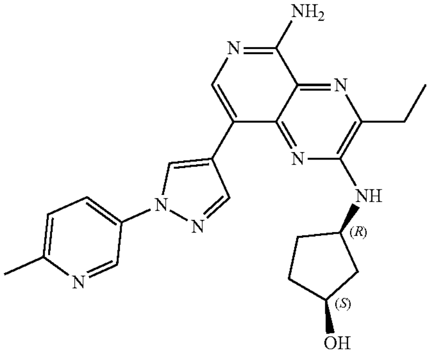

compound 177

Step 1: 4-Bromopyrazole (1.0 g, 6.8 mmol), cesium carbonate (6.6 g, 21 mmol), cuprous iodide (0.13 g, 0.60 mmol) and trans-N,N-dimethylcyclohexane-1,2-diamine (0.19 g, 1.3 mmol) were added to N,N-dimethylformamide (20 mL) solution containing 2-methyl-5-bromopyridine (2.3 g, 14 mmol). The mixture was stirred at 110° C. for 12 hours under nitrogen protection. At the end of the reaction, the mixture was cooled to room temperature and water (50 mL) was added. The solution was extracted three times (50 mL×3) with ethyl acetate. The organic phases were combined, dried over anhydrous sodium sulfate, filtered, and the filtrate was concentrated under reduced pressure. The resulting residue was purified by silica gel chromatography column (petroleum ether/ethyl acetate=70%: 30N) to obtain yellow oil (900 mg, yield 29%). (ESI) m/z. 238.1 $[M+H]^+$.

Steps 2 and 3: The method of Step 6 in Example 1 and the method of Step 2 in Example 2 were referred respectively. Borate intermediate was obtained by using 5-(4-bromo-1H-pyrazol-1-yl)-2-methylpyridine as the starting material, and then reacted with compound 151 to obtain yellow solid compound 177 (two-step yield 11%). $^1$H NMR (400 MHz, DMSO-$d_6$) δ 9.07 (s, 1H), 8.94 (d, J=2.8 Hz, 1H), 8.46 (s, 1H), 8.30 (s, 1H), 8.12-8.09 (m, 1H), 7.42 (d, J=8.4 Hz, 1H), 7.23 (d, J=6.8 Hz, 1H), 6.66 (s, 2H), 4.82 (d, J=3.6 Hz, 1H), 4.59-4.51 (m, 1H), 4.24-4.18 (m, 1H), 2.85-2.79 (m, 2H), 2.52 (s, 3H), 2.32-2.27 (m, 1H), 2.11-2.03 (i, 1H), 1.91-1.76 (t, 2H), 1.71-1.64 (m, 2H), 1.32 (t, J=7.2 Hz, 3H). LC-MS: Rt=1.051 m (ESI) m/z. 431.2 $[M+1]^+$.

The synthesis method of Example 22 was referred. The borate intermediate was obtained from the starting materials in the following table by the methods of Steps 1 and 2, and then reacted with compound 2 to obtain the corresponding compounds in the following table according to the method of Step 3:

| No | starting materials | structures | HNMR |
|---|---|---|---|
| 350 | 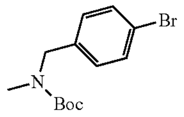 [SMILES: CN(Cc1ccc(Br)cc1)C(=O)OC(C)(C)C] | 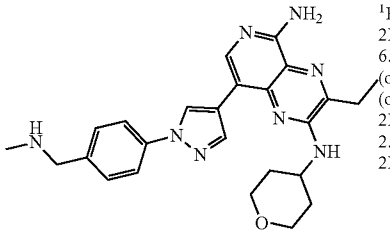 | $^1H$ NMR (400 MHz, DMSO-$d_6$) δ 8.89 (s, 1H), 8.29 (s, 2H), 7.77 (d, J = 8.4 Hz, 2H), 7.44 (d, J = 8.4 Hz, 2H), 6.84 (d, J = 7.2 Hz, 1H), 6.23 (s, 2H), 4.41-4.27 (m, 1H), 3.93 (d, J = 12.0 Hz, 2H), 3.71 (s, 2H), 3.40 (t, J = 10.8 Hz, 2H), 2.89-2.83 (m, 2H), 2.32 (s, 3H), 1.98 (d, J = 12.4 Hz, 2H), 1.78-1.67 (m, 2H), 1.33 (t, J = 7.2 Hz, 3H). |
| 347 | 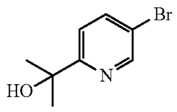 | 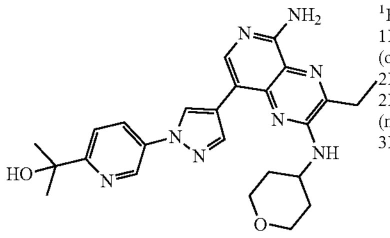 | $^1H$ NMR (400 MHz, DMSO-$d_6$) δ 9.03 (s, 2H), 8.42 (s, 1H), 8.31 (s, 1H), 8.25-8.22 (m, 1H), 8.17 (brs, 1H), 7.79 (d, J = 8.0 Hz, 1H), 7.12 (d, J = 8.0 Hz, 1H), 6.53 (brs, 2H), 5.31 (s, 1H), 4.39-4.29 (m, 1H), 3.93 (d, J = 8.0 Hz, 2H), 3.39-3.33 (m, 2H), 2.87-2.82 (m, 2H), 2.00-1.93 (m, 2H), 1.74-1.64 (m, 2H), 1.48 (s, 6H), 1.34-1.30 (m, 3H).formate |
| 349 | 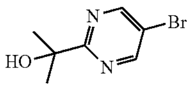 | 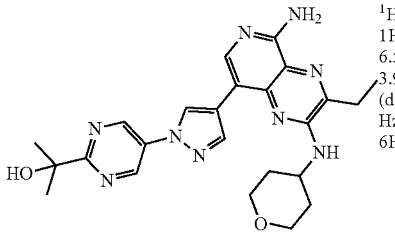 | $^1H$ NMR (400 MHz, DMSO-$d_6$) δ 9.32 (s, 2H), 9.10 (s, 1H), 8.51 (s, 1H), 8.31 (s, 1H), 7.13 (d, J = 8.0 Hz, 1H), 6.55 (brs, 2H), 5.19 (s, 1H), 4.35 (d, J = 7.2 Hz, 1H), 3.93 (d, J = 8.0 Hz, 2H), 3.40-3.38 (m, 2H), 2.85 (q, J = 7.2 Hz, 2H), 1.98-1.94 (m, 2H), 1.74-1.65 (m, 2H), 1.54 (s, 6H), 1.32 (t, J = 7.2 Hz, 3H). |

The borate intermediate was obtained according to the methods of Steps 1 and 2 of Example 22, and the corresponding compounds in the following table was obtained according to the methods of Steps 3 and 4 of Example 7:

| No | starting materials | structures | HNMR |
|---|---|---|---|
| 348 | 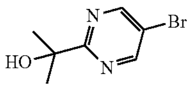 | 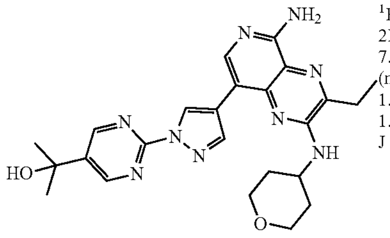 | $^1H$ NMR (400 MHz, DMSO-$d_6$) δ 9.46 (s, 1H), 8.93 (s, 2H), 8.50 (s, 1H), 8.29 (s, 1H), 8.11 (s, 2H), 7.85 (d, J = 7.2 Hz, 1H), 5.55 (s, 1H), 4.54-4.42 (m, 1H), 4.00-3.94 (m, 2H), 3.60-3.52 (m, 2H), 2.90 (q, J = 7.2 Hz, 2H), 1.96-1.92 (m, 2H), 1.78-1.72 (m, 2H), 1.54 (s, 6H), 1.35 (t, J = 7.2 Hz, 3H). |

The borate intermediate was obtained according to the methods of Steps 1 and 2 of Example 22, and the corresponding compounds in the following table was obtained according to the methods of Steps 3 and 4 of Example 17

| No | starting materials | structures | HNMR |
|---|---|---|---|
| 342 | 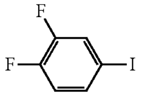 | 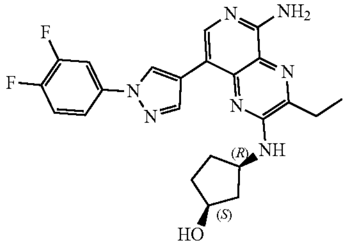 | $^1$H NMR (400 MHz, DMSO) δ 9.05 (s, 1H), 8.45 (s, 1H), 8.31 (s, 1H), 8.22 (s, 1H), 7.93-7.88 (m, 1H), 7.70-7.66 (m, 1H), 7.61-7.56 (m, 1H), 7.16 (d, J = 7.2 Hz, 1H), 6.50 (brs, 2H), 4.78 (s, 1H), 4.54-4.50 (m, 1H), 4.24-4.16 (m, 1H), 2.82 (q, J = 7.2 Hz, 2H), 2.32-2.25 (m, 1H), 2.07-2.04 (m, 1H), 1.88-1.76 (m, 2H), 1.67-1.60 (m, 2H), 1.32 (t, J = 7.2 Hz, 3H). $^1$F NMR (400 MHz, DMSO) δ -136.16 ( s, 1F),-142.40 (s, 1F). formate |
| 345 | 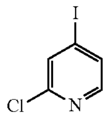 | 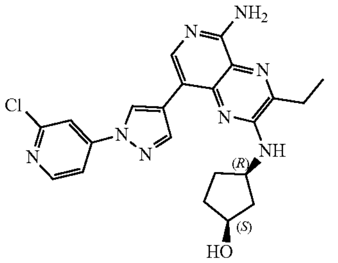 | $^1$H NMR (400 MHz, DMSO-d$_6$) δ 9.22 (s, 1H), 8.60 (s, 1H), 8.48 (d, J = 5.6 Hz, 1H), 8.34 (s, 1H), 8.24 (s, 1H), 7.92 (d, J = 2.0 Hz, 1H), 7.88 (dd, J = 5.6, 1.9 Hz, 1H), 7.18 (d, J = 7.2 Hz, 1H), 6.57 (s, 2H), 4.90-4.71 (m, 1H), 4.56-4.50 (m, 1H), 4.30-4.20 (m, 1H), 2.82 (d, J = 7.2 Hz, 2H), 2.36-2.26 (m, 1H), 2.12-2.02 (m, 1H), 1.85-1.70 (m, 2H), 1.68-1.60 (m, 2H), 1.32 (t, J = 7.2 Hz, 3H). formate |
| 329 | 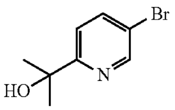 | 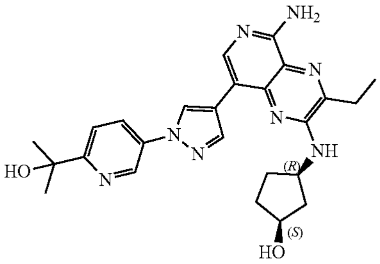 | $^1$H NMR (400 MHz, DMSO-d$_6$)) δ 9.07 (s, 1H), 8.99 (d, J = 4.0 Hz, 1H), 8.48 (s, 1H), 8.33 (s, 1H), 8.19-8.16 (m, 2H), 7.79 (d, J = 8.4 Hz, 1H), 7.15 (d, J = 6.4 Hz, 1H), 6.52 (s, 2H), 5.30 (s, 1H), 4.58-4.51(m, 1H), 4.28-4.14 (m, 1H), 2.85-2.79 (m, 2H), 2.34-2.28 (m, 1H), 2.12-2.06 (m, 1H), 1.92-1.76 (m, 2H), 1.73-1.62 (m, 2H), 1.48 (s, 6H), 1.32 (t, J = 7.2 Hz, 3H). formate |
| 318 | 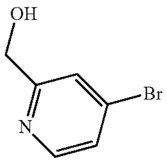 | 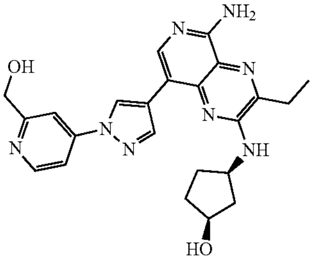 [SMILES: CCc1nc2c(N)ncc(-c3cnn(-c4ccnc(CO)c4)c3)c2nc1N[C@@H]1CC[C@H](O)C1] | $^1$H NMR (400 MHz, DMSO-d$_6$) δ 9.24 (s, 1H), 8.55 (s, 2H), 8.33 (s, 1H), 8.14 (brs, 0.8H), 7.92 (s, 1H), 7.69-7.67 (m, 1H), 7.32 (d, J = 6.8 Hz, 1H), 6.98 (s, 2H), 5.57 (s, 1H), 4.81 (s, 1H), 4.63 (s, 2H), 4.59-4.54 (m, 1H), 4.26-4.21 (m, 1H), 2.86-2.80 (m, 2H), 2.34-2.27 (m, 1H), 2.15-2.06 (m, 1H), 1.93-1.79 (m, 2H), 1.73-1.67 (m, 2H), 1.32 (t, J = 7.2 Hz, 3H). formate |
| 311 | 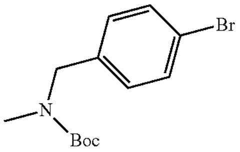 [SMILES: CN(Cc1ccc(Br)cc1)C(=O)OC(C)(C)C] | 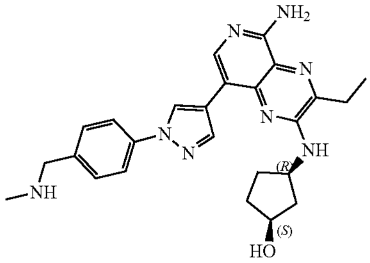 | $^1$H NMR (400 MHz, DMSO-d$_6$) δ 8.95 (s, 1H), 8.32 (d, J = 12.0 Hz, 2H), 7.73 (d, J = 8.4 Hz, 2H), 7.43 (d, J = 8.4 Hz, 2H), 6.91 (d, J = 7.2 Hz, 1H), 6.22 (s, 2H), 4.60-4.55 (m, 1H), 4.25 (s, 1H), 3.70 (s, 2H), 2.85-2.80 (m, 2H), 2.35-2.25 (m, 1H), 2.16-2.05 (m, 1H), 1.94-1.84 (m, 2H), 1.75-1.73 (m, 2H), 1.33 (t, J = 7.2 Hz, 3H). formate |

-continued

| No | starting materials | structures | HNMR |
|---|---|---|---|
| 310 | 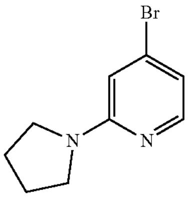 [SMILES: Brc1ccnc(N2CCCC2)c1] | 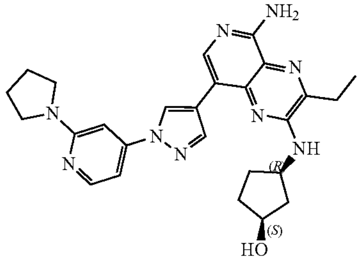 | $^1$H NMR (400 MHz, DMSO-$d_6$) δ 9.14 (s, 1H), 8.47 (s, 1H), 8.31 (s, 1H), 8.14 (brs, 1 H), 8.12 (d, J = 5.6 Hz, 1H), 7.25 (d, J = 7.2 Hz, 1H), 7.01-6.99 (m, 1H), 6.82-6.81 (m, 3H), 4.82 (s, 1H), 4.59-4.52 (m, 1H), 4.20-4.18 (m, 1H), 3.46-3.43 (m, 4H), 2.85-2.80 (m, 2H), 2.30-2.23 (m, 1H), 2.11-2.04 (m, 1H), 2.00-1.95 (m, 4H), 1.89-1.67 (m, 4H), 1.32 (t, J = 7.2 Hz, 3H). formate |
| 338 | 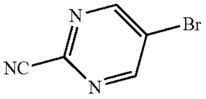 | 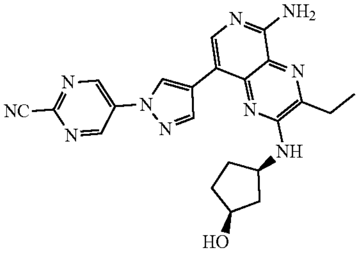 [SMILES: CCc1nc2c(N)ncc(-c3cnn(-c4cnc(C#N)nc4)c3)c2nc1N[C@@H]1CC[C@H](O)C1] | $^1$H NMR (400 MHz, DMSO-$d_6$) δ 9.58 (s, 1H), 9.30 (s, 1H), 8.64 (s, 1H), 8.44 (s, 1H), 8.18 (brs, 1H), 7.23 (d, J = 7.2 Hz, 1H), 6.61 (s, 2H), 4.56-4.48 (m, 1H), 4.33-4.28 (m, 1H), 2.85-2.80 (m, 2H), 2.43-2.40 (m, 1H), 2.22-2.13 (m, 1H), 1.96-1.84 (m, 2H), 1.74-1.64 (m, 2H), 1.32 (t, J = 7.2 Hz, 3H). formate |
| 278 | 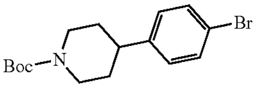 | 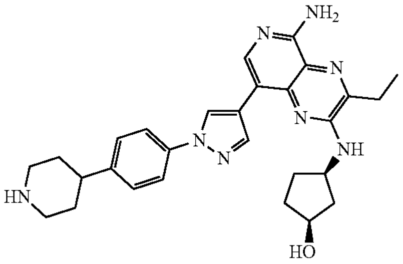 [SMILES: CCc1nc2c(N)ncc(-c3cnn(-c4ccc(C5CCNCC5)cc4)c3)c2nc1N[C@@H]1CC[C@H](O)C1] | $^1$H NMR (400 MHz, DMSO-$d_6$) δ 9.04 (s, 1H), 8.40 (s, 1H), 8.32 (s, 4H), 7.78 (d, J = 8.4 Hz, 2H), 7.37 (d, J = 8.4 Hz, 2H), 7.18 (d, J = 7.0 Hz, 1H), 6.52 (brs, 2H), 4.61-4.49 (m, 1H), 4.28-4.18 (m, 1H), 3.35-3.30 (m, 2H), 2.88-2.84 (m, 5H), 2.39-2.28 (m, 1H), 2.16-2.02 (m, 1H), 2.02-1.63 (m, 9H), 1.32 (t, J = 7.2 Hz, 3H). formate |

Compound 278 was reacted with the starting material in the following table to obtain the corresponding compound according to the method of Step 7 in Example 33:

| No | starting materials | structures | HNMR |
|---|---|---|---|
| 290 | Formaldehyde | 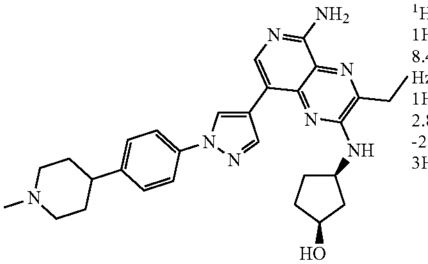 | $^1$H NMR (400 MHz, DMSO-$d_6$) δ 9.02 (s, 1H), 8.40 (s, 1H), 8.33 (s, 1H), 7.73 (d, J = 8.4 Hz, 2H), 7.38 (d, J = 8.4 Hz, 2H), 7.16 (d, J = 7.2 Hz, 1H), 6.47 (s, 2H), 4.82 (s, 1H), 4.54-4.50 (m, 1H), 4.27-4.20 (m, 1H), 3.17 (s, 1H), 2.84-2.80 (m, 4H), 2.33-2.30 (m, 1H), 2.20 (s, 3H), 2.14 -2.06 (m, 1H), 2.04-1.62 (m, 10H), 1.32 (t, J = 7.2 Hz, 3H). |

2-Methyl-5-bromopyridine was replaced with the starting materials in the following table to obtain the corresponding compounds according to the method of Example 22:

| No | starting materials | structures | HNMR |
|---|---|---|---|
| 275 | 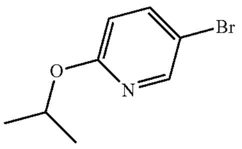 | 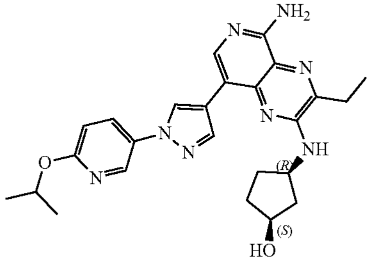 | $^1$H NMR (400 MHz, DMSO-$d_6$) δ 8.96 (s, 1H), 8.62-8.60 (m, 1H), 8.42 (s, 1H), 8.30 (s, 1H), 8.17 (brs, 1H), 8.14-8.10 (m, 1H), 7.13 (d, J = 7.2 Hz, 1H), 6.92-6.89 (m, 1H), 6.47 (brs, 2H), 5.30-5.23 (m, 1H), 4.57-4.48 (m, 1H), 4.22-4.16 (m, 1H), 2.81 (q, J = 7.2 Hz, 2H), 2.53-2.52 (m, 1H), 2.31-2.25 (m, 1H), 2.11-2.02 (m, 1H), 1.90-1.75 (m, 2H), 1.72-1.63 (m, 2H), 1.34-1.29 (m, 9H).formate |
| 343 | 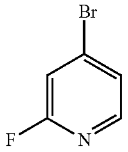 | 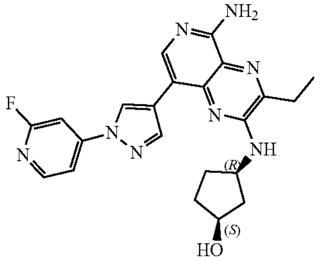 | $^1$H NMR (400 MHz, DMSO) δ 9.21 (s, 1H), 8.59 (s, 1H), 8.32 (s, 2H), 8.18 (s, 1H), 7.82 (d, J = 5.6 Hz, 1H), 7.57 (s, 1H), 7.18 (d, J = 7.2 Hz, 1H), 6.57 (brs, 2H), 4.79 (s, 1H), 4.55-4.50 (m, 1H), 4.28-4.17 (m, 1H), 2.82 (q, J = 7.2 Hz, 2H), 2.32-2.27 (m, 1H), 2.12-2.03 (m, 1H), 1.93-1.76 (m, 2H), 1.67-1.64 (m, 2H), 1.32 (t, J = 7.2 Hz, 3H). formate |
| 331 | 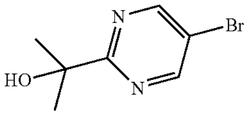 | 0.6 HCOOH 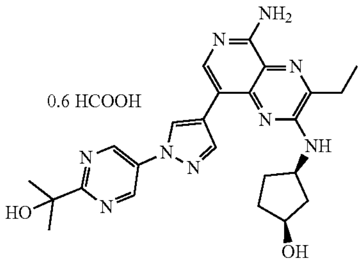 [SMILES: CCc1nc2c(N)ncc(-c3cnn(-c4cnc(C(C)(C)O)nc4)c3)c2nc1N[C@@H]1CC[C@H](O)C1] | $^1$H NMR (400 MHz, DMSO-$d_6$) δ 9.28 (s, 2H), 9.15 (s, 1H), 8.56 (s, 1H), 8.26 (s, 1H), 8.13 (brs, 0.3H), 7.42-7.35 (m, 1H), 7.17-7.00 (m, 2H), 5.17 (s, 1H), 4.81 (d, J = 3.2 Hz, 1H), 4.63-4.53 (m, 1H), 4.23-4.17 (m, 1H), 2.84 (q, J = 7.2 Hz, 2H), 2.30-2.23 (m, 1H), 2.11-2.01 (m, 1H), 1.91-1.76 (m, 2H), 1.73-1.65 (m, 2H), 1.55 (s, 6H), 1.33 (t, J = 7.2 Hz, 3H). formate |
| 351 | 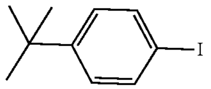 | 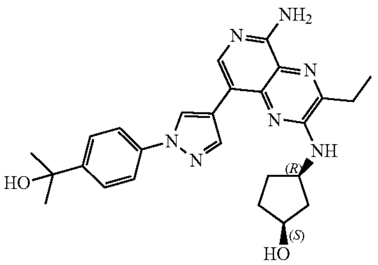 | $^1$H NMR (400 MHz, DMSO-$d_6$) δ 9.01 (s, 1H), 8.40 (s, 1H), 8.33 (s, 1H), 7.74 (d, J = 8.8 Hz, 2H), 7.52 (d, J = 8.8 Hz, 2H), 7.16 (d, J = 7.2 Hz, 1H), 6.50 (brs, 2H), 4.82 (d, J = 4.0 Hz, 1H), 4.58-4.53 (m, 1H), 4.23 (d, J = 4.0 Hz, 1H), 2.82 (q, J = 7.2 Hz, 2H), 2.34-2.29 (m, 1H), 2.11-2.07 (m, 1H), 1.89-1.78 (m, 2H), 1.73-1.65 (m, 2H), 1.34-1.31 (m, 12H). |
| 340 | 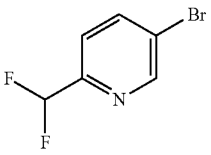 | 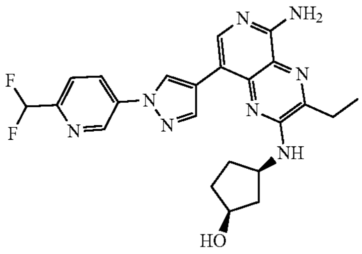 [SMILES: CCc1nc2c(N)ncc(-c3cnn(-c4ccc(C(F)F)nc4)c3)c2nc1N[C@@H]1CC[C@H](O)C1] | $^1$H NMR (400 MHz, DMSO-$d_6$) δ 9.20 (s, 2H), 8.56 (s, 1H), 8.42-8.40 (m, 1H), 8.33 (s, 1H), 8.14 (brs, 1 H), 7.87 (d, J = 8.8 Hz, 1H), 7.22 (d, J = 6.8 Hz, 1H), 7.17 (s, 0.25H), 7.03 (s, 0.5H), 6.90 (s, 0.25H), 6.69 (s, 2H), 4.80 (s, 1H), 4.59-4.54 (m, 1H), 4.24-4.19 (m, 1H), 2.85-2.80 (m, 2H), 2.34-2.27 (m, 1H), 2.12-2.05 (m, 1H), 1.91-1.76 (m, 2H), 1.71-1.65 (m, 2H), 1.32 (t, J = 7.2 Hz, 3H). formate |

-continued

| No | starting materials | structures | HNMR |
|---|---|---|---|
| 355 | 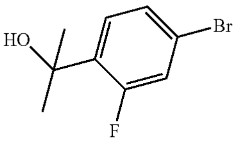 | 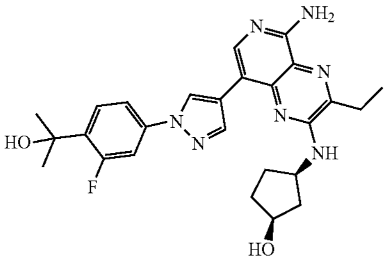 [SMILES: CCc1nc2c(N)ncc(-c3cnn(-c4ccc(C(C)(C)O)c(F)c4)c3)c2nc1N[C@@H]1CC[C@H](O)C1] | $^{1}$H NMR (400 MHz, DMSO-$d_6$) δ 9.06 (s, 1H), 8.44 (s, 1H), 8.33 (s, 1H), 7.76-7.70 (m, 1H), 7.65-7.55 (m, 2H), 7.16 (d, J = 7.2 Hz, 1H), 6.50 (brs, 2H), 5.37 (s, 1H), 4.81 (d, J = 3.6 Hz, 1H), 4.63-4.50 (m, 1H), 4.27-4.19 (m, 1H), 2.82 (q, J = 7.2 Hz, 2H), 2.35-2.30 (m, 1H), 2.15-2.05 (m, 1H), 1.93-1.77 (m, 2H), 1.74-1.63 (m, 2H), 1.52 (s, 6H), 1.32 (t, J = 7.2 Hz, 3H). |
| 353 | 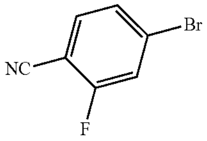 | 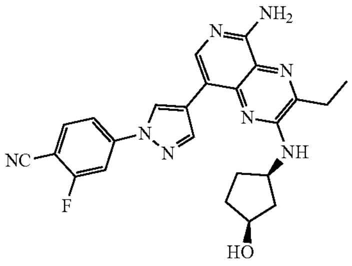 [SMILES: CCc1nc2c(N)ncc(-c3cnn(-c4ccc(C#N)c(F)c4)c3)c2nc1N[C@@H]1CC[C@H](O)C1] | $^{1}$H NMR (400 MHz, DMSO) δ 9.18 (s, 1H), 8.58 (s, 1H), 8.33 (s, 1H), 8.16 (brs, 1H), 8.11-8.05 (m, 1H), 7.99-7.95 (m, 1H), 7.89 (dd, J = 8.6, 2.0 Hz, 1H), 7.17 (d, J = 7.2 Hz, 1H), 6.57 (brs, 2H), 4.78 (s, 1H), 4.54-4.50 (m, 1H), 4.21-4.16 (m, 1H), 2.82 (q, J = 7.2 Hz, 2H), 2.34-2.25 (m, 1H), 2.12-2.01 (m, 1H), 1.83-1.72(m, 2H), 1.67-1.60 (m, 2H), 1.32 (t, J = 7.2 Hz, 3H). formate |
| 357 | 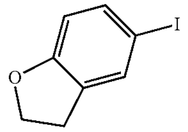 | 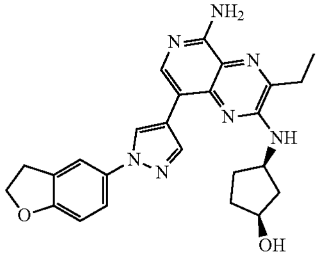 [SMILES: CCc1nc2c(N)ncc(-c3cnn(-c4ccc5c(c4)CCO5)c3)c2nc1N[C@@H]1CC[C@H](O)C1] | $^{1}$H NMR (400 MHz, DMSO-$d_6$) δ 8.93 (s, 1H), 8.32 (d, J = 6.8 Hz, 2H), 8.18 (brs, 1H), 7.66 (d, J = 2.0 Hz, 1H), 7.53-7.50 (m, 1H), 7.17 (d, J = 7.2 Hz, 1H), 6.87 (d, J = 8.4 Hz, 1H), 6.46 (s, 2H), 4.81 (s, 1H), 4.62-4.50 (m, 3H), 4.23-4.18 (m, 1H), 3.28-3.24 (m, 2H), 2.85-2.79 (m, 2H), 2.37-2.30 (m, 1H), 2.13-2.06 (m, 1H), 1.91-1.76 (m, 2H), 1.71-1.63 (m, 2H), 1.32 (t, J = 7.2 Hz, 3H). formate |
| 332 | 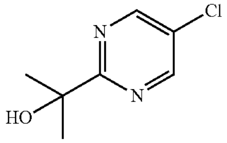 | 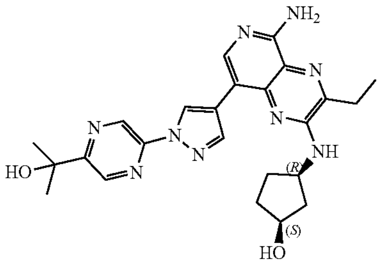 | $^{1}$H NMR (400 MHz, DMSO-$d_6$) δ 9.50 (brs, 1H), 9.14 (d, J = 4.0 Hz, 1H), 8.70 (d, J = 4.0 Hz, 1H), 8.54 (s, 1H), 8.42 (s, 1H), 8.15 (brs, 1H), 7.23 (d, J = 8.0 Hz, 1H), 6.54 (s, 2H), 5.54 (s, 1H), 4.80 (s, 1H), 4.57-4.52 (m, 1H), 4.31 (s, 1H), 2.83 (q, J = 7.2 Hz, 2H), 2.42 (d, J = 7.2 Hz, 1H), 2.20-2.15 (m, 1H), 1.94-1.86 (m, 2H), 1.74-1.66 (m, 2H), 1.51 (s, 6H), 1.32 (t, J = 7.2 Hz, 3H). formate |
| 308 | 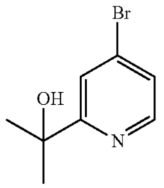 | 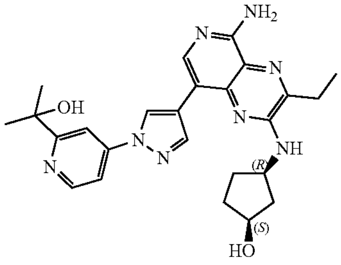 | $^{1}$H NMR (400 MHz, DMSO-$d_6$) δ 9.24 (s, 1H), 8.57-8.53 (m, 2H), 8.37 (s, 1H), 8.11 (d, J = 4.0 Hz, 1H), 7.67-7.65 (m, 1H), 7.16 (d, J = 8.0 Hz, 1H), 6.60 (brs, 2H), 5.36 (s, 1H), 4.80 (d, J = 4.0 Hz, 1H), 4.60-4.55 (m, 1H), 4.27-4.22 (m, 1H), 2.85-2.79 (m, 2H), 2.32-2.27 (m, 1H), 2.14-2.10 (m, 1H), 1.90-1.81 (m, 2H), 1.74-1.66 (m, 2H), 1.48 (s, 6H), 1.34-1.30 (m, 3H). |

-continued

| No | starting materials | structures | HNMR |
| --- | --- | --- | --- |
| 302 | 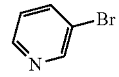 | 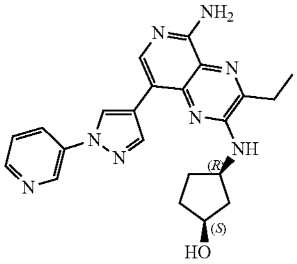 | $^1$H NMR (400 MHz, DMSO-$d_6$) δ 9.13 (s, 1H), 9.10 (d, J = 2.4 Hz, 1H), 8.53-8.50 (m, 2H), 8.33 (s, 1H), 8.26-8.21 (m, 2H), 7.58-7.55 (m, 1H), 7.16 (d, J = 7.2 Hz, 1H), 6.51 (brs, 2H), 4.58-4.53 (m, 1H), 4.23-4.18 (m, 1H), 2.85-2.79 (m, 2H), 2.34-2.27 (m, 1H), 2.12-2.02 (m, 1H), 1.91-1.72 (m, 2H), 1.69-1.64 (m, 2H), 1.32 (t, J = 7.2 Hz, 3H). formate |
| 299 | 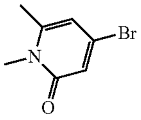 | 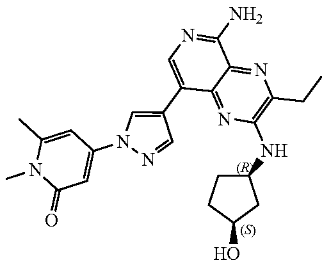 | $^1$H NMR (400 MHz, DMSO-$d_6$) δ 9.07 (s, 1H), 8.51 (s, 1H), 8.32 (s, 1H), 8.18 (brs, 1H), 7.17 (d, J = 8.0 Hz, 1H), 6.83 (d, J = 4.0 Hz, 1H), 6.59 (d, J = 4.0 Hz, 1H), 6.54 (brs, 2H), 4.80 (s, 1H), 4.55-4.49 (m, 1H), 4.25-4.21 (m, 1H), 3.45 (s, 3H), 2.85-2.79 (m, 2H), 2.45 (s, 3H), 2.29 (d, J = 8.0 Hz, 1H), 2.08-2.03 (m, 1H), 1.88-1.81 (m, 2H), 1.70-1.63 (m, 2H), 1.33-1.30 (m, 3H). formate |
| 295 | 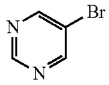 | 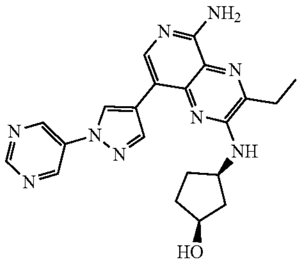 [SMILES: CCc1nc2c(N)ncc(-c3cnn(-c4cncnc4)c3)c2nc1N[C@@H]1CC[C@H](O)C1] | $^1$H NMR (400 MHz, DMSO-$d_6$) δ 9.31 (s, 2H), 9.18 (s, 1H), 9.13 (s, 1H), 8.58 (s, 1H), 8.33 (s, 1H), 8.15 (brs, 1H), 7.16 (d, J = 4.0 Hz, 1H), 6.55 (brs, 2H), 4.79 (s, 1H), 4.59-4.54 (m, 1H), 4.20 (s, 1H), 2.85-2.79 (m, 2H), 2.30-2.26 (m, 1H), 2.09-2.05 (m, 1H), 1.88-1.77 (m, 2H), 1.69-1.64 (m, 2H), 1.34-1.30 (m, 3H). formate |
| 333 | 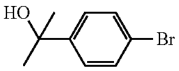 | 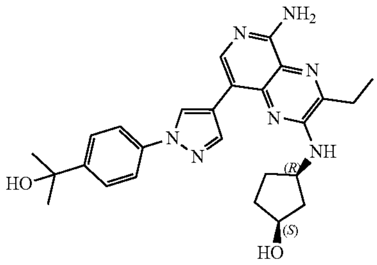 | $^1$H NMR (400 MHz, DMSO-$d_6$) δ 9.06 (s, 1H), 8.40 (s, 1H), 8.23 (s, 1H), 8.14 (brs, 1 H), 7.74 (d, J = 8.8 Hz, 2H), 7.67-7.39 (m, 5H), 5.12 (s, 1H), 4.84 (s, 1H), 4.58 (d, J = 7.2 Hz, 1H), 4.23 (s, 1H), 2.85 (t, J = 7.2 Hz, 2H), 2.33 (s, 1H), 2.14-2.01 (m, 1H), 1.95-1.76 (m, 2H), 1.74-1.67 (m, 2H), 1.47 (s, 6H), 1.33 (t, J = 7.2 Hz, 3H). formate |

The starting materials in the following table were used to obtain the corresponding compounds according to the method starting from Step 2 in Example 22.

| No | starting materials | structures | HNMR |
| --- | --- | --- | --- |
| 178 | 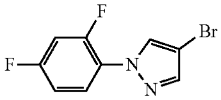 | 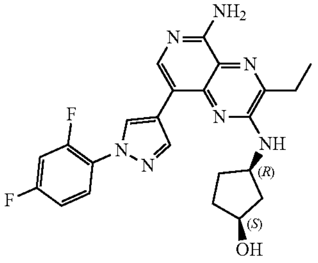 | $^1$H NMR (400 MHz, DMSO-$d_6$) δ 8.93 (d, J = 3.2 Hz, 1H), 8.43 (s, 1H), 8.34 (s, 1H), 8.25 (brs, 1H), 7.96-7.88 (m, 1H), 7.63-7.56 (m, 1H), 7.32-7.25 (m, 1H), 7.16 (d, J = 7.2 Hz, 1H), 6.49 (brs, 2H), 4.55-4.48 (m, 1H), 4.23-4.15 (m, 1H), 2.81 (q, J = 7.2 Hz, 2H), 2.53-2.51 (m, 1H), 2.30-2.23 (m, 1H), 2.09-1.97 (m, 1H), 1.89-1.73 (m, 2H), 1.70-1.61 (m, 2H), 1.31 (t, J = 7.2 Hz, 3H).formate |

-continued

| No | starting materials | structures | HNMR |
|---|---|---|---|
| 303 | 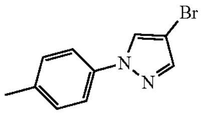 | 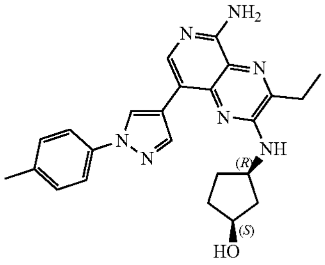 | $^1H$ NMR (400 MHz, DMSO-$d_6$) δ 9.02 (s, 1H), 8.38 (s, 1H), 8.33 (s, 1H), 8.19 (s, 1H), 7.70 (d, J = 8.4 Hz, 2H), 7.32 (d, J = 8.4 Hz, 2H), 7.16 (d, J = 7.2 Hz, 1H), 6.48 (s, 2H), 4.82 (s, 1H), 4.57-4.50 (m, 1H), 4.24-4.20 (m, 1H), 2.85-2.79 (m, 2H), 2.35 (s, 3H), 2.34-2.28 (m, 1H), 2.13-2.06 (m, 1H), 1.92-1.74 (m, 2H), 1.72-1.64 (m, 2H), 1.32 (t, J = 7.2 Hz, 3H). formate |

The synthesis method of compound 151 was referred, in step 1, (1S, 3R)-3-aminocyclopentanol hydrochloride was replaced with (1R, 3R)-3-aminocyclopentanol to obtain the following intermediate 356-A. Then the method of Example 22 was referred, 2-methyl-5-bromopyridine was replaced with the starting material in the following table and compound 151 was replaced with intermediate 356-A in step 3 to obtain the corresponding compound:

| No | starting materials | intermediate 356-A | structures | HNMR |
|---|---|---|---|---|
| 356 | 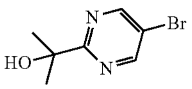 | 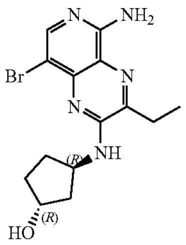 | 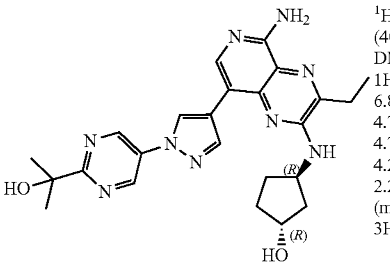 | $^1H$ NMR (400 MHz, DMSO-$d_6$) $^1H$ NMR (400 MHz, DMSO) δ $^1H$ NMR (400 MHz, DMSO) δ 9.29 (s, 2H), 9.12 (s, 1H), 8.61 (s, 1H), 8.34 (s, 1H), 8.15 (s, 1H), 7.12 (d, J = 6.8 Hz, 1H), 6.53 (brs, 2H), 5.17 (s, 1H), 4.78-4.75 (m, 1H), 4.58-4.55 (m, 1H), 4.28-4.25 (m, 1H), 2.83 (q, J = 7.2 Hz, 2H), 2.30-2.21 (m, 1H), 2.06-1.82 (m, 4H), 1.70-1.62 (m, 1H), 1.60 (s, 6H), 1.31 (t, J = 7.2 Hz, 3H).formate |

Example 23: (1S,3R)-3-((5-amino-3-ethyl-8-(1-(2-methylpyrimidin-4-yl)-1H-pyrazol-4-yl)pyridino[3,4-b]pyrazin-2-yl)amino)cyclopentan-1-ol (Compound 180)

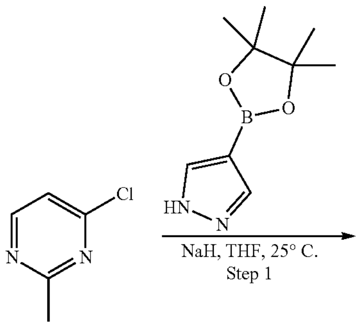

-continued

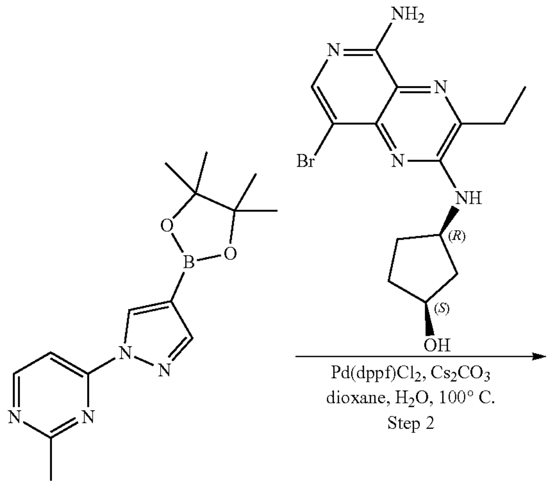

-continued

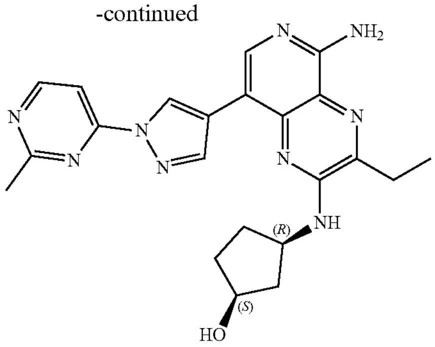

compound 180

Step 1: Sodium hydride (112 mg, 4.67 mmol) was added to the solution of tetrahydrofuran (20 mL) containing 4-pyrazole borate (498 mg, 2.6 mmol), then 4-chloro-2- methylpyrimidine (300 mg, 2.3 mmol) was added and the solution was stirred at 25° C. for 3 hours. After the reaction, water (30 mL) was added, and the solution was extracted with ethyl acetate (30 mL×3). The organic phases were combined, dried over anhydrous sodium sulfate, filtered, and the filtrate was concentrated under reduced pressure. The resulting residue was purified by silica gel chromatography column (dichloromethane/methanol=9:1) to obtain white solid (200 mg, yield 28%). (ESI) m/z. 287.2. $[M+H]^+$.

Step 2: The product of Step 1 (81 mg, 0.11 mmol) was reacted with the compound 151 (50 mg, 0.14 mmol) according to the method of Step 2 in Example 2 to obtain yellow solid compound 180 (7 mg, yield 12%). $^1$H NMR (400 MHz, DMSO-$d_6$) δ 9.55 (s, 1H), 8.74 (d, J=5.6 Hz, 1H), 8.58 (s, 1H), 8.43 (s, 1H), 8.17 (brs, 1H), 7.75 (d, J=5.6 Hz, 1H), 7.15 (d, J=7.2 Hz, 1H), 6.58 (brs, 2H), 4.62-4.57 (m, 1H), 4.31-4.27 (m, 1H), 2.84-2.80 (m, 2H), 2.64 (s, 3H), 2.40-2.35 (m, 1H), 2.29-2.22 (m, 1H), 1.99-1.81 (m, 2H), 1.79-1.66 (m, 2H), 1.33 (t, J=7.2 Hz, 3H). (ESI) m/z. 432.2

| No | starting materials | structures | HNMR |
|---|---|---|---|
| 337 | 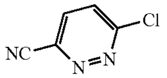 | 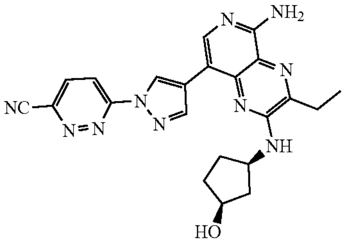 [SMILES: CCc1nc2c(N)ncc(-c3cnn(-c4ccc(C#N)nn4)c3)c2nc1N[C@@H]1CC[C@H](O)C1] | $^1$H NMR (400 MHz, DMSO-$d_6$) δ 9.76 (s, 1H), 8.72 (s, 1H), 8.49-8.37 (m, 3H), 7.27 (d, J = 7.2 Hz, 1H), 6.62 (brs, 2H), 4.76-4.72 (m, 1H), 4.57-4.50 (m, 1H), 4.30-4.24 (m, 1H), 2.84 (q, J = 7.2 Hz, 2H), 2.43-2.38 (m, 1H), 2.23-2.13 (m, 1H), 1.99-1.83 (m, 2H), 1.69-1.65 (m, 2H), 1.32 (t, J = 7.2 Hz, 3H). |
| 271 | 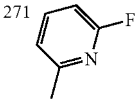 | 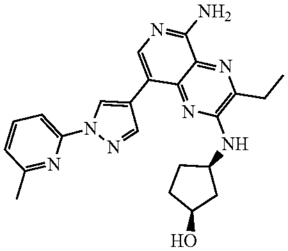 [SMILES: CCc1nc2c(N)ncc(-c3cnn(-c4cccc(C)n4)c3)c2nc1N[C@@H]1CC[C@H](O)C1] | $^1$H NMR (400 MHz, DMSO-$d_6$) δ 9.50 (s, 1H), 8.40 (d, J = 12.0 Hz, 2H), 8.18 (brs, 1H), 7.89-7.83 (m, 1H), 7.76 (d, J = 8.0 Hz, 1H), 7.19 (d, J = 8.0 Hz, 1H), 7.11 (d, J = 8.0 Hz, 1H), 6.51 (brs, 2H), 4.64-4.59 (m, 1H), 4.29-4.23 (m, 1H), 2.85-2.80 (m, 2H), 2.52-2.50 (m, 3H), 2.39-2.35 (m, 1H), 2.26-2.21 (m, 1H), 1.94-1.85 (m, 2H), 1.79-1.73 (m, 2H), 1.34-1.31 (m, 3H). formate |
| 270 | 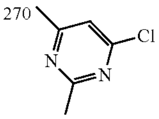 | 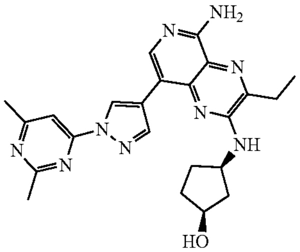 [SMILES: CCc1nc2c(N)ncc(-c3cnn(-c4cc(C)nc(C)n4)c3)c2nc1N[C@@H]1CC[C@H](O)C1] | $^1$H NMR (400 MHz, DMSO-$d_6$)) δ 9.53 (s, 1H), 8.55 (s, 1H), 8.42 (s, 1H), 8.14 (brs, 1H), 7.65 (s, 1H), 7.15 (d, J = 7.2 Hz, 1H), 6.58 (brs, 2H), 4.82 (s, 1H), 4.61-4.55 (m, 1H), 4.34-4.21 (m, 1H), 2.85-2.80 (m, 2H), 2.59 (s, 3H), 2.39-2.34 (m, 1H), 2.29-2.19 (m, 1H), 1.97-1.81 (m, 2H), 1.79-1.69 (m, 2H), 1.32 (t, J = 7.2 Hz, 3H). formate |

Example 24: (1S,3R)-3-((5-amino-3-ethyl-8-(1-(1-(isopropylsulfonyl)piperidin-4-yl)-1H-pyrazol-4-yl)pyridino[3,4b]pyrazin-2-yl)amino)cyclopentan-1-ol (Compound 187)

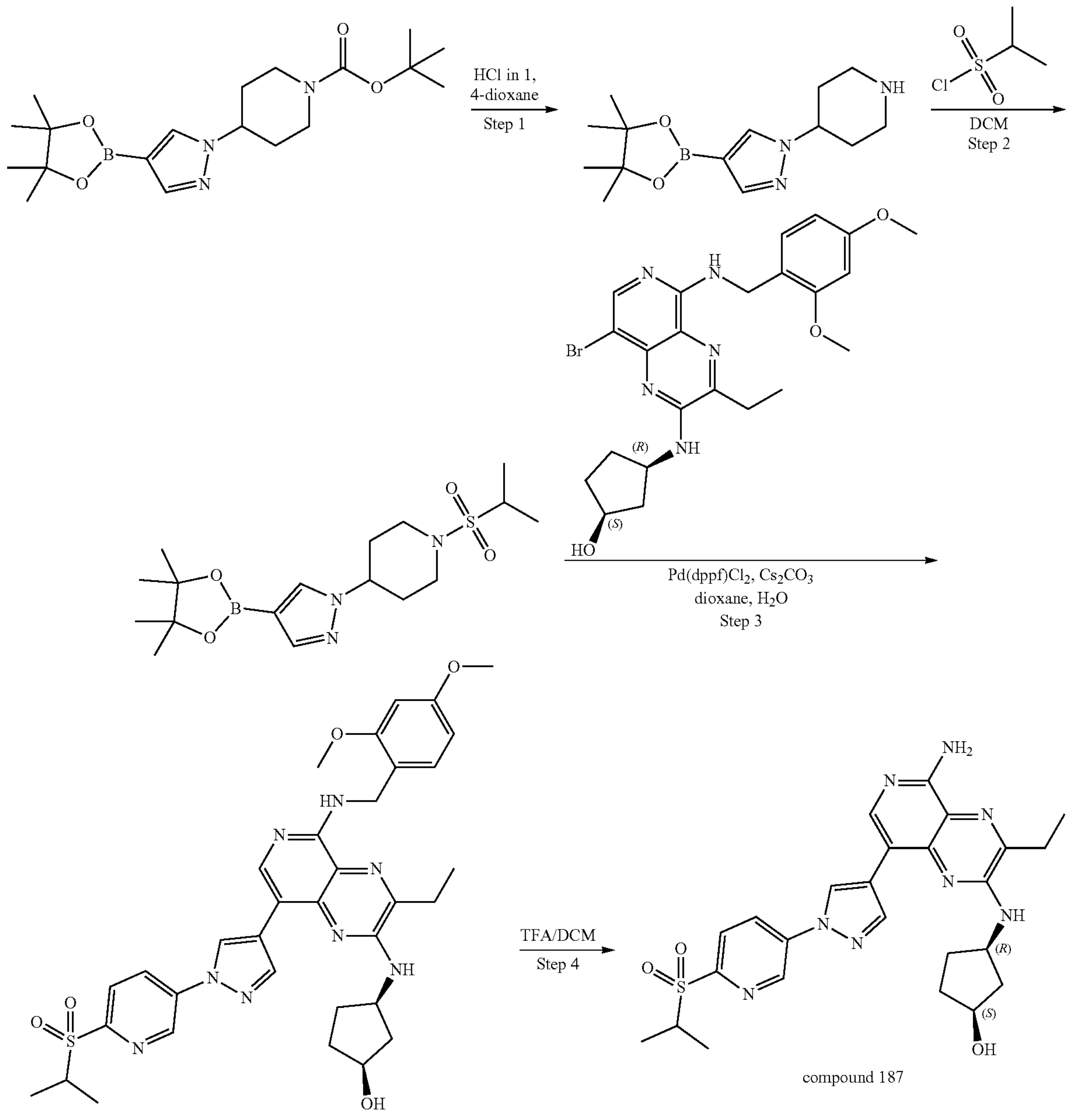

compound 187

Step 1: tert-butyl 4-(4-(4,4,5,5-Tetramethyl-1,3,2-dioxoborane-2-yl)-1H-pyrazol-1-yl)piperidine-1-carboxylate (1.0 g, 2.65 mmol) was dissolved in 1,4-dioxane (5 mL), and then 1,4-dioxane solution (4 M, 10 mL) of hydrochloric acid was added. The solution was stirred at 25° C. for 1 hour. After the reaction, the solution was concentrated under reduced pressure to obtain white solid compound (650 mg, 88%). (ESI) m/z 278.2. $[M+H]^+$.

Step 2: 2-Propane sulfonyl chloride (494 mg, 3.5 mmol) was added to the dichloromethane (10 mL) solution containing 4-(4,4,5,5-tetramethyl-1,3,2-dioxoborane-2-yl)-1H-pyrazol-1-yl)piperidine (800 mg, 2.9 mmol) and triethylamine (876 mg, 8.7 mmol). This mixture was stirred and reacted at 25° C. for 16 hours. After the reaction, water (30 mL) was added, and the solution was extracted three times with dichloromethane (20 mL×3). The organic phases were combined, dried over anhydrous sodium sulfate, filtered, and the filtrate was concentrated under reduced pressure to obtain yellow oil (400 mg, yield 95%). (ESI) m/z. 384.3. $[M+H]^+$.

Steps 3 and 4: The product of Step 2 (73 mg, 0.19 mmol) was used as starting material to react with intermediate D (80 mg, 0.16 mmol) according to the method starting from Step 3 in Example 17, thus obtaining the formate of the yellow solid compound 187 (30 mg, two-step yield 43%). $^1H$ NMR (400 MHz, DMSO-$d_6$) δ 8.43 (s, 1H), 8.19 (s, 1H), 8.14 (s, 1H), 8.07 (s, 1H), 7.12 (d, J=7.2 Hz, 1H), 6.47 (s, 2H), 4.79 (s, 1H), 4.52-4.46 (m 1H), 4.44-4.34 (m, 1H), 4.28-4.16 (m, 1H), 3.76 (d, J=12.0 Hz, 2H), 3.40 (d, J=6.4 Hz, 1H), 3.13 (t, J=12.0 Hz, 2H), 2.83-2.77 (m, 2H), 2.32-2.25 (m, 1H), 2.15 (d, J=12.0 Hz, 2H), 2.09-1.99 (m, 1H), 1.93-1.76 (m, 4H), 1.73-1.61 (m, 2H), 1.31 (t, J=7.2 Hz, 3H), 1.25 (d, J=6.4 Hz, 6H). (ESI) m/z. 529.3 $[M+1]^+$.

The starting material in the following table were used to obtain the corresponding borate intermediate, and then the borate intermediate reacted with compound 151 to obtain the compound in the following table according to the method of Example 24:

| No | starting materials | structures | HNMR |
|---|---|---|---|
| 168 | 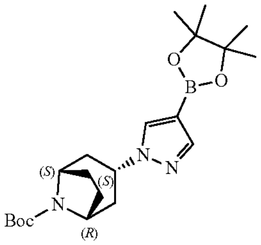 and methanesulfonyl chloride | 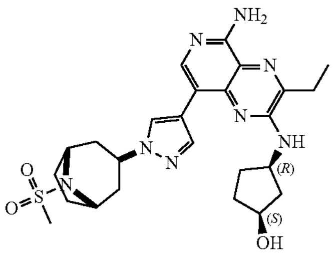 | $^1H$ NMR (400 MHz, DMSO-$d_6$) δ 8.41 (s, 1H), 8.17 (d, J = 8.0 Hz, 2H), 8.05 (s, 1H), 7.08 (d, J = 8.0 Hz, 1H), 6.39 (brs, 2H), 4.72-4.65 (m, 1H), 4.50-4.45 (m, 1H), 4.29-4.24 (m, 3H), 3.01 (s, 3H), 2.83-2.77 (m, 2H), 2.31-2.26 (m, 1H), 2.14-1.99 (m, 7H), 1.93-1.79 (m, 4H), 1.73-1.63 (m, 2H), 1.32-1.29 (m, 3H). formate |

2-Propanesulfonyl chloride was replaced with the starting material in the following table to obtain the corresponding compounds according to the method of Example 24:

| No | starting materials | structures | HNMR |
|---|---|---|---|
| 188 | 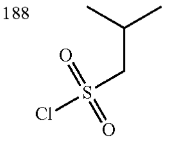 | 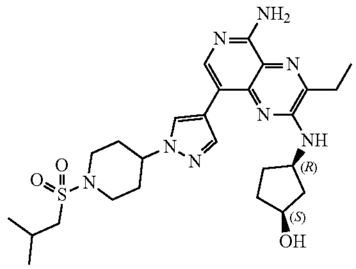 | $^1H$ NMR (400 MHz, DMSO-$d_6$) δ 8.43 (s, 1H), 8.19 (s, 1H), 8.08 (s, 1H), 7.11 (d, J = 8.0 Hz, 1H), 6.42 (brs, 2H), 4.79 (d, J = 4.0 Hz, 1H), 4.51-4.46 (m, 1H), 4.37-4.30 (m, 1H), 4.25-4.18 (m, 1H), 3.70 (d, J = 12.0 Hz, 2H), 3.05-2.93 (m, 4H), 2.83-2.77 (m, 2H), 2.31-2.26 (m, 1H), 2.20-2.03 (m, 4H), 1.96-1.77 (m, 4H), 1.72-1.62 (m, 2H), 1.32-1.29 (m, 3H), 1.05 (d, J = 4.0 Hz, 6H). |

Example 25: (S)-3-ethyl-8-(1-(piperidin-4-yl)-1H-pyrazol-4-yl)-N2-(tetrahydrofuran-3-yl)pyridino[3,4-b]pyrazin-2,5-diamine (Compound 259)

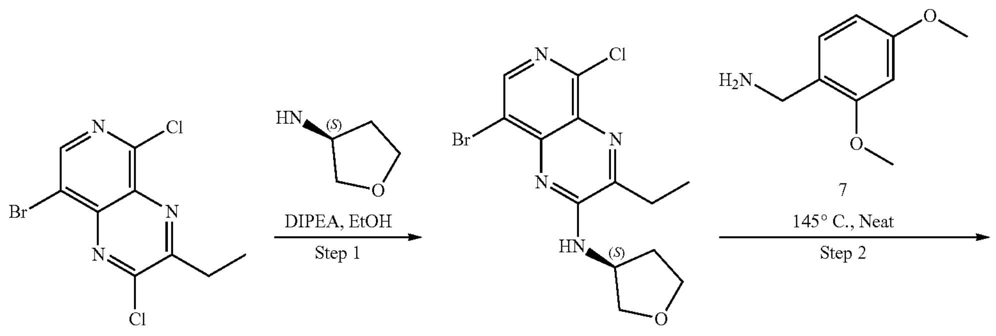

-continued

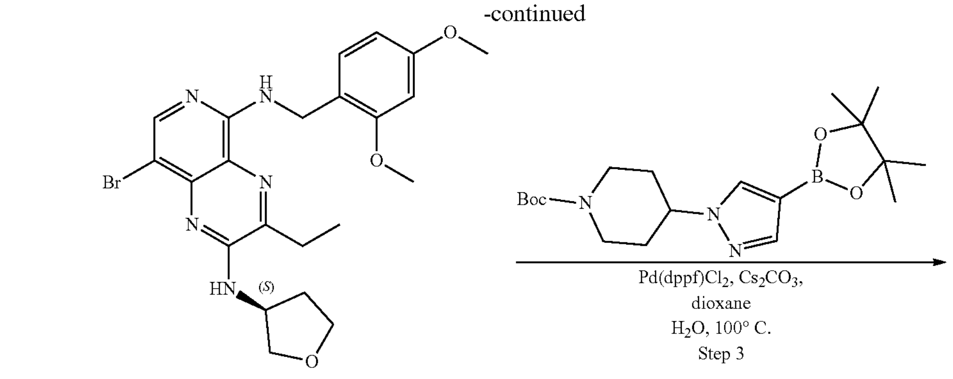

intermediate G

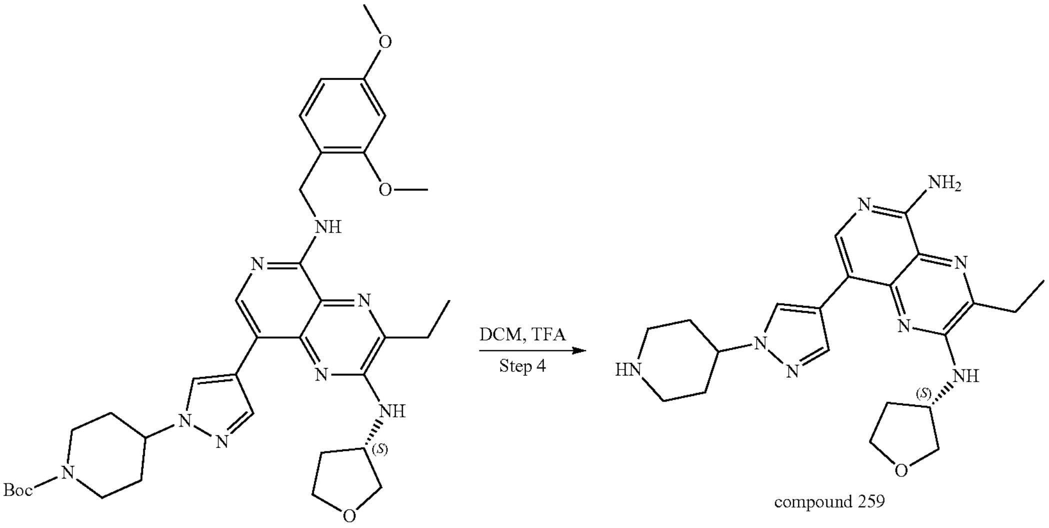

compound 259

Steps 1 and 2: Yellow solid intermediate G was prepared according to the synthesis method of intermediate D by using (S)-tetrahydrofuran-3-amine (two-step yield 28%). (ESI) m/z. 488.0. $[M+H]^+$.

Step 3: The intermediate G (200 mg, 0.41 mmol) was used as the starting material to react with tert-butyl 4-(4-(4,4,5,5-tetramethyl-1,3,2-dioxoboracyclopentan-2-yl)-1H-pyrazol-1-yl)piperidin-1-carboxylate (186 mg, 0.49 mmol) according to the method of Step 2 in Example 2 to obtain yellow oil intermediate H (280 mg, yield 94%). (ESI) m/z 659.3. $[M+H]^+$.

Step 4: Intermediate H (280 mg, 0.42 mmol) was used as the starting material to obtain yellow solid compound 259 (88 mg, 48% yield) according to the method of Step 12 in Example 1. $^1H$ NMR (400 MHz, DMSO-$d_6$) δ 8.34 (s, 1H), 8.18 (s, 1H), 8.03 (s, 1H), 7.25 (d, J=5.6 Hz, 1H), 6.39 (s, 1H), 4.71-4.67 (m, 1H), 4.21-4.01 (m, 1H), 4.04-4.00 (m, 1H), 3.94-3.90 (m, 1H), 3.82-3.76 (m, 1H), 3.74-3.71 (m, 1H), 3.06 (d, J=12.0 Hz, 2H), 2.87-2.82 (m, 2H), 2.68-2.59 (m, 2H), 2.54 (s, 1H), 2.33-2.25 (m, 1H), 2.14-2.06 (m, 1H), 2.02 (d, J=12.0 Hz, 2H), 1.84-1.75 (m, 2H), 1.31 (t, J=7.2 Hz, 3H). (ESI) m/z. 409.2 $[M+1]^+$.

(S)-Tetrahydrofuran-3-amine was replaced with starting material 1 in the following table to obtain the related intermediate according to the method of Example 25, and then the intermediate was reacted with starting material 2 to obtain the corresponding compound:

| No | starting material 1 | starting material 2 | structures | HNMR |
|---|---|---|---|---|
| 264 | 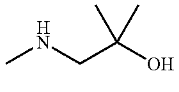 | 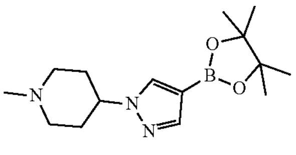 | 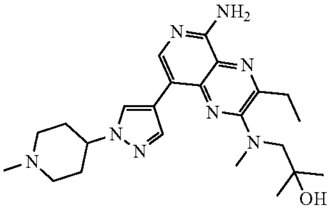 [SMILES: CCc1nc2c(N)ncc(-c3cnn(C4CCN(C)CC4)c3)c2nc1N(C)CC(C)(C)O] | $^1H$ NMR (400 MHz, DMSO-$d_6$) δ 8.35 (s, 1H), 8.21 (brs, 1H), 8.14 (s, 1H), 8.03 (s, 1H), 6.54 (brs, 2H), 4.50 (s, 1H), 4.25-4.12 (m, 1H), 3.74 (s, 2H), 3.28 (s, 3H), 3.02-2.97 (m, 4H), 2.49-2.48 (m, 3H), 2.34-2.32 (m, 2H), 2.17-1.93 (m, 4H), 1.31 (t, J = 7.2 Hz, 3H), 1.08 (s, 6H). formate |

(S)-Tetrahydrofuran-3-amine was replaced with starting material in the following table to obtain intermediate 261-A according to the method of Example 25. And then intermediate 261-A was reacted with methyl iodide to obtain the following table compound 261 according to the method of Example 11.

| No | starting material | intermediate 261-A | structures | HNMR |
|---|---|---|---|---|
| 261 | 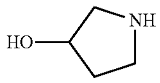 | 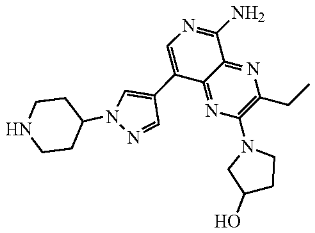 [SMILES: CCc1nc2c(N)ncc(-c3cnn(C4CCNCC4)c3)c2nc1N1CCC(O)C1] | 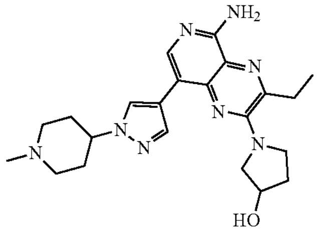 [SMILES: CCc1nc2c(N)ncc(-c3cnn(C4CCN(C)CC4)c3)c2nc1N1CCC(O)C1] | $^1$H NMR (400 MHz, DMSO-$d_6$) δ 8.40 (s, 1H), 8.22 (s, 1H), 8.12 (s, 1H), 6.52 (s, 1H), 5.06 (s, 1H), 4.43 (s, 1H), 4.29 (s, 1H), 3.93-3.87 (m, 2H), 3.82-3.76 (m, 1H), 3.61 (s, 1H), 3.15-3.11 (m, 2H), 3.10-3.06 (m, 2H), 2.57-2.52 (m, 5H), 2.18-1.95 (m, 6H), 1.29 (t, J = 7.2 Hz, 3H). |

(S)-Tetrahydrofuran-3-amine was replaced with the starting material in the following table to obtain the following table compound according to the method of Example 25.

| No | starting materials | structures | HNMR |
|---|---|---|---|
| 258 | 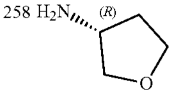 | 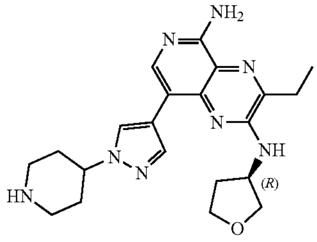 | $^1$H NMR (400 MHz, DMSO-$d_6$) δ 8.35 (s, 1H), 8.31 (s, 2H), 8.20 (brs, 2H), 8.10 (s, 1H), 7.29 (d, J = 4.0 Hz, 1H), 6.53 (s, 2H), 4.69 (s, 2H), 4.04-3.98 (m, 1H), 3.93 (d, J = 8.0 Hz, 1H), 3.83-3.72 (m, 2H), 3.39 (s, 2H), 3.07 (s, 2H), 2.88-2.83 (m, 2H), 2.37-1.98 (m, 7H), 1.33-1.29 (m, 3H). formate |

The starting material in the following table was used to react with compound 258 to obtain the following table compound according to the method of Step 2 in Example 6.

| No | starting materials | structures | HNMR |
|---|---|---|---|
| 250 | 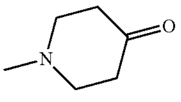 | 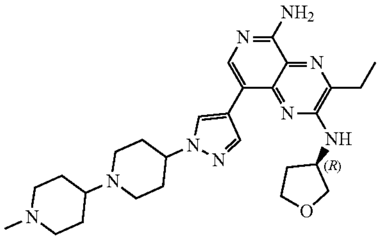 | $^1$H NMR (400 MHz, DMSO-$d_6$) δ 8.36 (s, 1H), 8.28 (brs, 3H), 8.17 (s, 1H), 8.06 (s, 1H), 7.37 (d, J = 4.0 Hz, 1H), 6.81 (brs, 2H), 4.89 (s, 2H), 4.70 (d, J = 4.0 Hz, 1H), 4.18 (s, 1H), 4.09-3.98 (m, 1H), 3.98-3.87 (m, 1H), 3.82-3.76 (m, 1H), 3.74-3.71 (m 1H), 3.24 (d, J = 12.0 Hz, 2H), 3.02 (d, J = 12.0 Hz, 2H), 2.88-2.83 (m, 2H), 2.71-2.63 (m, 2H), 2.57 (s, 2H), 2.43-2.37 (m, 2H), 2.32-2.27 (m, 1H), 2.10 (d, J = 8.0 Hz, 3H), 1.96 (d, J = 12.0 Hz, 2H), 1.88 (d, J = 12.0 Hz, 2H), 1.70 (d, J = 8.0 Hz, 2H), 1.33-1.30 (m, 3H). formate |

The starting material in the following table was used to obtain the following table compound according to the synthesis method of compound 250.

| No | starting materials | structures | HNMR |
|---|---|---|---|
| 247 | 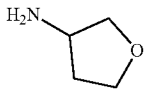 | 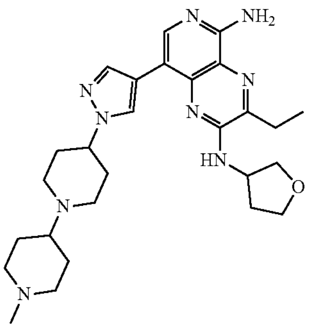 [SMILES: CCc1nc2c(N)ncc(-c3cnn(C4CCN(C5CCN(C)CC5)CC4)c3)c2nc1NC1CCOC1] | $^1$H NMR (400 MHz, DMSO-$d_6$) δ 8.35 (s, 1H), 8.19 (s, 3H), 8.18(s, 1H), 8.03 (s, 1H), 7.26 (d, J = 6.0 Hz, 1H), 6.42 (brs, 2H), 4.69-4.65 (m, 1H), 4.18-4.09 (m, 2H), 4.01-3.99 (m, 1H), 3.93-3.91 (m, 1H), 3.78-3.75 (m, 1H), 3.71-3.68 (m, 1H), 2.95-2.92 (m, 4H), 2.85-2.82 (m, 2H), 2.40-2.24 (m, 4H), 2.09-2.06 (m, 6H), 1.96-1.86 (m, 2H), 1.75-1.72 (m, 2H), 1.52-1.50 (m, 2H), 1.31 (t, J = 7.2 Hz, 3H). formate |

The starting materials in the following table was used to react with compound 259 to obtain the corresponding compounds according to the method of Step 2 in Example 6.

| No | starting materials | structures | HNMR |
|---|---|---|---|
| 248 | 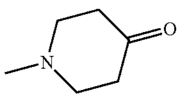 | 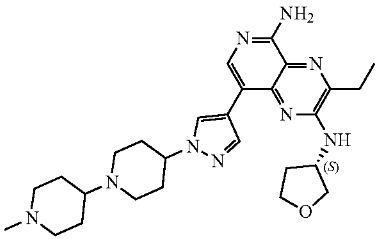 | $^1$H NMR (400 MHz, DMSO-$d_6$) δ 8.36 (s, 1H), 8.25 (s, 3H), 8.18 (s, 1H), 8.04 (s, 1H), 7.29 (d, J = 6.4 Hz, 1H), 6.53 (s, 2H), 4.73-4.66 (m, 1H), 4.18-4.12 (m, 1H), 4.03-4.00 (m, 1H), 3.96-3.90 (m, 1H), 3.81-3.76 (m, 1H), 3.74-3.70 (m, 1H), 3.09 (d, J = 12.0 Hz, 2H), 2.99 (d, J = 12.0 Hz, 2H), 2.88-2.82 (m, 2H), 2.42 (s, 3H), 2.41-2.21 (m, 6H), 2.13 (s, 1H), 2.08 (d, J = 6.4 Hz, 2H), 1.98-1.90 (m, 2H), 1.81 (d, J = 12.0 Hz, 2H), 1.66-1.57 (m, 2H), 1.33-1.29 (m, 3H). formate |
| 244 | 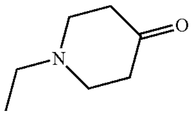 | 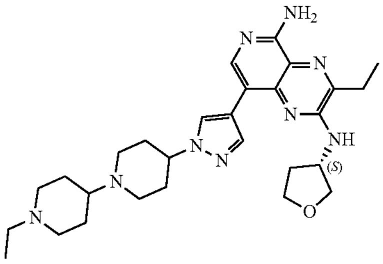 | $^1$H NMR (400 MHz, DMSO-$d_6$) δ 8.36 (s, 1H), 8.27 (brs, 3H), 8.18 (s, 1H), 8.05 (s, 1H), 7.32 (d, J = 6.4 Hz, 1H), 6.61 (brs, 2H), 4.71-4.66 (m, 1H), 4.19-4.13(m, 1H), 4.04-4.00 (m, 1H), 3.96-3.90 (m, 1H), 3.81-3.76 (m, 1H), 3.74-3.71 (m, 1H), 3.23 (d, J = 12.0 Hz, 2H), 3.00 (d, J = 12.0 Hz, 2H), 2.88-2.82 (m, 2H), 2.77-2.75 (d, J = 7.2 Hz, 2H), 2.46 (s, 2H), 2.40-2.25 (m, 4H), 2.12 (d, J = 12.0 Hz, 1H), 2.08 (s, 1H), 2.01-1.91 (m, 2H), 1.91-1.81 (m, 2H), 1.66 (d, J = 12.0 Hz, 2H), 1.33-1.29 (m, 3H), 1.14-1.11 (m, 3H). formate |
| 228 | 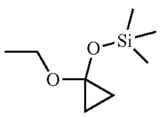 | 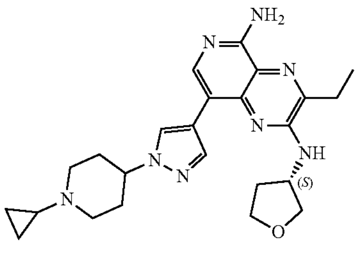 | $^1$H NMR (400 MHz, DMSO-$d_6$) δ 8.40 (s, 1H), 8.35 (s, 2H), 8.14 (s, 1H), 8.09 (d, J = 5.6 Hz, 1H), 8.04 (s, 1H), 4.74-4.70 (m, 2H), 4.56-4.52 (m, 2H), 4.00-3.90 (m, 3H), 3.80-3.76 (m, 2H), 3.68-3.64 (m, 2H), 3.38-3.35 (m, 2H), 2.91-2.88 (m, 2H), 2.32-2.10 (m, 4H), 1.34 (t, J = 7.2 Hz, 3H), 0.98-0.96 (m, 2H), 0.86-0.84 (m 2H). trifluoroacetate |

-continued

| No | starting materials | structures | HNMR |
|---|---|---|---|
| 224 | 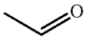 | 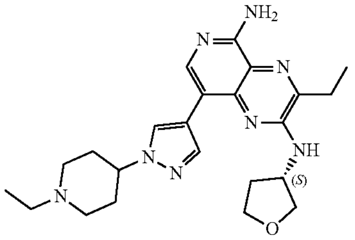 | $^{1}$H NMR (400 MHz, DMSO-$d_6$) δ 8.35 (s, 1H), 8.18 (brs, 4H), 8.06 (s, 1H), 7.27 (d, J = 5.6 Hz, 1H), 6.45 (brs, 1H), 4.70-4.66 (m, 2H), 4.20-4.16 (m, 1H), 4.06-4.00 (m, 1H), 3.98-3.87 (m, 1H), 3.86-3.68 (m, 3H), 3.08 (s, 2H), 2.85 (q, J = 7.2 Hz, 2H), 2.30-2.21 (m, 5H), 2.16-1.93 (m, 5H), 1.31 (t, J = 7.2 Hz, 3H), 1.06 (t, J = 7.2 Hz, 3H). formate |
| 227 | 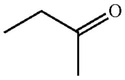 | 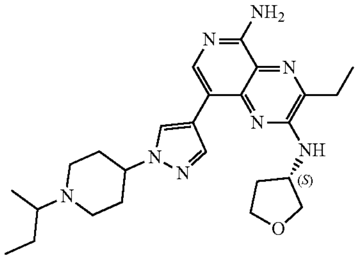 | $^{1}$H NMR (400 MHz, DMSO-$d_6$) δ 8.35 (s, 1H), 8.18 (brs, 1H), 8.14 (s, 1H), 8.09 (s, 1H), 7.32 (d, J = 5.6 Hz, 1H), 6.57 (brs, 2H), 4.68 (d, J = 6.4 Hz, 1H), 4.40 (s, 1H), 4.02-3.99 (m, 1H), 3.93 (d, J = 8.0 Hz, 1H), 3.80-3.74 (m, 2H), 3.26-3.23 (m, 2H), 3.02 (d, J = 12.0 Hz, 2H), 2.84 (d, J = 8.0 Hz, 1H), 2.56 (s, 2H), 2.33-2.11 (m, 6H), 1.78-1.64 (m, 1H), 1.50-1.37 (m, 1H), 1.33-1.29 (m, 3H), 1.15 (d, J = 6.4 Hz, 3H), 0.94-0.90 (m, 3H). formate |
| 226 | 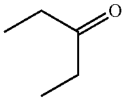 | 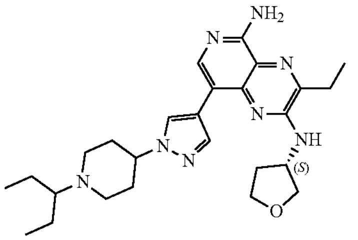 | $^{1}$H NMR (400 MHz, DMSO-$d_6$) δ 8.37 (s, 1H), 8.23-8.13 (m, 3H), 8.02 (s, 1H), 7.27 (d, J = 8.0 Hz, 1H), 6.43 (brs, 2H), 4.73-4.66 (m, 1H), 4.18-4.08 (m, 1H), 4.04-3.99 (m, 1H), 3.97-3.91 (m, 1H), 3.79-3.74 (m, 2H), 2.86-2.82 (m, 4H), 2.52 (d, J = 4.0 Hz, 1H), 2.42 (s, 1H), 2.32-2.23 (m, 2H), 2.14-2.04 (m, 1H), 2.08-2.02 (m, 2H), 1.88 (m, 2H), 1.52-1.42 (m,, 2H), 1.34-1.22 (m, 5H), 0.90-0.87 (m, 6H). formate |
| 225 | 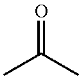 | 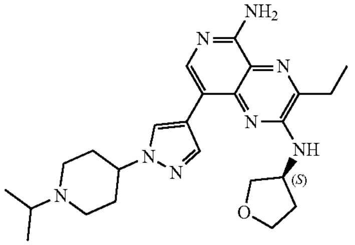 | $^{1}$H NMR (400 MHz, DMSO-$d_6$) δ 8.35 (s, 1H), 8.18 (s, 1H), 8.17 (brs, 3H), 8.05 (s, 1H), 7.26 (d, J = 5.6 Hz, 1H), 6.44 (brs, 2H), 4.73-4.66 (m, 1H), 4.23-4.16 (m, 1H), 4.03-3.99 (m, 1H), 3.93 (d, J = 7.2 Hz, 1H), 3.81-3.77 (m, 1H), 3.74-3.70 (m, 1H), 3.01 (d, J = 12.0 Hz, 2H), 2.95-2.89 (m, 1H), 2.87-2.82(m, 2H), 2.52 (s, 2H), 2.29-2.25 (m, 1H), 2.14-2.06 (m, 3H), 2.03-1.94 (m, 2H), 1.33-1.29 (m, 3H), 1.05 (d, J = 6.4 Hz, 6H). formate |
| 223 | paraformaldehyde | 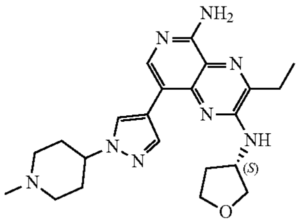 | $^{1}$H NMR (400 MHz, DMSO-$d_6$) δ 8.34 (s, 1H), 8.20 (brs, 2H), 8.16 (s, 1H), 8.04 (s, 1H), 7.26 (d, J = 5.6 Hz, 1H), 6.50 (brs, 2H), 4.71-4.65 (m, 2H), 4.12-4.15 (m, 1H), 4.01-3.98 (m, 1H), 3.94-3.88 (m, 1H), 3.79-3.74 (m, 1H), 3.72-3.69 (m, 1H), 2.97 (d, J = 12.0 Hz, 2H), 2.86-2.80 (m, 2H), 2.50 (s, 1H), 2.31 (s, 3H), 2.31-2.25 (m, 2H), 2.09 (s, 2H), 2.00 (d, J = 12.0 Hz, 2H), 1.29 (t, J = 7.2 Hz, 3H). formate |

(S)-Tetrahydrofuran-3-amine was replaced with the starting material in the following table to obtain the following table compound according to the synthesis method of compound 225.

| No | starting materials | structures | HNMR |
|---|---|---|---|
| 260 | 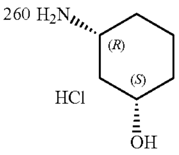 | 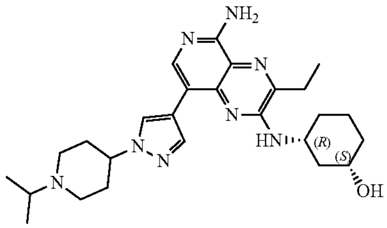 | $^1$H NMR (400 MHz, DMSO-$d_6$) δ 8.36 (s, 1H), 8.19 (d, J = 8.4 Hz, 3H), 8.02 (s, 1H), 7.13 (d, J = 7.2 Hz, 1H), 6.39 (brs, 2H), 4.14 (d, J = 4.0 Hz, 1H), 3.63 (d, J = 3.6 Hz, 1H), 2.95 (d, J = 12.0 Hz, 2H), 2.85-2.76 (m, 3H), 2.52 (d, J = 4.0 Hz, 1H), 2.39-2.28 (m, 3H), 2.6-2.07 (m, 1H), 2.01-1.77 (m, 1H), 1.47-1.35 (m, 3H), 1.30 (t, J = 7.2 Hz, 1H), 1.20 (d, J = 8.0 Hz, 1H), 1.02 (d, J = 6.4 Hz, 6H). formate |

Example 26: (1S,3R)-3-((5-amino-3-ethyl-8-(1-(1-(2-hydroxyethyl)piperidin-4-yl)-1H-pyrazol-4-yl) pyridino[3,4-b]pyrazin-2-yl)amino)cyclopentan-1-ol (Compound 207)

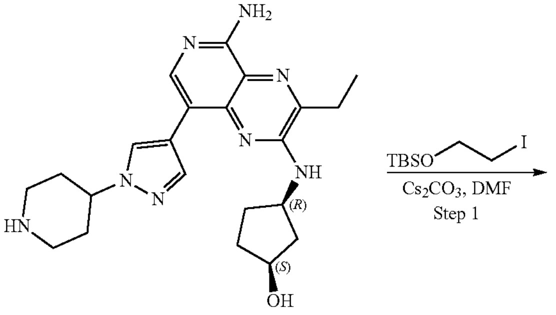

intermediate F

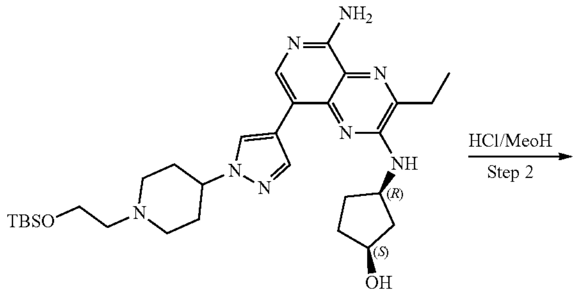

-continued

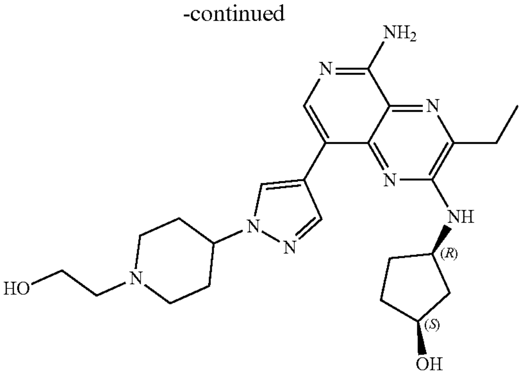

compound 207

Step 1: Tert-butyl (2-iodoethoxy)dimethylsilane (71 mg, 0.25 mmol) and cesium carbonate (161 mg, 0.50 mmol) were added to the N,N-dimethylformamide (5 mL) solution of intermediate F (50 mg, 0.10 mmol), and stirred at 45° C. for 12 hours. At the end of the reaction, the mixture was cooled to room temperature and water (1 mL) was added. The mixture was concentrated under reduced pressure. The resulting residue was purified by silica gel chromatography column (dichloromethane:methanol=3:1) to obtain yellow solid compound (40 mg, yield 41%). (ESI) m/z 581.3. $[M+H]^+$.

Step 2: The product of Step 1 (40 mg, 0.070 mmol) was used as the starting material to remove the protective group according to the method of Step 4 in Example 7 to obtain the formate salt of the yellow solid compound 207 (5 mg, 31% yield). $^1$H NMR (400 MHz, DMSO-$d_6$) δ 8.42 (s, 1H), 8.18 (s, 1H), 8.15 (brs, 2H), 8.05 (s, 1H), 7.12 (d, J=7.2 Hz, 1H), 6.42 (brs, 2H), 4.47-4.45 (m, 1H), 4.19-4.15 (m, 2H), 3.55-3.52 (m, 2H), 3.06-3.03 (m, 2H), 2.80-2.75 (m, 2H), 2.55-2.50 (m, 4H), 2.40-2.26 (m, 2H), 2.14-1.92 (m, 6H), 1.83-1.81 (m, 2H), 1.72-1.59 (m, 2H), 1.30 (t, J=7.2 Hz, 3H). (ESI) m/z 467.2 $[M+1]^+$.

Intermediate F was replaced with the starting materials in the following table to obtain the corresponding compounds by the method of Example 26.

| No | starting materials | structures | HNMR |
|---|---|---|---|
| 156 | Compound 58 | 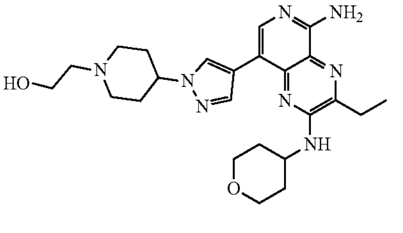 [SMILES: CCc1nc2c(N)ncc(-c3cnn(C4CCN(CCO)CC4)c3)c2nc1NC1CCOCC1] | $^{1}$H NMR (400 MHz, DMSO-$d_6$) δ 8.35 (s, 1H), 8.21 (brs, 2H), 8.18 (s, 1H), 8.01 (s, 1H), 7.04 (d, J = 7.2 Hz, 1H), 6.37 (brs, 2H), 4.30-4.28 (m, 2H), 4.21-4.10 (m, 2H), 3.98-3.95 (m, 2H), 3.54-3.35 (m, 2H), 3.01-2.98 (m, 2H), 2.82-2.78 (m, 2H), 2.46-2.42 (m, 2H), 2.22-2.12 (m, 2H), 2.08-1.88 (m, 6H), 1.71-1.69 (m, 2H), 1.31 (t, J = 7.2 Hz, 3H). formate |
| 229 | Compound 259 | 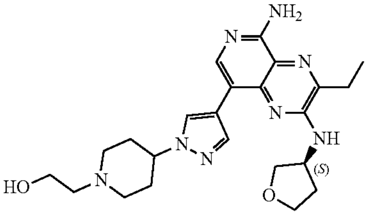 | $^{1}$H NMR (400 MHz, DMSO-$d_6$) δ 8.35 (s, 1H), 8.23 (brs, 2H), 8.17 (s, 1H), 8.05 (s, 1H), 7.30 (d, J = 6.0 Hz, 1H), 6.58 (brs, 2H), 4.71-4.65 (m, 1H), 4.26-4.19 (m, 1H), 4.03-4.00 (m, 1H), 3.96-3.90 (m, 1H), 3.82-3.76 (m, 1H), 3.74-3.71 (m, 1H), 3.59 (t, J = 6.0 Hz, 2H), 3.13 (d, J = 12.0 Hz, 2H), 2.88-2.82 (m, 2H), 2.63 (t, J = 6.0 Hz, 2H), 2.46-2.40 (m, 2H), 2.34-2.25 (m, 2H), 2.14-2.07 (m, 4H), 2.06-2.00 (m, 1H), 1.31 (t, J = 7.2 Hz, 3H). formate |
| 239 | Compound 160 | 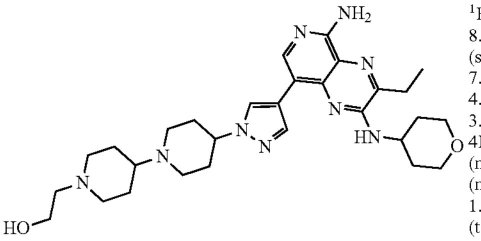 | $^{1}$H NMR (400 MHz, DMSO-$d_6$) δ 8.36 (s, 1H), 8.21 (brs, 4H), 8.18 (s, 1H), 8.00 (s, 1H), 7.06 (d, J = 7.6 Hz, 1H), 6.42 (brs, 2H), 4.37-4.25 (m, 1H), 4.20-4.12 (m, 1H), 3.98-3.95 (m, 2H), 3.51-3.48 (m, 4H), 3.03-2.99 (m, 4H), 2.82-2.78 (m, 2H), 2.55-2.50(m, 2H), 2.42-2.17 (m, 4H), 2.13-1.90 (m, 4H), 1.72-1.68 (m, 4H), 1.56-1.53 (m, 2H), 1.31 (t, J = 7.2 Hz, 3H). formate |

Example 27: (S)-3-ethyl-8-(1-(piperidin-4-yl)-1H-pyrazol-4-yl)-N2-(tetrahydrofuran-3-yl)pyridino[3,4-b]pyrazin-2,5-diamine (Compound 230)

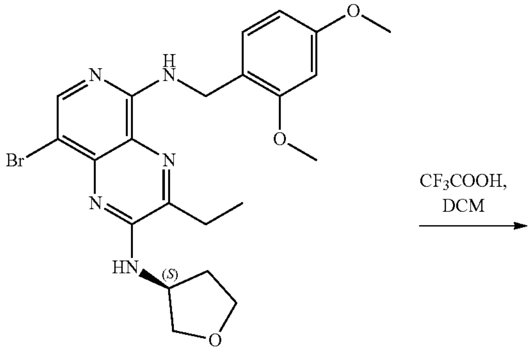

intermediate G

-continued

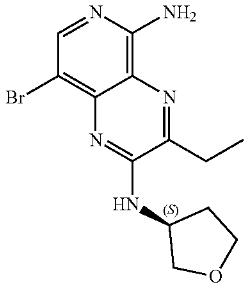

intermediate I

Yellow solid compound intermediate I (350 mg, yield 86%) was prepared from intermediate G (588 mg, 1.2 mmol) by the method of Step 12 in Example 1. (ESI) m/z 338.1. $[M+H]^+$.

The starting materials in the following table were reacted with intermediate I according to the method of Step 2 in Example 2 to obtain the corresponding compounds.

| No | starting materials | structures | HNMR |
|---|---|---|---|
| 230 | 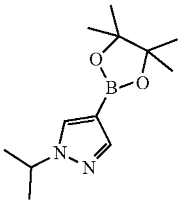 [SMILES: CC(C)n1cc(B2OC(C)(C)C(C)(C)O2)cn1] | 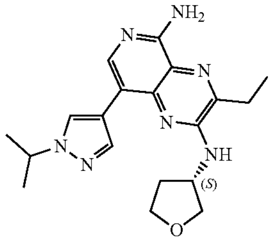 | $^1$H NMR (400 MHz, DMSO-$d_6$) δ 8.35 (s, 1H), 8.18 (brs, 1H), 8.15 (s, 1H), 8.01 (s, 1H), 7.26 (d, J = 6.0 Hz, 1H), 6.40 (brs, 2H), 4.73-4.67 (m, 1H), 4.55-4.48 (m, 1H), 4.05-4.01 (m, 1H), 3.95-3.88 (m, 1H), 3.81-3.76 (m, 1H), 3.73-3.69 (m, 1H), 2.85 (q, J = 7.2 Hz, 2H), 2.30-2.24 (m, 1H), 2.15-2.06 (m, 1H), 1.46 (d, J = 6.8 Hz, 6H), 1.31 (t, J = 7.2 Hz, 3H). formate |
| 281 | 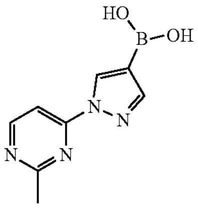 | 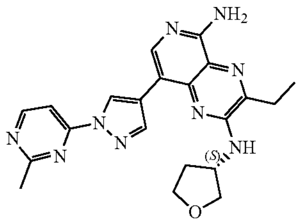 | $^1$H NMR (400 MHz, DMSO-$d_6$) δ 9.58 (s, 1H), 8.75 (d, J = 5.6 Hz, 1H), 8.58 (s, 1H), 8.44 (s, 1H), 8.19 (brs, 1 H), 7.7 (d, J = 5.6 Hz, 1H), 7.40 (d, J = 5.6 Hz, 1H), 6.62 (brs, 2H), 4.78 (brs, 1H), 4.27-4.23 (m, 1H), 3.98-3.93 (m, 1H), 3.89-3.75 (m, 2H), 2.91-2.85 (m, 2H), 2.64 (s, 3H), 2.44-2.41 (m, 1H), 2.21-2.13 (m 1H), 1.33 (t, J = 7.2 Hz, 3H). formate |

The starting material in the following table was reacted with intermediate G according to the method of step 3 to the end of Example 17 to obtain the corresponding compound

| No | starting materials | structures | HNMR |
|---|---|---|---|
| 231 | 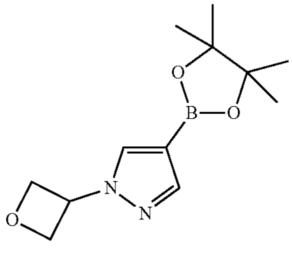 [SMILES: CC1(C)OB(c2cnn(C3COC3)c2)OC1(C)C] | 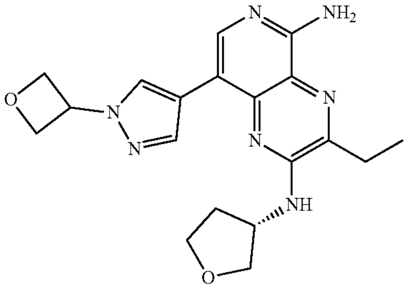 [SMILES: CCc1nc2c(N)ncc(-c3cnn(C4COC4)c3)c2nc1N[C@H]1CCOC1] | $^1$H NMR (400 MHz, DMSO-$d_6$) δ 8.49 (s, 1H), 8.19 (d, J = 2.8 Hz, 2H), 7.32 (d, J =6.0 Hz, 1H), 6.57 (brs, 2H), 5.65-5.58 (m, 1H), 4.98-4.90 (m, 4H), 4.74-4.64 (m, 1H), 4.02-3.98 (m, 1H), 3.95-3.89 (m, 1H), 3.81-3.74 (m, 2H), 2.88-2.83 (m, 2H), 2.33-2.25 (m, 1H), 2.14-2.06 (m, 1H), 1.31 (t, J =7.2 Hz, 3H). |

Example 28: 3-((5-amino-3-ethyl-8-(1-(1'-ethyl-[1,4'-bipiperidine]-4-yl)-1H-pyrazol-4-yl)pyridino[3,4-b]pyrazine-2-yl)amino)cyclohexan-1-ol (Compound 246)

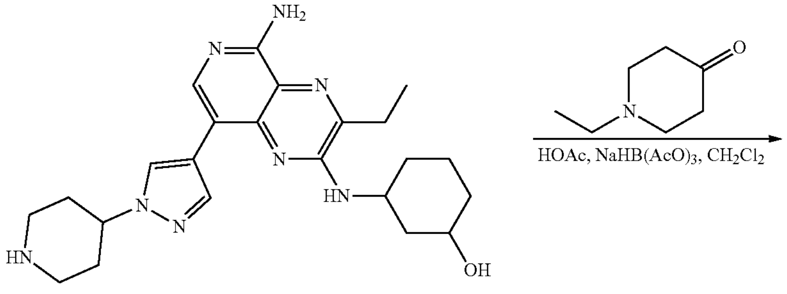

intermediate J

-continued

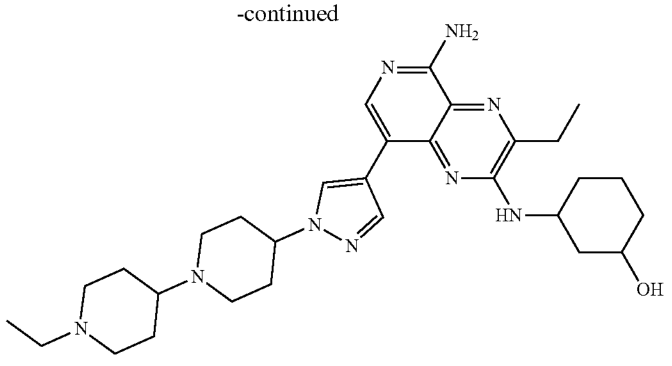

compound 246

(S)-tetrahydrofuran-3-amine was replaced with 3-aminocyclohexanol to obtain intermediate J by the method of Example 25, and then the intermediate J was used according to the method of Step 2 in Example 6 to obtain the formate of compound 246. $^1$H NMR (400 MHz, DMSO-$d_6$) δ 8.47 (s, 1H), 8.22-8.17 (m, 4H), 8.02 (s, 1H), 6.87 (d, J=7.6 Hz, 1H), 6.36 (brs, 2H), 4.63-4.56 (m, 1H), 4.16-4.13 (m, 1H), 4.08 (s, 1H), 3.12-2.93 (m, 6H), 2.80 (q, J=7.2 Hz, 2H), 2.35-2.27 (m, 4H), 2.11-1.41 (m, 18H), 1.29 (t, J=7.2 Hz, 3H), 1.08-1.01 (m, 3H). (ESI) m/z 548.3. [M+1]$^+$.

Example 29: 3-ethyl-8-(4-(4-(4-ethylpiperazine-1-yl)piperidine-1-yl)-3-methoxyphenyl)-N2-(tetrahydro-2H-pyran-4-yl)pyridino[3, 4-b]pyrazine-2, 5-diamine (Compound 315)

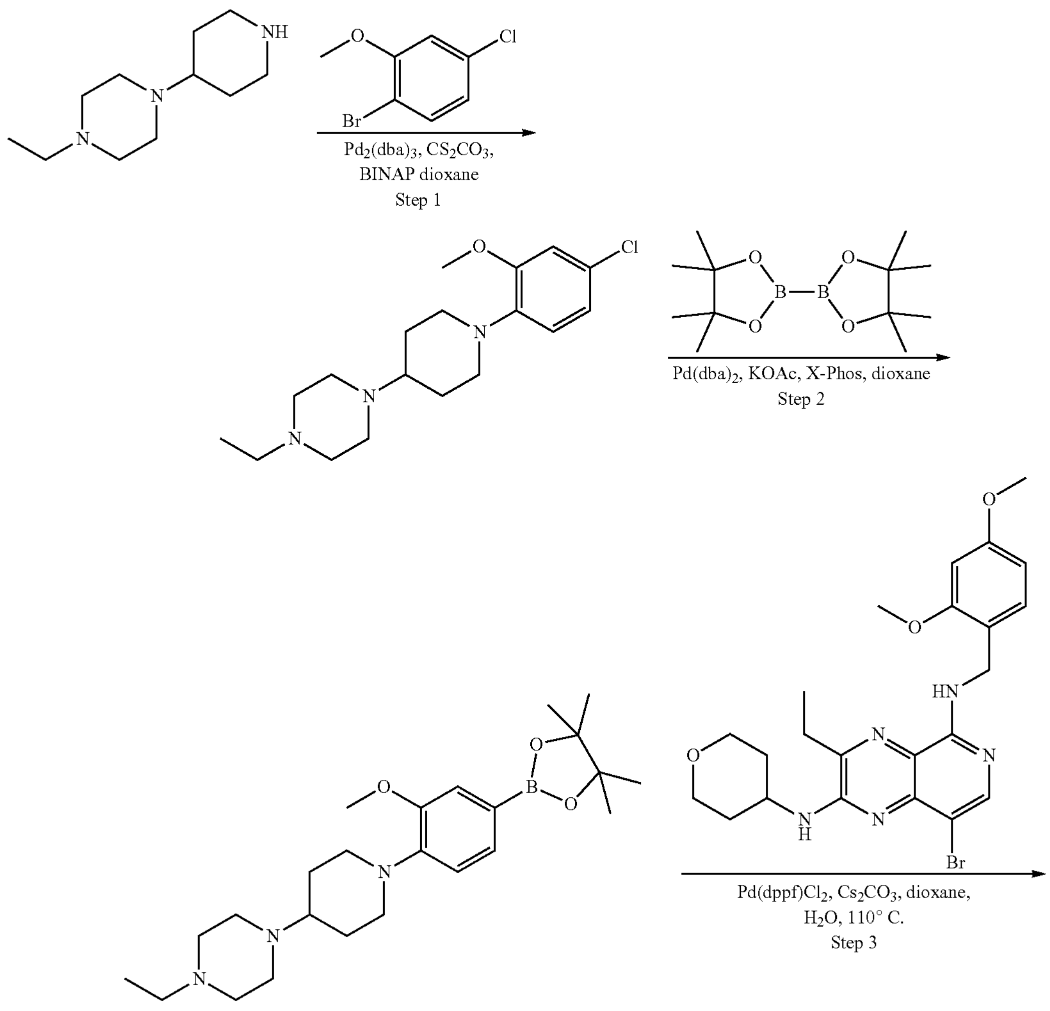

intermediate K

-continued

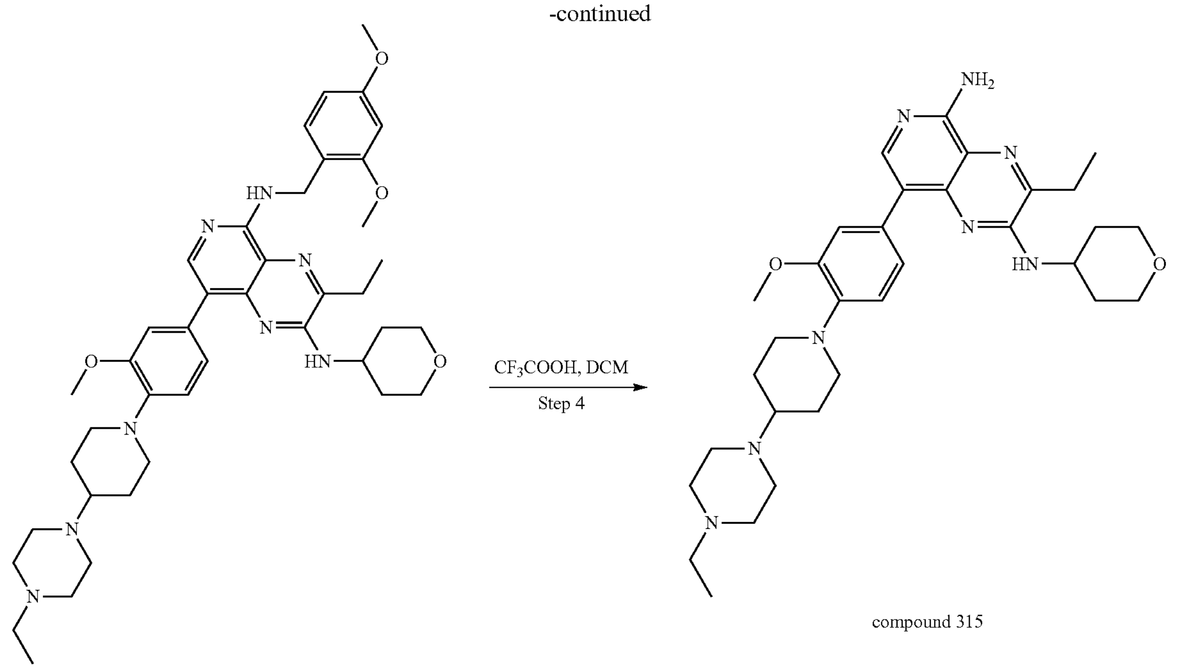

compound 315

Step 1: Cesium acetate (28 g, 87 mmol) and $Pd_2(dba)_3$ (4.0 g, 4.3 mmol), BINAP (5.4 g, 8.7 mmol) were added to the 1,4-dioxane (200 mL) mixture containing 1-ethyl-4-(piperidin-4-ylmethyl)piperazine (8.0 g, 40 mmol) and 1-bromo-4-chloro-2-methoxybenzene (9.6 g, 43 mmol). This mixture was stirred and reacted at 100° C. for 12 hours under nitrogen protection. At the end of the reaction, the mixture was cooled to room temperature and water (100 mL) was added. The solution was extracted three times (200 mL×3) with ethyl acetate. The organic phases were combined, dried over anhydrous sodium sulfate, filtered, and the filtrate was concentrated under reduced pressure. The resulting residue was purified by silica gel chromatography column (dichloromethane/methanol=4:1) to obtain yellow oil (7.0 g, yield 52%). (ESI) m/z 338.2 $[M+H]^+$.

Step 2: Potassium acetate (5.1 g, 62 mmol), $Pd_2(dba)_3$ (1.2 g, 2.1 mmol) and X-Phos (2.0 g, 4.1 mmol) were added to the 1, 4-dioxane (100 mL) mixture containing 1-(1-(4-chloro-2-methoxyphenyl) piperidin-4-yl)-4-ethylpiperazine (7.0 g, 21 mmol) and divaleryl diboron (7.9 g, 31 mmol). This mixture was stirred to react at 100° C. for 12 hours under nitrogen protection. At the end of the reaction, the mixture was cooled to room temperature and water (100 mL) was added. The mixture was extracted three times (300 mL×3) with ethyl acetate. The organic phases were combined, dried over anhydrous sodium sulfate, filtered, and the filtrate was concentrated under reduced pressure. The resulting residue was purified by silica gel chromatography column (dichloromethane/methanol=4:1) to obtain yellow oil intermediate K (7.0 g, yield 79%). (ESI) m/z 430.3. $[M+H]^+$.

Step 3: Cesium carbonate (2.7 g, 8.0 mmol) and Pd(dppf)$Cl_2$ (0.20 g, 0.20 mmol) were added to the 1,4-dioxane/water (8 mL, 4/1)) mixture containing 8-bromo-N5-(2,4-dimethoxy benzyl)-3-ethyl-N2-(tetrahydro-2H-pyran-4-yl)pyridino[3,4-b]pyrazine-2,5-diamine (1.4 g, 3.0 mmol) and intermediate K (4.0 g, 7.97 mmol). This mixture was reacted at microwave 100° C. for 1 hour under nitrogen protection. At the end of the reaction, the mixture was cooled to room temperature and water (50 mL) was added. The mixture was extracted three times (30 mL×3) with ethyl acetate. The organic phases were combined, dried over anhydrous sodium sulfate, filtered, and the filtrate was concentrated under reduced pressure. The resulting residue was purified by silica gel chromatography column (dichloromethane/methanol=10:1) to obtain yellow solid (900 mg, yield 42%). (ESI) m/z 725.4. $[M+H]^+$.

Step 4: The solution of trifluoroacetic acid/dichloromethane (5 mL, 3/1) containing N5-(2,4-dimethoxybenzyl)-3-ethyl-8-(4-(4-(4-ethylpiperazine-1-yl)piperidine-1-yl)-3-methoxyphenyl)-N2-(tetrahydro-2H-pyran-4-yl)pyridine[3,4-b]pyrazine-2,5-diamine (900 mg, 1.2 mmol) was stirred at 25° C. for 3 hours. At the end of the reaction, diisopropylethylamine (10 mL) was added to quench the reaction and the mixture was concentrated under reduced pressure. The residue was purified by preparative liquid chromatography to obtain yellow solid compound 315 as a formate (255 mg, 35% yield). $^1H$ NMR (400 MHz, DMSO-$d_6$) δ 8.14 (brs, 1H), 7.91 (s, 1H), 7.25-7.17 (m, 2H), 7.09 (d, J=8.0 Hz, 1H), 6.91 (d, J=8.0 Hz, 1H), 6.62 (brs, 2H), 4.14-4.10 (m, 1H), 3.91 (d, J=8.0 Hz, 2H), 3.82 (s, 3H), 3.48 (d, J=12.0 Hz, 3H), 3.26-3.24 (m, 2H), 2.82-2.78 (m, 2H), 2.61-2.51 (m, 6H), 2.49-2.44 (m, 6H), 1.88-1.84 (m, 4H), 1.64-1.60 (m, 4H), 1.31 (t, J=7.2 Hz, 3H), 1.14 (t, J=7.2 Hz, 3H). (ESI) m/z. 575.3 $[M+1]^+$.

1-Ethyl-4-(piperidin-4-ylmethyl)piperazine was replaced with the starting material in the following table to obtain the corresponding intermediate by the method of Example 29. And then the intermediate was reacted with compound 2 according to the method of Step 3 in Example 29 to obtain the following corresponding compound:

| No | starting materials | structures | HNMR |
|---|---|---|---|
| 314 | 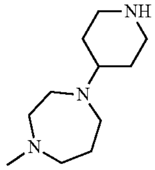 | 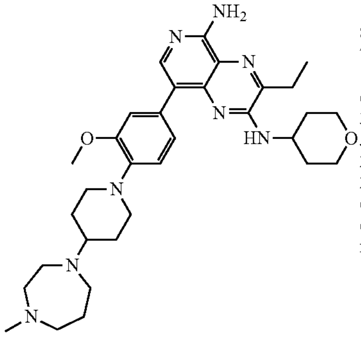 [SMILES: CCc1nc2c(N)ncc(-c3ccc(N4CCC(N5CCCN(C)CC5)CC4)c(OC)c3)c2nc1NC1CCOCC1] | $^1$H NMR (400 MHz, DMSO-d$_6$) δ 8.26 (brs, 1.5H), 7.92 (s, 1H), 7.22-7.18 (m, 2H), 7.01 (d, J = 7.2 Hz, 1H), 6.88 (d, J = 8.0 Hz, 1H), 6.46 (brs, 2H), 4.17-4.07 (m, 1H), 3.92-3.88 (m, 2H), 3.81 (s, 3H), 3.45 (d, J = 11.6 Hz, 3H), 3.29-3.24 (m, 3H), 2.83-2.76 (m, 6H), 2.68-2.62 (m, 4H), 2.56 (s, 1H), 2.34 (s, 3H), 1.88-1.84 (m, 2H), 1.79-1.73 (m, 4H), 1.66-1.56 (m, 4H), 1.30 (t, J = 7.2 Hz, 3H). formate |

1-Ethyl-4-(piperidin-4-ylmethyl) piperazine was replaced with the starting material 1 in the following table by the method of Example 29, and 1-bromo-4-chloro-2-methoxy-benzene was replaced with the starting material 2 in the following table to carry out the reaction to obtain the corresponding compound.

| No | starting material 1 | starting material 2 | structures | HNMR |
|---|---|---|---|---|
| 268 | 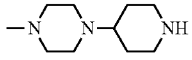 | 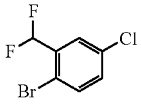 | 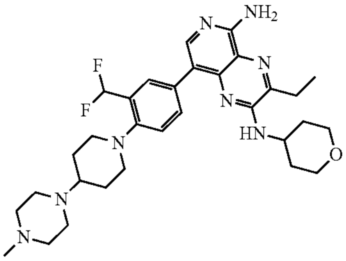 [SMILES: CCc1nc2c(N)ncc(-c3ccc(N4CCC(N5CCN(C)CC5)CC4)c(C(F)F)c3)c2nc1NC1CCOCC1] | $^1$H NMR (400 MHz, DMSO-d$_6$) δ 8.17 (brs, 3H), 8.02 (d, J = 1.6 Hz, 1H), 7.95 (s, 1H), 7.75-7.73 (m, 1H), 7.30 (d, J = 8.4 Hz, 1.25H), 7.18 (s, 0.5H), 7.04-7.00 (m, 1.25H), 6.54 (brs, 2H), 4.22-4.14 (m, 1H), 3.88-3.84 (m, 2H), 3.30 (s, 2H), 3.08 (d, J = 11.6 Hz, 2H), 2.80-2.74 (m, 4H), 2.55-2.54 (m, 3H), 2.41-2.35 (m, 6H), 2.19 (s, 3H), 1.87-1.78 (m, 4H), 1.70-1.57 (m, 4H), 1.31 (t, J = 7.2 Hz, 3H). formate |

1-Ethyl-4-(piperidin-4-ylmethyl)piperazine was replaced with the starting materials in the following table by the method of Step 1 and 2 in Example 29 to obtain the corresponding intermediates, and then the intermediate was reacted with intermediate D by the method of Step 3 and 4 in Example 29 to obtain the following corresponding compound.

| No | starting materials | structures | HNMR |
|---|---|---|---|
| 266 | 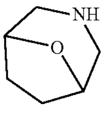 | 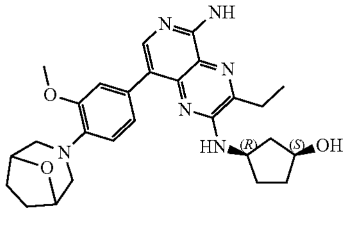 | $^1$H NMR (400 MHz, DMSO-d$_6$) δ 7.80 (s, 1H), 7.62 (s, 2H), 7.53 (d, J = 6.8 Hz, 1H), 7.29 (d, J = 2.0 Hz, 1H), 7.21-7.18 (m, 1H), 6.86 (d, J = 8.4 Hz, 1H), 4.78 (d, J = 3.6 Hz, 1H), 4.40-4.34 (m, 3H), 4.15-4.09 (m, 1H), 3.82 (s, 3H), 3.18 (d, J = 10.8 Hz, 2H), 2.84-2.80 (m, 4H), 2.17-2.11 (m, 1H), 2.03-2.00 (m, 2H), 1.94-1.87 (m, 1H), 1.83-1.80 (m, 2H), 1.76-1.57 (m, 4H), 1.32 (t, J = 7.2 Hz, 3H). |

-continued

| No | starting materials | structures | HNMR |
|---|---|---|---|
| 265 | 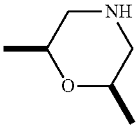 | 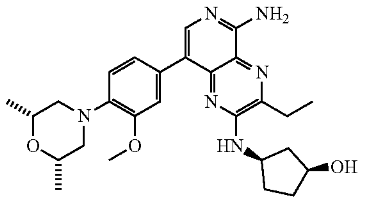 [SMILES: CCc1nc2c(N)ncc(-c3ccc(N4C[C@@H](C)O[C@@H](C)C4)c(OC)c3)c2nc1N[C@@H]1CC[C@H](O)C1] | $^1$H NMR (400 MHz, DMSO) δ 8.15 (s, 1H), 7.92 (s, 1H), 7.36 (d, J = 2.0 Hz, 1H), 7.20 (d, J = 8.2, 2.0 Hz, 1H), 7.02 (d, J = 7.2 Hz, 1H), 6.88 (d, J = 8.4 Hz, 1H), 6.45 (brs, 2H), 4.76 (s, 1H), 4.39-4.38 (m, 1H), 4.13 (s, 1H), 3.81 (s, 3H), 3.80-3.69 (m, 2H), 2.78 (q, J = 7.2 Hz, 2H), 2.26-2.20 (m, 2H), 2.19-2.10 (m, 1H), 1.98-1.87 (m, 1H), 1.83-1.54 (m, 5H), 1.31 (t, J = 7.2 Hz, 3H), 1.12 (d, J = 6.0 Hz, 6H). formate |

1-Ethyl-4-(piperidin-4-ylmethyl)piperazine was replaced with the starting material in the following table by the method of Step 1 and 2 in Example 29 to obtain the corresponding intermediate, and then the intermediate was reacted with compound 151 by the method of Step 3 in Example 29 to obtain the following corresponding compound.

| No | starting materials | structures | HNMR |
|---|---|---|---|
| 267 | 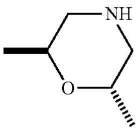 | 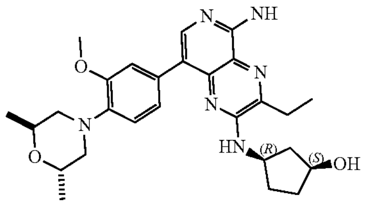 | $^1$H NMR (400 MHz, DMSO-$d_6$) δ 8.14 (brs, 1H), 7.91 (s, 1H), 7.37-7.34 (m, 1H), 7.22-7.18 (m, 1H), 7.01 (d, J = 7.2 Hz, 1H), 6.86 (d, J = 8.4 Hz, IH), 6.45 (brs, 2H), 4.45-4.35 (m, 1H), 4.17-4.10 (m, 1H), 4.07-4.01 (m, 2H), 3.81 (s, 3H), 2.98-2.92 (m, 2H), 2.82-2.75 (m, 4H), 2.18-2.11 (m, 1H), 1.97-1.90 (m, 1H), 1.82-1.54 (m, 5H), 1.31 (t, J = 7.2 Hz, 3H), 1.25 (d, J = 6.4 Hz, 6H). formate |

The starting material in the following table was used to obtain the corresponding compound by the method of Step 3 and 4 in Example 29.

| No | starting materials | structures | HNMR |
|---|---|---|---|
| 252 | intermediate G and intermediate K | 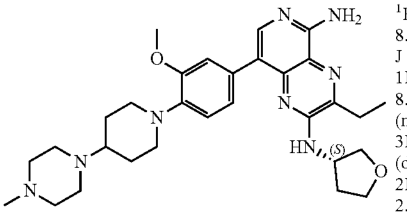 | $^1$H NMR (400 MHz, DMSO-$d_6$) δ 8.18 (s, 1H), 7.91 (s, 1H), 7.27 (d, J = 1.6 Hz, 1H), 7.21 (d, J = 5.6 Hz, 1H), 7.17-7.15 (m, 1H), 6.90 (d, J = 8.4 Hz, 1H), 6.48 (s, 2H), 4.51-4.45 (m, 1H), 3.91-3.85 (m, 2H), 3.81 (s, 3H), 3.70 (d, J = 6.4 Hz, 1H), 3.59 (d, J = 4.0 Hz, 2H), 3.30-3.21 (m, 2H), 2.85-2.83 (m, 2H), 2.57 (s, 4H), 2.43 (s, 4H), 2.33 (s, 2H), 2.22 (s, 3H), 2.18-2.09 (m, 1H), 2.08-1.97 (m, 1H), 1.84 (d, J = 12.0 Hz, 2H), 1.61-1.53 (m, 2H), 1.33-1.29 (m, 3H). formate |

The starting materials in the following table was used to react with intermediate K to obtain the corresponding compounds by the method of Example 29.

| No | starting materials | structures | HNMR |
|---|---|---|---|
| 325 | intermediate G | 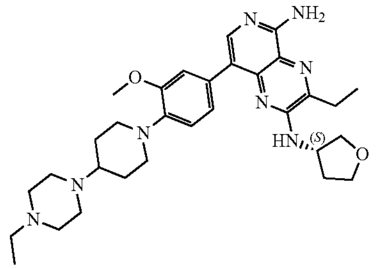 | $^1$H NMR (400 MHz, DMSO-$d_6$) δ 8.14 (brs, 0.8H), 7.91 (s, 1H), 7.27 (d, J = 2.0 Hz, 1H), 7.24 (d, J = 5.6 Hz, 1H), 7.19-7.14 (m, 1H), 6.92 (d, J = 8.4 Hz, 1H), 6.54 (s, 2H), 4.52-4.45 (m, 1H), 3.90-3.84 (m, 2H), 3.82 (s, 3H), 3.72-3.67 (m, 1H), 3.61-3.57 (m, 1H), 3.49-3.46 (m, 3H), 2.87-2.75 (m, 9H), 2.56-2.52 (m, 5H), 2.20-2.11 (m, 1H), 2.08-2.00 (m, 1H), 1.91-1.88 (m, 2H), 1.66-1.57 (m, 2H), 1.32 (t, J = 7.2 Hz, 3H), 1.11 (t, J = 7.2 Hz, 3H). formate |
| 253 | intermediate D | 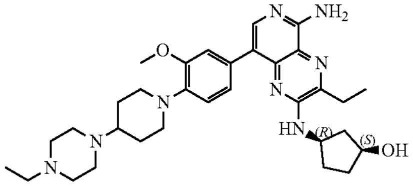 | $^1$H NMR (400 MHz, DMSO-$d_6$) δ 8.13 (brs, 1H), 7.89 (s, 1H), 7.34 (d, J = 1.6 Hz, 1H), 7.19-7.17 (m, 2H), 6.92 (d, J = 8.4 Hz, 1H), 6.72 (brs, 2H), 4.76 (d, J = 3.6 Hz, 1H), 4.41-4.35 (m, 1H), 4.15-4.09 (m, 1H), 3.81 (s, 3H), 3.48 (d, J = 9.2 Hz, 2H), 2.82-2.77 (m, 2H), 2.68-2.66 (m, 1H), 2.60-2.56 (m, 1H), 2.56-2.54 (m, 1H), 2.52-2.51 (m, 5H), 2.46-2.45 (m, 3H), 2.34-2.32 (m, 1H), 2.21-2.09 (m, 2H), 1.94-1.90 (m, 2H), 1.83-1.72 (m, 2H), 1.71-1.55 (m, 5H), 1.31 (t, J = 7.2 Hz, 3H), 1.15 (t, J = 12.0 Hz, 3H). formate |

Example 30: (1S,3R)-3-((5-amino-3-ethylpyridino[3,4-b]pyrazine-2-yl)amino)cyclopentan-1-ol (Compound 263)

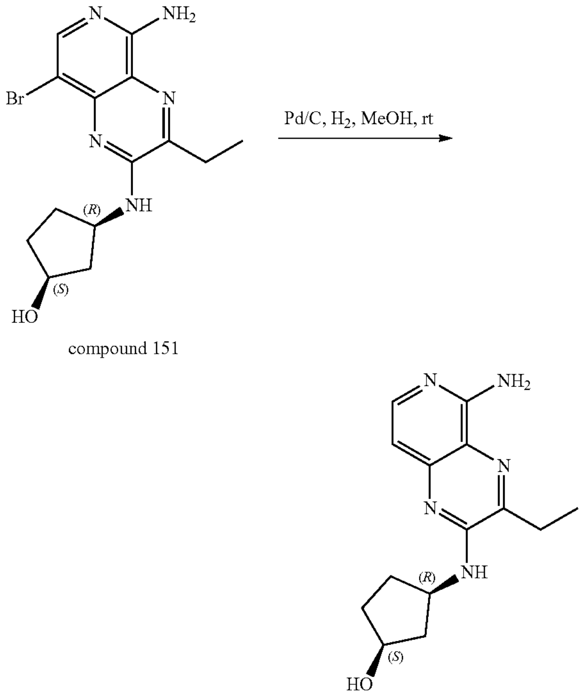

compound 151 compound 263

Compound 151 (100 mg, 0.28 mmol) was used as the starting material to obtain white solid compound 263 (20 mg, 25%) by the method of Step 4 in Example 1. $^1$H NMR (400 MHz, DMSO-$d_6$) δ 8.14 (brs, 1H), 7.75 (d, J=6.0 Hz, 1H), 7.01 (d, J=7.2 Hz, 1H), 6.59 (d, J=6.0 Hz, 1H), 6.51 (brs, 2H), 4.81 (s, 1H), 4.48-4.44 (m, 1H), 4.19-4.17 (m, 1H), 2.78-2.73 (m, 2H), 2.18-2.14 (m, 1H), 2.01-1.96 (m, 1H), 1.80-1.74 (m, 2H), 1.66-1.59 (m, 2H), 1.28 (t, J=7.2 Hz, 3H). (ESI) m/z. 274.1 [M+1]$^+$.

Example 31: (1S,3R)-3-((5-amino-3-ethyl-8-(1-(5-methylpyrimidin-4-yl)-1H-pyrazol-4-yl)pyridino[3,4-b]pyrazin-2-yl)amino)cyclopentan-1-ol (Compound 269)

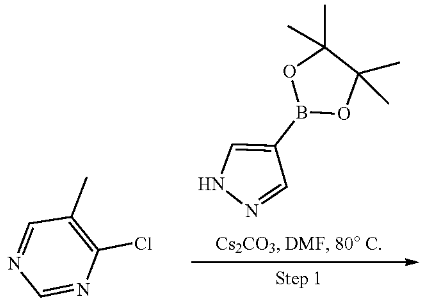

-continued

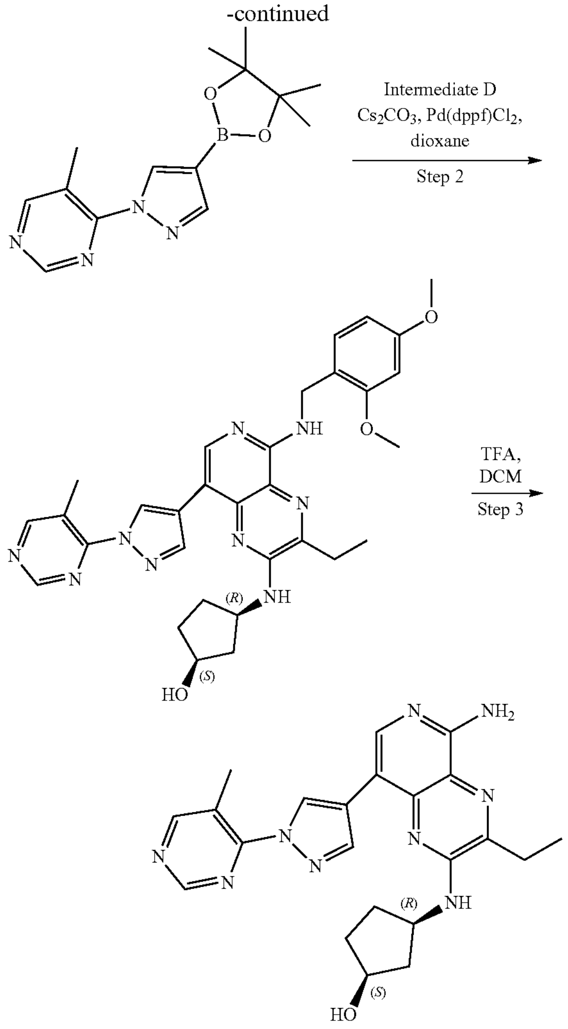

compound 269

Step 1: 4-(4,4,5,5-Tetramethyl-1,3,2-dioxoboran-2-yl) pyrazole (906 mg, 4.6 mmol) and cesium carbonate (2.3 g, 7.0 mmol) were added to the solution of N,N-dimethylformamide (15 mL) containing 4-chloro-5-methylpyrimidine (300 mg, 2.3 mmol). The mixture was stirred at 80° C. for 12 hours under nitrogen atmosphere. At the end of the reaction, the mixture was cooled to room temperature and water (50 mL) was added. The solution was extracted three times (50 mL×3) with ethyl acetate. The organic phases were combined, dried over anhydrous sodium sulfate, filtered, and the filtrate was concentrated under reduced pressure to obtain the product (200 mg, yield 30%). The product was directly used in the next step. (ESI) m/z. 287.2 [M+H].

Steps 2 and 3: The product of Step 1 was reacted with intermediate D by the method of Step 3 and 4 in Example 29 to obtain yellow solid compound 269 as a formate (two-step yield 46%). $^1$H NMR (400 MHz, DMSO-$d_6$) δ 9.61 (s, 1H), 8.90 (s, 1H), 8.77 (s, 1H), 8.56 (s, 1H), 8.38 (s, 1H), 8.14 (brs, 1H), 7.37 (d, J=7.2 Hz, 1H), 6.91 (s, 2H), 4.80 (s, 1H), 4.57-4.53 (in, 1H), 4.30-4.25 (in, 1H), 2.86-2.81 (m, 2H), 2.66 (s, 3H), 2.46-2.40 (m, 2H), 2.23-2.13 (in, 1H), 1.93-1.83 (m, 2H), 1.74-1.64 (m, 2H), 1.32 (t, J=7.2 Hz, 3H). (ESI) m/z. 432.2 $[M+1]^+$.

4-Chloro-5-methylpyrimidine was replaced with the starting material in the following table in the method of Example 31, while the two isomers of the product of step 1 were separated to obtain the corresponding compounds in the following table respectively.

| No | starting materials | structures | HNMR |
|---|---|---|---|
| 162 | 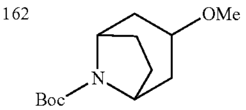 | 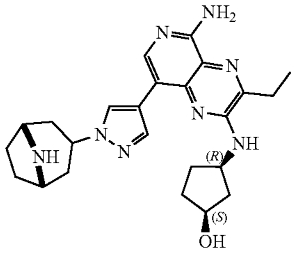 | $^1$H NMR (400 MHz, DMSO-$d_6$) δ $^1$H NMR (400 MHz, DMSO-$d_6$) δ 8.54 (s, 1H), 8.22 (s, 1H), 8.04 (s, 1H), 7.08 (d, J = 7.2 Hz, 1H), 6.35 (s, 2H), 4.83 (d, J = 3.6 Hz, 1H), 4.52-4.50 (m, 1H), 4.38-4.35 (m, 1H), 4.22-4.18 (m, 1H), 3.42 (s, 2H), 2.80 (q, J = 7.2 Hz, 2H), 2.35-2.17 (m, 7H), 2.05-2.02 ( , 1H), 1.77-1.70 (m, 5H), 1.61-1.45 (m, 4H), 1.31 (t, J = 7.3 Hz, 3H). |
| 163 | | 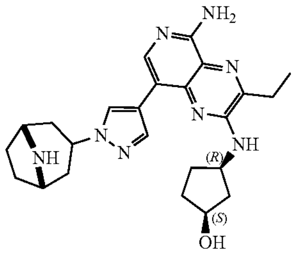 | $^1$H NMR (400 MHz, DMSO-$d_6$) δ 8.39 (s, 1H), 8.16 (s, 1H), 7.99 (s, 1H), 7.11 (d, J = 7.2 Hz, 1H), 6.34 (brs, 2H), 4.87-4.75 (m, 1H), 4.53-4.42 (m, 2H), 4.27-4.20 (m, 1H), 3.54 (s, 2H), 2.80 (q, J = 7.2 Hz, 2H), 2.55-2.52 (m, 1H), 2.38-2.28 (m, 2H), 2.12-2.02 (m, 2H), 1.97-1.80 (m, 6H), 1.77-1.60 (m, 6H), 1.30 (t, J = 7.2 Hz, 3H). |

The starting materials in the following table were used to obtain the corresponding compounds in the following table by the method of Step 2 in Example 6.

| No | starting materials | structures | HNMR |
|---|---|---|---|
| 164 | Compound 162 and formaldehyde | 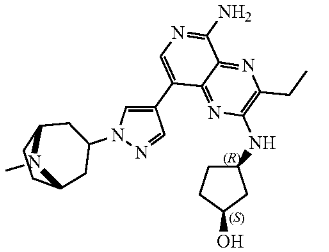 | $^1$H NMR (400 MHz, DMSO-$d_6$) δ 8.59 (s, 1H), 8.23 (s, 3H), 8.10 (s, 1H), 7.10 (d, J = 7.2 Hz, 1H), 6.42 (brs, 2H), 4.51-4.48 (m, 1H), 4.41-4.38 (m, 1H), 4.25-4.16 (m, 1H), 3.44 (s, 2H), 2.80 (q, J = 7.2 Hz, 2H), 2.68-2.64 (m, 2H), 2.44-2.37 (m, 5H), 2.27-2.25 (m, 1H), 2.09-1.99 (m, 1H), 1.95-1.63 (m, 7H), 1.57-1.52 (m, 2H), 1.31 (t, J = 7.2 Hz, 3H). formate |
| 165 | Compound 163 and formaldehyde | 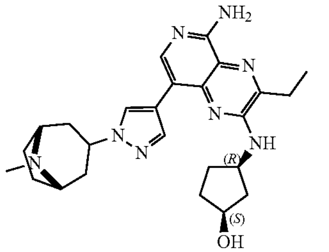 | $^1$H NMR (400 MHz, DMSO-$d_6$) δ 8.40 (s, 1H), 8.19 (brs, 3H), 8.17 (s, 1H), 8.02 (s, 1H), 7.12 (d, J = 7.2 Hz, 1H), 6.38 (brs, 2H), 4.55-4.46 (m, 2H), 4.25-4.22 (m, 1H), 3.39 (s, 2H), 2.80 (q, J = 7.2 Hz, 2H), 2.37 (s, 3H), 2.33-2.29 (m, 1H), 2.20-2.03 (m, 6H), 1.95-1.78 (m, 6H), 1.70-1.62 (m, 2H), 1.30 (t, J = 7.2 Hz, 3H). formate |
| 166 | Compound 163 and acetone | 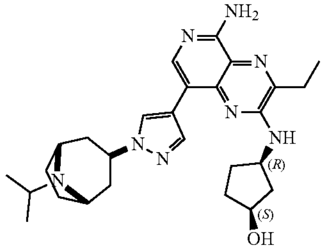 | $^1$H NMR (400 MHz, DMSO-$d_6$) δ 8.40 (s, 1H), 8.17 (s, 1H), 8.16 (s, 1H), 8.04 (s, 1H), 7.09 (d, J = 7.2 Hz, 1H), 6.37 (brs, 2H), 4.67-4.57 (m, 1H), 4.48-4.45 (m, 1H), 4.27-4.20 (m, 1H), 3.75 (s, 2H), 3.04-2.95 (m, 1H), 2.80 (q, J = 7.2 Hz, 2H), 2.30-2.26 (m, 1H), 2.18-2.15 (m, 2H), 2.06-2.00 (m, 2H), 1.99-1.75 (m, 7H), 1.68-1.65 (m, 2H), 1.30 (t, J = 7.2 Hz, 3H), 1.12 (d, J = 6.0 Hz, 6H). formate |
| 167 | Compound 163 and isobutyraldehyde | 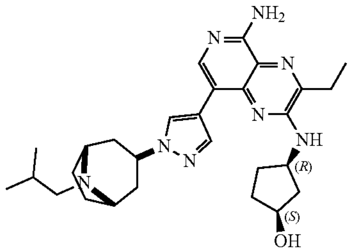 | $^1$H NMR (400 MHz, DMSO-$d_6$) δ 8.40 (s, 1H), 8.18 (s, 1H), 8.16 (s, 2H), 8.00 (s, 1H), 7.08 (d, J = 7.2 Hz, 1H), 6.37 (brs, 2H), 4.49-4.46 (m, 2H), 4.26-4.20 (m, 1H), 3.30 (s, 3H), 2.80 (q, J = 7.2 Hz, 2H), 2.33-2.24 (m, 1H), 2.20 (d, J = 7.2 Hz, 2H), 2.05-2.00 (m, 4H), 1.97-1.78 (m, 7H), 1.75-1.61 (m, 5H), 1.30 (t, J = 7.2 Hz, 3H), 0.91 (d, J = 6.8 Hz, 6H). formate |

4-Chloro-5-methylpyrimidine was replaced with the starting materials in the following table to obtain the corresponding compounds in the following table by the method of Example 31.

| No | starting materials | structures | HNMR |
|---|---|---|---|
| 272 | 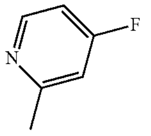 | 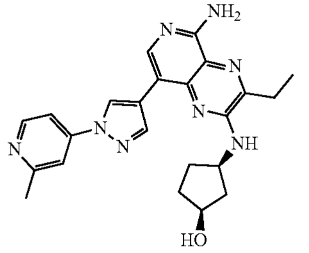 [SMILES: CCc1nc2c(N)ncc(-c3cnn(-c4ccnc(C)c4)c3)c2nc1N[C@@H]1CC[C@H](O)C1] | $^1$H NMR (400 MHz, DMSO-$d_6$) δ 9.21 (s, 1H), 8.55-8.49 (m, 2H), 8.23 (s, 1H), 8.14 (brs, 1H), 7.72 (d, J = 2.0 Hz, 1H), 7.68-7.49 (m, 4H), 4.83-4.80 (m, 1H), 4.58-4.50 (m, 1H), 4.20 (s, 1H), 2.86 (q, J = 7.2 Hz, 2H), 2.54 (s, 3H), 2.37-2.26 (m, 1H), 2.07-2.04 (m, 1H), 1.95-1.62 (m, 4H), 1.33 (t, J = 7.2 Hz, 3H). formate |
| 304 | 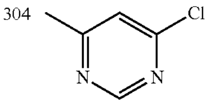 | 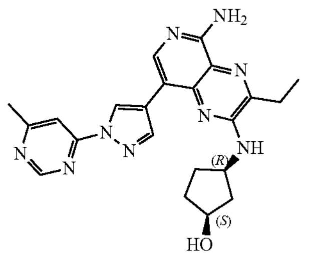 | $^1$H NMR (400 MHz, DMSO-$d_6$) δ 9.59 (s, 1H), 8.92 (s, 1H), 8.61 (s, 1H), 8.38 (s, 2H), 8.30 (s, 1H), 8.01 (d, J = 7.2 Hz, 1H), 7.88 (s, 1H), 4.92-4.70 (m, 1H), 4.60-4.50 (m, 1H), 4.35-4.26 (m, 1H), 2.90 (q, J = 7.2 Hz, 2H), 2.58 (s, 3H), 2.46-2.40 (m, 1H), 2.21-2.12 (m, 1H), 1.99-1.87 (m, 2H), 1.78-1.68 (m, 2H), 1.35 (t, J = 7.2 Hz, 3H). |
| 330 | 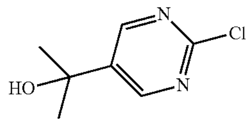 | 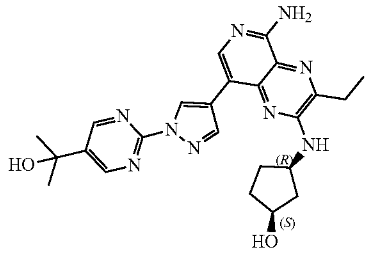 | $^1$H NMR (400 MHz, DMSO-$d_6$) δ 9.53 (s, 1H), 8.88 (s, 2H), 8.48 (s, 1H), 8.40 (s, 1H), 8.17 (brs, 1H), 7.22 (d, J = 7.2 Hz, 1H), 6.55 (brs, 2H), 5.48 (s, 1H), 4.61-4.51 (m, 1H), 4.33-4.27 (m, 1H), 2.83 (q, J = 7.2 Hz, 2H), 2.47-2.41 (m, 1H), 2.24-2.14 (m, 1H), 1.97-1.85 (m, 2H), 1.77-1.65 (m, 2H), 1.53 (s, 6H), 1.32 (t, J = 7.2 Hz, 3H). formate |
| 309 | 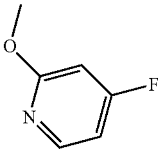 | 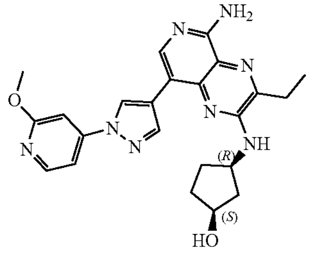 | $^1$H NMR (400 MHz, DMSO-$d_6$) δ 9.17 (s, 1H), 8.52 (s, 1H), 8.31 (s, 1H), 8.25 (d, J = 5.6 Hz, 1H), 8.14 (brs, 1H), 7.49-7.47 (m, 1H), 7.25 (d, J = 7.2 Hz, 1H), 7.19 (d, J = 1.6 Hz, 1H), 6.74 (s, 2H), 4.80 (s, 1H), 4.56-4.52 (m, 1H), 4.23-4.20 (m, 1H), 3.92 (s, 3H), 2.85-2.82 (m, 2H), 2.32-2.29 (m, 1H), 2.11-2.03 (m, 1H), 1.85-1.79 (m, 2H), 1.70-1.65 (m, 2H), 1.32 (t, J = 7.2 Hz, 3H). formate |

4-Chloro-5-methylpyrimidine was replaced with the starting materials in the following table to obtain the borate intermediate by the method of step 1 in Example 31. Then the borate intermediate was reacted with compound 151 according to the method of step 2 in Example 2 to obtain the corresponding compounds in the following table.

| No | starting materials | structures | HNMR |
|---|---|---|---|
| 205 | 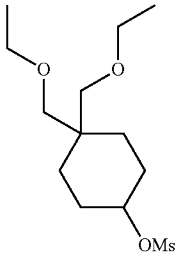 [SMILES: CCOCC1(COCC)CCC(OS(C)(=O)=O)CC1] | 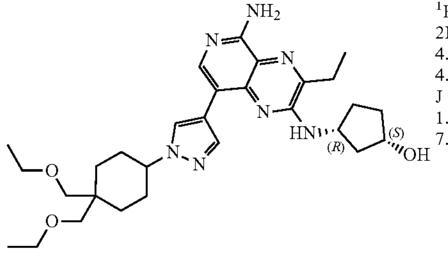 | $^1$H NMR (400 MHz, DMSO-$d_6$) δ 8.42 (s, 1H), 8.19 (s, 2H), 8.02 (s, 1H), 7.08 (d, J = 7.2 Hz, 1H), 6.36 (brs, 2H), 4.81 (s, 1H), 4.51-4.48 (m, 1H), 4.21-4.18 (m, 1H), 4.15-4.07 (m, 1H), 3.44-3.35(m, 6H), 3.17 (s, 2H), 2.80 (q, J = 7.2 Hz, 2H), 2.34-2.26 (m, 1H), 2.10-1.61 (m, 11H), 1.47-1.37 (m, 2H), 1.30 (t, J = 7.2 Hz, 3H), 1.12 (td, J = 7.2, 1.4 Hz, 6H). formate |

-continued

| No | starting materials | structures | HNMR |
|---|---|---|---|
| 344 | 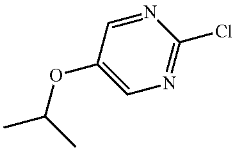 | 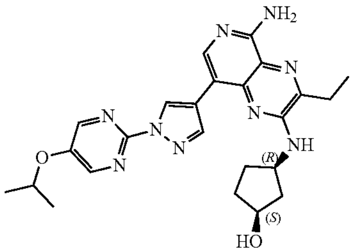 | $^1$H NMR (400 MHz, DMSO-$d_6$) δ 9.43 (s, 1H), 8.56 (s, 2H), 8.42 (s, 1H), 8.37 (s, 1H), 8.16 (brs, 1H), 7.20 (d, J = 8.0 Hz, 1H), 6.51 (brs, 2H), 4.86-4.80 (m, 1H), 4.55-4.50 (m, 1H), 4.30-4.26 (m, 1H), 2.83 (q, J = 7.2 Hz, 2H), 2.45-2.40 (m, 1H), 2.19-2.11 (m, 1H), 1.92-1.82 (m, 2H), 1.72-1.61 (m, 2H), 1.35-1.30 (m, 9H). formate |
| 354 | 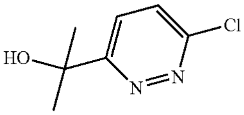 | 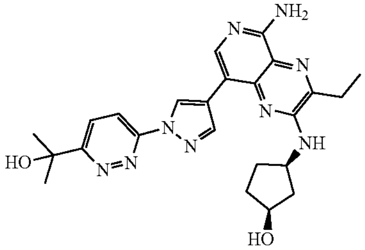 [SMILES: CCc1nc2c(N)ncc(-c3cnn(-c4ccc(C(C)(C)O)nn4)c3)c2nc1N[C@@H]1CC[C@H](O)C1] | $^1$H NMR (400 MHz, DMSO-$d_6$) δ 9.64 (s, 1H), 8.57 (s, 1H), 8.40 (s, 1H), 8.22 (d, J = 9.2 Hz, 1H), 8.14 (s, 1.1H), 8.08 (d, J = 9.2 Hz, 1H), 7.23 (d, J = 7.0 Hz, 1H), 6.57 (s, 2H), 5.56 (s, 1H), 4.72 (s, 1H), 4.57-4.51 (m, 1H), 4.27 (d, J = 4.4 Hz, 1H), 2.86-2.81 (m, 2H), 2.42-2.37 (m, 1H), 2.18-2.12 (m, 1H), 2.03-1.82 (m, 2H), 1.76-1.63 (m, 2H), 1.58 (s, 6H), 1.32 (t, J = 7.2 Hz, 3H). formate |
| 336 | 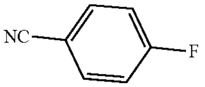 | 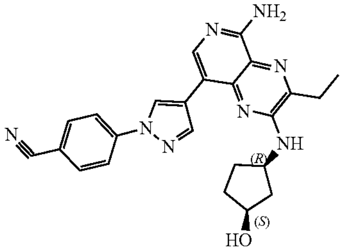 | $^1$H NMR (400 MHz, DMSO-$d_6$) δ 9.17 (s, 1H), 8.54 (s, 1H), 8.34 (s, 1H), 8.05-7.98 (m, 4H), 7.16 (d, J = 7.2 Hz, 1H), 6.54 (brs, 2H), 4.80 (d, J = 3.6 Hz, 1H), 4.58-4.48 (m, 1H), 4.25-4.18 (m, 1H), 2.82 (q, J = 7.2 Hz, 2H), 2.35-2.28 (m, 1H), 2.12-2.02 (m, 1H), 1.90-1.78 (m, 2H), 1.72-1.63 (m, 2H), 1.32 (t, J = 7.2 Hz, 3H). |
| 334 | 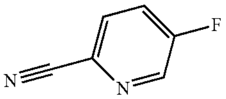 | 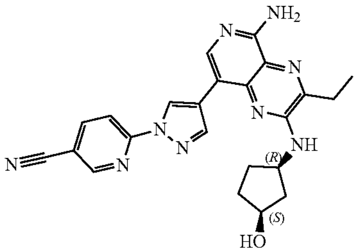 | $^1$H NMR (400 MHz, DMSO-$d_6$) δ 9.28 (d, J = 2.0 Hz, 1H), 9.24 (s, 1H), 8.62 (s, 1H), 8.45-8.43 (m, 1H), 8.32 (s, 1H), 8.22 (d, J = 8.0 Hz, 1H), 7.25 (d, J = 4.0 Hz, 1H), 6.75 (s, 2H), 4.80 (d, J = 4.0 Hz, 1H), 4.58-4.53 (m, 1H), 4.23-4.18 (m, 1H), 2.86-2.80 (m, 2H), 2.32-2.26 (m, 1H), 2.08-2.04 (m, 1H), 1.88-1.78 (m, 2H), 1.70-1.65 (m, 2H), 1.34-1.30 (m, 3H). |
| 282 | 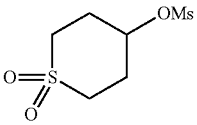 [SMILES: CS(=O)(=O)OC1CCS(=O)(=O)CC1] | 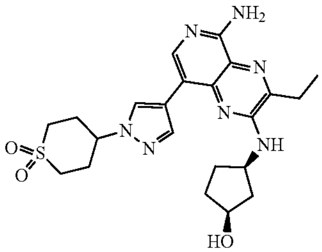 [SMILES: CCc1nc2c(N)ncc(-c3cnn(C4CCS(=O)(=O)CC4)c3)c2nc1N[C@@H]1CC[C@H](O)C1] | $^1$H NMR (400 MHz, DMSO-$d_6$)) δ 8.43 (s, 1H), 8.23 (d, J = 12.0 Hz, 2H), 8.11 (brs, 1H), 7.09 (d, J = 7.2 Hz, 1H), 6.39 (brs, 2H), 4.69-4.56 (m, 1H), 4.47 (d, J = 6.4 Hz, 1H), 4.34-4.16 (m, 1H), 3.49-3.42 (m, 3H), 3.22 (d, J = 12.0 Hz, 2H), 2.83-2.77 (m, 2H), 2.41-2.36 (m, 4H), 2.28-2.22 (m, 1H), 2.10-1.99 (m, 1H), 1.90-1.79 (m, 2H), 1.68-1.64 (m, 2H), 1.30 (t, J = 7.2 Hz, 3H). formate |
| 294 | 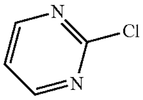 | 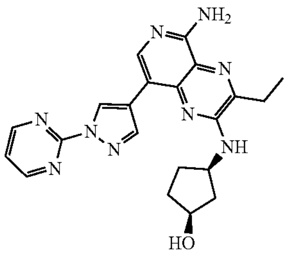 [SMILES: CCc1nc2c(N)ncc(-c3cnn(-c4ncccn4)c3)c2nc1N[C@@H]1CC[C@H](O)C1] | $^1$H NMR (400 MHz, DMSO-$d_6$) δ 9.56 (s, 1H), 8.85 (d, J = 4.8 Hz, 2H), 8.50 (s, 1H), 8.40 (s, 1H), 8.23 (brs, 1H), 7.45 (t, J = 4.8 Hz, 1H), 7.23 (d, J = 7.2 Hz, 1H), 6.54 (s, 2H), 4.58-4.52 (m, 1H), 4.230-4.26 (m, 1H), 2.86-2.80 (m, 2H), 2.41 (s, 1H), 2.20-2.14 (m, 1H), 1.891-1.84 (m, 2H), 1.74-1.63 (m, 2H), 1.32 (t, J = 7.2 Hz, 3H). formate |

-continued

| No | starting materials | structures | HNMR |
|---|---|---|---|
| 274 | 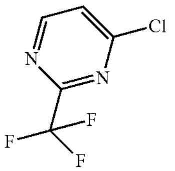 | 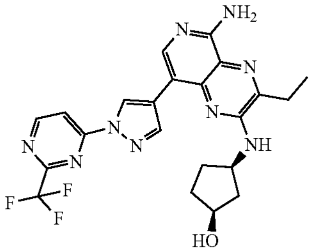 [SMILES: CCc1nc2c(N)ncc(-c3cnn(-c4ccnc(C(F)(F)F)n4)c3)c2nc1N[C@@H]1CC[C@H](O)C1] | $^1$H NMR (400 MHz, DMSO-$d_6$) δ 9.56 (s, 1H), 9.05 (d, J = 5.6 Hz, 1H), 8.72 (s, 1H), 8.48 (s, 1H), 8.19 (d, J = 5.6 Hz, 1H), 8.15 (brs, 1H), 7.10 (d, J = 7.2 Hz, 1H), 6.65 (brs, 2H), 4.65-4.58 (m, 1H), 4.28-4.22 (m, 1H), 2.82 (q, J = 7.2 Hz, 2H), 2.29-2.11 (m, 3H), 1.98-1.89 (m, 1H), 1.85-1.70 (m, 3H), 1.33 (t, J = 7.2 Hz, 3H). formate |
| 300 | 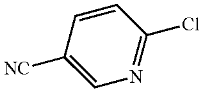 | 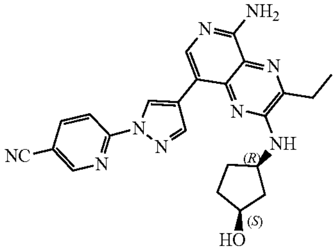 | $^1$H NMR (400 MHz, DMSO-$d_6$) δ 9.57 (s, 1H), 8.95-8.92 (m, 1H), 8.60 (s, 1H), 8.49-8.45 (m, 1H), 8.34 (s, 1H), 8.14 (brs, 1H), 8.11-8.08 (m, 1H), 7.71-7.65 (m, 1H), 7.62-7.40 (m, 2H), 4.85-4.81 (m, 1H), 4.58-4.50 (m, 1H), 4.34-4.27 (m, 1H), 2.86 (q, J = 7.2 Hz, 2H), 2.45-2.38 (m, 1H), 2.21-2.11 (m, 1H), 1.98-1.86 (m, 2H), 1.77-1.65 (m, 2H), 1.33 (t, J = 7.2 Hz, 3H). formate |
| 339 | 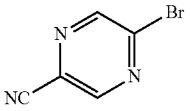 | 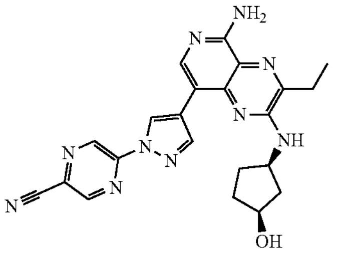 [SMILES: CCc1nc2c(N)ncc(-c3cnn(-c4cnc(C#N)cn4)c3)c2nc1N[C@@H]1CC[C@H](O)C1] | $^1$H NMR (400 MHz, DMSO-$d_6$) δ 9.53 (s, 1H), 9.34 (s, 1H), 9.07 (s, 1H), 8.72 (s, 1H), 8.46 (s, 1H), 7.26 (d, J = 7.2 Hz, 1H), 6.64 (brs, 2H), 4.79 (d, J = 4.0 Hz, 1H), 4.51-4.48 (m, 1H), 4.31-4.24 (m, 1H), 2.83 (q, J = 7.2 Hz, 2H), 2.40-2.36 (m, 1H), 2.19-2.11 (m, 1H), 1.91 ( m, 2H), 1.70-1.66 (m, 2H), 1.32 (t, J = 7.2 Hz, 3H). |
| 352 | 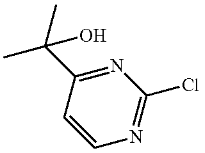 | 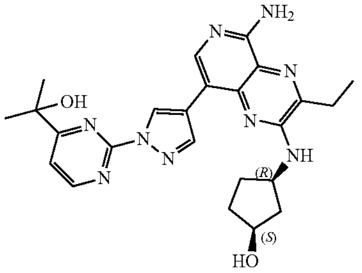 | $^1$H NMR (400 MHz, DMSO-$d_6$) δ 9.45 (s, 1H), 8.80 (d, J = 5.2 Hz, 1H), 8.48 (s, 1H), 8.39 (s, 1H), 8.15 (brs, 1H), 7.63 (d, J = 5.2 Hz, 1H), 7.13 (d, J = 6.8 Hz, 1H), 6.57 (brs, 2H), 5.56 (s, 1H), 4.95-4.70 (m, 1H), 4.63-4.53 (m, 1H), 4.29-4.22 (m, 1H), 2.82 (q, J = 7.2 Hz, 2H), 2.34-2.27 (m, 1H), 2.18-2.09 (m, 1H), 1.93-1.78 (m, 2H), 1.76-1.66 (m, 2H), 1.50 (s, 6H), 1.32 (t, J = 7.2 Hz, 3H). formate |

2-Methyl-5-bromopyridine was replaced with the starting materials in the following table to obtain the borate intermediates by the method of Example 2. Then the borate intermediates were reacted with intermediate D according to the method of step 2 and 3 in Example 31 to obtain the corresponding compounds in the following table.

| No | starting materials | structures | HNMR |
|---|---|---|---|
| 273 | 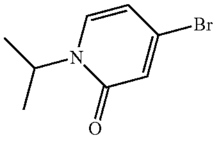 | 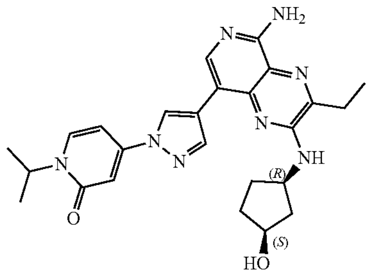 | $^1$H NMR (400 MHz, DMSO-$d_6$) δ 9.09 (s, 1H), 8.53 (s, 1H), 8.33 (s, 1H), 8.16 (brs, 1H), 7.90 (d, J = 7.6 Hz, 1H), 7.17 (d, J = 7.2 Hz, 1H), 6.91-6.88 (m, 1H), 6.67 (d, J = 2.4 Hz, 1H), 6.56 (brs, 2H), 5.09-5.04 (m, 1H), 4.55-4.50 (m, 1H), 4.27-4.22 (m, 1H), 2.84-2.79 (m, 2H), 2.33-2.28 (m, 1H), 2.11-2.02 (m, 1H), 1.92-1.81 (m, 2H), 1.73-1.64 (m, 2H), 1.31 (t, J = 6.8 Hz, 9H). formate |

-continued

| No | starting materials | structures | HNMR |
|---|---|---|---|
| 296 | 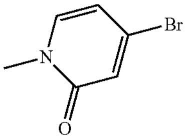 | 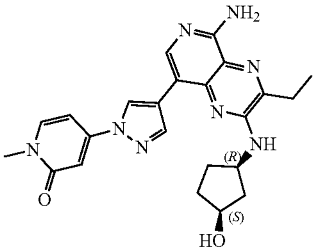 | $^1$H NMR (400 MHz, DMSO-$d_6$) δ 9.09 (s, 1H), 8.53 (s, 1H), 8.33 (s, 1H), 8.18 (brs, 1H), 7.87 (d, J = 8.0 Hz, 1H), 7.19 (d, J = 8.0 Hz, 1H), 6.86-6.84 (m, 1H), 6.70 (d, J = 2.4 Hz, 1H), 6.56 (brs, 2H), 4.81 (s, 1H), 4.55-4.50 (m, 1H), 4.25-4.21 (m, 1H), 3.45 (s, 3H), 2.84-2.79 (m, 2H), 2.32-2.28 (m, 1H), 2.08-2.04 (m, 1H), 1.88-1.81 (m, 2H), 1.70-1.63 (m, 2H), 1.33-1.29 (m, 3H). formate |
| 291 | 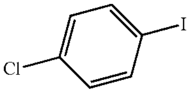 | 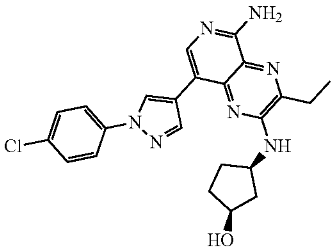 [SMILES: CCc1nc2c(N)ncc(-c3cnn(-c4ccc(Cl)cc4)c3)c2nc1N[C@@H]1CC[C@H](O)C1] | $^1$H NMR (400 MHz, DMSO-$d_6$) δ 9.06 (s, 1H), 8.45 (s, 1H), 8.33 (s, 1H), 8.20 (brs, 1H), 7.89-7.80 (m, 2H), 7.65-7.54 (m, 2H), 7.16 (d, J = 7.2 Hz, 1H), 6.50 (brs, 2H), 4.81 (s, 1H), 4.54-4.50 (m, 1H), 4.21 (d, J = 4.4 Hz, 1H), 2.84-2.79 (m, 2H), 2.32-2.27 (m, 1H), 2.09-2.05 (m, 1H), 1.891-1.76 (m, 2H), 1.70-1.65 (m, 2H), 1.32 (t, J = 7.2 Hz, 3H). formate |
| 277 | 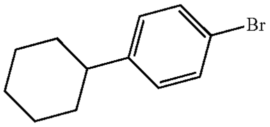 [SMILES: Brc1ccc(C2CCCCC2)cc1] | 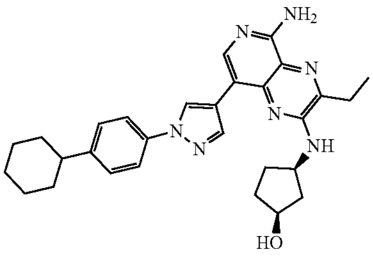 [SMILES: CCc1nc2c(N)ncc(-c3cnn(-c4ccc(C5CCCCC5)cc4)c3)c2nc1N[C@@H]1CC[C@H](O)C1] | $^1$H NMR (400 MHz, DMSO-$d_6$) δ 9.01 (s, 1H), 8.35 (d, J = 22.4 Hz, 3H), 7.71 (d, J = 8.4 Hz, 2H), 7.35 (d, J = 8.4 Hz, 2H), 7.16 (d, J = 7.2 Hz, 1H), 6.46 (s, 2H), 4.57-4.52 (m, 1H), 4.24-4.20 (m, 1H), 3.88-3.69 (m, 2H), 2.85-2.79 (m, 2H), 2.12-2.06 (m, 1H), 1.83-1.78 (m, 4H), 1.74-1.65 (m, 3H), 1.49-1.37 (m, 4H), 1.32 (t, J = 7.2 Hz, 3H), 1.27-1.23 (m, 2H), 0.98 (d, J = 6.4 Hz, 1H). formate |
| 279 | 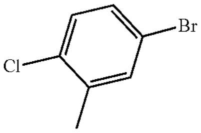 | 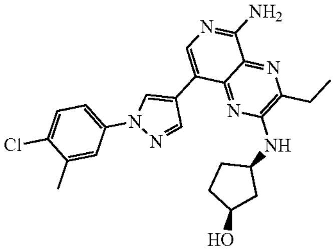 [SMILES: CCc1nc2c(N)ncc(-c3cnn(-c4ccc(Cl)c(C)c4)c3)c2nc1N[C@@H]1CC[C@H](O)C1] | $^1$H NMR (400 MHz, DMSO-$d_6$) δ 9.05 (s, 1H), 8.43 (s, 1H), 8.32 (s, 1H), 8.17 (brs, 1H), 7.86 (d, J = 2.4 Hz, 1H), 7.69-7.67 (m, 1H), 7.54 (d, J = 8.8 Hz, 1H), 7.16 (d, J = 7.2 Hz, 1H), 6.50 (brs, 2H), 4.57-4.52 (m, 1H), 4.23-4.17 (m, 1H), 2.84-2.79 (m, 2H), 2.42 (s, 3H), 2.33-2.28 (m, 1H), 2.12-2.04 (m, 1H), 1.83-1.75 (m, 2H), 1.71-1.64 (m, 2H), 1.31 (t, J = 7.2 Hz, 3H). formate |
| 276 | 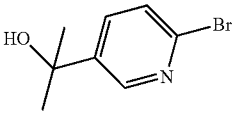 | 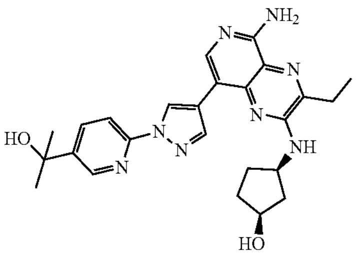 [SMILES: CCc1nc2c(N)ncc(-c3cnn(-c4ccc(C(C)(C)O)cn4)c3)c2nc1N[C@@H]1CC[C@H](O)C1] | $^1$H NMR (400 MHz, DMSO-$d_6$) $^1$H NMR (400 MHz, DMSO) δ 9.50 (s, 1H), 8.52 (s, 1H), 8.42 (s, 1H), 8.39 (s, 1H), 8.02 (dd, J = 8.6, 2.4 Hz, 1H), 7.89 (d, J = 8.5 Hz, 1H), 7.21 (d, J = 7.0 Hz, 1H), 6.50 (brs, 2H), 5.30 (s, 1H), 4.79-4.77 (m, 1H), 4.57-4.52 (m, 1H), 4.30-4.25 (m, 1H), 2.83 (q, J = 7.2Hz, 2H), 2.47-2.40 (m, 1H), 2.24-2.17 (m, 1H), 1.90 (m, 2H), 1.78-1.64 (m, 2H), 1.50 (s, 6H), 1.32 (t, J = 7.3 Hz, 3H). |
| 301 | 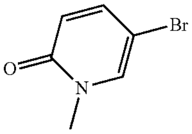 | 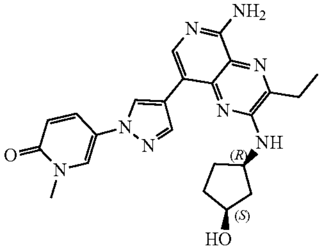 | $^1$H NMR (400 MHz, DMSO-$d_6$) δ 8.79 (s, 1H), 8.38 (s, 1H), 8.32-8.25 (m, 2H), 7.95 (dd, J = 9.7, 2.8 Hz, 1H), 7.15 (d, J = 7.2Hz, 1H), 6.55 (d, J = 9.6 Hz, 1H), 6.47 (brs, 2H), 4.80 (s, 1H), 4.51-4.48 (m, 2H), 4.19-4.14 (m, 1H), 3.52 (s, 3H), 2.81 (q, J = 7.2 Hz, 2H), 2.28-2.25 (m, 1H), 2.05-2.02 (m, 1H), 1.89-1.59 (m, 4H), 1.31 (t, J = 7.2 Hz, 3H). |

4-Chloro-2-methylpyrimidine was replaced with the starting material in the following table to obtain intermediate 335-A by the method of Step 1 in Example 23. Then intermediate 335-A was reacted with intermediate D according to the method of Step 2 and 3 in Example 31 to obtain the corresponding compound in the following table.

| No | starting materials | intermediate 335-A | structure | HNMR |
|---|---|---|---|---|
| 335 | 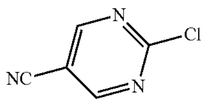 | 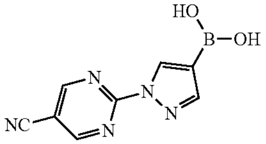 [SMILES: N#Cc1cnc(-n2cc(B(O)O)cn2)nc1] | 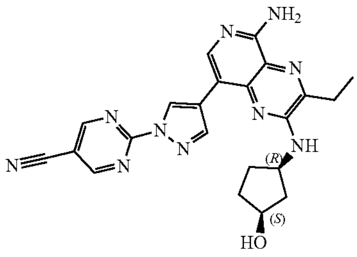 | $^1$H NMR (400 MHz, DMSO-$d_6$) δ 9.59-9.57 (m, 1H), 9.33-9.28 (m, 2H), 8.65 (s, 1H), 8.44 (s, 1H), 8.17 (brs, 1H), 7.24 (d, J = 7.2 Hz, 1H), 6.62 (brs, 2H), 4.57-4.48 (m, 1H), 4.33-4.27 (m, 1H), 2.83 (q, J = 7.2 Hz, 2H), 2.45-2.38 (m, 1H), 2.22-2.12 (m, 1H), 1.96-1.84 (m, 2H), 1.75-1.64 (m, 2H), 1.32 (t, J = 7.2 Hz, 3H). |

4-Chloro-2-methylpyrimidine was replaced with the starting material in the following table to obtain intermediate 346-A by the method of Step 1 in Example 23. Then intermediate 346-A was used to obtain the corresponding compound in the following table by the method of Step 3 and 4 in Example 7.

| No | register No # starting material | intermediate 346-A | structures | HNMR |
|---|---|---|---|---|
| 268 | 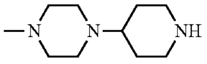 | 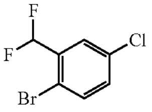 [SMILES: FC(F)c1cc(Cl)ccc1Br] | 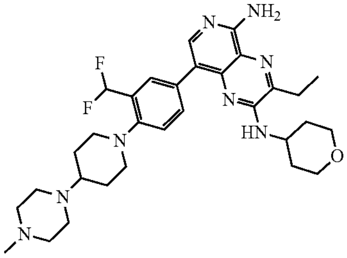 [SMILES: CCc1nc2c(N)ncc(-c3ccc(N4CCC(N5CCN(C)CC5)CC4)c(C(F)F)c3)c2nc1NC1CCOCC1] | $^1$H NMR (400 MHz, DMSO-$d_6$) δ 8.17 (brs, 3H), 8.02 (d, J = 1.6 Hz, 1H), 7.95 (s, 1H), 7.75-7.73 (m, 1H), 7.30 (d, J = 8.4 Hz, 1.25H), 7.18 (s, 0.5H), 7.04-7.00 (m, 1.25H), 6.54 (brs, 2H), 4.22-4.14 (m, 1H), 3.88-3.84 (m, 2H), 3.30 (s, 2H), 3.08 (d, J = 11.6 Hz, 2H), 2.80-2.74 (m, 4H), 2.55-2.54 (m, 3H), 2.41-2.35 (m, 6H), 2.19 (s, 3H), 1.87-1.78 (m, 4H), 1.70-1.57 (m, 4H), 1.31 (t, J = 7.2 Hz, 3H). formate |

Example 32: 8-Bromo-3-ethyl-N2-(tetrahydro-2H-pyran-4-yl)pyridino[3,4-b]pyrazine-2, 5-diamine (Compound 2)

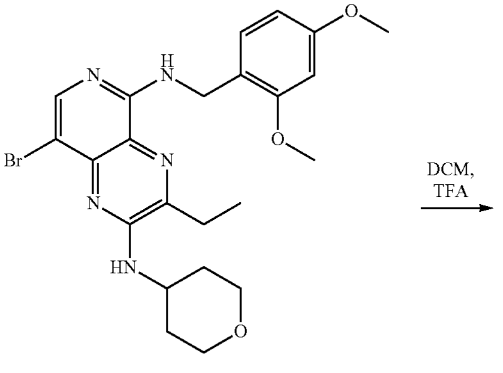

-continued

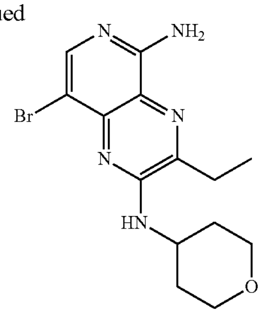

compound 2

8-Bromo-N5-(2,4-dimethoxybenzyl)-3-ethyl-N2-(tetrahydro-2H-pyran-4-yl)pyridino[3,4-b]pyrazin-2,5-diamine (1.0 g, 2.0 mmol) was used as starting material to obtain yellow solid compound 2 (650 mg, yield 93%) according to the method of Step 12 in Example 1. (ESI) m/z 352.0. $[M+H]^+$.

The starting materials in the following table was reacted with compound 2 according to the method of Example 23 to obtain the corresponding compounds in the following table.

| No | starting materials | structures | HNMR |
|---|---|---|---|
| 59 | 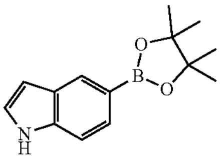 [SMILES: CC1(C)OB(c2ccc3[nH]ccc3c2)OC1(C)C] | 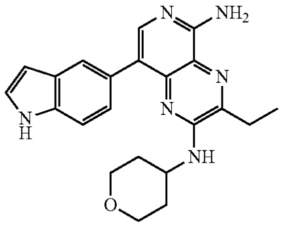 [SMILES: CCc1nc2c(N)ncc(-c3ccc4[nH]ccc4c3)c2nc1NC1CCOCC1] | $^1$H NMR (400 MHz, DMSO-$d_6$) δ 11.02 (brs, 1H), 7.96 (s, 1H), 7.88 (s, 1H), 7.45-7.42 (m, 2H), 7.34-7.32 (m, 1H), 6.99 (d, J = 8.0Hz, 1H), 6.42-6.38 (m, 3H), 4.15-3.99 (m, 1H), 3.93-3.90 (m, 2H), 3.30-3.24 (m, 2H), 2.82-2.79 (m, 2H), 1.95-1.85 (m, 2H), 1.67-1.57 (m, 2H), 1.34-1.30 (m, 3H). |
| 60 | 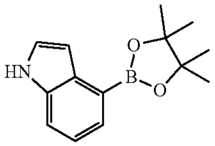 [SMILES: CC1(C)OB(c2cccc3[nH]ccc23)OC1(C)C] | 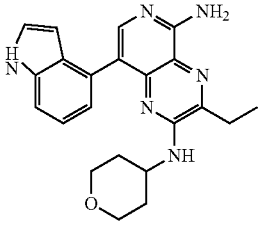 [SMILES: CCc1nc2c(N)ncc(-c3cccc4[nH]ccc34)c2nc1NC1CCOCC1] | $^1$H NMR (400 MHz, DMSO-$d_6$) δ 11.02 (brs, 1H), 8.02 (s, 1H), 7.33 (d, J = 8.0 Hz, 1H), 7.27 (t, J = 2.8 Hz, 1H), 7.17 (d, J = 6.4 Hz, 1H), 7.09 (t, J = 7.6 Hz, 1H), 6.92 (d, J = 7.2 Hz, 1H), 6.45 (brs, 2H), 6.25 (s, 1H), 3.93-3.86 (m, 1H), 3.82-3.78 (m, 2H), 3.04 (t, J = 11.2 Hz, 2H), 2.83-2.77 (m, 2H), 1.74 (d, J = 12.4 Hz, 2H), 1.56-1.46 (m, 2H), 1.31 (t, J = 7.2 Hz, 3H). |
| 280 | 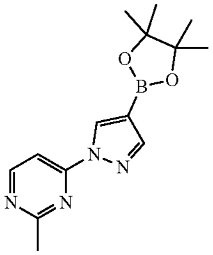 [SMILES: Cc1nccc(-n2cc(B3OC(C)(C)C(C)(C)O3)cn2)n1] | 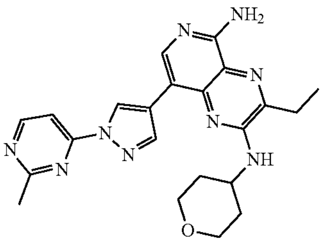 [SMILES: CCc1nc2c(N)ncc(-c3cnn(-c4ccnc(C)n4)c3)c2nc1NC1CCOCC1] | $^1$H NMR (400 MHz, DMSO-$d_6$) δ 9.29 (s, 1H), 8.75 (d, J = 8.0 Hz, 1H), 8.57 (s, 1H), 8.43 (s, 1H), 8.19 (brs, 1H), 7.79 (d, J = 4.0 Hz, 1H), 7.19 (d, J = 8.0 Hz, 1H), 6.60 (brs, 2H), 4.42-4.34 (m, 1H), 3.96 (d, J = 12.0 Hz, 2H), 3.69-3.64 (m, 2H), 2.88-2.83 (m, 2H), 2.69 (s, 3H), 2.01 (d, J = 8.0 Hz, 2H), 1.76-1.66 (m, 2H), 1.35-1.31 (m, 3H). formate |

Example 33:3-ethyl-8-(3-methoxy-4-(4-(8-methyl-3,8-diazabicyclo[3.2.1]octan-3-yl)piperidin-1-yl)phenyl)-N2-(tetrahydro-2H-pyran-4-yl)pyridino [3,4-b]pyrazin-2,5-diamine (Compound 293) and 8-(4-(4-(3,8-diazabicyclo[3.2.1]octane-3-yl)piperidin-1-yl)-3-methoxyphenyl)-3-ethyl-N2-(tetrahydro-2H-pyran-pyridin-4-yl)pyridino [3,4-b]pyrazine-2,5-diamine (Compound 319)

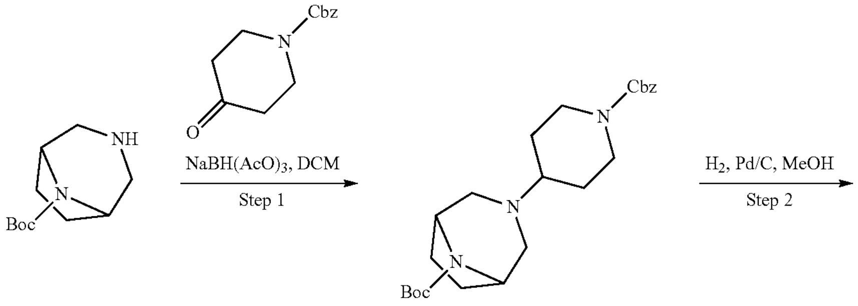

-continued
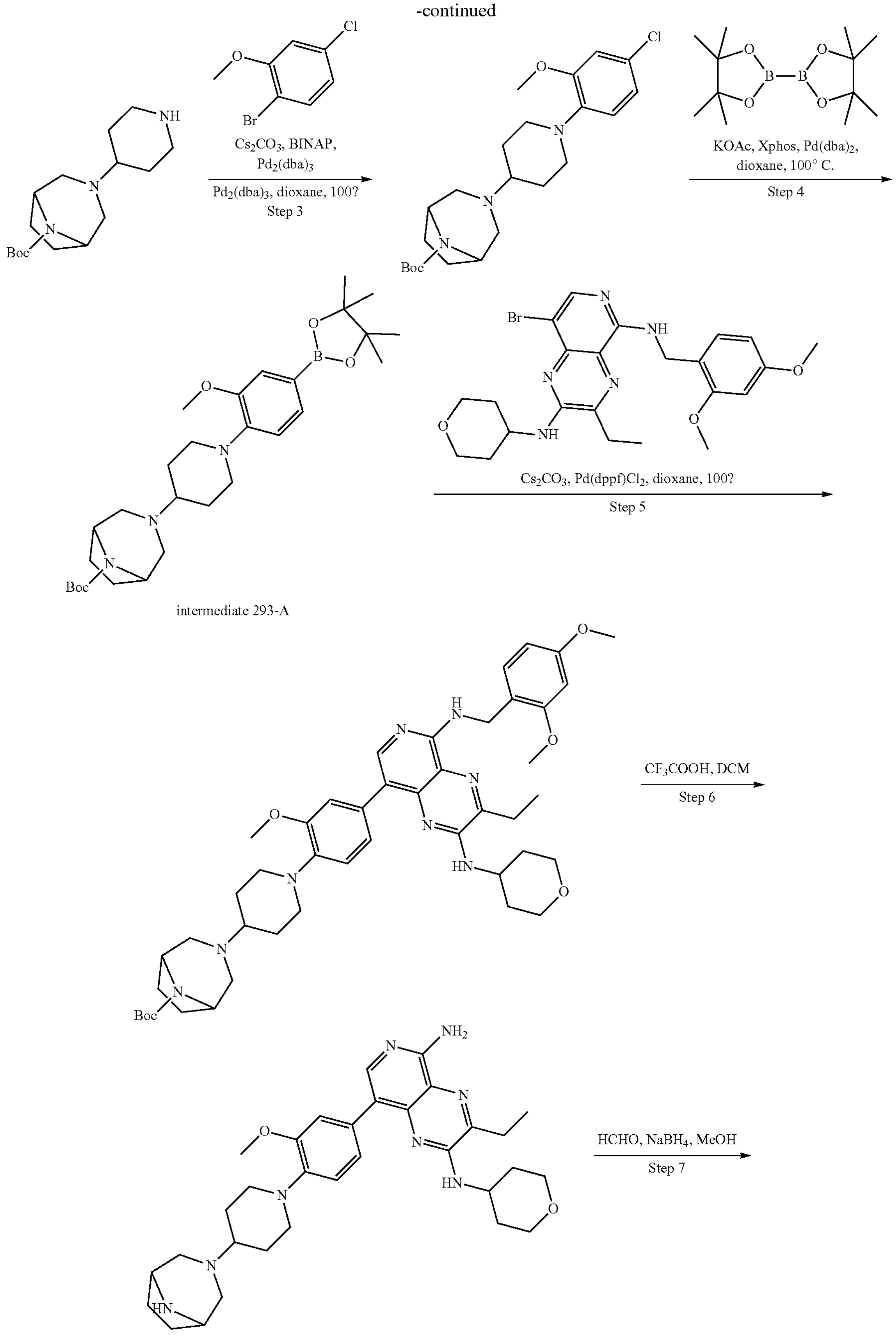
intermediate 293-A
compound 319

-continued

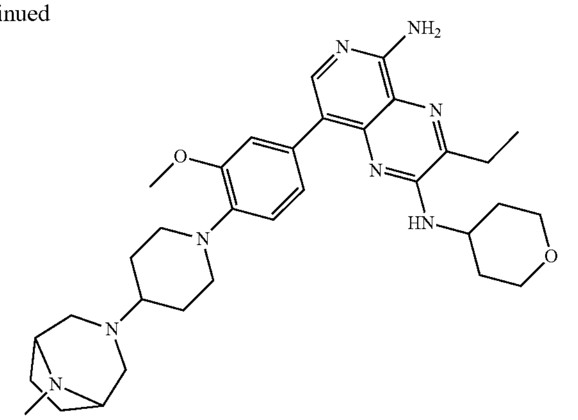

compound 293

Steps 1 and 2: Tert-butyl 3,8-diazabicyclo[3.2.1]octane-8-carboxylate (3.5 g, 0.016 mol) and benzyl 4-oxo-piperidin-1-carboxylate (5.7 g, 0.025 mol) were used as starting materials to obtain yellow oil (3 g, two-step yield 61%) by the methods of Step 1 and Step 2 of Example 1. (ESI) m/z 296.3 $[M+H]^+$.

Steps 3 and 4: Tert-butyl 3-(piperidin-4-yl)-3,8-diazabicyclo[3.2.1]octane-8-carboxylate was used as starting material to obtain brown oil intermediate 293-A (two-step yield 66%) by the methods of Step 1 and Step 2 of Example 7. (ESI) m/z 528.3. $[M+H]^+$.

Step 5 and 6: Intermediate 293-A was reacted with 8-bromo-N5-(2,4-dimethoxy benzyl)-3-ethyl-N2-(tetrahydro-2H-pyran-4-yl) pyridino [3,4-b]pyrazine-2,5-diamine according to the synthesis method of compound 8 suggested in Example 2 to obtain yellow solid compound 319 (two-step yield 35%). 1H NMR (400 MHz, DMSO-$d_6$) δ 8.31 (s, 2H), 7.92 (s, 1H), 7.22-7.18 (m, 2H), 7.01 (d, J=7.2 Hz, 1H), 6.89 (d, J=8.4 Hz, 1H), 6.45 (s, 2H), 4.17-4.07 (m, 1H), 3.92-3.88 (m, 2H), 3.81 (s, 3H), 3.77 (s, 2H), 3.41 (d, J=11.6 Hz, 3H), 3.27 (t, J=11.2 Hz, 3H), 2.83-2.74 (m, 4H), 2.60-2.54 (m, 2H), 2.32-2.29 (m, 1H), 1.88-1.75 (m, 8H), 1.66-1.54 (m, 4H), 1.31 (t, J=7.2 Hz, 3H). (ESI) m/z. 573.3 $[M+1]^+$.

Step 7: The solution of methanol (10 mL) containing compound 319 (100 mg, 0.17 mmol) and formaldehyde (8.0 mg, 0.27 mmol) was stirred at 25° C. for 10 minutes, and then sodium borohydride was added (20 mg, 0.52 mmol). The mixture was stirred at 25° C. for 30 minutes and concentrated under reduced pressure. The resulting residue was purified by silica gel chromatography column (dichloromethane/methanol=1:1) to obtain yellow solid compound 293 (40 mg, yield 39%). $^1H$ NMR (400 MHz, DMSO-$d_6$) δ 7.92 (s, 1H), 7.27-7.12 (m, 2H), 7.00 (d, J=7.2 Hz, 1H), 6.88 (d, J=8.0 Hz, 1H), 6.44 (brs, 2H), 4.19-4.01 (m, 1H), 3.92-3.88 (m, 2H), 3.88 (s, 3H), 3.39 (d, J=12.0 Hz, 2H), 3.30-3.22 (m, 2H), 3.10 (s, 2H), 2.83-2.78 (m, 2H), 2.66-2.54 (m, 4H), 2.38 (d, J=8.0 Hz, 2H), 2.22 (d, J=12.0 Hz, 4H), 1.87-1.77 (m, 6H), 1.70-1.50 (m, 6H), 1.31 (t, J=7.2 Hz, 3H). (ESI) m/z. 587.3 $[M+1]^+$.

Example 34: (1S, 3R)-3-((5-amino-3-ethyl-8-(3-methoxy-4-(1-(1-methylpiperidin-4-yl)-1H-pyrazol-4-yl) phenyl) pyridino [3,4-b] pyrazin-2-yl) amino) cyclopentan-1-ol (Compound 312)

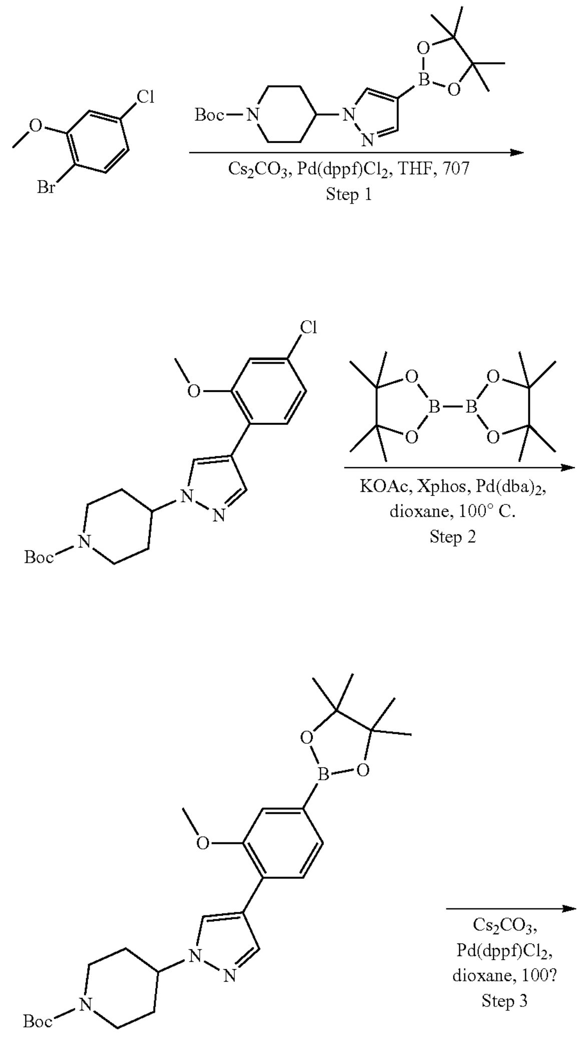

-continued

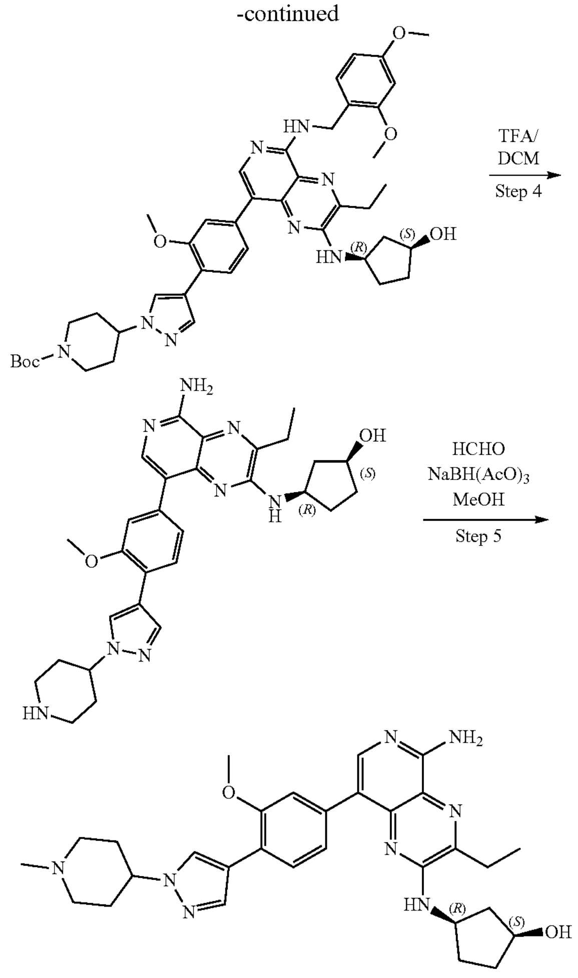

compound 312

Step 1: Cesium carbonate (5.18 g, 15.0 mmol) and Pd(dppf)$Cl_2$ (0.39 g, 0.50 mmol) were added to the tetrahydrofuran/water (50 mL) mixture containing 4-(4-(4, 4, 5, 5-tetramethyl-1, 3, 2-dioxoborane-2-yl)-1H-pyrazol-1-yl) piperidine-1-carboxylic acid tert-butyl ester (2.0 g, 5.0 mmol) and 1-bromo-4-chloro-2-methoxybenzene (1.8 g, of 7.0 mmol). This mixture was stirred at 70° C. for 1 hour under nitrogen protection. At the end of the reaction, the mixture was cooled to room temperature and water (20 mL) was added. The solution was extracted three times (10 mL×3) with ethyl acetate. The organic phases were combined, dried over anhydrous sodium sulfate, filtered, and the filtrate was concentrated under reduced pressure. The resulting residue was purified by silica gel chromatography column (petroleum ether/ethyl acetate=70%/30%) to obtain yellow oil (1.8 g, yield 83%). (ESI) m/z. 392.1 $[M+H]^+$.

Step 2 to Step 5: The product of Step 1 was reacted according to the method of Step 4 to Step 7 of Example 33 to obtain yellow solid compound 312 formate (four-step yield 1.3%). $^1$H NMR (400 MHz, DMSO-$d_6$) δ 8.18 (d, J=4.0 Hz, 3H), 8.00 (s, 1H), 7.94 (s, 1H), 7.60 (d, J=8.0 Hz, 1H), 7.43 (d, J=1.2 Hz, 1H), 7.31-7.29 (m, 1H), 7.05 (d, J=7.2 Hz, 1H), 6.53 (s, 2H), 4.44-4.39 (m, 1H), 4.20-4.09 (m, 2H), 3.91 (s, 3H), 2.89 (s, 2H), 2.79 (m, 2H), 2.24 (s, 3H), 2.19-1.98 (m, 7H), 1.96-1.91 (m, 1H), 1.84-1.54 (m, 5H), 1.31 (t, J=7.2 Hz, 3H). (ESI) m/z. 543.3. $[M+H]^+$.

Example 35: 3-ethyl-8-(3-methoxy-4-(3-methyl-4-(4-methylpiperazine-1-yl)piperidine-1-yl)phenyl)-N2-(tetrahydro-2H-pyran-4-yl)pyridino[3,4-b]pyrazine-2,5-diamine (Compound 287)

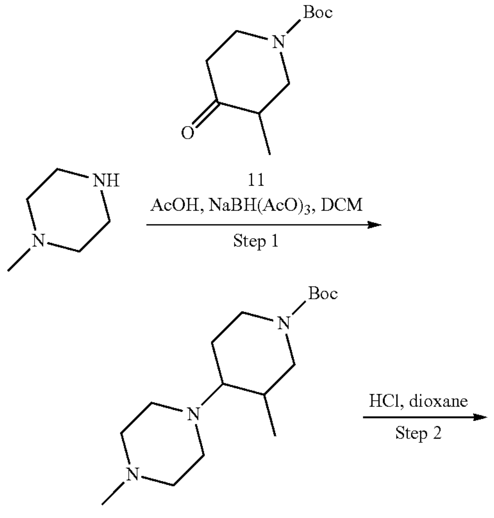

intermediate 267-A

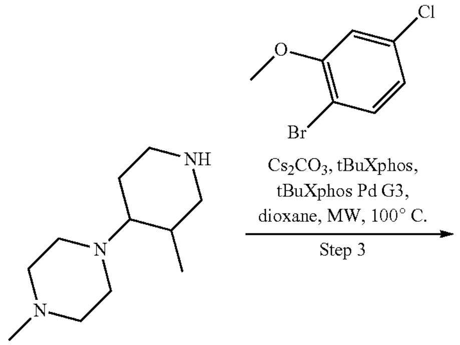

intermediate 267-B

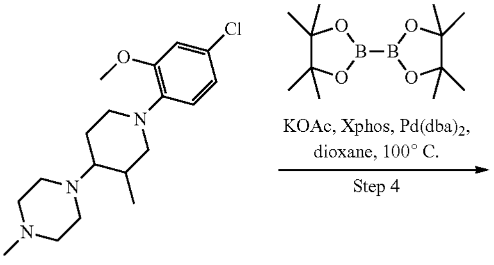

intermediate 267-C

-continued

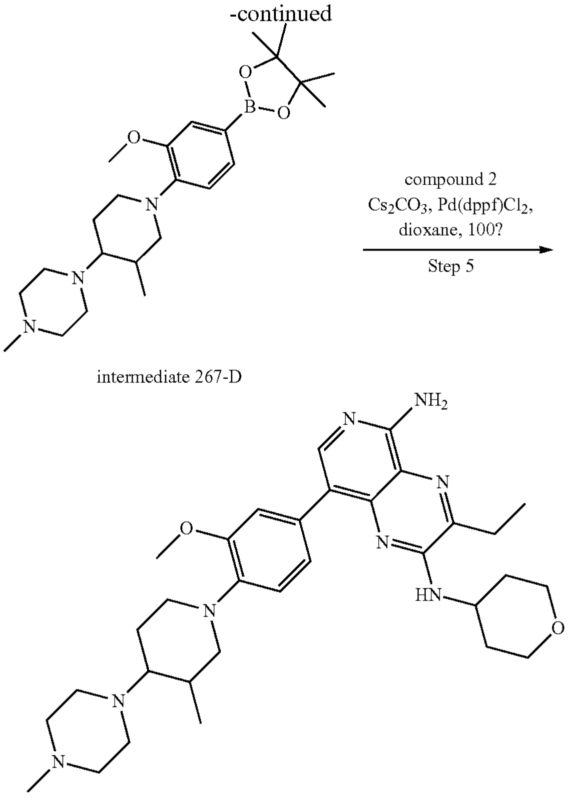

intermediate 267-D compound 267

Step 1:1-Methylpiperazine (1.5 g, 15 mmol) and N-Boc-3-methyl-4-piperidone (3.2 g, 15 mmol) were used as starting materials to obtain white solid intermediate 287-A (2.5 g, yield 53%) by the method of Step 2 of Example 6. (ESI) m/z. 298.3 $[M+1]^+$.

Step 2: Intermediate 287-A (2.5 g, 8.0 mmol) was used as starting material to obtain white solid intermediate 287-B (1.7 g, yield 87%) by the method of Step 4 of Example 7. (ESI) m/z. 198.3 $[M+1]^+$.

Step 3: Potassium tert-butanol (438 mg, 4.6 mmol), tBuXPhos Pd G3 (120 mg, 0.15 mmol) and tBuXPhos (129 mg, 0.30 mmol) were added to the mixture of 1,4-dioxane (10 mL) containing intermediate 287-B (300 mg, 1.5 mmol) and 1-bromo-4-chloro-2-methoxybenzene (336 mg, 1.5 mmol). This mixture was stirred at 100° C. for 1 hour under nitrogen atmosphere and microwave. At the end of the reaction, the mixture was cooled to room temperature and water (30 mL) was added. The solution was extracted three times (30 mL×3) with ethyl acetate. The organic phases were combined, dried over anhydrous sodium sulfate, filtered, and the filtrate was concentrated under reduced pressure. The resulting residue was purified by silica gel chromatography column (dichloromethane/methanol=70%:30%)) to obtain yellow oil intermediate 287-C (280 mg, yield 54%). (ESI) m/z 338.2. $[M+1]^+$.

Steps 4 and 5: Intermediate 287-C was reacted according to the method of Step 2 of Example 7 to obtain intermediate 287-D, then the intermediate 287-D was reacted with compound 2 to obtain yellow solid compound 287 formate according to the method of Step 2 of Example 2 (two-step yield 37%). $^1$H NR (400 MHz, DMSO-$d_6$) δ 8.14 (brs, 1H), 7.91 (s, 1H), 7.22-7.20 (m, 2H), 7.05 (d, J=7.2 Hz, 1H), 6.88-6.85 (m, 1H), 6.55 (s, 2H), 4.14-4.10 (m, 1H), 3.92-3.89 (m, 2H), 3.82 (s, 3H), 3.41-3.37 (m, 5H), 3.30-3.24 (m, 5H), 2.84-2.78 (m, 3H), 2.54-2.52 (m, 2H), 2.51 (s, 3H), 2.17 (s, 3H), 1.88-1.84 (m, 3H), 1.63-1.57 (m, 3H), 1.31 (t, J=7.2 Hz, 3H), 1.09 (d, J=6.8 Hz, 3H). (ESI) m/z. 575.3 $[M+1]^+$.

Example 36: (1S, 3R)-3-((5-amino-3-ethyl-8-(3-methoxy-4-(8-methyl-3,8-diazabicyclo[3.2.1]octyl-3-yl)phenyl)pyridino[3,4-b]pyrazine-2-yl)amino) cyclopentan-1-ol (Compound 286)

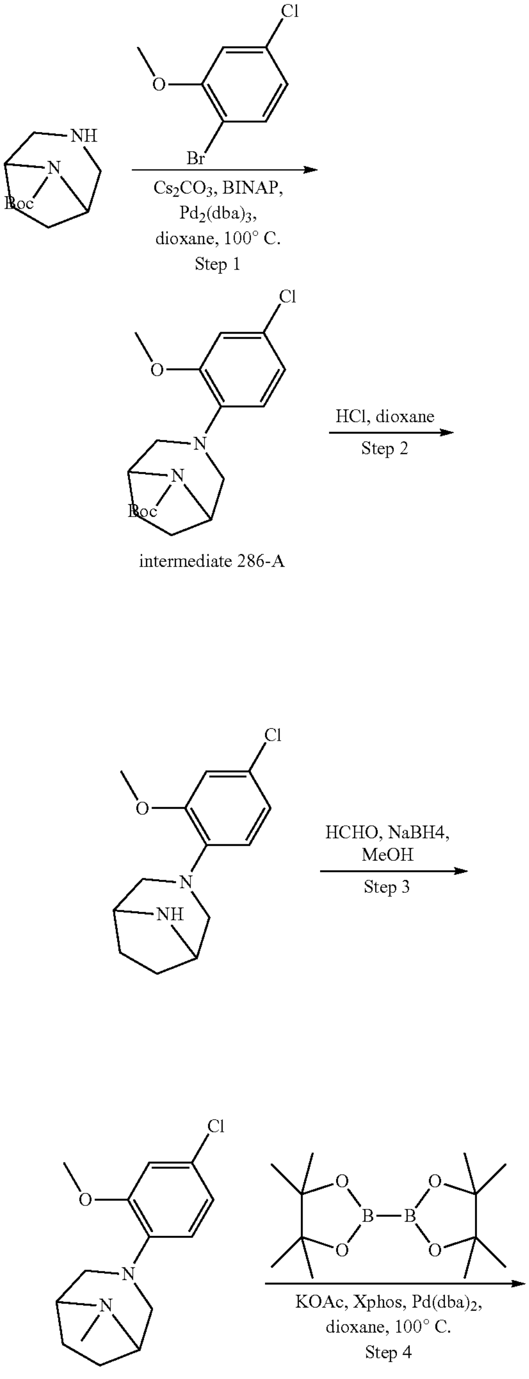

intermediate 286-A intermediate 286-C

-continued

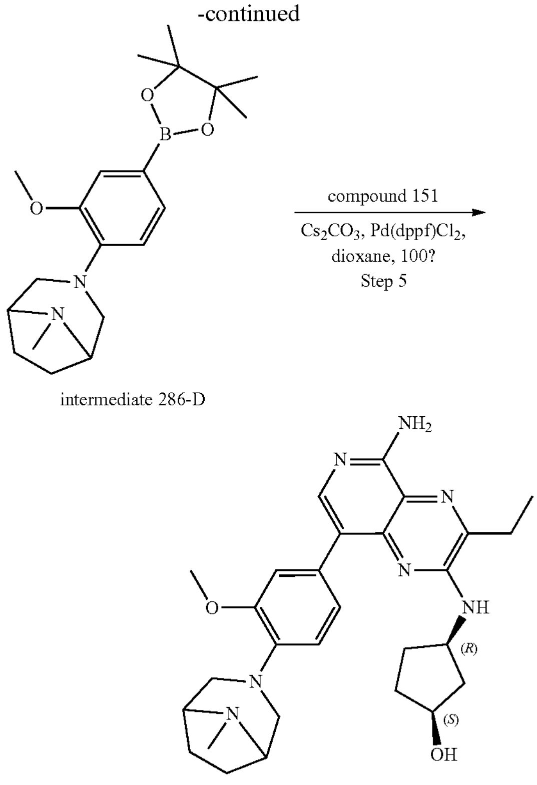

intermediate 286-D compound 286

Step 1: Tert-butyl 3, 8-diazabicyclo[3.2.1]octane-8-formate (1.1 g, 5.2 mmol) was used to obtain yellow oil intermediate 286-A (0.97 g, yield 50%) by the method of Step 1 of Example 7. (ESI) m/z. 353.3 $[M+1]^+$.

Step 2: Intermediate 286-A (970 mg, 2.7 mmol) was used as the starting material to obtain white solid intermediate 287-B (450 mg, yield 65%) according to the method of Step 4 of Example 7. (ESI) m/z. 253.1 $[M+1]^+$.

Step 3: Intermediate 286-B (450 mg, 1.8 mmol) was used as the starting material to obtain white solid intermediate 286-C (370 mg, yield 74%) according to the method of Step 7 of Example 33. (ESI) m/z 267.1. $[M+H]^+$.

Steps 4 and 5: Intermediate 286-C was used to obtain intermediate 286-D according to the method of Step 2 of Example 7, then intermediate 286-D was reacted with compound 151 according to the method of Step 2 of Example 2 to obtain yellow solid compound 286 (two-step yield 2.8%). 1H NMR (400 MHz, DMSO-$d_6$)) δ 7.90 (s, 1H), 7.32 (d, J=1.6 Hz, 1H), 7.19-7.16 (m, 1H), 7.00 (d, J=7.2 Hz, 1H), 6.81 (d, J=8.4 Hz, 1H), 6.41 (s, 2H), 4.75 (d, J=3.6 Hz, 1H), 4.42-4.37 (m, 1H), 4.13 (d, J=4.4 Hz, 1H), 3.81 (s, 3H), 3.21-3.06 (m, 4H), 2.85-2.72 (m, 4H), 2.21 (s, 3H), 2.16-2.11 (m, 1H), 1.96-1.81 (m, 5H), 1.77-1.54 (m, 4H), 1.30 (t, J=7.2 Hz, 3H). (ESI) m/z. 504.3. $[M+H]^+$.

Example 37:3-ethyl-8-(3-methoxy-4-(4-(3-methyl-3, 8-diazabicyclo[3.2.1]octyl-8-yl)piperidin-1-yl)phenyl)-N2-(tetrahydro-2H-pyran-4-yl)pyridino[3,4-b] pyrazine-2,5-diamine (Compound 327)

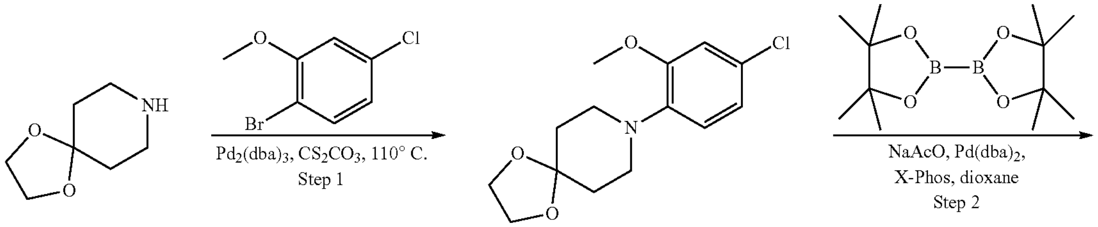

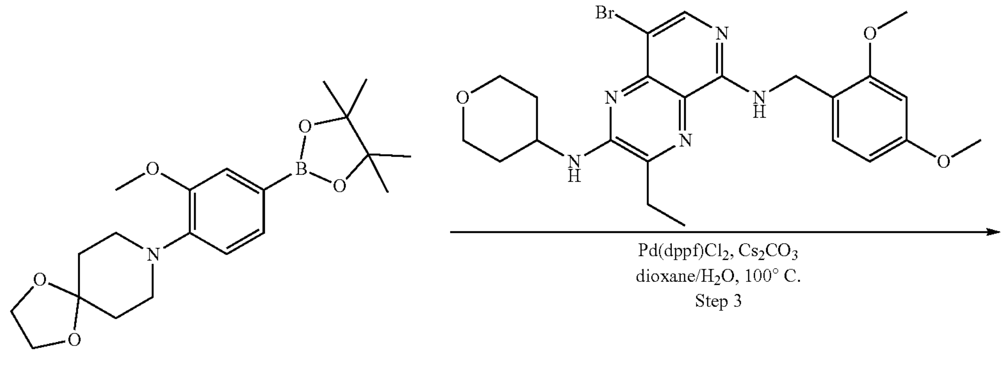

-continued

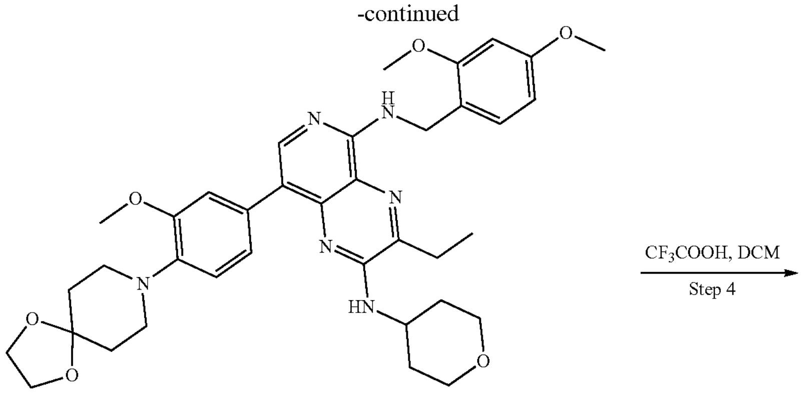

intermediate 327-A

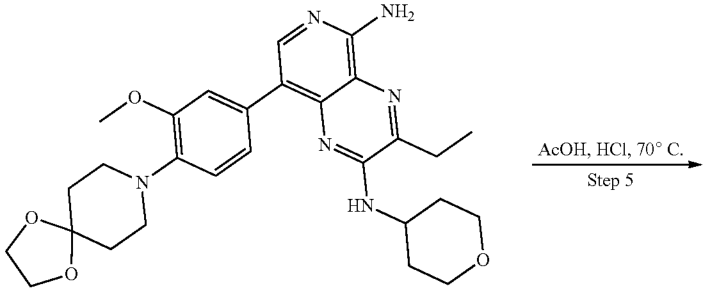

intermediate 327-B

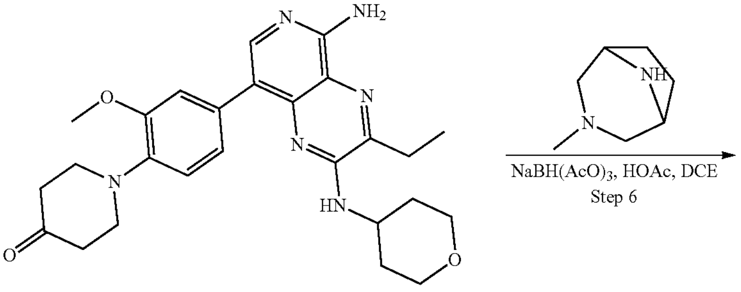

intermediate L

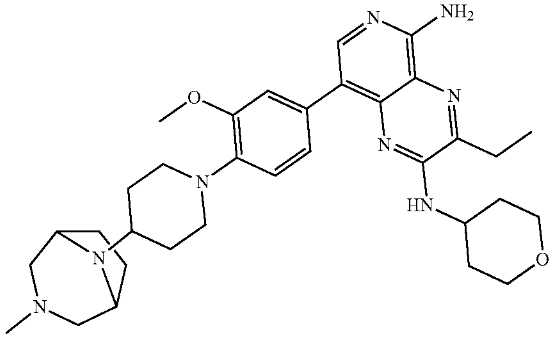

compound 327

Step 1 to Step 3:1,4-Dioxa-8-azanolo[4.5]decane was used to obtain yellow solid intermediate 327-A (three-step yield 20%) according to the method of Step 1 to Step 3 of Example 7. (ESI) m/z. 671.3 $[M+1]^+$.

Step 4: Trifluoroacetic acid/dichloromethane (1 mL/10 mL) solution of intermediate 327-A (1.0 g, 1.5 mmol) was stirred at 25° C. for 1.5 hours. After the reaction, the solution was concentrated under reduced pressure. The resulting residue was purified by silica gel chromatography column (1% ammonia methanol solution/dichloromethane=30%/70%) to obtain yellow solid intermediate 327-B (750 mg, yield 92%). (ESI) m/z. $[M+H]^+$521.4.

Step 5: Acetic acid (3 mL) was added to 6 N hydrochloric acid (6 mL) solution of intermediate 327-B (600 mg, 1.2 mmol), and then the solution was stirred at 70° C. for 3 hours. After the reaction, the solution was concentrated under reduced pressure, and ammonia methanol solution (20 mL) was added to basify, then the solution was concentrated under reduced pressure again. The resulting residue was purified by silica gel chromatography column (1% ammonia methanol solution/dichloromethane=30%/70%) to obtain yellow solid intermediate L (350 mg, yield 32%). (ESI) m/z. $[M+H]^+$477.2.

Step 6: Sodium triacetoxyborohydride (200 mg, 0.90 mmol) was added to the mixture of 1,2-dichloroethane (20 mL) containing intermediate L (150 mg, 0.30 mmol) and 3-methyl-3,8-diazabicyclo[3.2.1]octane (79 mg, 0.60 mmol). The solution was stirred at 80° C. for 16 hours. At the end of the reaction, the mixture was cooled to room temperature and then concentrated under reduced pressure. The resulting residue was purified by preparative liquid chromatography to obtain yellow solid compound 327 as a formate (17 mg, yield 9%). 1H NMR (400 MHz, DMSO-$d_6$) δ 8.20 (brs, 1.8H), 7.92 (s, 1H), 7.26-7.17 (m, 2H), 7.01 (d, J=7.2 Hz, 1H), 6.89 (d, J=8.0 Hz, 1H), 6.45 (brs, 2H), 4.14-4.10 (m, 1H), 3.91 (d, J=8.4 Hz, 2H), 3.82 (s, 3H), 3.48 (s, 4H), 3.25-3.20 (m, 2H), 2.80 (t, J=7.2 Hz, 2H), 2.64-2.52 (m, 4H), 2.48-2.41 (m, 4H), 2.22 (d, J=12.0 Hz, 2H), 1.96 (d, J=12.0 Hz, 2H), 1.86 (d, J=12.4 Hz, 2H), 1.75-1.57 (m, 6H), 1.50-1.39 (m, 2H), 1.31 (t, J=7.2 Hz, 3H). (ESI) m/z. 587.4 $[M+H]^+$.

The starting materials in the following table was used to react with intermediate L according to the method of reductive-amination in Step 6 of Example 37 to obtain the corresponding compounds in the following table.

| No | starting materials | structures | HNMR |
|---|---|---|---|
| 328 | 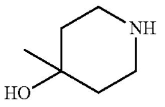 | 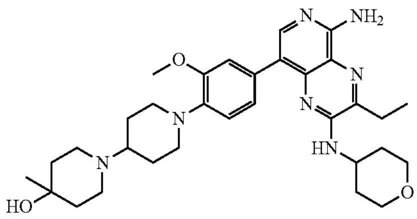 [SMILES: CCc1nc2c(N)ncc(-c3ccc(N4CCC(N5CCC(C)(O)CC5)CC4)c(OC)c3)c2nc1NC1CCOCC1] | $^1$H NMR (400 MHz, DMSO-$d_6$) δ 8.21 (brs, 2.5H), 7.92 (s, 1H), 7.24-7.15 (m, 2H), 7.01 (d, J = 7.2 Hz, 1H), 6.89 (d, J = 8.0 Hz, 1H), 6.47 (s, 2H), 4.14-4.10 (m, 1H), 3.91 (d, J = 8.4 Hz, 2H), 3.82 (s, 3H), 3.48 (d, J = 12.0 Hz, 2H), 3.29 (d, J = 12.0 Hz, 2H), 2.83-2.78 (m, 2H), 2.74-2.68 (m, 4H), 2.63-2.51 (m, 4H), 1.88 (t, J = 12.4 Hz, 4H), 1.75-1.58 (m, 4H), 1.55 (t, J = 12.0 Hz, 4H), 1.31 (t, J = 7.2 Hz, 3H), 1.12 (s, 3H). formate |
| 121 | 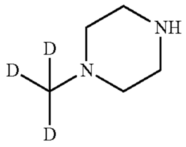 | 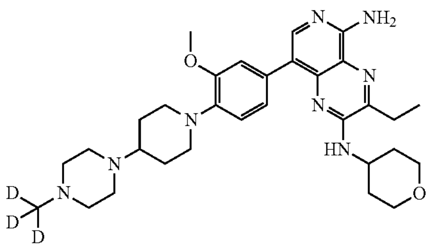 [SMILES: [2H]C([2H])([2H])N1CCN(C2CCN(c3ccc(-c4cnc(N)c5nc(CC)c(NC6CCOCC6)nc45)cc3OC)CC2)CC1] | $^1$H NMR (400 MHz, DMSO-$d_6$) δ 8.14 (brs, 0.7H), 7.89 (s, 1H), 7.22-7.19 (m, 3H), 6.92-6.86 (m, 3H), 4.16-4.08 (m, 1H), 3.91-3.89 (m, 2H), 3.82 (s, 3H), 3.48 (d, J = 10.8 Hz, 3H), 3.28-3.23 (m, 7H), 2.84-2.79 (m, 3H), 2.60-2.54 (m, 4H), 1.90-1.83 (m, 4H), 1.66-1.57 (m, 4H), 1.31 (t, J = 7.2 Hz, 3H). formate |
| 323 | 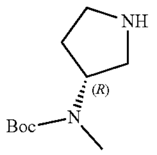 | 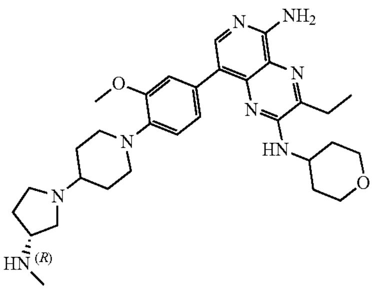 | $^1$H NMR (400 MHz, DMSO-$d_6$) δ 8.14 (brs, 3H), 7.83 (s, 1H), 7.71 (d, J = 7.2 Hz, 1H), 7.21 (d, J = 6.4 Hz, 2H), 6.95 (d, J = 8.8 Hz, 1H), 4.17-4.05 (m, 1H), 3.96-3.90 (m, 2H), 3.83 (s, 3H), 3.75 (s, 1H), 3.47-3.44 (m, 2H), 3.23-3.18 (m, 3H), 3.10 (s, 3H), 2.85 (q, J = 7.2 Hz, 2H), 2.66-2.56 (m, 6H), 2.23-2.19 (m, 1H), 2.11-2.00 (m, 3H), 1.98-1.77 (m, 3H), 1.65-1.60 ( m, 4H), 1.33 (t, J = 7.2 Hz, 3H). formate |
| 324 | 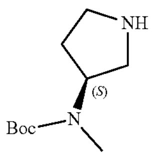 | 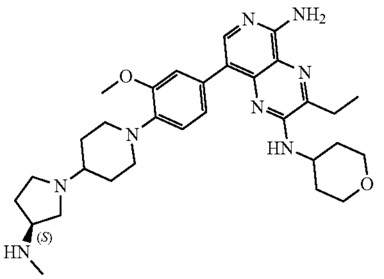 | $^1$H NMR (400 MHz, DMSO-$d_6$) δ 8.25 (brs, 2H), 8.14 (s, 1H), 7.82 (s, 1H), 7.75 (d, J = 6.8 Hz, 1H), 7.21 (d, J = 6.8 Hz, 2H), 6.95 (d, J = 8.8 Hz, 1H), 4.21-4.07 (m, 1H), 3.91-3.84 (m, 3H), 3.83 (s, 3H), 3.49-3.30 (m, 6H), 3.26 (m, 3H), 2.86 (q, J = 7.2 Hz, 2H), 2.70-2.55 (m, 6H), 2.29-2.25 (m, 1H), 1.91 (m, 6H), 1.65-1.60 (m, 4H), 1.33 (t, J = 7.2 Hz, 3H). formate |

Example 38:3-ethyl-8-(3-methoxy-4-(4-(4-methylpiperazine-1-yl)piperidine-1-yl)phenyl)-N2-(tetrahydro-2H-pyran-4-yl)-1,6-naphthyridine-2,5-diamine (Compound 113)
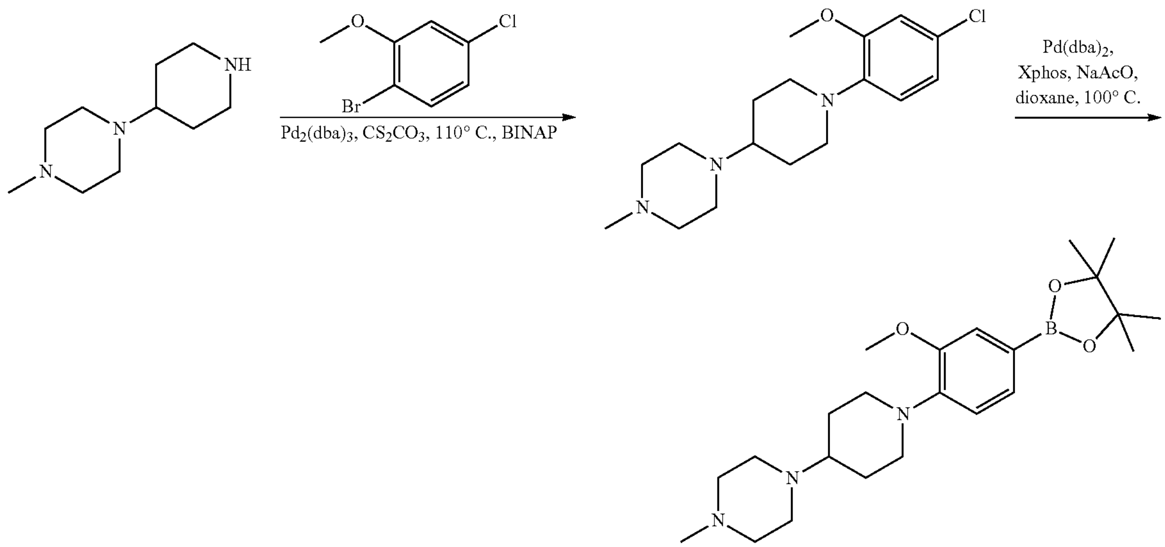
intermediate M
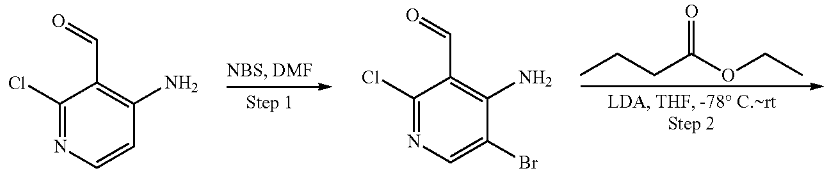
intermediate 113-A
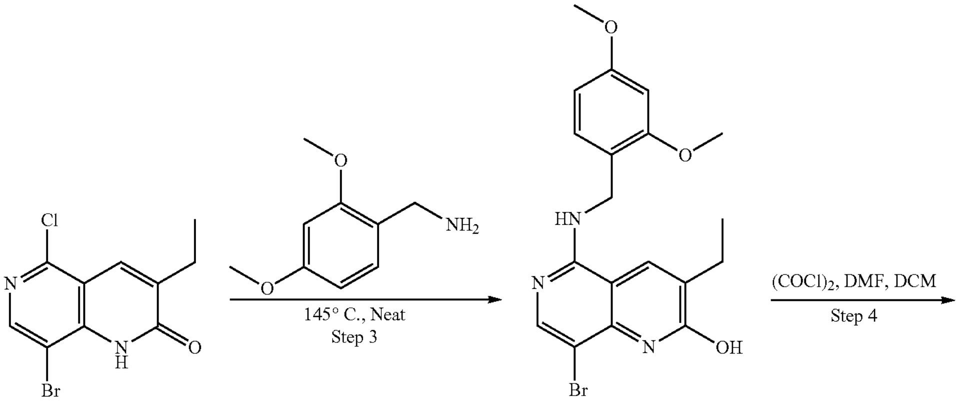
intermediate 113-B
intermediate 113-C
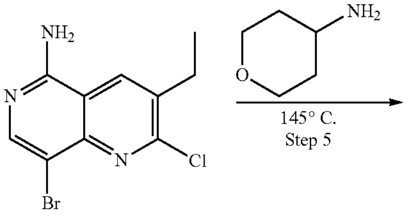
intermediate 113-D -continued

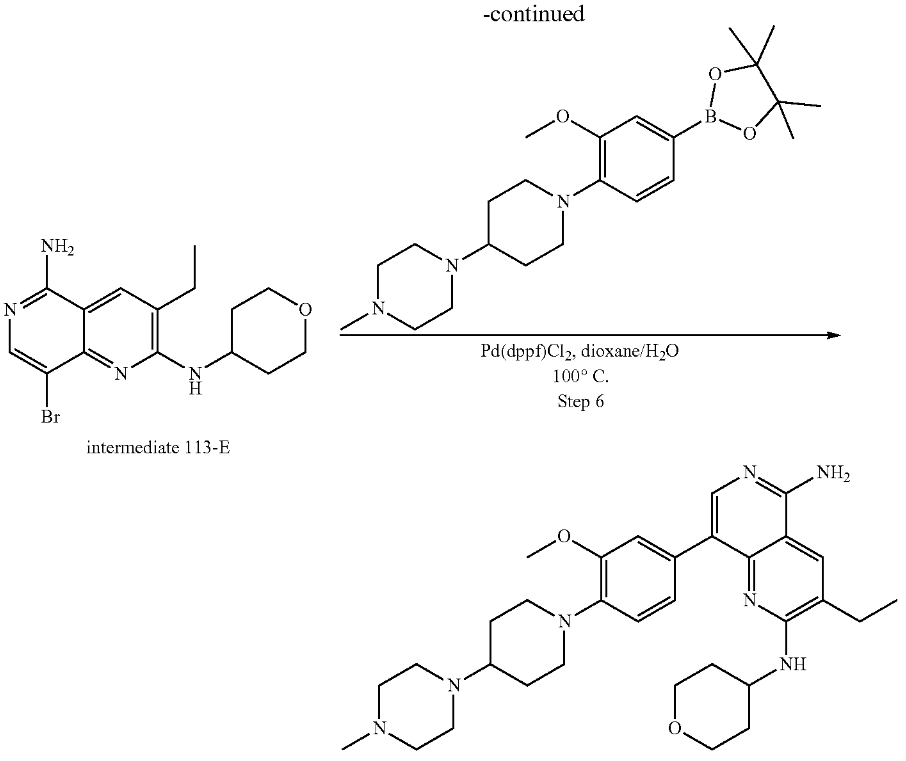

intermediate 113-E compound 113

Synthesis of Intermediate M: 1-methyl-4-(4-piperidinyl) piperazine (5.0 g, 30 mmol) was used to obtain yellow solid intermediate M by the method of Step 1 and Step 2 of Example 7 (two-step yield 24%). 1H NMR (400 MHz, $CDCl_3$) δ 7.39 (d, J=8.0 Hz, 1H), 7.25 (s, 1H), 6.92 (d, J=8.0 Hz, 1H), 3.90 (s, 3H), 2.51-2.34 (m, 13H), 2.34 (s, 3H), 1.89-1.76 (m, 4H), 1.33 (s, 12H). (ESI) m/z. $[M+1]^+$ 416.2.

Step 1: NBS (260 mg, 1.5 mmol) was added to the solution of N, N-dimethylformamide (5 mL) of 4-amino-2-chloropyridine-3-formaldehyde (200 mg, 1.3 mmol). The reaction was stirred under 25° C. for 5 hours, and then poured into water (10 mL). The solid was precipitated, filtered and dried to obtain white solid intermediate 113-A (215 mg, yield 72%). 1H NMR (400 MHz, $CDCl_3$) δ 10.39 (brs, 1H), 9.24 (s, 1H), 8.24 (s, 1H), 5.73 (s, 1H). (ESI) m/z 234.9 $[M+H]^+$ Step 2: LDA solution (1.9 mL, 3.8 mmol, 2 mol/L) was added to the solution of tetrahydrofuran (10 mL) of ethyl butyrate (440 mg, 3.8 mmol) at −78° C. The reaction was stirred at −78° C. for 1 hour, and then intermediate 113-A (0.21 g, 0.90 mmol) was added. The reaction was stirred at 25° C. for 14 hours and added to saturated ammonium chloride solution (10 mL). The solution was extracted three times (10 mL×3) with ethyl acetate. The organic phases were combined, dried over anhydrous sodium sulfate, filtered, and the filtrate was concentrated under reduced pressure. The resulting residue was purified by silica gel chromatography column (petroleum ether/ethyl acetate=10:1) to obtain white solid intermediate 113-B (88 mg, yield 40%). 1H NMR (400 MHz, DMSO-$d_6$) δ 11.51 (brs, 1H), 8.50 (s, 1H), 7.85 (s, 1H), 2.59 (dd, J=14.8, 7.2 Hz, 2H), 1.19 (t, J=7.2 Hz, 3H). (ESI) m/z 286.9 $[M+H]^+$ Step 3: intermediate 113-B (88 mg, 0.31 mmol) was used as the starting material to obtain light yellow solid intermediate 113-C according to the method of Step 1 of Example 2 (80 mg, yield 62%). (ESI) m/z 418.0 $[M+H]^+$.

Step 4: intermediate 113-C (80 mg, 0.19 mmol) was used as the starting material to obtain brown solid intermediate 113-D according to the method of Step 8 of Example 1 (90 mg, the crude product was directly used for the next reaction).

Step 5: The mixture of intermediate 113-D (90 mg) and tetrahydropyran-4-amine (412 mg, 4.1 mmol) was stirred at 145° C. for 1 hour. At the end of the reaction, the mixture was cooled to room temperature and concentrated under reduced pressure. The resulting residue was purified by silica gel chromatography column (petroleum ether/ethyl acetate=1:1) to obtain brown solid intermediate 113-E (60 mg, yield 89%). (ESI) m/z 353.0 $[M+H]^+$.

Step 6: intermediate 113-E (60 mg, 0.17 mmol) and intermediate M (142 mg, 0.34 mmol) were used as the starting materials to obtain yellow solid compound 113 formate according to the method of Step 2 of Example 2 (23 mg, 23% yield). 1H NMR (400 MHz, DMSO-$d_6$) δ 8.20 (brs, 3H), 8.00 (s, 1H), 7.81 (s, 1H), 7.23-7.13 (m, 2H), 6.88 (d, J=8.0 Hz, 1H), 6.75 (s, 2H), 6.45 (d, J=7.2 Hz, 1H), 4.19-4.11 (m, 1H), 3.92-3.84 (m, 2H), 3.84-3.77 (m, 3H), 3.45 (d, J=11.2 Hz, 2H), 3.23 (t, J=11.2 Hz, 2H), 2.62-2.54 (m, 6H), 2.53-2.51 (m, 1H), 2.48-2.20 (m, 2H), 2.22 (s, 3H), 1.90-1.76 (m, 4H), 1.65-1.48 (m, 4H), 1.25 (dd, J=12.0, 4.8 Hz, 3H). (ESI) m/z. 560.3 $[M+1]^+$.

The starting material in the following table was used to react with intermediate M to obtain the corresponding compound in the following table by synthesis method of Step 6 of Example 38.

| No | starting materials | structures | HNMR |
|---|---|---|---|
| 114 | 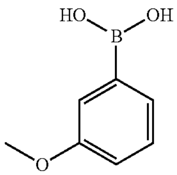 | 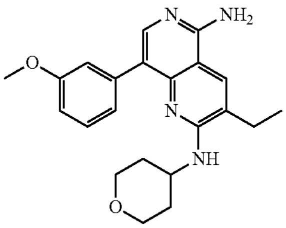 [SMILES: CCc1cc2c(N)ncc(-c3cccc(OC)c3)c2nc1NC1CCOCC1] | $^1$H NMR (400 MHz, DMSO-$d_6$) δ 8.29 (s, 2H), 7.99 (s, 1H), 7.87 (s, 1H), 7.32-7.21 (m, 3H), 6.85 (d, J = 7.6 Hz, 1H), 6.56 (s, 2H), 6.41 (d, J = 7.2 Hz, 1H), 4.19-4.12 (m, 1H), 3.90-3.85 (m, 2H), 3.79 (s, 3H), 3.29 (d, J = 10.4 Hz, 2H), 2.58-2.54 (m, 2H), 1.82 (d, J = 10.4 Hz, 2H), 1.57 (dt, J = 12.0, 7.6 Hz, 2H), 1.25 (t, J = 7.2 Hzs, 3H). formate |
Example 39:3-ethyl-8-(3-methoxyphenyl)-N2-(tetrahydro-2H-pyran-4-yl)pyrazino[2,3-d]pyridazine-2,5-diamine (Compound 116)
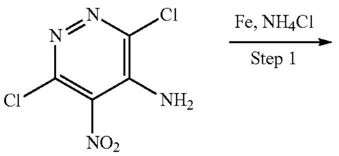
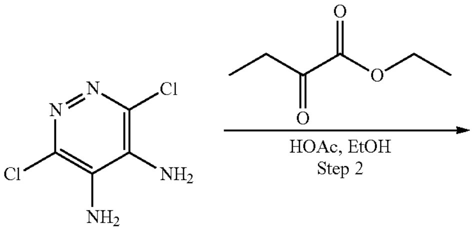
intermediate 116-A
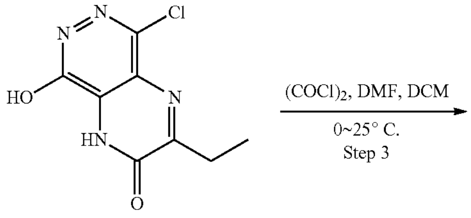
intermediate 116-B
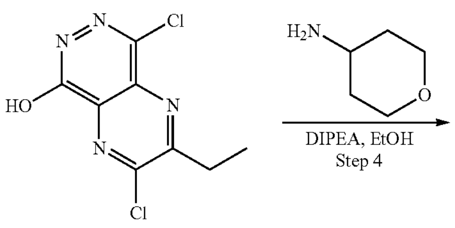
intermediate 116-C
-continued
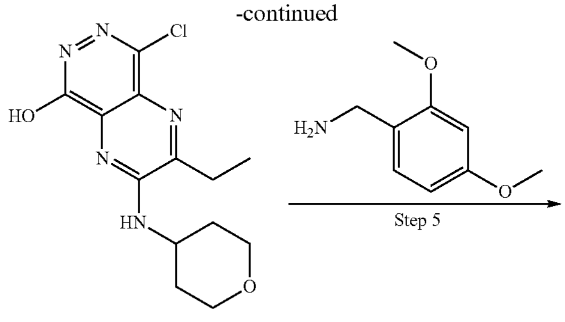
intermediate 116-D
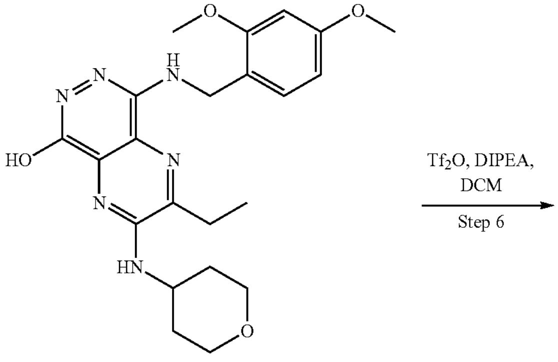
intermediate 116-E
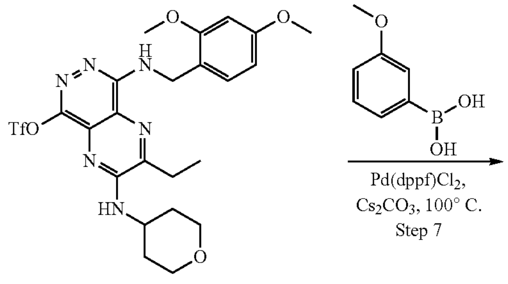
intermediate 116-F
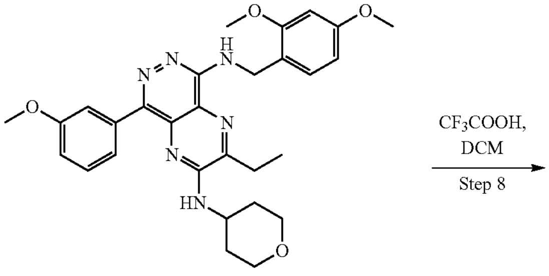
intermediate 116-G -continued

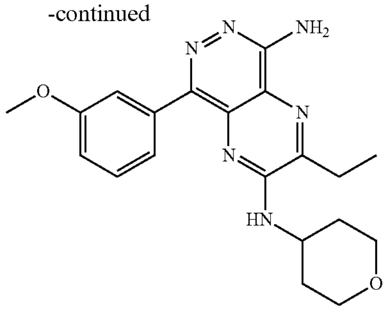

compound 116

Step 1: Iron powder (12 g, 0.21 mol) was added to the solution of ethanol (40 mL) and saturated ammonium chloride (40 mL) containing 3, 6-dichloro-5-nitropyridine-4-amine (4.4 g, 21 mmol). The reaction was stirred at 25° C. for 18 hours, filtered, and the filter cake was washed with ethanol (40 mL). The filtrate was evaporated to remove ethanol, and the residue was extracted three times (100 mL×3) with ethyl acetate. The organic phases were combined, dried over anhydrous sodium sulfate, filtered, and the filtrate was concentrated under reduced pressure. The resulting residue was purified by silica gel chromatography column (dichloromethane:methanol=20:1) to obtain yellow solid intermediate 116-A (1.8 g, yield 43%). (ESI) m/z 178.9 $[M+H]^+$ Step 2 to Step 4: Intermediate 116-D was obtained according to the method of Step 7 to step 9 of Example 1 by using intermediate 116-A, white solid (three-step yield 2.2%). (ESI) m/z 312.1 $[M+H]^+$ Step 5: Intermediate 116-E was obtained according to the method of Step 1 of Example 8 by using intermediate 116-D (66 mg, 0.21 mmol), yellow solid (60 mg, yield 61%). (ESI) m/z 441.1 $[M+H]^+$ Step 6: Intermediate 116-E was obtained according to the method of Step 1 of Example 17 by using intermediate 116-E (50 mg, 0.12 mmol) to react with trifluoromethanesulfonic anhydride (40 mg, 0.14 mmol), yellow solid (50 mg, yield 65%). (ESI) m/z 573.0 $[M+H]^+$ Step 7 and Step 8: Intermediate 116-E (70 mg, 0.12 mmol) was reacted with (3-methoxyphenyl) boric acid (37 mg, 0.24 mmol) according to the method of Step 1 of Example 17 to obtain white solid compound 116 formate (5 mg, two-step yield 11%). 1H NMR (400 MHz, DMSO-$d_6$) δ 8.23 (s, 1H), 7.73-7.71 (m, 2H), 7.41 (d, J=7.2 Hz, 1H), 7.38-7.34 (m, 1H), 7.00-6.97 (m, 1H), 6.70 (s, 2H), 4.16-4.12 (m, 1H), 3.96-3.92 (m, 2H), 3.82 (s, 3H), 3.42 (s, 2H), 2.90-2.84 (m, 2H), 1.89 (d, J=12.0 Hz, 2H), 1.67-1.61 (m, 2H), 1.35-1.31 (m, 3H). (ESI) m/z. 381.1 $[M+1]^+$.

Methoxyphenylboronic acid was replaced with intermediate M in step 7 to obtain the following table compound by synthesis method of Example 39.

| No | structures | HNMR |
| --- | --- | --- |
| 115 | 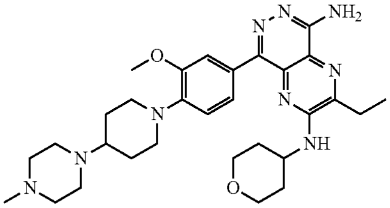 [SMILES: CCc1nc2c(N)nnc(-c3ccc(N4CCC(N5CCN(C)CC5)CC4)c(OC)c3)c2nc1NC1CCOCC1] | $^1$H NMR (400 MHz, DMSO-$d_6$) δ 8.18 (brs, 2H), 7.77 (dd, J = 8.4, 2.0 Hz, 1H), 7.65 (d, J = 2.0 Hz, 1H), 7.37 (d, J = 7.2 Hz, 1H), 6.93 (d, J = 8.4 Hz, 1H), 6.63 (brs, 2H), 4.23-4.14 (m, 1H), 3.94 (d, J = 8.0 Hz, 2H), 3.85 (s, 3H), 3.51 (d, J = 11.2 Hz, 2H), 3.35 (t, J = 11.2 Hz, 3H), 2.89-2.83 (m, 2H), 2.62-2.54 (m, 6H), 2.43-2.31 (m, 4H), 2.19 (s, 3H), 1.93-1.82 (m, 4H), 1.72-1.52 (m, 4H), 1.33 (t, J = 7.2 Hz, 3H). formate |

Example 40: (1S,3R)-3-((5-amino-3-ethyl-8-(3-methoxy-4-(2-methylpyrimidine-4-yl)phenyl)pyrido[3,4-b]pyrazine-2-yl)amino)cyclopentan-1-ol (Compound 288)

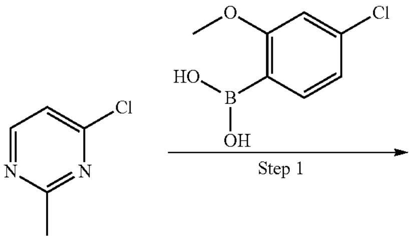

-continued

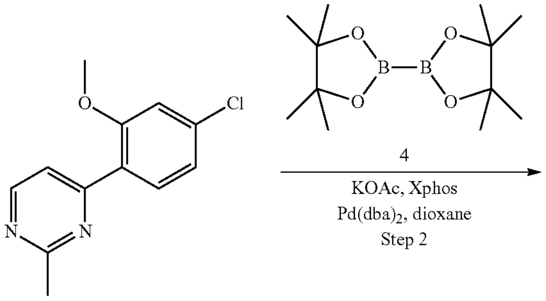

intermediate 288-A

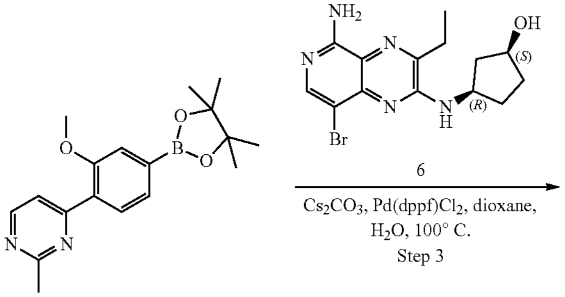

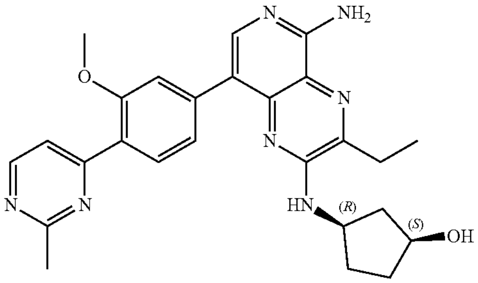

compound 288

Step 1:4-Chloro-2-methylpyrimidine (1.0 g, 7.8 mmol) was reacted with (4-chloro-2-methoxyphenyl) boric acid (1.7 g, 9.3 mmol) according to the method of Step 2 of Example 2 to obtain brown solid intermediate 288-A (1.6 g, yield 87%).

Steps 2 and 3: Intermediate 288-A was used to obtain intermediate according to the method of Step 2 of Example 7 and then the intermediate was reacted with compound 151 according to the method of Step 2 of Example 2 to obtain yellow solid compound 288 formate (two-step yield was about 59%). 1H NMR (400 MHz, DMSO-$d_6$) δ 8.67 (d, J=5.6 Hz, 1H), 8.14 (brs, 1H), 8.07 (s, 1H), 8.01 (d, J=8.4 Hz, 1H), 7.87 (d, J=5.6 Hz, 1H), 7.58-7.54 (m, 1H), 7.51-7.47 (m, 1H), 7.16 (d, J=7.2 Hz, 1H), 6.81 (brs, 2H), 4.87-4.65 (m, 1H), 4.46-4.38 (m, 1H), 4.17-4.09 (m, 1H), 3.94 (s, 3H), 2.81 (q, J=7.2 Hz, 2H), 2.67 (s, 3H), 2.20-2.11 (m, 1H), 1.97-1.88 (m, 1H), 1.82-1.58 (m, 4H), 1.32 (t, J=7.2 Hz, 3H). (ESI) m/z 472.2. $[M+1]^+$.

The starting material in the following table was reacted according to the methods of Step 1 and Step 2 of Example 40 to obtain borate ester intermediate, and then the borate ester intermediate was reacted with intermediate D according the Step 2 to the end of synthesis method of compound 8 to obtain the corresponding compound in the following table

| No | starting materials | structures | HNMR |
|---|---|---|---|
| 313 | 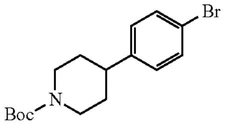 [SMILES: CC(C)(C)OC(=O)N1CCC(c2ccc(Br)cc2)CC1] | 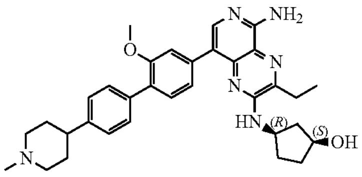 | $^1$H NMR (400 MHz, DMSO) δ 7.97 (s, 3H), 7.64 (d, J = 8.0 Hz, 1H), 7.51 (d, J = 8.0 Hz, 2H), 7.44 (s, 1H), 7.40-7.30 (m, 4H), 4.80 (d, J = 4.0 Hz, 1H), 4.44-4.33 (m, 1H), 4.11 (s, 1H), 3.82 (s, 3H), 3.54 (d, J = 12.0 Hz, 2H), 3.13-3.07 (m, 2H), 2.88-2.83 (m, 6H), 2.21-2.11 (m, 1H), 2.09-1.78 (m, 6H), 1.73-1.57 (m, 3H), 1.35-1.32 (m, 3H). |

Example 41: Cis and trans 4-(4-(5-amino-3-ethyl-2-(((1R,3S)-3-hydroxycyclopentyl)amino)pyridino[3,4-b]pyrazin-8-yl)-1H-pyrazol-1-yl)-1-methylcyclohexyl-1-ol (Compounds 284 and 285)

According to the following route, the cis and trans starting materials of were reacted respectively to obtain compound 284 and compound 285

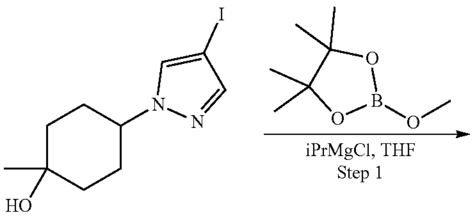

cis or trans

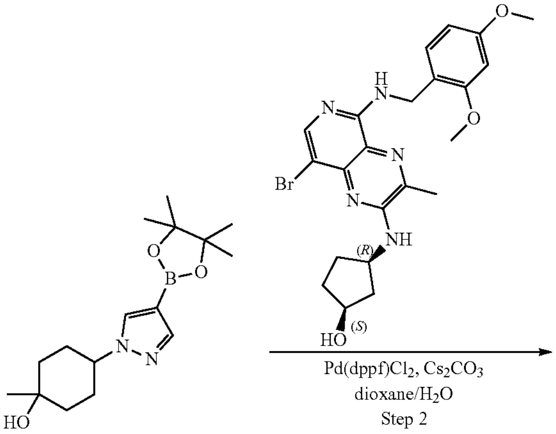

cis or trans
intermediate N

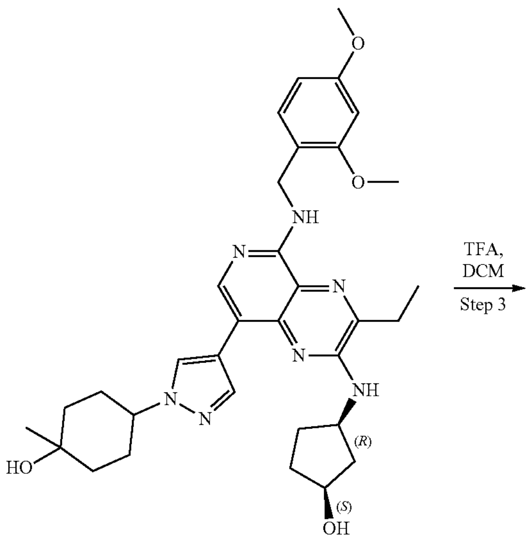

cis or trans

-continued

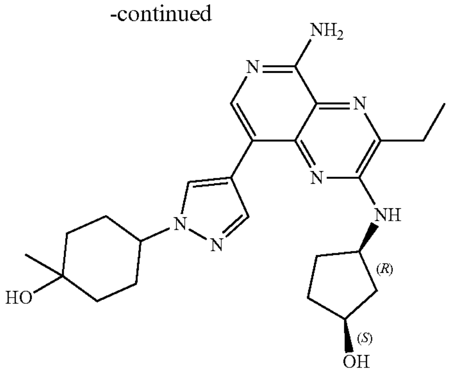

cis or trans
compound 284 and compound 285

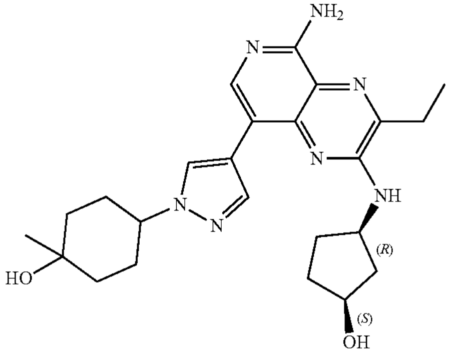

Step 1: Isopropyl magnesium chloride (about 5 equivalents) was added to the tetrahydrofuran solution of cis or trans 4-(4-iodo-1H-pyrazol-1-yl)-1-methylcyclohexan-1-ol at 0° C. This mixture was stirred at 0° C. under nitrogen atmosphere for 1 hour, and then 2-methoxy-4,4,5,5-tetramethyl-1,3,2-dioxapentaborane (about 5.5 equivalents) was added. The mixture was stirred at 0° C. for 1 hour under nitrogen atmosphere, and then heated to 25° C. and stirred for 3 hours. After the reaction, the mixture was concentrated under reduced pressure, and the residue was purified by silica gel chromatography column (petroleum ether:ethyl acetate=3:7 to ethyl acetate) to obtain colorless oil intermediate N (yield about 72%). (ESI) m/z. 307.2. $[M+H]^+$.

Steps 2 and 3: Intermediate N was reacted with intermediate D according to the methods of Step 2 and Step 3 of Example 31 to obtain compound 284 (two-step yield 30%) and compound 285 (two-step yield 6.5%), both of them were yellow solids. Compound 284: 1H NMR (400 MHz, DMSO-$d_6$) δ 8.45 (s, 1H), 8.17-8.13 (m, 2H), 8.01 (s, 1H), 7.28 (d, J=6.8 Hz, 1H), 6.82 (s, 2H), 4.92-4.65 (m, 1H), 4.54-4.46 (m, 1H), 4.26-4.07 (m, 3H), 2.82 (q, J=7.2 Hz, 2H), 2.34-2.27 (m, 1H), 2.12-2.03 (m, 3H), 1.88-1.80 (m, 4H), 1.71-1.63 (m, 4H), 1.53-1.46 (m, 2H), 1.31 (t, J=7.2 Hz, 3H), 1.16 (s, 3H). (ESI) m/z 452.3. $[M+1]^+$. Compound 285: 1H NMR (400 MHz, DMSO-$d_6$) δ 8.43 (s, 1H), 8.19 (s, 2H), 8.02 (s, 1H), 7.10 (d, J=7.2 Hz, 1H), 6.38 (brs, 2H), 4.50-4.47 (m, 1H), 4.28-4.11 (m, 2H), 2.80 (q, J=7.2 Hz, 2H), 2.35-2.25 (m, 1H), 2.05-2.00 (m, 3H), 2.00-1.52 (m, 11H), 1.30 (t, J=7.2 Hz, 3H), 1.19 (s, 3H). (ESI) m/z. 452.3 $[M+1]^+$.

Example 42: (1S, 3R)-3-((5-amino-3-ethyl-8-(1-(4-((1-methylpiperidin-4-yl)oxy)phenyl)-1H-pyrazol-4-yl)pyridino[3,4-b]pyrazin-2-yl)amino)cyclopentan-1-ol (Compound 292)

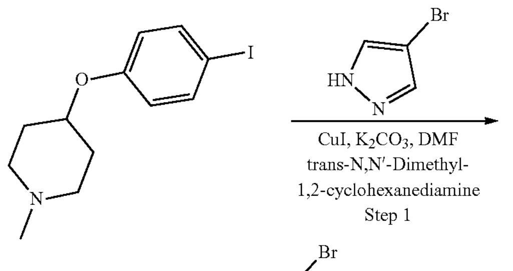

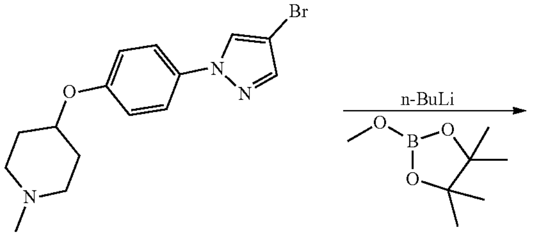

intermediate 292-A

Step 2

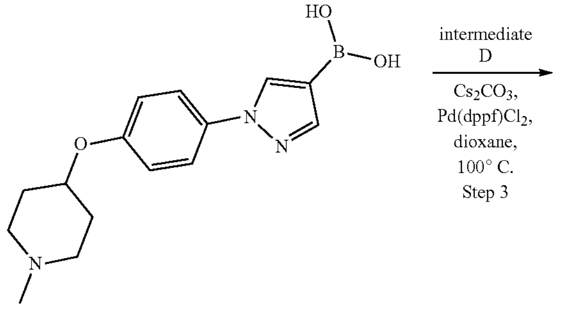

intermediate 292-B

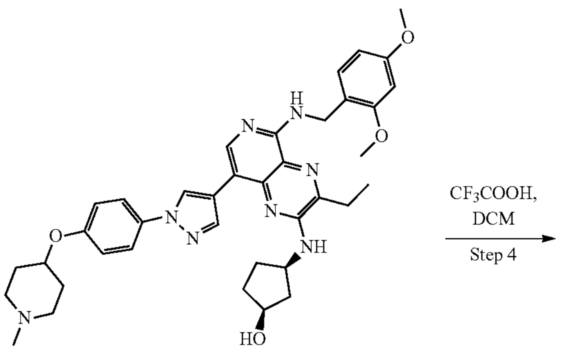

-continued

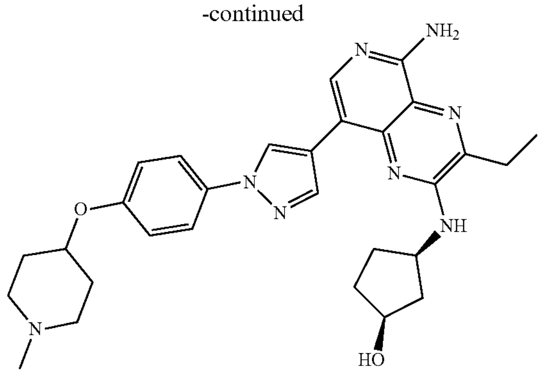

compound 292

Step 1:4-(4-Iodophenoxy)-1-methylpiperidine (800 mg, 2.5 mmol) reacted with 4-bromo-1H-pyrazole (389 mg, 2.6 mmol) according to the method of Step 1 of Example 22 to obtain yellow solid intermediate 292-A (410 mg, 48%). (ESI) m/z 336.1 $[M+H]^+$.

Step 2: n-Butyl solution (0.5 ml, 2.4 N) was added dropwise to tetrahydrofuran (10 mL) solution of intermediate 292-A (350 mg, 1.04 mmol) under −78° C. and nitrogen atmosphere. The solution was stirred for 20 minutes, and 2-methoxy-4, 4, 5, 5-tetramethyl-1, 3, 2-dioxpentaborane (328 mg, 2.08 mmol) in tetrahydrofuran (5 mL) was added. The mixture was stirred at −78° C. for 1 hour under nitrogen atmosphere, and then heated to 0° C. and stirred for 1 hour. At the end of the reaction, methanol (2 mL) was added to quench and the solution was concentrated under reduced pressure. The residue was purified by silica gel chromatography column (dichloromethane:methanol=9:1) to obtain yellow oily intermediate 292-B (150 mg, yield 86%). (ESI) m/z. 302.2. $[M+H]^+$.

Steps 3 and 4: Intermediate 292-B (114 mg, 0.398 mmol) was reacted with intermediate D (100 mg, 0.199 mmol) according to the methods of Step 2 and Step 3 of Example 31 to obtain yellow solid compound 292 formate (38 mg, two-step yield 3.9%). 1H NMR (400 MHz, DMSO-$d_6$) δ 7.77-7.70 (m, 2H), 7.22-7.15 (m, 4H), 6.91 (d, J=8.8 Hz, 2H), 6.52 (d, J=1.6 Hz, 1H), 4.72-4.68 (m, 1H), 4.60-4.54 (m, 1H), 4.09 (s, 1H), 4.00-3.96 (m, 1H), 3.34-3.20 (m, 4H), 2.79 (s, 3H), 2.73-2.66 (m, 2H), 2.14-1.85 (m, 5H), 1.76-1.53 (m, 5H), 1.48-1.38 (m, 1H), 1.25 (t, J=7.2 Hz, 3H). (ESI) m/z. 529.3. $[M+H]^+$.

Example 43: (S,E)-N-(1-((2-((4-(5-amino-3-ethyl-2-((tetrahydro-2H-pyran-4-yl)amino)pyridino[3,4b] pyrazine-8-yl)-2-methoxyphenyl)amino)ethyl) amino)-1-oxopropane-2-yl)-4-(dimethylamino)-N-methylbutyl-2-enamide (Compound 358)

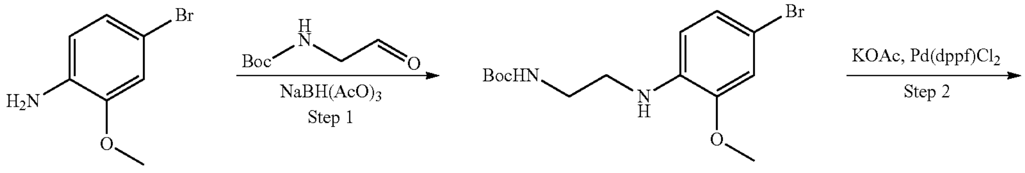

intermediate 358-A

-continued
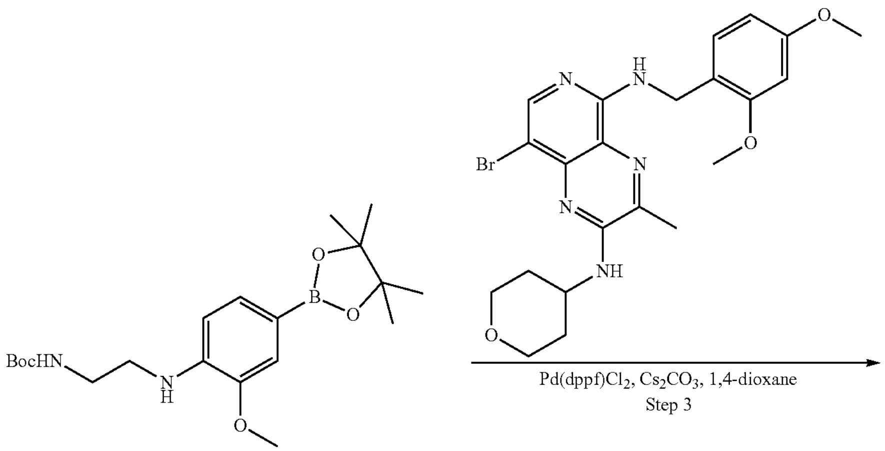
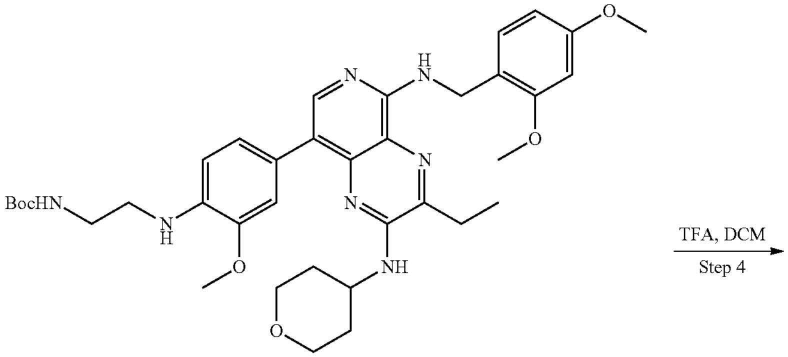
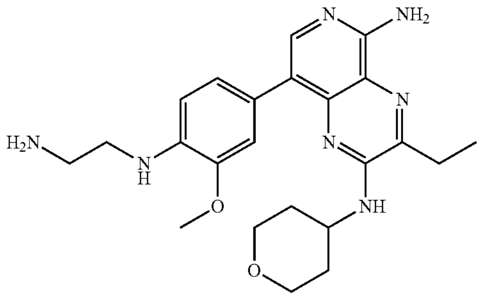
intermediate 358-B
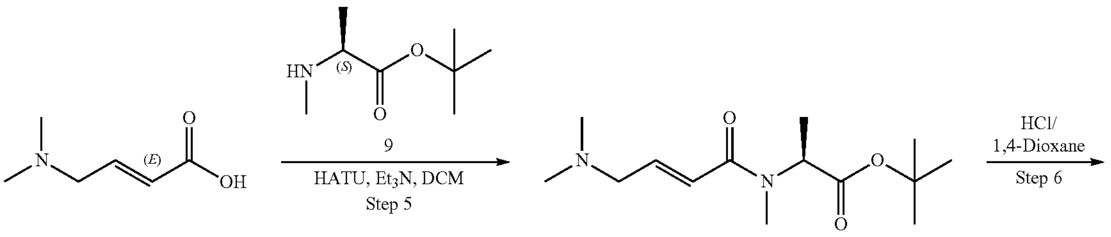
intermediate 358-C
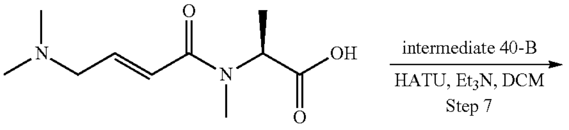
intermediate 358-D -continued

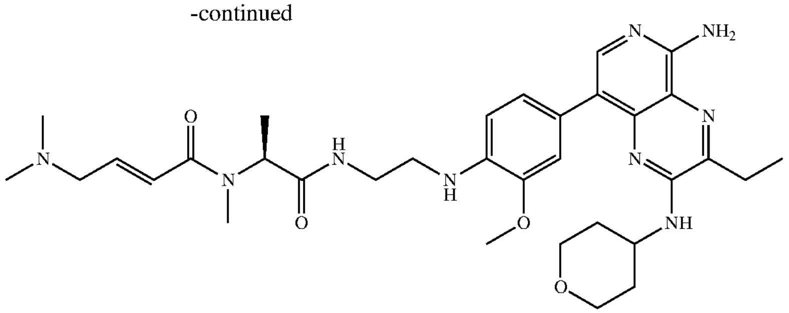

compound 358

Step 1:4-Bromo-2-methoxyaniline (8.0 g, 39 mmol) was reacted with tert-butyl (2-oxyethyl) carbamate (6.6 g, 41 mmol) according to the method of Step 2 of Example 6 to obtain yellow solid intermediate 358-A (4.5 g, 30%). (ESI) m/z 346.1 $[M+H]^+$.

Steps 2 to 4: Intermediate 358-A was reacted according to the method of Step 2 to 4 of Example 7 to obtain yellow solid intermediate 358-B (three-step yield 23%). (ESI) m/z. 438.2. $[M+H]^+$.

Step 5: HATU (1.9 g, 5.0 mmol) and triethylamine (0.77 g, 7.7 mmol) were added to (E)-4-(dimethylamino)butyl-2-enoic acid (500 mg, 3.9 mmol) and (2S)-2-(methylamino) propionate (678 mg, 4.3 mmol) in dichloromethane solution (10 mL). The mixture was stirred at 25° C. for 4 hours, then concentrated under reduced pressure. The resulting residue was purified by silica gel chromatography column (methanol (containing 1% ammonia)/dichloromethane=from 0% to 100% in 20 minutes) to obtain yellow solid intermediate 358-C (980 mg, yield 84%). (ESI) m/z. 271.1. $[M+H]^+$.

Step 6: Intermediate 358-C (500 mg, 1.9 mmol) was reacted according to the method of Step 1 of Example 24 to obtain yellow solid intermediate 358-D (350 mg, yield 88%). (ESI) m/z. 215.1. $[M+H]^+$.

Step 7: Intermediate 358-D (62 mg, 0.29 mmol) was reacted with intermediate 358-B (120 mg, 0.27 mmol) according to the method of Step 1 of this Example to obtain yellow solid compound 358 (18.5 mg, 11% yield). $^1$H NMR (400 MHz, DMSO-$d_6$) δ 8.17 (s, 2H), 7.98 (s, 1H), 7.88 (s, 1H), 7.15 (d, J=6.0 Hz, 2H), 6.98 (d, J=7.2 Hz, 1H), 6.67-6.59 (m, 2H), 6.52 (s, 1H), 6.42 (s, 2H), 5.04-5.00 (m, 2H), 4.22-4.11 (m, 1H), 3.96-3.87 (m, 2H), 3.81 (s, 3H), 3.31-3.28 (m, 3H), 3.16-3.12 (m, 2H), 3.10-3.00 (m, 2H), 2.90 (s, 2H), 2.80-2.75 (m, 3H), 2.16-2.10 (m, 6H), 1.87-1.84 (m, 2H), 1.63-1.60 (m, 2H), 1.31 (t, J=7.2 Hz, 1H), 1.23 (d, J=7.2 Hz, 1H). (ESI) m/z. 634.3. $[M+H]^+$.

Biological Test Example 1: FLT3 Kinase In Vitro Inhibitory Activity Experiment Reagents and Consumables

| Reagent name | Supplier | catalogNo. | lot No. |
|---|---|---|---|
| FLT3 | Carna | 08-145 | 10CBS-0917U |
| Kinase substrate 2 | GL | 112394 | P191104-TL112394 |
| 384-well plate | Corning | 3573 | 12619003 |

Instruments

Centrifuge (manufacturer: Eppendorf, model: 5430), microplate reader (manufacturer: Perkin Elmer, model: Caliper EZ Reader II), Echo 550 (manufacturer: Labcyte, model: Echo 550)

Experimental Methods

1. Kinase Reaction Process
   (1) 1×Kinase buffer was prepared.
   (2) Preparation of the serial compound dilutions: the initial stock (the concentration of the tested compound was 1 μM) was diluted by 3-fold into 10 concentrations, and was single-well detected. The compounds were series diluted to solutions of 10 different concentration (100-folds final concentration) in 384-well plates. 250 nl of solution was transferred to each well of 384-well plate by Echo550. 100% DMSO (250 nl) was added to negative control wells and positive control wells respectively.
   (3) Kinase solution (2.5 times final concentration) was prepared with 1×Kinase buffer.
   (4) 10 μL of kinase solution (2.5 times final concentration) was added to compound wells and positive control wells respectively: 1×Kinase buffer (10 μL) was added to the negative control wells.
   (5) The solution was centrifuged at 1000 rpm for 30 seconds, shaked and mixed, and incubated at room temperature for 10 minutes.
   (6) The mixed solution of ATP and Kinase substrate 2 (25/15 times final concentration) was prepared with 1×Kinase buffer.
   (7) 15 μL of mixed solution ATP and Kinase substrate 2 (25/15 times final concentration) was added to initiated the reaction.
   (8) 384 well plate was centrifuged at 1000 rpm for 30 seconds, shaked and mixed, then incubated at room temperature for 30 minutes.
   (9) Stop solution (30 μL) was added to stop kinase reaction, and the solution was centrifuged at 1000 rpm for 30 seconds, shaked and mixed.
   (10) The conversion rate was read with Caliper EZ Reader II.
2. Data Analysis Formula for Calculation $$\% \text{ Inhibition} = \frac{\text{Conversion\%\_max} - \text{Conversion\%\_sample}}{\text{Conversion\%\_max} - \text{Conversion\%\_min}} \times 100$$

Wherein: Conversion %_sample is the reading of the sample conversion; Conversion %_min: negative control well.

Biological Test Example 2: MV4;11 In Vitro Inhibition of Proliferation Assay

Experimental Materials

The MV4;11 cell lines were purchased from the cell bank of the Chinese Academy of Sciences, IMDM medium (Gibco, catalog number 12440), fetal bovine serum (Gibco, catalog number 10099141C), penicillin-streptomycin antibiotics (Gibco, catalog number 15140122), DMSO (Sigma, catalog number D2650), Celltiter-Glo kit (CTG) (Promega, catalog number G7573), 384-well clear flat-bottom black cell culture plate (Corning, catalog number 3764), D300e digital dispenser (Tecan, catalog number D300e), SpectraMax i3x microplate reader (MOLECULAR DEVICES, catalog number i3x)

Experimental Methods

Cell Culture:

MV4;11 cell was cultivated in IMDM, 10% fetal bovine serum, 1% penicillin-streptomycin antibiotics, and cell density was kept less than 1.0*10E6 cells per ml to ensure that it was always in logarithmic growth phase. Cell viability was greater than 95%.

Compound Preparation:

The compounds to be tested was diluted by 3 times from 10 uM with DMSO to 9 concentrations. 60 nl diluted compound was added to the cell culture plate and three duplicates were set up.

Compound Treated Cells:

The prepared MV4;11 cell suspension was added to the 384-well plate, and 20 microliters of cell suspension was added per well, i.e., each well contained 2000 MV4;11 cells, of which the final concentration of DMSO was 0.3%. The cell culture plate was placed in 37° C. and incubated in a 5% carbon dioxide incubator for 72 hours.

20 μL of Promega CellTiter-Glo reagent was added to per well, and the plate was incubated at room temperature for 10 minutes when the luminescence signals were stable. SpectraMax i3x microplate reader was used to read signals.

Data Analysis:

The original data was converted into inhibition rate, and the $IC_{50}$ value (half inhibition concentration) of the compound was determined by fitting the nonlinear four-parameter curve.

The following table recorded the test results in Biological Test Example 1 and Biological Test Example 2. The results showed that the sample compound of the present invention has strong inhibitory effect on FLT3 kinase, and has excellent inhibitory activity to MV4;11 cell proliferation.

A: $IC_{50} \leq 10$ nM;

B: 10 nM$<IC_{50} \leq 100$ nM;

C: 100 nM$<IC_{50} \leq 500$ nM;

D: >500 nM

The activity of some compounds were shown in the following table.

| No. | Enzyme activity FLT3 | Inhibitory activity of cell proliferation MV4;11 |
|---|---|---|
| 1 | D | D |
| 2 | C | D |
| 3 | B | D |
| 7 | A | B |
| 8 | A | B |
| 11 | B | D |
| 13 | A | B |
| 14 | A | B |
| 15 | A | B |
| 16 | A | B |
| 17 | A | B |
| 18 | B | |
| 19 | A | |
| 21 | B | C |
| 22 | A | B |
| 23 | A | B |
| 25 | B | |
| 26 | B | C |
| 27 | A | B |
| 28 | A | B |
| 31 | A | B |
| 32 | A | B |
| 33 | A | B |
| 35 | A | B |
| 36 | A | B |
| 37 | A | B |
| 38 | A | B |
| 39 | A | B |
| 43 | B | C |
| 44 | B | D |
| 45 | A | B |
| 46 | A | B |
| 48 | A | B |
| 56 | B | |
| 57 | B | |
| 58 | A | B |
| 61 | B | |
| 65 | A | B |
| 66 | A | B |
| 67 | A | B |
| 68 | A | B |
| 69 | A | C |
| 70 | A | A |
| 71 | A | B |
| 72 | A | A |
| 76 | B | |
| 77 | A | B |
| 78 | A | B |
| 79 | A | B |
| 82 | A | B |
| 83 | A | B |
| 85 | A | B |
| 92 | A | B |
| 121 | A | B |
| 134 | A | B |
| 135 | A | B |
| 136 | A | B |
| 137 | A | |
| 138 | C | D |
| 139 | A | B |
| 151 | C | |
| 154 | A | |
| 155 | A | B |
| 156 | A | B |
| 157 | A | B |
| 158 | A | B |
| 159 | A | B |
| 160 | A | B |
| 162 | A | C |
| 163 | A | B |
| 164 | A | B |
| 165 | A | A |
| 166 | A | A |
| 167 | A | A |
| 168 | A | A |
| 169 | A | A |
| 170 | A | A |
| 171 | A | A |

-continued

| No. | Enzyme activity FLT3 | Inhibitory activity of cell proliferation MV4;11 |
|---|---|---|
| 172 | A | A |
| 173 | A | |
| 174 | A | A |
| 175 | A | A |
| 176 | A | B |
| 177 | A | A |
| 178 | A | A |
| 179 | A | A |
| 180 | A | A |
| 181 | A | A |
| 182 | A | A |
| 183 | A | A |
| 184 | A | A |
| 185 | A | A |
| 186 | A | A |
| 187 | A | A |
| 188 | A | A |
| 189 | A | A |
| 190 | A | A |
| 191 | A | A |
| 192 | A | A |
| 193 | A | A |
| 194 | A | A |
| 195 | B | B |
| 196 | A | B |
| 197 | A | B |
| 198 | A | B |
| 199 | A | A |
| 200 | A | A |
| 201 | A | A |
| 202 | A | A |
| 203 | A | B |
| 204 | A | A |
| 205 | A | A |
| 206 | A | B |
| 207 | A | A |
| 208 | A | A |
| 209 | A | A |
| 210 | A | A |
| 211 | A | A |
| 212 | A | A |
| 213 | A | A |
| 214 | A | A |
| 215 | A | A |
| 216 | A | A |
| 217 | A | A |
| 218 | A | A |
| 219 | A | A |
| 220 | A | A |
| 221 | A | A |
| 222 | A | A |
| 223 | A | A |
| 224 | A | A |
| 225 | A | A |
| 226 | A | A |
| 227 | A | A |
| 228 | A | B |
| 229 | A | |
| 230 | A | |
| 231 | A | |
| 232 | A | A |
| 233 | A | A |
| 234 | A | A |
| 235 | A | A |
| 236 | A | B |
| 237 | A | B |
| 238 | A | B |
| 239 | A | B |
| 240 | A | B |
| 241 | A | B |
| 242 | A | B |
| 243 | A | A |
| 244 | A | B |
| 245 | A | A |
| 246 | A | A |

-continued

| No. | Enzyme activity FLT3 | Inhibitory activity of cell proliferation MV4;11 |
|---|---|---|
| 247 | A | B |
| 248 | A | B |
| 249 | A | A |
| 250 | A | |
| 251 | A | B |
| 252 | A | B |
| 253 | A | A |
| 254 | A | A |
| 255 | A | |
| 256 | A | |
| 257 | A | A |
| 258 | A | |
| 259 | A | |
| 260 | A | A |
| 261 | A | B |
| 262 | B | |
| 263 | D | |
| 264 | A | |
| 265 | A | B |
| 266 | A | B |
| 267 | A | B |
| 268 | A | B |
| 269 | A | A |
| 270 | A | B |
| 271 | A | B |
| 272 | A | A |
| 273 | A | A |
| 274 | A | B |
| 275 | A | B |
| 276 | A | A |
| 277 | B | C |
| 278 | A | A |
| 279 | B | B |
| 280 | A | A |
| 281 | B | B |
| 282 | A | B |
| 283 | A | B |
| 284 | A | A |
| 285 | A | A |
| 286 | A | A |
| 287 | A | B |
| 288 | A | B |
| 290 | A | A |
| 291 | A | B |
| 292 | D | C |
| 293 | A | B |
| 294 | A | A |
| 295 | A | A |
| 296 | A | A |
| 299 | A | B |
| 300 | A | A |
| 301 | A | A |
| 302 | A | A |
| 303 | A | B |
| 304 | A | A |
| 306 | A | A |
| 308 | A | A |
| 309 | A | A |
| 310 | A | B |
| 311 | A | A |
| 312 | A | B |
| 313 | A | B |
| 314 | B | B |
| 315 | A | B |
| 318 | A | A |
| 319 | A | B |
| 320 | A | B |
| 321 | A | B |
| 322 | A | B |
| 323 | A | B |
| 324 | A | B |
| 325 | A | B |
| 326 | B | B |
| 327 | A | B |
| 328 | A | B |

-continued

| No. | Enzyme activity FLT3 | Inhibitory activity of cell proliferation MV4;11 |
|---|---|---|
| 329 | A | A |
| 330 | A | B |
| 331 | A | A |
| 332 | A | A |
| 333 | A | A |
| 334 | A | A |
| 335 | A | A |
| 336 | A | A |
| 337 | A | B |
| 338 | A | A |
| 339 | A | B |
| 340 | A | B |
| 341 | A | A |
| 342 | A | B |
| 343 | A | A |
| 344 | A | A |
| 345 | A | A |
| 346 | A | B |
| 347 | A | B |
| 348 | A | B |
| 349 | A | B |
| 350 | A | A |
| 351 | A | B |
| 352 | A | B |
| 353 | A | B |
| 354 | A | B |
| 355 | A | A |
| 356 | A | B |
| 357 | A | A |
| 358 | B | C |

All literature mentioned in the present invention is incorporated by reference herein, as though each piece of literature were individually incorporated by reference. In addition, it is understood that after reading the above teaching content, those skilled in the art can make various alterations or modifications, and these equivalents also fall within the scope defined by the claims appended to this application.

The invention claimed is:

1. A compound as shown in the following formula II, or a pharmaceutically acceptable salt or deuterated product thereof:

II

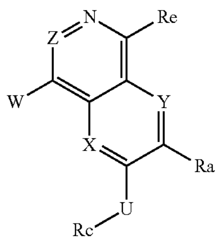

wherein, X and Y are N, and Z is CH;

Ra is H, substituted or unsubstituted $C_1$-$C_6$ alkyl;

U is chemical bond or —NH—; and when U is chemical bond, Rc is pyrrolidine;

Rc is selected from the group consisting of substituted or unsubstituted $C_1$-$C_6$ alkyl, substituted or unsubstituted $C_3$-$C_8$ carbocyclic ring, substituted or unsubstituted 3-8 membered heterocyclic ring containing 1-3 heteroatoms selected from oxygen, sulfur and nitrogen, substituted or unsubstituted $C_6$-$C_{10}$ aryl, and substituted or unsubstituted 5-12 membered heteroaromatic ring containing 1-3 heteroatoms selected from oxygen, sulfur, and nitrogen;

Re is —NHR; wherein R is selected from the group consisting of H, substituted or unsubstituted $C_1$-$C_6$ alkyl, and substituted or unsubstituted phenyl;

W is substituted or unsubstituted $C_6$-$C_{10}$ aryl, or substituted or unsubstituted 5-12 membered heteroaromatic ring containing 1-3 heteroatoms selected from the group consisting of oxygen, sulfur, and nitrogen;

the W group is substituted by at least one group having the structure of -M-A, wherein M is selected from the group consisting of chemical bond, —$CH_2$—;

A is selected from the group consisting of substituted or unsubstituted $C_1$-$C_6$ alkyl, substituted or unsubstituted $C_1$-$C_6$ alkoxy, substituted or unsubstituted $C_6$-$C_{10}$ aryl, substituted or unsubstituted 4-12 membered heterocyclic ring containing 1-3 heteroatoms selected from oxygen, sulfur and nitrogen, substituted or unsubstituted 5-12 membered heteroaromatic ring containing 1-3 heteroatoms selected from oxygen, sulfur and nitrogen, and substituted or unsubstituted $C_3$-$C_{12}$ cycloalkyl;

wherein, in the definition of A, the substitution means substituted by one or more groups selected from group B consisting of H, halogen, cyano, hydroxyl, aldehyde, carboxyl, substituted or unsubstituted $C_1$-$C_6$ alkyl, substituted or unsubstituted $C_1$-$C_6$ alkoxy, substituted or unsubstituted 3-12 membered heterocyclic ring containing 1-3 heteroatoms selected from oxygen, sulfur and nitrogen, substituted or unsubstituted 5-12 membered heteroaromatic ring containing 1-3 heteroatoms selected from oxygen, sulfur and nitrogen, substituted or unsubstituted-$C_1$-$C_6$ alkyl-phenyl, substituted or unsubstituted $C_3$-$C_{12}$ cycloalkyl, substituted or unsubstituted $C_2$-$C_{10}$ acyl, substituted or unsubstituted $C_2$-$C_{10}$ ester group, substituted or unsubstituted $C_1$-$C_6$ amide, and substituted or unsubstituted $C_1$-$C_4$ alkyl-S$(O)_2$—, and in the group B, the substitution means substituted by one or more R groups;

wherein R is selected from the group consisting of H, halogen, cyano, amino, nitro, hydroxyl, substituted or unsubstituted $C_1$-$C_6$ alkyl, substituted or unsubstituted $C_1$-$C_6$ alkoxy, substituted or unsubstituted $C_3$-$C_{12}$ cycloalkyl, substituted or unsubstituted $C_2$-$C_{10}$ ester group;

unless otherwise specified, in the above formulae, the substitution means that the hydrogen atom on the corresponding group is replaced by one or more substituents selected from the group consisting of deuterium, halogen, hydroxyl, amino, $C_1$-$C_6$ amide, cyano, unsubstituted or halogenated $C_1$-$C_6$ alkyl, $C_1$-$C_6$ alkoxy, $C_1$-$C_6$ alkyl-amino, $C_1$-$C_{12}$ alkylaminocarbonyl, unsubstituted or halogenated $C_2$-$C_{10}$ acyl, and unsubstituted or halogenated $C_1$-$C_4$ alkyl-S$(O)_2$—.

2. The compound of claim 1, or the pharmaceutically acceptable salt or deuterated form thereof, wherein the compound has the structure as shown in formula IIa:

IIa

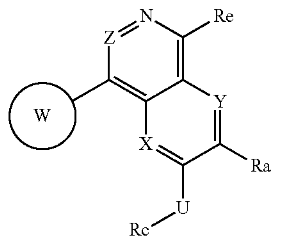

wherein, W is selected from the group consisting of a substituted or unsubstituted phenyl, substituted or unsubstituted pyridine, and substituted or unsubstituted pyrazolyl; wherein in the definition of W, said substitution means substituted by one or more groups selected from A.

3. The compound of claim 1, or the pharmaceutically acceptable salt or deuterated form thereof, wherein W is a substituted or unsubstituted phenyl.

4. The compound of claim 1, or the pharmaceutically acceptable salt or deuterated form thereof, wherein W is a substituted or unsubstituted

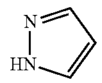

5. The compound of claim 1, or the pharmaceutically acceptable salt or deuterated product thereof, wherein the compound has the structure as shown in formula III:

III

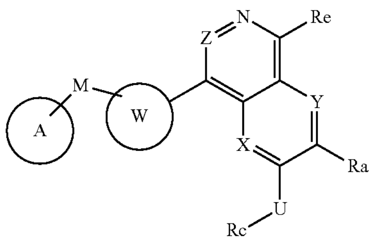

wherein, A is selected from the group consisting of substituted or unsubstituted 4-12 membered heterocyclic ring containing 1-3 heteroatoms selected from oxygen, sulfur and nitrogen, substituted or unsubstituted 5-12 membered heteroaromatic ring containing 1-3 heteroatoms selected from oxygen, sulfur and nitrogen, substituted or unsubstituted $C_6$ aryl, and substituted or unsubstituted $C_3$-$C_{12}$ cycloalkyl;

M is a chemical bond, or $—CH_2—$.

6. The compound of claim 5, or the pharmaceutically acceptable salt or deuterated product thereof, wherein the compound has the structure as shown in the following formula:

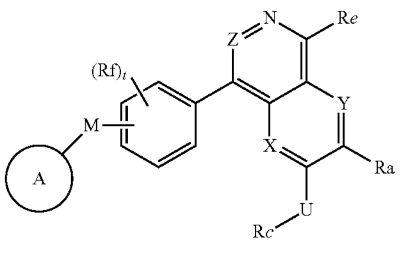

wherein,

Rf is selected from the group consisting of H, halogen, cyano, amino, hydroxyl, $C_1$-$C_4$ alkyl-$S(O)_2$—, substituted or unsubstituted $C_1$-$C_6$ alkyl, and substituted or unsubstituted $C_1$-$C_6$ alkoxy;

t is 0, 1, 2, 3 or 4;

A is selected from the group consisting of substituted or unsubstituted 5-12 membered saturated ring, and substituted or unsubstituted $C_6$-$C_{10}$ aryl; and A has at least one heteroatom selected from N and O.

7. The compound of claim 5, or the pharmaceutically acceptable salt or deuterated product thereof, wherein the compound has the structure as shown in the following formula:

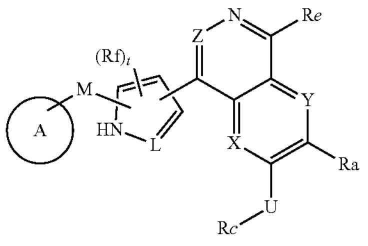

wherein,

Rf is H;

t is 0, 1, 2, 3 or 4;

L is N;

A is selected from the group consisting of a substituted or unsubstituted 4-12 membered heterocyclic ring containing 1-3 heteroatoms selected from oxygen, sulfur and nitrogen, a substituted or unsubstituted $C_3$-$C_{12}$ cycloalkyl, a substituted or unsubstituted 5-12 membered heteroaromatic ring containing 1-3 heteroatoms selected from oxygen, sulfur and nitrogen, and a substituted or unsubstituted $C_6$-$C_{10}$ aryl.

8. The compound, or the pharmaceutically acceptable salt or deuterated product thereof of claim 5, the compound has the structure as shown in the following formula IV:

IV

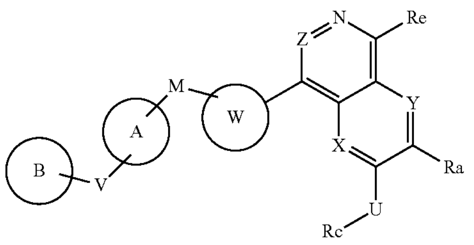

wherein, A is substituted or unsubstituted 4-12 membered heterocyclic ring containing 1-3 heteroatoms selected from oxygen, sulfur and nitrogen substituted or unsubstituted $C_6$ aryl;

M is a chemical bond;

B is substituted or unsubstituted 4-12 membered heterocyclic ring containing 1-3 heteroatoms selected from oxygen, sulfur and nitrogen;

V is a chemical bond.

9. The compound of claim 5, or the pharmaceutically acceptable salt or deuterated product thereof, wherein A has at least one substituent G, and G is selected from the group consisting of amino, =O, substituted or unsubstituted 4-7 membered heterocyclic ring containing 1-3 heteroatoms selected from oxygen and nitrogen, substituted or unsubstituted $C_2$-$C_{10}$ ester, and substituted or unsubstituted $C_1$-$C_6$ amide.

10. The compound of claim 1, or the pharmaceutically acceptable salt or deuterated product thereof of, wherein the compound is selected from the following compounds;
| No | structure |
|---|---|
| 3 | 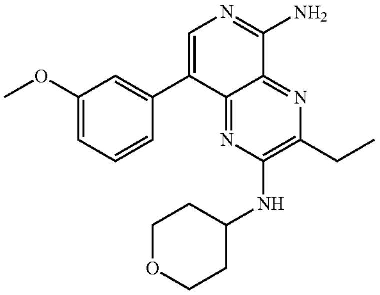 |
| 4 | 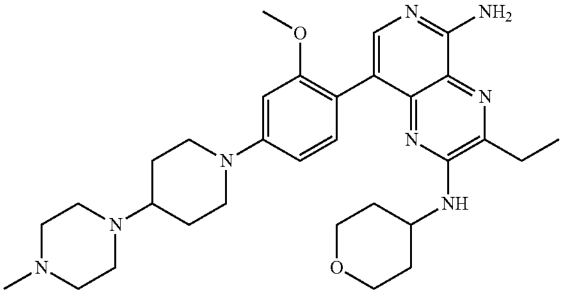 [SMILES: CCc1nc2c(N)ncc(-c3ccc(N4CCC(N5CCN(C)CC5)CC4)cc3OC)c2nc1NC1CCOCC1] |
| 5 | 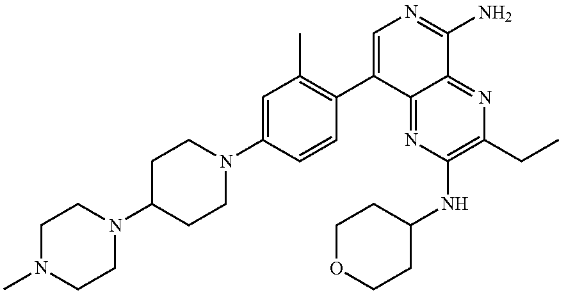 [SMILES: CCc1nc2c(N)ncc(-c3ccc(N4CCC(N5CCN(C)CC5)CC4)cc3C)c2nc1NC1CCOCC1] |
| 6 | 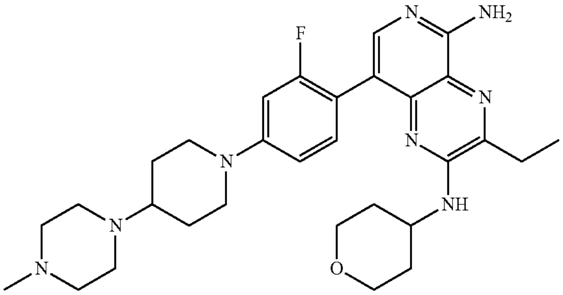 |
| 7 | 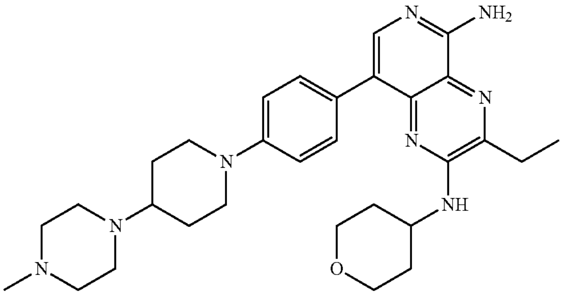 |

-continued
| No | structure |
|---|---|
| 8 | 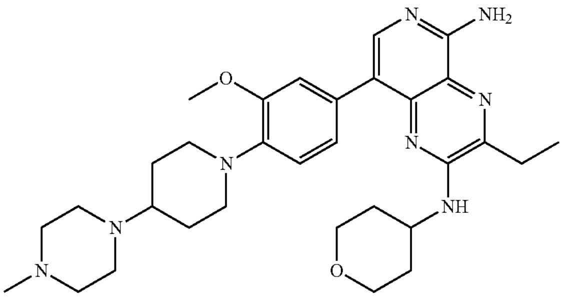 [SMILES: CCc1nc2c(N)ncc(-c3ccc(N4CCC(N5CCN(C)CC5)CC4)c(OC)c3)c2nc1NC1CCOCC1] |
| 14 | 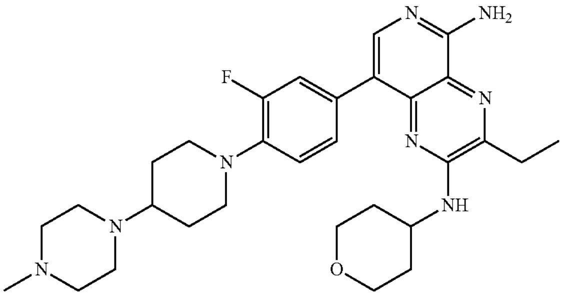 [SMILES: CCc1nc2c(N)ncc(-c3ccc(N4CCC(N5CCN(C)CC5)CC4)c(C)c3)c2nc1NC1CCOCC1] |
| 13 | 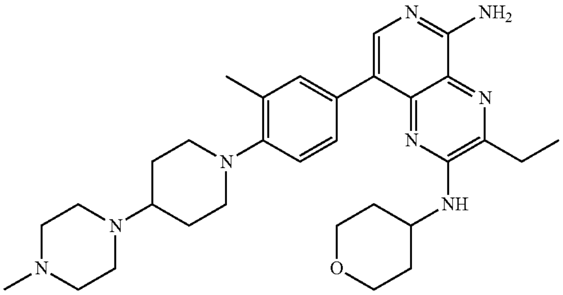 |
| 16 | 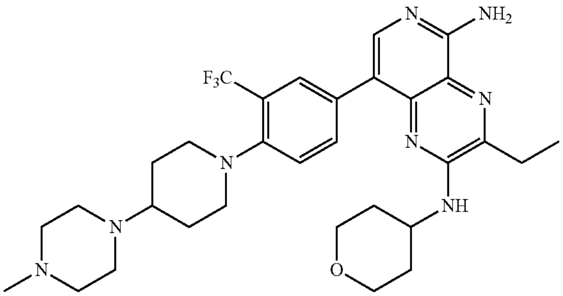 |
| 15 | 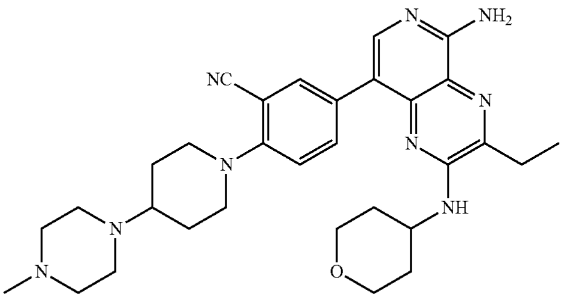 [SMILES: CCc1nc2c(N)ncc(-c3ccc(N4CCC(N5CCN(C)CC5)CC4)c(C#N)c3)c2nc1NC1CCOCC1] |

-continued
| No | structure |
|---|---|
| 18 | 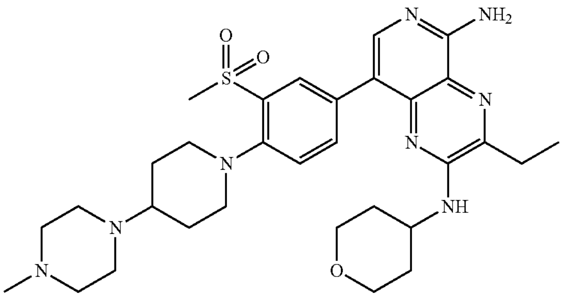 [SMILES: CCc1nc2c(N)ncc(-c3ccc(N4CCC(N5CCN(C)CC5)CC4)c(S(C)(=O)=O)c3)c2nc1NC1CCOCC1] |
| 17 | 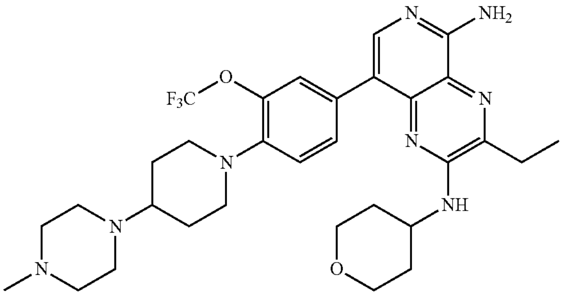 [SMILES: CCc1nc2c(N)ncc(-c3ccc(N4CCC(N5CCN(C)CC5)CC4)c(OC(F)(F)F)c3)c2nc1NC1CCOCC1] |
| 20 | 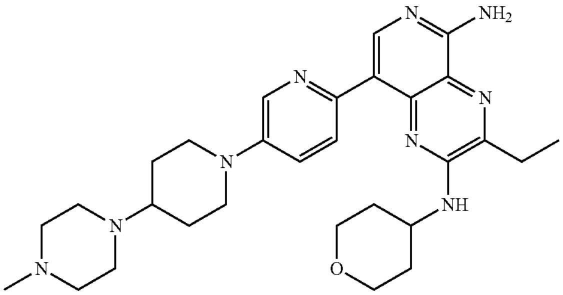 [SMILES: CCc1nc2c(N)ncc(-c3ccc(N4CCC(N5CCN(C)CC5)CC4)cn3)c2nc1NC1CCOCC1] |
| 19 | 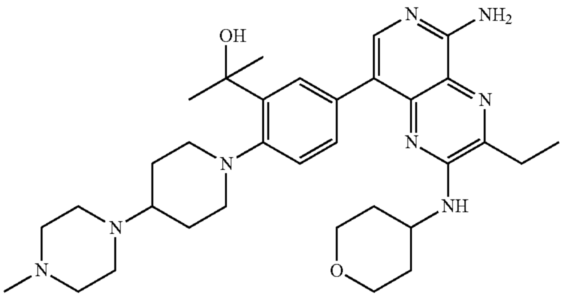 [SMILES: CCc1nc2c(N)ncc(-c3ccc(N4CCC(N5CCN(C)CC5)CC4)c(C(C)(C)O)c3)c2nc1NC1CCOCC1] |
| 22 | 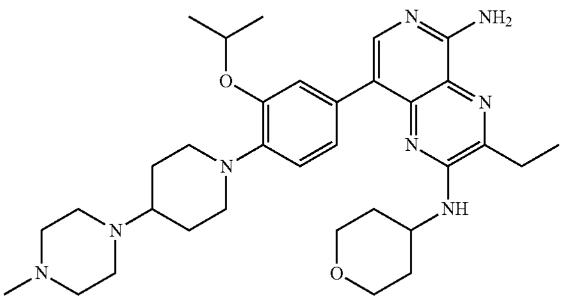 [SMILES: CCc1nc2c(N)ncc(-c3ccc(N4CCC(N5CCN(C)CC5)CC4)c(OC(C)C)c3)c2nc1NC1CCOCC1] |

-continued
| No | structure |
|---|---|
| 21 | 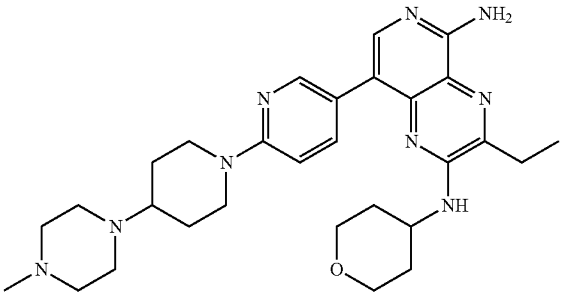 [SMILES: CCc1nc2c(N)ncc(-c3ccc(N4CCC(N5CCN(C)CC5)CC4)nc3)c2nc1NC1CCOCC1] |
| 24 | 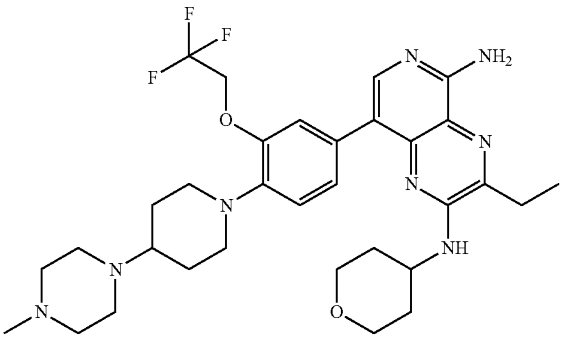 [SMILES: CCc1nc2c(N)ncc(-c3ccc(N4CCC(N5CCN(C)CC5)CC4)c(OCC(F)(F)F)c3)c2nc1NC1CCOCC1] |
| 23 | 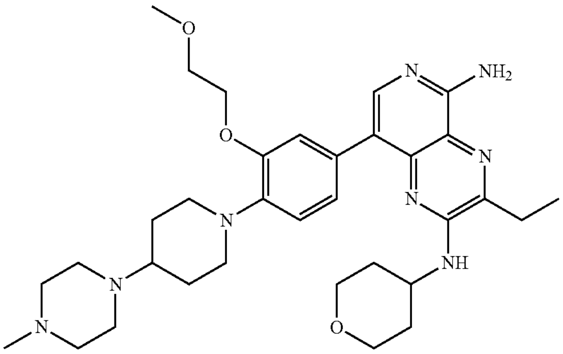 [SMILES: CCc1nc2c(N)ncc(-c3ccc(N4CCC(N5CCN(C)CC5)CC4)c(OCCOC)c3)c2nc1NC1CCOCC1] |
| 26 | 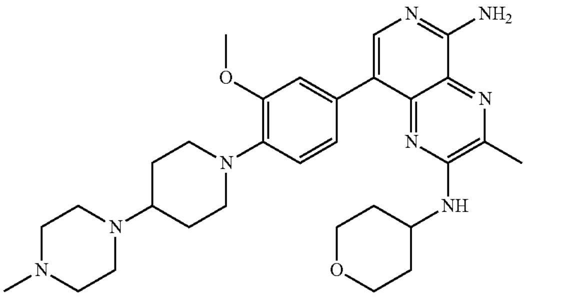 |
| 25 | 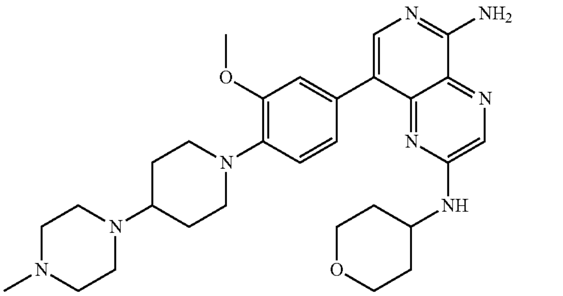 [SMILES: COc1cc(-c2cnc(N)c3ncc(NC4CCOCC4)nc23)ccc1N1CCC(N2CCN(C)CC2)CC1] |

-continued
| No | structure |
|---|---|
| 28 | 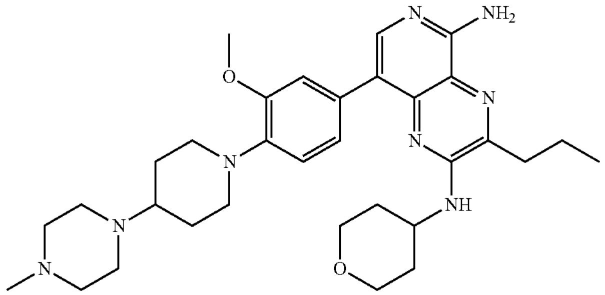 [SMILES: CCCc1nc2c(N)ncc(-c3ccc(N4CCC(N5CCN(C)CC5)CC4)c(OC)c3)c2nc1NC1CCOCC1] |
| 27 | 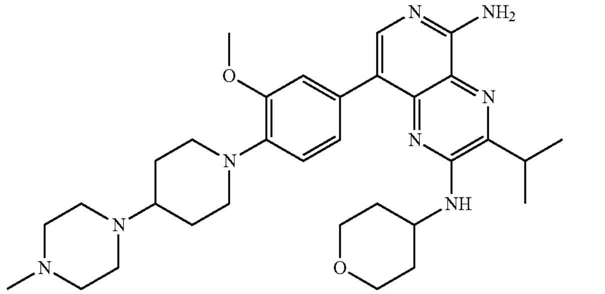 [SMILES: COc1cc(-c2cnc(N)c3nc(C(C)C)c(NC4CCOCC4)nc23)ccc1N1CCC(N2CCN(C)CC2)CC1] |
| 30 | 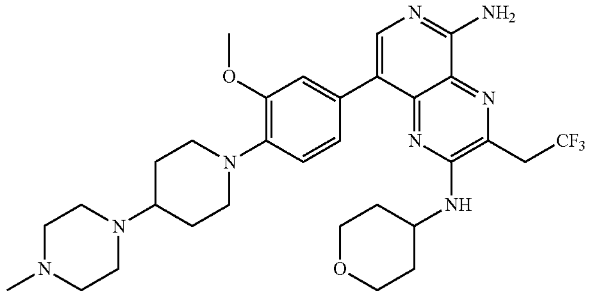 [SMILES: COc1cc(-c2cnc(N)c3nc(CC(F)(F)F)c(NC4CCOCC4)nc23)ccc1N1CCC(N2CCN(C)CC2)CC1] |
| 31 | 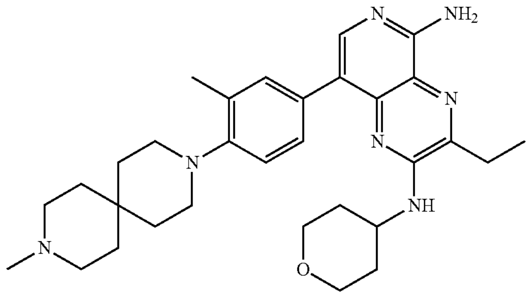 [SMILES: CCc1nc2c(N)ncc(-c3ccc(N4CCC5(CCN(C)CC5)CC4)c(C)c3)c2nc1NC1CCOCC1] |
| 32 | 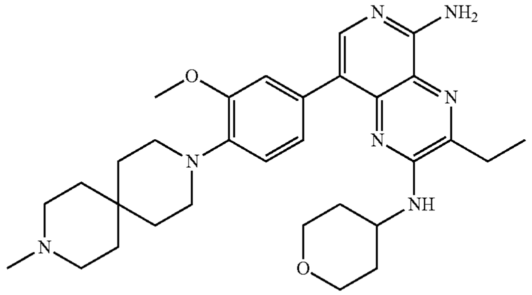 [SMILES: CCc1nc2c(N)ncc(-c3ccc(N4CCC5(CCN(C)CC5)CC4)c(OC)c3)c2nc1NC1CCOCC1] |

-continued
| No | structure |
|---|---|
| 33 | 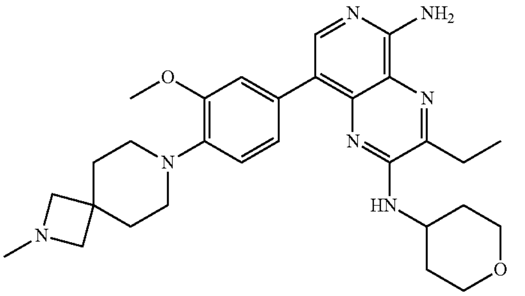 [SMILES: CCc1nc2c(N)ncc(-c3ccc(N4CCC5(CC4)CN(C)C5)c(OC)c3)c2nc1NC1CCOCC1] |
| 34 | 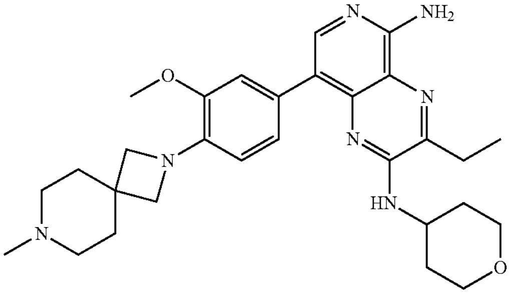 [SMILES: CCc1nc2c(N)ncc(-c3ccc(N4CC5(CCN(C)CC5)C4)c(OC)c3)c2nc1NC1CCOCC1] |
| 35 | 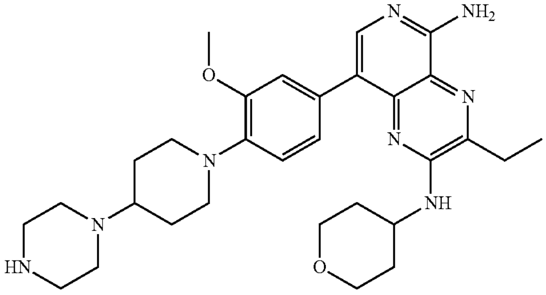 [SMILES: CCc1nc2c(N)ncc(-c3ccc(N4CCC(N5CCNCC5)CC4)c(OC)c3)c2nc1NC1CCOCC1] |
| 36 | 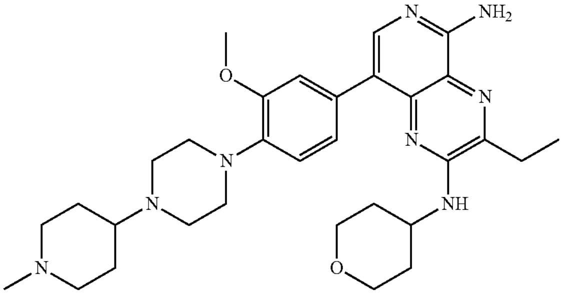 [SMILES: CCc1nc2c(N)ncc(-c3ccc(N4CCN(C5CCN(C)CC5)CC4)c(OC)c3)c2nc1NC1CCOCC1] |
| 37 | 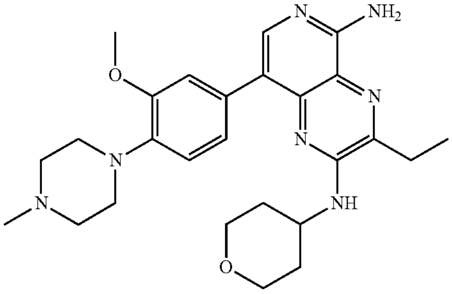 [SMILES: CCc1nc2c(N)ncc(-c3ccc(N4CCN(C)CC4)c(OC)c3)c2nc1NC1CCOCC1] |

-continued
| No | structure |
| --- | --- |
| 38 | 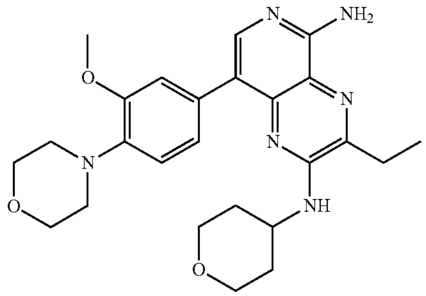 [SMILES: CCc1nc2c(N)ncc(-c3ccc(N4CCOCC4)c(OC)c3)c2nc1NC1CCOCC1] |
| 39 | 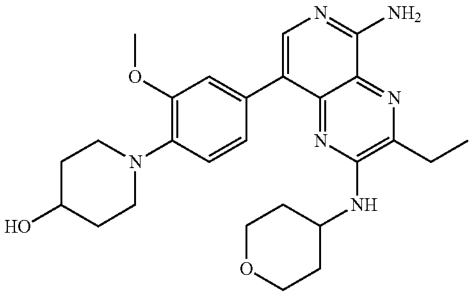 [SMILES: CCc1nc2c(N)ncc(-c3ccc(N4CCC(O)CC4)c(OC)c3)c2nc1NC1CCOCC1] |
| 40 | 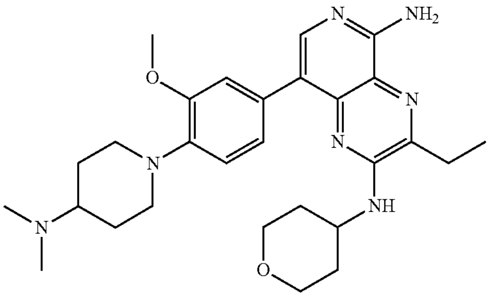 [SMILES: CCc1nc2c(N)ncc(-c3ccc(N4CCC(N(C)C)CC4)c(OC)c3)c2nc1NC1CCOCC1] |
| 41 | 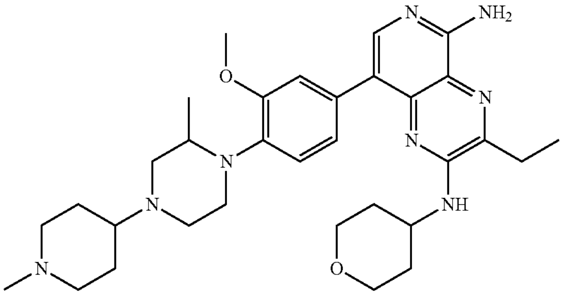 |
| 42 | 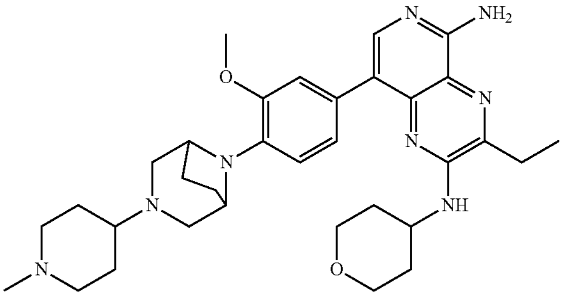 [SMILES: CCc1nc2c(N)ncc(-c3ccc(N4C5CCC4CN(C4CCN(C)CC4)C5)c(OC)c3)c2nc1NC1CCOCC1] |

-continued
| No | structure |
|---|---|
| 43 | 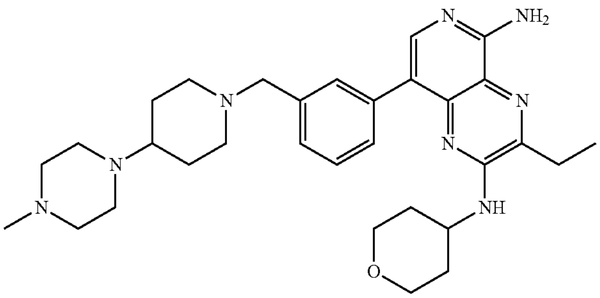 [SMILES: CCc1nc2c(N)ncc(-c3cccc(CN4CCC(N5CCN(C)CC5)CC4)c3)c2nc1NC1CCOCC1] |
| 44 | 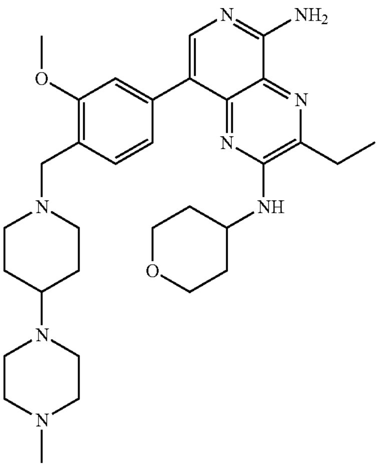 [SMILES: CCc1nc2c(N)ncc(-c3ccc(CN4CCC(N5CCN(C)CC5)CC4)c(OC)c3)c2nc1NC1CCOCC1] |
| 47 | 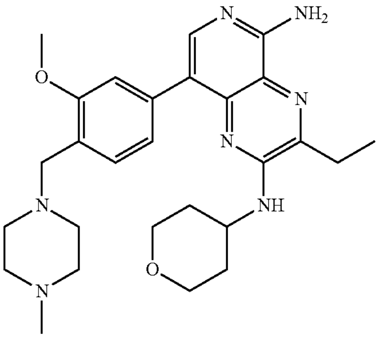 [SMILES: CCc1nc2c(N)ncc(-c3ccc(CN4CCN(C)CC4)c(OC)c3)c2nc1NC1CCOCC1] |
| 46 | 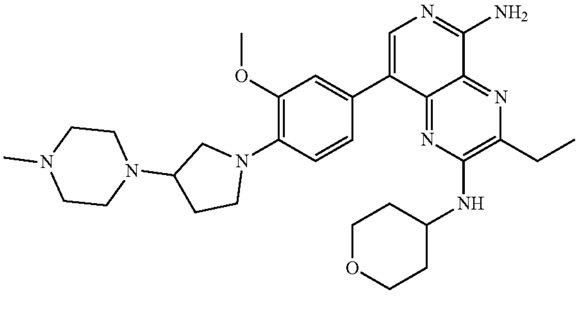 [SMILES: CCc1nc2c(N)ncc(-c3ccc(N4CCC(N5CCN(C)CC5)C4)c(OC)c3)c2nc1NC1CCOCC1] |

-continued
| No | structure |
|---|---|
| 49 | 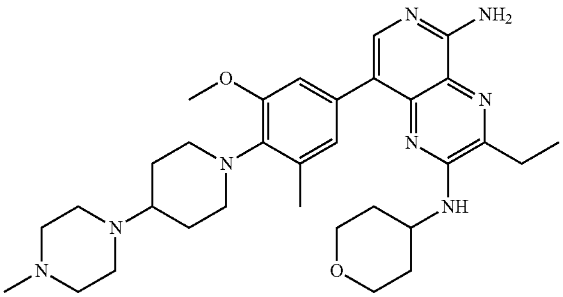 [SMILES: CCc1nc2c(N)ncc(-c3cc(C)c(N4CCC(N5CCN(C)CC5)CC4)c(OC)c3)c2nc1NC1CCOCC1] |
| 57 | 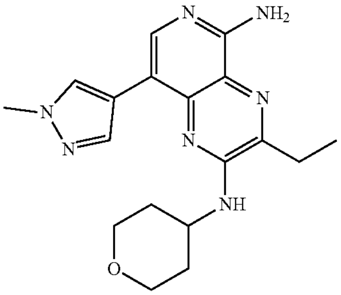 [SMILES: CCc1nc2c(N)ncc(-c3cnn(C)c3)c2nc1NC1CCOCC1] |
| 63 | 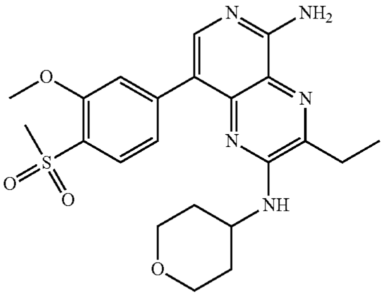 [SMILES: CCc1nc2c(N)ncc(-c3ccc(S(C)(=O)=O)c(OC)c3)c2nc1NC1CCOCC1] |
| 58 | 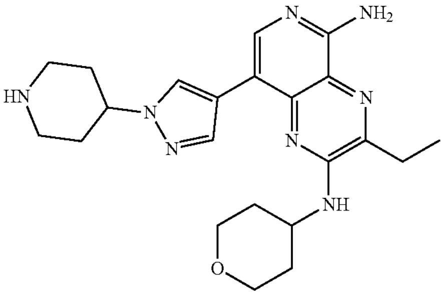 [SMILES: CCc1nc2c(N)ncc(-c3cnn(C4CCNCC4)c3)c2nc1NC1CCOCC1] |
| 65 | 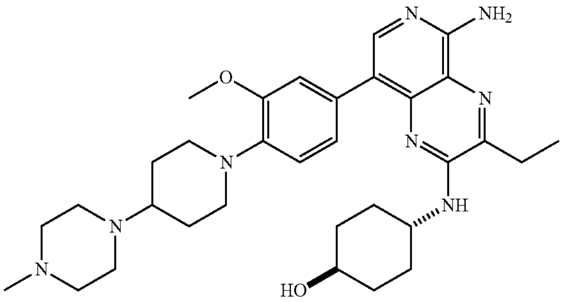 |

-continued
| No | structure |
|---|---|
| 64 | 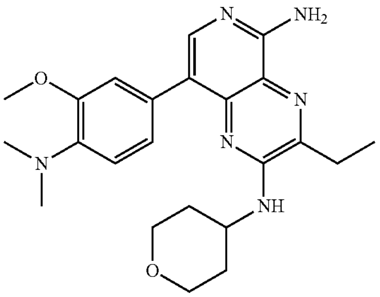 |
| 67 | 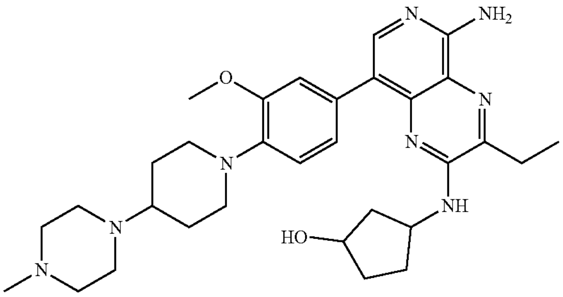 [SMILES: CCc1nc2c(N)ncc(-c3ccc(N4CCC(N5CCN(C)CC5)CC4)c(OC)c3)c2nc1NC1CCC(O)C1] |
| 66 | 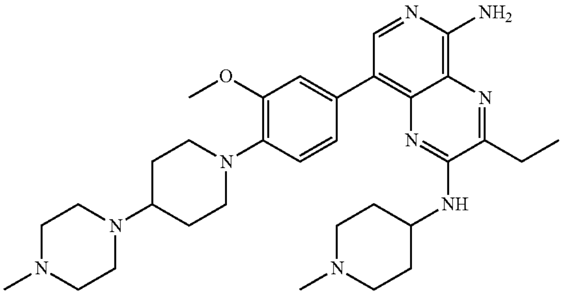 [SMILES: CCc1nc2c(N)ncc(-c3ccc(N4CCC(N5CCN(C)CC5)CC4)c(OC)c3)c2nc1NC1CCN(C)CC1] |
| 69 | 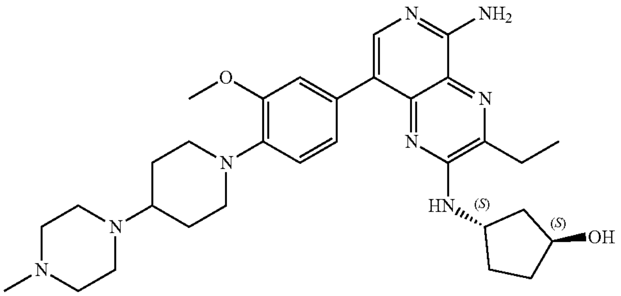 |
| 68 | 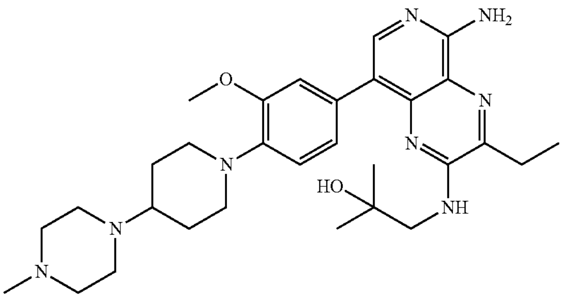 [SMILES: CCc1nc2c(N)ncc(-c3ccc(N4CCC(N5CCN(C)CC5)CC4)c(OC)c3)c2nc1NCC(C)(C)O] |

-continued
| No | structure |
|---|---|
| 71 | 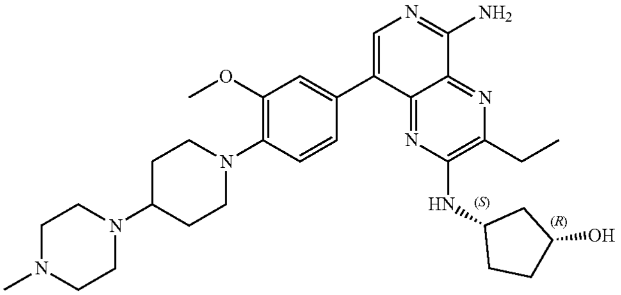 |
| 70 | 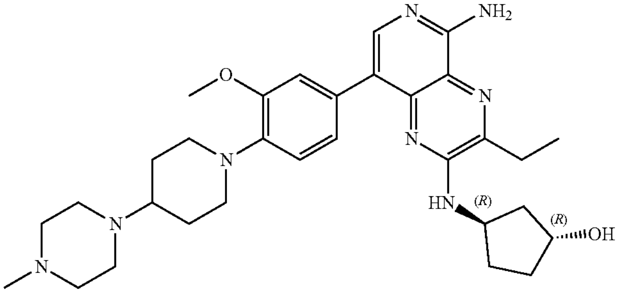 |
| 76 | 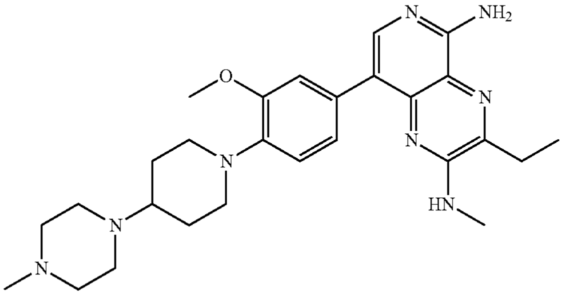 [SMILES: CCc1nc2c(N)ncc(-c3ccc(N4CCC(N5CCN(C)CC5)CC4)c(OC)c3)c2nc1NC] |
| 72 | 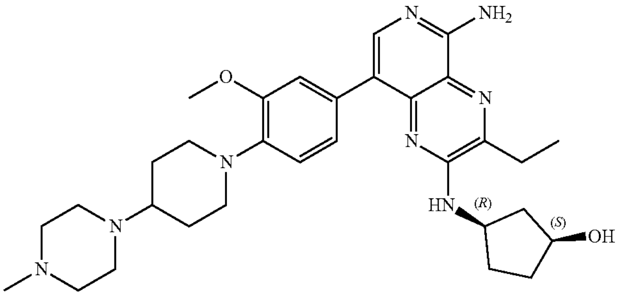 |
| 78 | 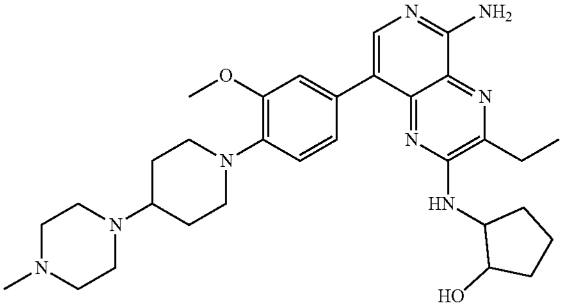 [SMILES: CCc1nc2c(N)ncc(-c3ccc(N4CCC(N5CCN(C)CC5)CC4)c(OC)c3)c2nc1NC1CCCC1O] |

-continued
| No | structure |
|---|---|
| 77 | 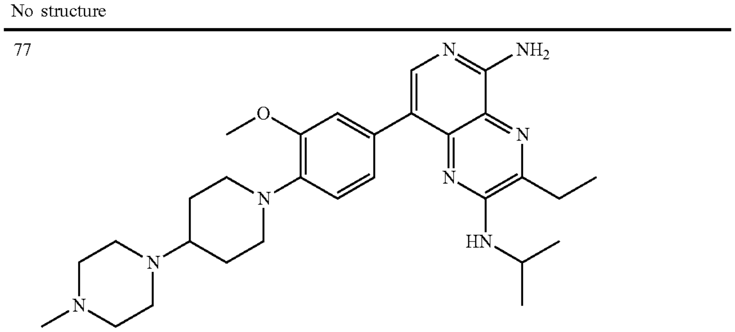 |
| 80 | 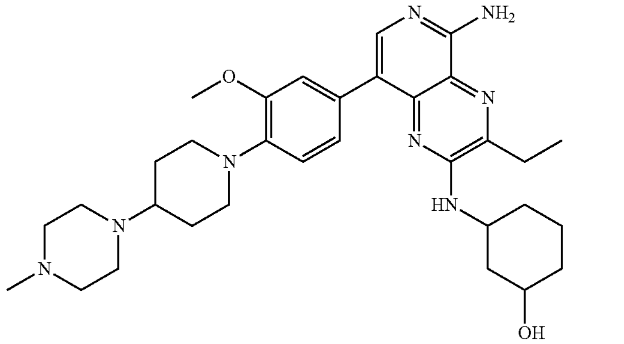 [SMILES: CCc1nc2c(N)ncc(-c3ccc(N4CCC(N5CCN(C)CC5)CC4)c(OC)c3)c2nc1NC1CCCC(O)C1] |
| 79 | 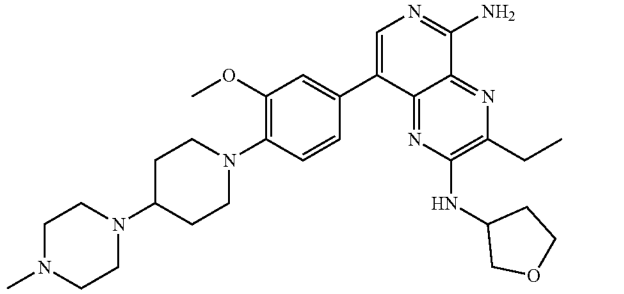 |
| 82 | 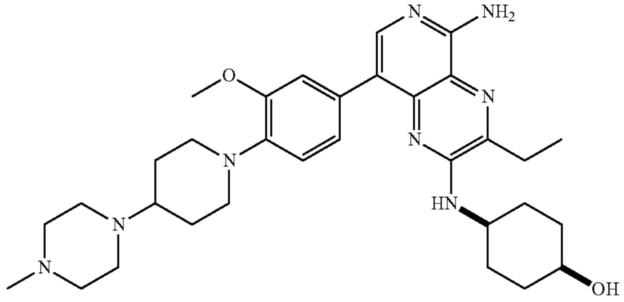 |
| 81 | 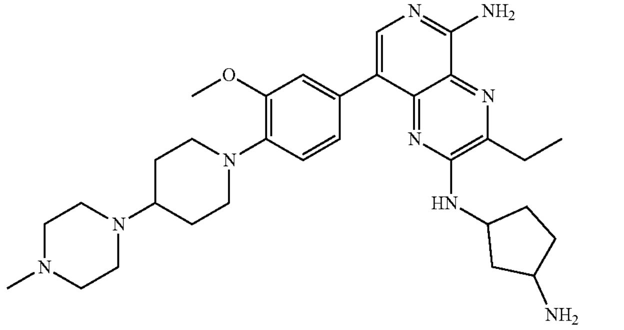 [SMILES: CCc1nc2c(N)ncc(-c3ccc(N4CCC(N5CCN(C)CC5)CC4)c(OC)c3)c2nc1NC1CCC(N)C1] |

-continued
| No | structure |
|---|---|
| 84 | 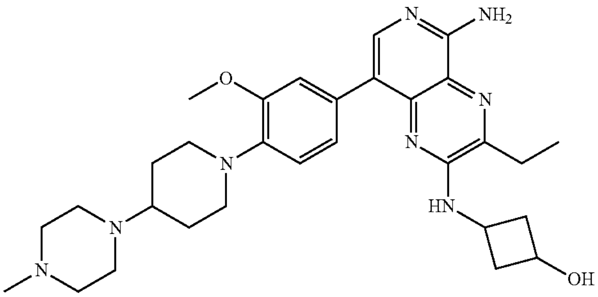 [SMILES: CCc1nc2c(N)ncc(-c3ccc(N4CCC(N5CCN(C)CC5)CC4)c(OC)c3)c2nc1NC1CC(O)C1] |
| 83 | 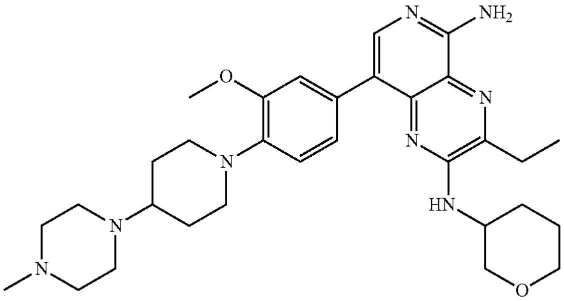 [SMILES: CCc1nc2c(N)ncc(-c3ccc(N4CCC(N5CCN(C)CC5)CC4)c(OC)c3)c2nc1NC1CCCOC1] |
| 88 | 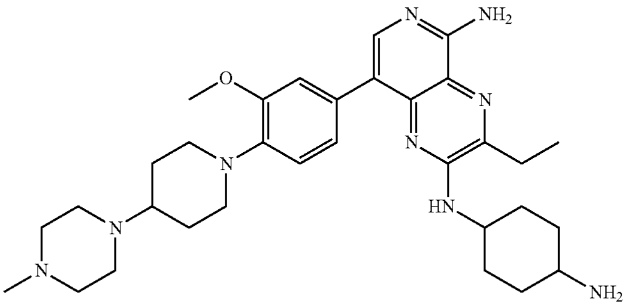 [SMILES: CCc1nc2c(N)ncc(-c3ccc(N4CCC(N5CCN(C)CC5)CC4)c(OC)c3)c2nc1NC1CCC(N)CC1] |
| 85 | 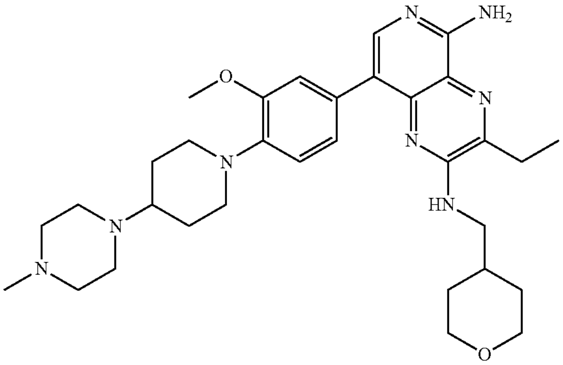 [SMILES: CCc1nc2c(N)ncc(-c3ccc(N4CCC(N5CCN(C)CC5)CC4)c(OC)c3)c2nc1NCC1CCOCC1] |

-continued
| No | structure |
|---|---|
| 90 | 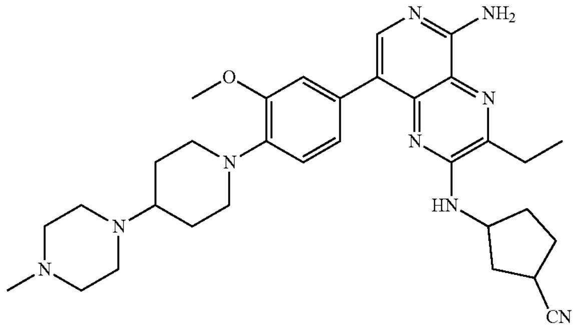 [SMILES: CCc1nc2c(N)ncc(-c3ccc(N4CCC(N5CCN(C)CC5)CC4)c(OC)c3)c2nc1NC1CCC(C#N)C1] |
| 87 | 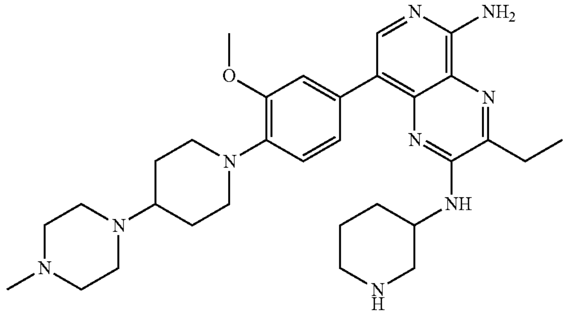 [SMILES: CCc1nc2c(N)ncc(-c3ccc(N4CCC(N5CCN(C)CC5)CC4)c(OC)c3)c2nc1NC1CCCNC1] |
| 92 | 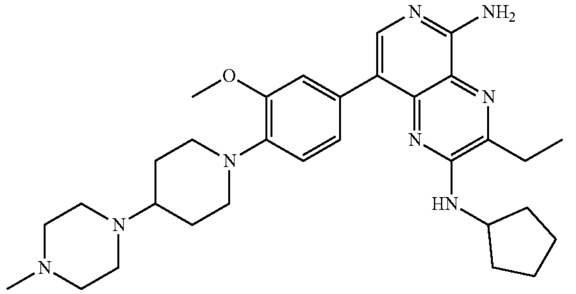 |
| 89 | 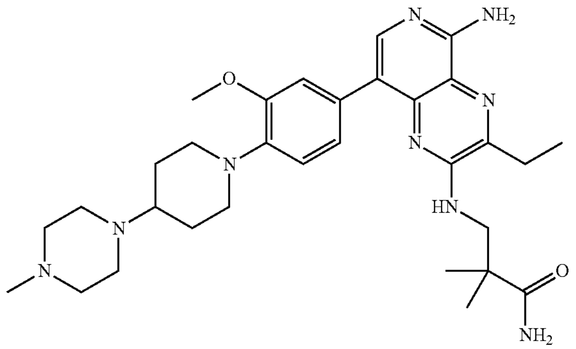 [SMILES: CCc1nc2c(N)ncc(-c3ccc(N4CCC(N5CCN(C)CC5)CC4)c(OC)c3)c2nc1NCC(C)(C)C(N)=O] |

-continued
| No | structure |
|---|---|
| 135 | 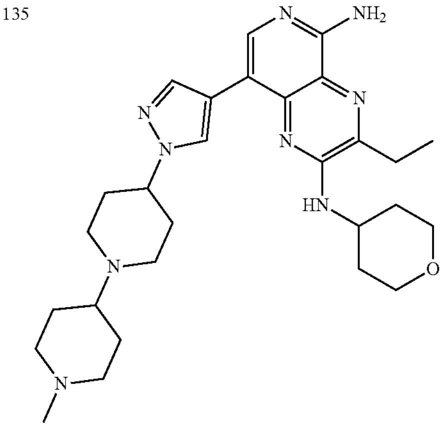 |
| 91 | 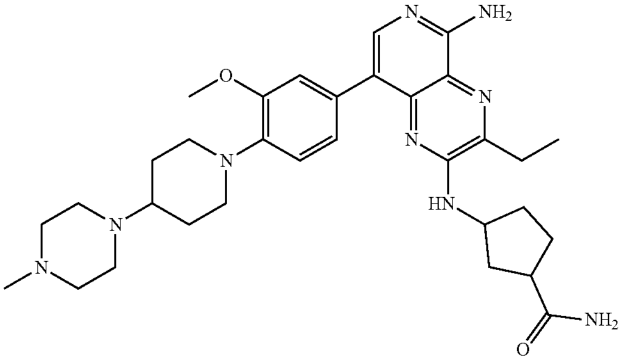 [SMILES: CCc1nc2c(N)ncc(-c3ccc(N4CCC(N5CCN(C)CC5)CC4)c(OC)c3)c2nc1NC1CCC(C(N)=O)C1] |
| 137 | 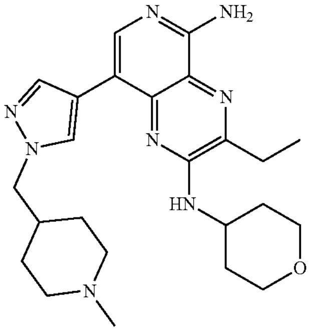 [SMILES: CCc1nc2c(N)ncc(-c3cnn(CC4CCN(C)CC4)c3)c2nc1NC1CCOCC1] |
| 93 | 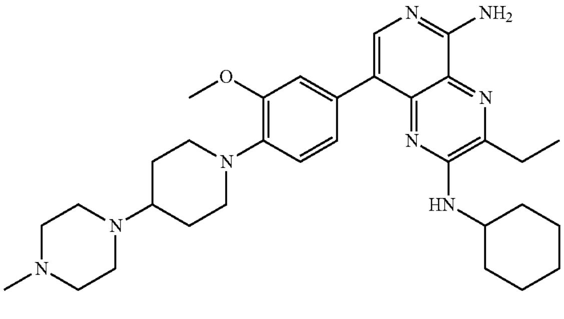 [SMILES: CCc1nc2c(N)ncc(-c3ccc(N4CCC(N5CCN(C)CC5)CC4)c(OC)c3)c2nc1NC1CCCCC1] |

-continued
| No | structure |
|---|---|
| 139 | 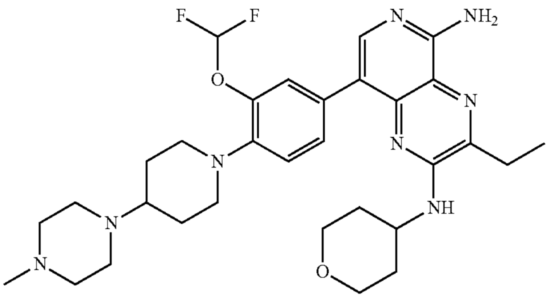 [SMILES: CCc1nc2c(N)ncc(-c3ccc(N4CCC(N5CCN(C)CC5)CC4)c(OC(F)F)c3)c2nc1NC1CCOCC1] |
| 121 | 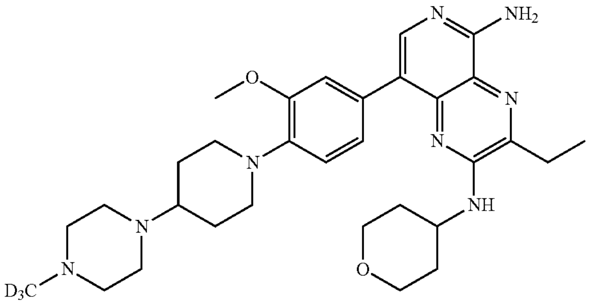 [SMILES: [2H]C([2H])([2H])N1CCN(C2CCN(c3ccc(-c4cnc(N)c5nc(CC)c(NC6CCOCC6)nc45)cc3OC)CC2)CC1] |
| 154 | 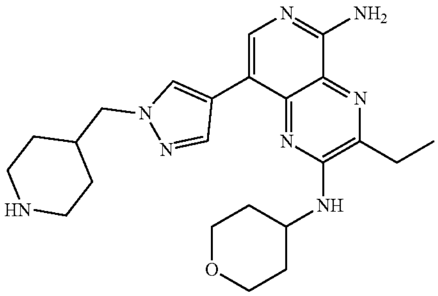 [SMILES: CCc1nc2c(N)ncc(-c3cnn(CC4CCNCC4)c3)c2nc1NC1CCOCC1] |
| 134 | 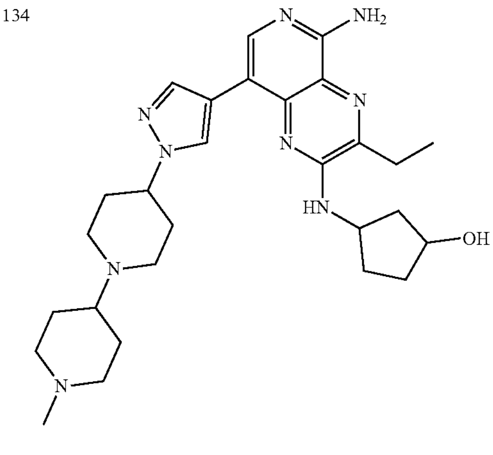 |

-continued
| No | structure |
|---|---|
| 156 | 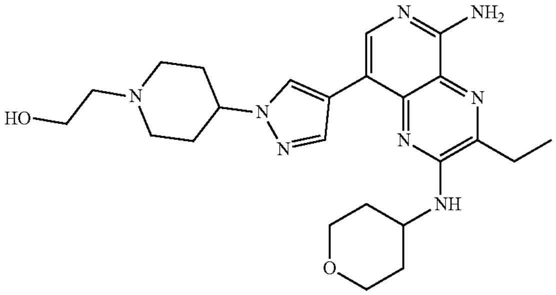 [SMILES: CCc1nc2c(N)ncc(-c3cnn(C4CCN(CCO)CC4)c3)c2nc1NC1CCOCC1] |
| 136 | 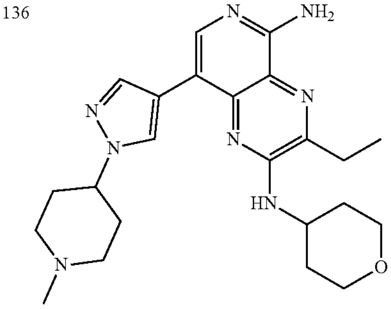 |
| 160 | 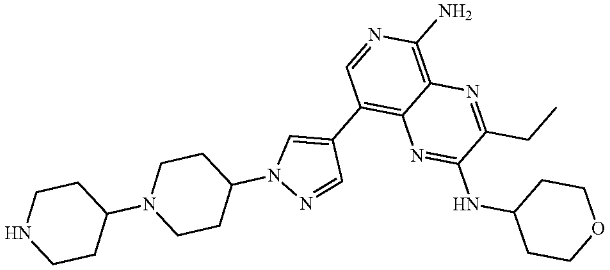 [SMILES: CCc1nc2c(N)ncc(-c3cnn(C4CCN(C5CCNCC5)CC4)c3)c2nc1NC1CCOCC1] |
| 138 | 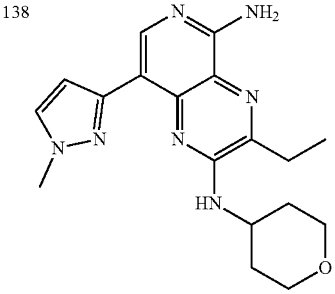 |
| 162 | 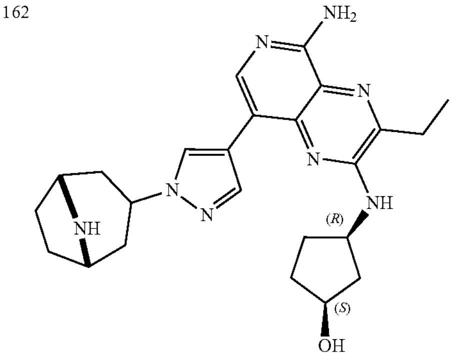 |

-continued
| No | structure |
|---|---|
| 155 | 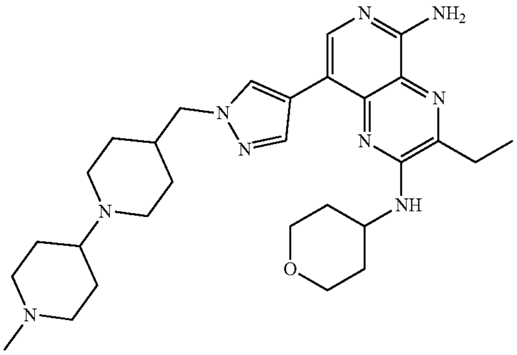 [SMILES: CCc1nc2c(N)ncc(-c3cnn(CC4CCN(C5CCN(C)CC5)CC4)c3)c2nc1NC1CCOCC1] |
| 164 | 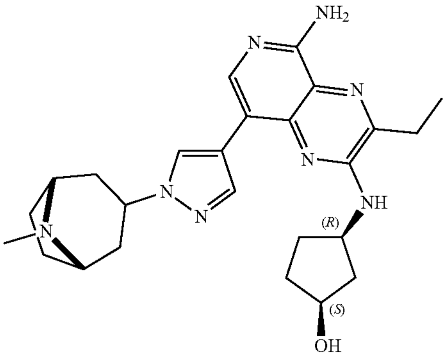 |
| 159 | 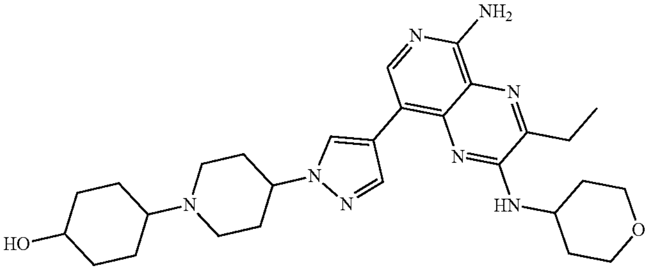 [SMILES: CCc1nc2c(N)ncc(-c3cnn(C4CCN(C5CCC(O)CC5)CC4)c3)c2nc1NC1CCOCC1] |
| 166 | 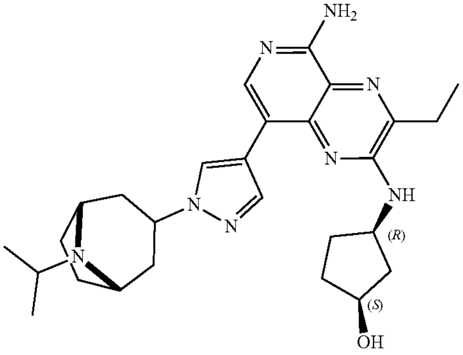 |

-continued
| No | structure |
|---|---|
| 163 | 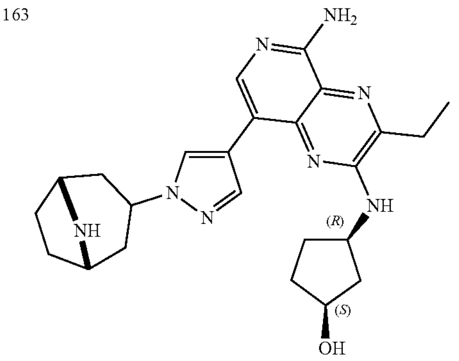 |
| 168 | 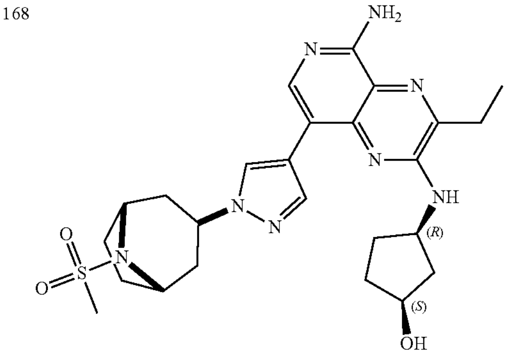 |
| 165 | 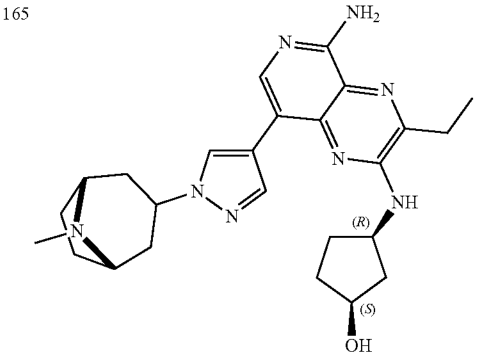 |
| 170 | 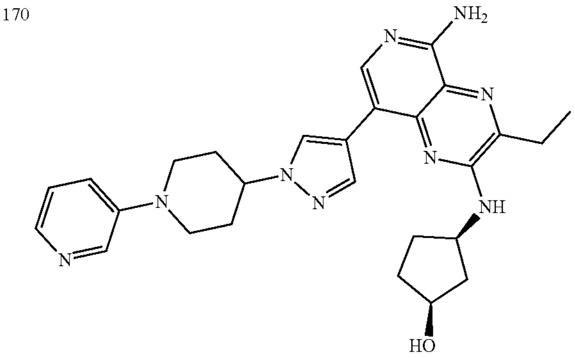 |

-continued
| No | structure |
|---|---|
| 167 | 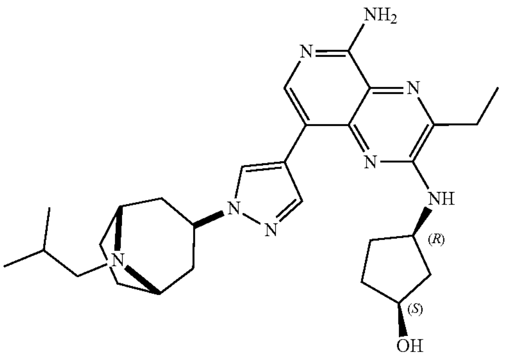 |
| 172 | 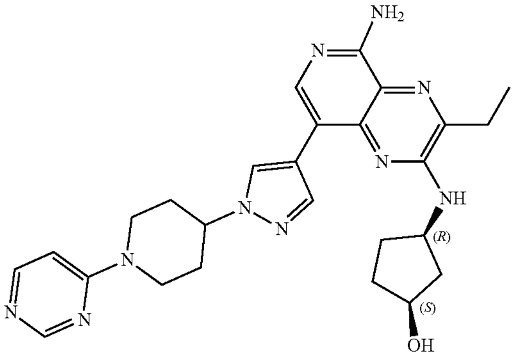 |
| 169 | 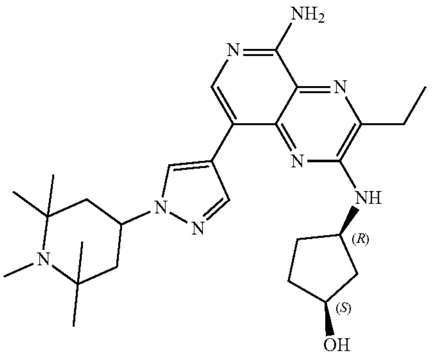 |
| 174 | 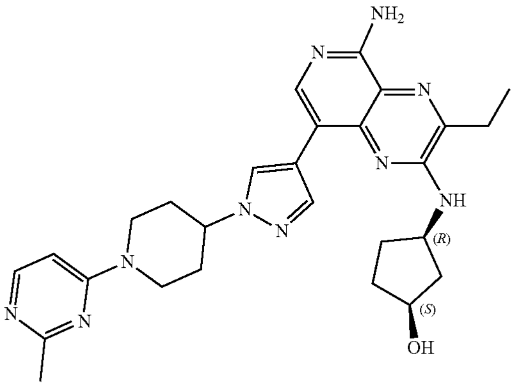 |

-continued
| No | structure |
|---|---|
| 171 | 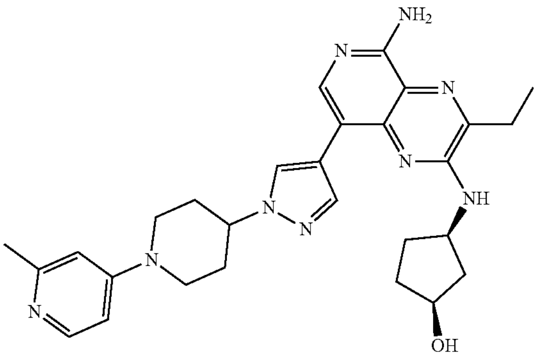 [SMILES: CCc1nc2c(N)ncc(-c3cnn(C4CCN(c5ccnc(C)c5)CC4)c3)c2nc1N[C@@H]1CC[C@H](O)C1] |
| 176 | 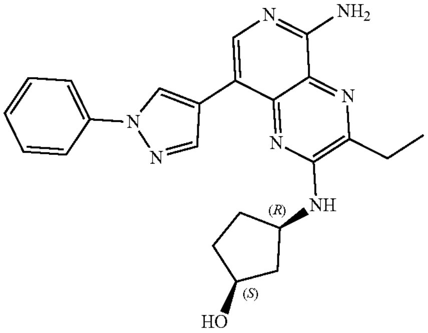 |
| 173 | 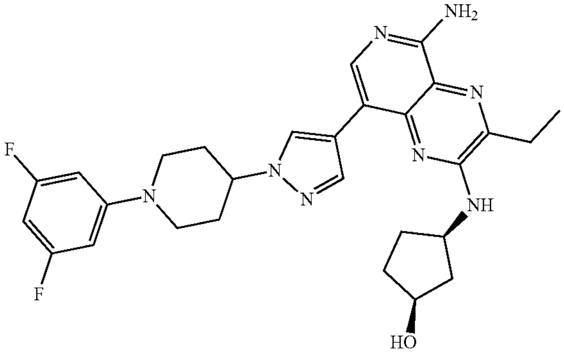 [SMILES: CCc1nc2c(N)ncc(-c3cnn(C4CCN(c5cc(F)cc(F)c5)CC4)c3)c2nc1N[C@@H]1CC[C@H](O)C1] |
| 178 | 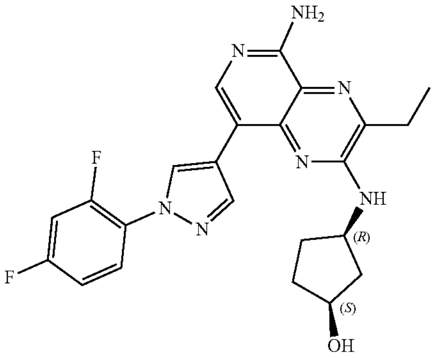 |

-continued
| No | structure |
|---|---|
| 175 | 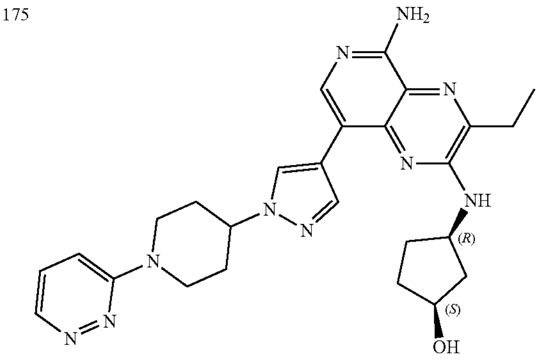 |
| 180 | 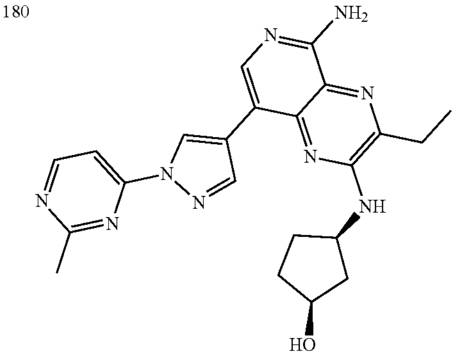 |
| 177 | 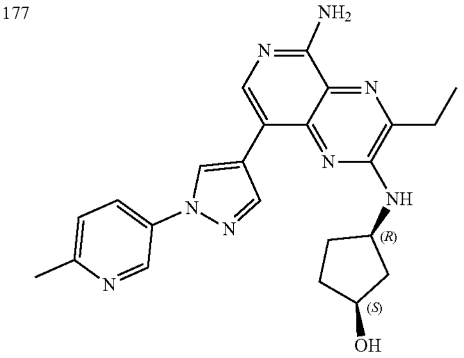 |
| 182 | 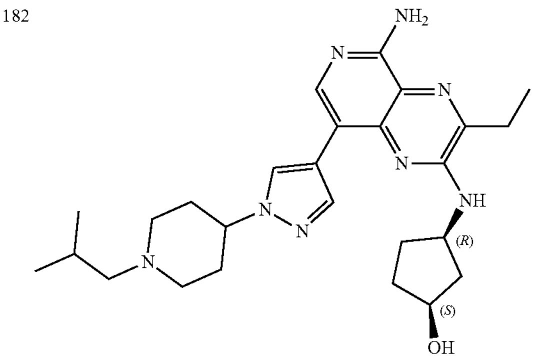 |

-continued
| No | structure |
|---|---|
| 179 | 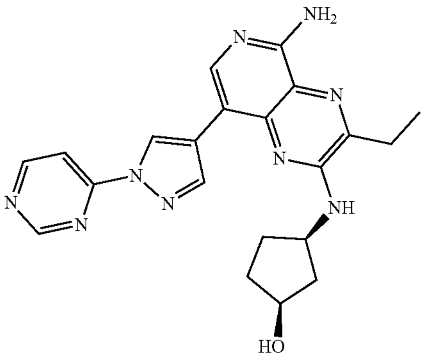 [SMILES: CCc1nc2c(N)ncc(-c3cnn(-c4ccncn4)c3)c2nc1N[C@@H]1CC[C@H](O)C1] |
| 184 | 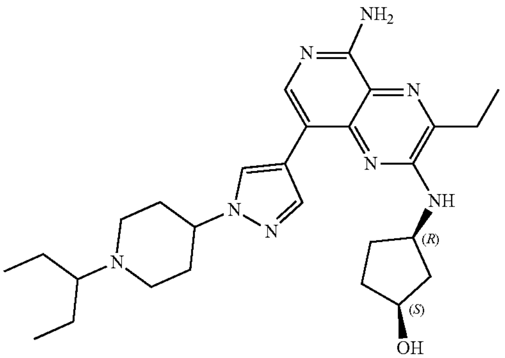 |
| 181 | 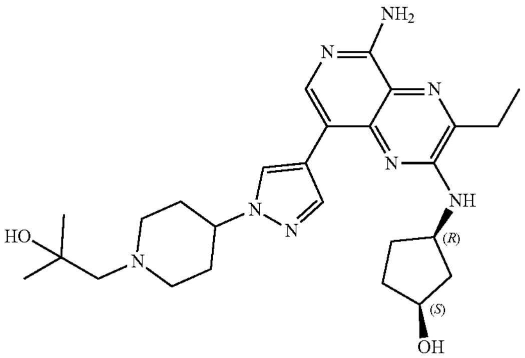 |
| 186 | 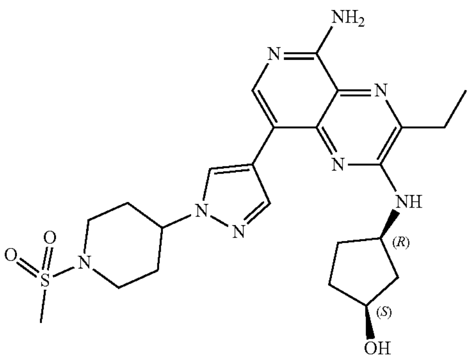 |

-continued
| No | structure |
|---|---|
| 183 | 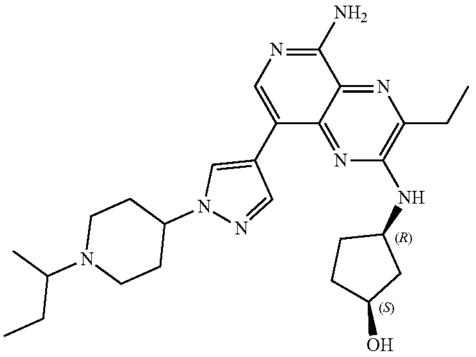 |
| 188 | 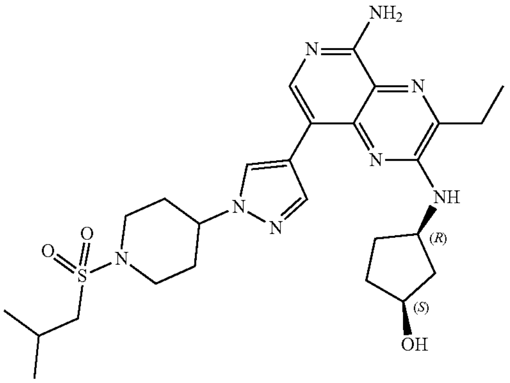 |
| 185 | 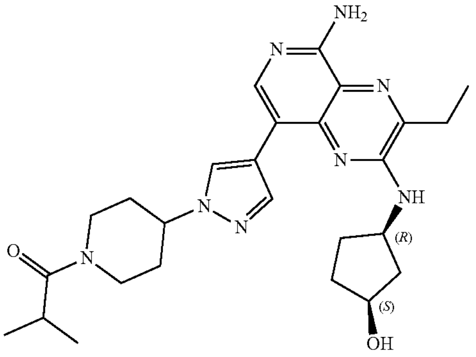 |
| 190 | 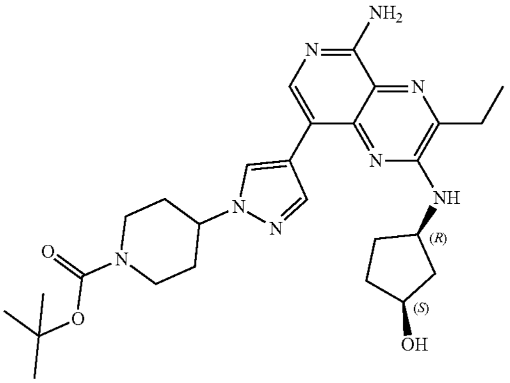 |

-continued
| No | structure |
| --- | --- |
| 187 | 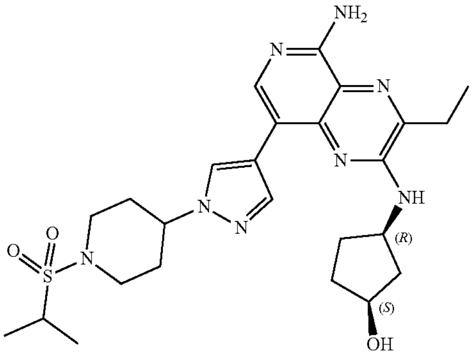 |
| 192 | 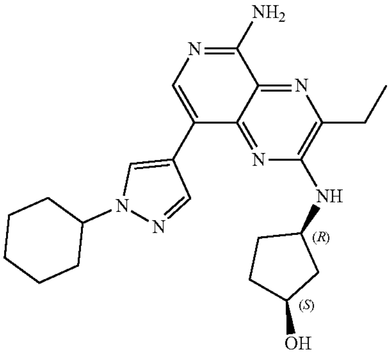 |
| 189 | 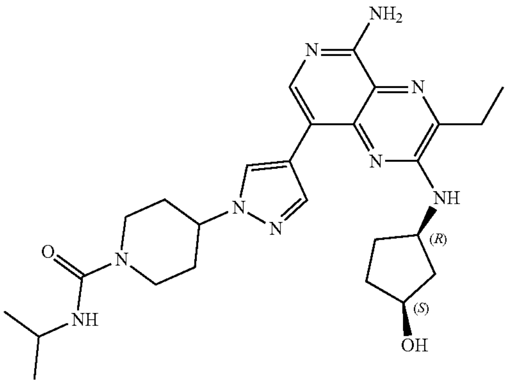 |
| 194 | 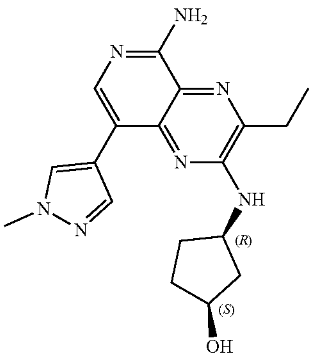 |

-continued
| No | structure |
|---|---|
| 191 | 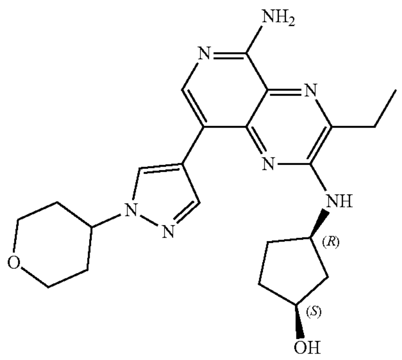 |
| 196 | 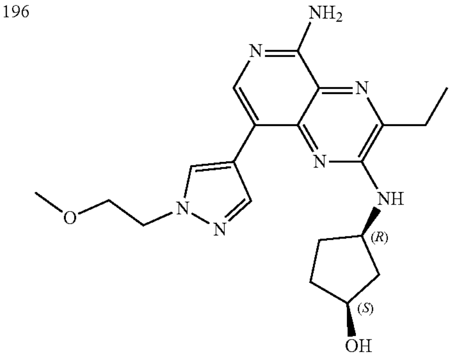 |
| 193 | 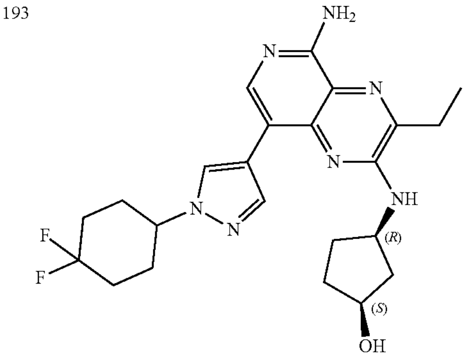 |
| 198 | 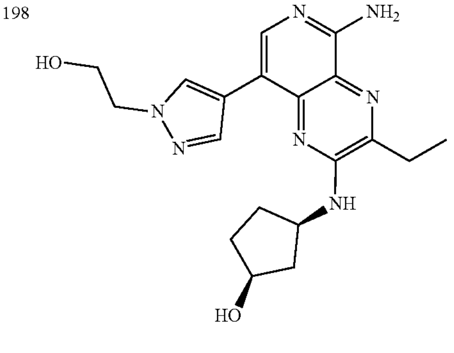 |

-continued
| No | structure |
|---|---|
| 195 | 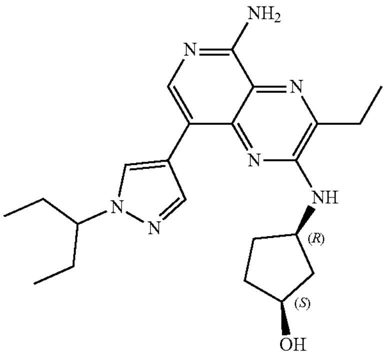 |
| 200 | 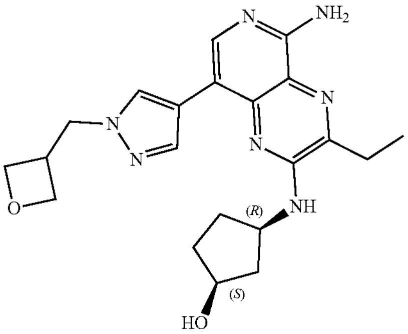 |
| 197 | 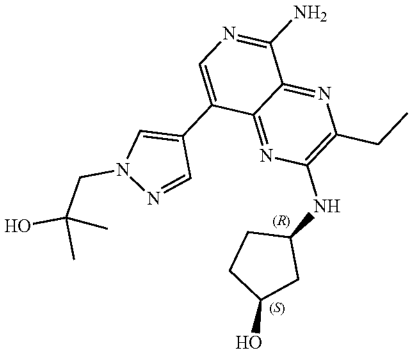 |
| 202 | 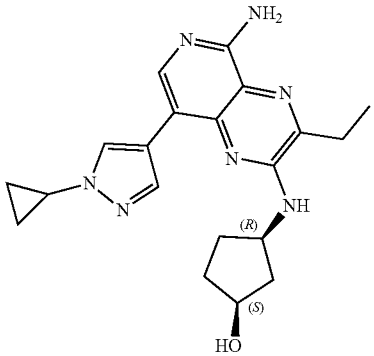 |

-continued
| No | structure |
| --- | --- |
| 199 | 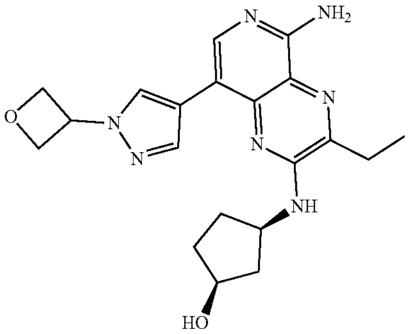 [SMILES: CCc1nc2c(N)ncc(-c3cnn(C4COC4)c3)c2nc1N[C@@H]1CC[C@H](O)C1] |
| 204 | 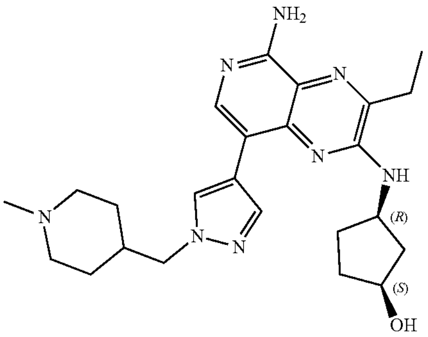 |
| 201 | 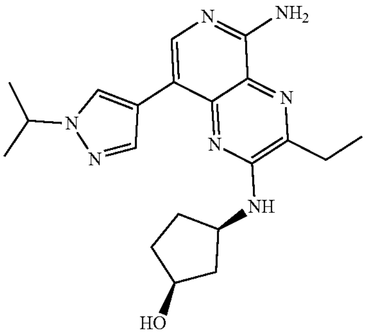 [SMILES: CCc1nc2c(N)ncc(-c3cnn(C(C)C)c3)c2nc1N[C@@H]1CC[C@H](O)C1] |
| 206 | 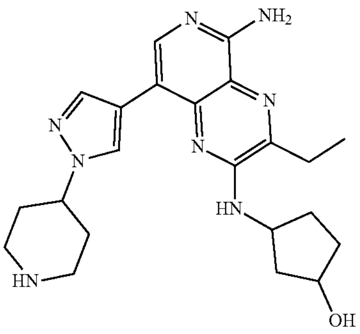 [SMILES: CCc1nc2c(N)ncc(-c3cnn(C4CCNCC4)c3)c2nc1NC1CCC(O)C1] |

-continued
| No | structure |
|---|---|
| 203 | 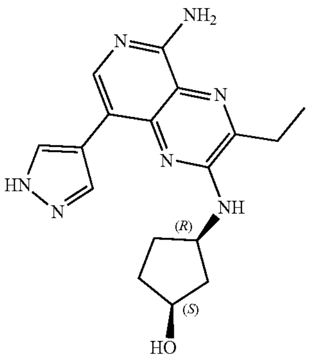 |
| 208 | 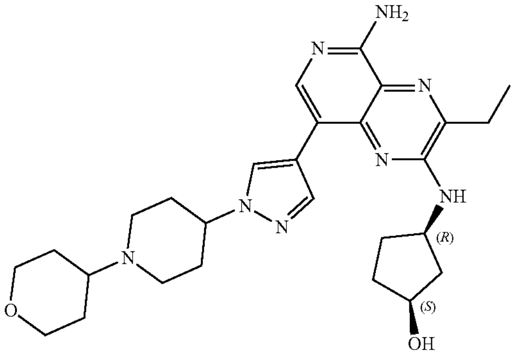 |
| 205 | 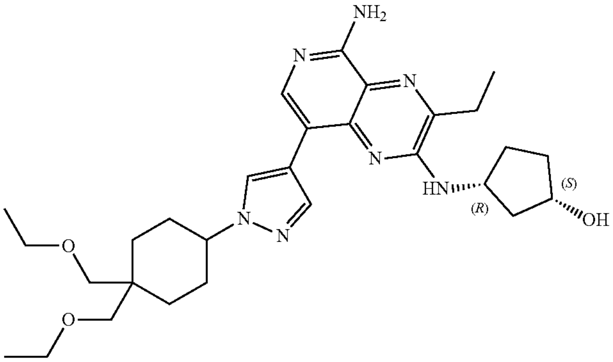 |
| 210 | 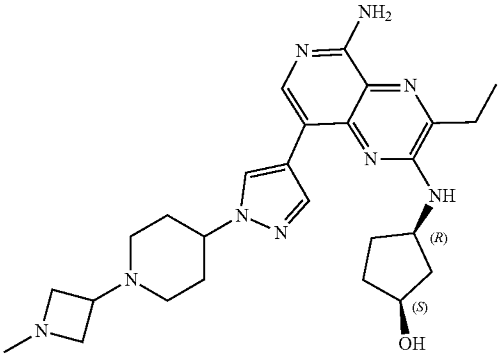 |

-continued
| No | structure |
|---|---|
| 207 | 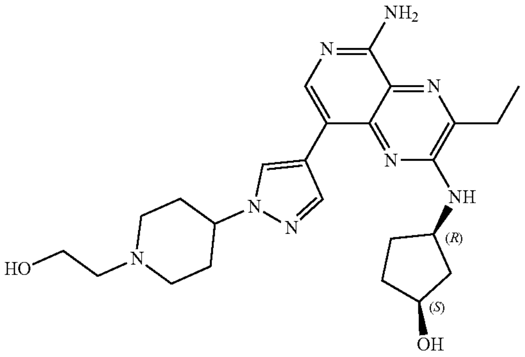 |
| 212 | 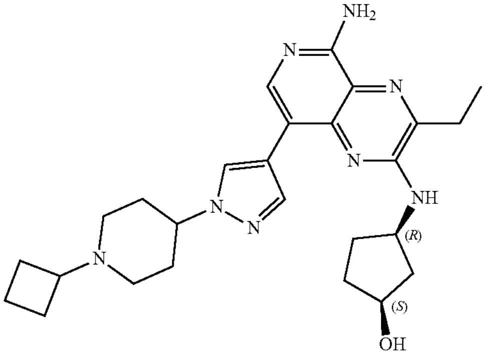 |
| 209 | 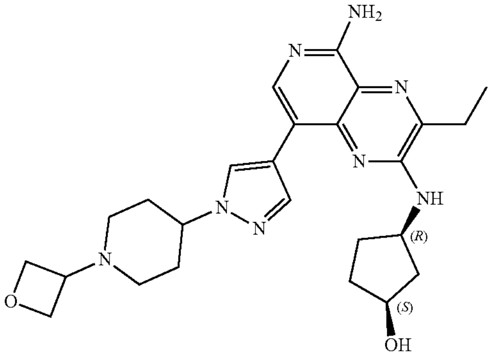 |
| 214 | 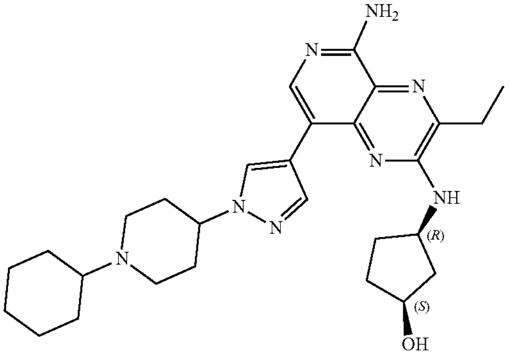 |

-continued
| No | structure |
|---|---|
| 211 | 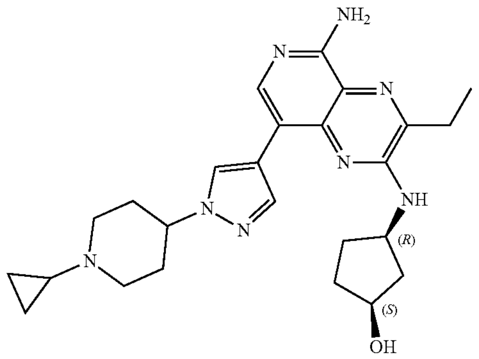 |
| 216 | 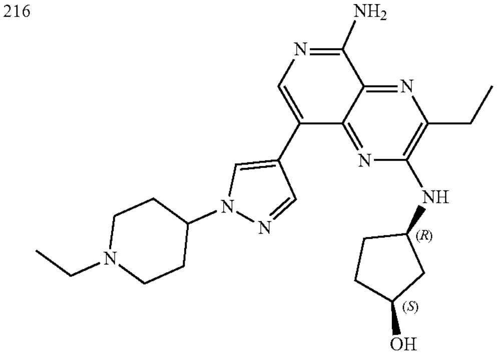 |
| 213 | 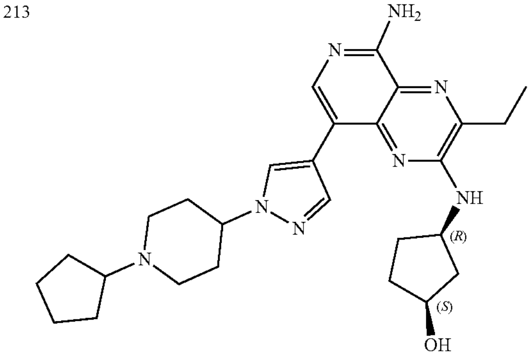 |
| 218 | 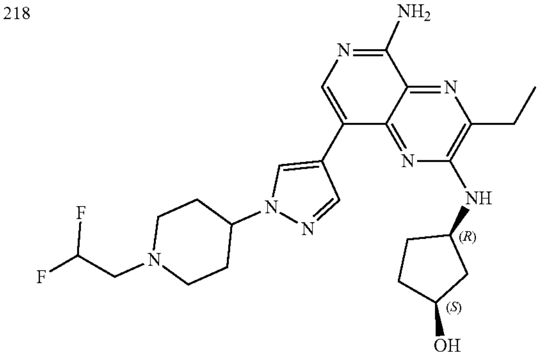 |

-continued
| No | structure |
|---|---|
| 215 | 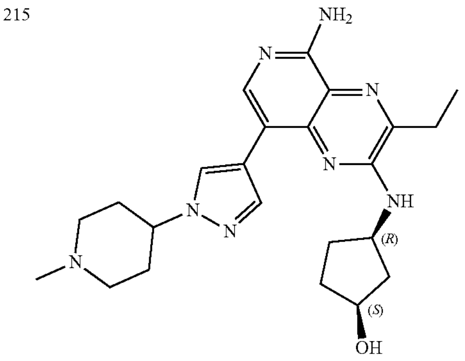 |
| 220 | 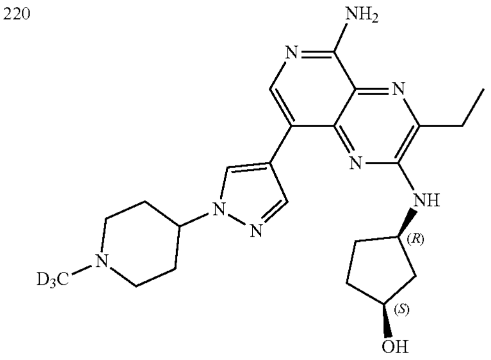 |
| 217 | 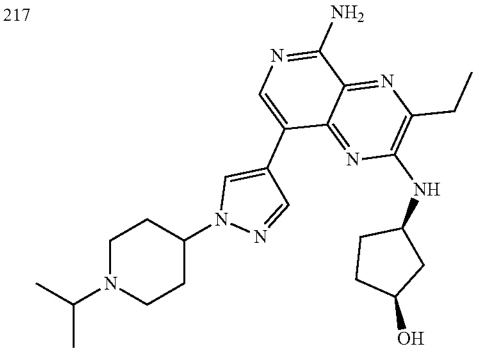 |
| 222 | 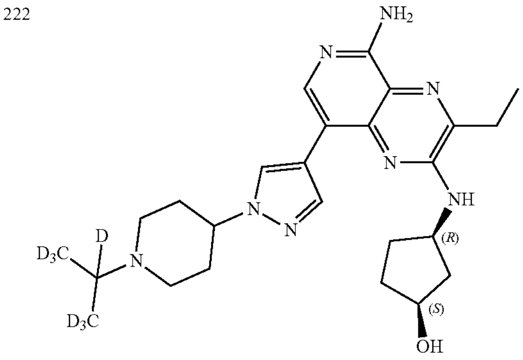 |

-continued
| No | structure |
|---|---|
| 219 | 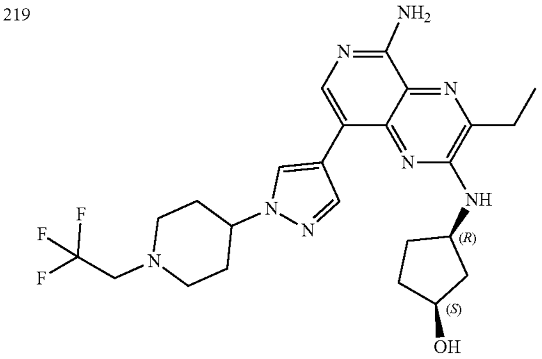 |
| 224 | 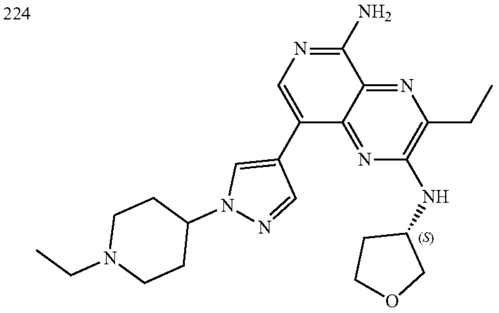 |
| 221 | 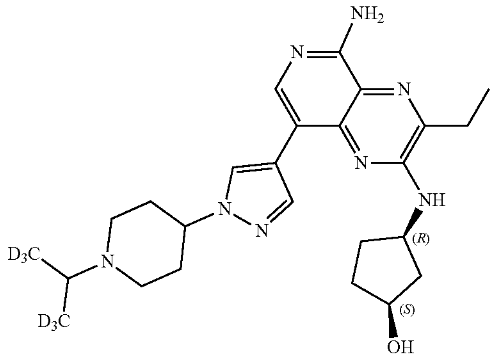 |
| 226 | 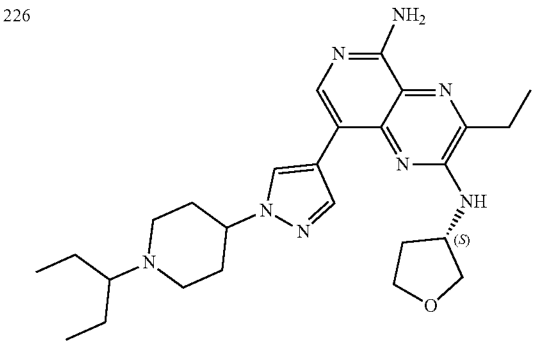 |

-continued
| No | structure |
|---|---|
| 223 | 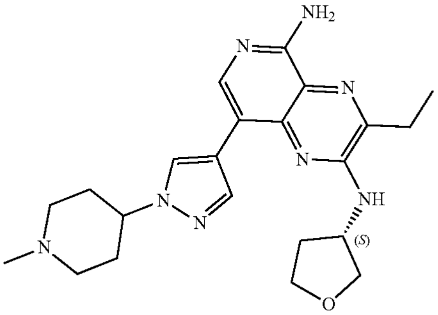 |
| 228 | 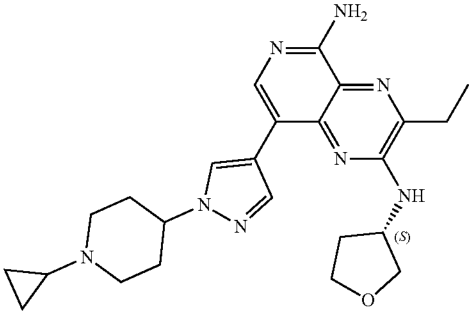 |
| 225 | 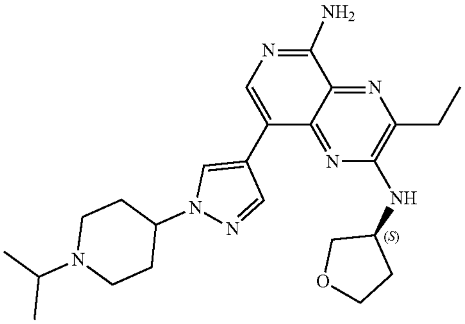 |
| 230 | 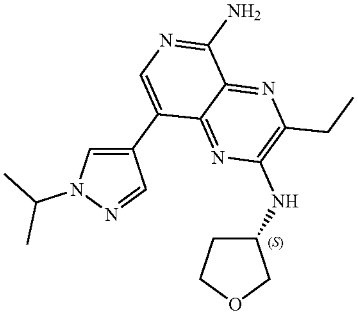 |

-continued
| No | structure |
|---|---|
| 227 | 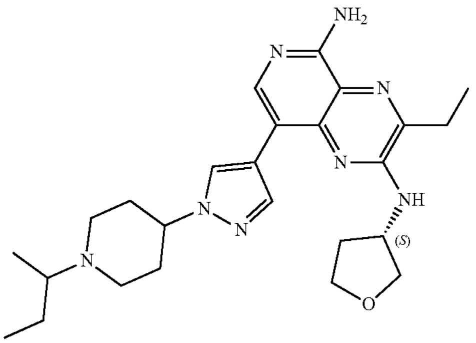 |
| 232 | 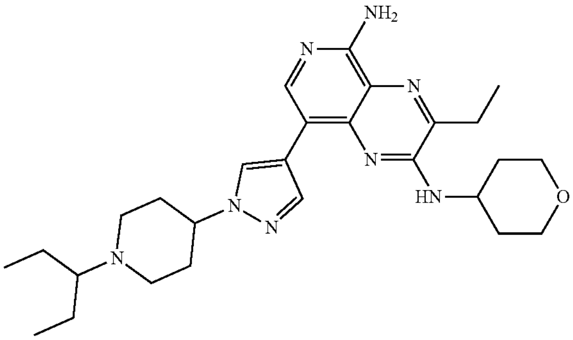 [SMILES: CCc1nc2c(N)ncc(-c3cnn(C4CCN(C(CC)CC)CC4)c3)c2nc1NC1CCOCC1] |
| 229 | 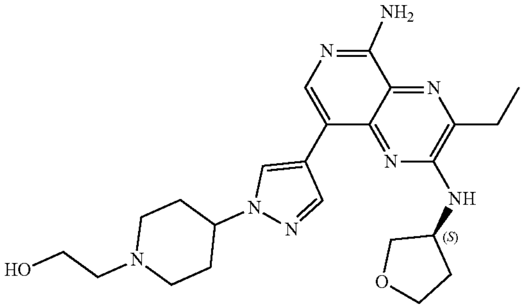 |
| 234 | 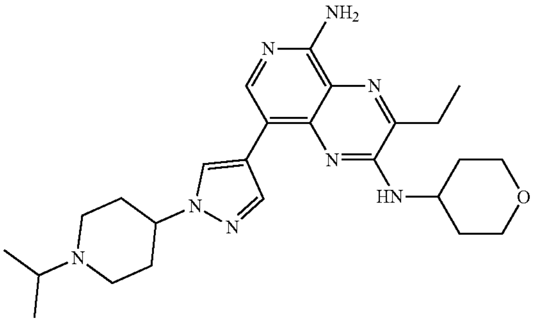 [SMILES: CCc1nc2c(N)ncc(-c3cnn(C4CCN(C(C)C)CC4)c3)c2nc1NC1CCOCC1] |

-continued
| No | structure |
|---|---|
| 231 | 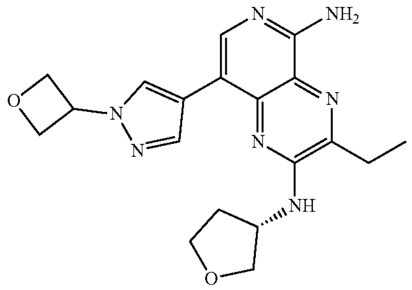 [SMILES: CCc1nc2c(N)ncc(-c3cnn(C4COC4)c3)c2nc1N[C@H]1CCOC1] |
| 236 | 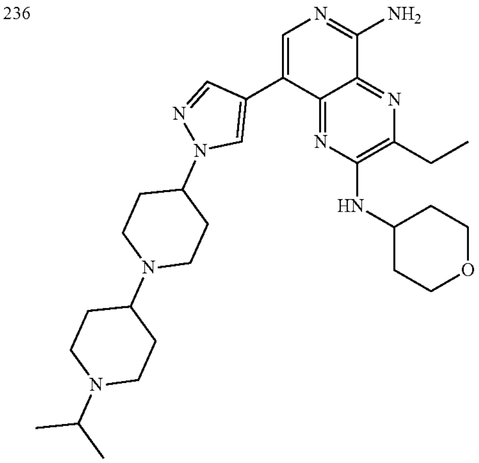 |
| 233 | 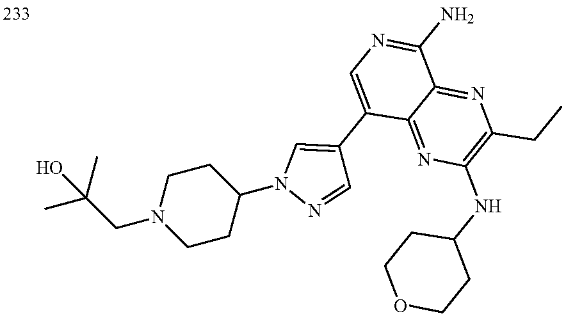 |
| 238 | 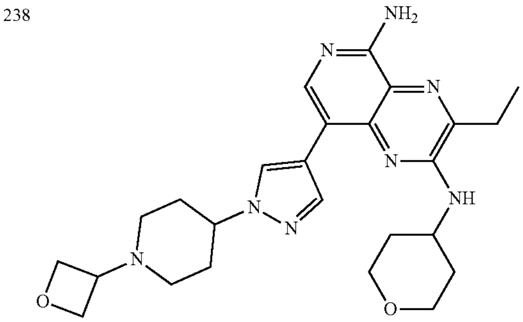 |

-continued
| No | structure |
| --- | --- |
| 235 | 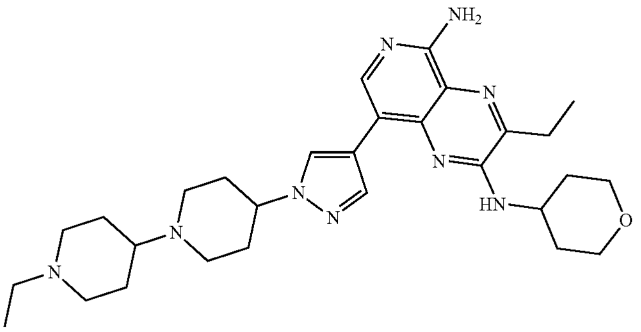 [SMILES: CCc1nc2c(N)ncc(-c3cnn(C4CCN(C5CCN(CC)CC5)CC4)c3)c2nc1NC1CCOCC1] |
| 240 | 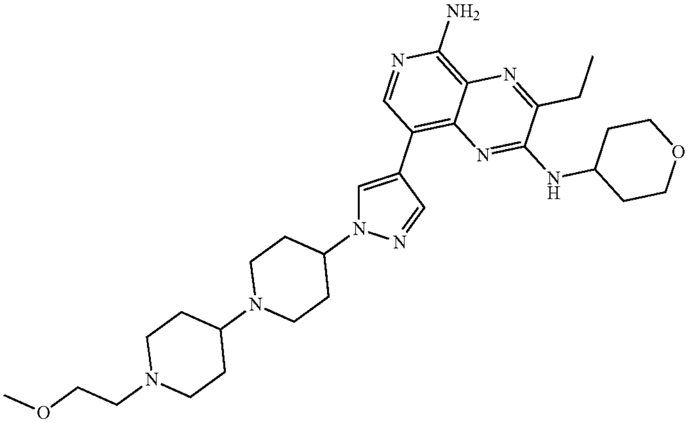 [SMILES: CCc1nc2c(N)ncc(-c3cnn(C4CCN(C5CCN(CCOC)CC5)CC4)c3)c2nc1NC1CCOCC1] |
| 237 | 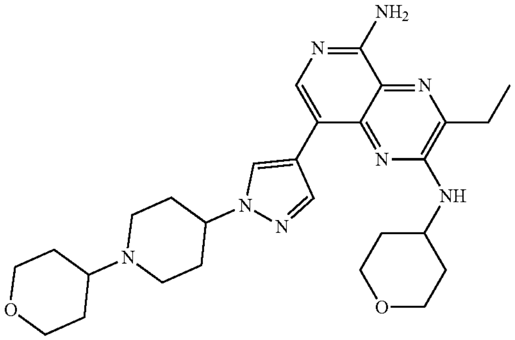 [SMILES: CCc1nc2c(N)ncc(-c3cnn(C4CCN(C5CCOCC5)CC4)c3)c2nc1NC1CCOCC1] |
| 242 | 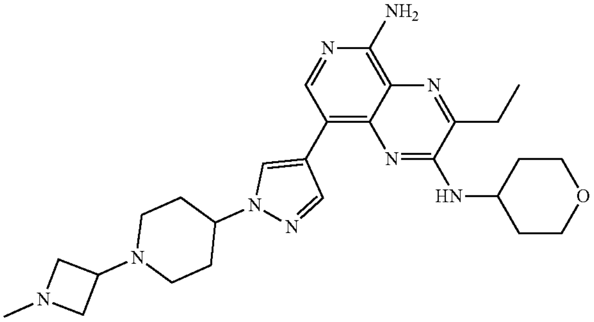 [SMILES: CCc1nc2c(N)ncc(-c3cnn(C4CCN(C5CN(C)C5)CC4)c3)c2nc1NC1CCOCC1] |

-continued
| No | structure |
|---|---|
| 239 | 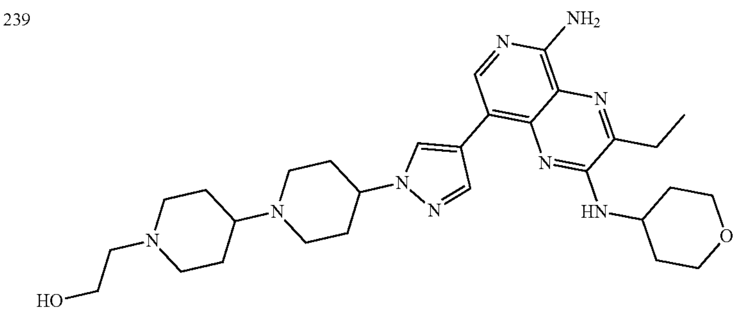 |
| 244 | 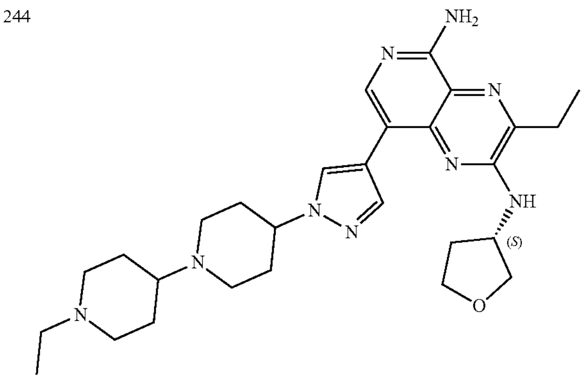 |
| 241 | 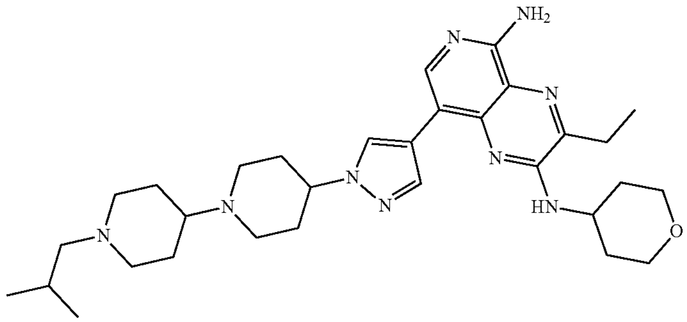 [SMILES: CCc1nc2c(N)ncc(-c3cnn(C4CCN(C5CCN(CC(C)C)CC5)CC4)c3)c2nc1NC1CCOCC1] |
| 246 | 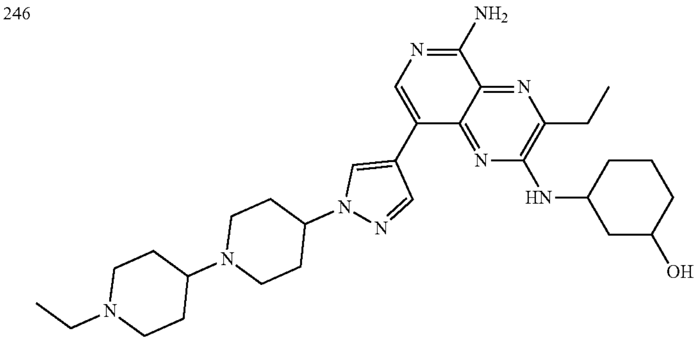 |

-continued
| No | structure |
|---|---|
| 243 | 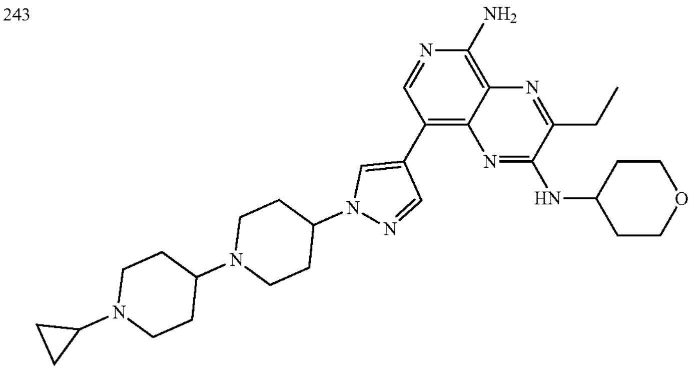 |
| 248 | 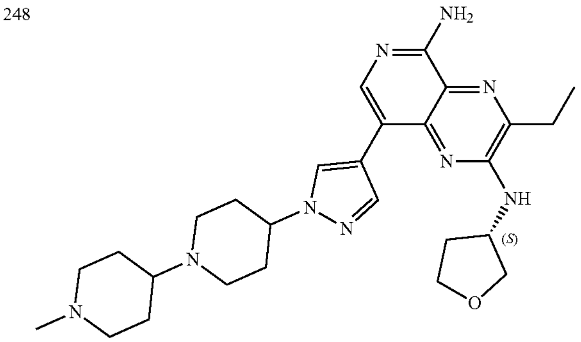 |
| 245 | 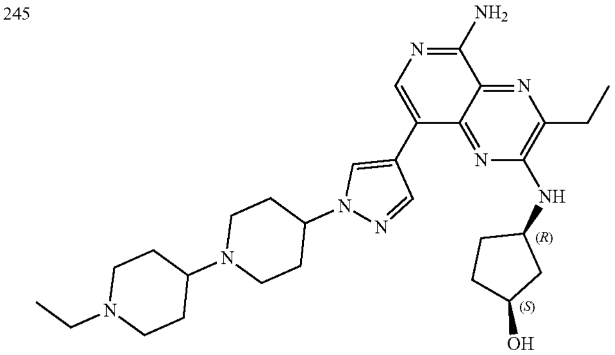 |
| 250 | 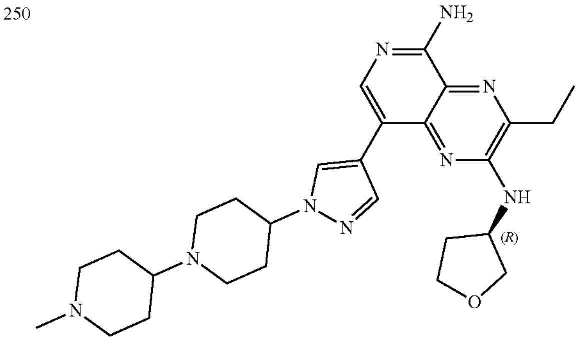 |

-continued
| No | structure |
|---|---|
| 247 | 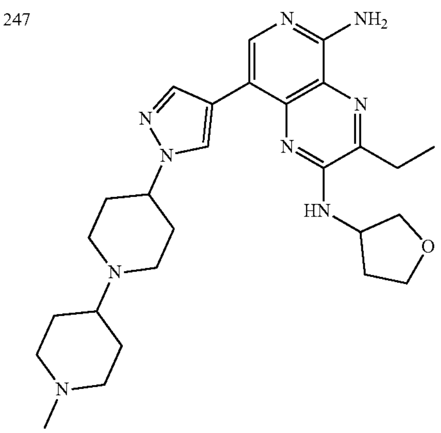 |
| 252 | 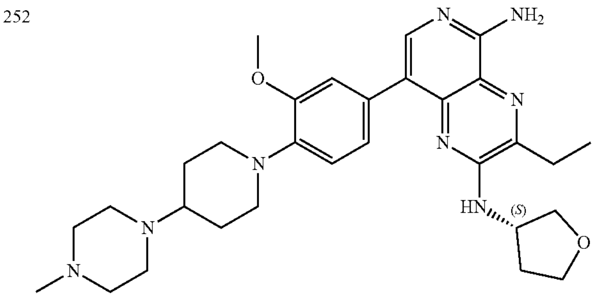 |
| 249 | 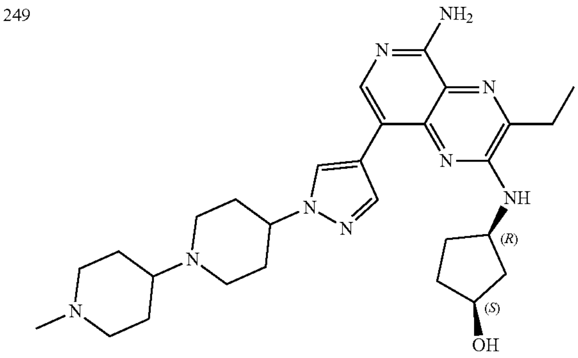 |
| 255 | 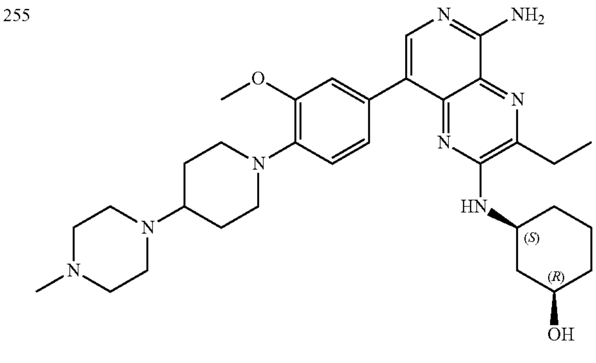 |

-continued
| No | structure |
|---|---|
| 251 | 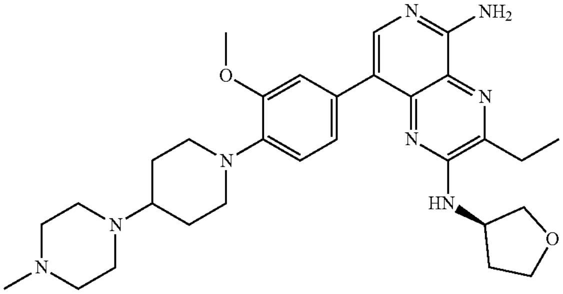 [SMILES: CCc1nc2c(N)ncc(-c3ccc(N4CCC(N5CCN(C)CC5)CC4)c(OC)c3)c2nc1N[C@@H]1CCOC1] |
| 257 | 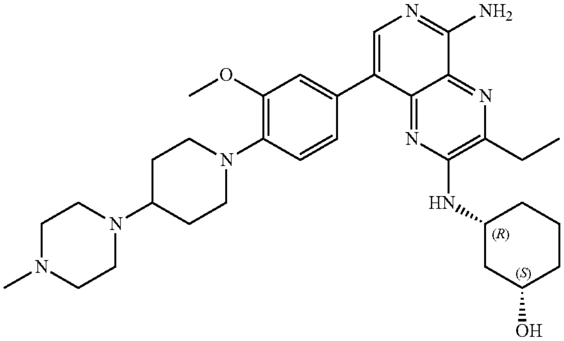 |
| 253 | 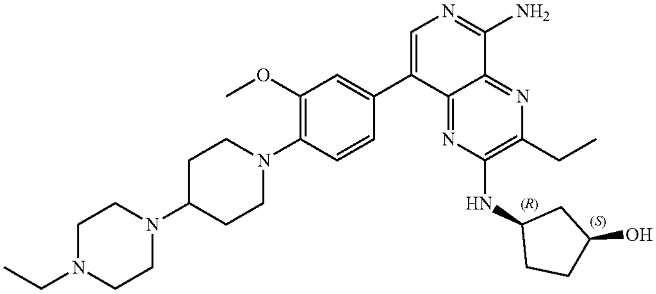 |
| 259 | 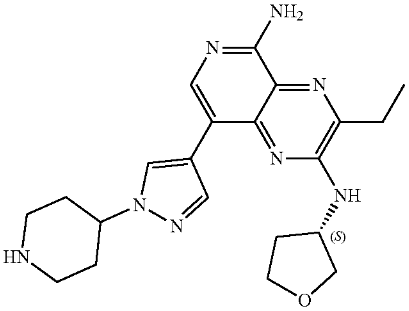 |

-continued
| No | structure |
|---|---|
| 256 | 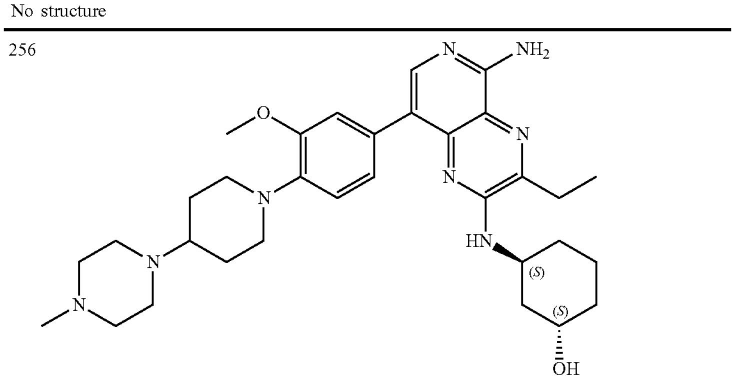 |
| 261 | 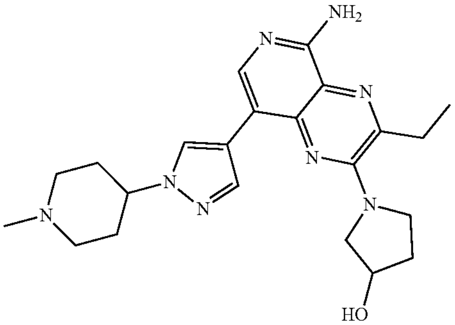 [SMILES: CCc1nc2c(N)ncc(-c3cnn(C4CCN(C)CC4)c3)c2nc1N1CCC(O)C1] |
| 258 | 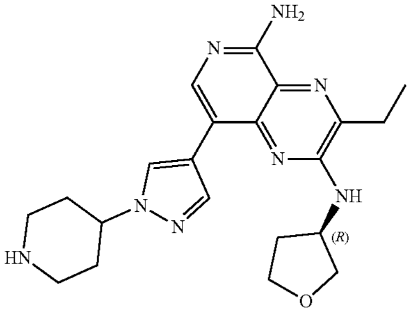 |
| 266 | 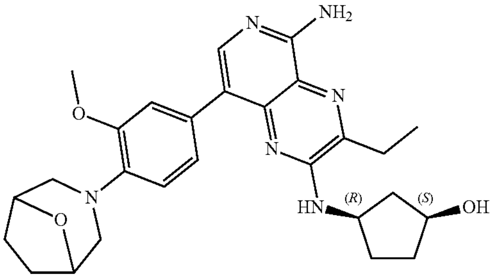 |
| 260 | 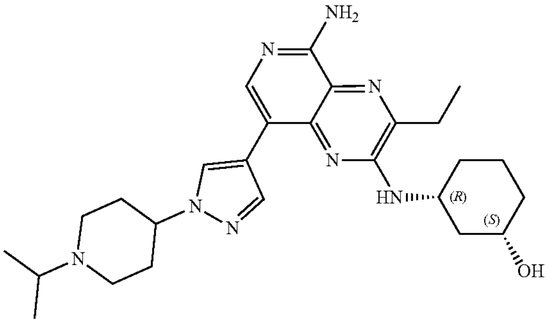 |

-continued
| No | structure |
|---|---|
| 268 | 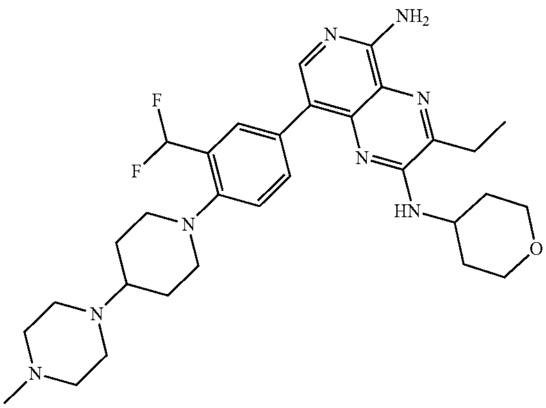 [SMILES: CCc1nc2c(N)ncc(-c3ccc(N4CCC(N5CCN(C)CC5)CC4)c(C(F)F)c3)c2nc1NC1CCOCC1] |
| 265 | 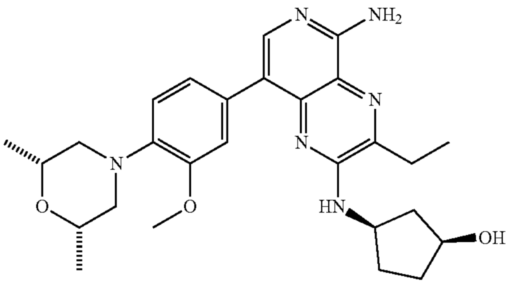 [SMILES: CCc1nc2c(N)ncc(-c3ccc(N4C[C@@H](C)O[C@@H](C)C4)c(OC)c3)c2nc1N[C@@H]1CC[C@H](O)C1] |
| 270 | 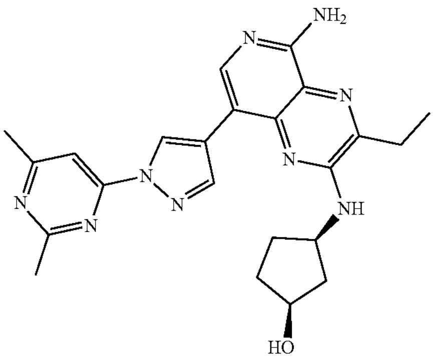 [SMILES: CCc1nc2c(N)ncc(-c3cnn(-c4cc(C)nc(C)n4)c3)c2nc1N[C@@H]1CC[C@H](O)C1] |
| 267 | 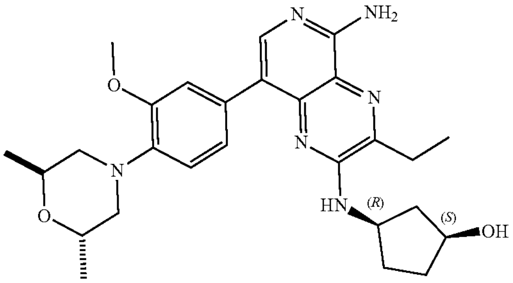 |

-continued
| No | structure |
|---|---|
| 272 | 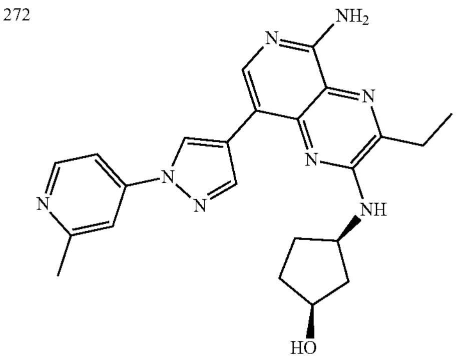 |
| 269 | 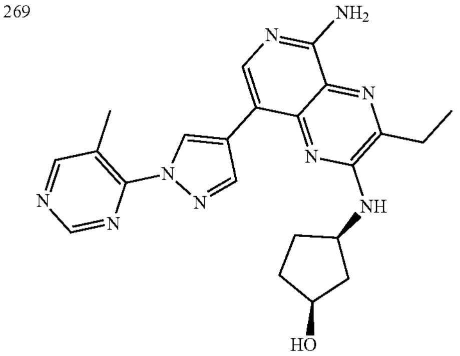 |
| 274 | 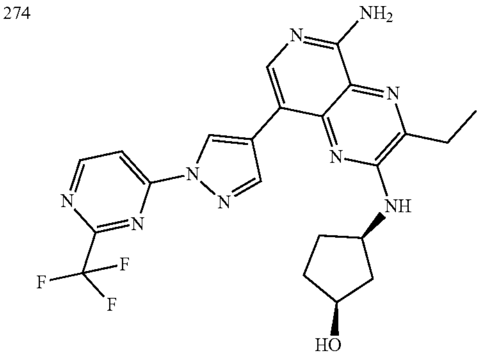 |
| 271 | 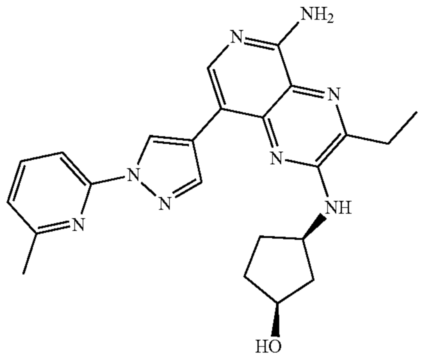 [SMILES: CCc1nc2c(N)ncc(-c3cnn(-c4cccc(C)n4)c3)c2nc1N[C@@H]1CC[C@H](O)C1] |

-continued
| No | structure |
|---|---|
| 276 | 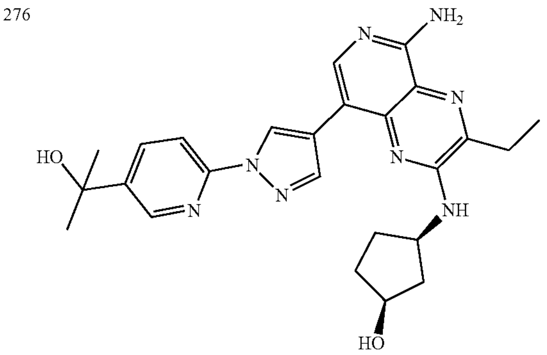 |
| 273 | 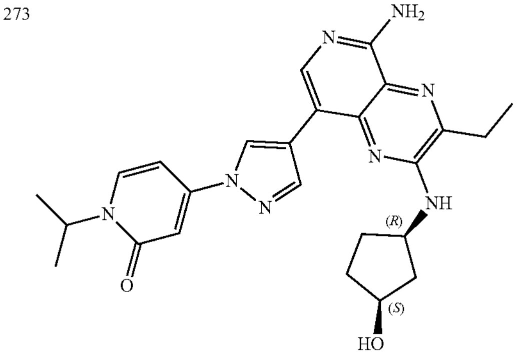 |
| 278 | 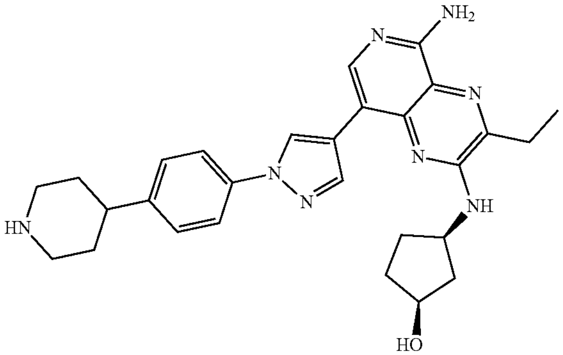 [SMILES: CCc1nc2c(N)ncc(-c3cnn(-c4ccc(C5CCNCC5)cc4)c3)c2nc1N[C@@H]1CC[C@H](O)C1] |
| 275 | 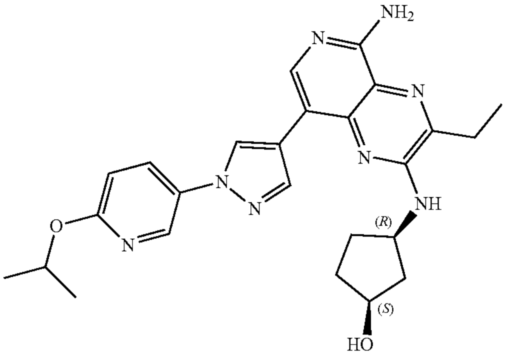 |

-continued
| No | structure |
|---|---|
| 280 | 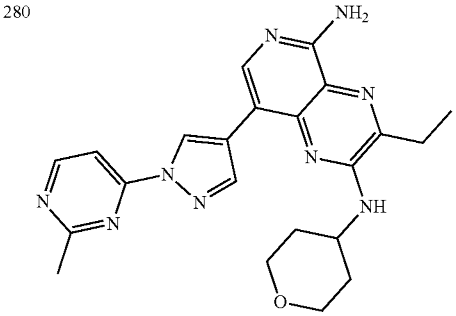 |
| 277 | 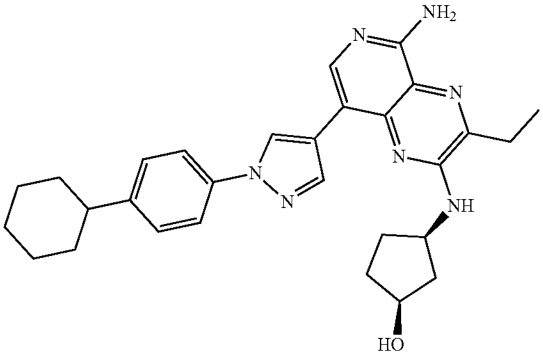 [SMILES: CCc1nc2c(N)ncc(-c3cnn(-c4ccc(C5CCCCC5)cc4)c3)c2nc1N[C@@H]1CC[C@H](O)C1] |
| 282 | 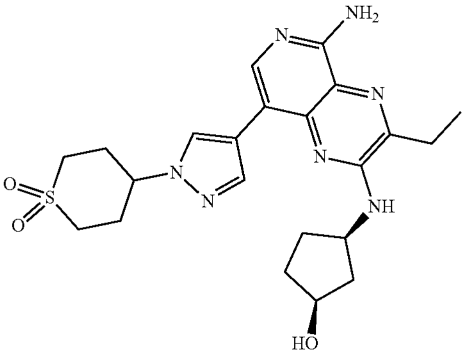 [SMILES: CCc1nc2c(N)ncc(-c3cnn(C4CCS(=O)(=O)CC4)c3)c2nc1N[C@@H]1CC[C@H](O)C1] |
| 279 | 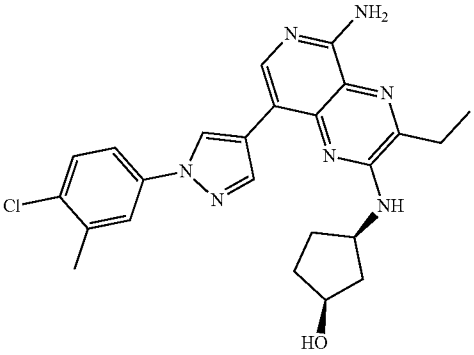 [SMILES: CCc1nc2c(N)ncc(-c3cnn(-c4ccc(Cl)c(C)c4)c3)c2nc1N[C@@H]1CC[C@H](O)C1] |

-continued
| No | structure |
|---|---|
| 284 | 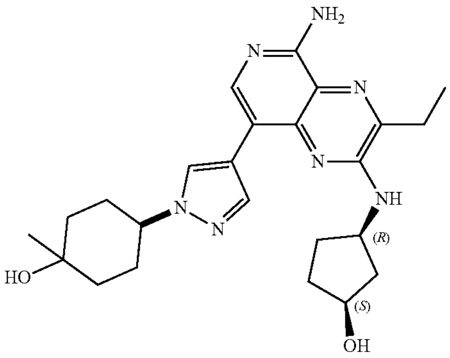 |
| 281 | 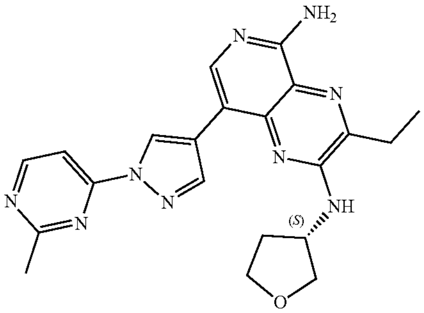 |
| 286 | 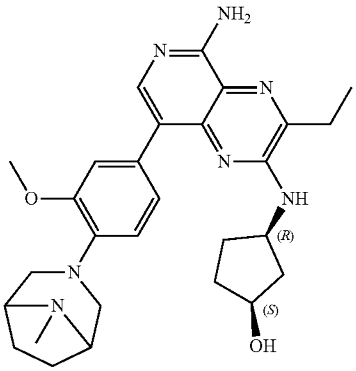 |
| 285 | 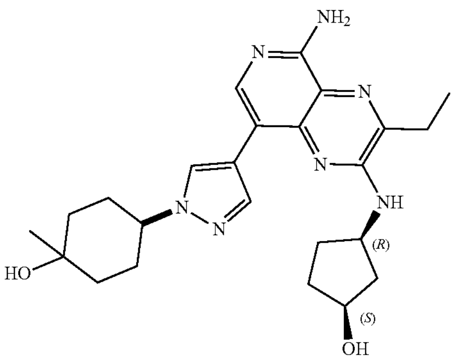 |

-continued
| No | structure |
|---|---|
| 288 | 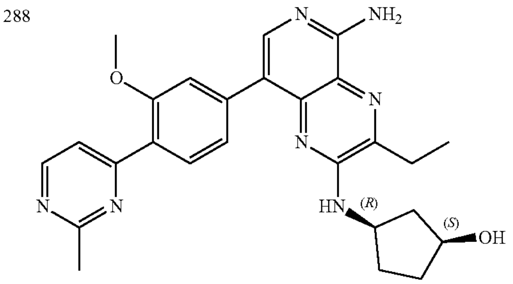 |
| 287 | 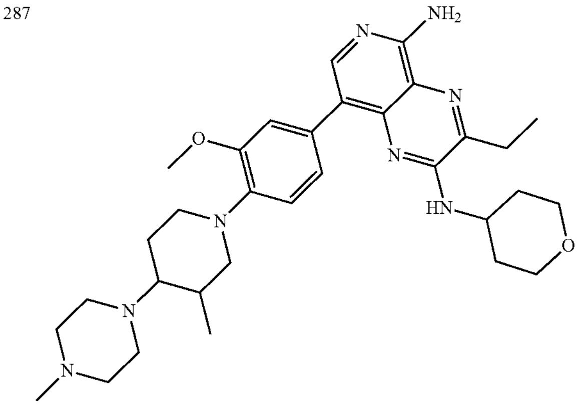 |
| 290 | 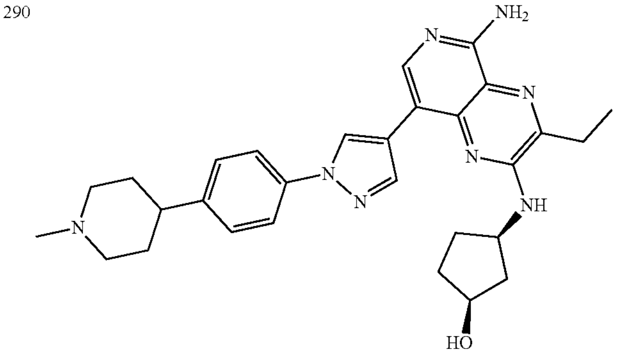 |
| 289 | 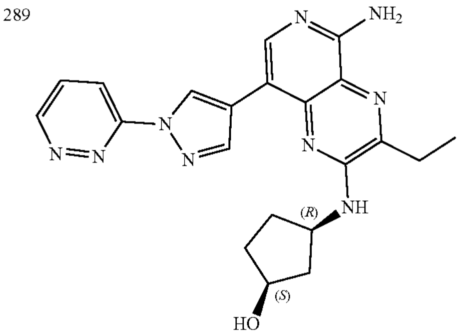 |

-continued
| No | structure |
|---|---|
| 294 | 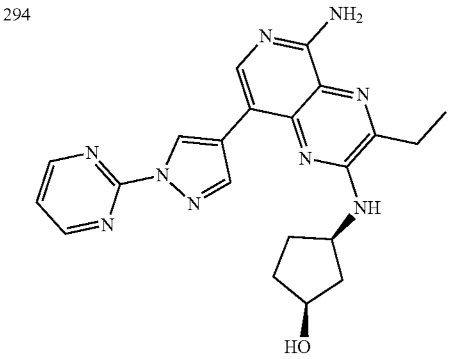 |
| 291 | 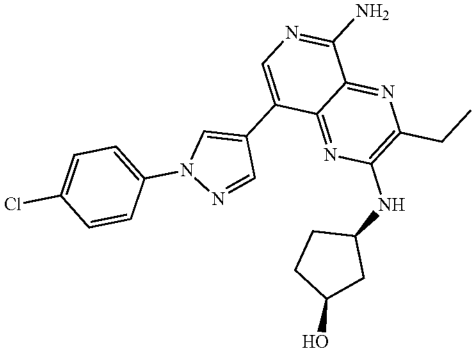 [SMILES: CCc1nc2c(N)ncc(-c3cnn(-c4ccc(Cl)cc4)c3)c2nc1N[C@@H]1CC[C@H](O)C1] |
| 296 | 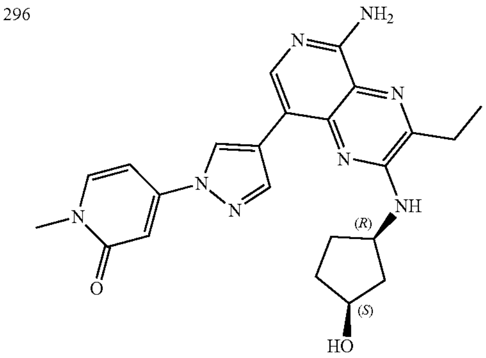 |
| 293 | 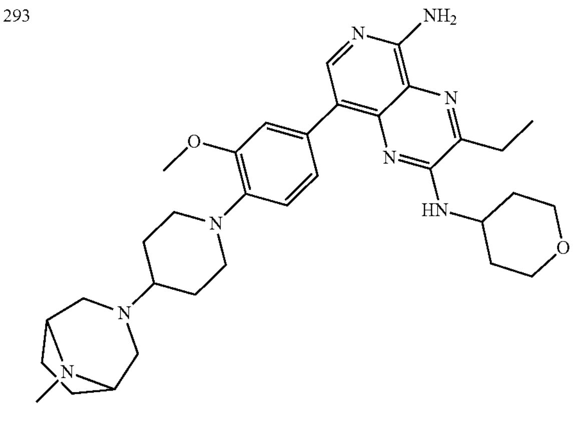 |

-continued
| No | structure |
|---|---|
| 298 | 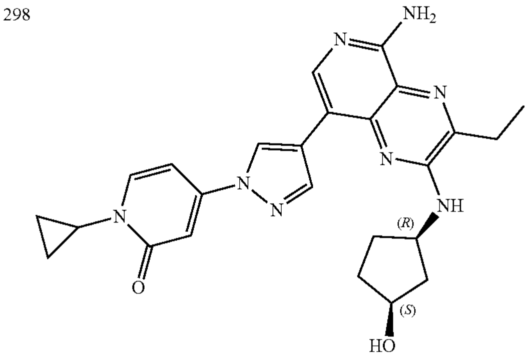 |
| 295 | 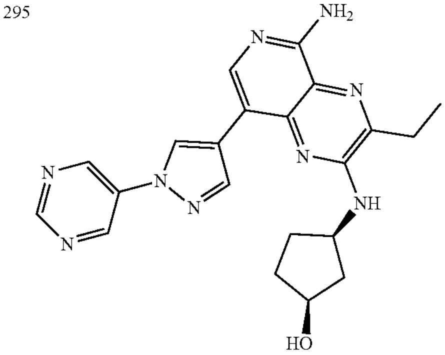 |
| 300 | 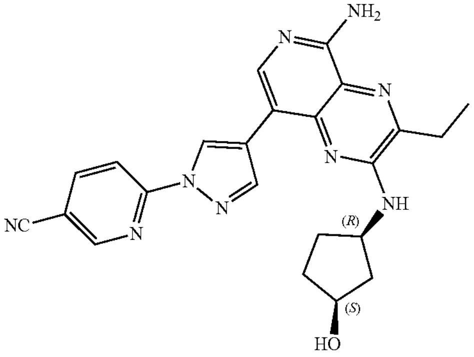 |
| 297 | 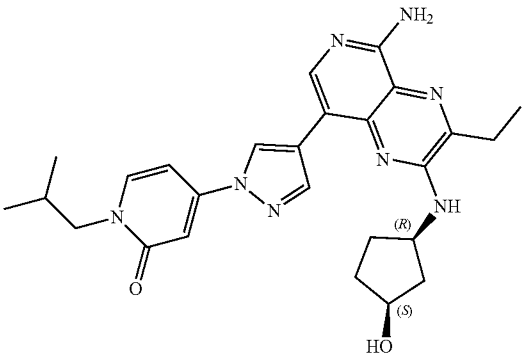 |

-continued
| No | structure |
|---|---|
| 302 | 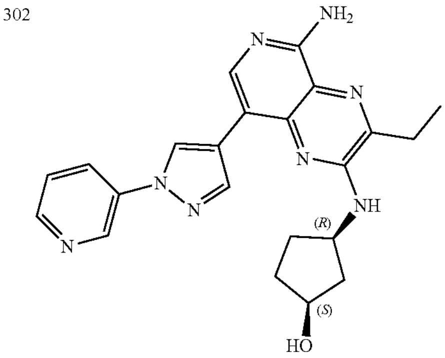 |
| 299 | 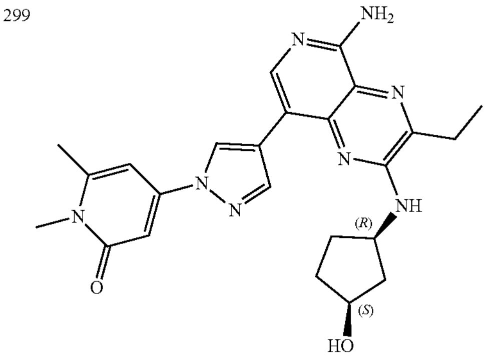 |
| 304 | 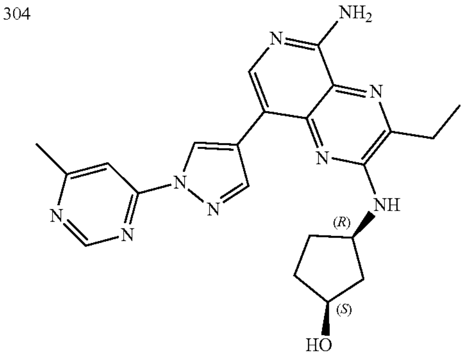 |
| 301 | 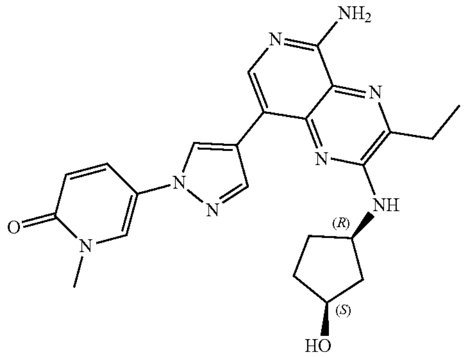 |

-continued
| No | structure |
| --- | --- |
| 306 | 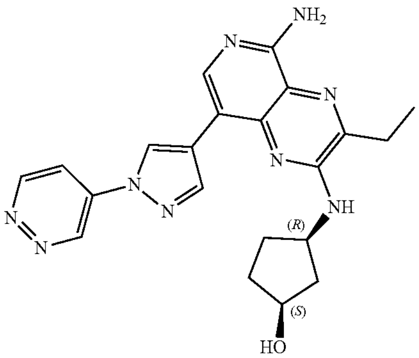 |
| 303 | 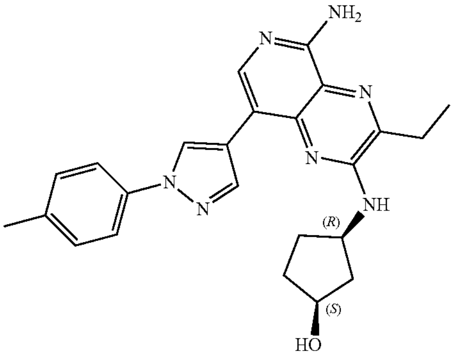 |
| 308 | 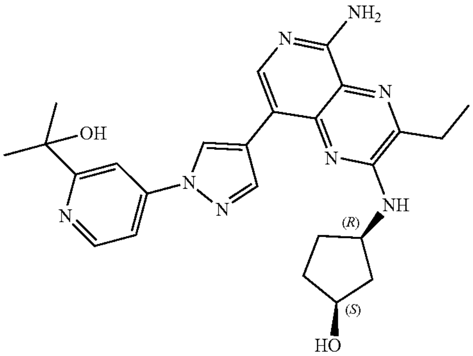 |
| 305 | 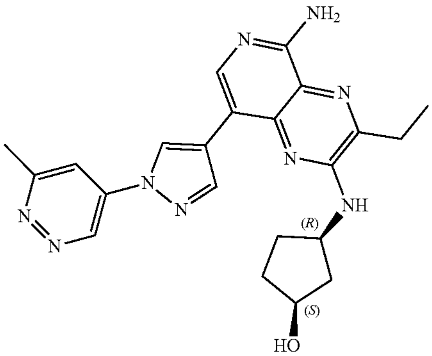 |

-continued
| No structure | |
|---|---|
| 310 | 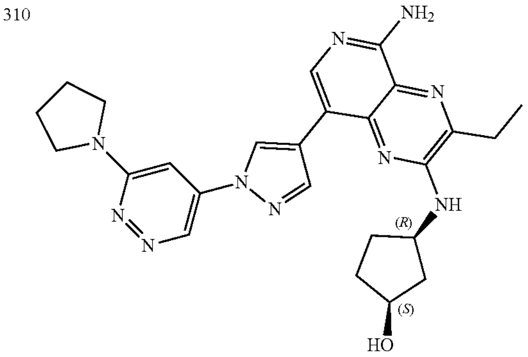 |
| 307 | 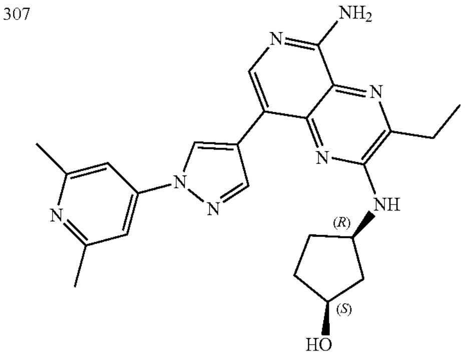 |
| 312 | 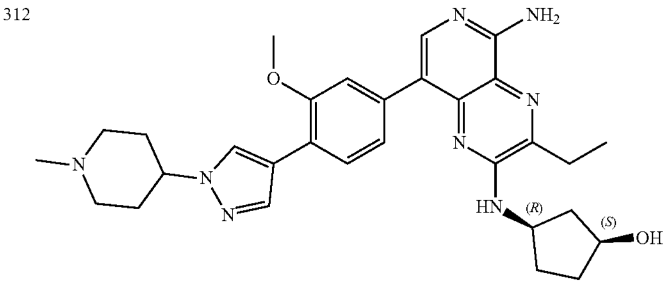 |
| 309 | 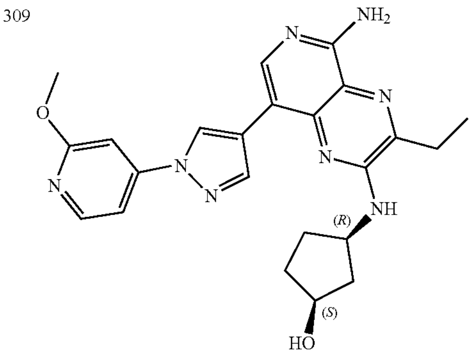 |

-continued
| No | structure |
|---|---|
| 322 | 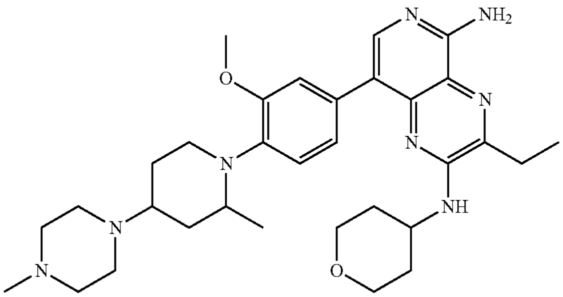 [SMILES: CCc1nc2c(N)ncc(-c3ccc(N4CCC(N5CCN(C)CC5)CC4C)c(OC)c3)c2nc1NC1CCOCC1] |
| 311 | 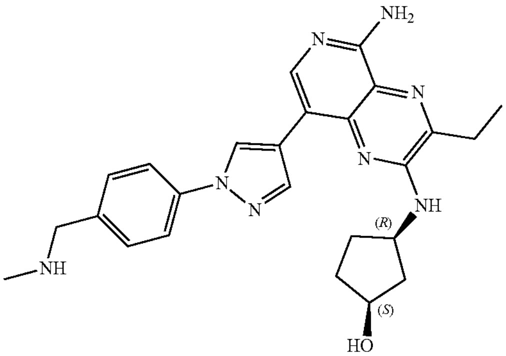 |
| 324 | 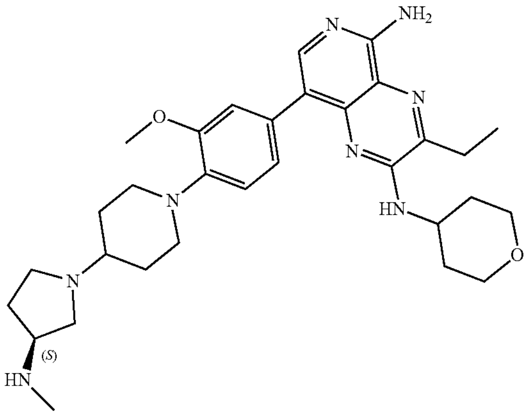 |
| 313 | 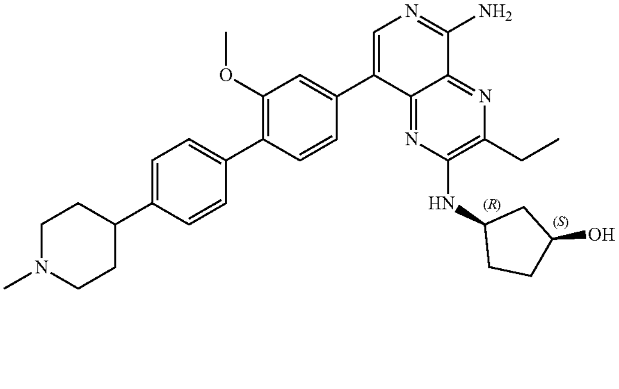 |

-continued
| No | structure |
|---|---|
| 326 | 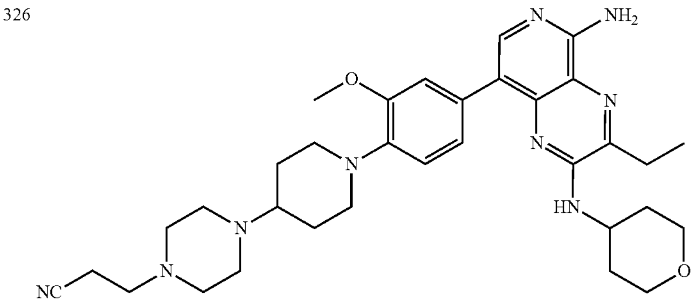 |
| 323 | 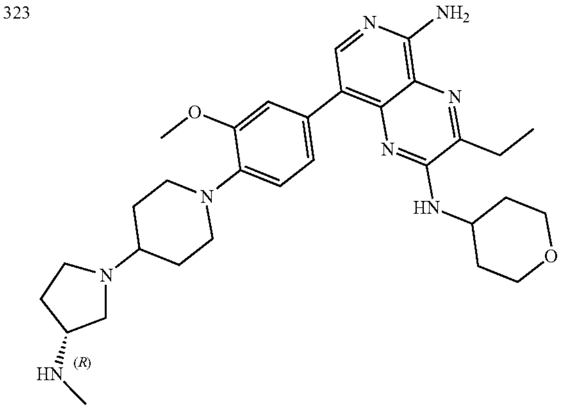 |
| 333 | 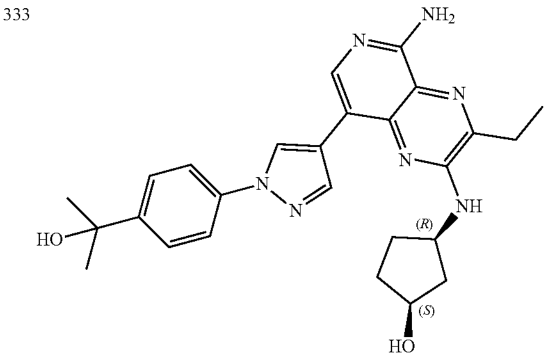 |
| 325 | 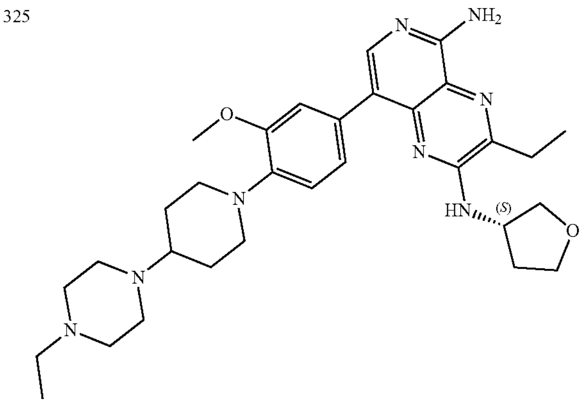 |

-continued
| No | structure |
|---|---|
| 335 | 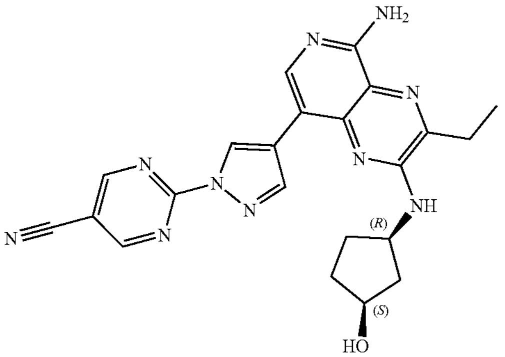 |
| 332 | 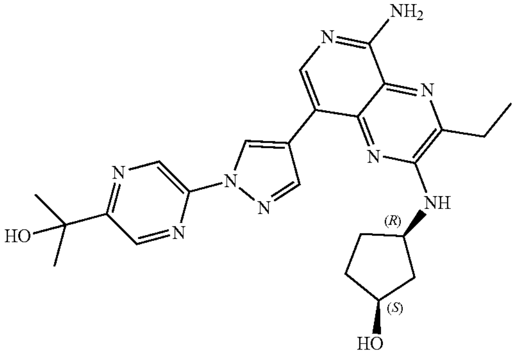 |
| 337 | 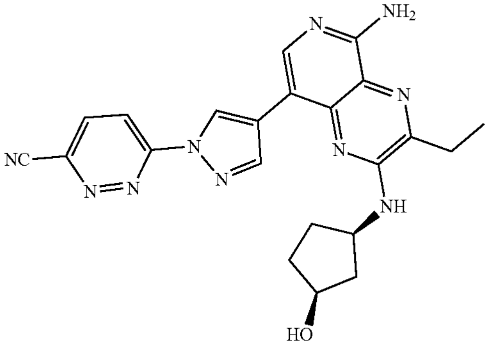 [SMILES: CCc1nc2c(N)ncc(-c3cnn(-c4ccc(C#N)nn4)c3)c2nc1N[C@@H]1CC[C@H](O)C1] |
| 334 | 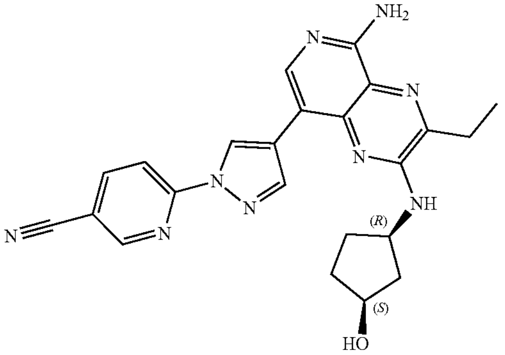 |

-continued
| No | structure |
|---|---|
| 339 | 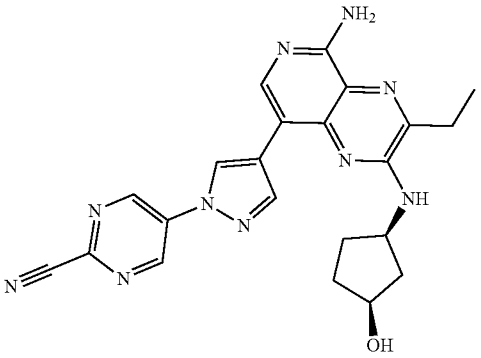 [SMILES: CCc1nc2c(N)ncc(-c3cnn(-c4cnc(C#N)nc4)c3)c2nc1N[C@@H]1CC[C@H](O)C1] |
| 336 | 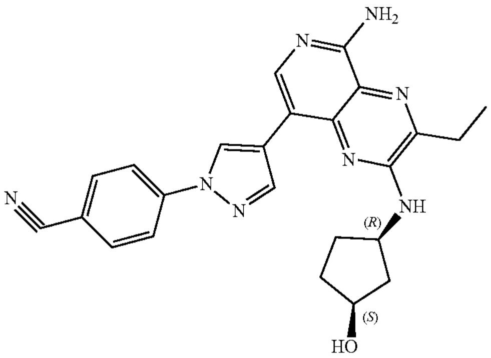 |
| 341 | 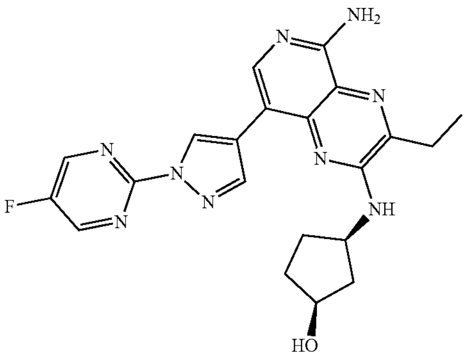 [SMILES: CCc1nc2c(N)ncc(-c3cnn(-c4ncc(F)cn4)c3)c2nc1N[C@@H]1CC[C@H](O)C1] |
| 338 | 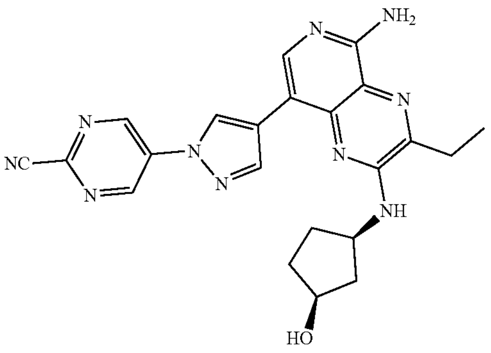 [SMILES: CCc1nc2c(N)ncc(-c3cnn(-c4cnc(C#N)nc4)c3)c2nc1N[C@@H]1CC[C@H](O)C1] |

-continued
| No | structure |
|---|---|
| 343 | 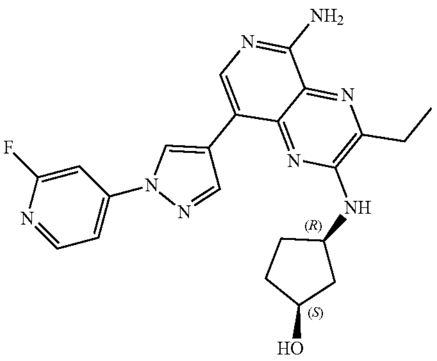 |
| 340 | 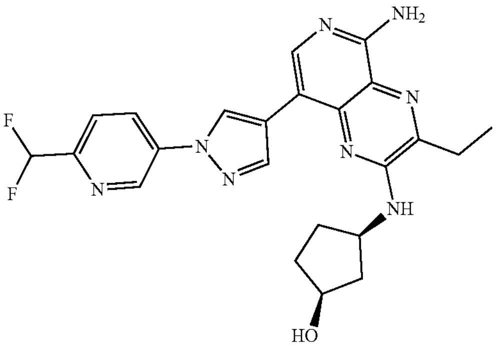 [SMILES: CCc1nc2c(N)ncc(-c3cnn(-c4ccc(C(F)F)nc4)c3)c2nc1N[C@@H]1CC[C@H](O)C1] |
| 345 | 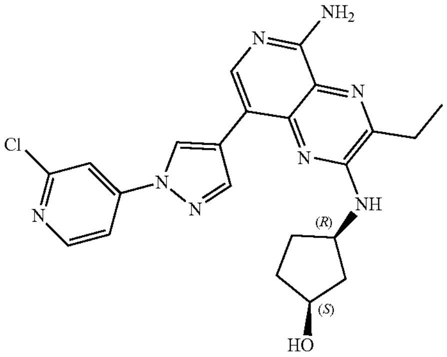 |
| 342 | 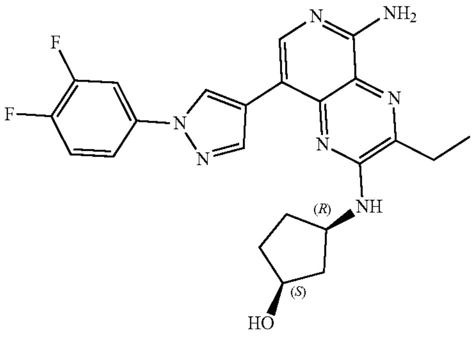 |

-continued
| No | structure |
| --- | --- |
| 347 | 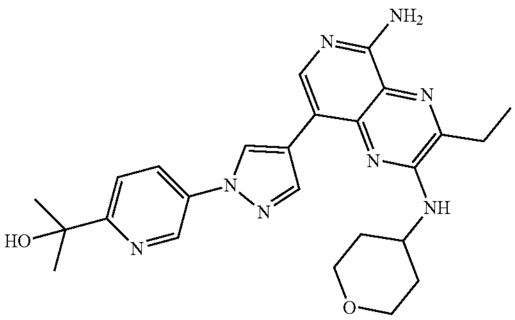 [SMILES: CCc1nc2c(N)ncc(-c3cnn(-c4ccc(C(C)(C)O)nc4)c3)c2nc1NC1CCOCC1] |
| 344 | 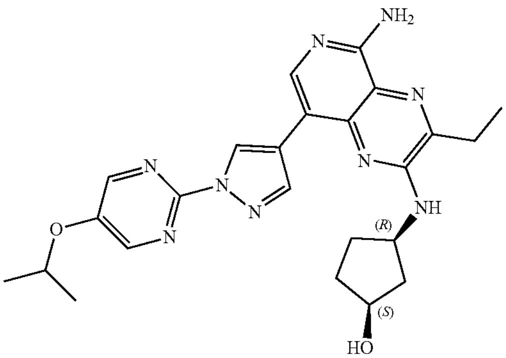 |
| 349 | 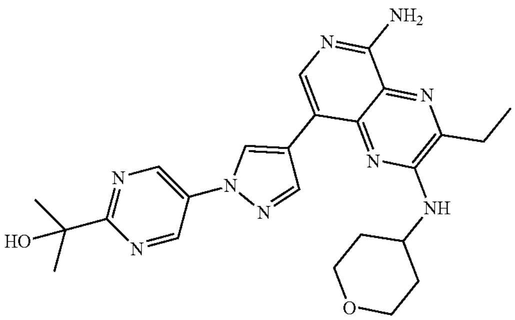 [SMILES: CCc1nc2c(N)ncc(-c3cnn(-c4cnc(C(C)(C)O)nc4)c3)c2nc1NC1CCOCC1] |
| 346 | 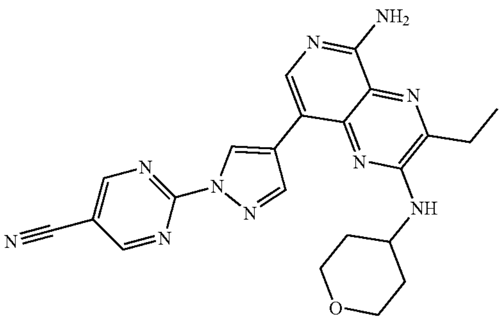 [SMILES: CCc1nc2c(N)ncc(-c3cnn(-c4ncc(C#N)cn4)c3)c2nc1NC1CCOCC1] |

-continued
| No | structure |
|---|---|
| 351 | 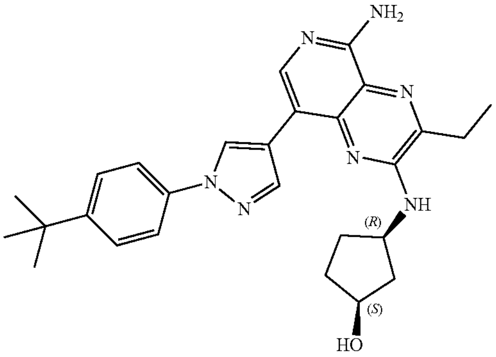 |
| 348 | 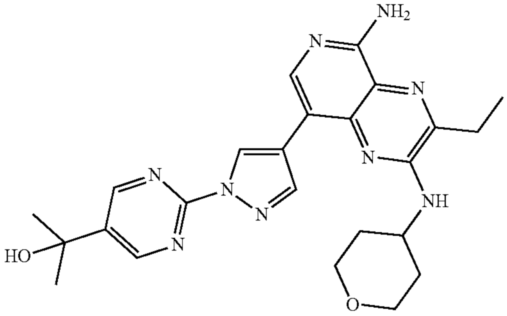 [SMILES: CCc1nc2c(N)ncc(-c3cnn(-c4ncc(C(C)(C)O)cn4)c3)c2nc1NC1CCOCC1] |
| 353 | 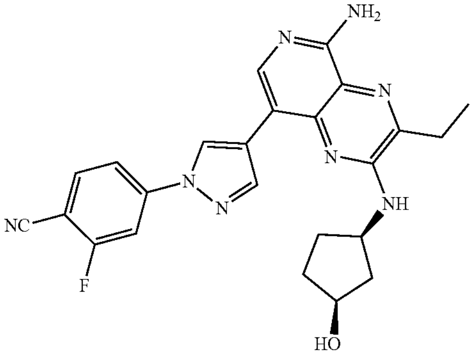 [SMILES: CCc1nc2c(N)ncc(-c3cnn(-c4ccc(C#N)c(F)c4)c3)c2nc1N[C@@H]1CC[C@H](O)C1] |
| 350 | 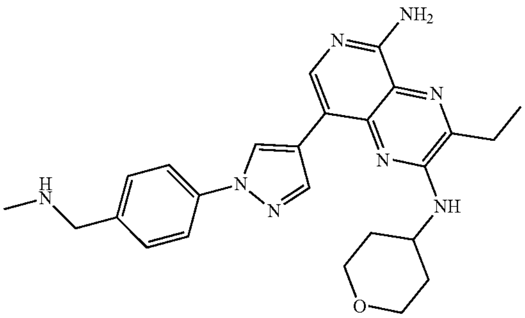 [SMILES: CCc1nc2c(N)ncc(-c3cnn(-c4ccc(CNC)cc4)c3)c2nc1NC1CCOCC1] |

-continued
| No | structure |
|---|---|
| 355 | 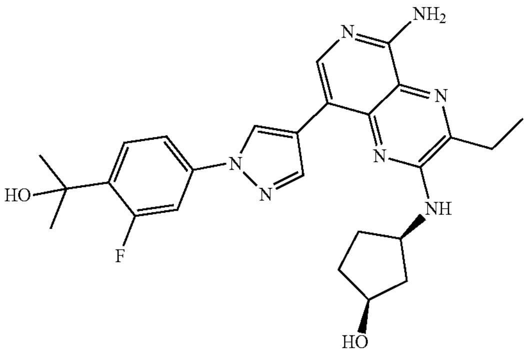 [SMILES: CCc1nc2c(N)ncc(-c3cnn(-c4ccc(C(C)(C)O)c(F)c4)c3)c2nc1N[C@@H]1CC[C@H](O)C1] |
| 352 | 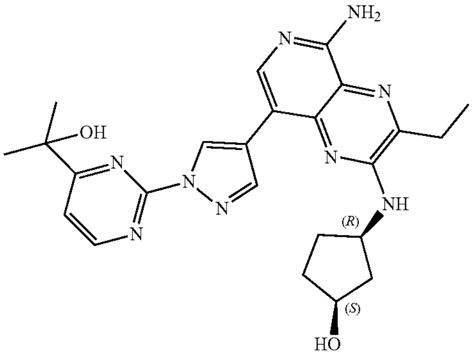 |
| 356 | 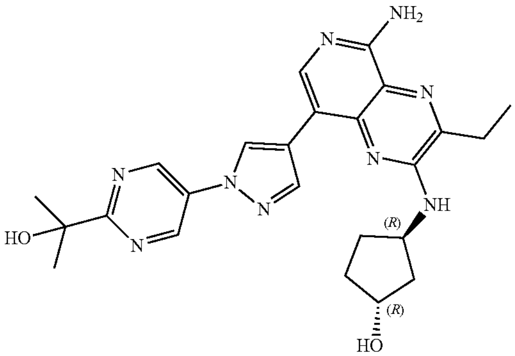 |
| 354 | 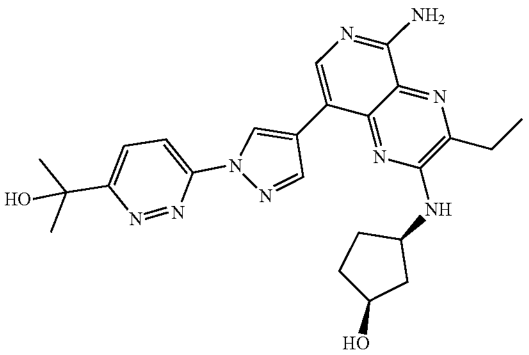 [SMILES: CCc1nc2c(N)ncc(-c3cnn(-c4ccc(C(C)(C)O)nn4)c3)c2nc1N[C@@H]1CC[C@H](O)C1] |

-continued
| No | structure |
|---|---|
| 327 | 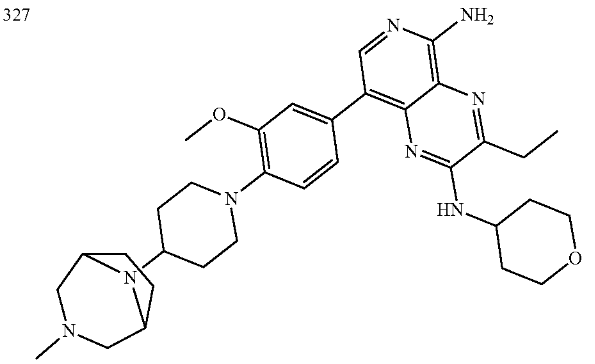 |
| 314 | 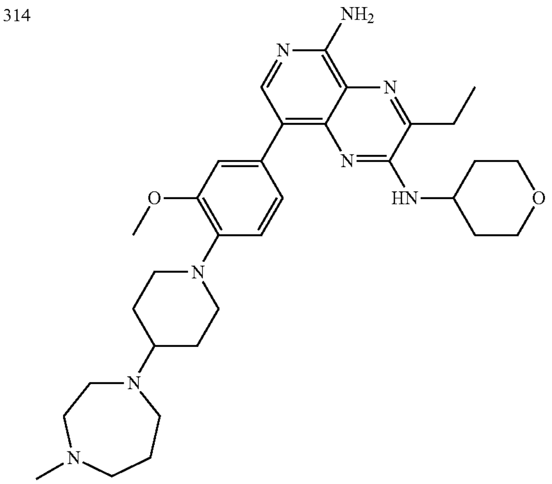 |
| 328 | 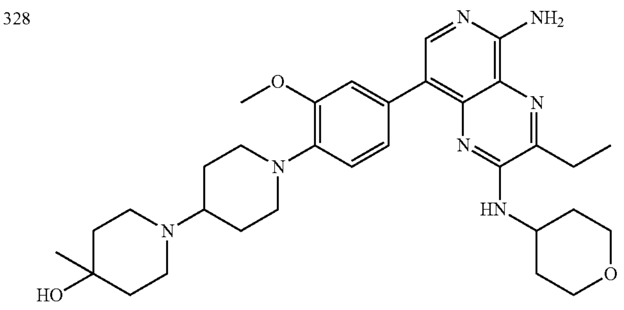 |

-continued
| No | structure |
| --- | --- |
| 315 | 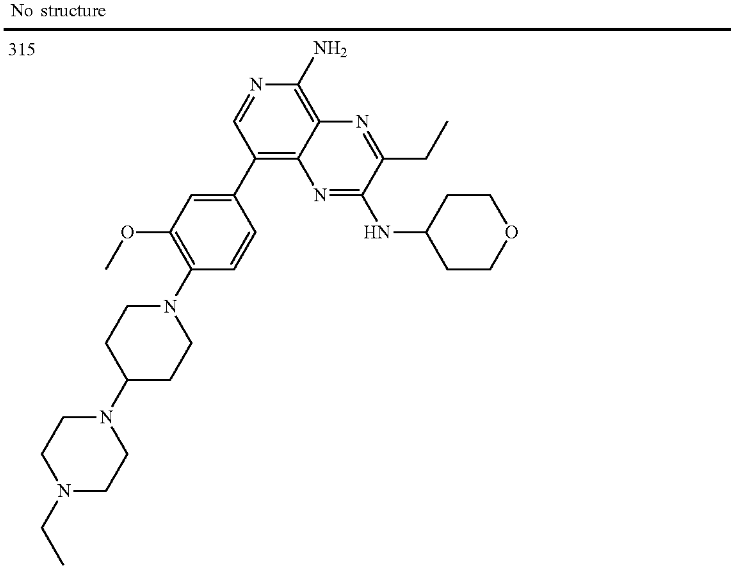 |
| 329 | 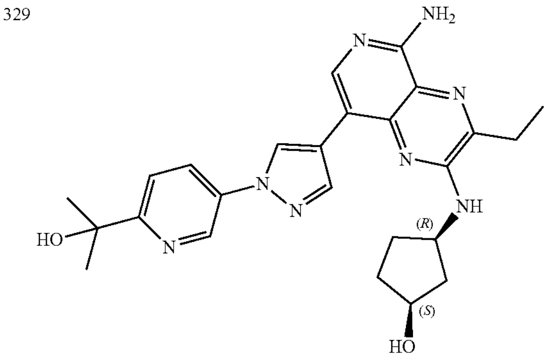 |
| 316 | 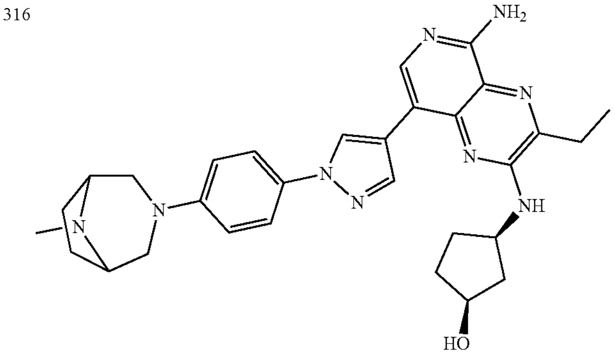 |
| 330 | 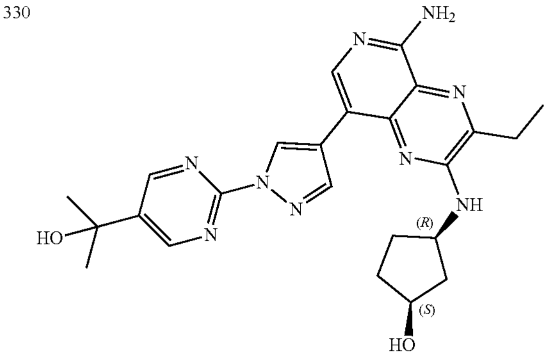 |

-continued
| No | structure |
|---|---|
| 317 | 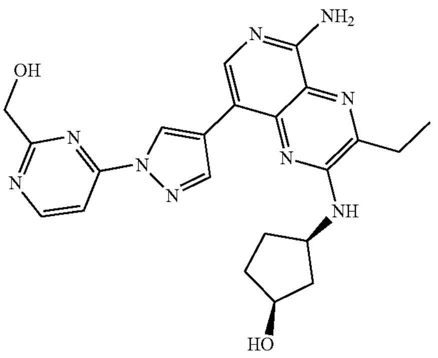 [SMILES: CCc1nc2c(N)ncc(-c3cnn(-c4ccnc(CO)n4)c3)c2nc1N[C@@H]1CC[C@H](O)C1] |
| 331 | 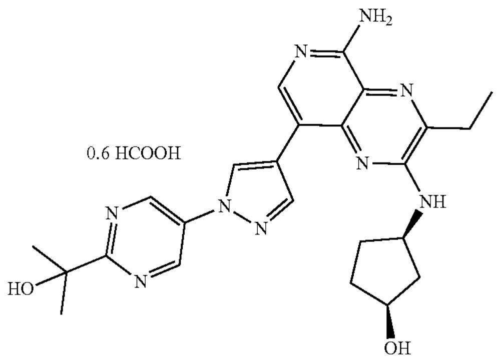 [SMILES: CCc1nc2c(N)ncc(-c3cnn(-c4cnc(C(C)(C)O)nc4)c3)c2nc1N[C@@H]1CC[C@H](O)C1] |
| 318 | 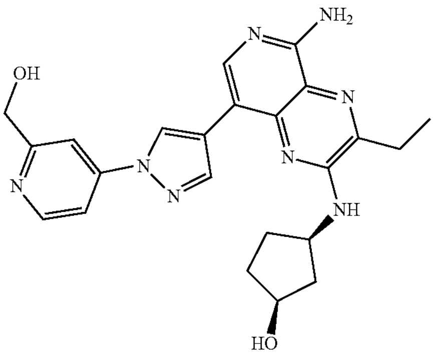 [SMILES: CCc1nc2c(N)ncc(-c3cnn(-c4ccnc(CO)c4)c3)c2nc1N[C@@H]1CC[C@H](O)C1] |
| 320 | 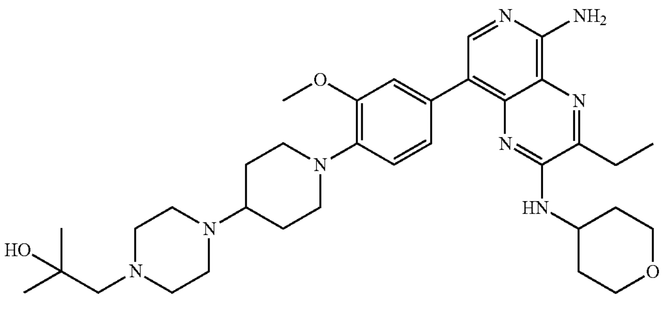 [SMILES: CCc1nc2c(N)ncc(-c3ccc(N4CCC(N5CCN(CC(C)(C)O)CC5)CC4)c(OC)c3)c2nc1NC1CCOCC1] |

-continued

| No | structure |
| --- | --- |
| 319 | 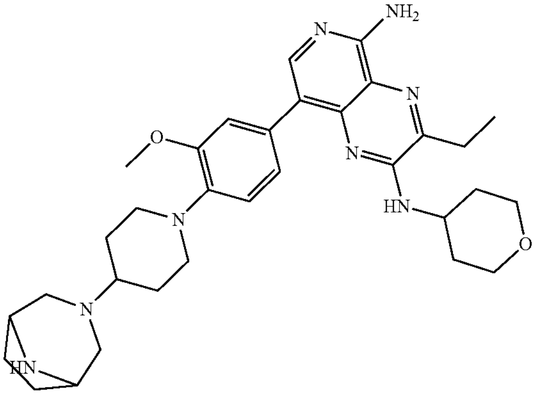 [SMILES: CCc1nc2c(N)ncc(-c3ccc(N4CCC(N5CC6CCC(C5)N6)CC4)c(OC)c3)c2nc1NC1CCOCC1] |
| 321 | 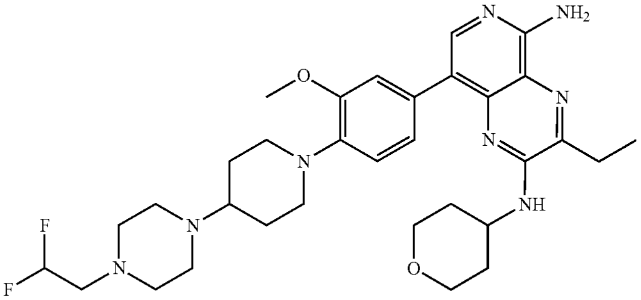 [SMILES: CCc1nc2c(N)ncc(-c3ccc(N4CCC(N5CCN(CC(F)F)CC5)CC4)c(OC)c3)c2nc1NC1CCOCC1] |
| 56 | 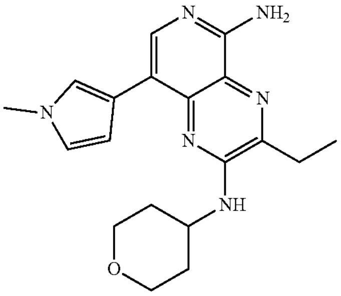 [SMILES: CCc1nc2c(N)ncc(-c3ccn(C)c3)c2nc1NC1CCOCC1] |

11. A pharmaceutical composition comprising an effective amount of one or more of the compound of claim 1, or the pharmaceutically acceptable salt, racemate, R-isomer and S-isomer, stereoisomer or a tautomer thereof, and one or more pharmaceutically acceptable carriers, excipients, adjuvants, excipients and/or diluents.

12. A method of treating or preventing a disease, the method comprising administering to the subject an effective amount of the compound of claim 1, or the racemate, R-isomer, S-isomer or the pharmaceutically acceptable salt thereof; wherein the disease is selected from the group consisting of acute myeloid leukemia, neurofibroma type I, multiple myeloma, non-small cell lung cancer, liver cancer, hepatocellular carcinoma, cervical cancer, lymphoma, bone metastases, hormone refractory prostate cancer, hormone dependent prostate cancer, thyroid adenoma, medullary thyroid carcinoma, mesothelioma, glioblastoma, sphincter metastases, Merkel cell carcinoma, urogenital tract tumor, bladder cancer, papillary thyroid cancer, breast cancer, soft tissue sarcoma, glioma, neuroendocrine tumor, renal cell carcinoma, advanced solid tumor, undifferentiated astrocytic cell carcinoma, gastrointestinal stromal tumor, Hipper-Lindau syndrome, small cell lung cancer, pancreatic cancer, pancreatic endocrine carcinoma, central nervous system tumor, metastatic renal cancer, endometrioid carcinoma, endometrioid adenocarcinoma, lung cancer, colorectal cancer, ovarian cancer, rhabdomyosarcoma, melanoma, retinoblastoma, tumors of the central and peripheral nervous system, acute leukemia, chronic leukemia, cholangiocarcinoma, bronchiocarcinoma, esophageal cancer, testicular cancer, skin cancer, oral cancer, neuroblastoma, and anaplastic large cell lymphoma.

13. A compound of the formula IV, or the pharmaceutically acceptable salts or deuterated products thereof,

IV

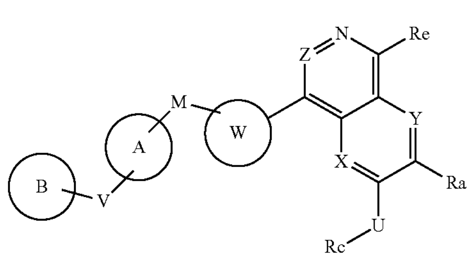

wherein, X and Y are N, and Z is CH;

Ra is selected from the group consisting of H, and substituted or unsubstituted $C_1$-$C_6$ alkyl;

U is —NH—;

Rc is selected from the group consisting of substituted or unsubstituted $C_1$-$C_6$ alkyl, substituted or unsubstituted $C_3$-$C_8$ carbocyclic ring, substituted or unsubstituted 3-8 membered heterocyclic ring containing 1-3 heteroatoms selected from oxygen, sulfur and nitrogen, substituted or unsubstituted $C_6$-$C_{10}$ aryl, and substituted or unsubstituted 5-12 membered heteroaromatic ring containing 1-3 heteroatoms selected from oxygen, sulfur, and nitrogen;

Re is —$NH_2$;

W is substituted or unsubstituted $C_6$-$C_{10}$ aryl, or substituted or unsubstituted 5-12 membered heteroaromatic ring containing 1-3 heteroatoms selected from the group consisting of oxygen, sulfur, and nitrogen;

the W group is substituted by at least one group having the structure of -M-A, wherein M is selected from the group consisting of chemical bond, —$CH_2$—;

the A ring is selected from the group consisting of substituted or unsubstituted 4-12 membered heterocyclic ring containing 1-3 heteroatoms selected from oxygen, and substituted or unsubstituted $C_6$ aryl;

M is a chemical bond, —$CH_2$—;

B ring is substituted or unsubstituted 4-12 membered heterocyclic ring containing 1-3 heteroatoms selected from oxygen, sulfur and nitrogen; and in the group B, the substitution means substituted by one or more R groups;

wherein R is selected from the group consisting of H, halogen, cyano, amino, nitro, hydroxyl, substituted or unsubstituted C1-C6 alkyl, substituted or unsubstituted C1-C6 alkoxy, substituted or unsubstituted C3-C12 cycloalkyl, and substituted or unsubstituted C2-C10 ester group;

V is —$CH_2$—;

unless otherwise specified, in the above formulae, the substitution means that the hydrogen atom on the corresponding group is replaced by one or more substituents selected from the group consisting of deuterium, halogen, hydroxyl, amino, $C_1$-$C_6$ amide, cyano, unsubstituted or halogenated $C_1$-$C_6$ alkyl, $C_1$-$C_6$ alkoxy, $C_1$-$C_6$ alkyl-amino, $C_1$-$C_{12}$ alkylaminocarbonyl, unsubstituted or halogenated $C_2$-$C_{10}$ acyl, and unsubstituted or halogenated $C_1$-$C_4$ alkyl-$S(O)_2$—.

14. A compound selected from the group consisting of:

45

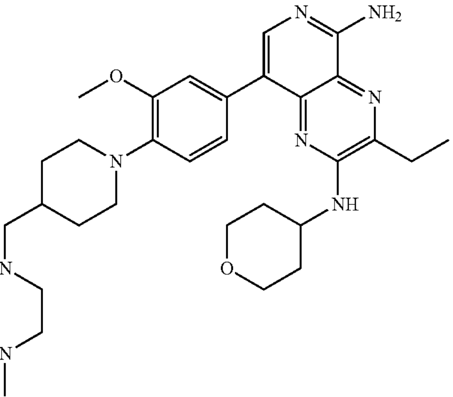

158

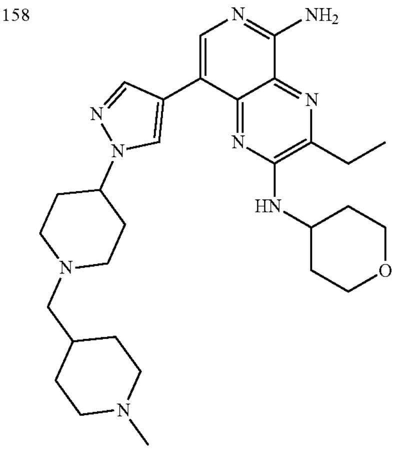

-continued
48
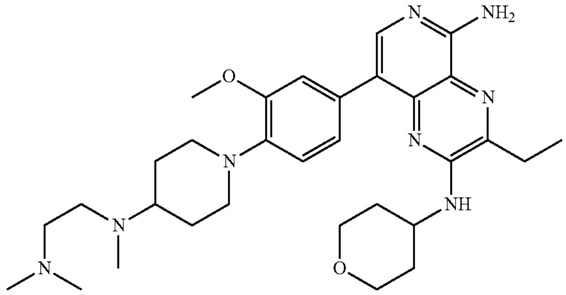 [SMILES: CCc1nc2c(N)ncc(-c3ccc(N4CCC(N(C)CCN(C)C)CC4)c(OC)c3)c2nc1NC1CCOCC1]
262
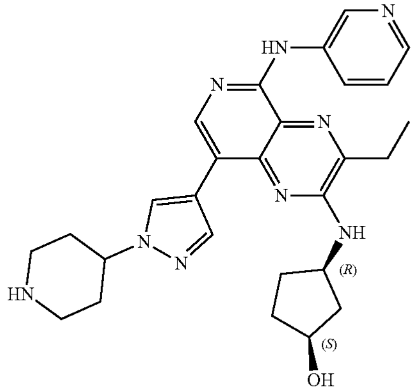
59
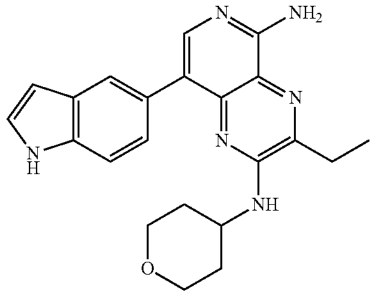 [SMILES: CCc1nc2c(N)ncc(-c3ccc4[nH]ccc4c3)c2nc1NC1CCOCC1]
264
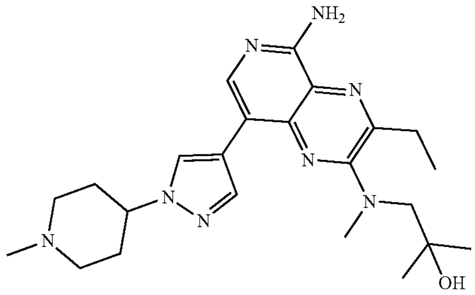 [SMILES: CCc1nc2c(N)ncc(-c3cnn(C4CCN(C)CC4)c3)c2nc1N(C)CC(C)(C)O]
61
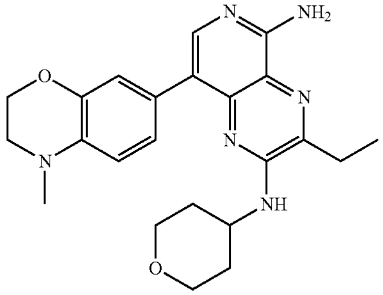 [SMILES: CCc1nc2c(N)ncc(-c3ccc4c(c3)OCCN4C)c2nc1NC1CCOCC1]

-continued
283
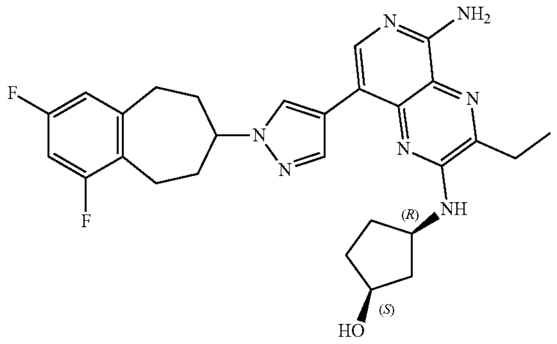
62
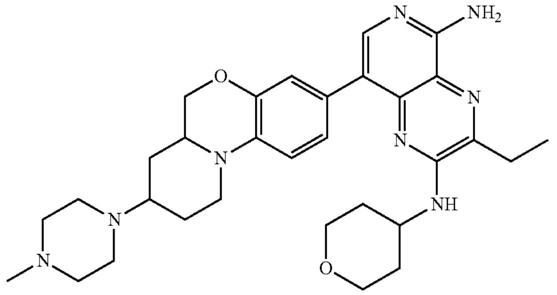 [SMILES: CCc1nc2c(N)ncc(-c3ccc4c(c3)OCC3CC(N5CCN(C)CC5)CCN43)c2nc1NC1CCOCC1]
357
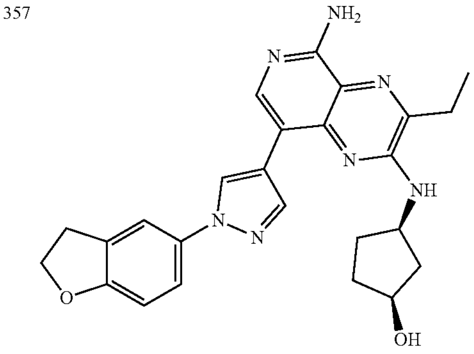
157
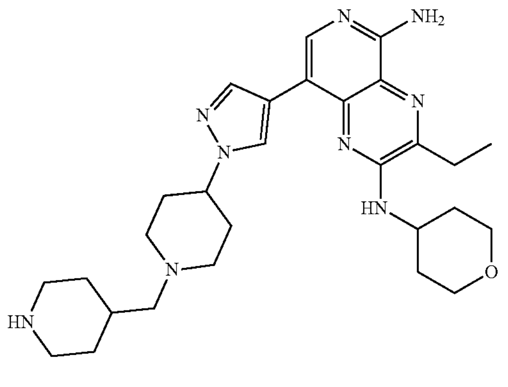 [SMILES: CCc1nc2c(N)ncc(-c3cnn(C4CCN(CC5CCNCC5)CC4)c3)c2nc1NC1CCOCC1]

-continued
358
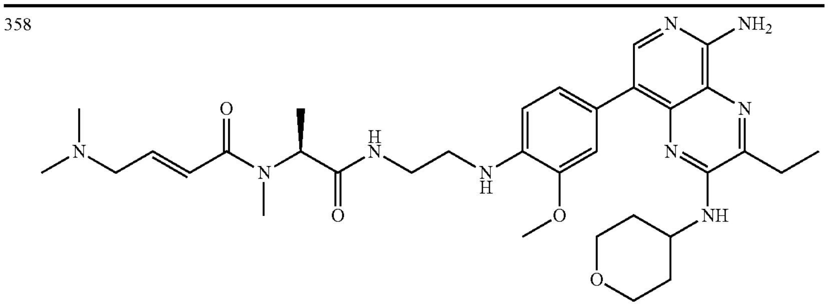
11
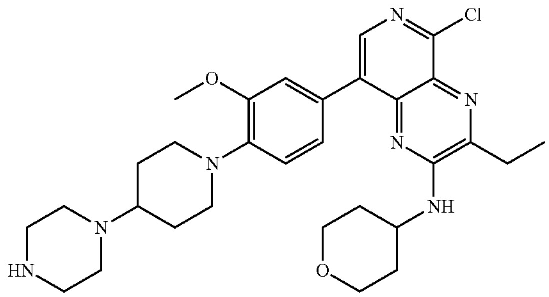 [SMILES: CCc1nc2c(Cl)ncc(-c3ccc(N4CCC(N5CCNCC5)CC4)c(OC)c3)c2nc1NC1CCOCC1]
* * * * *